United States Patent
Charrier et al.

(10) Patent No.: US 9,701,674 B2
(45) Date of Patent: Jul. 11, 2017

(54) SUBSTITUTED PYRAZINES AS ATR KINASE INHIBITORS

(71) Applicant: Vertex Pharmaceuticals Incorporated, Boston, MA (US)

(72) Inventors: Jean-Damien Charrier, Wantage (GB); Steven Durrant, Abingdon (GB); David Kay, Purton (GB); Ronald Knegtel, Abingdon (GB); Somhairle MacCormick, Ealing (GB); Michael Mortimore, Burford (GB); Michael O'Donnell, Abingdon (GB); Joanne Pinder, Didcot (GB); Alistair Rutherford, Abingdon (GB); Anisa Nizarali Virani, Thatcham (GB); Stephen Young, Oxford (GB); Philip Michael Reaper, Richmond (GB)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

(21) Appl. No.: 14/467,175

(22) Filed: Aug. 25, 2014

(65) Prior Publication Data

US 2015/0051187 A1    Feb. 19, 2015

Related U.S. Application Data

(62) Division of application No. 12/642,447, filed on Dec. 18, 2009, now Pat. No. 8,841,308.
(Continued)

(51) Int. Cl.
*A61K 31/4965* (2006.01)
*C07D 241/28* (2006.01)
(Continued)

(52) U.S. Cl.
CPC .......... *C07D 413/14* (2013.01); *C07D 241/28* (2013.01); *C07D 401/04* (2013.01);
(Continued)

(58) Field of Classification Search
CPC .......................... A61K 31/4965; C07D 241/28
(Continued)

(56) References Cited

U.S. PATENT DOCUMENTS 4,309,430 A    1/1982 Bock et al.
5,143,824 A    9/1992 Yamakawa et al.
(Continued)

FOREIGN PATENT DOCUMENTS

CN    1551869 A    12/2004
CN    101001606 A    7/2007
(Continued)

OTHER PUBLICATIONS

International Search Report and Written Opinion mailed Jul. 19, 2011 for Application No. PCT/US2011/036246.
(Continued)

*Primary Examiner* — Douglas M Willis
(74) *Attorney, Agent, or Firm* — Andrea L. C. Reid; Dechert LLP

(57) ABSTRACT

The present invention relates to pyrazine compounds useful as inhibitors of ATR protein kinase. The invention also relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and methods of using the compounds in in vitro applications, such as the study of kinases in biological and pathological phenomena; the study of intracellular signal transduction pathways mediated by such kinases; and the comparative evaluation of new kinase inhibitors.

Certain compounds of this invention are of formula II, V, and/or VII:

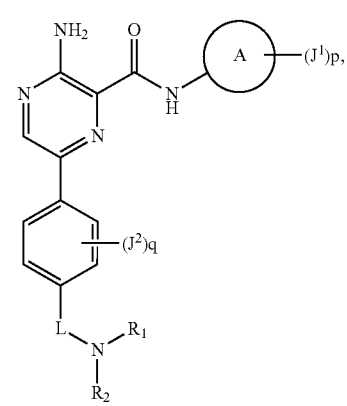

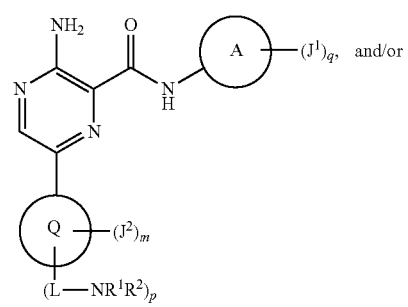

(Continued)

-continued

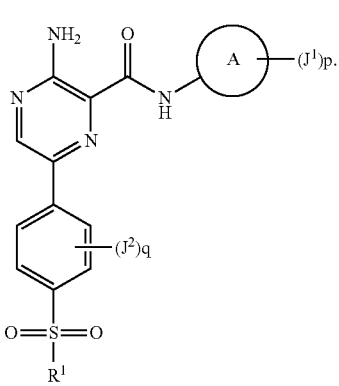

VII wherein the variables are as defined herein.

61 Claims, No Drawings

Related U.S. Application Data

(60) Provisional application No. 61/139,420, filed on Dec. 19, 2008, provisional application No. 61/139,424, filed on Dec. 19, 2008, provisional application No. 61/139,426, filed on Dec. 19, 2008, provisional application No. 61/139,429, filed on Dec. 19, 2008, provisional application No. 61/181,794, filed on May 28, 2009, provisional application No. 61/219,100, filed on Jun. 22, 2009.

(51) Int. Cl.
| | |
|---|---|
| C07D 413/14 | (2006.01) |
| C07D 401/14 | (2006.01) |
| C07D 403/12 | (2006.01) |
| C07D 409/14 | (2006.01) |
| C07D 413/12 | (2006.01) |
| C07D 417/04 | (2006.01) |
| C07D 417/12 | (2006.01) |
| C07D 471/04 | (2006.01) |
| C07D 401/10 | (2006.01) |
| C07D 403/04 | (2006.01) |
| C07D 403/14 | (2006.01) |
| C07D 405/14 | (2006.01) |
| C07D 417/14 | (2006.01) |
| C07D 401/04 | (2006.01) |
| C07D 403/10 | (2006.01) |
| C07D 405/04 | (2006.01) |
| C07D 405/12 | (2006.01) |
| C07D 409/04 | (2006.01) |

(52) U.S. Cl.
CPC ......... C07D 401/10 (2013.01); C07D 401/14 (2013.01); C07D 403/04 (2013.01); C07D 403/10 (2013.01); C07D 403/12 (2013.01); C07D 403/14 (2013.01); C07D 405/04 (2013.01); C07D 405/12 (2013.01); C07D 405/14 (2013.01); C07D 409/04 (2013.01); C07D 409/14 (2013.01); C07D 413/12 (2013.01); C07D 417/04 (2013.01); C07D 417/12 (2013.01); C07D 417/14 (2013.01); C07D 471/04 (2013.01)

(58) Field of Classification Search
USPC .................................... 514/255.06; 544/407
See application file for complete search history.

(56) References Cited

U.S. PATENT DOCUMENTS

| | | | |
|---|---|---|---|
| 6,420,367 B1 | 7/2002 | Ueda et al. | |
| 6,469,002 B1 | 10/2002 | Ohshima et al. | |
| 6,660,753 B2 | 12/2003 | Van Wagenen et al. | |
| 6,790,935 B1 | 9/2004 | Mutter et al. | |
| 6,858,600 B2 | 2/2005 | Hamilton et al. | |
| 6,992,087 B2 | 1/2006 | Verhoest et al. | |
| 7,041,672 B2 | 5/2006 | Verhoest et al. | |
| 7,043,079 B2 | 5/2006 | Malvar et al. | |
| 7,145,002 B2 | 12/2006 | Brands et al. | |
| 7,199,123 B2 * | 4/2007 | Munchhof | 514/255.05 |
| 7,277,118 B2 | 10/2007 | Foote | |
| 7,385,626 B2 | 6/2008 | Aggarwal et al. | |
| 7,394,926 B2 | 7/2008 | Bryll et al. | |
| 7,452,993 B2 | 11/2008 | Arnold et al. | |
| 7,574,131 B2 | 8/2009 | Chang et al. | |
| 7,622,583 B2 | 11/2009 | Ungashe et al. | |
| 7,626,021 B2 | 12/2009 | Arnold et al. | |
| 7,700,601 B2 | 4/2010 | Chan et al. | |
| 7,704,995 B2 | 4/2010 | Buhr et al. | |
| 7,829,558 B2 | 11/2010 | Arnold et al. | |
| 7,872,031 B2 | 1/2011 | Lauffer et al. | |
| 7,902,197 B2 | 3/2011 | Elworthy et al. | |
| 7,932,254 B2 | 4/2011 | Dubois et al. | |
| 7,939,531 B2 | 5/2011 | Bamberg et al. | |
| 7,981,893 B2 | 7/2011 | Mortensen et al. | |
| 8,063,032 B2 | 11/2011 | Chytil et al. | |
| 8,106,197 B2 | 1/2012 | Cui et al. | |
| 8,410,112 B2 | 4/2013 | Charrier et al. | |
| 8,492,582 B2 | 7/2013 | Yokotani et al. | |
| 8,765,751 B2 | 7/2014 | Charrier et al. | |
| 8,841,308 B2 | 9/2014 | Charrier et al. | |
| 8,841,337 B2 | 9/2014 | Charrier et al. | |
| 8,841,449 B2 | 9/2014 | Charrier et al. | |
| 8,841,450 B2 | 9/2014 | Charrier et al. | |
| 8,846,686 B2 | 9/2014 | Charrier et al. | |
| 8,846,917 B2 | 9/2014 | Charrier et al. | |
| 8,846,918 B2 | 9/2014 | Charrier et al. | |
| 8,853,217 B2 | 10/2014 | Charrier et al. | |
| 8,877,759 B2 | 11/2014 | Charrier et al. | |
| 8,912,198 B2 | 12/2014 | Charrier et al. | |
| 8,962,631 B2 | 2/2015 | Charrier et al. | |
| 8,969,356 B2 | 3/2015 | Charrier et al. | |
| 8,999,632 B2 | 4/2015 | Falcon et al. | |
| 9,035,053 B2 | 5/2015 | Charrier et al. | |
| 9,062,008 B2 | 6/2015 | Charrier et al. | |
| 9,096,584 B2 | 8/2015 | Charrier et al. | |
| 9,334,244 B2 | 5/2016 | Charrier et al. | |
| 9,365,557 B2 | 6/2016 | Charrier et al. | |
| 2002/0064314 A1 | 5/2002 | Comaniciu et al. | |
| 2002/0068828 A1 | 6/2002 | Schnatterer et al. | |
| 2002/0158984 A1 | 10/2002 | Brodsky et al. | |
| 2002/0180759 A1 | 12/2002 | Park et al. | |
| 2002/0195563 A1 | 12/2002 | Iida et al. | |
| 2003/0008882 A1 | 1/2003 | Hamilton et al. | |
| 2003/0055085 A1 | 3/2003 | Wagenen et al. | |
| 2003/0199511 A1 | 10/2003 | Li et al. | |
| 2004/0034037 A1 | 2/2004 | Harbeson et al. | |
| 2004/0075741 A1 | 4/2004 | Berkey et al. | |
| 2004/0100560 A1 | 5/2004 | Stavely et al. | |
| 2004/0175042 A1 | 9/2004 | Kroeker et al. | |
| 2004/0180905 A1 | 9/2004 | Munchhof | |
| 2004/0202382 A1 | 10/2004 | Pilu | |
| 2004/0252193 A1 | 12/2004 | Higgins | |
| 2004/0264793 A1 | 12/2004 | Okubo | |
| 2005/0116968 A1 | 6/2005 | Barrus et al. | |
| 2005/0123902 A1 | 6/2005 | Meneses et al. | |
| 2005/0207487 A1 | 9/2005 | Monroe | |
| 2005/0261339 A1 | 11/2005 | Ohi et al. | |
| 2005/0276765 A1 | 12/2005 | Nghiem et al. | |
| 2006/0046991 A1 | 3/2006 | Cui et al. | |

(56) References Cited

U.S. PATENT DOCUMENTS

| | | |
|---|---|---|
| 2006/0083440 A1 | 4/2006 | Chen |
| 2006/0142307 A1 | 6/2006 | Hellberg et al. |
| 2006/0211709 A1 | 9/2006 | Buhr et al. |
| 2007/0032501 A1 | 2/2007 | Augeri et al. |
| 2007/0037794 A1 | 2/2007 | Ungashe et al. |
| 2007/0092245 A1 | 4/2007 | Bazakos et al. |
| 2007/0120954 A1 | 5/2007 | Allen et al. |
| 2007/0149547 A1* | 6/2007 | Bonnefous et al. ..... 514/255.05 |
| 2007/0254868 A1 | 11/2007 | Lauffer et al. |
| 2007/0270420 A1 | 11/2007 | Harbeson et al. |
| 2007/0287711 A1 | 12/2007 | Arnold et al. |
| 2008/0132698 A1 | 6/2008 | Fagnou et al. |
| 2008/0176892 A1 | 7/2008 | Heinrich et al. |
| 2009/0001843 A1 | 1/2009 | Enomoto et al. |
| 2009/0005381 A1 | 1/2009 | Brown et al. |
| 2009/0143410 A1 | 6/2009 | Patel |
| 2009/0156512 A1 | 6/2009 | Umemura et al. |
| 2009/0215724 A1 | 8/2009 | DuBois et al. |
| 2009/0215750 A1 | 8/2009 | Bamberg et al. |
| 2009/0215785 A1 | 8/2009 | DuBois et al. |
| 2009/0215788 A1 | 8/2009 | Elworthy et al. |
| 2009/0306087 A1 | 12/2009 | Ibrahim et al. |
| 2010/0036118 A1 | 2/2010 | Arnold et al. |
| 2010/0168138 A1 | 7/2010 | DeGoey et al. |
| 2010/0179194 A1 | 7/2010 | Mihara et al. |
| 2010/0190980 A1 | 7/2010 | Umemiya et al. |
| 2010/0204214 A1 | 8/2010 | Chytil et al. |
| 2010/0222318 A1 | 9/2010 | Charrier et al. |
| 2010/0233091 A1 | 9/2010 | Neumann et al. |
| 2010/0249387 A1 | 9/2010 | Inouye |
| 2011/0015231 A1 | 1/2011 | Al-Abed et al. |
| 2011/0059936 A1 | 3/2011 | Lauffer et al. |
| 2011/0098325 A1 | 4/2011 | Raynham et al. |
| 2011/0275797 A1 | 11/2011 | Yokotani et al. |
| 2011/0288067 A1 | 11/2011 | Hendricks et al. |
| 2011/0288097 A1 | 11/2011 | Hendricks et al. |
| 2012/0025805 A1 | 2/2012 | Matsushita et al. |
| 2012/0027874 A1 | 2/2012 | Charrier et al. |
| 2012/0035407 A1 | 2/2012 | Charrier et al. |
| 2012/0035408 A1 | 2/2012 | Charrier et al. |
| 2012/0040020 A1 | 2/2012 | Charrier et al. |
| 2012/0046295 A1 | 2/2012 | Charrier et al. |
| 2012/0065247 A1 | 3/2012 | Thompson et al. |
| 2012/0115874 A1 | 5/2012 | Wang et al. |
| 2012/0122884 A1 | 5/2012 | Charrier et al. |
| 2012/0177748 A1 | 7/2012 | Charrier et al. |
| 2012/0178756 A1 | 7/2012 | Charrier et al. |
| 2012/0178915 A1 | 7/2012 | Xu |
| 2012/0220587 A1 | 8/2012 | Emde et al. |
| 2012/0225857 A1 | 9/2012 | Augeri et al. |
| 2012/0238518 A1 | 9/2012 | Maciag et al. |
| 2013/0017273 A1 | 1/2013 | Everitt et al. |
| 2013/0018035 A1 | 1/2013 | MacCormick et al. |
| 2013/0034616 A1 | 2/2013 | Storck et al. |
| 2013/0089624 A1 | 4/2013 | Charrier et al. |
| 2013/0089625 A1 | 4/2013 | Charrier et al. |
| 2013/0089626 A1 | 4/2013 | Pollard et al. |
| 2013/0095193 A1 | 4/2013 | Charrier et al. |
| 2013/0096139 A1 | 4/2013 | Charrier et al. |
| 2013/0115310 A1 | 5/2013 | Charrier et al. |
| 2013/0115311 A1 | 5/2013 | Charrier et al. |
| 2013/0115312 A1 | 5/2013 | Charrier et al. |
| 2013/0115313 A1 | 5/2013 | Charrier et al. |
| 2013/0115314 A1 | 5/2013 | Charrier et al. |
| 2013/0172273 A1 | 7/2013 | Aizpurua Iparraguirre et al. |
| 2013/0184292 A1 | 7/2013 | Charrier et al. |
| 2014/0044802 A1 | 2/2014 | Pollard et al. |
| 2014/0107093 A1 | 4/2014 | Charrier et al. |
| 2014/0113005 A1 | 4/2014 | Charrier et al. |
| 2014/0134596 A1 | 5/2014 | Falcon et al. |
| 2014/0187529 A1 | 7/2014 | Shetty et al. |
| 2014/0356456 A1 | 12/2014 | Pollard et al. |
| 2015/0031661 A1 | 1/2015 | Charrier et al. |
| 2015/0239874 A1 | 8/2015 | Charrier et al. |
| 2015/0247866 A1 | 9/2015 | Falcon et al. |
| 2015/0274710 A1 | 10/2015 | Charrier et al. |
| 2016/0030424 A1 | 2/2016 | Pollard et al. |
| 2016/0271129 A1 | 9/2016 | Charrier et al. |
| 2016/0311809 A1 | 10/2016 | Charrier et al. |

FOREIGN PATENT DOCUMENTS

| | | |
|---|---|---|
| CN | 101479255 A | 7/2009 |
| CN | 101537007 A | 9/2009 |
| CN | 101652354 A | 2/2010 |
| CN | 101671336 A | 3/2010 |
| CN | 103373996 A | 10/2013 |
| EP | 0313724 A2 | 5/1989 |
| EP | 1217000 A1 | 6/2002 |
| EP | 2157090 A1 | 2/2010 |
| JP | 62/270623 A2 | 11/1987 |
| JP | 63/208520 A2 | 8/1988 |
| JP | H02-72370 A | 3/1990 |
| JP | H02-72372 A | 3/1990 |
| JP | H03-74370 A | 3/1991 |
| JP | H10-77286 A | 3/1998 |
| JP | 2002/072370 A | 3/2002 |
| JP | 2002/072372 A | 3/2002 |
| JP | 2002/518389 A | 6/2002 |
| JP | 2003/074370 A | 3/2003 |
| JP | 2003/516974 A | 5/2003 |
| JP | 2005/511531 A | 4/2005 |
| JP | 2005/530760 A | 10/2005 |
| JP | 2006/156445 A | 6/2006 |
| JP | 2006/516124 A | 6/2006 |
| JP | 2006/519232 A | 8/2006 |
| JP | 2006/519833 A | 8/2006 |
| JP | 2006/520794 A | 9/2006 |
| JP | 2006/521357 A | 9/2006 |
| JP | 2007/524682 A | 8/2007 |
| JP | 2008/510790 A | 4/2008 |
| JP | 2008/510792 A | 4/2008 |
| JP | 2008/517945 A | 5/2008 |
| JP | 2008/525453 A | 7/2008 |
| JP | 2008/543754 A | 12/2008 |
| JP | 2009/503103 A | 1/2009 |
| JP | 2009/027904 A | 2/2009 |
| JP | 2009/530233 A | 8/2009 |
| JP | 2009/532356 A | 9/2009 |
| JP | 2009/533327 A | 9/2009 |
| JP | 2009/541247 A | 11/2009 |
| JP | 2009/541268 A | 11/2009 |
| JP | 2010/506934 A | 3/2010 |
| JP | 2010/509356 A | 3/2010 |
| JP | 2010/077286 A | 4/2010 |
| JP | 2010/513433 A | 4/2010 |
| JP | 2010/180180 A | 8/2010 |
| JP | 2011/500778 A | 1/2011 |
| JP | 2011/042639 A | 3/2011 |
| JP | 2012/508260 A | 4/2012 |
| JP | 2012/513398 A | 6/2012 |
| JP | 2012/533248 A | 12/2012 |
| JP | 2013/501720 A | 1/2013 |
| JP | 2013/505900 A | 2/2013 |
| JP | 2013/517264 A | 5/2013 |
| JP | 2013/525476 A | 6/2013 |
| JP | 2014/510072 A | 4/2014 |
| JP | 2014/518545 A | 7/2014 |
| JP | 2014/165380 A | 9/2014 |
| NZ | 593316 | 6/2013 |
| NZ | 593969 A | 11/2013 |
| WO | WO 97/43267 A1 | 11/1997 |
| WO | WO 98/42701 A1 | 10/1998 |
| WO | WO 99/44609 A1 | 9/1999 |
| WO | WO 00/04014 A1 | 1/2000 |
| WO | WO 00/76982 A1 | 12/2000 |
| WO | WO 01/44206 A1 | 6/2001 |
| WO | WO 02/09648 A2 | 2/2002 |
| WO | WO 02/80899 A1 | 10/2002 |
| WO | WO 03/004472 A1 | 1/2003 |
| WO | WO 03/004475 A1 | 1/2003 |
| WO | WO 03/032971 A1 | 4/2003 |
| WO | WO 03/045924 A1 | 6/2003 |
| WO | WO 03/076422 A1 | 9/2003 |

(56) References Cited

FOREIGN PATENT DOCUMENTS

| | | |
|---|---|---|
| WO | WO 03/080610 A1 | 10/2003 |
| WO | WO 03/087057 A1 | 10/2003 |
| WO | WO 03/092686 A1 | 11/2003 |
| WO | WO 03/093297 A2 | 11/2003 |
| WO | WO 03/101968 A1 | 12/2003 |
| WO | WO 2004/000318 A2 | 12/2003 |
| WO | WO 2004/000820 A2 | 12/2003 |
| WO | WO 2004/033431 A2 | 4/2004 |
| WO | WO 2004/055005 A1 | 7/2004 |
| WO | WO 2004/055006 A1 | 7/2004 |
| WO | WO 2004/076412 A2 | 9/2004 |
| WO | WO 2004/080982 A1 | 9/2004 |
| WO | WO 2004/084813 A2 | 10/2004 |
| WO | WO 2004/084824 A2 | 10/2004 |
| WO | WO 2004/085409 A2 | 10/2004 |
| WO | WO 2004/103279 A2 | 12/2004 |
| WO | WO 2004/103369 A1 | 12/2004 |
| WO | WO 2004/103991 A1 | 12/2004 |
| WO | WO 2005/028475 A2 | 3/2005 |
| WO | WO 2005/058876 A1 | 6/2005 |
| WO | WO 2005/079802 A1 | 9/2005 |
| WO | WO 2005/123672 A2 | 12/2005 |
| WO | WO 2006/015124 A2 | 2/2006 |
| WO | WO 2006/021886 A1 | 3/2006 |
| WO | WO 2006/047504 A1 | 5/2006 |
| WO | WO 2006/053342 A2 | 5/2006 |
| WO | WO 2006/058074 A1 | 6/2006 |
| WO | WO 2006/067462 A1 | 6/2006 |
| WO | WO 2006/071548 A2 | 7/2006 |
| WO | WO 2006/075152 A1 | 7/2006 |
| WO | WO 2006/088837 A2 | 8/2006 |
| WO | WO 2006/114180 A1 | 11/2006 |
| WO | WO 2006/120573 A2 | 11/2006 |
| WO | WO 2006/124874 A2 | 11/2006 |
| WO | WO 2006/135604 A2 | 12/2006 |
| WO | WO 2007/015632 A1 | 2/2007 |
| WO | WO 2007/016674 A2 | 2/2007 |
| WO | WO 2007/058850 A2 | 5/2007 |
| WO | WO 2007/063012 A1 | 6/2007 |
| WO | WO 2007/066805 A1 | 6/2007 |
| WO | WO 2007/076360 A1 | 7/2007 |
| WO | WO 2007/095588 A1 | 8/2007 |
| WO | WO 2007/096151 A2 | 8/2007 |
| WO | WO 2007/096764 A2 | 8/2007 |
| WO | WO 2007/096765 A1 | 8/2007 |
| WO | WO 2007/102770 A1 | 9/2007 |
| WO | WO 2007/111904 A2 | 10/2007 |
| WO | WO 2007/126964 A2 | 11/2007 |
| WO | WO 2007/147746 A1 | 12/2007 |
| WO | WO 2007/147874 A1 | 12/2007 |
| WO | WO 2008/025820 A1 | 3/2008 |
| WO | WO 2008/037477 A1 | 4/2008 |
| WO | WO 2008/038010 A1 | 4/2008 |
| WO | WO 2008/040651 A1 | 4/2008 |
| WO | WO 2008/051493 A2 | 5/2008 |
| WO | WO 2008/060907 A2 | 5/2008 |
| WO | WO 2008/071456 A2 | 6/2008 |
| WO | WO 2008/074997 A1 | 6/2008 |
| WO | WO 2008/079291 A2 | 7/2008 |
| WO | WO 2008/079903 A1 | 7/2008 |
| WO | WO 2008/079906 A1 | 7/2008 |
| WO | WO 2008/103277 A2 | 8/2008 |
| WO | WO 2008/106692 A1 | 9/2008 |
| WO | WO 2008/122375 A2 | 10/2008 |
| WO | WO 2008/124850 A1 | 10/2008 |
| WO | WO 2008/141065 A1 | 11/2008 |
| WO | WO 2008/144463 A1 | 11/2008 |
| WO | WO 2008/144464 A1 | 11/2008 |
| WO | WO 2008/156174 A1 | 12/2008 |
| WO | WO 2008/157191 A2 | 12/2008 |
| WO | WO 2009/005638 A2 | 1/2009 |
| WO | WO 2009/007390 A2 | 1/2009 |
| WO | WO 2009/012482 A2 | 1/2009 |
| WO | WO 2009/014637 A2 | 1/2009 |
| WO | WO 2009/016460 A2 | 2/2009 |
| WO | WO 2009/024825 A1 | 2/2009 |
| WO | WO 2009/037247 A1 | 3/2009 |
| WO | WO 2009/053737 A2 | 4/2009 |
| WO | WO 2009/099982 A1 | 8/2009 |
| WO | WO 2009/106885 A1 | 9/2009 |
| WO | WO 2009/111280 A1 | 9/2009 |
| WO | WO 2009/115517 A2 | 9/2009 |
| WO | WO 2010/015803 A1 | 2/2010 |
| WO | WO 2010/016005 A1 | 2/2010 |
| WO | WO 2010/017055 A2 | 2/2010 |
| WO | WO 2010/048131 A1 | 4/2010 |
| WO | WO 2010/054398 A1 | 5/2010 |
| WO | WO 2010/063634 A1 | 6/2010 |
| WO | WO 2010/068483 A2 | 6/2010 |
| WO | WO 2010/071837 A1 | 6/2010 |
| WO | WO 2010/073034 A1 | 7/2010 |
| WO | WO 2010/075200 A1 | 7/2010 |
| WO | WO 2011/008830 A1 | 1/2011 |
| WO | WO 2011/017513 A1 | 2/2011 |
| WO | WO 2011/035855 A1 | 3/2011 |
| WO | WO 2011/044157 A1 | 4/2011 |
| WO | WO 2011/086531 A2 | 7/2011 |
| WO | WO 2011/117145 A2 | 9/2011 |
| WO | WO 2011/124998 A1 | 10/2011 |
| WO | WO 2011/130689 A1 | 10/2011 |
| WO | WO 2011/138751 A2 | 11/2011 |
| WO | WO 2011/143399 A1 | 11/2011 |
| WO | WO 2011/143419 A1 | 11/2011 |
| WO | WO 2011/143422 A1 | 11/2011 |
| WO | WO 2011/143423 A2 | 11/2011 |
| WO | WO 2011/143425 A2 | 11/2011 |
| WO | WO 2011/143426 A1 | 11/2011 |
| WO | WO 2011/144584 A1 | 11/2011 |
| WO | WO 2011/144585 A1 | 11/2011 |
| WO | WO 2012/158785 A1 | 11/2012 |
| WO | WO 2013/049722 A1 | 4/2013 |
| WO | WO 2013/049726 A2 | 4/2013 |
| WO | WO 2013/049859 A1 | 4/2013 |

OTHER PUBLICATIONS

International Search Report and Written Opinion mailed Aug. 23, 2013 for Application No. PCT/US2013/035466.
International Search Report and Written Opinion mailed Apr. 23, 2013 for Application No. PCT/US2012/058127.
International Search Report and Written Opinion mailed Jan. 11, 2012 for Application No. PCT/US2011/036243.
International Search Report and Written Opinion mailed Oct. 12, 2011 for Application No. PCT/US2011/036239.
International Search Report and Written Opinion mailed Dec. 20, 2013 for Application No. PCT/US2013/063254.
International Search Report and Written Opinion mailed Dec. 28, 2011 for Application No. PCT/US2011/036245.
International Search Report and Written Opinion mailed Jan. 8, 2013 for Application No. PCT/US2012/058374.
International Search Report and Written Opinion mailed Jun. 28, 2011 for Application No. PCT/US2011/036242.
International Search Report and Written Opinion mailed Mar. 4, 2010 for Application No. PCT/US2009/068827.
International Search Report and Written Opinion mailed Mar. 15, 2010 for Application No. PCT/US2009/063922.
International Search Report and Written Opinion mailed Jan. 30, 2013 for Application No. PCT/US2012/058117.
International Search Report and Written Opinion mailed Feb. 15, 2013 for Application No. PCT/US2012/064421.
International Search Report and Written Opinion mailed Jun. 17, 2011 for Application No. PCT/US2011/036214.
International Search Report and Written Opinion mailed Aug. 10, 2012 for Application No. PCT/US2012/032438.
International Search Report and Written Opinion mailed Nov. 12, 2012 for Application No. PCT/US2012/058121.
International Search Report and Written Opinion mailed Nov. 12, 2012 for Application No. PCT/US2012/058119.
International Search Report and Written Opinion mailed Feb. 1, 2013 for Application No. PCT/US2012/064426.

(56) References Cited

OTHER PUBLICATIONS

International Search Report and Written Opinion mailed Feb. 1, 2013 for Application No. PCT/US2012/064430.
International Search Report and Written Opinion mailed Feb. 26, 2013 for Application No. PCT/US2012/064433.
International Search Report and Written Opinion mailed Jan. 30, 2013 for Application No. PCT/US2012/064435.
International Search Report and Written Opinion mailed Feb. 27, 2014 for Application No. PCT/US2013/064920.
Non-Final Office Action dated Aug. 8, 2013 in U.S. Appl. No. 13/631,727.
Non-Final Office Action dated Aug. 8, 2013 in U.S. Appl. No. 13/631,732.
Abdel-Magid, Inhibitors of ATR Kinase for Treatment of Cancer. ACS Med Chem Lett. Jun. 13, 2013;4(8):688-9. doi: 10.1021/ml4002198. eCollection 2013.
Adamczyk et al., Synthesis of 3,7-dihydroimidazo[1,2a]pyrazine-3-ones and their chemiluminescent properties. Tetrahedron. 2003;59(41):8129-42.
Ammar et al., 3-Ethoxycarbonylmethylenequinoxalin-2-one in heterocyclic synthesis. Part 1: Synthesis of new substituted and condensed quinoxalines. Afinidad 2005;62(516):151-60.
Bracher et al., Total Synthesis of the Indolizidinium Alkaloid Ficuseptine. Eur J Org Chem. 2002:2288-91.
Buscemi et al., DNA damage-induced cell cycle regulation and function of novel Chk2 phosphoresidues. Mol Cell Biol. Nov. 2006;26(21):7832-45. Epub Aug. 28, 2006.
Campone et al., Phase I and pharmacokinetic trial of AP5346, a DACH-platinum-polymer conjugate, administered weekly for three out of every 4 weeks to advanced solid tumor patients. Cancer Chemother Pharmacol. Sep. 2007;60(4):523-33. Epub Feb. 17, 2007.
Charrier et al, Discovery of potent and selective inhibitors of ataxia telangiectasia mutated and Rad3 related (ATR) protein kinase as potential anticancer agents. J Med Chem. Apr. 14, 2011;54(7):2320-30. doi: 10.1021/jm101488z. Epub Mar. 17, 2011.
Charrier et al., Discovery of Potent and Selective Inhibitors of ATR (Ataxia Telangiectasia Mutated and Rad3 Related) as Potential AntiCancer Agents. Supplementary Information, Apr. 14, 2011: 47 pages.
Charrier, Discovery of potent and selective inhibitors of Ataxia Telangiectasia mutated and Rad3 related (ATR) protein kinase as potential anticancer agents. Presentation, ACS Denver 2011. Aug. 28, 2011. 21 pages.
Chen et al., Development of biomarker of ATR activity in surrogate human tissues. Newcastle University. Poster. Nov. 2012. 1 page.
Chen et al., Targeting the S and G2 checkpoint to treat cancer. Drug Discov Today. Mar. 2012;17(5-6):194-202. doi: 10.1016/j.drudis.2011.12.009. Epub Dec. 15, 2011.
Clark et al., Mass spectrometry of pyrrolo [2, 3- b] pyrazines and pyrazino [2, 3- b]indole. Organic Mass Spectrometry. 1977;12(7):421-3.
Curtin, Inhibiting the DNA damage response as a therapeutic manoeuvre in cancer. Br J Pharmacol. 2013;1-52.
Curtin, Inhibiting the DNA damage response as a therapeutic manoeuvre in cancer. Br J Pharmacol. Aug. 2013;169(8):1745-65. doi: 10.1111/bph.12244.
Darabantu et al., Synthesis of new polyaza heterocycles. Part 42: Diazines. Tetrahedron. 2005;61(11):2897-905.
De Wergifosse et al., Coelenterazine: a two-stage antioxidant in lipid micelles. Free Radical Biol Med. 2004;36(3):278-87.
Dias et al., Synthesis of 2,6-diphenylpyrazine derivatives and their DNA binding and cytotoxic properties. Eur J Med Chem. 2005;40:1206-13.
El-Emary, Synthesis and Biological Activity of Some New Pyrazolo[3,4-b]pyrazines. J Chinese Chem Soc (Taipei, Taiwan). 2006;53(2): 391-401.
Erickson et al., Structure-guided expansion of kinase fragment libraries driven by support vector machine models. Biochim Biophys Acta. Mar. 2010;1804(3):642-52. doi: 10.1016/j.bbapap.2009.12.002. Epub Dec. 11, 2009.
Fernandes et al., Synthesis and Biological Activity of Heterocyclic Derivatives derived from Ethyl-2-hydroxy-quinoxaline-3-carboxylate. J Indian Chem Soc. 1986;63(4):427-9.
Finlay et al., Modulation of DNA repair by pharmacological inhibitors of the PIKK protein kinase family. Bioorg Med Chem Lett. Sep. 1, 2012;22(17):5352-9. doi: 10.1016/j.bmcl.2012.06.053. Epub Jul. 1, 2012.
Fokas et al., Targeting ATR in DNA damage response and cancer therapeutics. Cancer Treat Rev. Feb. 2014;40(1):109-17. doi: 10.1016/j.ctrv.2013.03.002. Epub Apr. 11, 2013.
Fokas et al., Targeting ATR in vivo using the novel inhibitor VE-822 results in selective sensitization of pancreatic tumors to radiation. Cell Death Dis. Dec. 6, 2012;3:e441. doi: 10.1038/cddis.2012.181.
Gentili et al., Alpha2-adrenoreceptors profile modulation. 4. From antagonist to agonist behavior. J Med Chem. Jul. 24, 2008;51(14):4289-99. doi: 10.1021/jm800250z. Epub Jun. 25, 2008.
Goto et al.,Squid bioluminescence I. Structure of watasenia oxyluciferin, a possible light-emitter in the bioluminescence of watasenia scintillans. Tetrahedron Lett. 1974;15(26):2321-4.
Hall-Jackson et al., ATR is a caffeine-sensitive, DNA-activated protein kinase with a substrate specificity distinct from DNA-PK. Oncogene. Nov. 18, 1999;18(48):6707-13.
Hart et al., Renilla Reinformis Bioluminescence: Luciferase-Catalyzed Production of Nonradiating Excited States from Luciferin Analogues and Elucidation of the Excited State Species Involved in Energy Transfer to Renilla Green Fluorescent Protein. Biochemistry. 1979;18:2204-10.
Hickson et al., Identification and characterization of a novel and specific inhibitor of the ataxia-telangiectasia mutated kinase ATM. Cancer Res. Dec. 15, 2004;64(24):9152-9.
Hilton et al., Identification and characterisation of 2-aminopyridine inhibitors of checkpoint kinase 2. Bioorg Med Chem. Jan. 15, 2010;18(2):707-18. doi: 10.1016/j.bmc.2009.11.058. Epub Dec. 6, 2009.
Hirano et al., Bioluminescent properties of fluorinated semi-synthetic aequorins. Tetrahedron Lett. 1998;39(31):5541-4.
Jia et al., A Facile Preparation of 2,6-Diarylpyrazines. Heteroatom Chemistry. 1998;9(3):341-5.
Jiang et al., Synthesis and cytotoxicity evaluation of novel indolylpyrimidines and indolylpyrazines as potential antitumor agents. Bioorg Med Chem. May 2001;9(5):1149-54.
Jones et al., A Suzuki Coupling Approach to Pyrazines Related to Coelenterazine. Synlett. 1996;(6):509-10.
Kao et al., Inhibition of γ-H2AX after ionizing radiation as a biological surrogate of impaired upstream DNA damage signaling and radiosensitivity. J Cancer Mol. 2010;5(2):49-54.
Katritzky et al., Efficient synthesis of 3,5-functionalized isoxazoles and isoxazolines via 1,3-dipolar cycloaddition reactions of 1-propargyl- and 1-allylbenzotriazoles. J Heterocyclic Chem. 2000;37(6):1505-10.
Kim et al., Substrate specificities and identification of putative substrates of ATM kinase family members. J Biol Chem. Dec. 31, 1999;274(53):37538-43.
Klicnar, J., et al., "Studien in der chinoxalinreihe III. Synthese, reaktionen und ir-spektren einiger 3-hydroxy-2-carboxymethylchinoxalin-derivate", Collection Czechoslovak. Chem. Commun. 1965; 30(9): 3092-3101.
Kumpaty et al., Synthesis of N-methyl secondary amines. Synth Commun. 2003;33(8):1411-6.
Kurasawa et al., Revised Structure for the Product from the Reaction of 3-Hydrazinocarbonylmethylene-2-oxo-1,2,3,4-tetrahydroquinoxaline with Nitrous Acid. Chem. Pharm. Bull. 1984;32(10):4140-3.
Lima et al., Bioisosterism: a useful strategy for molecular modification and drug design. Curr Med Chem. 2005;12(1):23-49.
Ling et al., Mechanism of Cell Cycle G2/M Arrest in Human Gastric Cancer BGC823 Cells Induced by Diallyl Disulfide. Chinese J Clin Oncol. Feb. 28, 2010;(3):121-5.
Liu et al., Chemical Biology Foundation. Science Press. Sep. 30, 2010;213-8.

(56) References Cited

OTHER PUBLICATIONS

Luo et al., Molecular dynamics-based self-organizing molecular field analysis on 3-amino-6-arylpyrazines as the ataxia telangiectasia mutated and Rad3 related (ATR) protein kinase inhibitors. Med Chem Res. 2013; 1-12.
March, J., Mar.'s Advanced Organic Chemistry, 2007, John Wiley and Sons, Chapter 16.
McKenna, G., et al., "Evaluation of the first potent and highly selective inhibitor of ATR inhibitor, VE-821: an approach to selectively sensitize cancer cells to ionizing radiation and hypoxia", Poster, Mar. 31, 2012.
McKenna, G., et al., "Evaluation of the first potent and highly selective inhibitor of ATR kinase: an approach to selectively sensitize cancer cells to ionizing radiation and hypoxia", Abstract, Mar. 31, 2012.
Middleton et al., ATR as a Therapeutic Target. Cancer Drug Discovery and Development. 2013. Author's Proof. 20 pages.
Middleton et al., ATR as a Therapeutic Target. In: Advances in DNA Repair in Cancer Therapy. Cancer Drug Discovery and Development. 2013;72:211-28.
Middleton et al., Chemosensitisation by, and Single Agent Activity of, ATR Inhibitor VE-821 in Human Breast Cancer Cells. Eur J Canc. Nov. 1, 2012;85-6.
Muslimovic et al., An optimized method for measurement of gamma-H2AX in blood mononuclear and cultured cells. Nat Protoc. 2008;3(7):1187-93. doi: 10.1038/nprot.2008.93.
Nakamura et al., Bimodal Chemiluminescence of 8-Chlorostyryl-6-phenylethynylimidazopyrazinone: Large Bathochromic Shift Caused by a Styryl Group at 8-Position. Tetrahedron Letters. 1998;39:301-4.
Nowotnik et al., ProLindac (AP5346): a review of the development of an HPMA DACH platinum Polymer Therapeutic. Adv Drug Deliv Rev. Nov. 12, 2009;61(13):1214-9. doi: 10.1016/j.addr.2009.06.004. Epub Aug. 9, 2009. Review.
Patani et al., Bioisosterism: A Rational Approach in Drug Design. Chem Rev. Dec. 19, 1996;96(8):3147-76.
Pires et al., Targeting radiation-resistant hypoxic tumour cells through ATR inhibition. Br J Cancer. Jul. 10, 2012;107(2):291-9. doi: 10.1038/bjc.2012.265. Epub Jun. 19, 2012.
Pollard, Inhibition of the DNA Damage Response Kinase, ATR, as a Promising Anti-Cancer Approach. Presentation, Mar. 8, 2012. 28 pages.
Prevo et al., The novel ATR inhibitor VE-821 increases sensitivity of pancreatic cancer cells to radiation and chemotherapy. Cancer Biol Ther. Sep. 2012;13(11):1072-81. doi: 10.4161/cbt.21093. Epub Jul. 24, 2012.
Qi et al., Chemi- and Bio-Iuminescence of Coelenterazine Analogues with Phenyl Homologues at the C-2 Position. J Chem Soc. Perkin Trans 1. 1992:1607-11.
Reaper et al., Selective killing of ATM- or p53-deficient cancer cells through inhibition of ATR. Nat Chem Biol. Apr. 13, 2011;7(7):428-30. doi: 10.1038/nchembio.573.
Reaper, et al., Selective killing of ATM- or p53-deficient cancer cells through inhibition of ATR. Nat Chem Biol. Apr. 13, 2011;7(7):428-30. doi: 10.1038/nchembio.573. Supplementary Information.
Reaper, P.M., et al., "Evaluation of a potent and highly selective inhibitor of ATR kinase: an approach to selectively sensitize cancer cells to genotoxic drugs", Abstract, Mar. 31, 2012.
Reaper, P.M., et al., "Evaluation of a Potent and Highly Selective Inhibitor of ATR Kinase: An Approach to Selectively Sensitize Cancer Cells to Genotoxic Drugs", Poster, Mar. 31, 2012.
Reaper, P.M., et al., "Selective Killing of ATM- or p53-deficient cancer cells through inhibition of ATR", Presentation, Nov. 21, 2011.
Reaper, P.M., et al., "Selective Killing of ATM- or p53-deficient cancer cells through inhibition of ATR", Presentation, Nov. 29, 2011.
Reaper, P.M., et al., "Selective Killing of ATM- or p53-deficient cancer cells through inhibition of ATR", Supplementary Information, *Nature Chemical Biology*, Apr. 13, 2011 (DOI: 10.1038/NCHEMBIO.573).
Redon et al., γ-H2AX as a biomarker of DNA damage induced by ionizing radiation in human peripheral blood lymphocytes and artificial skin. Adv Space Res. 2009;43(8):1171-8.
Registry (STN), 2004, RN 726138-31-4.
Richards et al., An Autoinhibitory Tyrosine Motif in the Cell-Cycle-Regulated Nek7 Kinase Is Released through Binding of Nek9. Molec Cell. 2009;36:560-70.
Saito et al., Synthesis and in vitro evaluation of botryllazine B analogues as a new class of inhibitor against human aldose reductase. Tetrahedron. 2009;65(15):3019-26.
Sarkaria et al., Inhibition of ATM and ATR kinase activities by the radiosensitizing agent, caffeine. Cancer Res. Sep. 1, 1999;59(17):4375-82.
Schultheiss et al., Facile Synthesis of Diarylpyrazines Using Suzuki Coupling of Dichloropyrazines with Aryl Boronic Acids. Heterocycles. 2003;60(8):1891-7.
Sevilla et al., Microwave-assisted synthesis of 1,3-dihydro-[1,2,5]thiadiazolo[3,4-b]pyrazine-2,2-dioxides. Tetrahedron Letters. 2006;47(48):8603-6.
Shimomura et al., Semi-synthetic aequorins with improved sensitivity to Ca2+ ions. Biochem J. Aug. 1, 1989;261(3):913-20.
Sugimoto et al., Imidazopteridines. I. Synthesis of Imidazo[1,2-c]pteridine and Its Alkyl Derivatives. Bull Chem Soc Japan. 1977;50(10):2744-7.
Teranishi et al., Synthesis and Chemiluminescence of Coelenterazine (Oplophorus Luciferin) Analogues. Bulletin Chem Soc Japan. 1990;63(11):3132-40.
Tutin, CCLVII.—Syntheses in the epinephrine series. Part II. The formation and properties of some 2:5- and 2:6-substituted pyrazines and their conversion into amino-ketones and imino-diketones. J Chem Soc Trans. 1910;97:2495-524.
Vicent, Polymer Anticancer Drug Conjugates: Use as Single Agents and as Combination Therapy. 2007 AACR Annual Meeting. Apr. 14-18, 2007:56-62.
Ward et al., Histone H2AX is phosphorylated in an ATR-dependent manner in response to replicational stress. J Biol Chem. Dec. 21, 2001;276(51):47759-62. Epub Oct. 22, 2001.
Wu et al., Chemi- and bioluminescence of coelenterazine analogues with a conjugated group at the C-8 position. Tetrahedron Lett. 2001;42(16):2997-3000.
Wuts et al., Protection for the Amino Group. Chapter 7. In: Greene's Protective Groups in Organic Synthesis, 4th Edition. John Wiley & Sons, Inc. 2007. 235 pages.
Wuts et al., Protection for the Carbonyl Group. Chapter 4. In: Greene's Protective Groups in Organic Synthesis, 4th Edition. John Wiley & Sons, Inc. 2007. 106 pages.
Bastin et al., Salt Selection and Optimisation Procedures for Pharmaceutical New Chemical Entities. Organic Process Research and Development. American Chemical Society. 2000;4(5):427-35.
Biss et al., Selective tumor killing based on specific DNA-damage response deficiencies. Cancer Biology & Therapy. Mar. 2012; 239-46.
Caira, Crystalline Polymorphism of Organic Compounds. Topics in Current Chemistry. Design of Organic Solids. 1998;198:163-208.
Hilfiker et al., Relevance of Solid-state Properties for Pharmaceutical Products. Polymorphism: in the Pharmaceutical Industry. 2006;1-19.
Kumar et al., Salt selection in drug development. Pharmaceutical Technology. 2008;32(3):128-46.
Peasland et al., Identification and evaluation of a potent novel ATR inhibitor, NU6027, in breast and ovarian cancer cell lines. British Journal of Cancer. Jul. 2011; 105(3):372-81.
Serajuddin, Salt formation to improve drug solubility. Advanced Drug Delivery Reviews. 2007; 59(7):603-16.
U.S. Appl. No. 13/106,476, filed May 12, 2011, Charrier et al.
U.S. Appl. No. 13/857,658, filed Apr. 5, 2013, Pollard et al.
U.S. Appl. No. 14/816,432, filed Aug. 3, 2015, Pollard et al.
U.S. Appl. No. 13/631,759, filed Sep. 28, 2012, Charrier et al.
U.S. Appl. No. 14/678,489, filed Apr. 3, 2015, Charrier et al.

(56) References Cited

OTHER PUBLICATIONS

U.S. Appl. No. 13/106,337, filed May 12, 2011, Charrier et al.
U.S. Appl. No. 13/106,173, filed May 12, 2011, Charrier et al.
U.S. Appl. No. 14/045,373, filed Oct. 3, 2013, Falcon et al.
U.S. Appl. No. 14/633,394, filed Feb. 27, 2015, Falcon et al.
U.S. Appl. No. 13/106,184, filed May 12, 2011, Charrier et al.
U.S. Appl. No. 15/074,375, filed Mar. 18, 2016, Charrier et al.
U.S. Appl. No. 15/400,725, filed Jan. 6, 2017, Charrier et al.
U.S. Appl. No. 13/633,114, filed Oct. 1, 2012, Pollard et al.
U.S. Appl. No. 14/193,845, filed Feb. 28, 2014, Pollard et al.
U.S. Appl. No. 13/106,178, filed May 12, 2011, Charrier et al.
U.S. Appl. No. 14/562,965, filed Dec. 8, 2014, Charrier et al.
U.S. Appl. No. 12/642,447, filed Dec. 18, 2009, Charrier et al.
U.S. Appl. No. 14/223,109, filed Mar. 24, 2014, Charrier et al.
U.S. Appl. No. 15/142,286, filed Apr. 29, 2016, Charrier et al.
U.S. Appl. No. 13/104,291, filed Oct. 27, 2011, Charrier et al.
U.S. Appl. No. 13/742,948, filed Jan. 16, 2013, Charrier et al.
U.S. Appl. No. 13/631,730, filed Sep. 28, 2012, Charrier et al.
U.S. Appl. No. 13/672,937, filed Nov. 9, 2012, Charrier et al.
U.S. Appl. No. 13/106,167, filed May 12, 2011, Charrier et al.
U.S. Appl. No. 13/440,981, filed Sep. 4, 2012, Charrier et al.
U.S. Appl. No. 13/631,732, filed Sep. 28, 2012, Charrier et al.
U.S. Appl. No. 13/631,727, filed Sep. 28, 2012, Charrier et al.
U.S. Appl. No. 13/672,944, filed Nov. 9, 2012, Charrier et al.
U.S. Appl. No. 13/672,949, filed Nov. 9, 2012, Charrier et al.
U.S. Appl. No. 13/672,954, filed Nov. 9, 2012, Charrier et al.
U.S. Appl. No. 13/672,958, filed Nov. 9, 2012, Charrier et al.
U.S. Appl. No. 14/053,737, filed Oct. 15, 2013, Charrier et al.
Brittain, editor. Polymorphism in pharmaceutical solids. CRC Press; 2009, Chapters 7 (p. 233-281) and 12 (p. 436-480).
Cholodov et al., Clinical Pharmokinetics Part M: Medicine. 1985. pp. 83-98, 134-8, 160, 378-80.
Hancock et al., Characteristics and significance of the amorphous state in pharmaceutical systems. J Pharm Sci. Jan. 1997;86(1):1-12.
Morgan et al., Mechanism of radiosensitization by the Chk1/2 inhibitor AZD7762 involves abrogation of the G2 checkpoint and inhibition of homologous recombinational DNA repair. Cancer Res. Jun. 15, 2010;70(12):4972-81. doi: 10.1158/0008-5472.CAN-09-3573.
Pollard et al., Defining optimal dose schedules for ATR inhibitors in combination with DNA damaging drugs: Informing clinical studies of VX-970, the first-in-class ATR inhibitor. Proceedings: AACR Annual Meeting. Apr. 16-20, 2016.
Sergeev, Brief course of Molecular Pharmacology. Moscow Medical Institute. 1975. p. 10.

* cited by examiner

SUBSTITUTED PYRAZINES AS ATR KINASE INHIBITORS

CROSS REFERENCE TO RELATED APPLICATIONS

This application is a divisional of U.S. application Ser. No. 12/642,447, filed on Dec. 18, 2009, which claims the benefit of U.S. Provisional Application Nos. 61/139,420 filed on Dec. 19, 2008; 61/139,424 filed on Dec. 19, 2008; 61/139,426 filed on Dec. 19, 2008; 61/139,429 filed on Dec. 19, 2008; 61/181,794 filed on May 28, 2009; and 61/219,100 filed on Jun. 22, 2009; the entire teachings of each of which are incorporated herein by reference.

SEQUENCE LISTING

The instant application contains a Sequence Listing which has been submitted in ASCII format via EFS-Web and is hereby incorporated by reference in its entirety. Said ASCII copy, created on Mar. 19, 2014, is named VPI_08-149 US_Sequence Listing.txt and is 1 kilobyte in size.

BACKGROUND OF THE INVENTION

ATR ("ATM and Rad3 related") kinase is a protein kinase involved in cellular responses to DNA damage. ATR kinase acts with ATM ("ataxia telangiectasia mutated") kinase and many other proteins to regulate a cell's response to DNA damage, commonly referred to as the DNA Damage Response ("DDR"). The DDR stimulates DNA repair, promotes survival and stalls cell cycle progression by activating cell cycle checkpoints, which provide time for repair. Without the DDR, cells are much more sensitive to DNA damage and readily die from DNA lesions induced by endogenous cellular processes such as DNA replication or exogenous DNA damaging agents commonly used in cancer therapy.

Healthy cells can rely on a host of different proteins for DNA repair including the DDR kinase ATR. In some cases these proteins can compensate for one another by activating functionally redundant DNA repair processes. On the contrary, many cancer cells harbour defects in some of their DNA repair processes, such as ATM signaling, and therefore display a greater reliance on their remaining intact DNA repair proteins which include ATR.

In addition, many cancer cells express activated oncogenes or lack key tumour suppressors, and this can make these cancer cells prone to dysregulated phases of DNA replication which in turn cause DNA damage. ATR has been implicated as a critical component of the DDR in response to disrupted DNA replication. As a result, these cancer cells are more dependent on ATR activity for survival than healthy cells. Accordingly, ATR inhibitors may be useful for cancer treatment, either used alone or in combination with DNA damaging agents, because they shut down a DNA repair mechanism that is more important for cellular survival in many cancer cells than in healthy normal cells. In fact, ATR inhibition has been shown to be effective in cancer cells as single agents and as potent sensitizers to radiotherapy and genotoxic chemotherapy.

ATR peptide can be expressed and isolated using a variety of methods known in the literature (see e.g., Ünsal-Kaçmaz et al, PNAS 99: 10, pp 6673-6678, May 14, 2002; see also Kumagai et al. Cell 124, pp 943-955, Mar. 10, 2006; Unsal-Kacmaz et al. Molecular and Cellular Biology, February 2004, p 1292-1300; and Hall-Jackson et al. Oncogene 1999, 18, 6707-6713).

For all of these reasons, there is a need for the development of potent and selective ATR inhibitors for the treatment of cancer, either as single agents or as combination therapies with radiotherapy or genotoxic chemotherapy.

SUMMARY OF THE INVENTION

The present invention relates to pyrazine compounds useful as inhibitors of ATR protein kinase. The invention also relates to pharmaceutically acceptable compositions comprising the compounds of this invention; methods of treating of various diseases, disorders, and conditions using the compounds of this invention; processes for preparing the compounds of this invention; intermediates for the preparation of the compounds of this invention; and methods of using the compounds in in vitro applications, such as the study of kinases in biological and pathological phenomena; the study of intracellular signal transduction pathways mediated by such kinases; and the comparative evaluation of new kinase inhibitors. These compounds have an unexpected ability to treat cancer as single agents. These compounds also show surprising synergy with other cancer agents, such as cisplatin, in combination therapies.

DETAILED DESCRIPTION OF THE INVENTION

One aspect of this invention provides a compound of Formula IA:

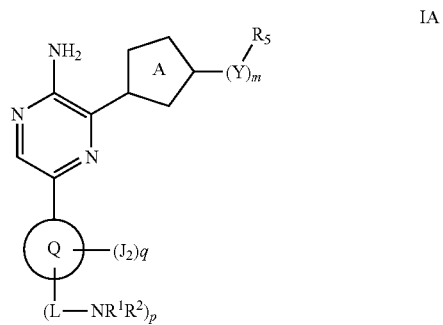

or a pharmaceutically acceptable salt thereof; wherein
Y is a $C_1$-$C_{10}$ aliphatic chain wherein up to three methylene units of the aliphatic chain are optionally replaced with O, $NR^o$, S, C(O) or $S(O)_2$;
Ring A is a 5 membered heteroaryl ring selected from

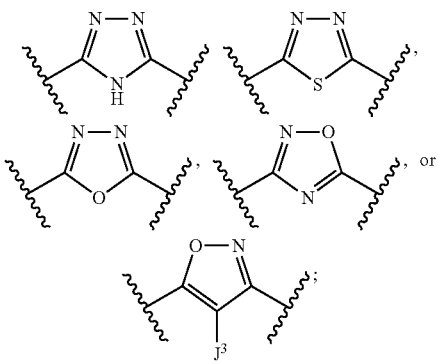

$J^3$ is H or $C_{1-4}$alkyl wherein 1 methylene unit of the alkyl group can optionally be replaced with O, NH, $N(C_{1-4}$alkyl), or S and optionally substituted with 1-3 halo;

Q is a 5-6 membered monocyclic aromatic ring containing 0-4 heteroatoms independently selected from nitrogen, oxygen, or sulfur; or an 8-10 membered bicyclic aromatic ring containing 0-6 heteroatoms independently selected from nitrogen, oxygen, or sulfur;

$R^5$ is H; a 3-7 membered monocyclic fully saturated, partially unsaturated, or aromatic ring containing 0-4 heteroatoms independently selected from nitrogen, oxygen, or sulfur; an 8-10 membered bicyclic fully saturated, partially unsaturated, or aromatic ring containing 0-6 heteroatoms independently selected from nitrogen, oxygen, or sulfur; $R^5$ is optionally substituted with 1-5 $J^5$ groups;

L is a $C_{1-4}$alkyl chain wherein up to two methylene units of the alkyl chain are optionally replaced with O, $NR^6$, S, —C(O)—, —SO—, or —SO$_2$—;

$R^0$ is H or $C_1$-$C_6$alkyl wherein one methylene unit of the alkyl chain can be optionally replaced with O, NH, $N(C_{1-4}$alkyl), or S;

$R^1$ is H or $C_1$-$C_6$alkyl;

$R^2$ is H, $C_1$-$C_6$alkyl, —($C_2$-$C_6$alkyl)-Z or a 4-8 membered cyclic ring containing 0-2 nitrogen atoms; wherein said ring is bonded via a carbon atom and is optionally substituted with one occurrence of $J^Z$;

or $R^1$ and $R^2$, taken together with the atom to which they are bound, form a 4-8 membered heterocyclic ring containing 1-2 heteroatoms selected from oxygen, nitrogen, or sulfur; wherein said heterocyclic ring is optionally substituted with one occurrence of $J^{Z1}$;

$J^{Z1}$ is halo, CN, $C_1$-$C_8$aliphatic, —(X)$_t$—CN, or —(X)$_r$—Z; wherein said up to two methylene units of said $C_1$-$C_8$aliphatic can be optionally replaced with O, NR, S, P(O), C(O), S(O), or S(O)$_2$; wherein said $C_1$-$C_8$aliphatic is optionally substituted with halo, CN, or NO$_2$;

X is $C_1$-$C_4$alkyl;

each t, r and m is independently 0 or 1;

Z is —$NR^3R^4$;

$R^3$ is H or $C_1$-$C_2$alkyl;

$R^4$ is H or $C_1$-$C_6$alkyl;

or $R^3$ and $R^4$, taken together with the atom to which they are bound, form a 4-8 membered heterocyclic ring containing 1-2 heteroatoms selected from oxygen, nitrogen, or sulfur; wherein said ring is optionally substituted with one occurrence of $J^Z$;

$R^6$ is H, or $C_1$-$C_6$alkyl;

$J^Z$ is independently NH$_2$, NH($C_{1-4}$aliphatic), N($C_{1-4}$aliphatic)$_2$, halogen, $C_{1-4}$aliphatic, OH, O($C_{1-4}$aliphatic), NO$_2$, CN, CO$_2$H, CO($C_{1-4}$aliphatic), CO$_2$($C_{1-4}$aliphatic), O(halo$C_{1-4}$ aliphatic), or halo$C_{1-4}$ aliphatic;

$J^5$ is halo, oxo, CN, NO$_2$, $X^1$—R, or —(X)$_p$-$Q^4$;

$X^1$ is $C_{1-10}$aliphatic; wherein 1-3 methylene units of said $C_{1-10}$aliphatic are optionally replaced with —NR'—, —O—, —S—, C(=NR'), C(O), S(O)$_2$, or S(O); wherein $X^1$ is optionally and independently substituted with 1-4 occurrences of NH$_2$, NH($C_{1-4}$aliphatic), N($C_{1-4}$aliphatic)$_2$, halogen, $C_{1-4}$aliphatic, OH, O($C_{1-4}$aliphatic), NO$_2$, CN, CO$_2$H, CO$_2$($C_{1-4}$aliphatic), C(O)NH$_2$, C(O)NH($C_{1-4}$aliphatic), C(O)N($C_{1-4}$aliphatic)$_2$, SO($C_{1-4}$aliphatic), SO$_2$($C_{1-4}$aliphatic), SO$_2$NH($C_{1-4}$aliphatic), SO$_2$NH($C_{1-4}$aliphatic), NHC(O)($C_{1-4}$aliphatic), N($C_{1-4}$aliphatic)C(O)($C_{1-4}$aliphatic), wherein said $C_{1-4}$aliphatic is optionally substituted with 1-3 occurrences of halo;

$Q^4$ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each $Q^4$ is optionally substituted with 1-5 $J^{Q4}$;

$J^{Q4}$ is halo, CN, or $C_{1-4}$alkyl wherein up to 2 methylene units are optionally replaced with O, NR*, S, C(O), S(O), or S(O)$_2$;

R is H or $C_{1-4}$alkyl wherein said $C_{1-4}$alkyl is optionally substituted with 1-4 halo;

$J^2$ is halo; CN; a 5-6 membered aromatic or nonaromatic monocyclic ring having 0-3 heteroatoms selected from oxygen, nitrogen, or sulfur; or a $C_{1-10}$aliphatic group wherein up to 2 methylene units are optionally replaced with O, NR", C(O), S, S(O), or S(O)$_2$; wherein said $C_{1-10}$aliphatic group is optionally substituted with 1-3 halo or CN; and said monocyclic ring is optionally substituted with 1-3 occurences of halo; CN; a $C_{3-6}$cycloalkyl; a 3-7 membered heterocyclyl containing 0-2 heteroatoms selected from oxygen, nitrogen, or sulfur; or a $C_{1-4}$alkyl wherein up to one methylene unit of the alkyl chain is optionally replaced with O, NR", or S; and wherein said $C_{1-4}$alkyl is optionally substituted with 1-3 halo;

q is 0, 1, or 2;

p is 0 or 1;

R', R", and R* are each independently H, $C_{1-4}$alkyl, or is absent; wherein said $C_{1-4}$alkyl is optionally substituted with 1-4 halo.

In some embodiments,

Y is a $C_1$-$C_6$aliphatic chain wherein one methylene unit of the alkyl chain is optionally replaced with C(O) or —$NR^0$—; and $R^5$ is a 3-7 membered monocyclic fully saturated, partially unsaturated, or aromatic ring containing 0-4 heteroatoms independently selected from nitrogen, oxygen, or sulfur; or an 8-10 membered bicyclic fully saturated, partially unsaturated, or aromatic ring containing 0-6 heteroatoms independently selected from nitrogen, oxygen, or sulfur; $R^5$ is optionally substituted with 1-5 $J^5$ groups, provided that when Ring A is

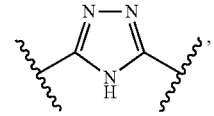 [SMILES: *c1nnc(*)[nH]1]

p is 1; and $R^5$ is aromatic.

In some embodiments, Ring A is a 5 membered heteroaryl ring selected from

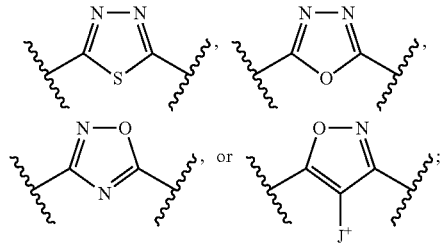

In some embodiments, ring A is

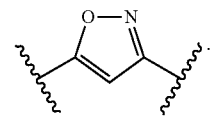 [SMILES: *c1cc(*)on1]

In other embodiments, ring A is

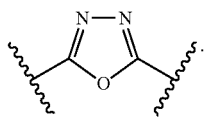 [SMILES: *c1nnc(*)o1]

It should be understood that Ring A structures can be bound to the pyrazine ring in two different ways: as drawn, and the reverse (flipped). For example, when Ring A is

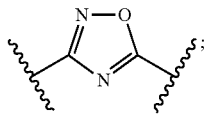 [SMILES: *c1noc(*)n1]

it can be bound to the pyrazine ring as shown below:

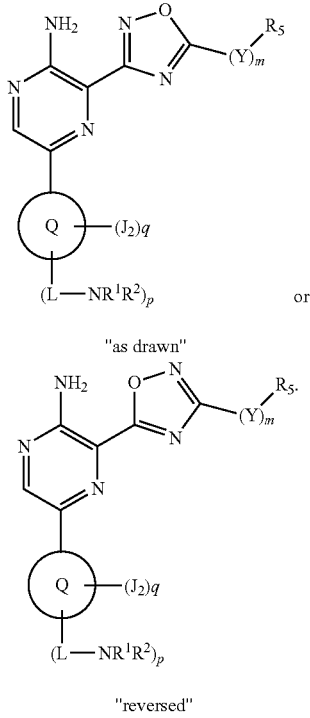

Similarly, when Ring A is

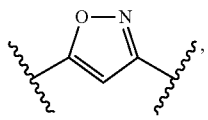 [SMILES: *c1cc(*)on1]

it can also be bound to the pyrazine ring in two ways—as drawn and reversed. In some embodiments, the Ring A structures are bound as drawn.

In other embodiments, $J^3$ is H.

In yet other embodiments, Y is a $C_{1-2}$alkyl chain wherein one methylene unit of the alkyl chain is optionally replaced with —$NR^0$—.

In some embodiments, $J^5$ is a $C_{1-6}$aliphatic group wherein up to 2 methylene units are optionally replaced with O or NR'R" where each R' and R" is independently H or alkyl; or R' and R" taken together to form a 3-6 membered heterocyclic ring; $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO(C_{1-4}aliphatic)$, $CO_2(C_{1-4}aliphatic)$, $O(haloC_{1-4}aliphatic)$, or $haloC_{1-4}aliphatic$;

In other embodiments, $J^2$ is halo, $C_1$-$C_2$alkyl optionally substituted with 1-3 fluoro, CN, or a $C_{1-4}$alkyl group wherein up to 2 methylene units are optionally replaced with S(O), $S(O)_2$, C(O), or NR'.

In yet another embodiment,

Y is NH;

$R^5$ is 5-6 membered monocyclic aryl or heteroaryl ring having 0-3 heteroatoms independently selected from nitrogen, oxygen, or sulfur, $R^5$ is optionally fused to a 5-6 membered aromatic ring containing 0-2 heteroatoms selected from N, O, or S; each $R^5$ is optionally substituted with 1-5 $J^5$ groups;

L is —C(O)— or —$SO_2$—;

$R^1$ is H, or $C_1$-$C_6$alkyl;

$R^2$ is —($C_2$-$C_6$alkyl)-Z or a 4-8 membered cyclic ring containing 0-2 nitrogen atoms; wherein said ring is bonded via a carbon atom and is optionally substituted with one occurrence of $J^Z$;

or $R^1$ and $R^2$, taken together with the atom to which they are bound, form a 4-8 membered heterocyclic ring containing 1-2 nitrogen atoms; wherein said heterocyclic ring is optionally substituted with one occurrence of $J^{Z1}$;

$J^{Z1}$-is —$(X)_r$—CN, $C_1$-$C_6$alkyl or —$(X)_r$—Z;

$R^3$ is H or $C_1$-$C_2$alkyl;

$R^4$ is H or $C_1$-$C_6$alkyl;

or $R^3$ and $R^4$, taken together with the atom to which they are bound, form a 4-8 membered heterocyclic ring containing 1-2 heteroatoms selected from oxygen, nitrogen, or sulfur; wherein said ring is optionally substituted with one occurrence of $J^Z$;

$J^5$ is halogen, $NO_2$, CN, $O(haloC_{1-4}aliphatic)$, $haloC_{1-4}aliphatic$, or a $C_{1-6}aliphatic$ group wherein up to 2 methylene units are optionally replaced with C(O), O, or NR'; and $J^2$ is halo, $C_1$-$C_2$alkyl optionally substituted with 1-3 fluoro, or CN.

According to another embodiment, L is —C(O)—, m is 0, and $R^1$ and $R^2$, taken together with the atom to which they are bound, form a 4-8 membered heterocyclic ring containing 1-2 nitrogen atoms. In some embodiments, said heterocyclyl is pyrrolidinyl, piperidinyl, piperazinyl, azepanyl, or 1,4-diazepanyl.

According to another embodiment, m is 0, q is 0, and -L-$NR^1R^2$ is C(O)pyrrolidinyl, C(O)piperidinyl, C(O)piperazinyl, C(O) azepanyl, C(O) 1,4-diazepanyl, C(O)NH-piperidinyl, C(O)NHCH$_2$CH$_2$-pyrrolidinyl, C(O)NHCH$_2$CH$_2$-piperidinyl, CON(CH$_3$)CH$_2$CH$_2$N(CH$_3$)$_2$, wherein said pyrrolidinyl, piperidinyl, piperazinyl, azepanyl or 1,4-diazepanyl is optionally substituted with $C_{1-4}$alkyl or N($C_{1-4}$alkyl)$_2$.

According to yet another embodiment, $J^2$ is halo; CN; phenyl; oxazolyl; or a $C_{1-6}$aliphatic group wherein up to 2 methylene units are optionally replaced with O, NR", C(O), S, S(O), or $S(O)_2$; said $C_{1-6}$aliphatic group is optionally substituted with 1-3 fluoro or CN.

Another embodiment provides a compound of Formula IA':

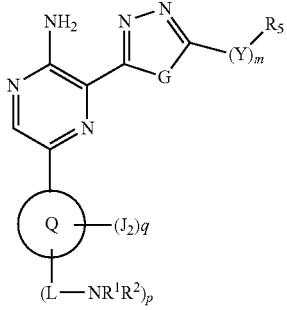

IA' or a pharmaceutically acceptable salt thereof; wherein
Y is a $C_1$-$C_4$alkyl chain wherein one methylene unit of the alkyl chain is optionally replaced with —$NR^0$—;
G is O or S;
Q is a 5-6 membered monocyclic aromatic ring containing 0-4 heteroatoms independently selected from nitrogen, oxygen, or sulfur; or an 8-10 membered bicyclic aromatic ring containing 0-6 heteroatoms independently selected from nitrogen, oxygen, or sulfur;
$R^5$ is a 3-7 membered monocyclic fully saturated, partially unsaturated, or aromatic ring containing 0-4 heteroatoms independently selected from nitrogen, oxygen, or sulfur; or an 8-10 membered bicyclic fully saturated, partially unsaturated, or aromatic ring containing 0-6 heteroatoms independently selected from nitrogen, oxygen, or sulfur; $R^5$ is optionally substituted with 1-5 $J^5$ groups;
L is $C_{1-4}$alkyl chain wherein up to two methylene units of the alkyl chain are optionally replaced with O, $NR^6$, S, —C(O)—, —SO—, or —$SO_2$—;
$R^0$ is H or $C_1$-$C_6$alkyl;
$R^1$ is H or $C_1$-$C_6$alkyl;
$R^2$ is H, $C_1$-$C_6$alkyl, —($C_2$-$C_6$alkyl)-Z or a 4-8 membered cyclic ring containing 0-2 nitrogen atoms; wherein said ring is bonded via a carbon atom and is optionally substituted with one occurrence of $J^Z$;
or $R^1$ and $R^2$, taken together with the atom to which they are bound, form a 4-8 membered heterocyclic ring containing 1-2 heteroatoms selected from nitrogen, sulfur, or oxygen; wherein said heterocyclic ring is optionally substituted with one occurrence of $J^{Z1}$;
$J^{Z1}$ is —(X)$_t$—CN, $C_1$-$C_6$alkyl or —(X)$_r$—Z;
X is $C_1$-$C_4$alkyl;
each t, r and m is independently 0 or 1;
Z is —$NR^3R^4$;
$R^3$ is H or $C_1$-$C_2$alkyl;
$R^4$ is H or $C_1$-$C_6$alkyl;
or $R^3$ and $R^4$, taken together with the atom to which they are bound, form a 4-8 membered heterocyclic ring containing 1-2 nitrogen atoms; wherein said ring is optionally substituted with one occurrence of $J^Z$;
$R^6$ is H, or $C_1$-$C_6$alkyl;
$J^Z$ is independently $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO(C_{1-4}aliphatic)$, $CO_2(C_{1-4}aliphatic)$, $O(haloC_{1-4}\ aliphatic)$, or $haloC_{1-4}\ aliphatic$;
$J^5$ is halo, oxo, CN, $NO_2$, $X^1$—R, or —($X^1$)$_p$-$Q^4$,
$X^1$ is $C_{1-10}aliphatic$; wherein 1-3 methylene units of said $C_{1-10}aliphatic$ are optionally replaced with —NR'—, —O—, —S—, C(O), $S(O)_2$, or S(O); wherein $X^1$ is optionally and independently substituted with 1-4 occurrences of $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO_2(C_{1-4}aliphatic)$, $C(O)NH_2$, $C(O)NH(C_{1-4}aliphatic)$, $C(O)N(C_{1-4}aliphatic)_2$, $SO(C_{1-4}aliphatic)$, $SO_2(C_{1-4}aliphatic)$, $SO_2NH(C_{1-4}aliphatic)$, $SO_2NH(C_{1-4}aliphatic)$, $NHC(O)(C_{1-4}aliphatic)$, $N(C_{1-4}aliphatic)C(O)(C_{1-4}aliphatic)$, wherein said $C_{1-4}aliphatic$ is optionally substituted with 1-3 occurrences of halo;
$Q^4$ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each $Q^4$ is optionally substituted with 1-5 $J^{Q4}$;
$J^{Q4}$ is halo, CN, or $C_{1-4}alkyl$ wherein up to 2 methylene units are optionally replaced with O, NR*, S, C(O), S(O), or $S(O)_2$;
R is H or $C_{1-4}alkyl$ wherein said $C_{1-4}alkyl$ is optionally substituted with 1-4 halo;
$J^2$ is halo; CN; a 5-6 membered aromatic or nonaromatic monocyclic ring having 0-3 heteroatoms selected from oxygen, nitrogen, or sulfur; or a $C_{1-10}aliphatic$ group wherein up to 2 methylene units are optionally replaced with O, NR", C(O), S, S(O), or $S(O)_2$; wherein said $C_{1-10}aliphatic$ group is optionally substituted with 1-3 halo or CN; and said monocyclic ring is optionally substituted with 1-3 halo; CN; a $C_{3-6}cycloalkyl$; a 3-7 membered heterocyclyl containing 0-2 heteroatoms selected from oxygen, nitrogen, or sulfur; or a $C_{1-4}alkyl$ wherein up to one methylene unit of the alkyl chain is optionally replaced with O, NR", or S;
R', R", and R* are each independently H, $C_{1-4}alkyl$, or is absent; wherein said $C_{1-4}alkyl$ is optionally substituted with 1-4 halo.
q is 0, 1, or 2,
p is 0 or 1.

In some embodiments, $J^5$ is halogen, $NO_2$, CN, $O(haloC_{1-4}aliphatic)$, $haloC_{1-4}aliphatic$, or a $C_{1-6}aliphatic$ group wherein up to 2 methylene units are optionally replaced with C(O), O, or NR'. In other embodiments, $J^5$ is halo, CN, phenyl, oxazolyl, or a $C_{1-6}aliphatic$ group wherein up to 2 methylene units are optionally replaced with O, NR', C(O), S, S(O), or $S(O)_2$; said $C_{1-6}aliphatic$ group is optionally substituted with 1-3 fluoro or CN.

In yet other embodiments, $J^2$ is halo; CN; phenyl; oxazolyl; or a $C_{1-6}aliphatic$ group wherein up to 2 methylene units are optionally replaced with O, NR", C(O), S, S(O), or $S(O)_2$; said $C_{1-6}aliphatic$ group is optionally substituted with 1-3 fluoro or CN.

In some embodiments, Y is a $C_1$-$C_2$alkyl chain wherein one methylene unit of the alkyl chain is optionally replaced with $NR^0$.

In some embodiments, p is 0 and Q is phenyl, indolyl, pyridyl, naphthyl or benzothienyl, or quinolinyl. In certain embodiments, Q is phenyl, indolyl, pyridyl, or quinolinyl. In some embodiments, Q is phenyl or pyridyl. In some embodiments, phenyl. In other embodiments, pyridyl.

$J^2$ is —$OCH_3$, —$OCH_2CH_2N(CH_3)_2$, —$NHCH_2CH_2N(CH_3)_2$, or piperazinyl.

The compound according to claim 19, wherein Q is substituted in the ortho position, the para position, or in both the ortho and the para position.

The compound according to claim 19, wherein Q is substituted at the para position with $J^2$, wherein the $J^2$ is a $C_{1-6}aliphatic$ group wherein the methylene group bonded to Ring Q is replaced with —$SO_2$—.

The compound of claim 19 wherein at least one more methylene unit of the $C_{1-6}$ aliphatic group is optionally replaced with a heteroatom selected from the group consisting of O, NR", and S.

The compound according to claim 19, wherein Q is substituted at the para position with —SO$_2$(C$_{1-4}$alkyl), —SO$_2$(C$_{1-4}$alkyl)N(C$_{1-4}$alkyl)$_2$, C(O)N(C$_{1-4}$alkyl)$_2$, C(O)(1,4-diazepanyl), CO(azepanyl), C(O)(piperazinyl), or C(O)(piperidinyl).

The compound of claim 21, wherein at least one more methylene unit of the $C_{1-6}$ aliphatic group is optionally replaced with a heteroatom selected from the group consisting of O, NR", and S.

In some embodiments, Q is optionally substituted in the ortho-position with one $J^2$, wherein $J^2$ is C$_1$-C$_4$alkyl, NH$_2$, NHC(O)CH$_3$, O(C$_1$-C$_4$alkyl), CH$_2$OH, CH$_2$OCH$_3$, CH$_2$CH$_2$OCH$_3$, CH$_2$CN, CN, CH$_2$C(O)NH$_2$, OH, OCF$_3$, CF$_3$, CHF$_2$, —CH═CHF, NHCOCH$_3$, COCH$_3$, CONH$_2$, SCH$_3$, SOCH$_3$, SOCH$_2$CH$_3$, SO$_2$CH(CH$_3$)$_2$, —C≡CH, oxazolyl, or phenyl. In some embodiments, $J^2$ is substituted in the ortho position with CH$_2$OH, CHF$_2$, S(O)CH$_3$, or S(O)CH$_2$CH$_3$.

In yet other embodiments, Q is optionally substituted in the ortho-position with $J^2$, wherein $J^2$ is C$_{1-4}$alkyl, —C≡C—(C$_{1-4}$alkyl), CH═CH$_2$, CH═CHF, O(C$_{1-4}$alkyl), NH(C$_{1-4}$alkyl), N(C$_{1-4}$alkyl)$_2$, —(C$_{1-4}$alkyl)OH, —(C$_{1-4}$alkyl)O(C$_{1-4}$alkyl), —(C$_{1-4}$alkyl)NH$_2$, —(C$_{1-4}$alkyl)NH(C$_{1-4}$alkyl), —(C$_{1-4}$alkyl)N(C$_{1-4}$alkyl)$_2$, —(C$_{1-4}$alkyl)CN, CO(C$_{1-4}$alkyl), CON(C$_{1-4}$alkyl)$_2$, C(O)O(C$_{1-4}$alkyl), S(C$_{1-4}$alkyl), —S—(C$_{1-4}$alkyl)NH$_2$, S(O)(C$_{1-4}$alkyl)NH$_2$, S(O)$_2$(C$_{1-4}$alkyl)OH, S(O)(C$_{1-4}$alkyl)NHC(O)O(t-butyl), NHS(O)$_2$(C$_{1-4}$alkyl), halo, or CN.

In some embodiments, $J^2$ is CH$_2$CH$_2$OH, SCH(CH$_3$)$_2$, —C≡CCH$_3$, halo, CN, CON(CH$_3$)$_2$, CH$_2$CN, S(O)CH$_2$CH$_2$NH$_2$, SCH$_2$CH$_2$NH$_2$, C(O)OCH$_3$, CH$_2$N(CH$_3$)$_2$, S(O)CH$_2$CH$_2$NHBOC, N(CH$_3$)$_2$, NHSO$_2$CH$_3$, CH═CHF, CH$_2$OCH$_3$, CH═CH$_2$, SCH$_2$CH$_3$, or —CH═CH.

In other embodiments, Q is optionally substituted in the para position with $J^2$, wherein $J^2$ is —SO$_2$(C$_{1-4}$alkyl), —SO$_2$(C$_{3-6}$cycloalkyl), —SO$_2$(3-6 membered heterocyclyl), —SO$_2$(C$_{1-4}$alkyl)N(C$_{1-4}$alkyl)$_2$, —C(O)(C$_{1-4}$alkyl), —(C$_{1-4}$alkyl)N(C$_{1-4}$alkyl)$_2$, or —NHC(O)(C$_{1-4}$alkyl).

In some embodiments, said 3-6 membered heterocyclyl is tetrahydrofuranyl, tetrahydropyranyl, azetidinyl, pyrrolidinyl, or piperidinyl.

In yet other embodiments, Q is optionally substituted in the meta position with $J^2$ wherein $J^2$ is C$_{1-4}$alkyl, C$_{1-4}$alkoxy, halo, haloC$_{1-4}$alkyl, haloC$_{1-4}$alkoxyl, CN, SO$_2$ (C$_{1-4}$alkyl), NHSO$_2$(C$_{1-4}$alkyl), C(O)(C$_{1-4}$alkyl), C(O)NH$_2$, NHC(O)(C$_{1-4}$alkyl), —(C$_{1-4}$alkyl)-OH, —(C$_{1-4}$alkyl)-O(C$_{1-4}$alkyl), —(C$_{1-4}$alkyl)-NH$_2$, —(C$_{1-4}$alkyl)-N(C$_{1-4}$alkyl)$_2$, or —(C$_{1-4}$alkyl)NH(C$_{1-4}$alkyl).

In some embodiments, Q is naphthyl or benzothienyl.

In another embodiment, Q is pyridyl. In some embodiments, Q is substituted in the ortho-position with one $J^2$, wherein $J^2$ is CN.

In some embodiments, Q is substituted with one or two $J^2$, wherein $J^2$ is a C$_{1-6}$aliphatic group wherein up to 2 methylene units are optionally replaced with O or NR".

In some embodiments, $J^2$ is —OCH$_3$, —OCH$_2$CH$_2$N(CH$_3$)$_2$, —NHCH$_2$CH$_2$N(CH$_3$)$_2$, or piperazinyl.

In another embodiment, p is 1. In some embodiments, Q is phenyl, pyridyl, or naphthyl. In some embodiments, said pyridyl is 3-pyridyl or 4-pyridyl. In other embodiments, Q is phenyl.

In some embodiments, Q comprises Q$^1$ and optionally Q$^2$ as shown in formula IA-i, wherein Q$^1$ is a six membered ring and -LNR$^1$R$^2$ is substituted in the para-position as shown below:

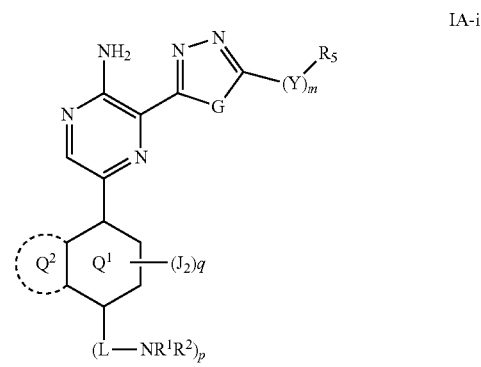

In some embodiments, $J^5$ is halogen, NO$_2$, CN, O(haloC$_{1-4}$aliphatic), haloC$_{1-4}$aliphatic, or a C$_{1-6}$aliphatic group wherein up to 2 methylene units are optionally replaced with C(O), O, or NR'.

In some embodiments, Q$^1$ is phenyl or pyridyl. In other embodiments, Q$^1$-Q$^2$ is naphthyl.

In some embodiments, Y is a C$_1$-C$_2$alkyl chain wherein one methylene unit of the alkyl chain is optionally replaced with NR$^0$.

In other embodiments, L is —C(O)— or —SO$_2$—.

In yet other embodiments, R$^1$ and R$^2$, taken together with the atom to which they are bound, form a 4-8 membered heterocyclic ring containing 1-2 heteroatoms selected from nitrogen, sulfur, or oxygen. In some embodiments, said heterocyclic ring is selected from pyrrolidinyl, piperidinyl, piperazinyl, morpholinyl, 1,4-diazepanyl, or 1,4-oxazepanyl. In yet other embodiments, R$^1$ is C$_1$-C$_6$alkyl. In some embodiments, said heterocyclic ring is optionally substituted with halo, CN, C$_{1-6}$ aliphatic, haloC$_{1-6}$ aliphatic, —C(O)O(C$_{1-6}$ aliphatic), C(O)H, C(O)(C$_{1-6}$aliphatic), P(O)(OC$_{1-4}$alkyl)$_2$, NH(C$_{1-6}$aliphatic), or N(C$_{1-6}$aliphatic)$_2$.

In some embodiments, R$^2$ is C$_1$-C$_6$alkyl. In other embodiments, R$^2$ is —(C$_2$-C$_6$alkyl)-Z.

According to another embodiment, m is 0.

According to yet another embodiment, q is 0.

In some embodiments, L is —C(O)—.

In some embodiments, R$^1$ and R$^2$, taken together with the atom to which they are bound, form a 4-8 membered heterocyclic ring containing 1-2 nitrogen atoms. In some embodiments, said heterocyclic ring is selected from pyrrolidinyl, piperidinyl, piperazinyl, azepanyl, or 1,4-diazepanyl. In other embodiments, said heterocyclic ring is selected from

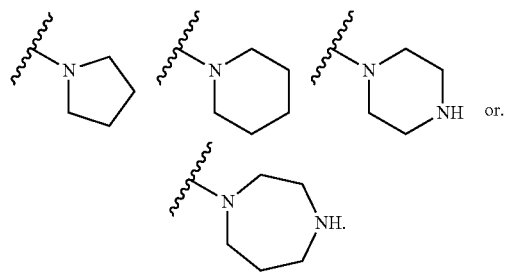

In some embodiments, t is 1. In other embodiments, t is 0.

In other embodiments, $R^1$ is H or $C_1$-$C_6$alkyl; and $R^2$ is —($C_2$-$C_6$alkyl)-Z. In some embodiments, $R^1$ is $C_1$-$C_6$alkyl. In some embodiments, Z is —$NR^3R^4$, wherein $R^3$ and $R^4$ are both $C_1$-$C_2$alkyl. In other embodiments, $R^3$ and $R^4$, taken together with the atom to which they are bound, form a ring selected from pyrrolidinyl, piperidinyl, piperazinyl, azepanyl, or 1,4-diazepanyl. In some embodiments, said ring is pyrrolidinyl or piperidinyl.

In some embodiments, said ring is optionally substituted with one $J^{Z1}$. In some embodiments, $J^{Z1}$ is $(X)_r$—Z. In other embodiments, $J^{Z1}$ is $C_{1-4}$alkyl or $N(C_{1-4}$alkyl$)_2$.

In one embodiment, p is 0, q is 0, and -L-$NR^1R^2$ is C(O)pyrrolidinyl, C(O)piperidinyl, C(O)piperazinyl, C(O) azepanyl, C(O)1,4-diazepanyl, C(O)NH-piperidinyl, C(O)NHCH$_2$CH$_2$-pyrrolidinyl, C(O)NHCH$_2$CH$_2$-piperidinyl, CON(CH$_3$)CH$_2$CH$_2$N(CH$_3$)$_2$, wherein said pyrrolidinyl, piperidinyl, piperazinyl, azepanyl, or 1,4-diazepanyl is optionally substituted with $C_{1-4}$alkyl or $N(C_{1-4}$alkyl$)_2$. In one embodiment, -L-$NR^1R^2$ is C(O)1,4-diazepanyl.

According to another aspect, m is 0. In some embodiments, $R^5$ is thienyl, thiazolyl, furanyl, pyrrolidinyl, azetidinyl, piperidinyl, piperazinyl, morpholinyl, pyridinonyl, pyridyl, tetrahydropyridinyl, tetrahydroisoquinolinyl, 1,4-diazepanyl, azabicyclo[2.2.1]heptanyl, or phenyl. In other embodiments, $R^5$ is phenyl, piperidinyl or thienyl. In some embodiments, Q is optionally substituted in the para position with —SO$_2$(C$_{1-4}$alkyl), —SO$_2$(C$_{1-4}$alkyl)N(C$_{1-4}$alkyl)$_2$, C(O)N(C$_{1-4}$alkyl)$_2$, C(O)(1,4-diazepanyl), C(O)(piperazinyl), or C(O)(piperidinyl).

According to another aspect, $R^5$ is phenyl. In some embodiments, $R^5$ is optionally substituted with 1-2 $J^5$ groups, wherein $J^5$ is selected from halo, CN, NO$_2$, $X^1$—R, or —$(X^1)_p$-$Q^4$; p is 0-1; $X^1$ is a $C_{1-10}$aliphatic wherein 1-3 methylene units of said $C_{1-6}$aliphatic are optionally replaced with —NR'—, —O—, —S—, C(=NH)—, C(O), S(O)$_2$, or S(O); R is H; and $Q^4$ is a 3-6 membered monocyclic ring containing 0-2 heteroatoms selected from O or N, wherein $X^1$ is optionally substituted with 1-3 occurrences of halo or CN.

In other embodiments, $J^5$ is a $C_{1-10}$aliphatic chain wherein 1-2 methylene units of $X^1$ are replaced with —O— or —NR'—.

According to another aspect, $R^5$ is piperidinyl optionally substituted with NH$_2$ or —(C$_{1-4}$alkyl)NH$_2$. According to yet another aspect, $R^5$ is thienyl optionally substituted with CN, $C_{1-6}$ alkyl, —(C$_{1-4}$ alkyl)NH$_2$, —(C$_{1-4}$ alkyl)NH(C$_{1-6}$ alkyl), —(C$_{1-4}$ alkyl)N(C$_{1-6}$ alkyl)$_2$, O(C$_{1-6}$alkyl), pyrrolidinyl, wherein said alkyl is optionally substituted with 1-3 halo.

In some embodiments, $Q^4$ is an optionally substituted 3-6 membered cycloalkyl ring. In other embodiments, $Q^4$ is an optionally substituted 3-6 membered heterocyclic ring selected from pyrrolidinyl, azetidinyl, or thienyl.

In some embodiments, $J^5$ is halo, $C_{1-6}$alkyl, NO$_2$, CN, $C_{1-6}$alkyl, —CH=CH$_2$, OH, OCH$_3$, OCH$_2$CH$_3$, OCH(CH$_3$)$_2$, NH$_2$, CH$_2$NH$_2$, CH$_2$OH, CH(CH$_3$)NHCH$_3$, C(CH$_3$)$_2$NH$_2$, CH$_2$CH$_2$NH$_2$, CH$_2$CH$_2$OH, CH$_2$NHCH$_3$, CH$_2$N(CH$_3$)$_2$, CH(CH$_3$)NH$_2$, CH(CH$_3$)NHC(O)O(CH$_3$)$_3$, CH$_2$NHC(CH$_3$)$_2$, CH$_2$NHCH$_2$CHF$_2$, CH$_2$NHCH$_2$CH(CH$_3$) OH, CH$_2$NHCH$_2$C(CH$_3$)$_2$OH, CH$_2$NHCH$_2$CH(OH)-cyclopropyl, CH$_2$NHCH$_2$CH$_2$N(CH$_3$)$_2$, CH$_2$NHCH(CH$_3$)$_3$, CH$_2$NHCH$_3$, CH$_2$NHCH$_2$CH$_3$, CH$_2$NHCH$_2$CH$_2$CH$_3$, CH$_2$NH-cyclopropyl, CH$_2$NHCH$_2$CH$_2$OH, CH$_2$NHCH$_2$CH$_2$OCH$_3$, CH$_2$NHCH$_2$CH$_2$OCH$_2$CH$_2$OH, azetidinyl, pyrrolidinyl, CF$_3$, C(=NH)NH$_2$, C(=NH)NH(CH$_3$), thienyl, CH$_2$NH-cyclopropyl, CH$_2$NH(CH$_2$OH)$_3$, OCH$_2$CH$_2$OH, OCH$_2$CH$_2$CH$_2$OH, OCH$_2$CH$_2$NHC(O)OC(CH$_3$)$_3$, CH$_2$NHC(O)O(CH$_3$)$_3$, or CH$_2$OC(O)CH$_3$.

According to another aspect, m is 1.

In some embodiments, $R^5$ is H.

In some embodiments, Y is —NH—, —NHCH$_2$—, —NHC(O)—, C(O)NH, C(O)NHCH$_2$, C(O), —NHCH(CH$_3$)— or —N(CH$_3$)CH$_2$—; and $R^5$ is phenyl. In some embodiments, $R^5$ is optionally substituted with halo or $C_{1-4}$alkyl, wherein up to 1 methylene unit is optionally replaced with O, NR', or S.

Another embodiment provides a compound of Formula IIA:

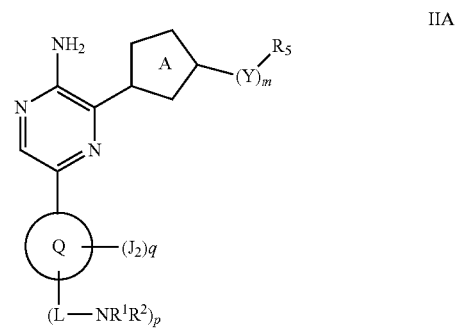

IIA or a pharmaceutically acceptable salt thereof; wherein Ring A is a 5 membered heteroaryl ring selected from

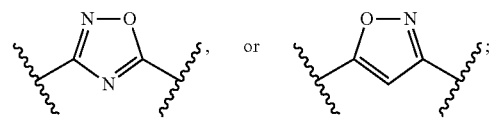 [SMILES: *c1noc(*)n1 ; *c1cc(*)on1]

Y is a $C_1$-$C_4$alkyl chain wherein one methylene unit of the alkyl chain is optionally replaced with —NR$^O$—;

Q is a 5-6 membered monocyclic aromatic ring containing 0-4 heteroatoms independently selected from nitrogen, oxygen, or sulfur; or an 8-10 membered bicyclic aromatic ring containing 0-6 heteroatoms independently selected from nitrogen, oxygen, or sulfur;

$R^5$ is 5-6 membered monocyclic aryl or heteroaryl ring having 0-3 heteroatoms independently selected from nitrogen, oxygen, or sulfur, $R^5$ is optionally fused to a 5-6 membered aromatic ring containing 0-2 heteroatoms selected from N, O, or S; each $R^5$ is optionally substituted with 1-5 $J^5$ groups;

L is —C(O)— or —SO$_2$—;

$R^1$ is H, or $C_1$-$C_6$alkyl;

$R^O$ is H or $C_1$-$C_6$alkyl;

$R^2$ is $C_1$-$C_6$alkyl, —(C$_2$-$C_6$alkyl)-Z or a 4-8 membered cyclic ring containing 0-2 nitrogen atoms; wherein said ring is bonded via a carbon atom and is optionally substituted with one occurrence of $J^Z$;

or $R^1$ and $R^2$, taken together with the atom to which they are bound, form a 4-8 membered heterocyclic ring containing 1-2 heteroatoms selected from nitrogen, sulfur, or oxygen; wherein said heterocyclic ring is optionally substituted with one occurrence of $J^{Z1}$;

$J^{Z1}$ is $(X)_r$—CN, $C_1$-$C_6$alkyl or —$(X)_r$—Z;

X is $C_1$-$C_4$alkyl;

each t, r and m is independently 0 or 1;

Z is —$NR^3R^4$;

$R^3$ is H or $C_1$-$C_2$alkyl;

$R^4$ is H or $C_1$-$C_6$alkyl;

or $R^3$ and $R^4$, taken together with the atom to which they are bound, form a 4-8 membered heterocyclic ring containing 1-2 nitrogen atoms; wherein said ring is optionally substituted with one occurrence of $J^Z$;

$J^Z$ is $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO(C_{1-4}aliphatic)$, $CO_2(C_{1-4}aliphatic)$, $O(haloC_{1-4}aliphatic)$, or $haloC_{1-4}aliphatic$;

$J^5$ is halogen, $NO_2$, CN, $O(haloC_{1-4}aliphatic)$, $haloC_{1-4}aliphatic$, or a $C_{1-6}aliphatic$ group wherein up to 2 methylene units are optionally replaced with C(O), O, or NR';

$J^2$ is halo; CN; phenyl; oxazolyl; or a $C_{1-6}aliphatic$ group wherein up to 2 methylene units are optionally replaced with O, NR", C(O), S, S(O), or $S(O)_2$; said $C_{1-6}aliphatic$ group is optionally substituted with 1-3 fluoro or CN;

R' and R" are each independently H or $C_1$-$C_4$ alkyl;

q is 0, 1, or 2, p is 0 or 1.

In some embodiments, Q is phenyl or pyridyl.

In other embodiments, Y is a $C_1$-$C_2$alkyl chain wherein one methylene unit of the alkyl chain is optionally replaced with $NR^O$.

Another embodiment provides a Compound from Table IIA-2:

TABLE IIA-2

IIA-1

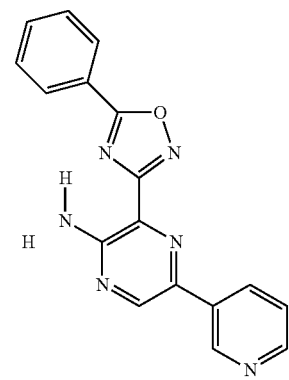

IIA-2

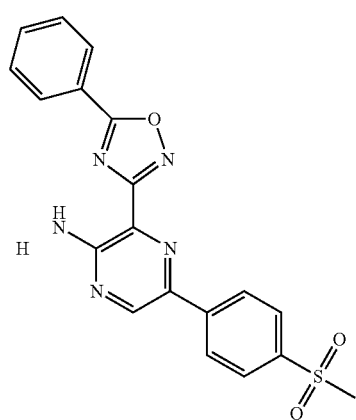

TABLE IIA-2-continued

IIA-3

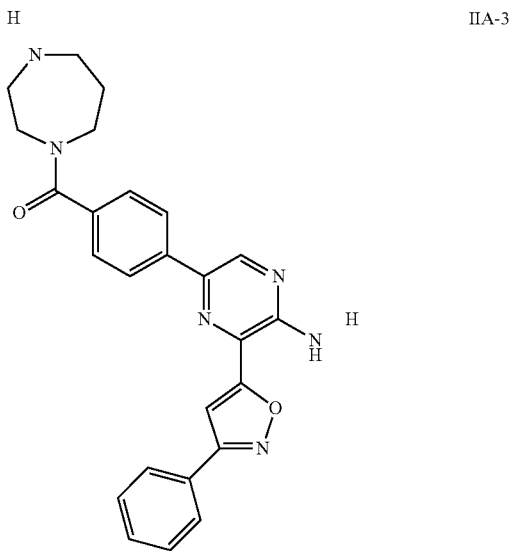

IIA-4

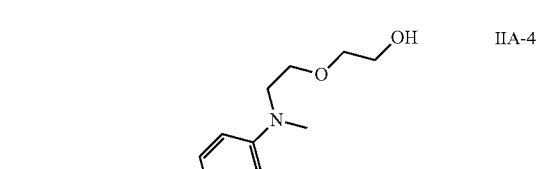

IIA-5

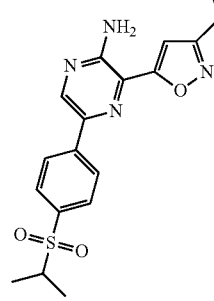

TABLE IIA-2-continued
IIA-6
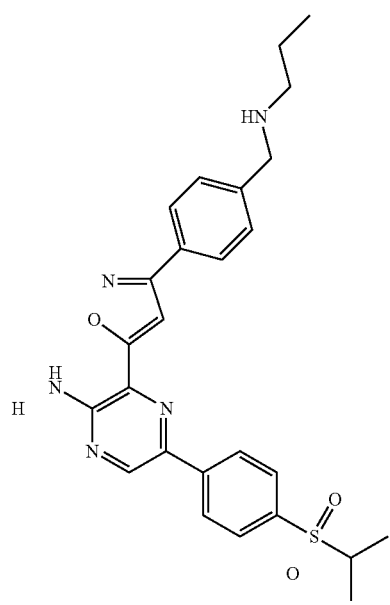
IIA-8
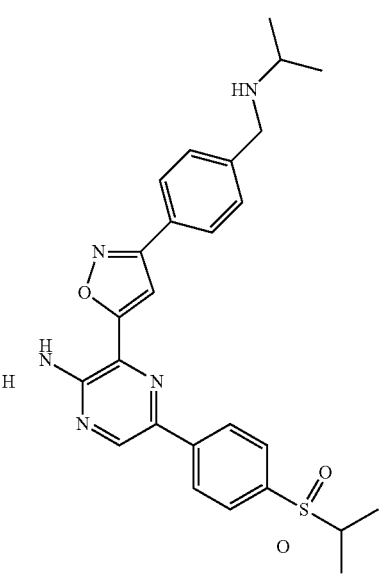
IIA-7
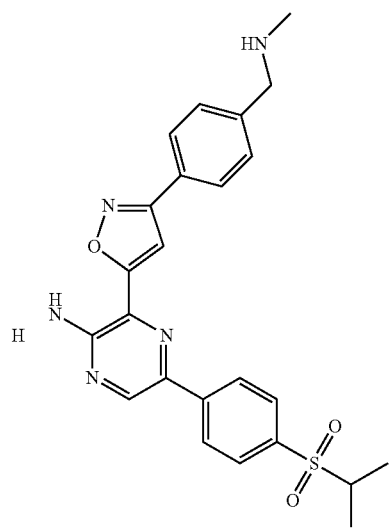
IIA-9
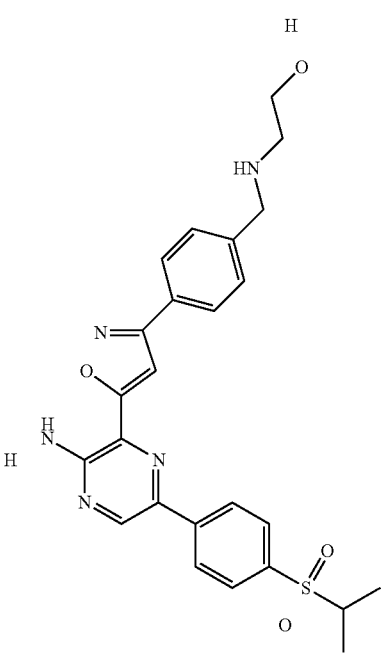

TABLE IIA-2-continued
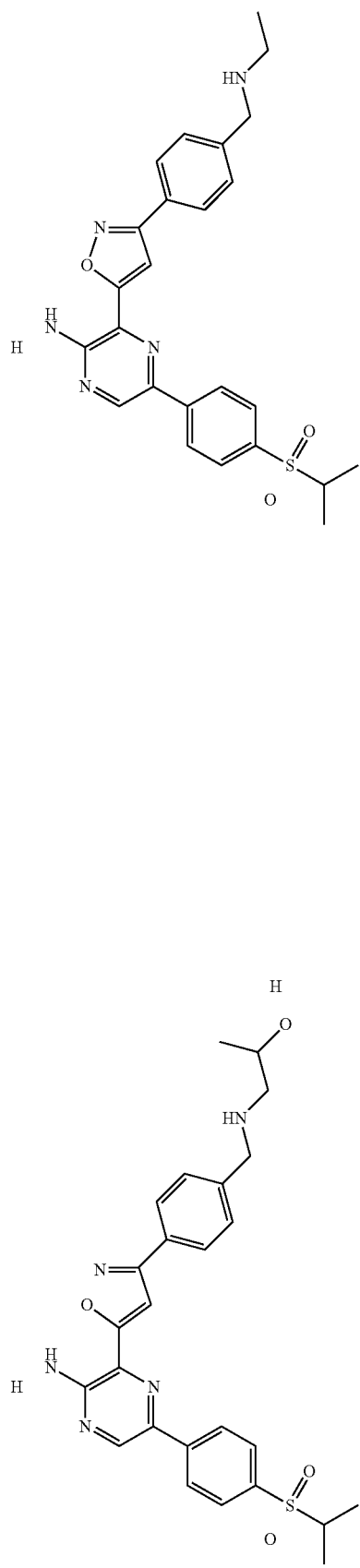
IIA-10
IIA-11
TABLE IIA-2-continued
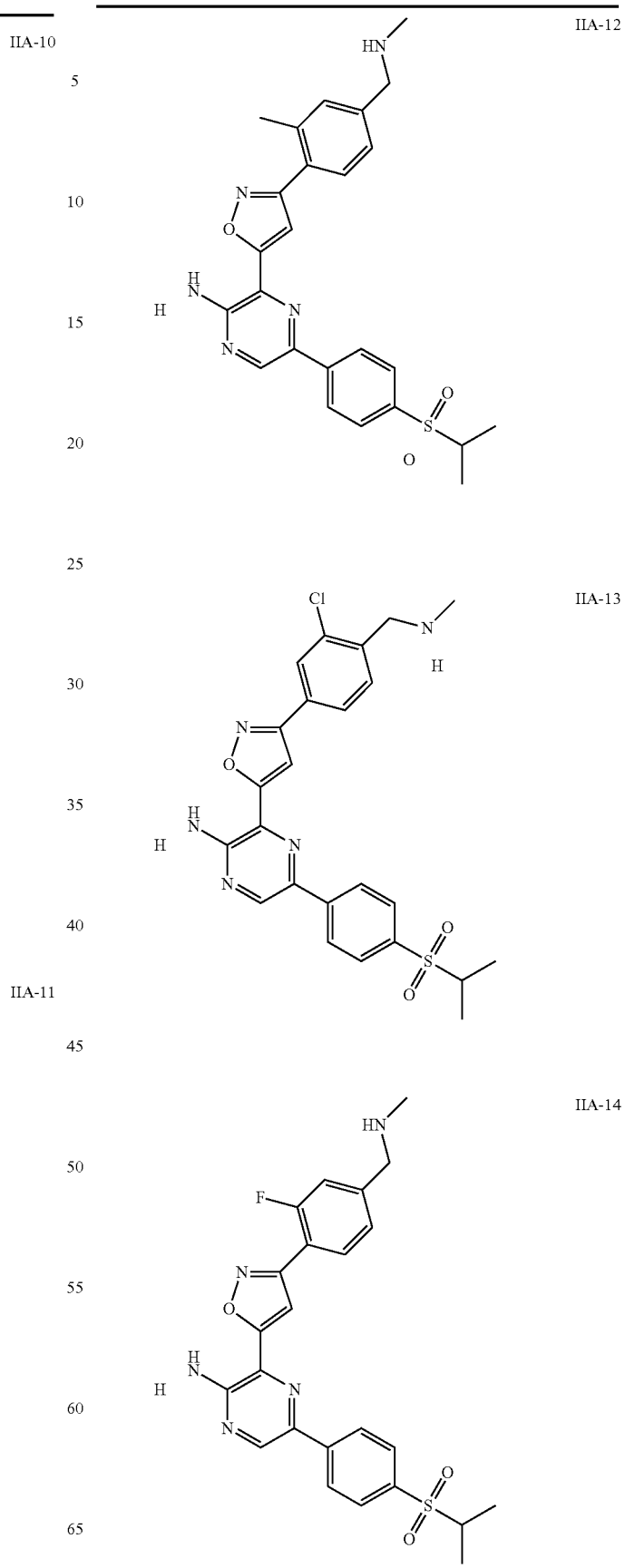
IIA-12
IIA-13
IIA-14

TABLE IIA-2-continued

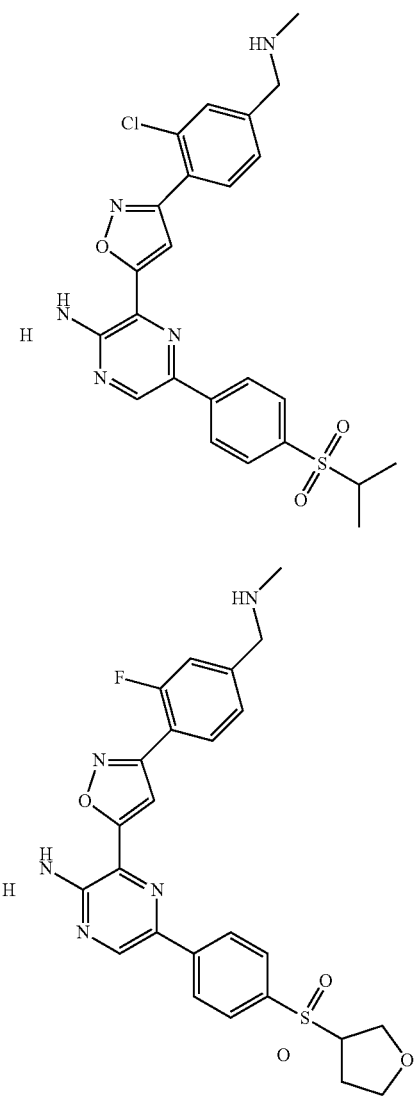

Another embodiment provides a compound of Formula IIIA:

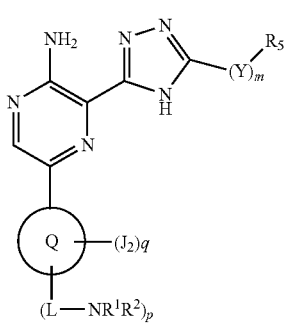

or a pharmaceutically acceptable salt thereof; wherein

Y is a $C_1$-$C_4$alkyl chain wherein one methylene unit of the alkyl chain is optionally replaced with —$NR^o$—;

Q is phenyl or pyridyl;

$R^5$ is 5-6 membered monocyclic aryl or heteroaryl ring having 0-3 heteroatoms independently selected from nitrogen, oxygen, or sulfur, $R^5$ is optionally fused to a 5-6 membered aromatic ring containing 0-2 heteroatoms selected from N, O, or S; each $R^5$ is optionally substituted with 1-5 $J^5$ groups;

L is —C(O)— or —$SO_2$—;

$R^1$ is H, or $C_1$-$C_6$alkyl;

$R^o$ is H or $C_1$-$C_6$alkyl;

$R^2$ is $C_1$-$C_6$alkyl, —($C_2$-$C_6$alkyl)-Z or a 4-8 membered cyclic ring containing 0-2 nitrogen atoms; wherein said ring is bonded via a carbon atom and is optionally substituted with one occurrence of $J^Z$;

or $R^1$ and $R^2$, taken together with the atom to which they are bound, form a 4-8 membered heterocyclic ring containing 1-2 heteroatoms selected from nitrogen, sulfur, or oxygen; wherein said heterocyclic ring is optionally substituted with one occurrence of $J^{Z1}$;

$J^{Z1}$ is —$(X)_t$—CN, $C_1$-$C_6$alkyl or —$(X)_t$—Z;

X is $C_1$-$C_4$alkyl;

each t, r and m is independently 0 or 1;

Z is —$NR^3R^4$;

$R^3$ is H or $C_1$-$C_2$alkyl;

$R^4$ is H or $C_1$-$C_6$alkyl;

or $R^3$ and $R^4$, taken together with the atom to which they are bound, form a 4-8 membered heterocyclic ring containing 1-2 nitrogen atoms; wherein said ring is optionally substituted with one occurrence of $J^Z$;

$J^Z$ is $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO(C_{1-4}aliphatic)$, $CO_2(C_{1-4}aliphatic)$, $O(haloC_{1-4}aliphatic)$, or $haloC_{1-4}aliphatic$;

$J^5$ is halogen, $NO_2$, CN, $O(haloC_{1-4}aliphatic)$, $haloC_{1-4}aliphatic$, or a $C_{1-6}aliphatic$ group wherein up to 2 methylene units are optionally replaced with C(O), O, or NR';

$J^2$ is halo; CN; phenyl; oxazolyl; or a $C_{1-6}aliphatic$ group wherein up to 2 methylene units are optionally replaced with O, NR", C(O), S, S(O), or $S(O)_2$; said $C_{1-6}aliphatic$ group is optionally substituted with 1-3 fluoro or CN;

R' and R" are each independently H or $C_1$-$C_4$ alkyl;

q is 0, 1, or 2, p is 0 or 1.

In some embodiments, Y is a $C_1$-$C_2$alkyl chain wherein one methylene unit of the alkyl chain is optionally replaced with $NR^o$.

In other embodiments, p is 0 and Q is pyridyl. In some embodiments, m is 0.

In yet other embodiments, $R^5$ is phenyl or thienyl. In some embodiments, $R^5$ is phenyl optionally substituted with one occurrence of $NH_2$, $C_1$-$C_4$alkyl, or $CH_2NH_2$.

Another embodiment provides a compound selected from Table IIIA:

TABLE IIIA
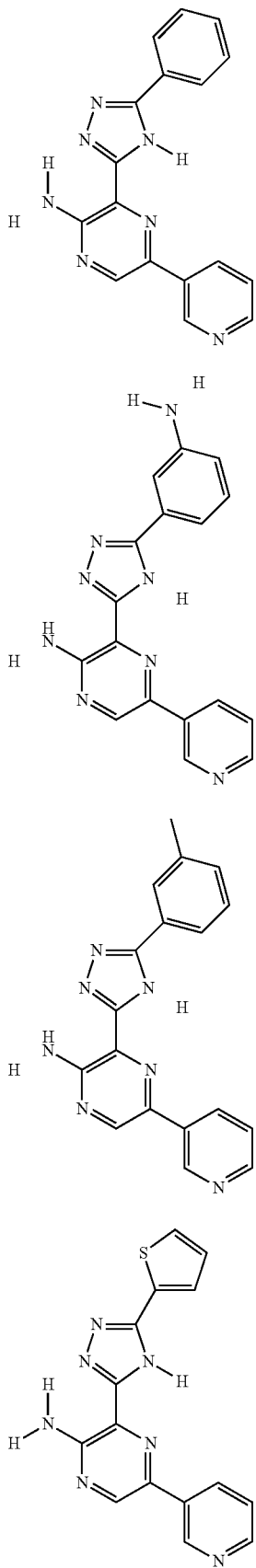
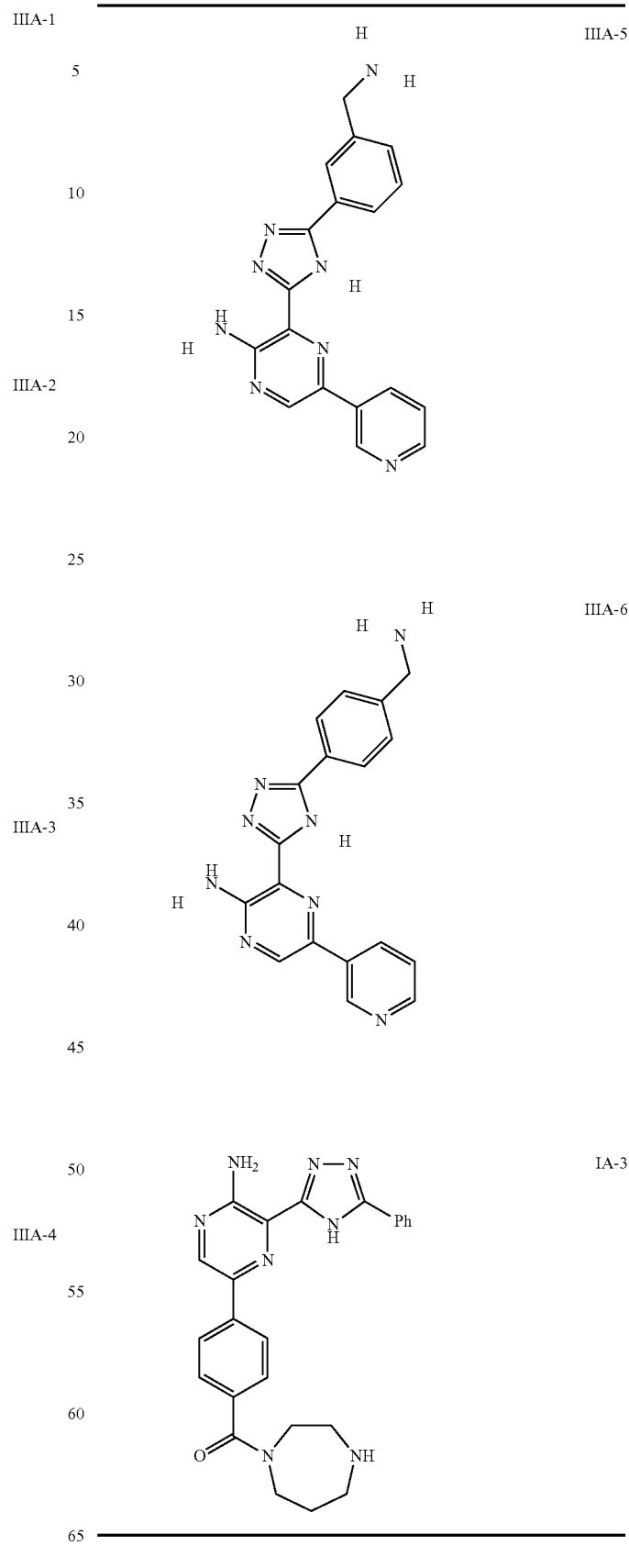

Another aspect provides a compound of formula IA-ii:

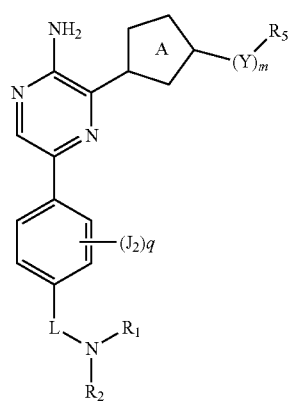

IA-ii or a pharmaceutically acceptable salt thereof; wherein
Y is NH;
Ring A is a 5 membered heteroaryl ring selected from

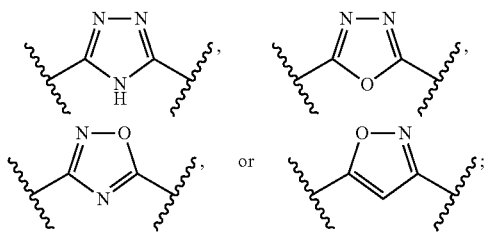

$R^5$ is 5-6 membered monocyclic aryl or heteroaryl ring having 0-3 heteroatoms independently selected from nitrogen, oxygen, or sulfur, $R^5$ is optionally fused to a 5-6 membered aromatic ring containing 0-2 heteroatoms selected from N, O, or S; each $R^5$ is optionally substituted with 1-5 $J^5$ groups;
L is —C(O)— or —SO$_2$—;
$R^1$ is H, or $C_1$-$C_6$alkyl;
$R^2$ is —($C_2$-$C_6$alkyl)-Z or a 4-8 membered cyclic ring containing 0-2 nitrogen atoms; wherein said ring is bonded via a carbon atom and is optionally substituted with one occurrence of $J^Z$;
or $R^1$ and $R^2$, taken together with the atom to which they are bound, form a 4-8 membered heterocyclic ring containing 1-2 nitrogen atoms; wherein said heterocyclic ring is optionally substituted with one occurrence of $J^{Z1}$;
$J^{Z1}$ is —(X)$_t$—CN, $C_1$-$C_6$alkyl or —(X)$_r$—Z;
X is $C_1$-$C_4$alkyl;
each t, r and m is independently 0 or 1;
Z is —NR$^3$R$^4$;
$R^3$ is H or $C_1$-$C_2$alkyl;
$R^4$ is H or $C_1$-$C_6$alkyl;
or $R^3$ and $R^4$, taken together with the atom to which they are bound, form a 4-8 membered heterocyclic ring containing 1-2 nitrogen atoms; wherein said ring is optionally substituted with one occurrence of $J^Z$;
each $J^Z$, $J^1$, and $J^5$ is independently NH$_2$, NH($C_{1-4}$aliphatic), N($C_{1-4}$aliphatic)$_2$, halogen, $C_{1-4}$aliphatic, OH, O($C_{1-4}$aliphatic), NO$_2$, CN, CO$_2$H, CO($C_{1-4}$aliphatic), CO$_2$($C_{1-4}$aliphatic), O(halo$C_{1-4}$ aliphatic), or halo$C_{1-4}$aliphatic;
$J^2$ is halo, $C_1$-$C_2$alkyl optionally substituted with 1-3 fluoro, or CN;
q is 0, 1, or 2.

According to one embodiment, Ring A is

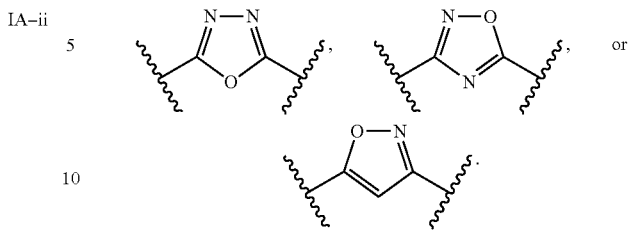

According to another embodiment, m is 0.

According to another embodiment, q is 0.

In some embodiments, L is —C(O)—.

In some embodiments, $R^1$ and $R^2$, taken together with the atom to which they are bound, form a 4-8 membered heterocyclic ring containing 1-2 nitrogen atoms. In some embodiments, said heterocyclic ring is selected from pyrrolidinyl, piperidinyl, piperazinyl, azepanyl, or 1,4-diazepanyl. In other embodiments, said heterocyclic ring is selected from

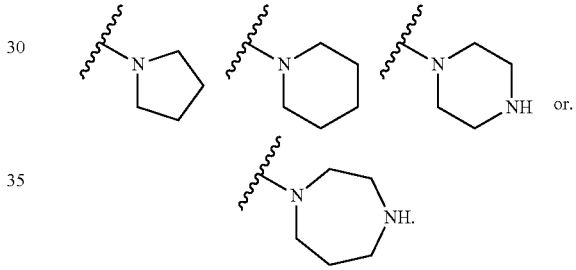

In some embodiments, t is 1. In other embodiments, t is 0.

In other embodiments, $R^1$ is H or $C_1$-$C_6$alkyl; and $R^2$ is —($C_2$-$C_6$alkyl)-Z. In some embodiments, $R^1$ is $C_1$-$C_6$alkyl. In some embodiments, Z is —NR$^3$R$^4$, wherein R$^3$ and R$^4$ are both $C_1$-$C_2$alkyl. In other embodiments, R$^3$ and R$^4$, taken together with the atom to which they are bound, form a ring selected from pyrrolidinyl, piperidinyl, piperazinyl, azepanyl, or 1,4-diazepanyl. In some embodiments, said ring is pyrrolidinyl or piperidinyl.

In some embodiments, said ring is optionally substituted with one $J^{Z1}$. In some embodiments, $J^{Z1}$ is (X)$_r$—Z. In other embodiments, $J^{Z1}$ is $C_{1-4}$alkyl or N($C_{1-4}$alkyl)$_2$.

In one embodiment, p is 0, q is 0, and -L-NR$^1$R$^2$ is C(O)pyrrolidinyl, C(O)piperidinyl, C(O)piperazinyl, C(O)azepanyl, C(O)1,4-diazepanyl, C(O)NH-piperidinyl, C(O)NHCH$_2$CH$_2$-pyrrolidinyl, C(O)NHCH$_2$CH$_2$-piperidinyl, CON(CH$_3$)CH$_2$CH$_2$N(CH$_3$)$_2$, wherein said pyrrolidinyl, piperidinyl, piperazinyl, azepanyl, or 1,4-diazepanyl is optionally substituted with $C_{1-4}$alkyl or N($C_{1-4}$alkyl)$_2$. In one embodiment, -L-NR$^1$R$^2$ is C(O)1,4-diazepanyl.

Another embodiment provides a compound selected from Table IA:

TABLE IA

IA-1

IA-2

Another embodiment provides a compound of Formula IA-iii:

IA-iii or a pharmaceutically acceptable salt thereof wherein;

Ring A is

<img/> or <img/>, $J^5o$ is H, F, Cl, $C_{1-4}$aliphatic, O($C_{1-3}$aliphatic), or OH;

$J^5p$ is

<img/>

$J^5p1$ is H, $C_{1-4}$aliphatic, oxetanyl, tetrahydrofuranyl, tetrahydropyranyl; wherein $J^5p2$ is optionally substituted with 1-2 occurrences of OH or halo;

$J^5p2$ is H, methyl, ethyl, $CH_2F$, $CF_3$, or $CH_2OH$;

$J^2o$ is H, CN, or $SO_2CH_3$;

$J^2m$ is H, F, Cl, or methyl;

$J^2p$ is —$SO_2(C_{1-6}$ alkyl), —$SO_2(C_{3-6}$ cycloalkyl), —$SO_2$ (4-6 membered heterocyclyl), —$SO_2(C_{1-4}$alkyl)N($C_{1-4}$ alkyl)$_2$, or —$SO_2(C_{1-4}$alkyl)-(4-6 membered heterocyclyl), wherein said heterocyclyl contains 1 heteroatom selected from the group consisting of O, N, and S; and wherein said $J^2p$ is optionally substituted with 1-3 occurences halo, OH, or O($C_{1-4}$ alkyl).

In some embodiments, Ring A is

<img/>

In other embodiments, Ring A is

<img/>

Another embodiments provides a compound from one of the following Tables:

TABLE IA-2

IA-4

IA-5

TABLE IA-2-continued
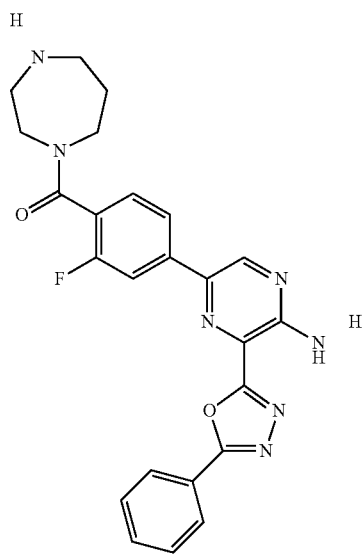
IA-6
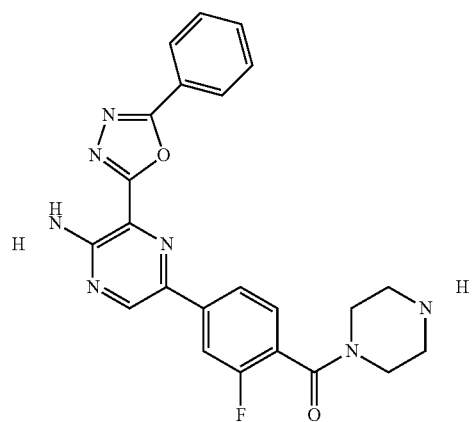
IA-7
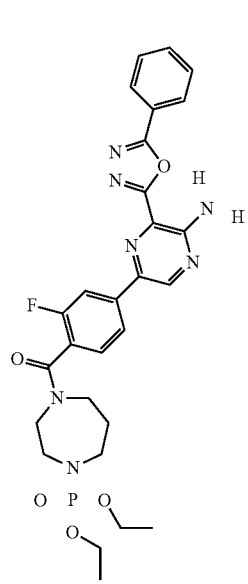
IA-8
TABLE IA-2-continued
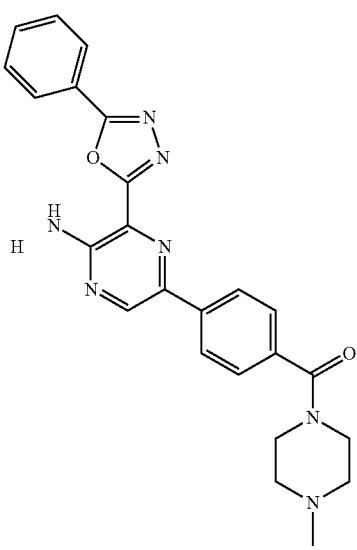
IA-9
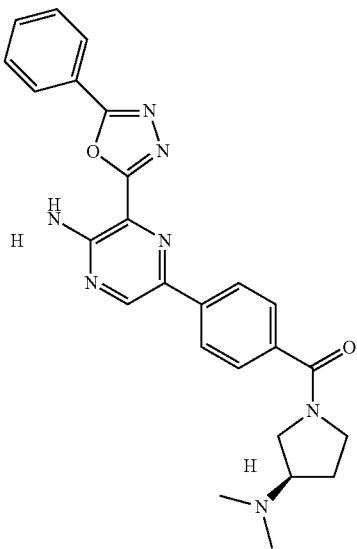
IA-10

TABLE IA-2-continued
IA-11
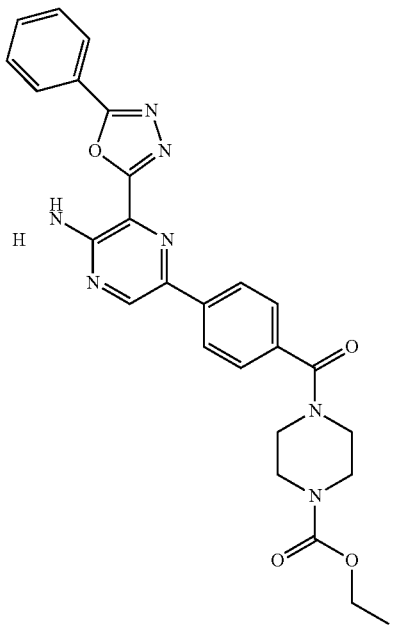
IA-12
IA-13
TABLE IA-2-continued
IA-14
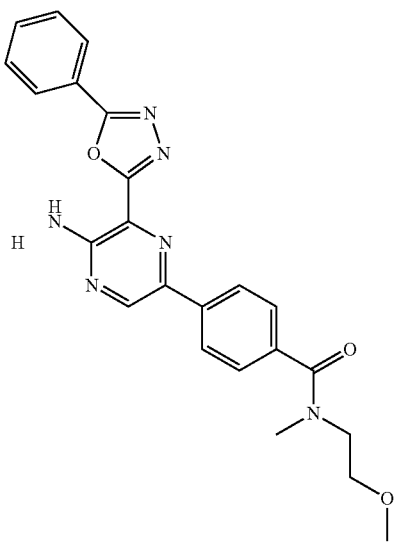
IA-15
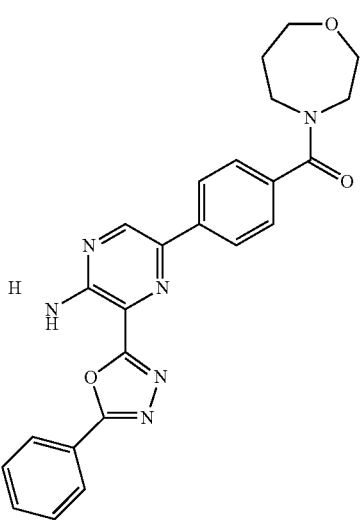
IA-16
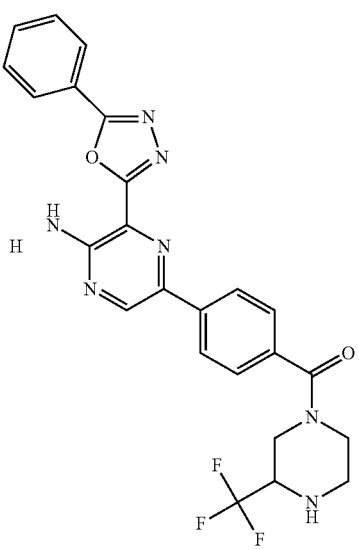

TABLE IA-2-continued
IA-17
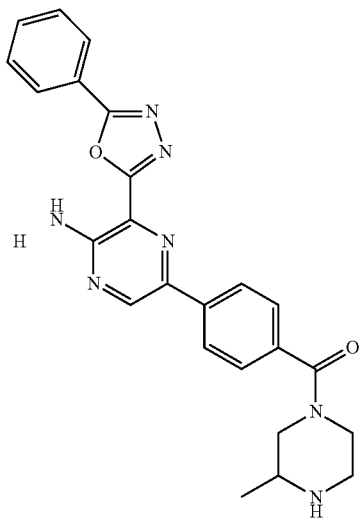
IA-18
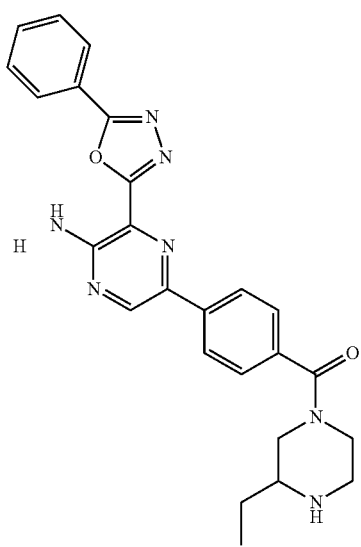
IA-19
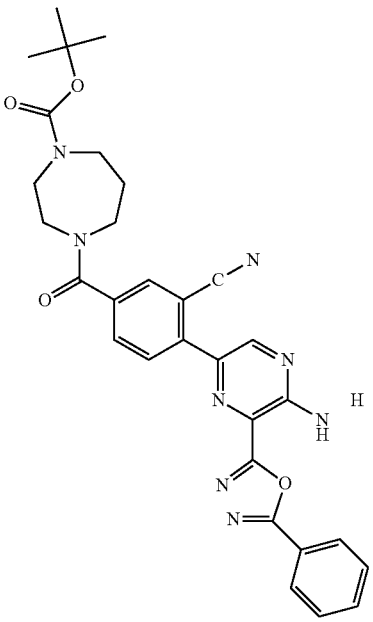
IA-20
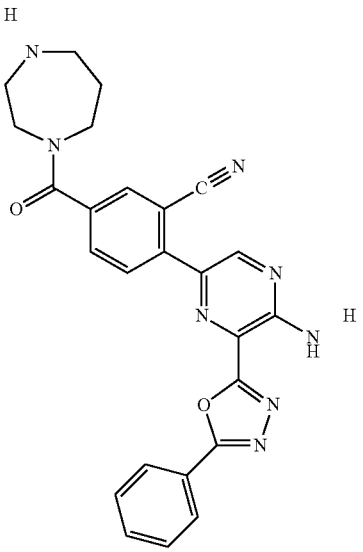
IA-21
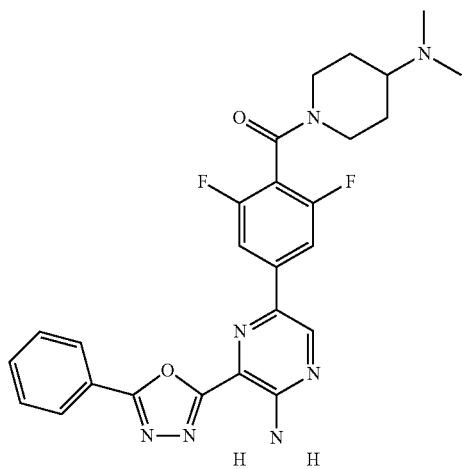

TABLE IA-2-continued
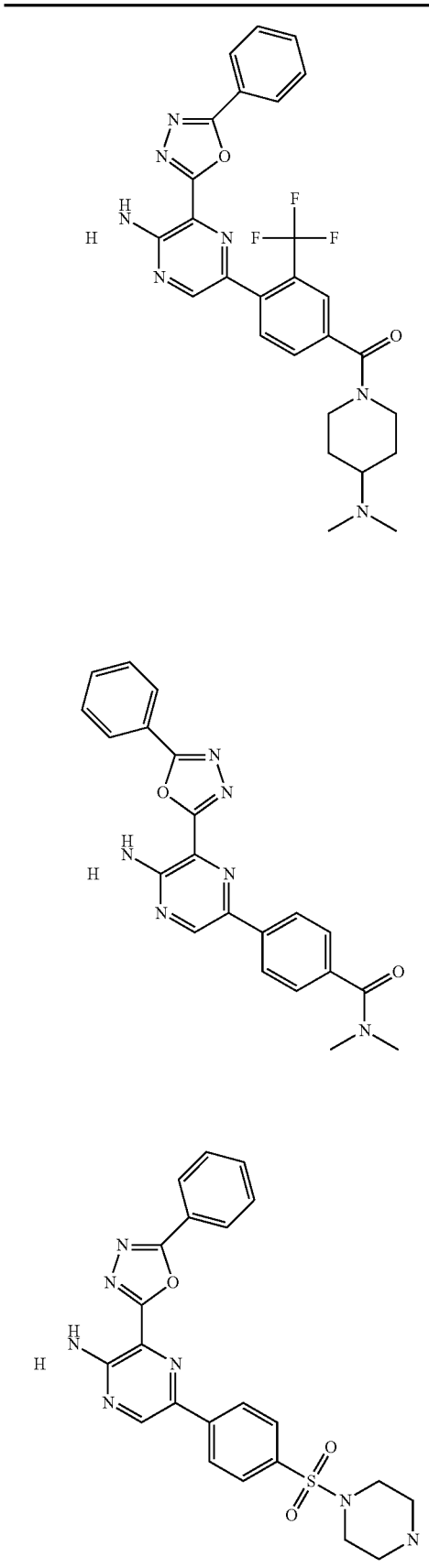
IA-22
IA-23
IA-24
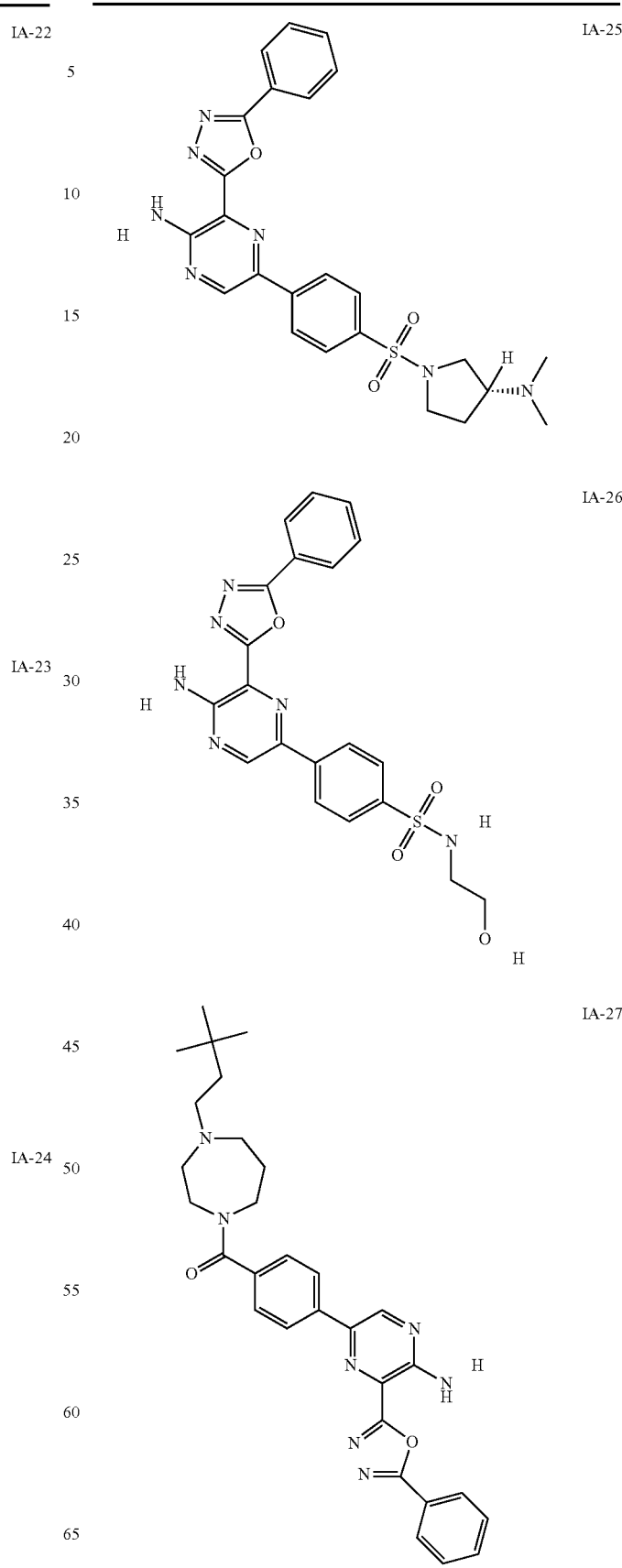
IA-25
IA-26
IA-27

TABLE IA-2-continued
IA-28
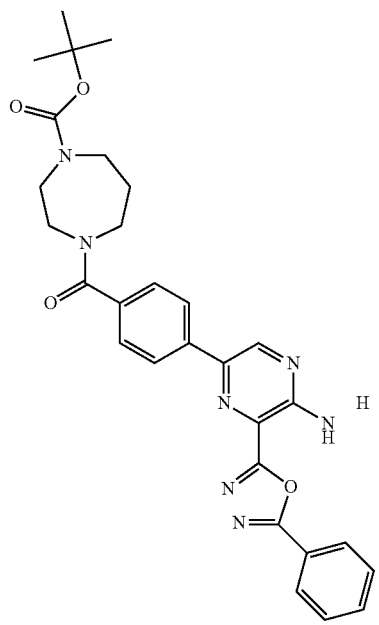
IA-29
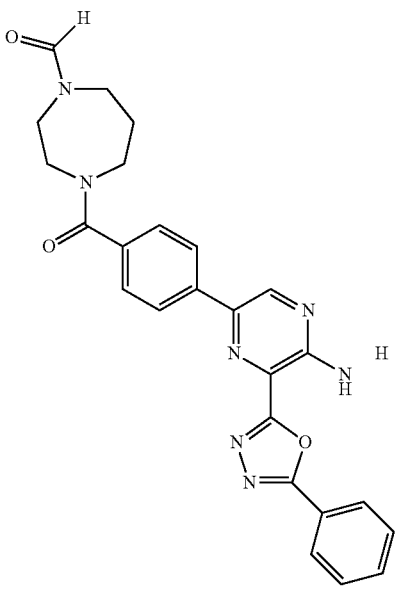
IA-30
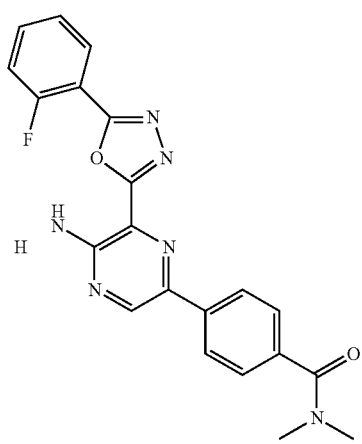
IA-31
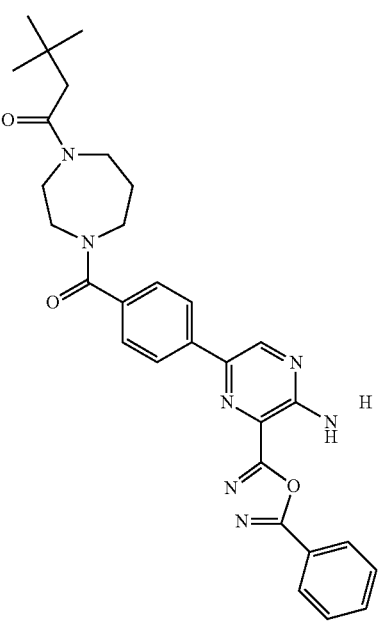
IA-32
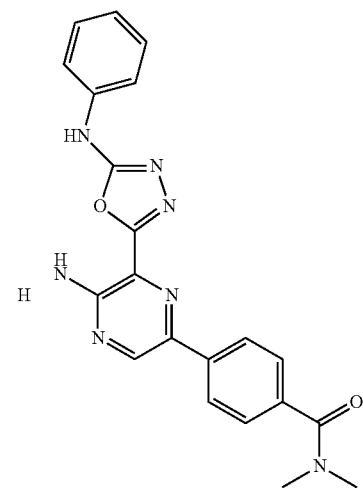
IA-33
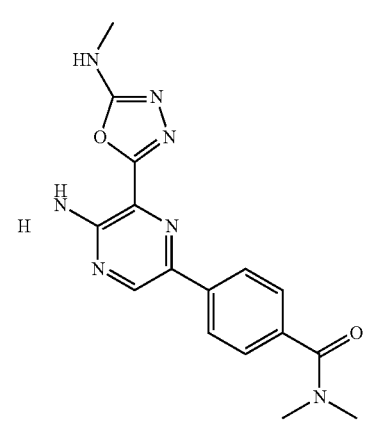

TABLE IA-2-continued
IA-34
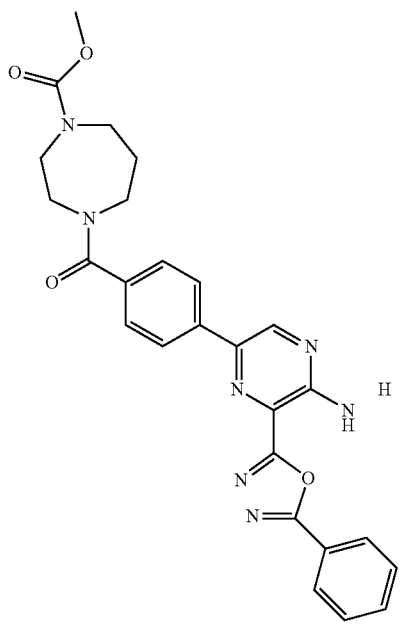
IA-35
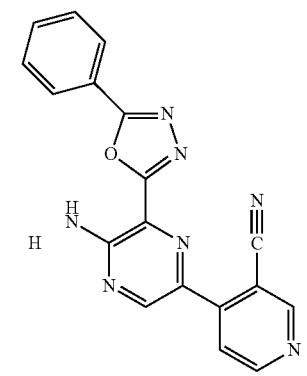
IA-36
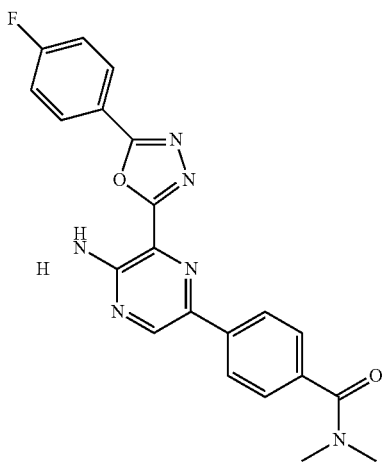
TABLE IA-2-continued
IA-37
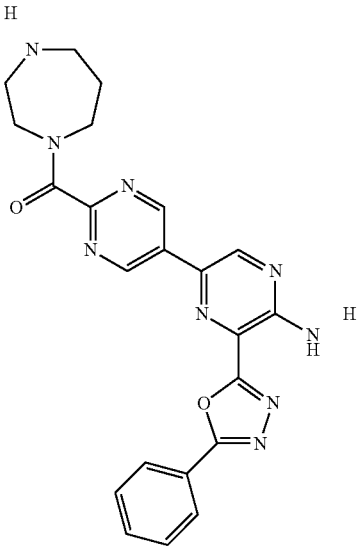
IA-38
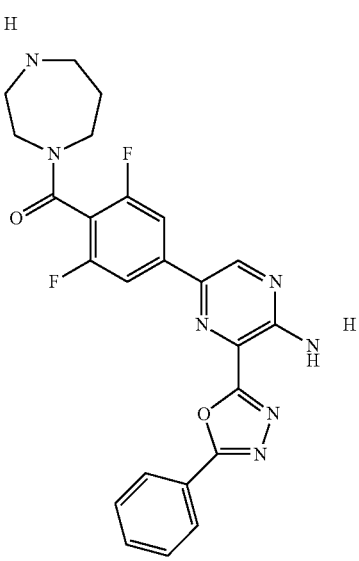
IA-39
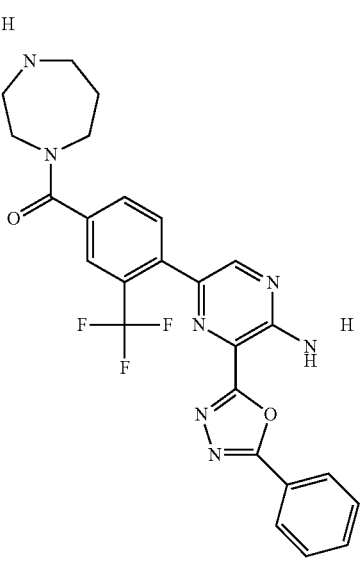

TABLE IA-2-continued
IA-40
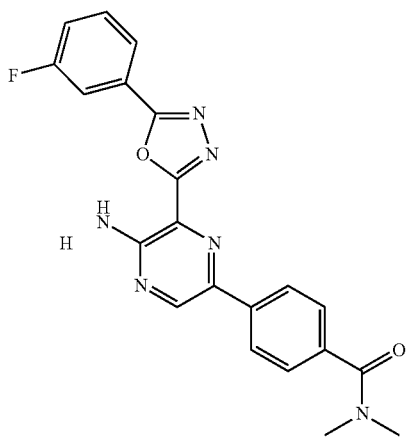
IA-41
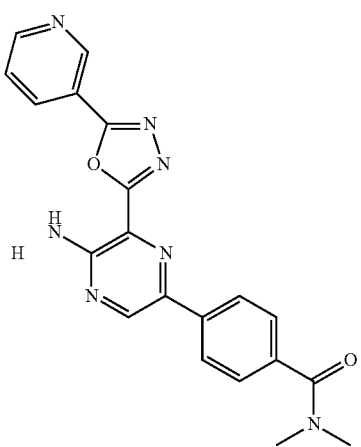
IA-42
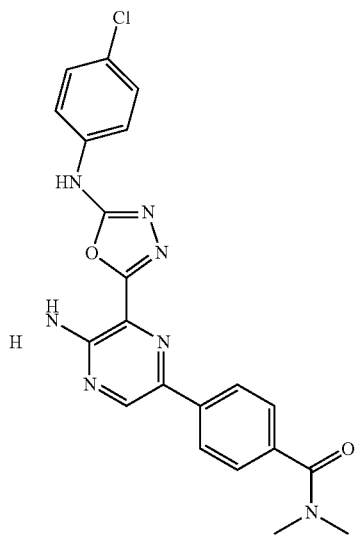
TABLE IA-2-continued
IA-43
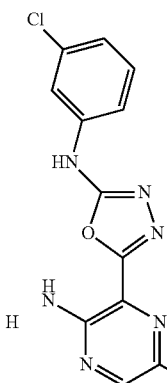
IA-44
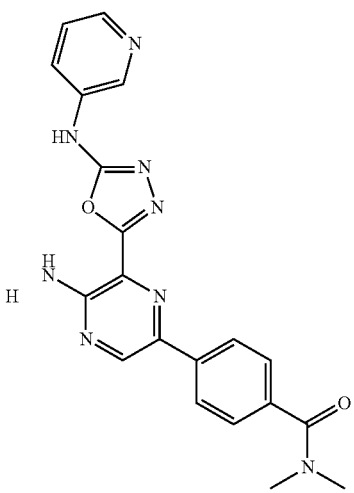
IA-45
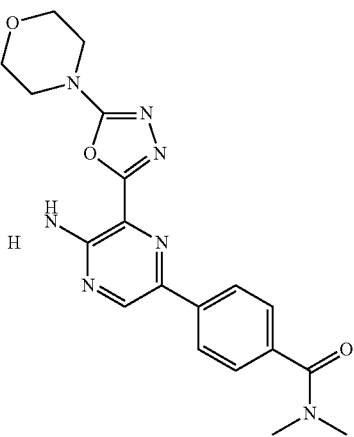

TABLE IA-2-continued
IA-46
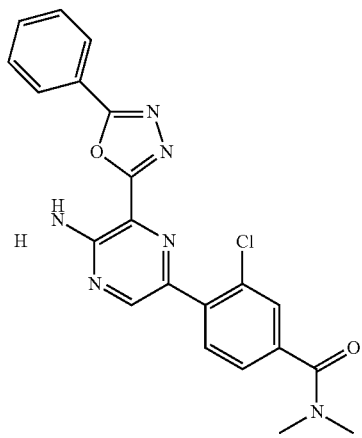
IA-47
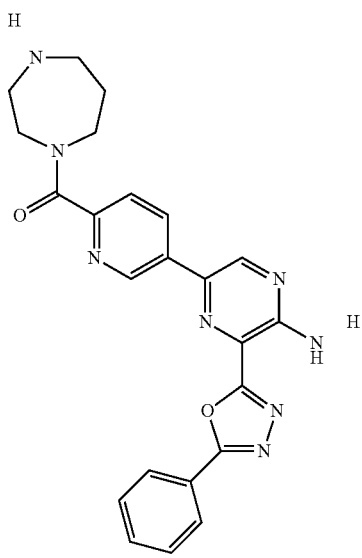
IA-48
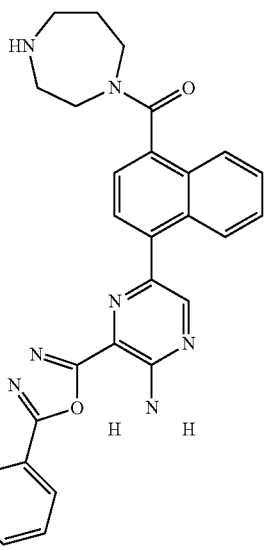
TABLE IA-2-continued
IA-49
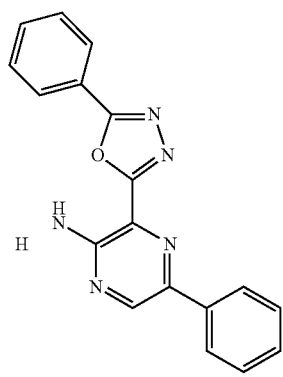
IA-50
IA-51
IA-52

TABLE IA-2-continued
IA-53
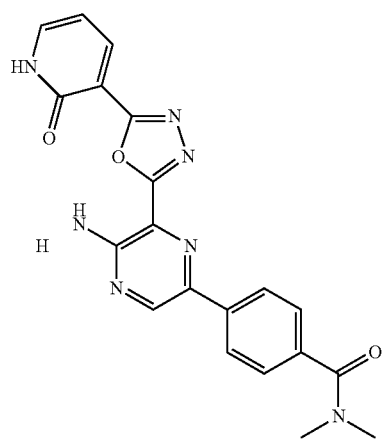
IA-54
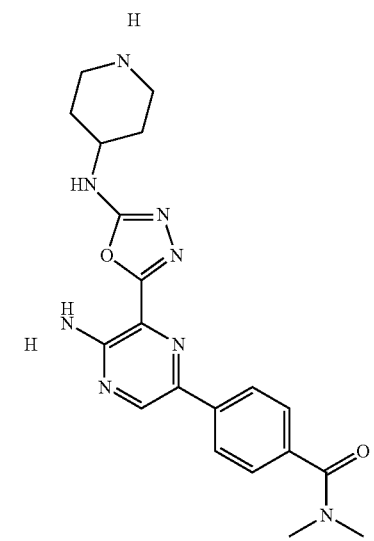
IA-55
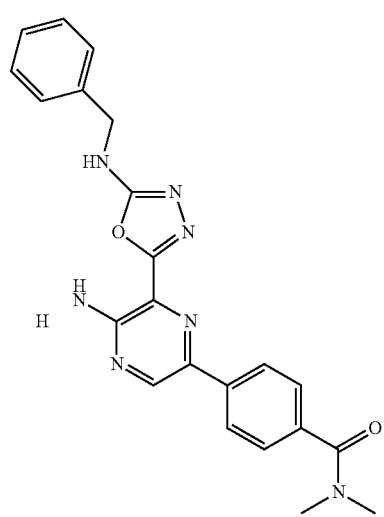
IA-56
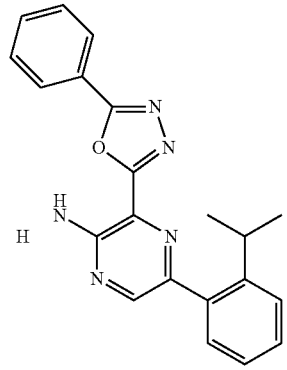
IA-57
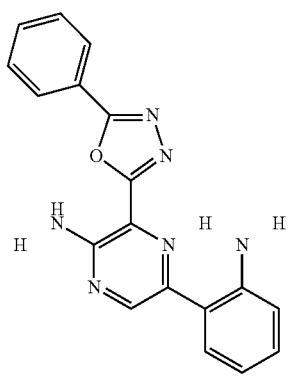
IA-58
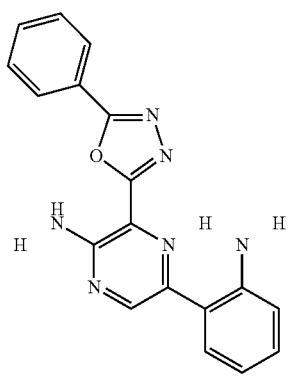
IA-59
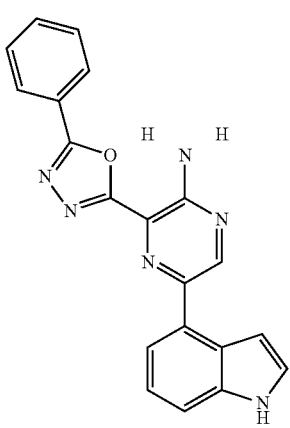

TABLE IA-2-continued
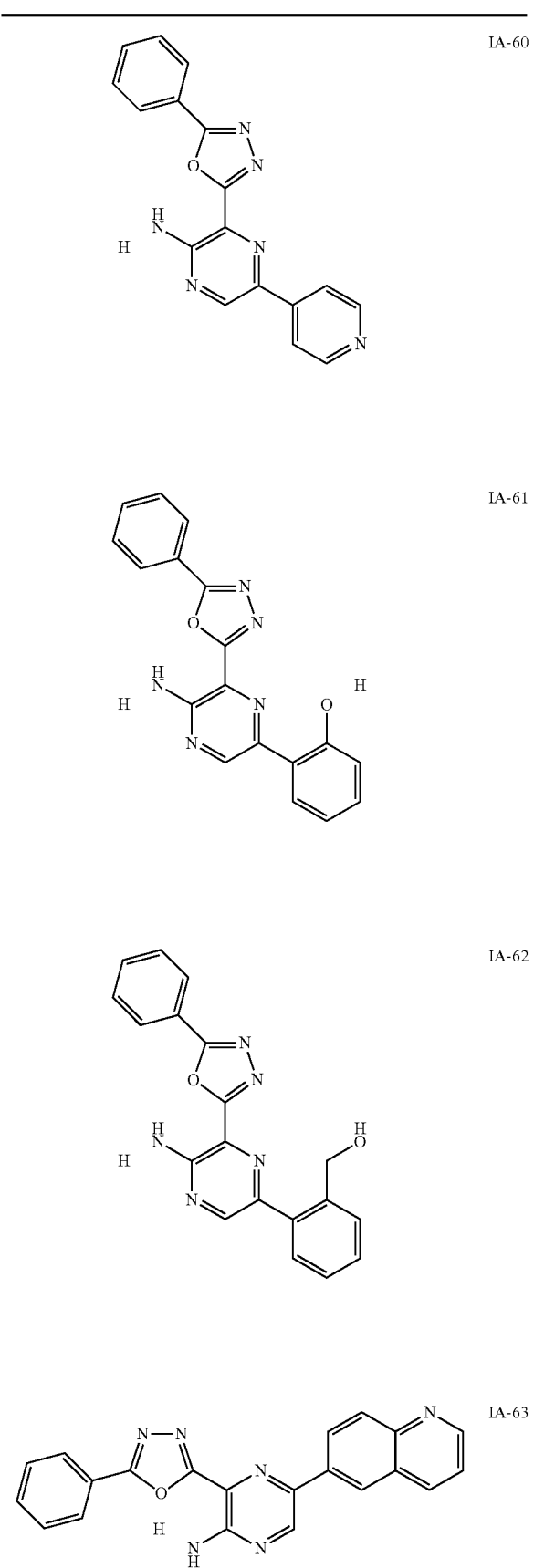
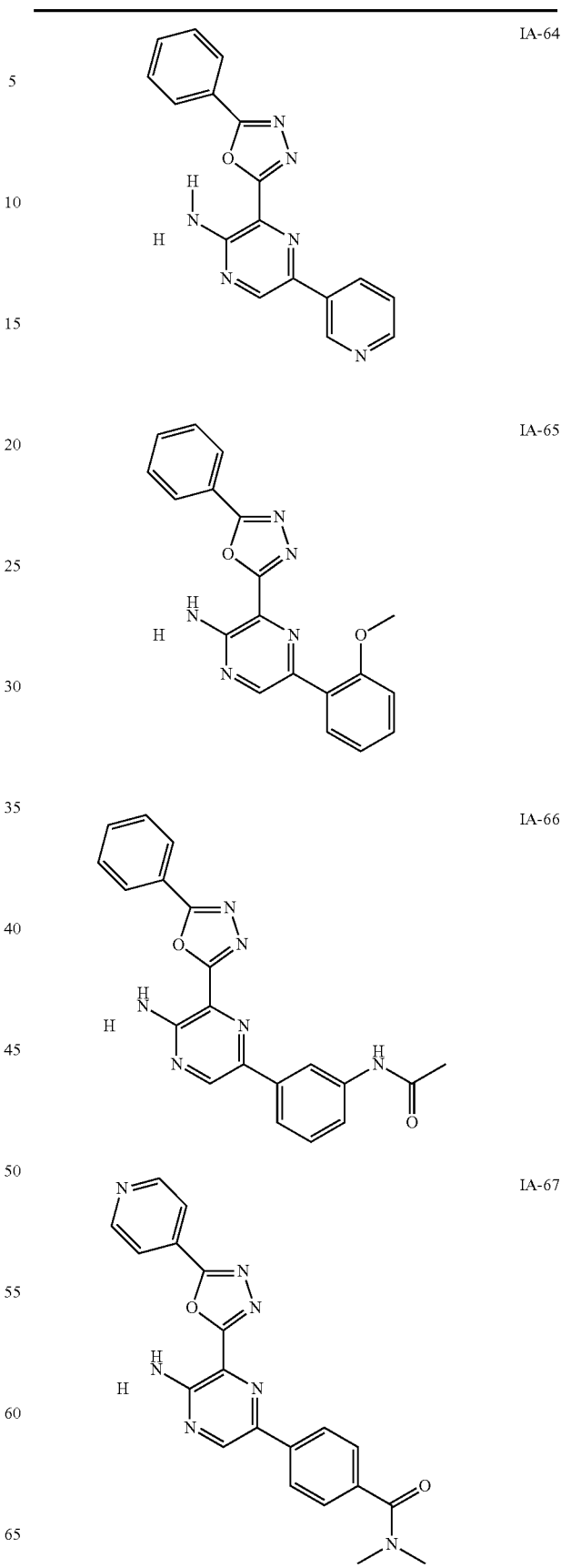

TABLE IA-2-continued
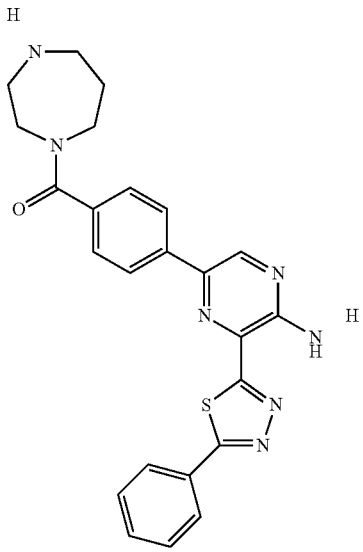
IA-68
TABLE IA-3
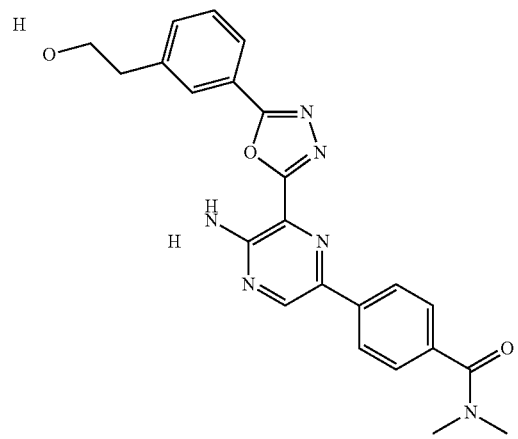
IA-69
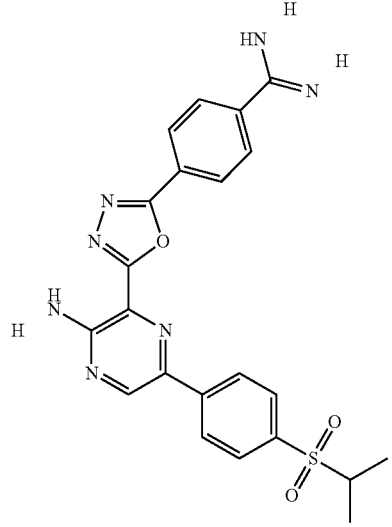
IA-70
TABLE IA-3-continued
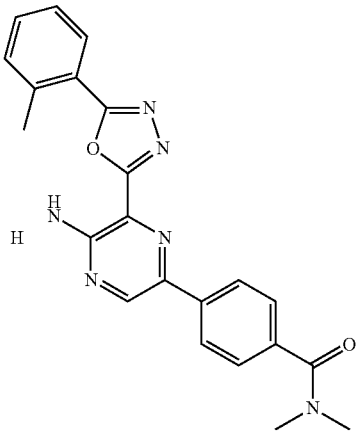
IA-71
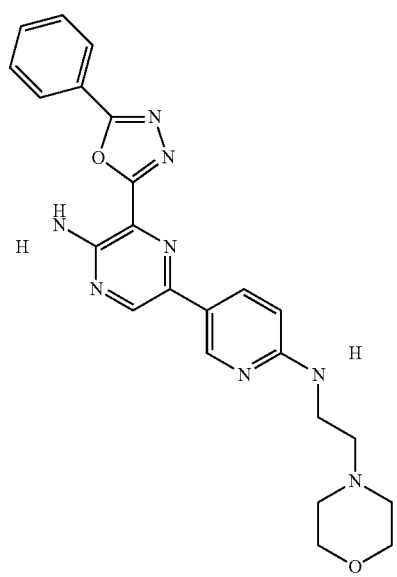
IA-72
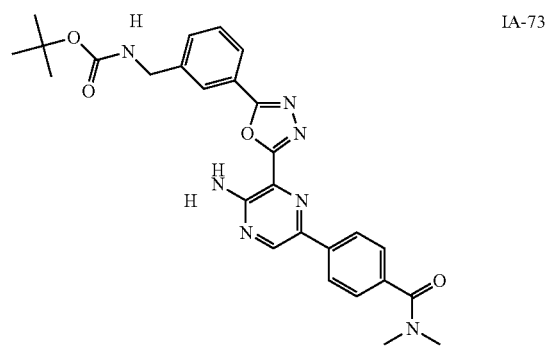
IA-73

TABLE IA-3-continued
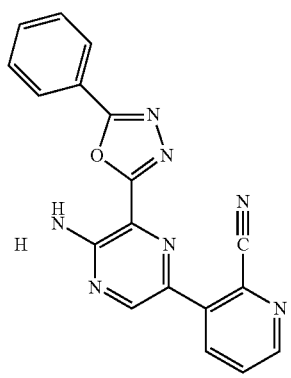
IA-74
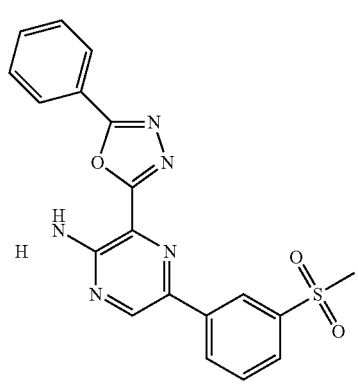
IA-75
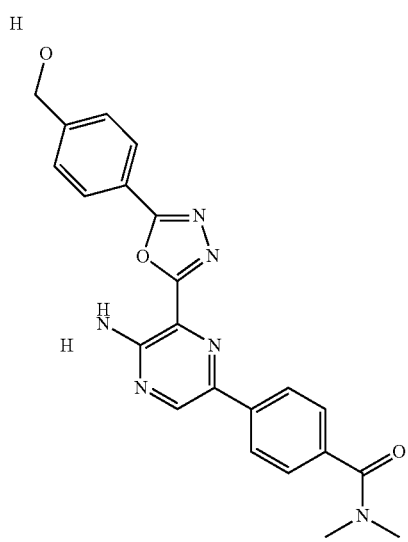
IA-76
TABLE IA-3-continued
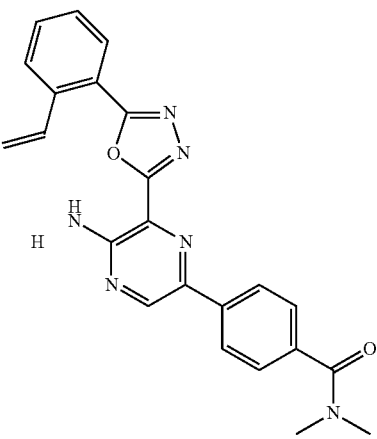
IA-77
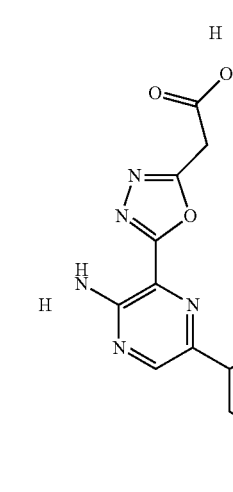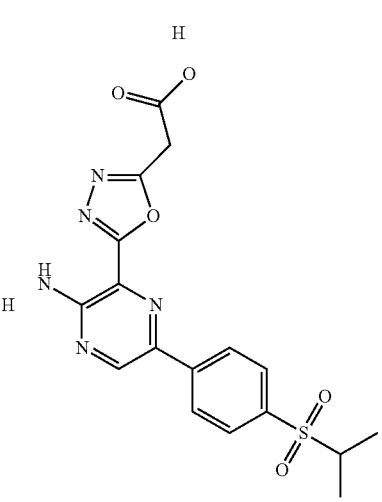
IA-78
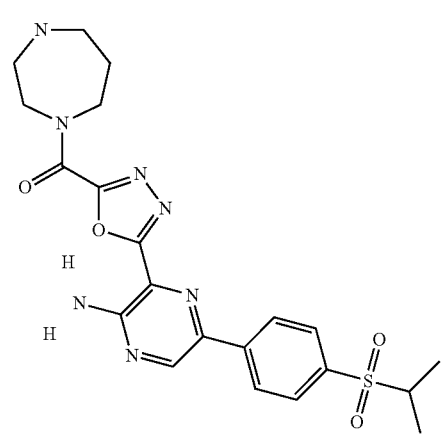
IA-79

TABLE IA-3-continued
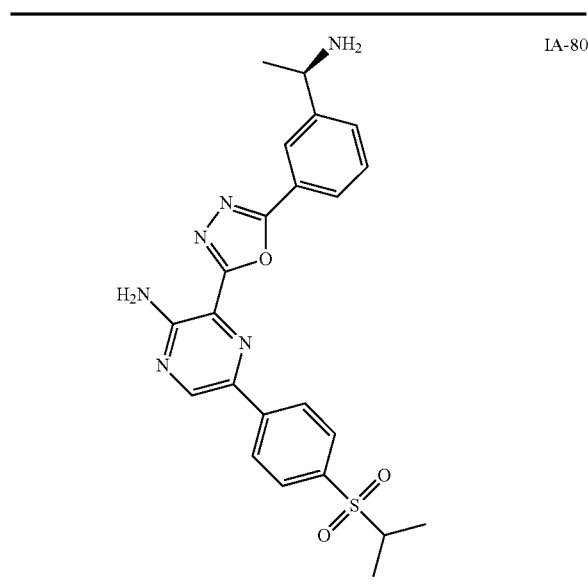
IA-80
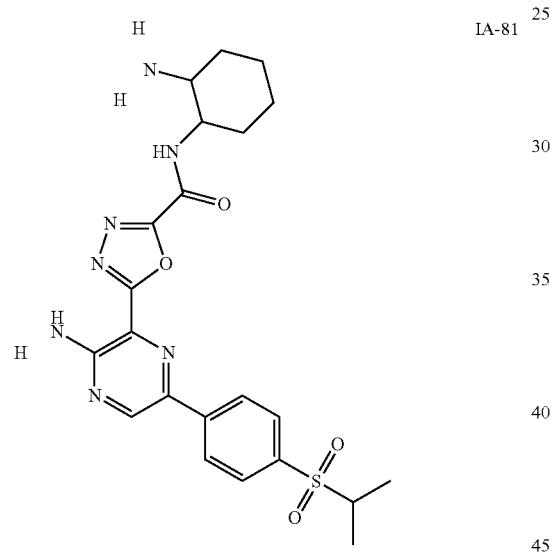
IA-81
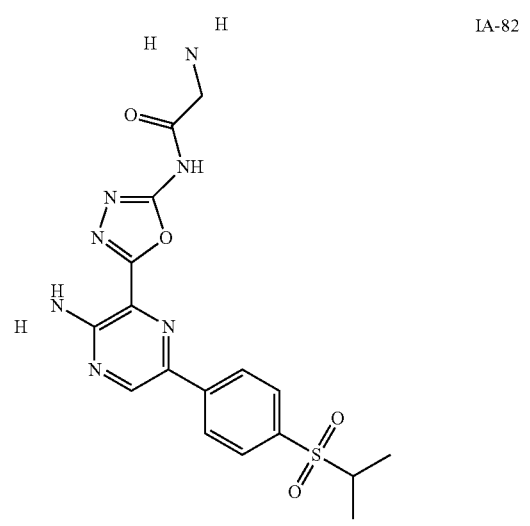
IA-82
TABLE IA-3-continued
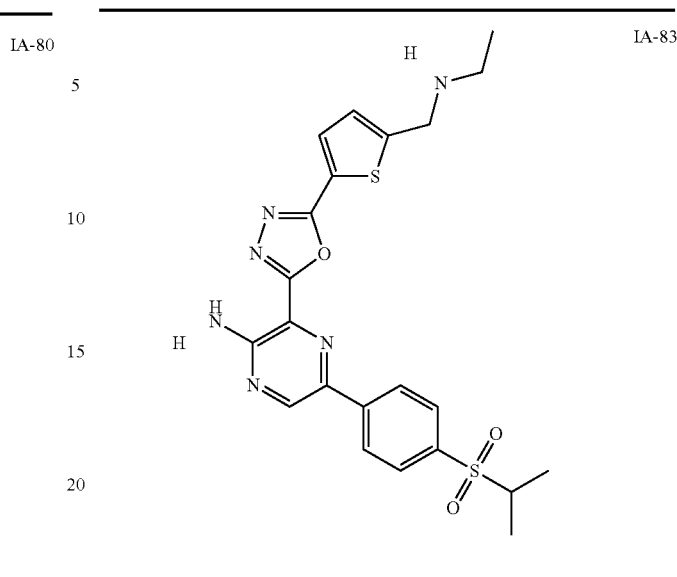
IA-83
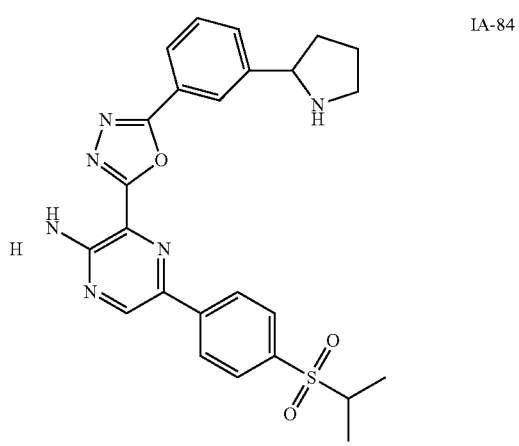
IA-84
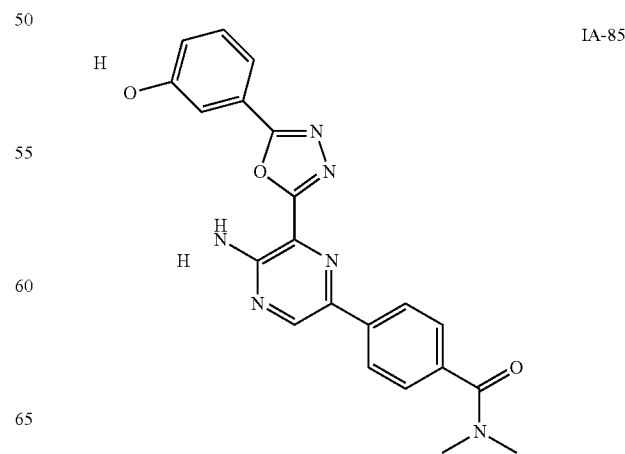
IA-85

TABLE IA-3-continued
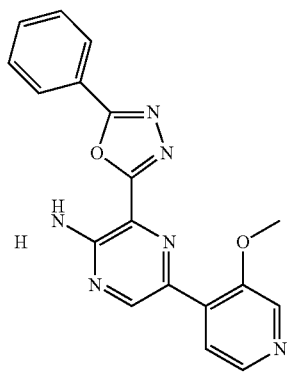
IA-86
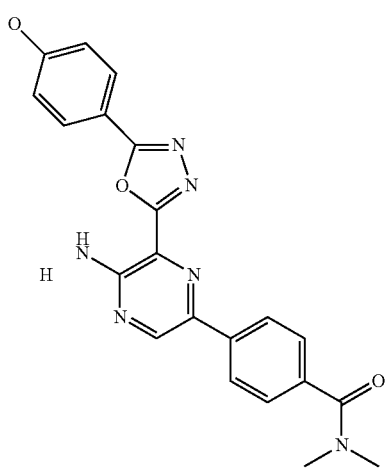
IA-87
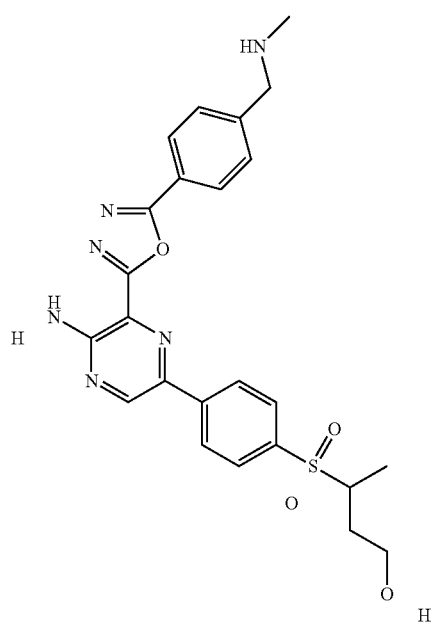
IA-88
TABLE IA-3-continued
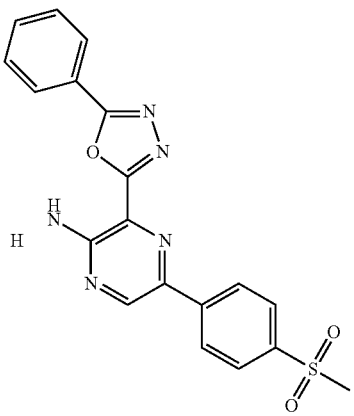
IA-89
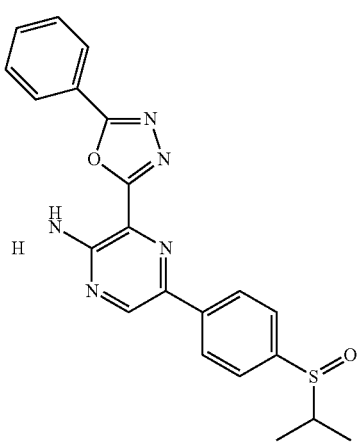
IA-90
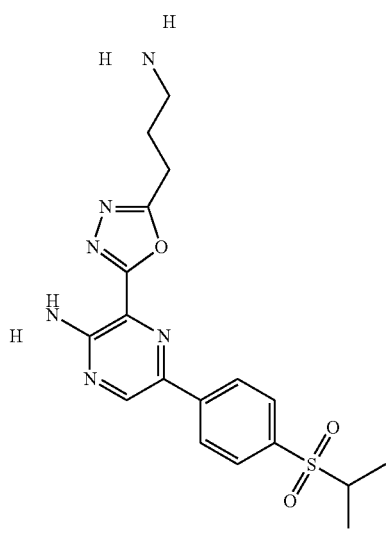
IA-91

TABLE IA-3-continued
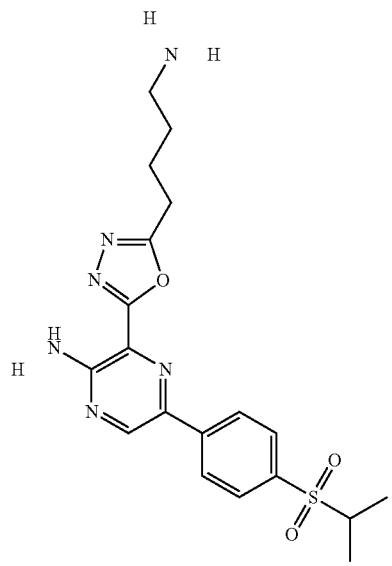
IA-92
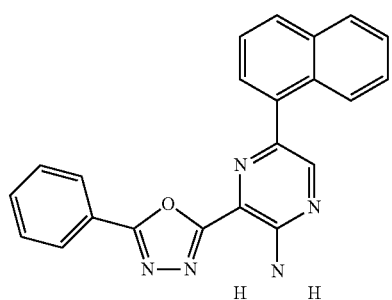
IA-93
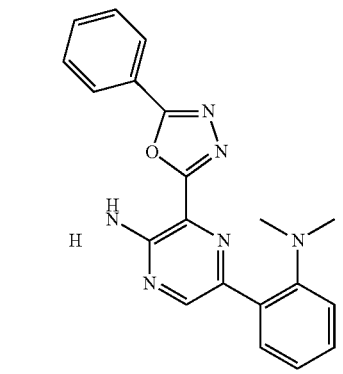
IA-94
TABLE IA-3-continued
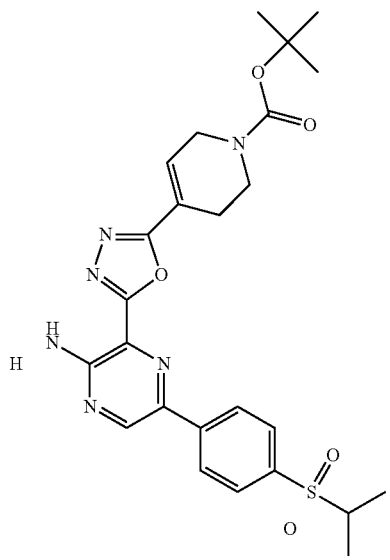
IA-95
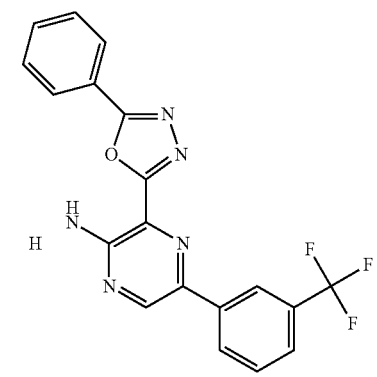
IA-96
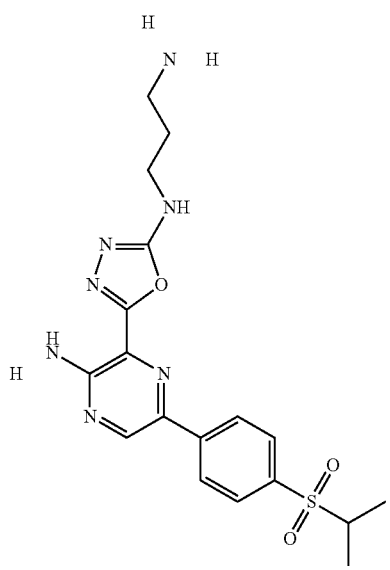
IA-97

TABLE IA-3-continued
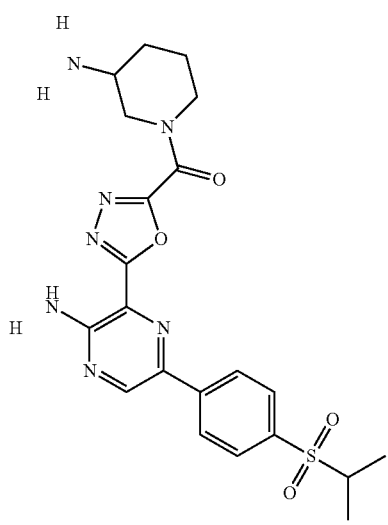
IA-98
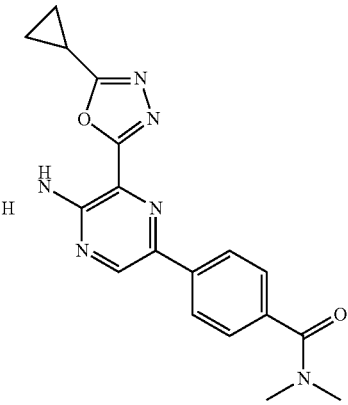
IA-101
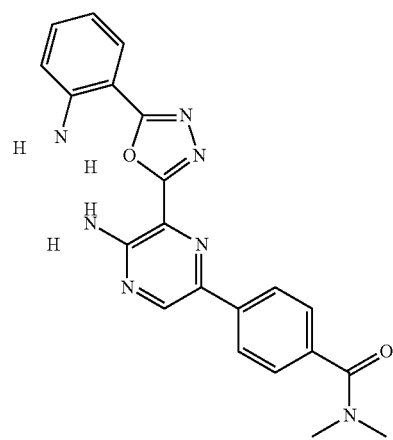
IA-99
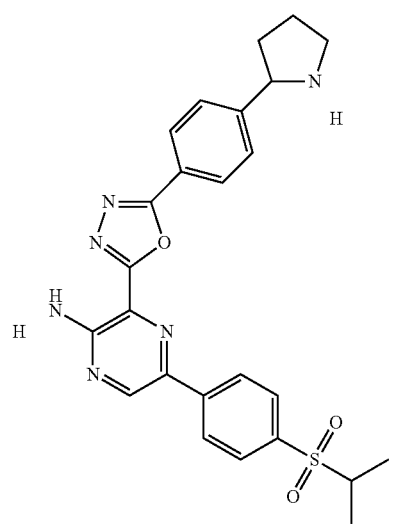
IA-102
IA-100
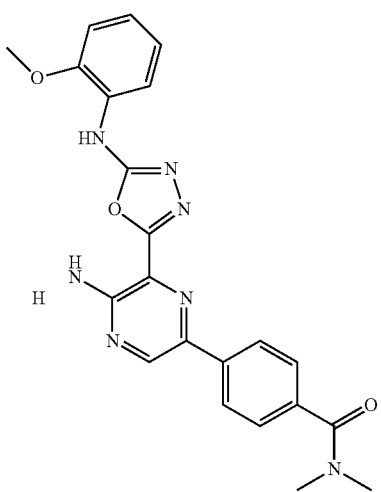
IA-103

TABLE IA-3-continued
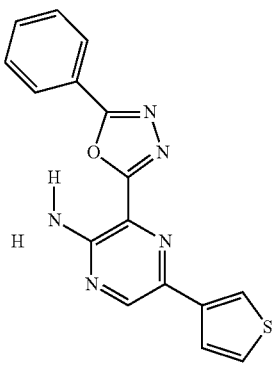
IA-104
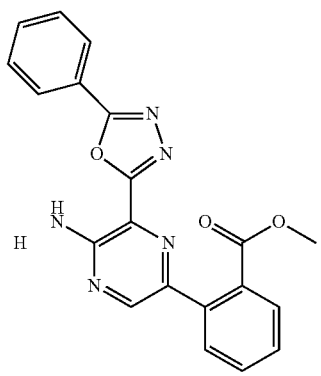
IA-105
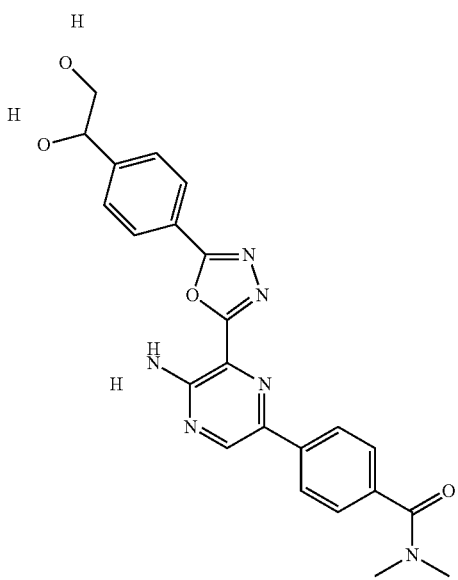
IA-106
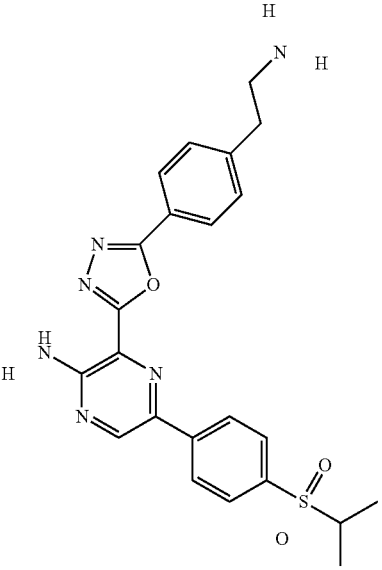
IA-107
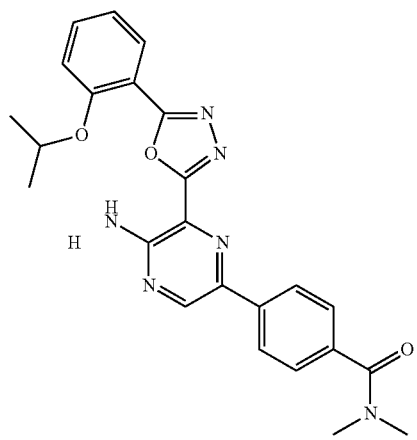
IA-108
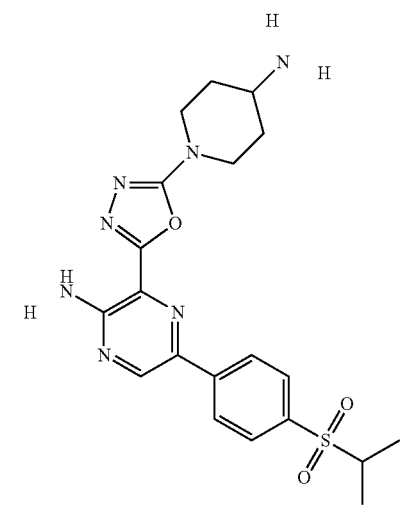
IA-109

TABLE IA-3-continued
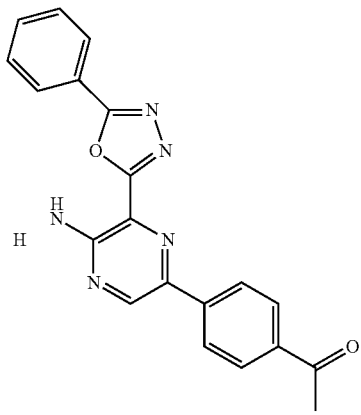
IA-110
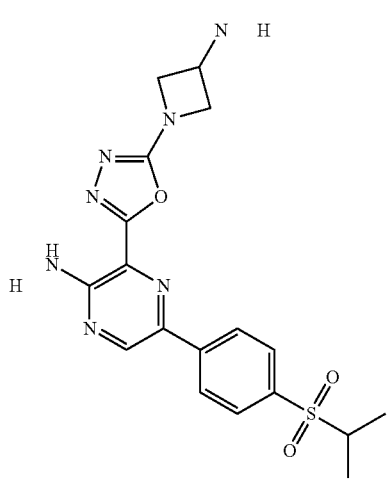
IA-111
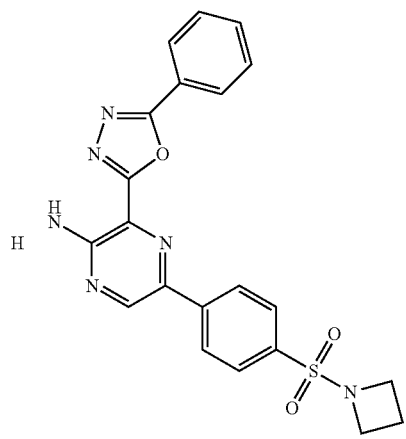
IA-112
TABLE IA-3-continued
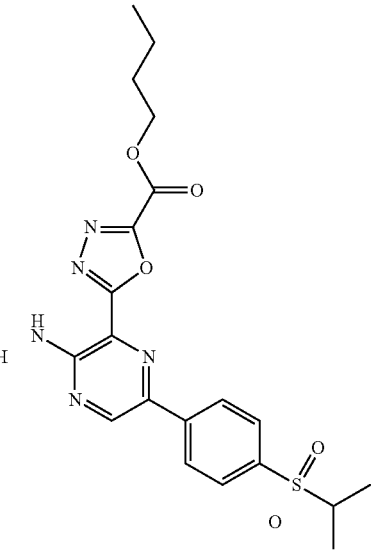
IA-113
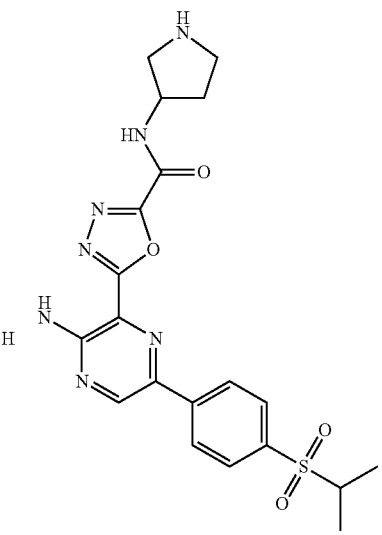
IA-114
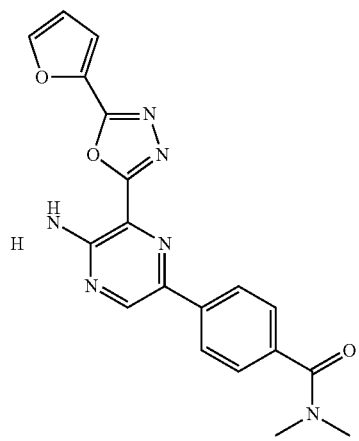
IA-115

TABLE IA-3-continued
IA-116
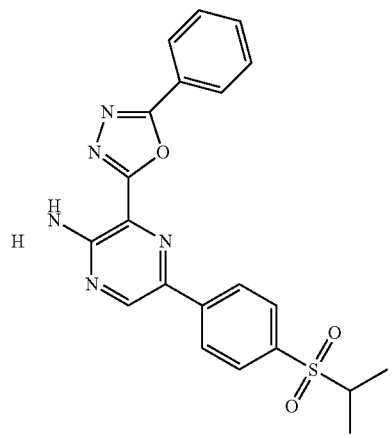
IA-117
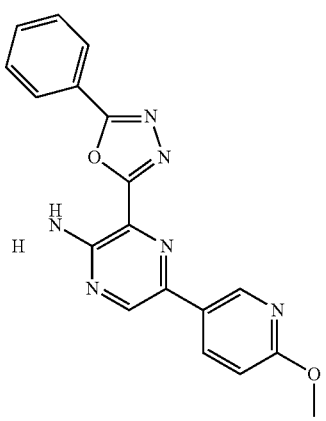
IA-118
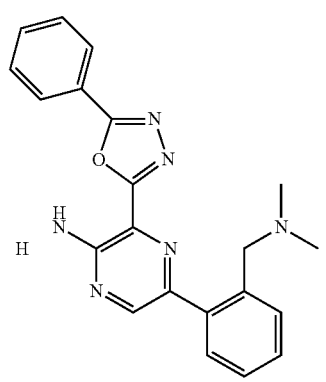
TABLE IA-3-continued
IA-119
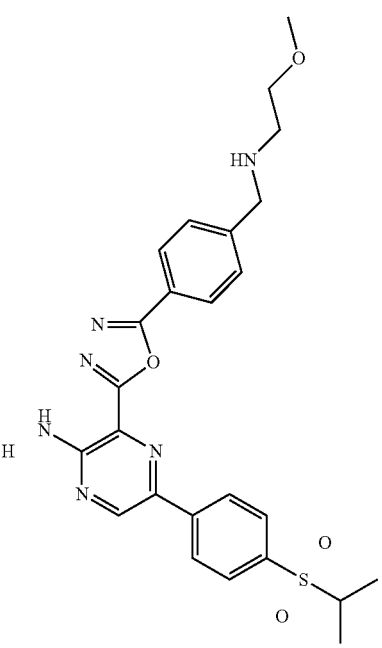
IA-120
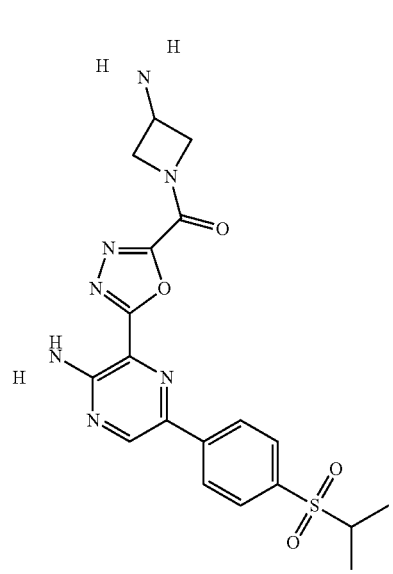
IA-121
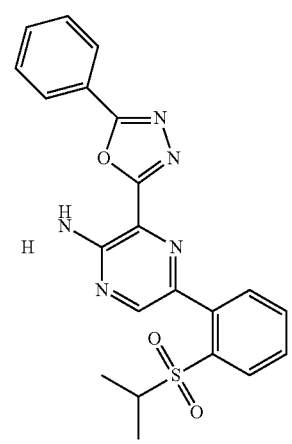

TABLE IA-3-continued
IA-122
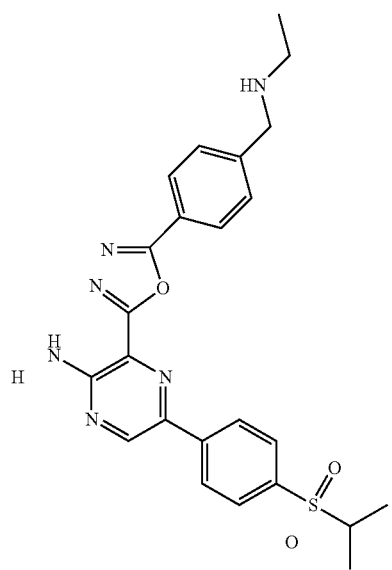
IA-123
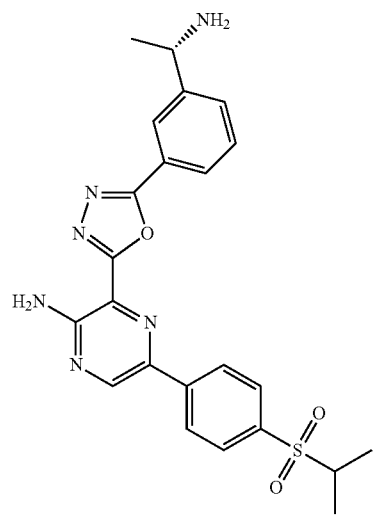 [SMILES: CC(C)S(=O)(=O)c1ccc(-c2cnc(N)c(-c3nnc(-c4cccc([C@H](C)N)c4)o3)n2)cc1]
IA-124
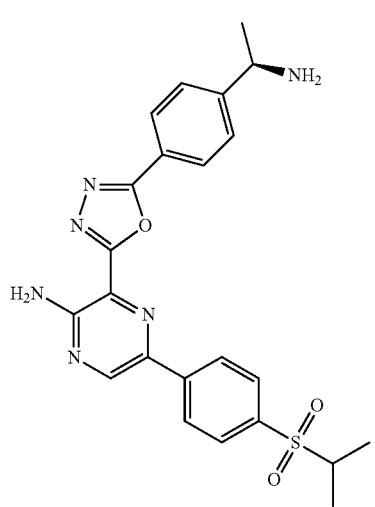 [SMILES: CC(C)S(=O)(=O)c1ccc(-c2cnc(N)c(-c3nnc(-c4ccc([C@@H](C)N)cc4)o3)n2)cc1]
TABLE IA-3-continued
IA-125
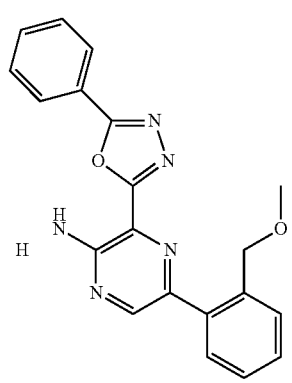
IA-126
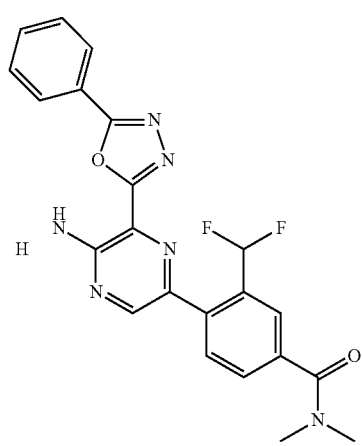
IA-127
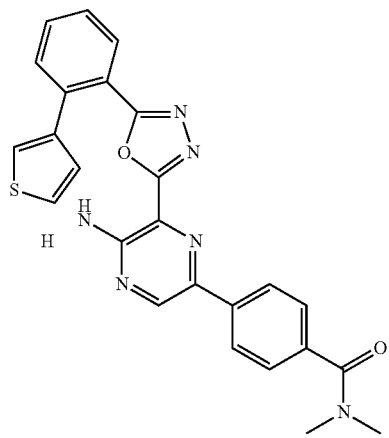

TABLE IA-3-continued
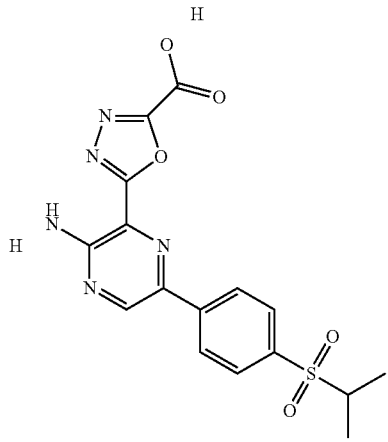
IA-128
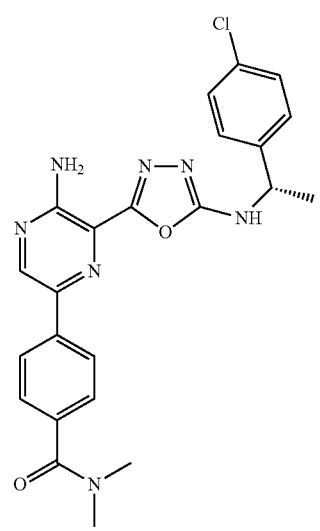 [SMILES: C[C@H](Nc1nnc(-c2nc(-c3ccc(C(=O)N(C)C)cc3)cnc2N)o1)c1ccc(Cl)cc1]
IA-129
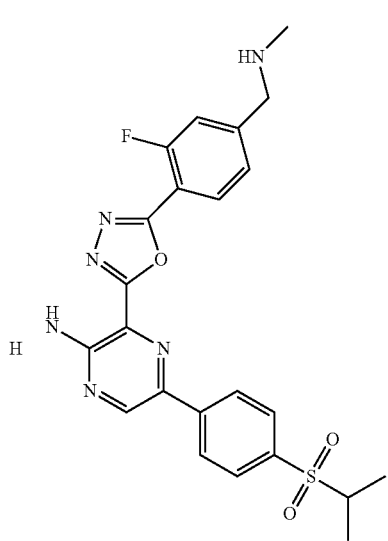
IA-130
TABLE IA-3-continued
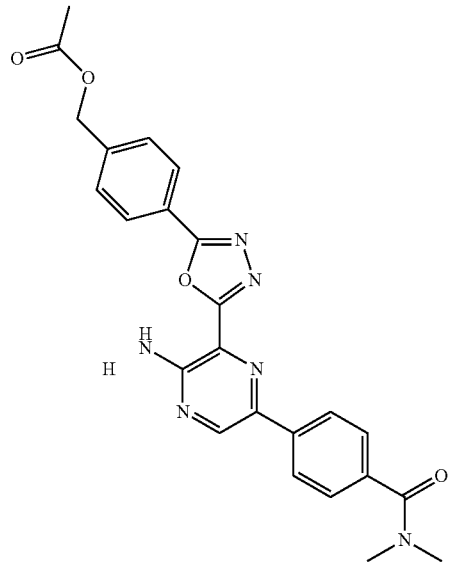
IA-131
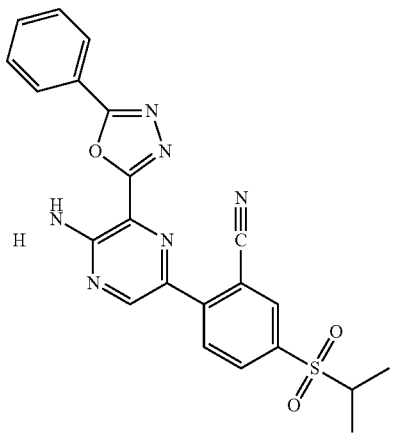
IA-132
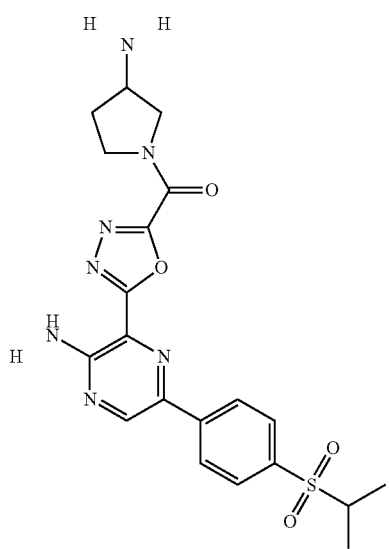
IA-133

TABLE IA-3-continued
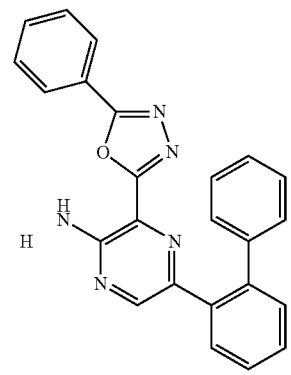
IA-134
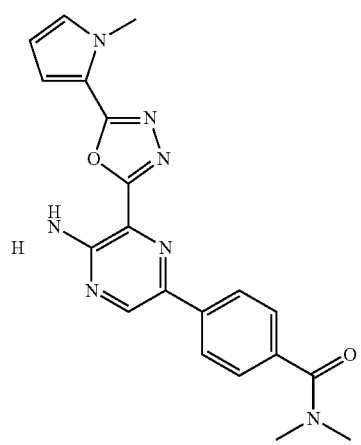
IA-135
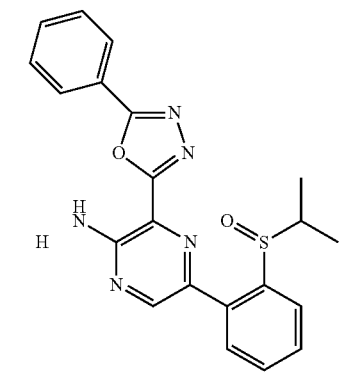
IA-136
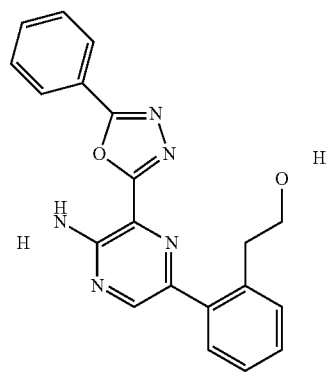
IA-137
TABLE IA-3-continued
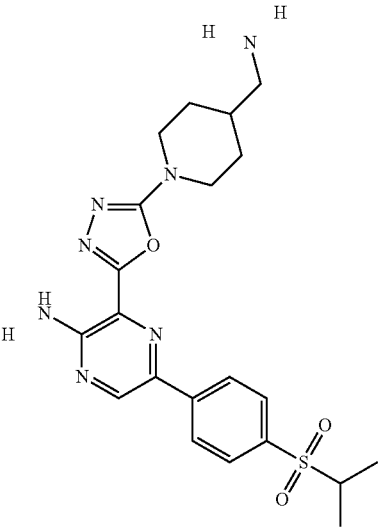
IA-138
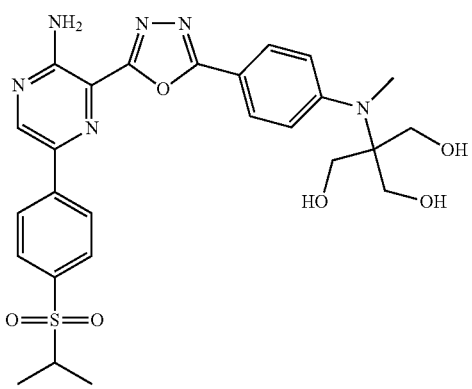 [SMILES: CC(C)S(=O)(=O)c1ccc(-c2cnc(N)c(-c3nnc(-c4ccc(N(C)C(CO)(CO)CO)cc4)o3)n2)cc1]
IA-139
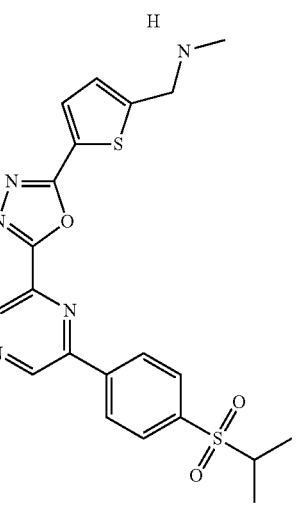
IA-140

TABLE IA-3-continued
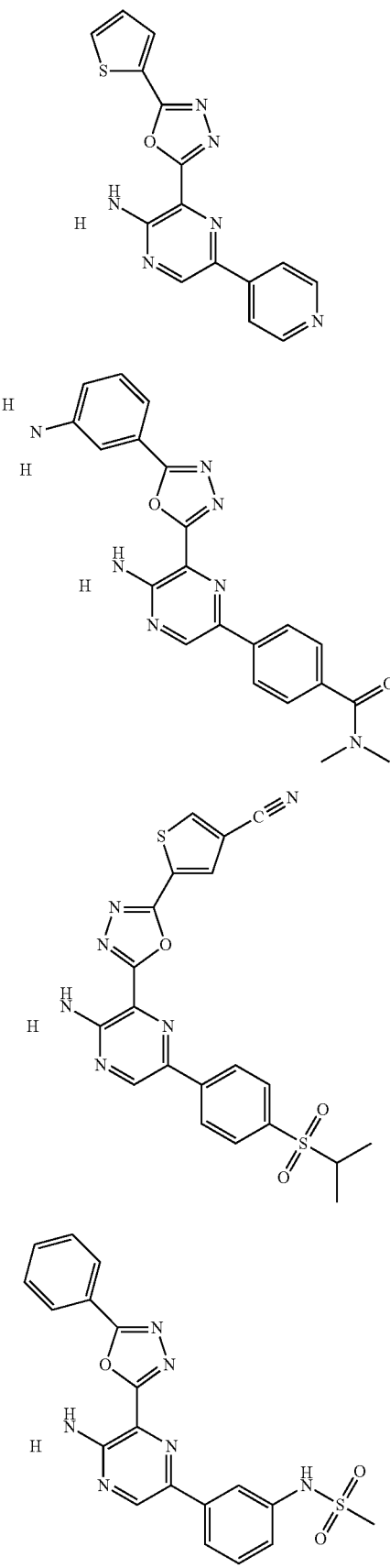
IA-141
IA-142
IA-143
IA-144
TABLE IA-3-continued
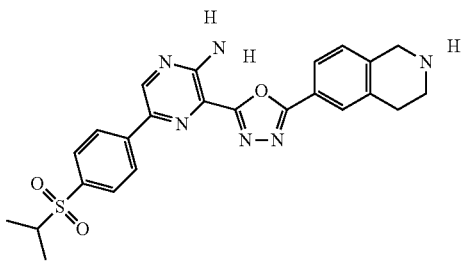
IA-145
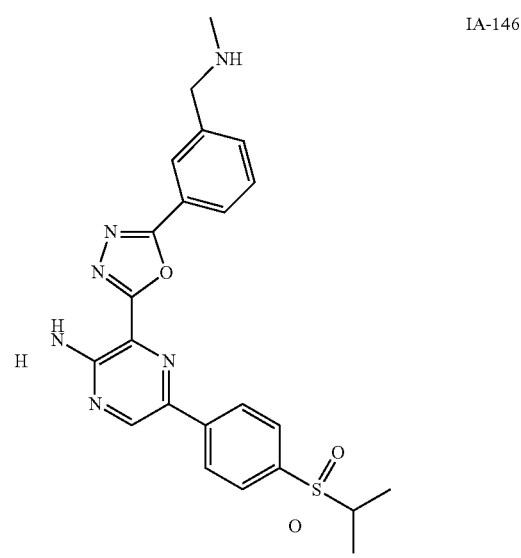
IA-146
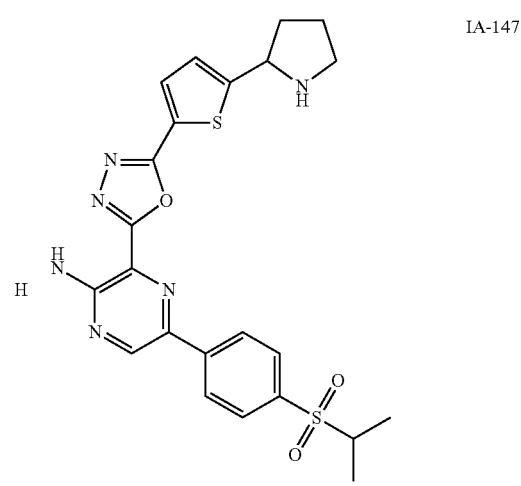
IA-147

TABLE IA-3-continued
IA-148
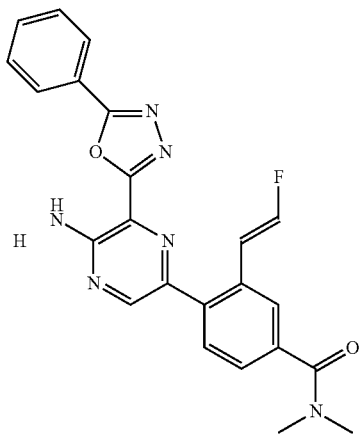
IA-149
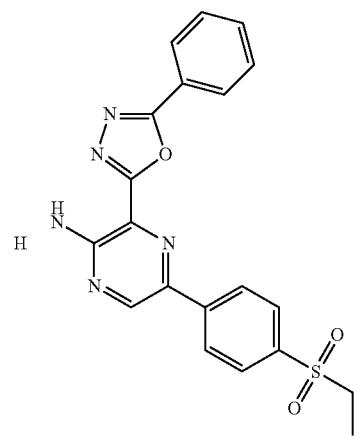
IA-150
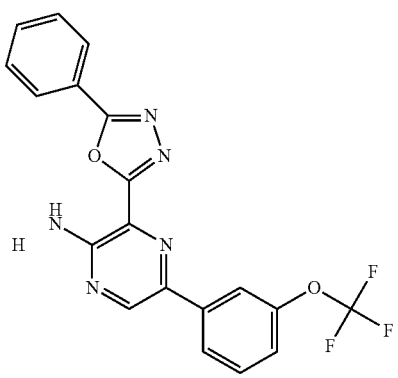
TABLE IA-3-continued
IA-151
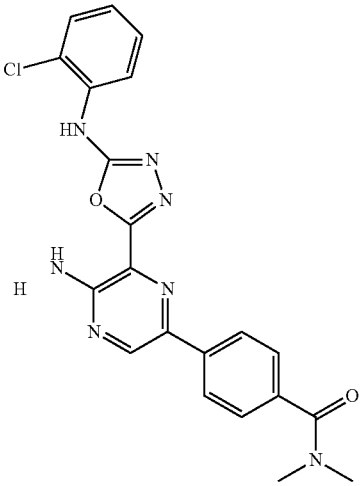
IA-152
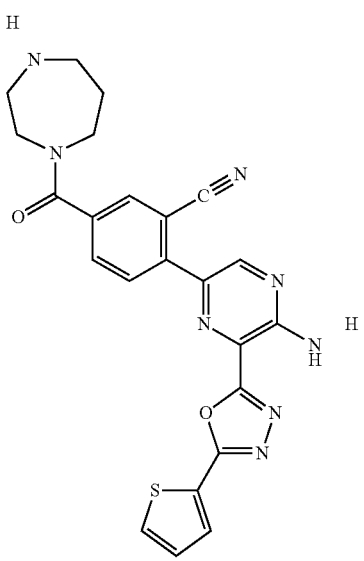
IA-153
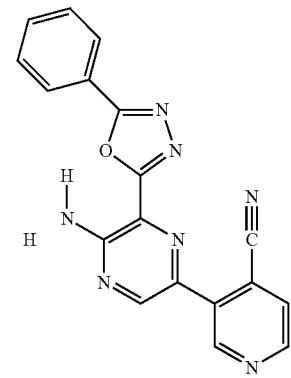

TABLE IA-3-continued
IA-154
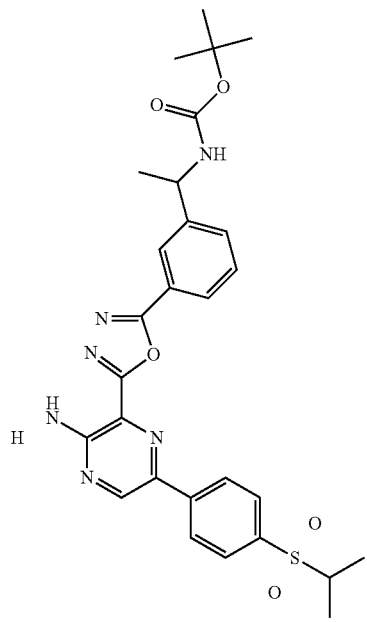
IA-155
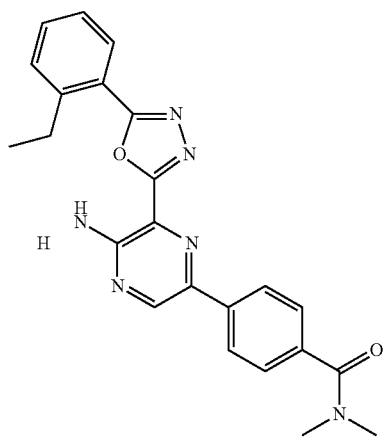
IA-156
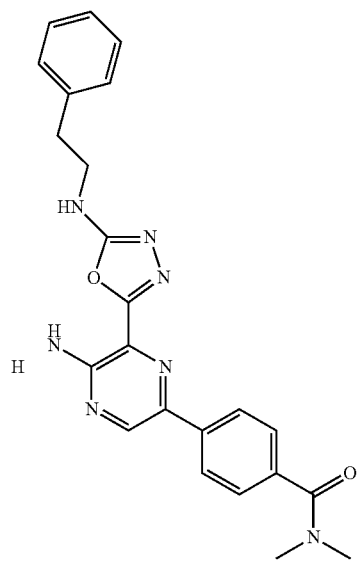
TABLE IA-3-continued
IA-157
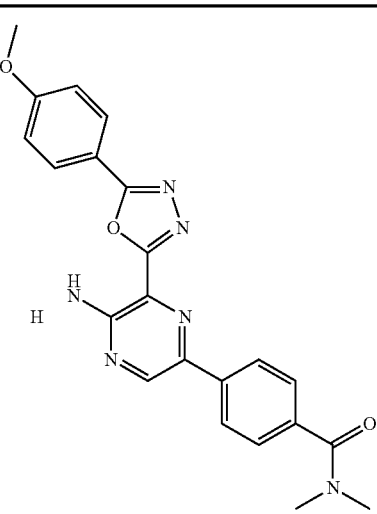
IA-158
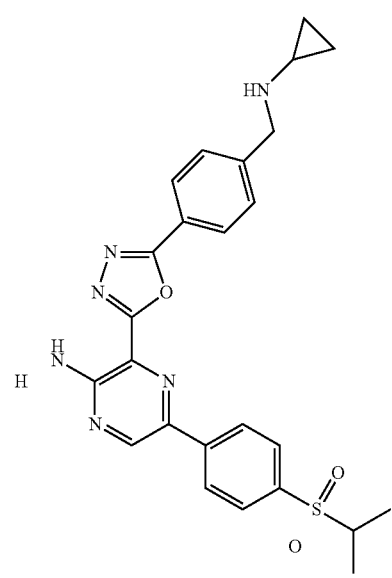
IA-159
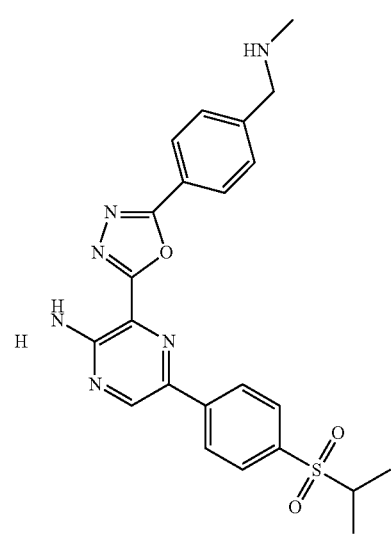

TABLE IA-3-continued
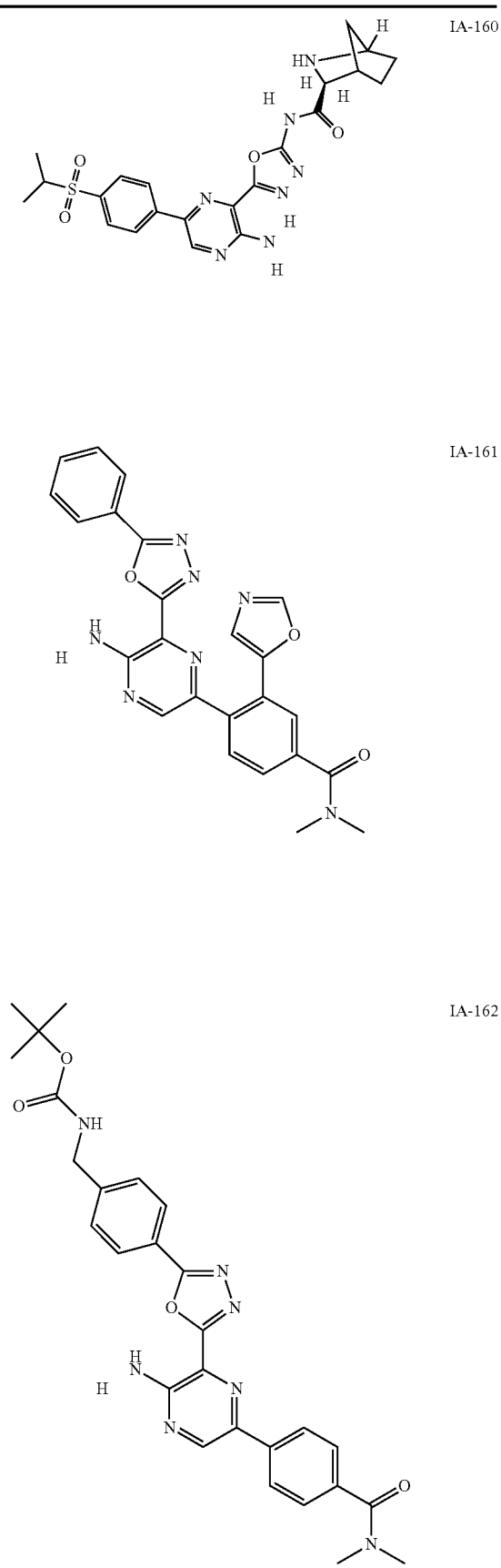
IA-160
IA-161
IA-162
TABLE IA-3-continued
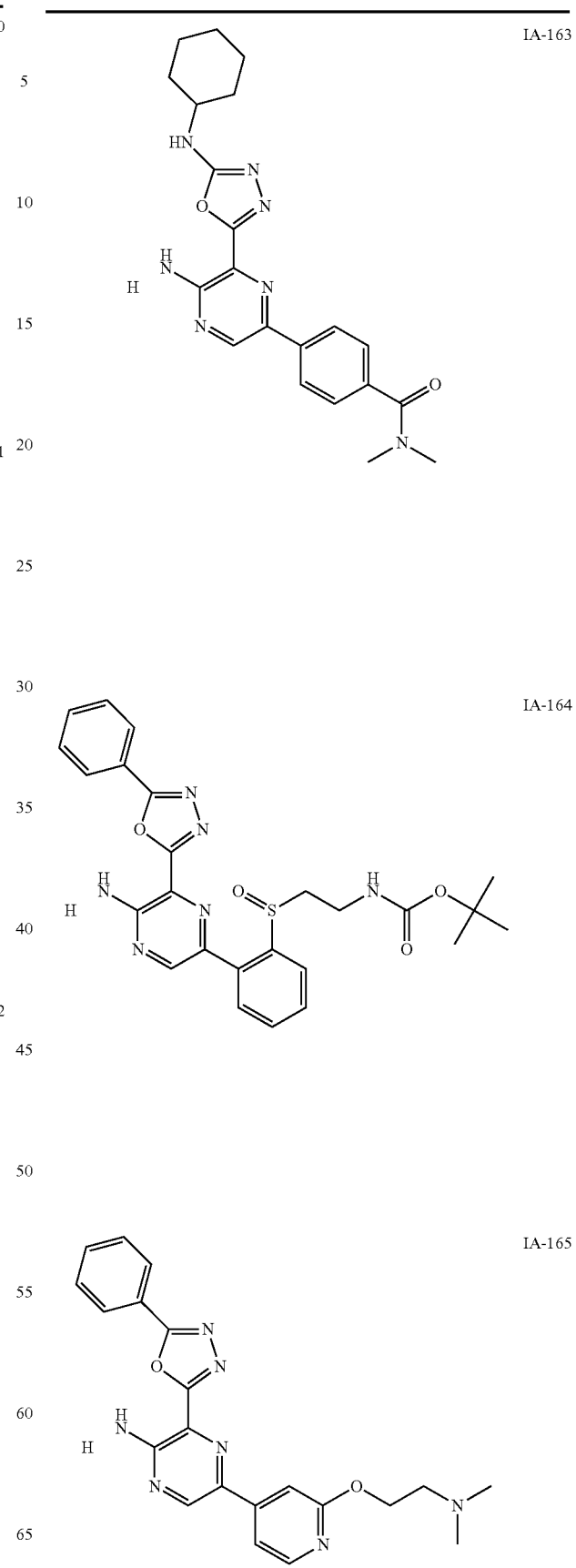
IA-163
IA-164
IA-165

TABLE IA-3-continued
IA-166
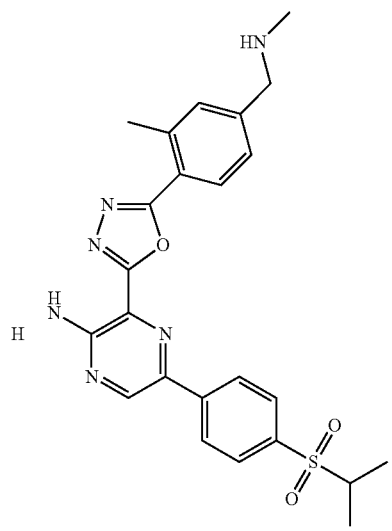
IA-167
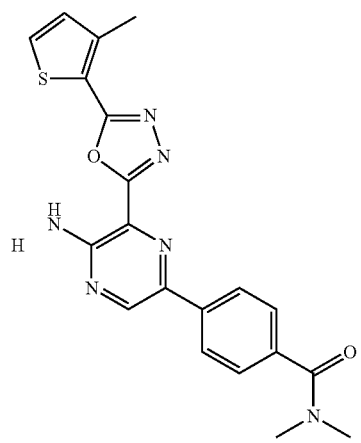
IA-168
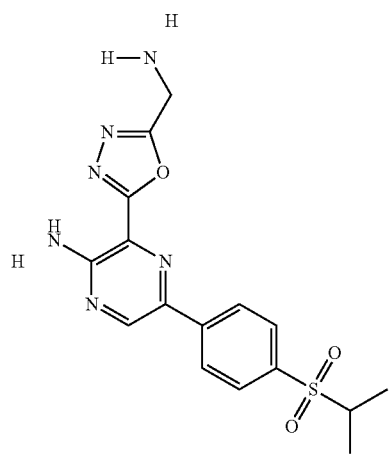
TABLE IA-3-continued
IA-169
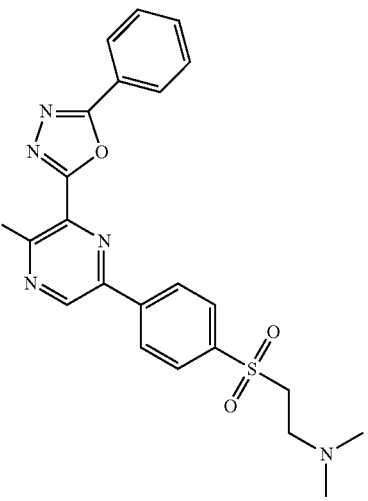
IA-170
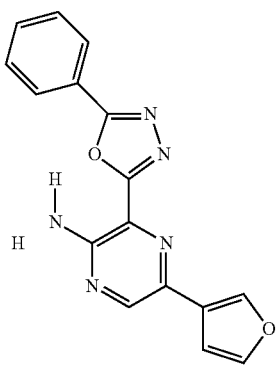
IA-171
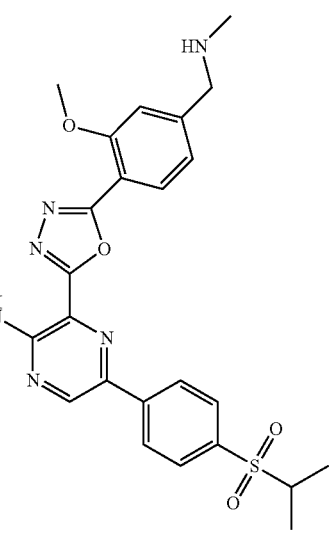

TABLE IA-3-continued
IA-172
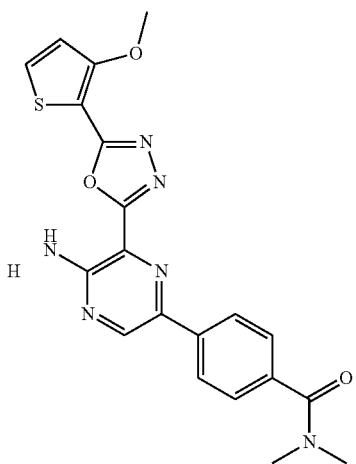
IA-173
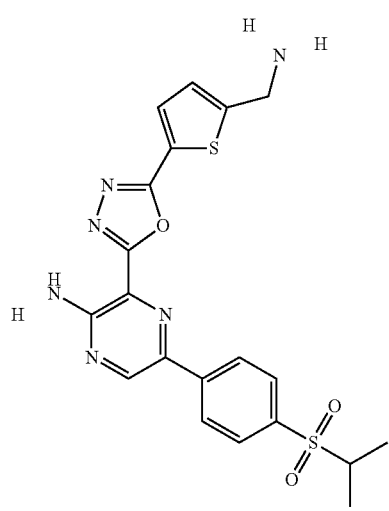
IA-174
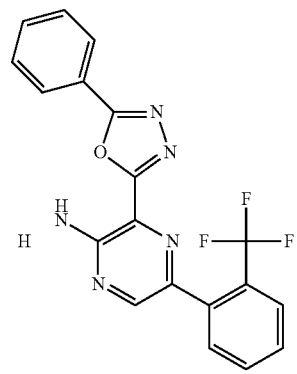
TABLE IA-3-continued
IA-175
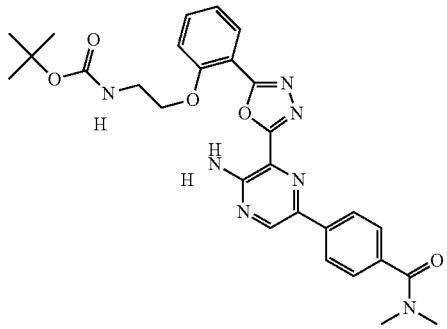
IA-176
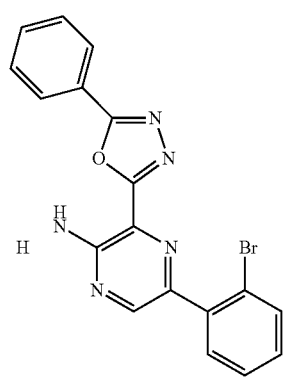
IA-177
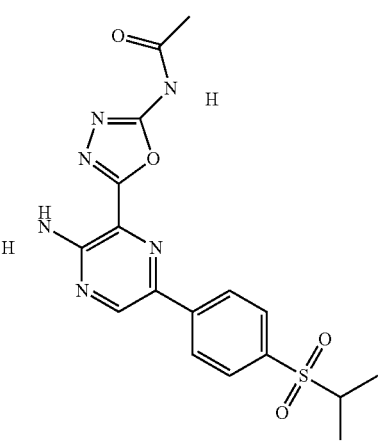

TABLE IA-3-continued
IA-178
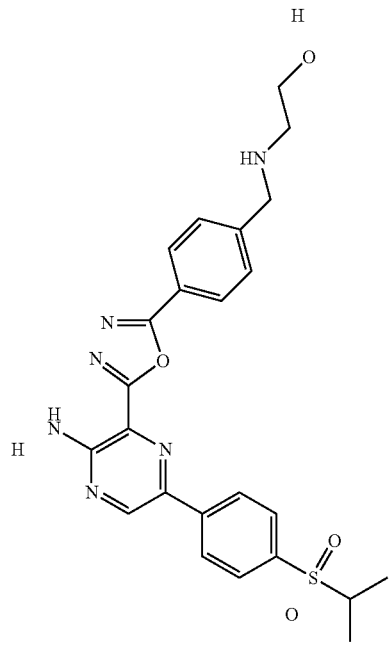
IA-181
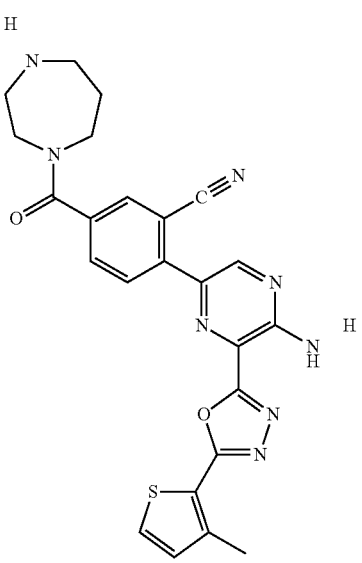
IA-179
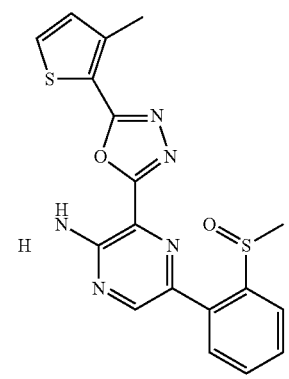
IA-182
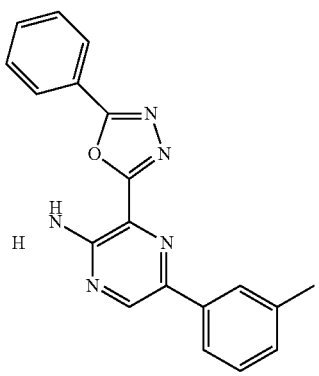
IA-180
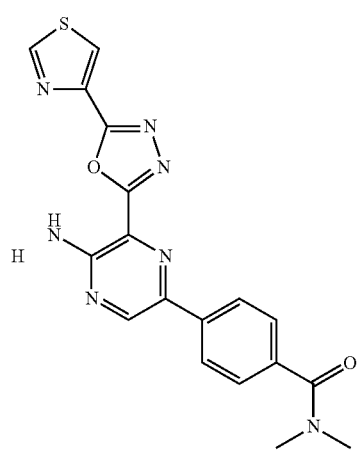
IA-183
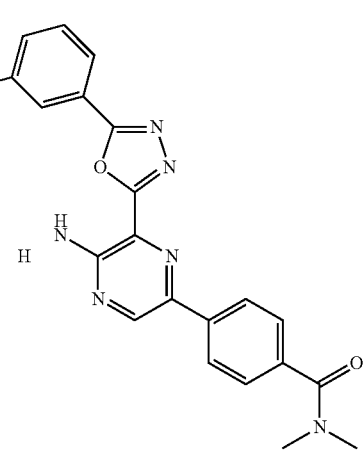

TABLE IA-3-continued
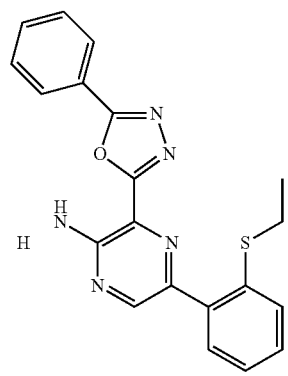
IA-184
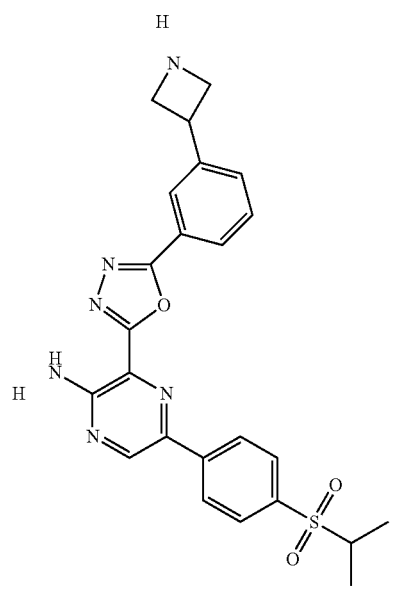
IA-185
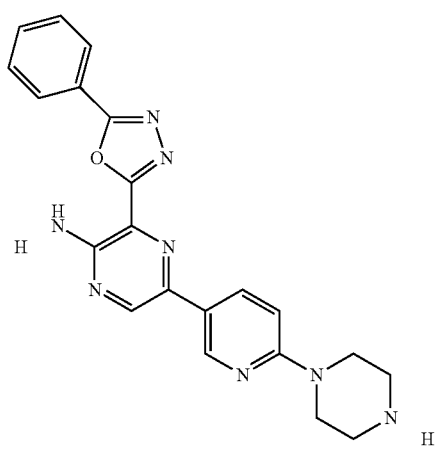
IA-186
TABLE IA-3-continued
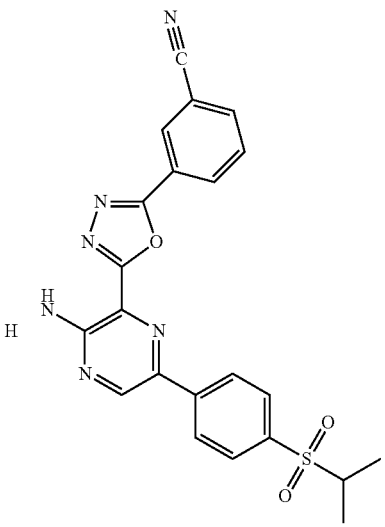
IA-187
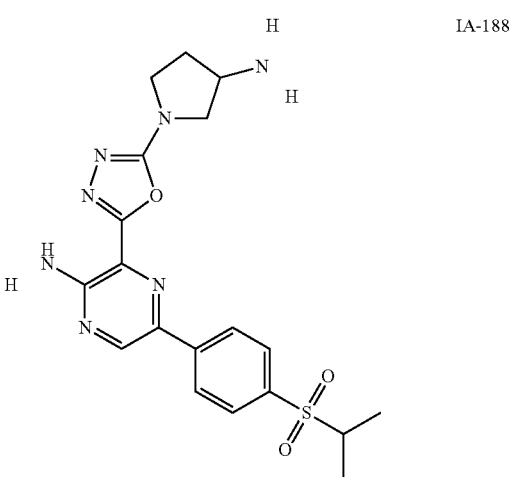
IA-188
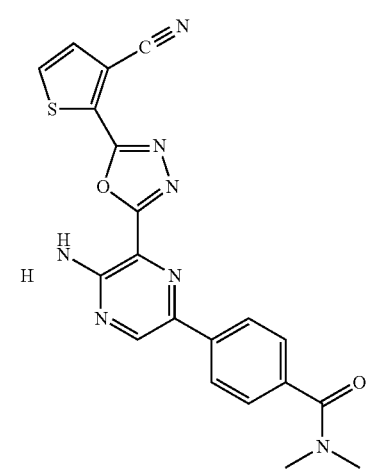
IA-189

TABLE IA-3-continued
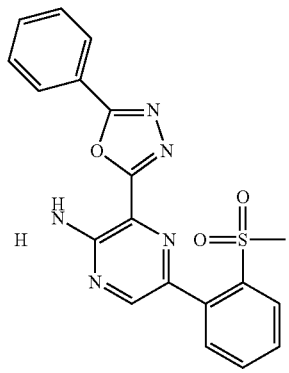
IA-190
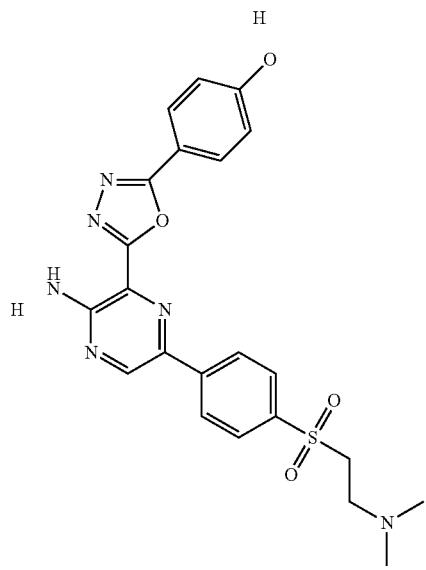
IA-191
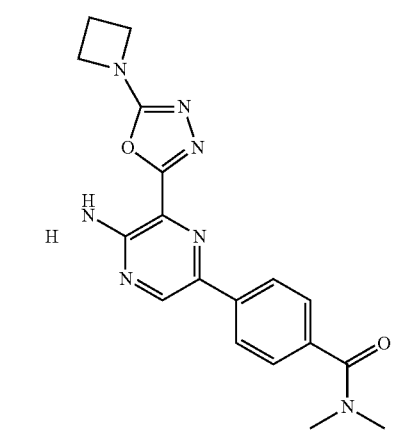
IA-192
TABLE IA-3-continued
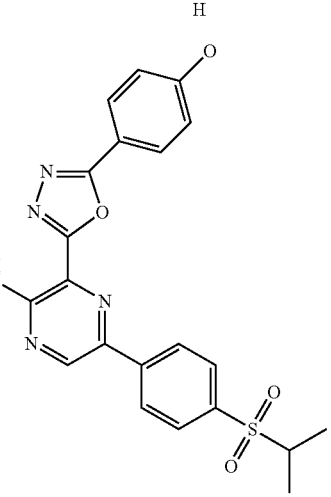
IA-193
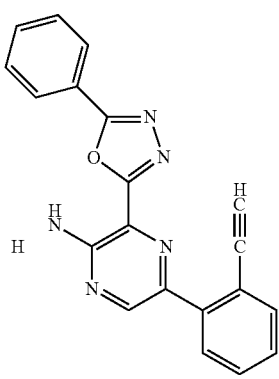
IA-194
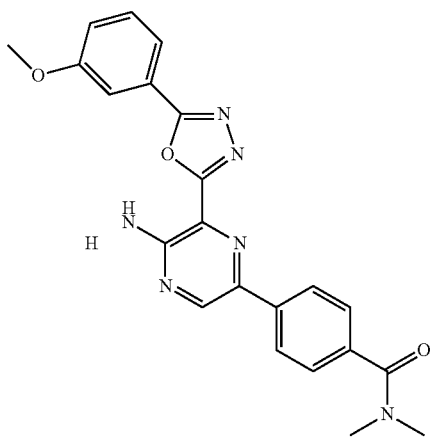
IA-195

TABLE IA-3-continued
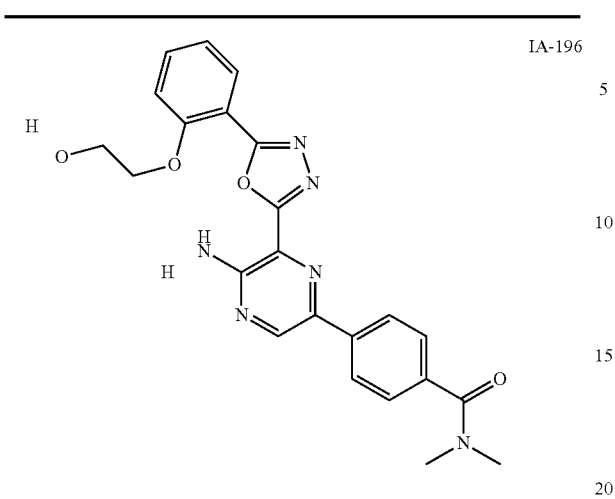
IA-196
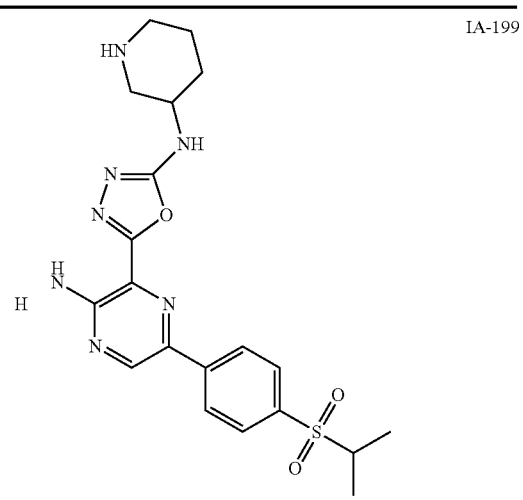
IA-199
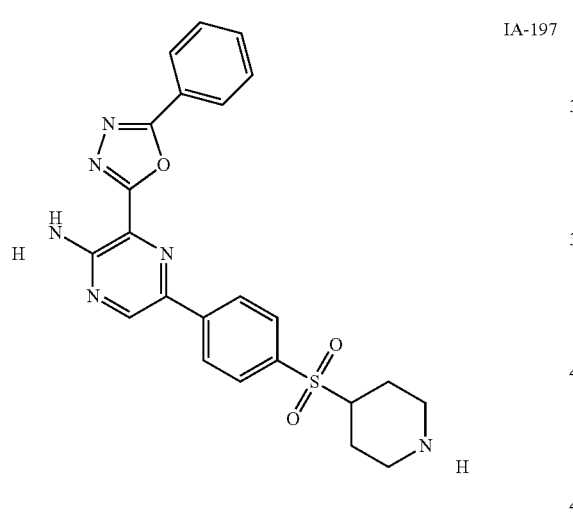
IA-197
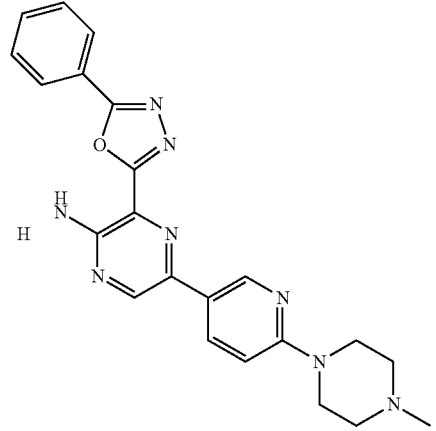
IA-200
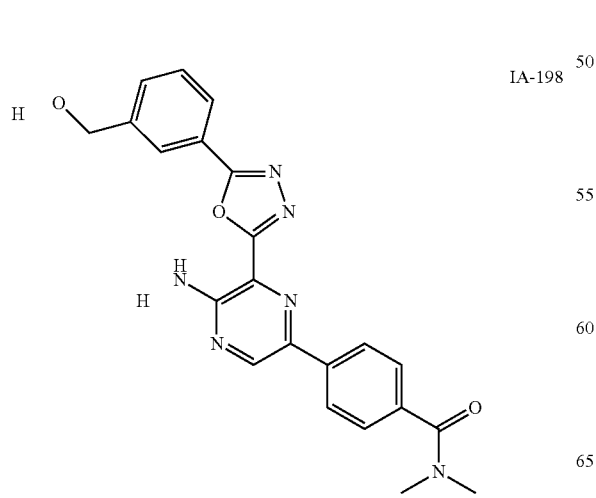
IA-198
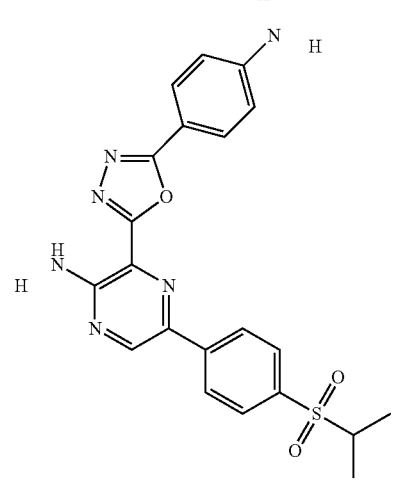
IA-201

TABLE IA-3-continued
IA-202
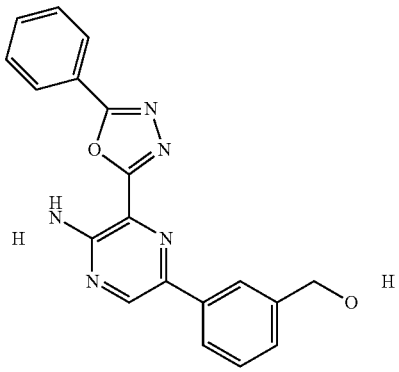
IA-203
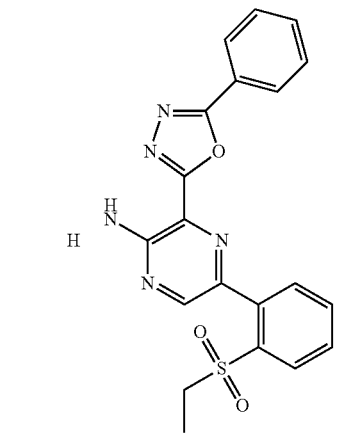
IA-204
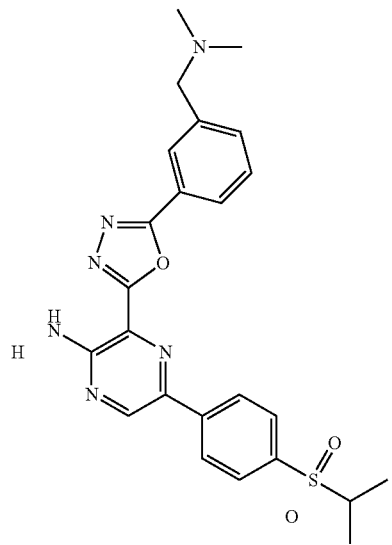
TABLE IA-3-continued
IA-205
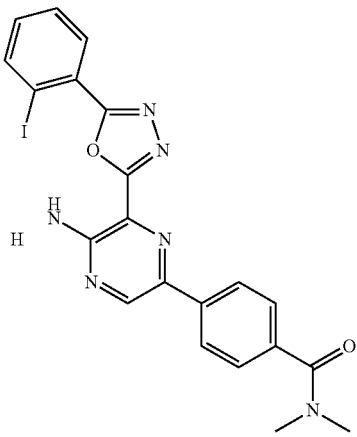
IA-206
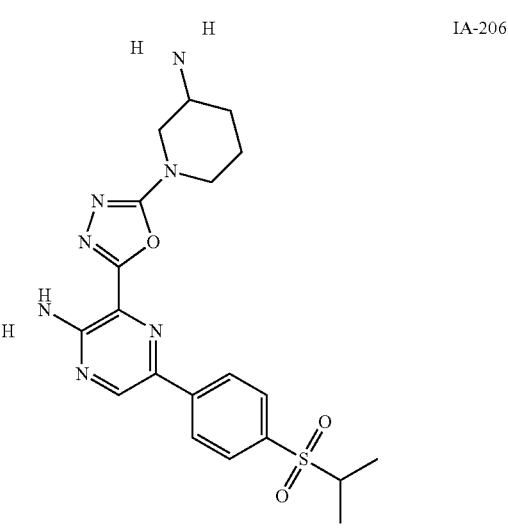
IA-207
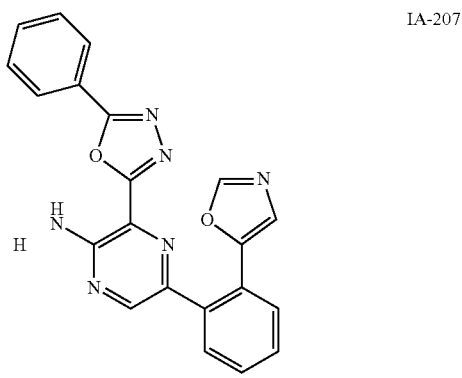

TABLE IA-3-continued
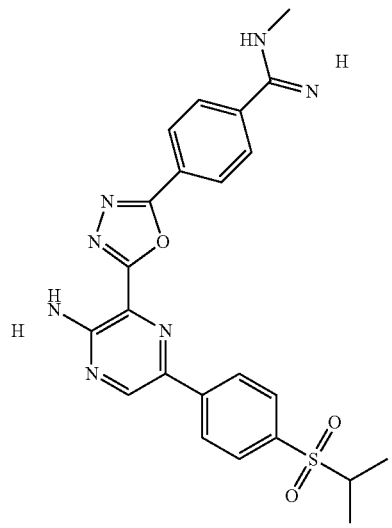
IA-208
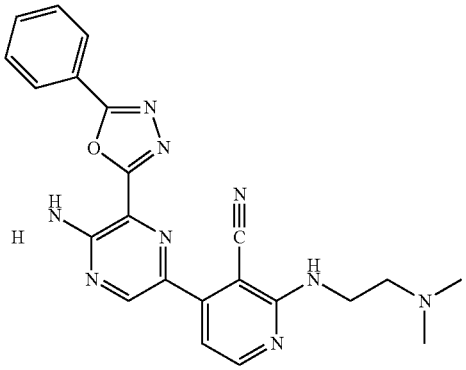
IA-209
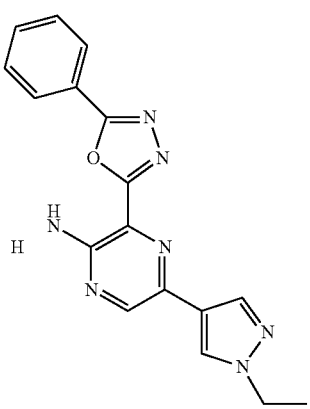
IA-210
TABLE IA-3-continued
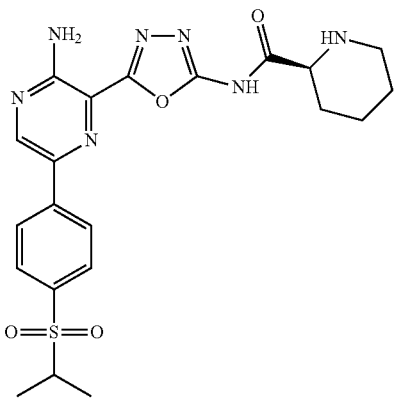 [SMILES: CC(C)S(=O)(=O)c1ccc(-c2cnc(N)c(-c3nnc(NC(=O)[C@@H]4CCCCN4)o3)n2)cc1]
IA-211
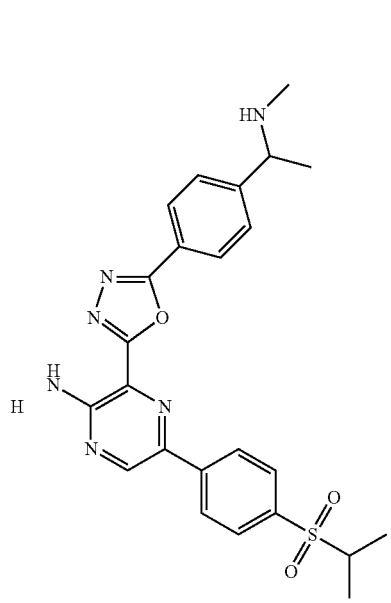
IA-212
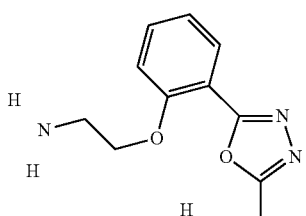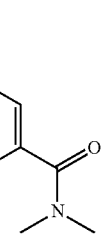
IA-213

TABLE IA-3-continued
IA-214
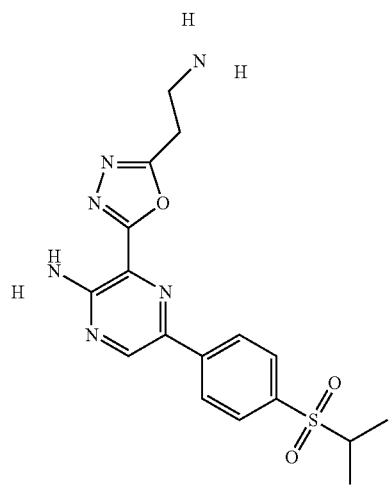
IA-215
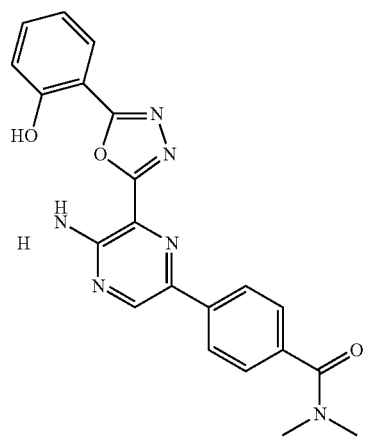
IA-216
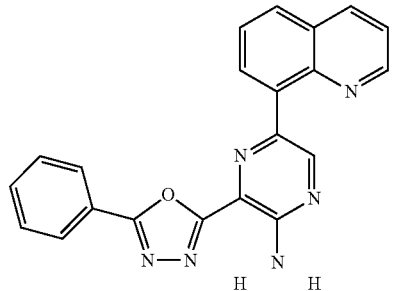
IA-217
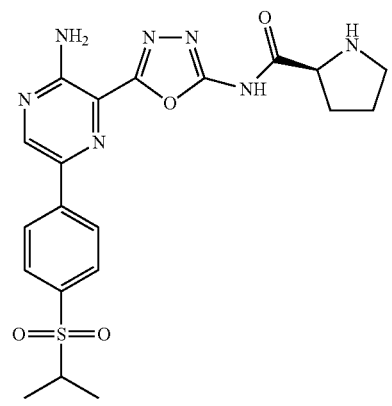 [SMILES: CC(C)S(=O)(=O)c1ccc(-c2cnc(N)c(-c3nnc(NC(=O)[C@@H]4CCCN4)o3)n2)cc1]
TABLE IA-3-continued
IA-218
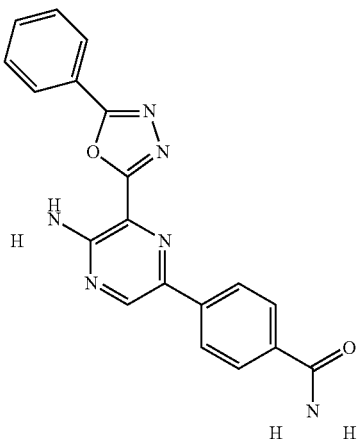
IA-219
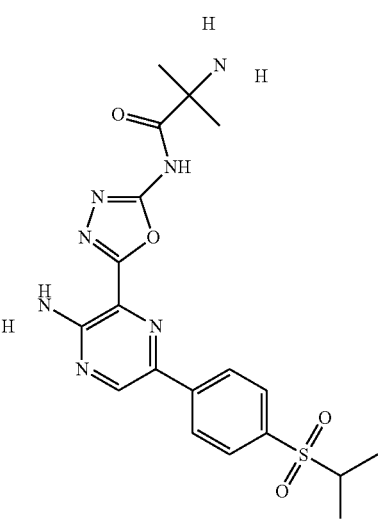
IA-220
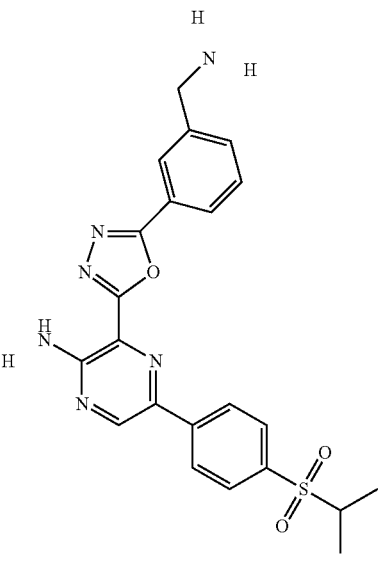

TABLE IA-3-continued
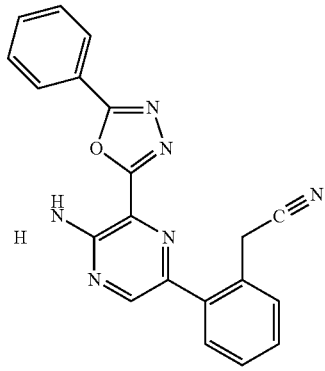
IA-221
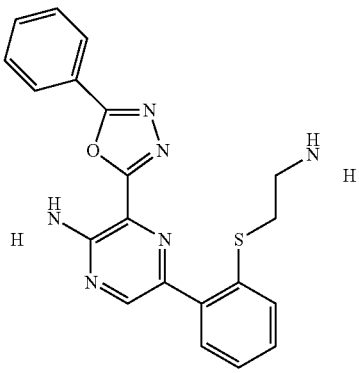
IA-224
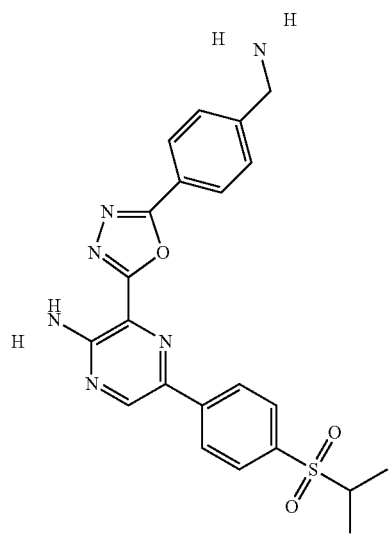
IA-222
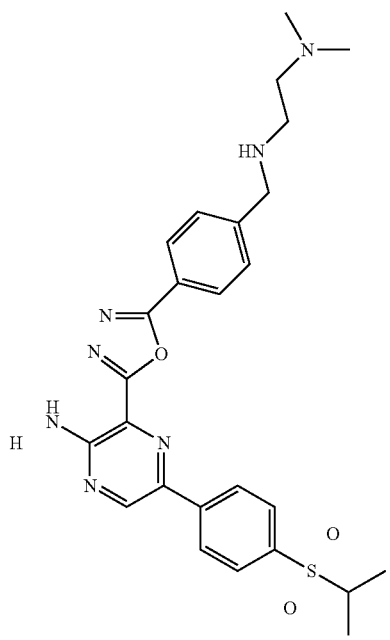
IA-225
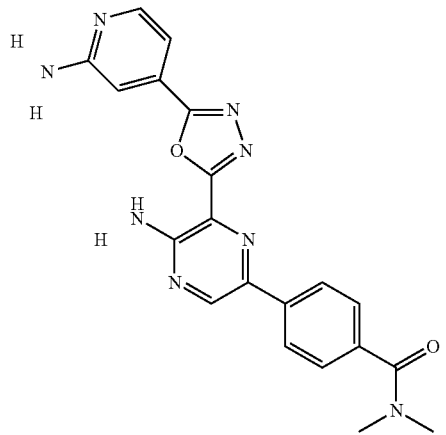
IA-223
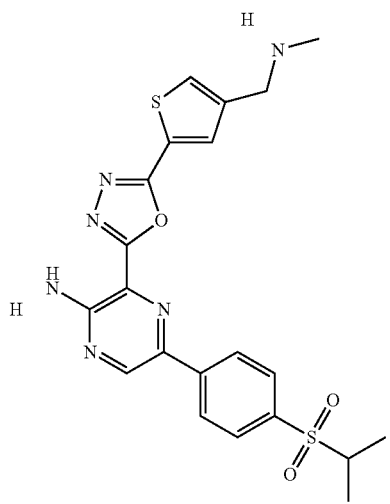
IA-226

TABLE IA-3-continued
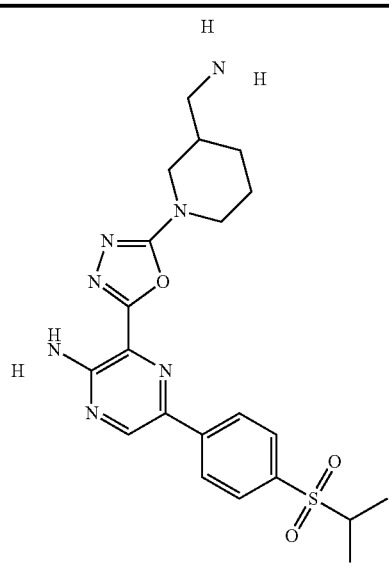
IA-227
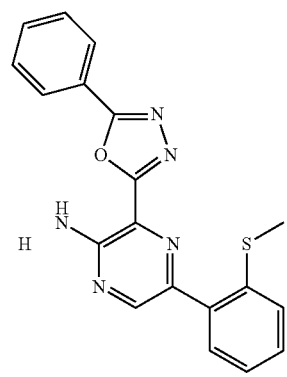
IA-230
IA-228
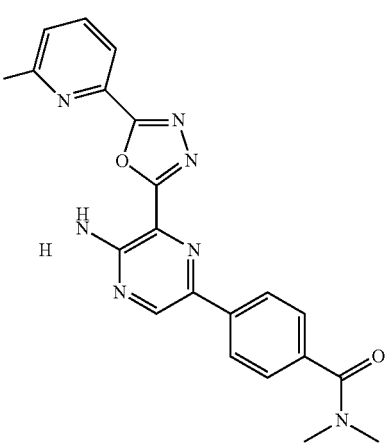
IA-231
IA-229
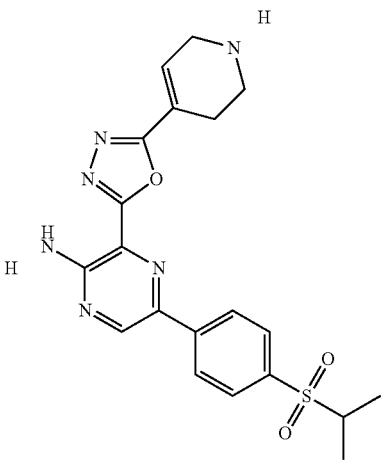
IA-232

TABLE IA-3-continued
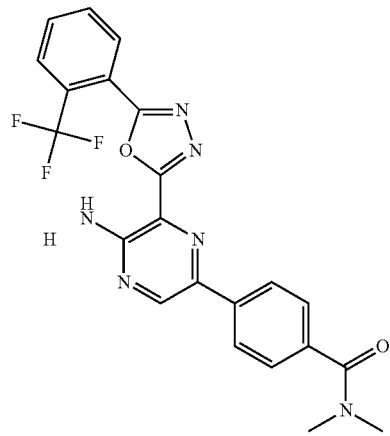
IA-233
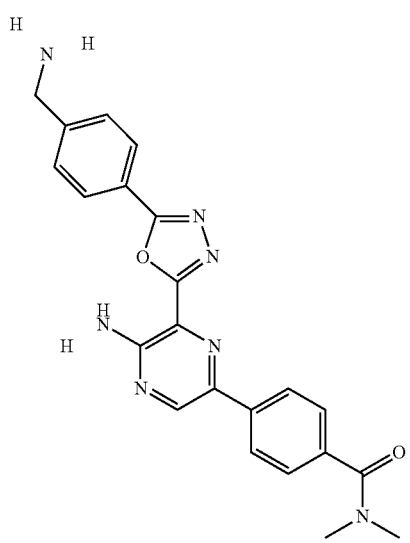
IA-234
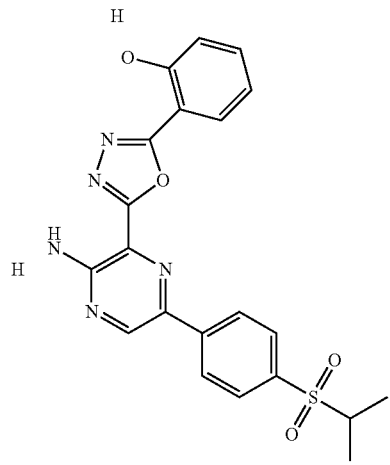
IA-235
TABLE IA-3-continued
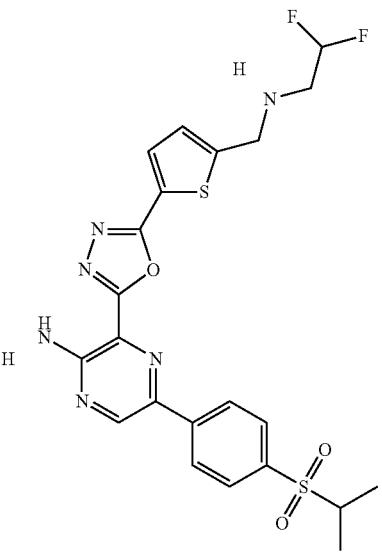
IA-236
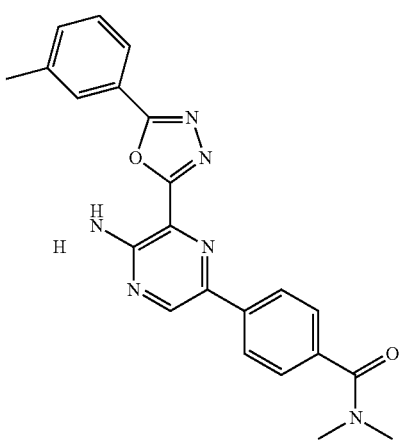
IA-237
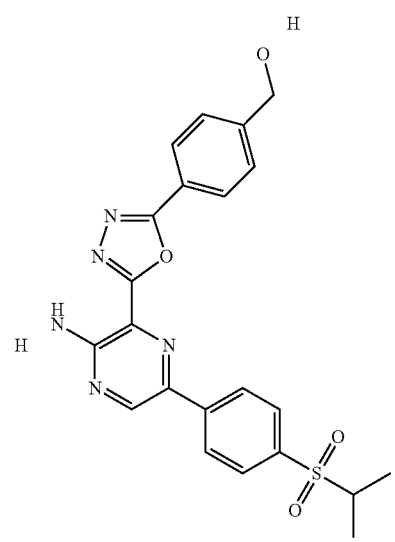
IA-238

104
TABLE IA-3-continued
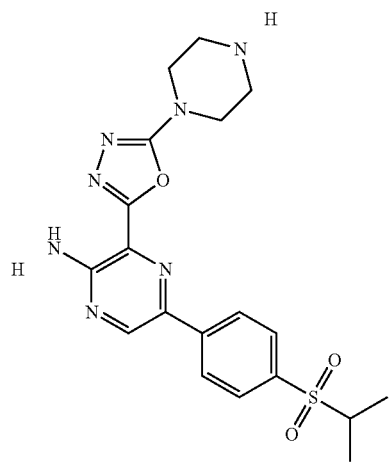
IA-239
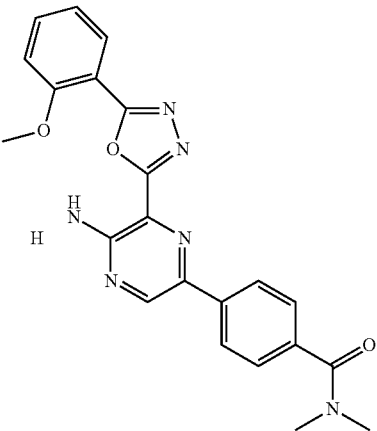
IA-242
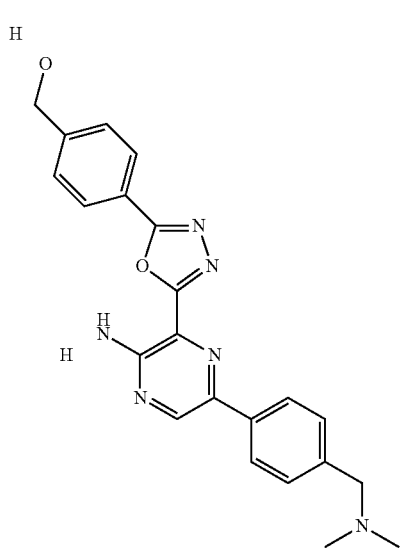
IA-240
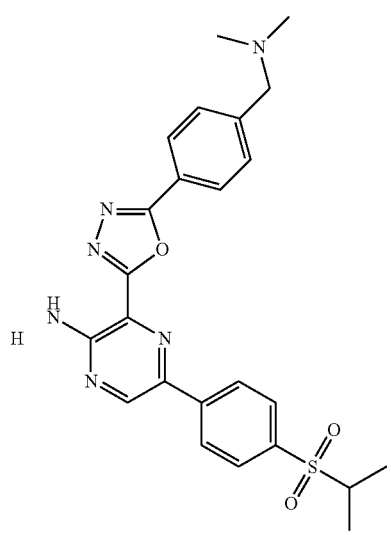
IA-243
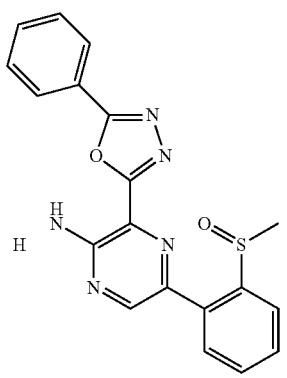
IA-241
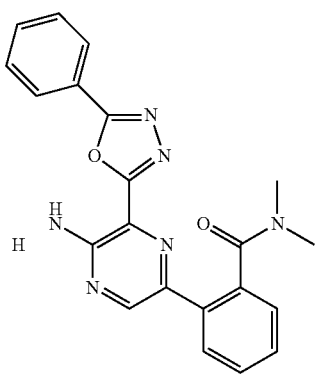
IA-244

TABLE IA-3-continued
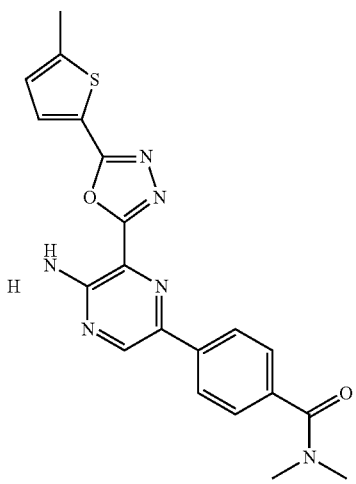
IA-245
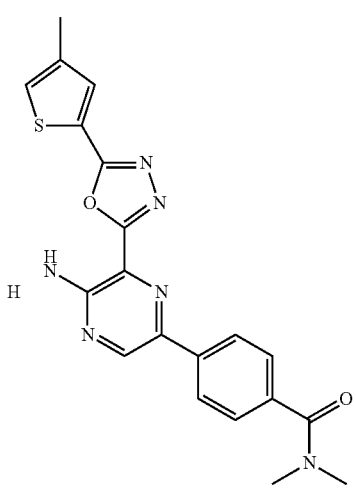
IA-246
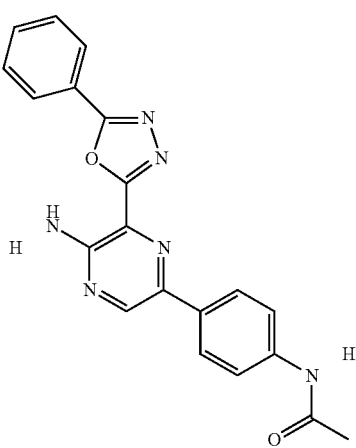
IA-247
TABLE IA-3-continued
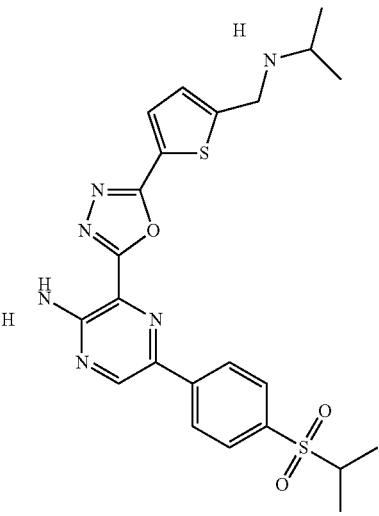
IA-248
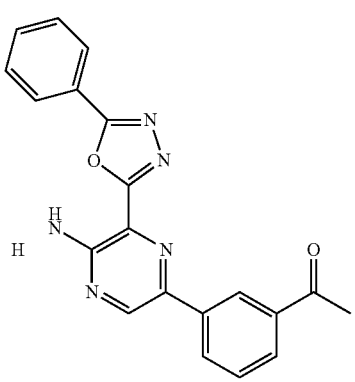
IA-249
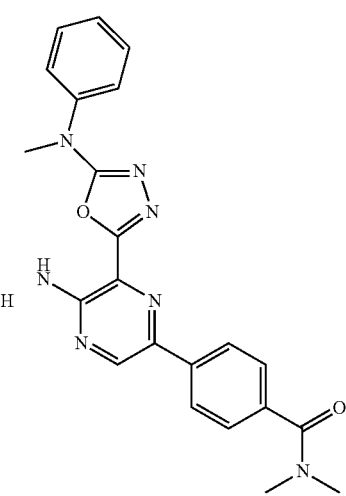
IA-250

TABLE IA-3-continued
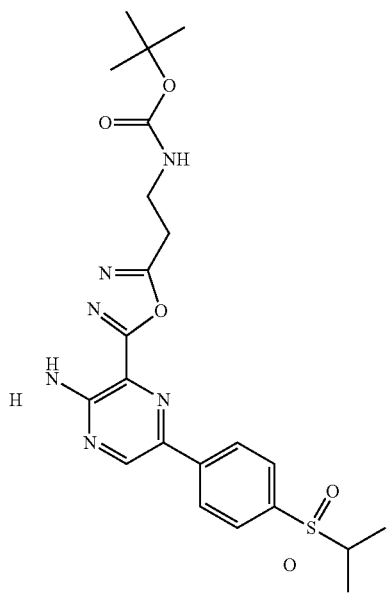
IA-251
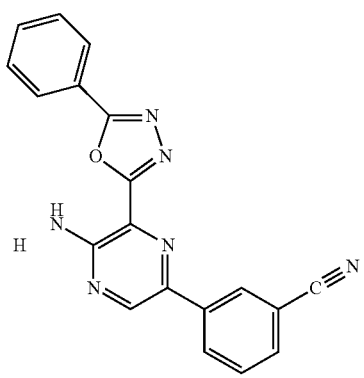
IA-252
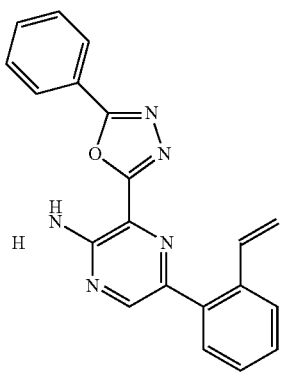
IA-253
TABLE IA-3-continued
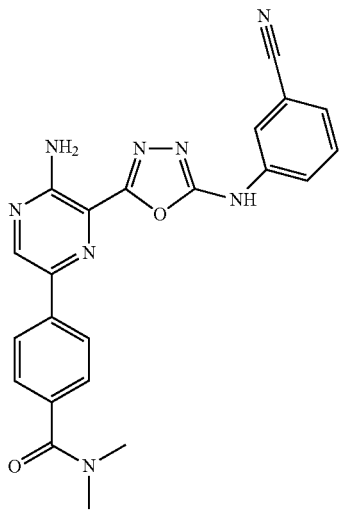 [SMILES: CN(C)C(=O)c1ccc(-c2cnc(N)c(-c3nnc(Nc4cccc(C#N)c4)o3)n2)cc1]
IA-254
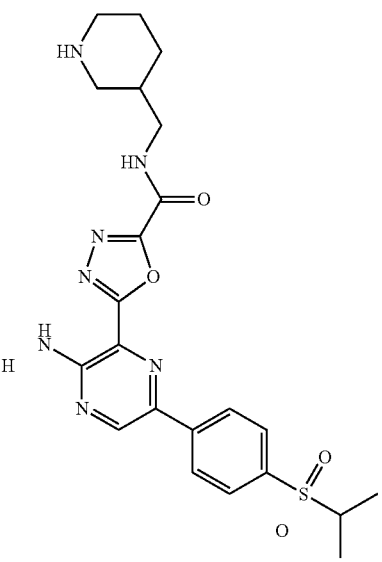
IA-255
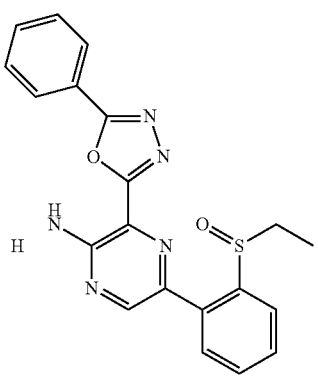
IA-256

TABLE IA-3-continued
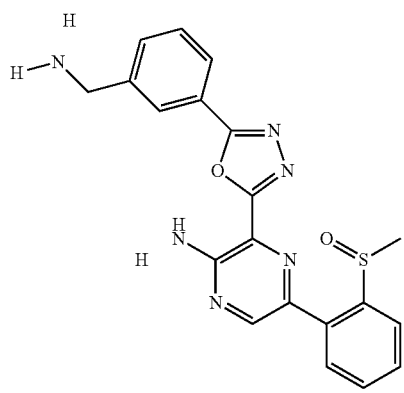
IA-257
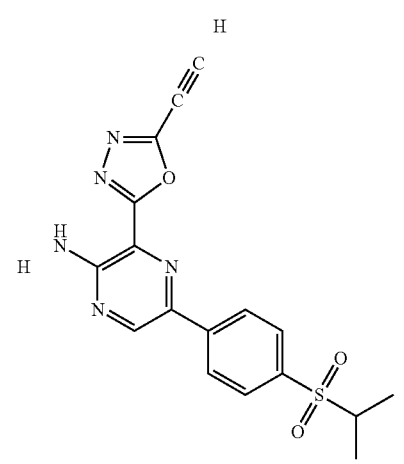
IA-258
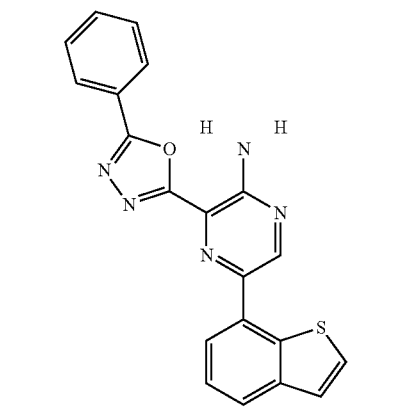
IA-259
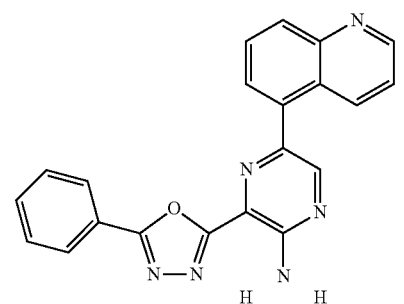
IA-260
TABLE IA-3-continued
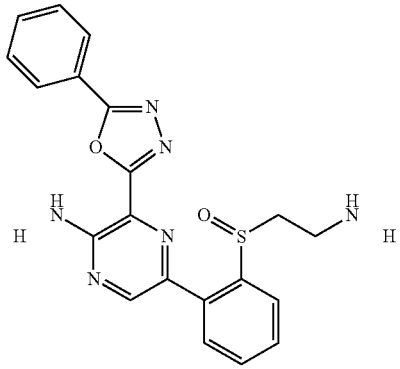
IA-261
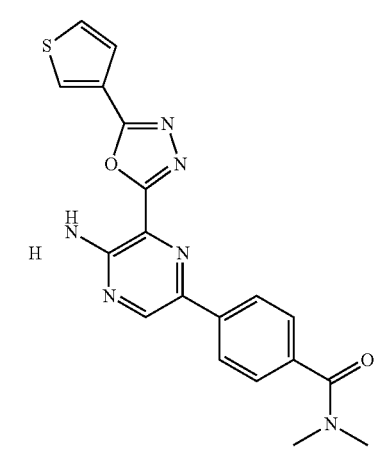
IA-262
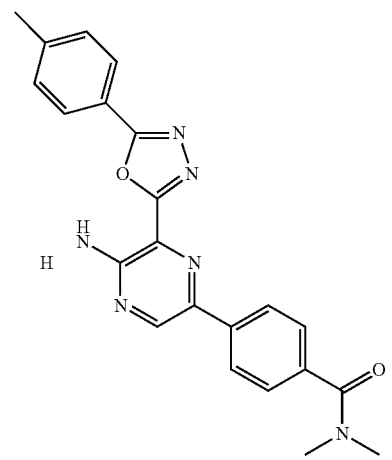
IA-263

TABLE IA-3-continued
IA-264
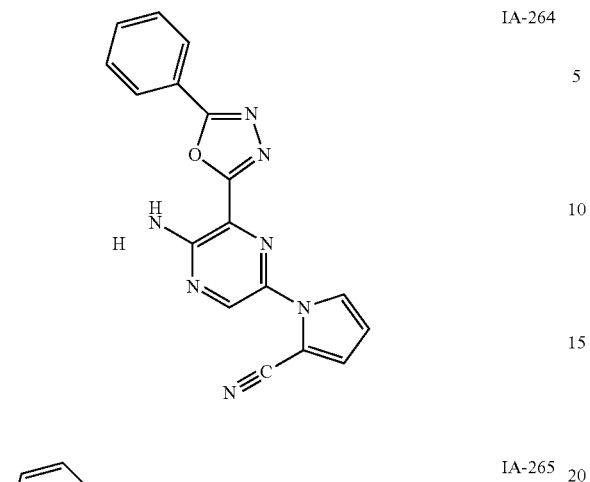
IA-265
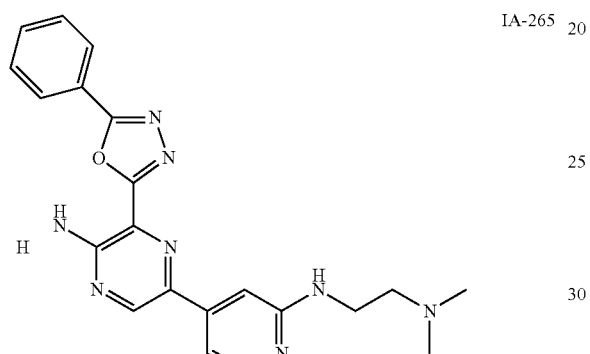
IA-266
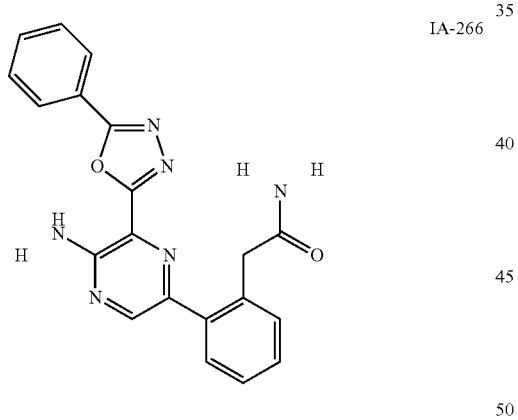
IA-267
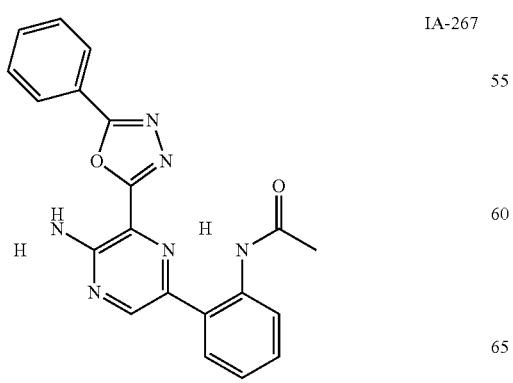
TABLE IA-3-continued
IA-268
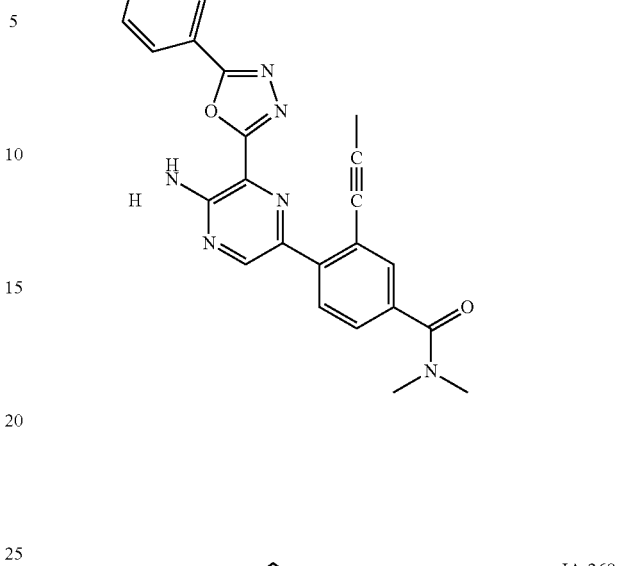
IA-269
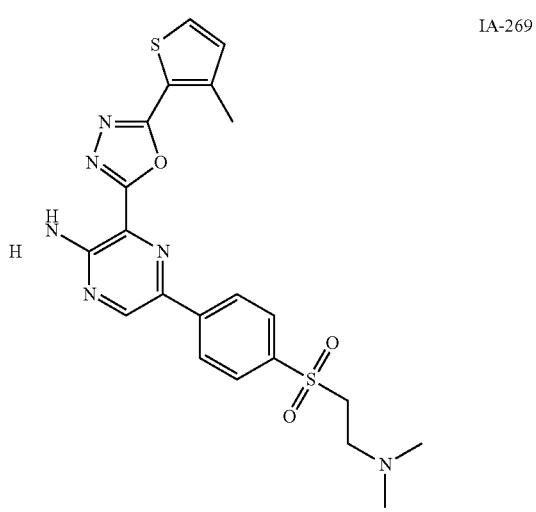
IA-270
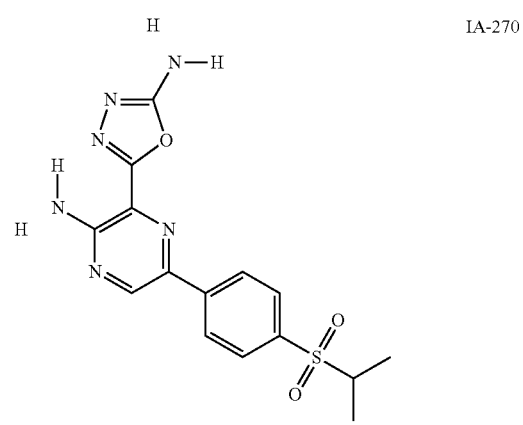

TABLE IA-3-continued
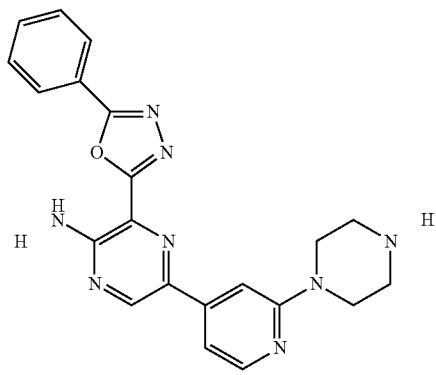
IA-271
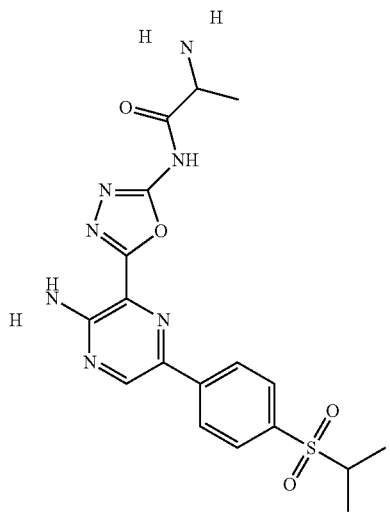
IA-272
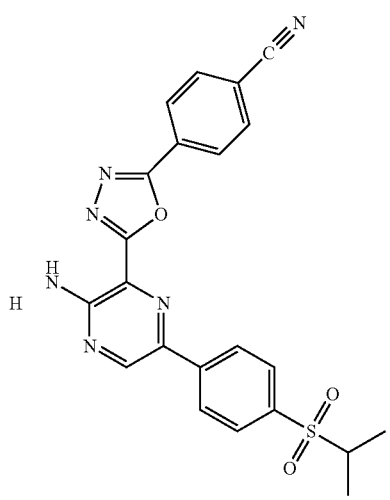
IA-273
TABLE IA-3-continued
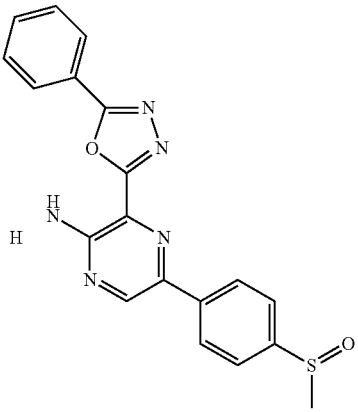
IA-274
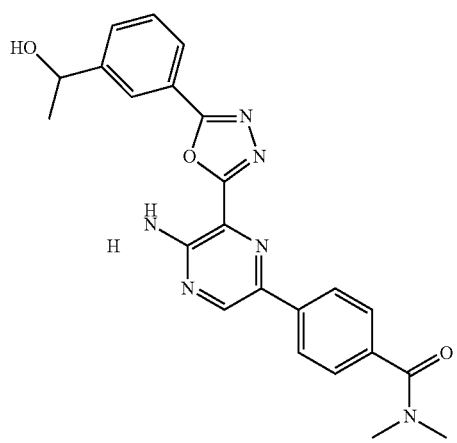
IA-275
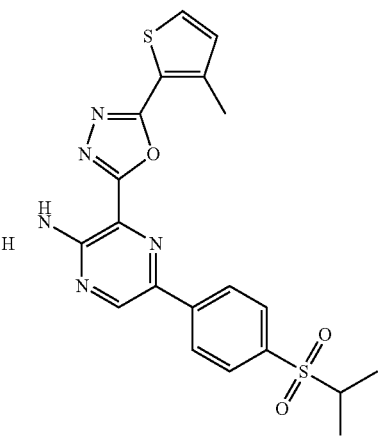
IA-276

TABLE IA-3-continued
IA-277
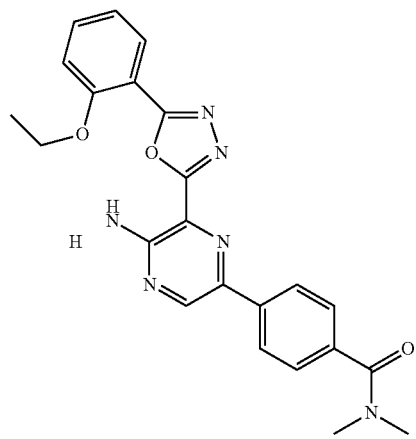
IA-278
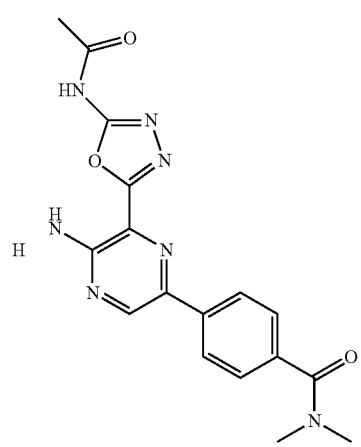
IA-279
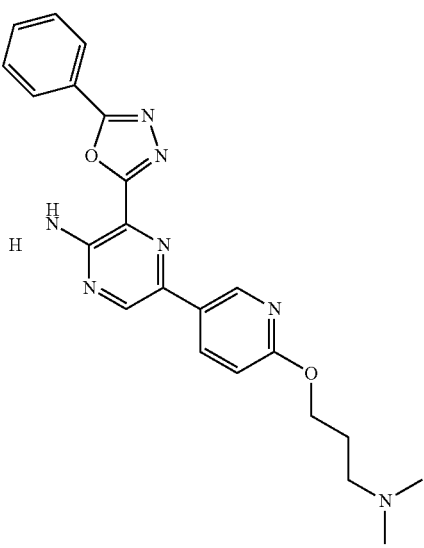
IA-280
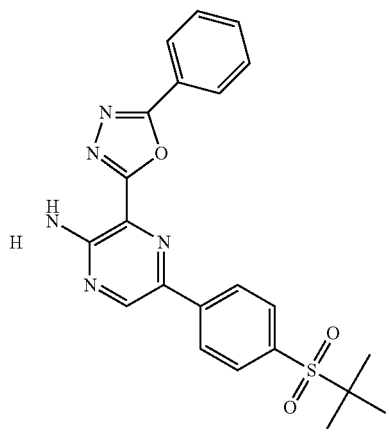
IA-281
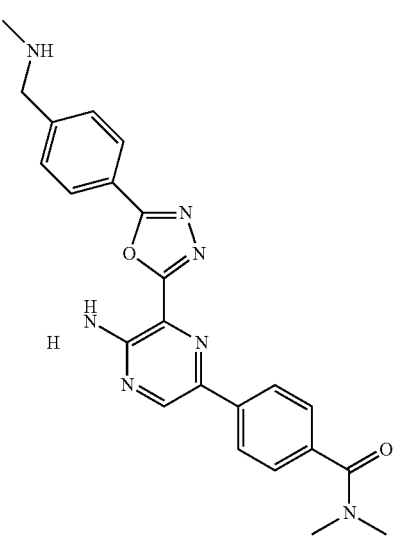
IA-282
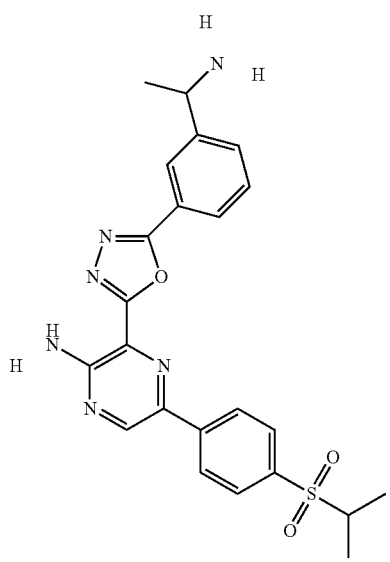

TABLE IA-3-continued
IA-283
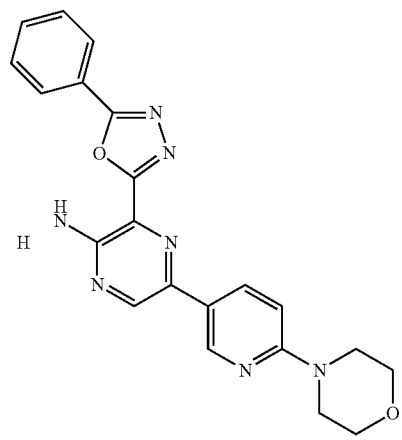
IA-284
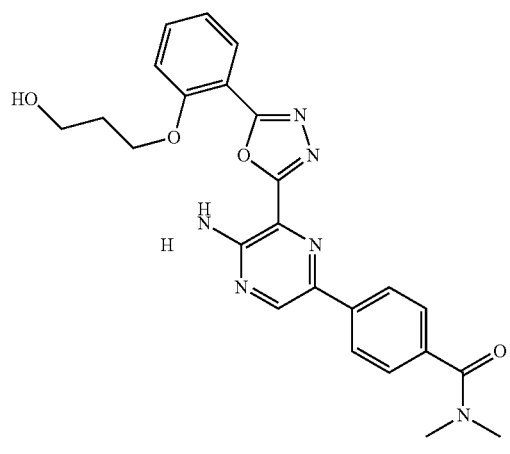
IA-285
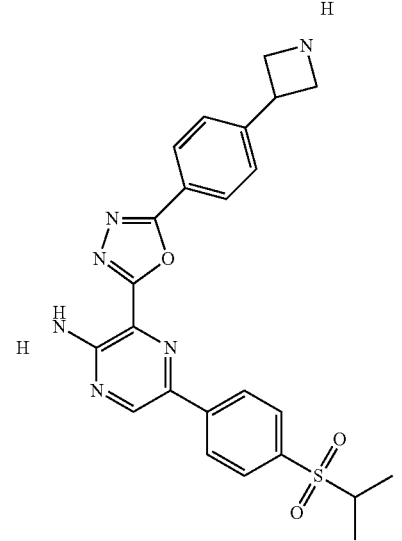
TABLE IA-3-continued
IA-286
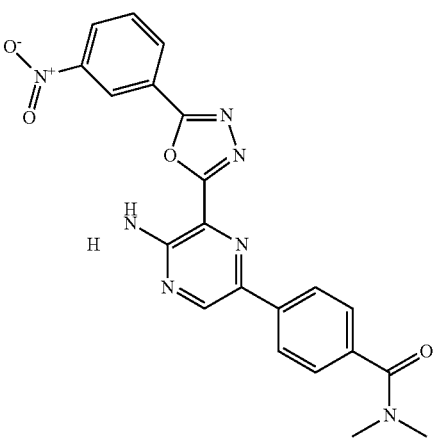
IA-287
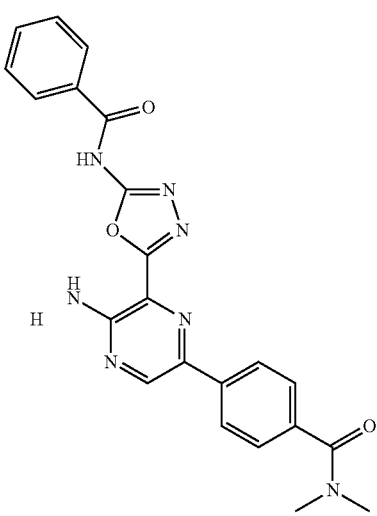
IA-288
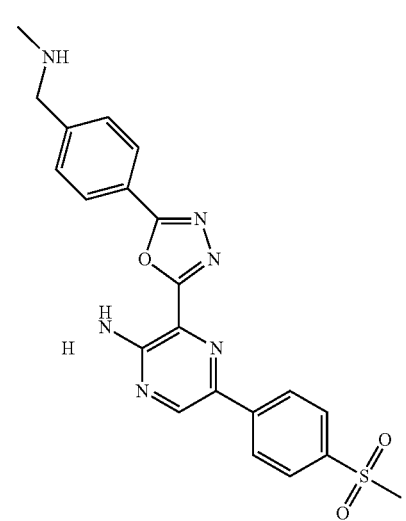

TABLE IA-3-continued
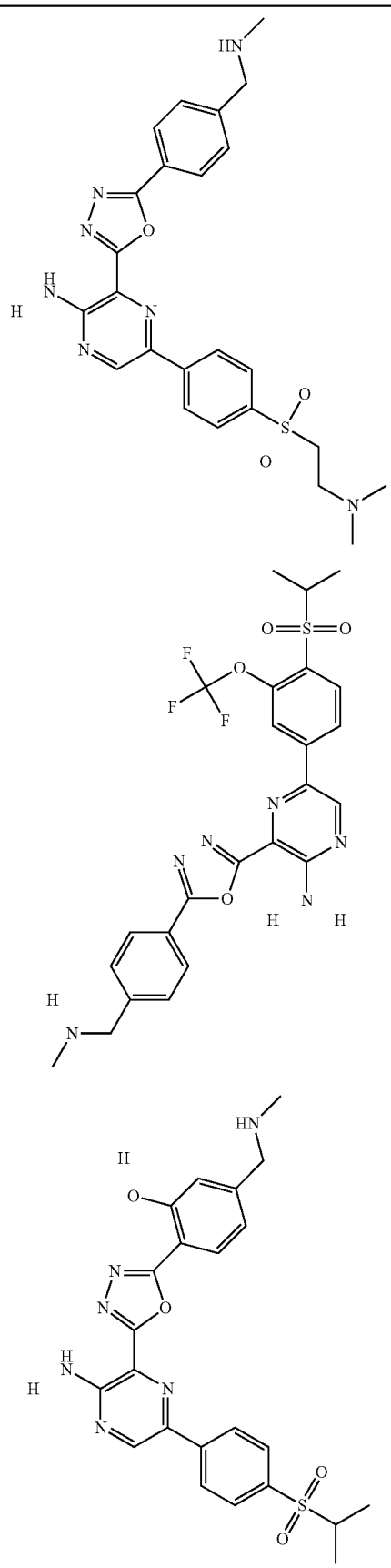
IA-289
IA-290
IA-291
TABLE IA-3-continued
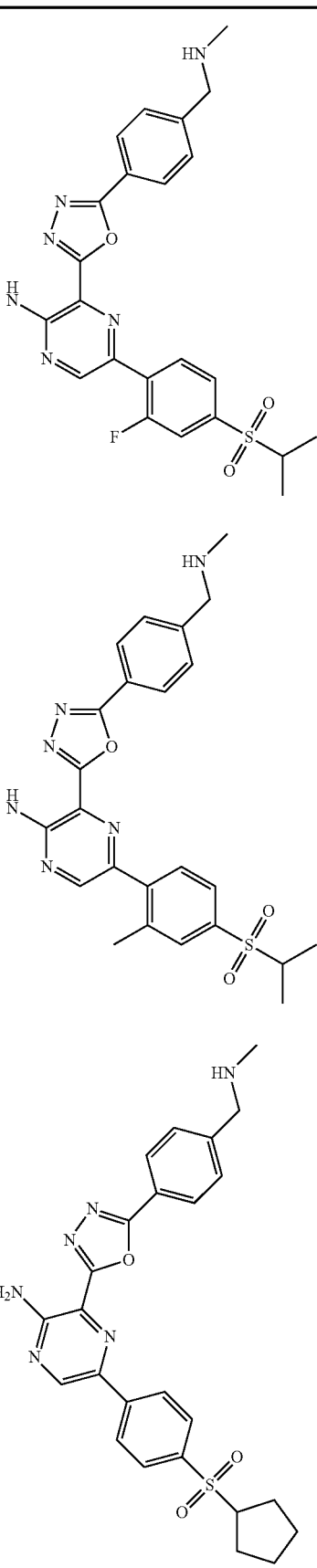
IA-292
IA-293
IA-294

TABLE IA-3-continued
IA-295
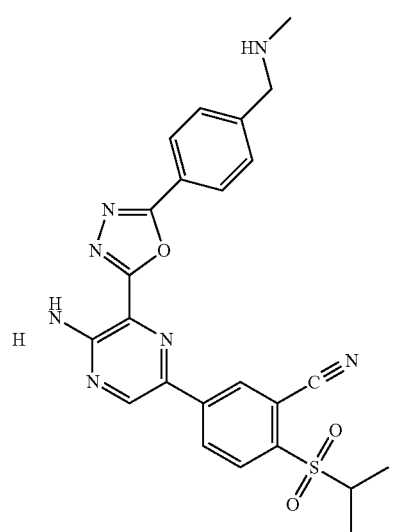
IA-298
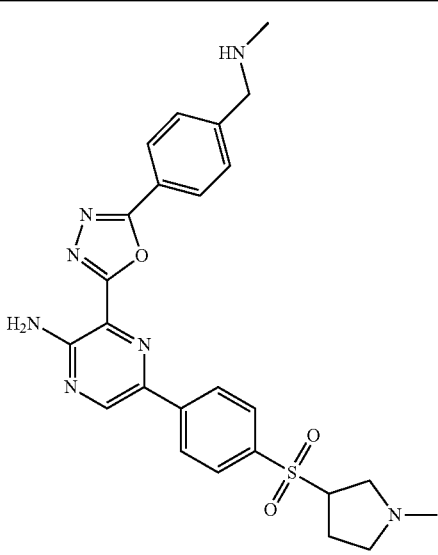
IA-296
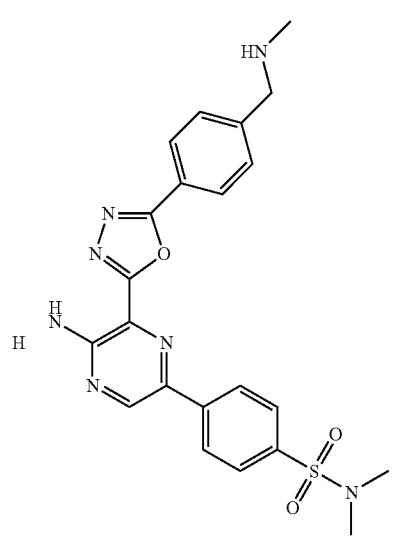
IA-299
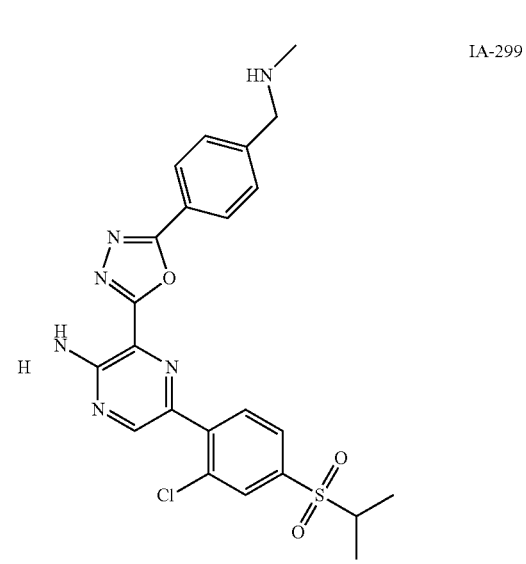
IA-297
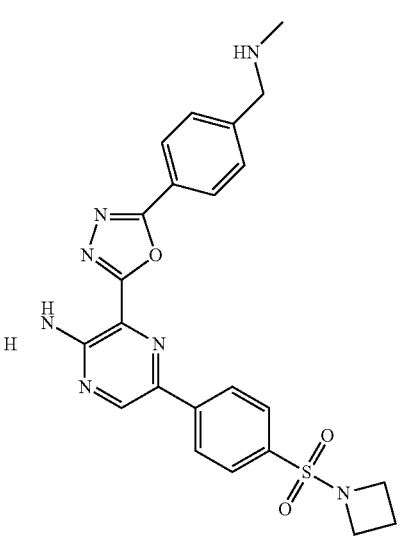
IA-300
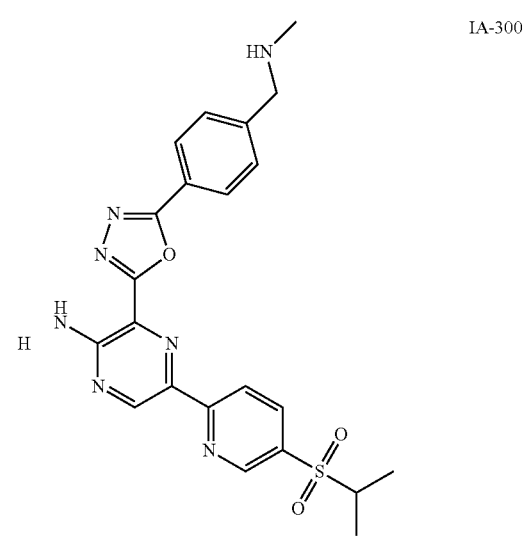

TABLE IA-3-continued
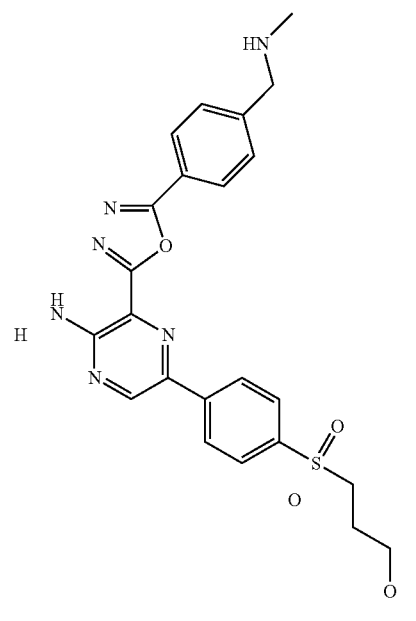
IA-301
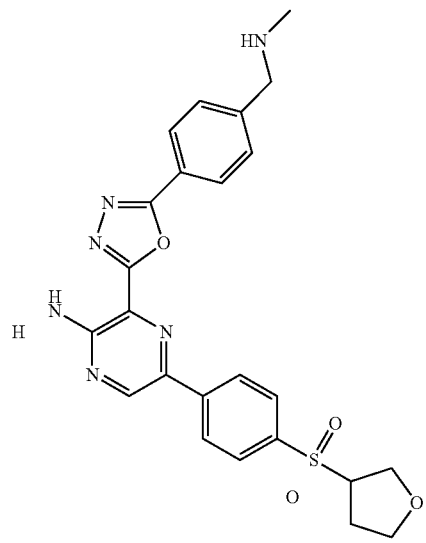
IA-302
TABLE IA-3-continued
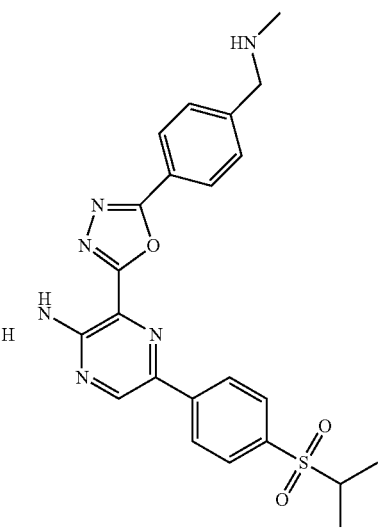
IA-303
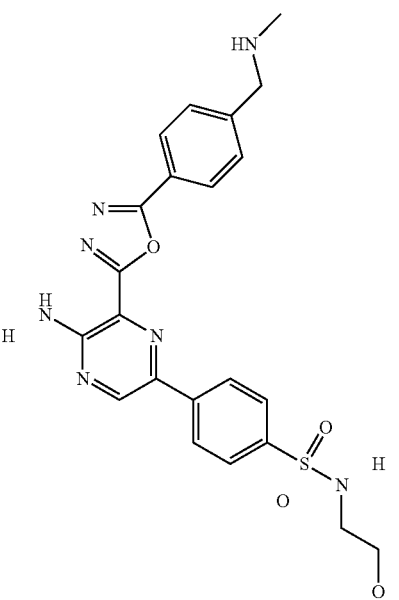
IA-304
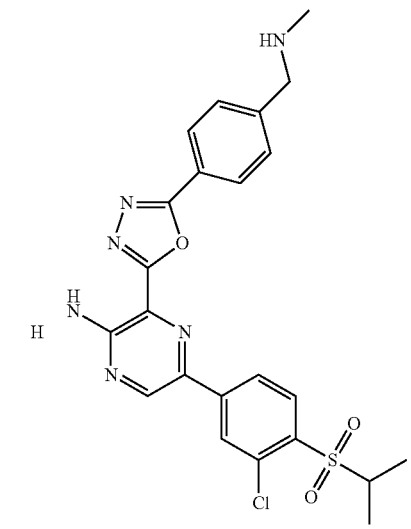
IA-305

TABLE IA-3-continued
IA-306
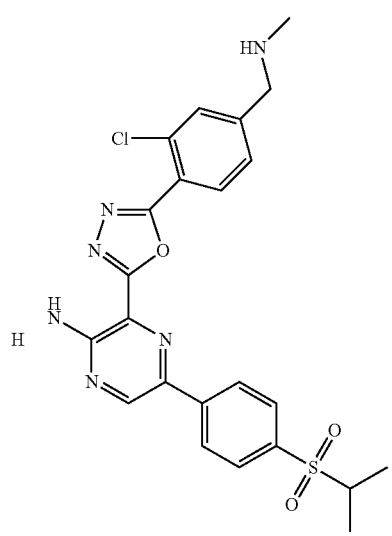
IA-307
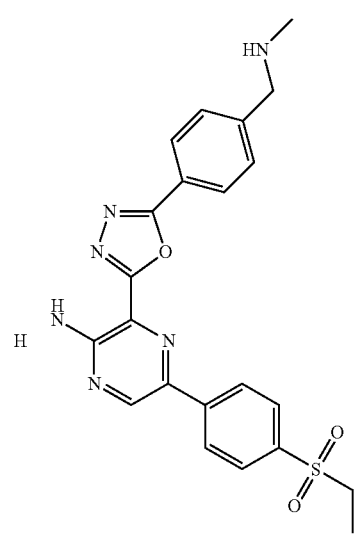
IA-308
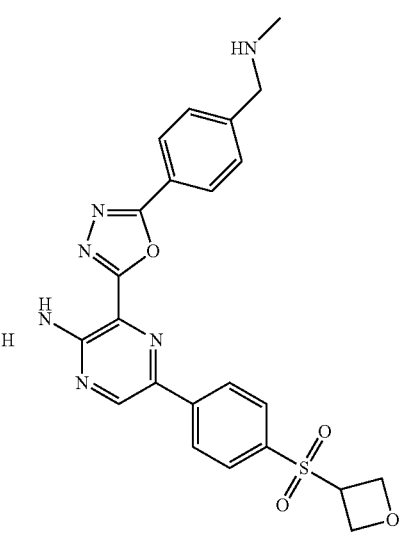
TABLE IA-3-continued
IA-309
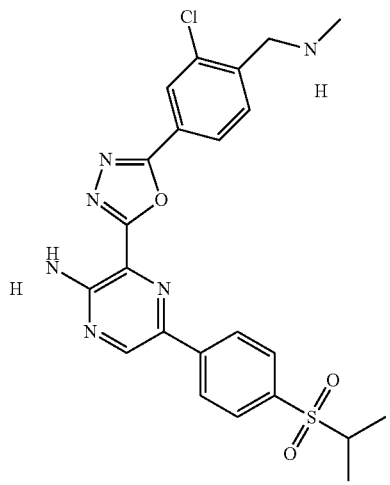
IA-310
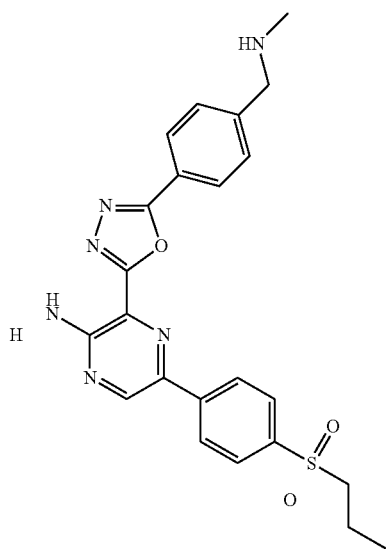
IA-311
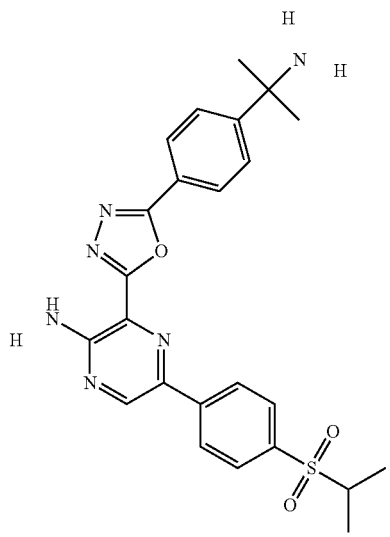

TABLE IA-3-continued
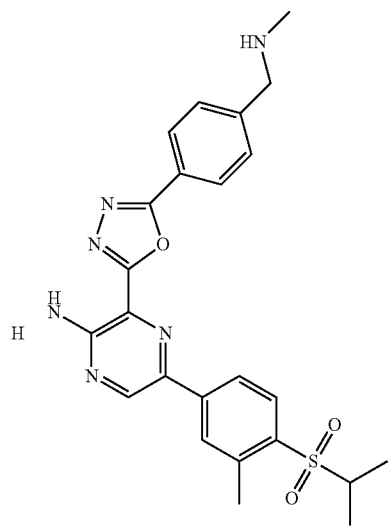
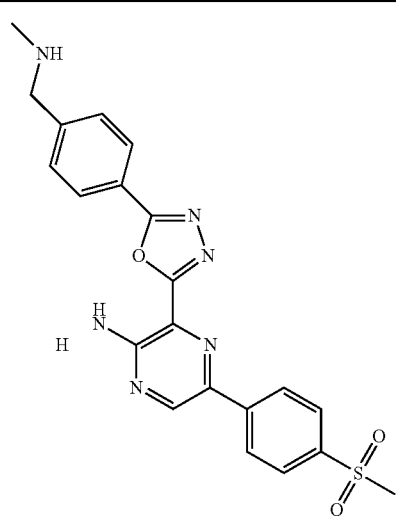

TABLE IA-3-continued
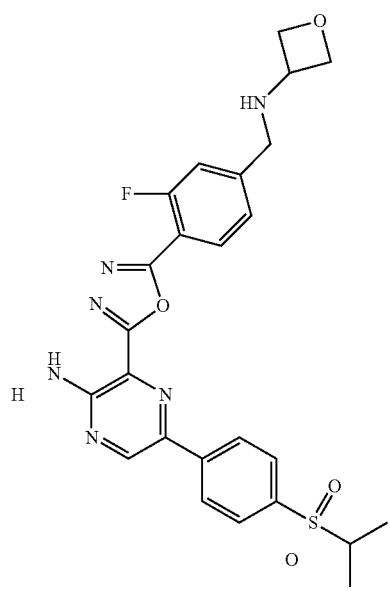
IA-319
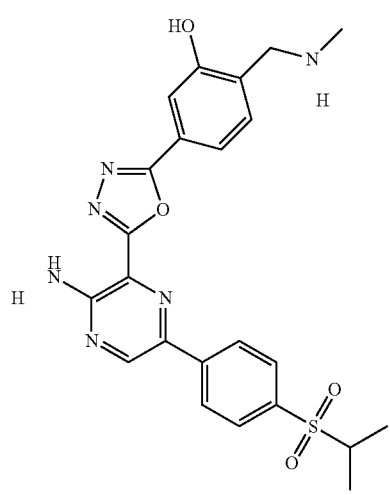
IA-320
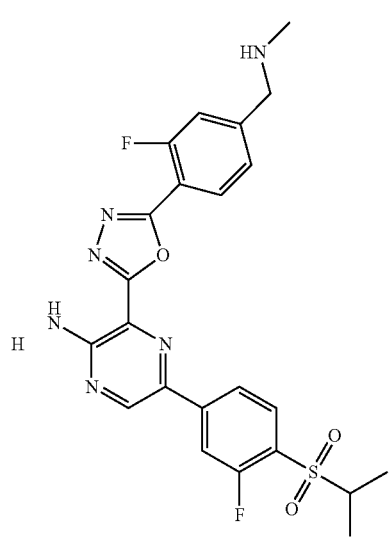
IA-321
TABLE IA-3-continued
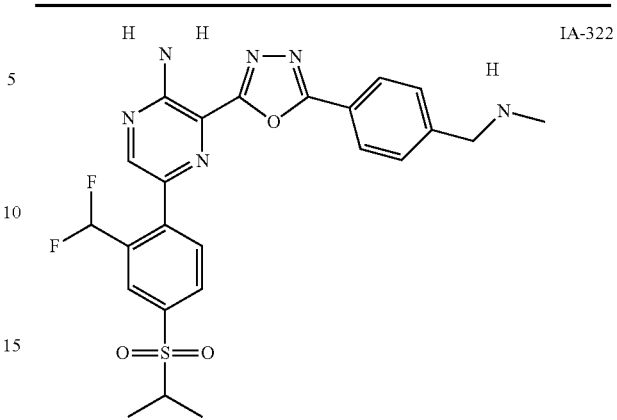
IA-322
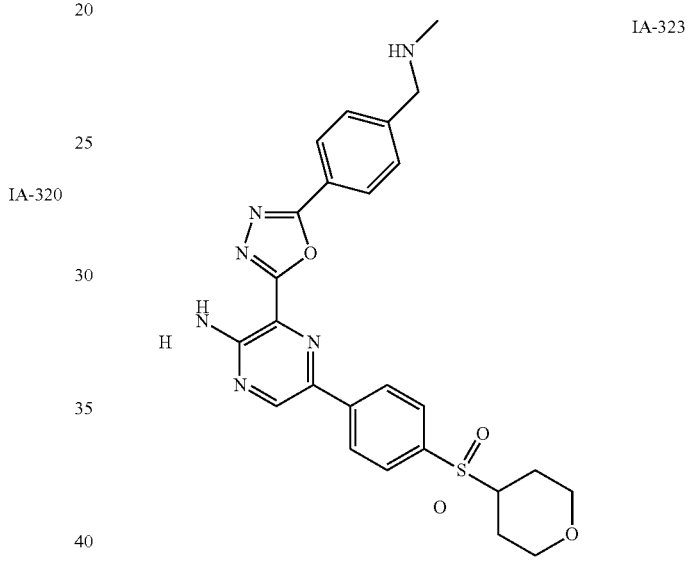
IA-323
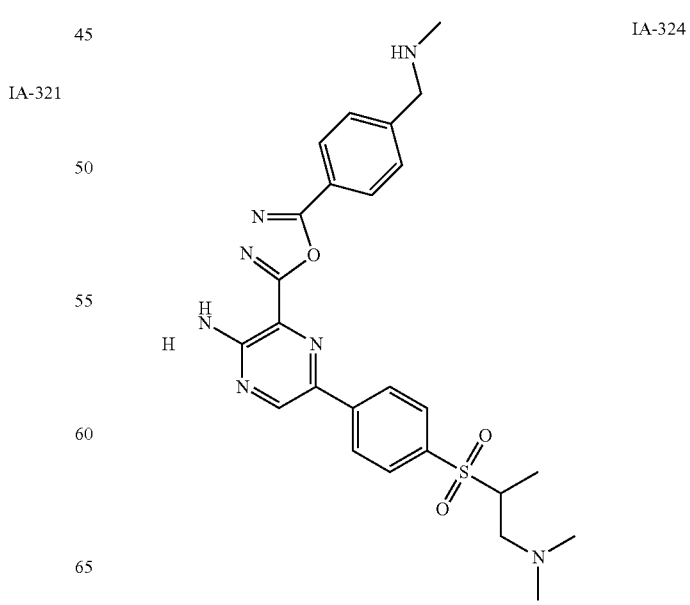
IA-324

TABLE IA-3-continued
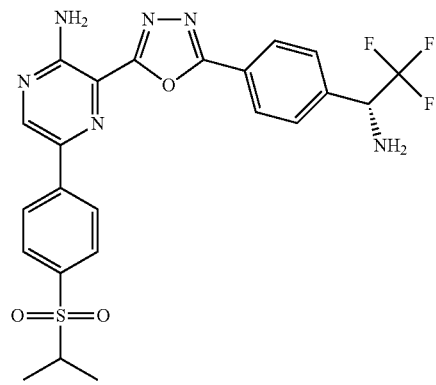 [SMILES: CC(C)S(=O)(=O)c1ccc(-c2cnc(N)c(-c3nnc(-c4ccc([C@@H](N)C(F)(F)F)cc4)o3)n2)cc1]
IA-325
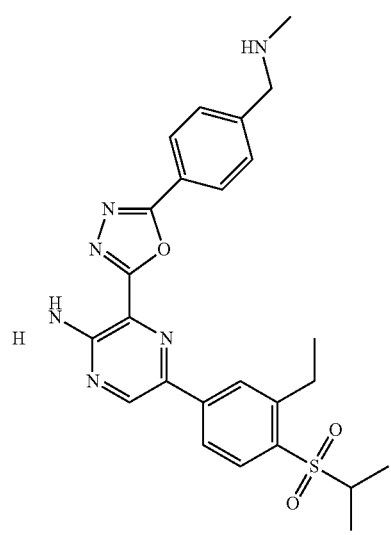
IA-326
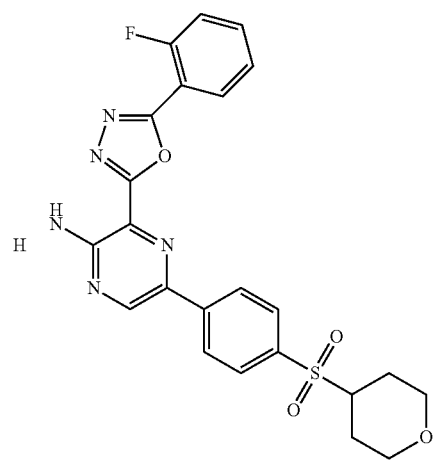
IA-327
TABLE IA-3-continued
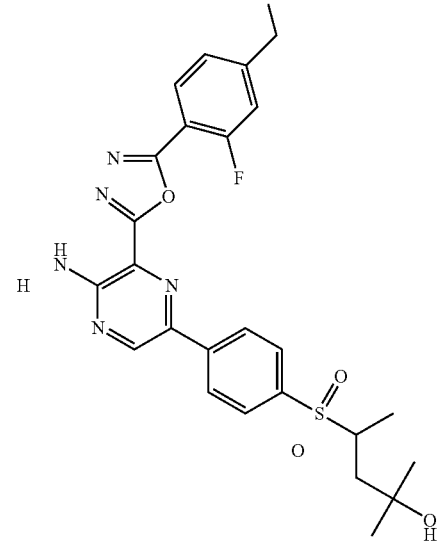
IA-328
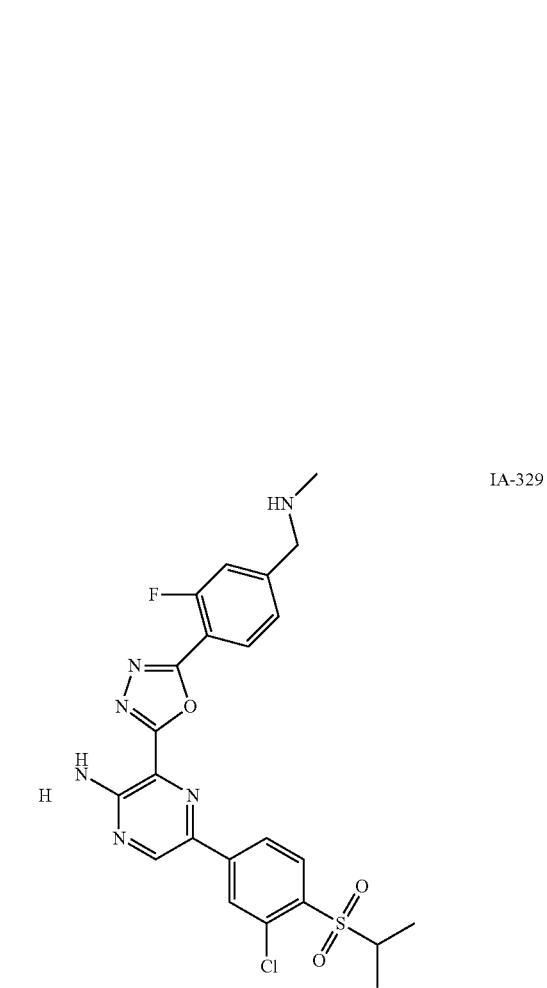
IA-329

TABLE IA-3-continued
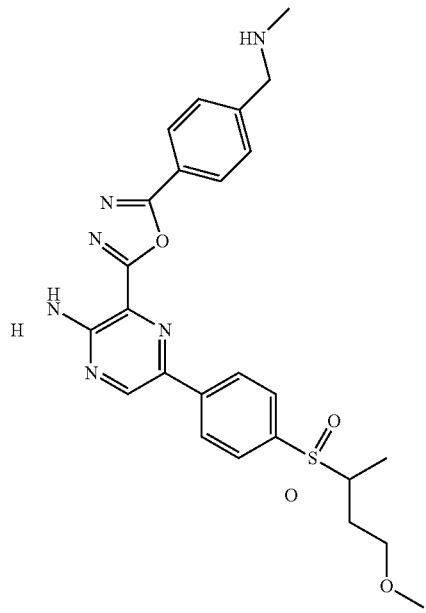
IA-330
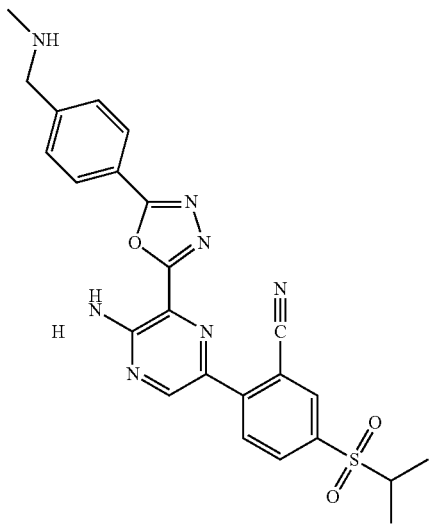
IA-331
TABLE IA-3-continued
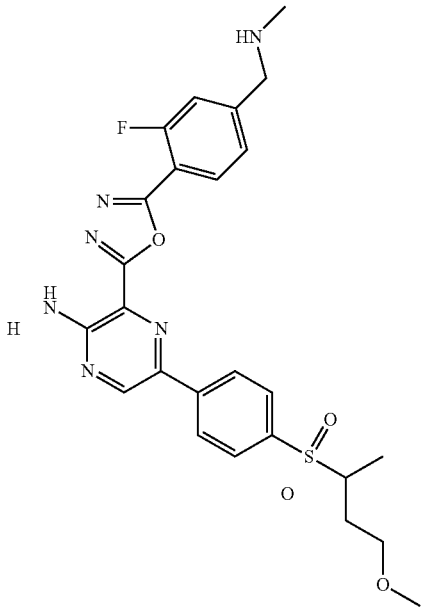
IA-332
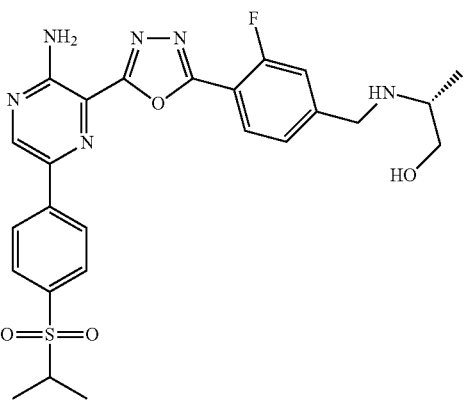 [SMILES: CC(C)S(=O)(=O)c1ccc(-c2cnc(N)c(-c3nnc(-c4ccc(CN[C@H](C)CO)cc4F)o3)n2)cc1]
IA-333
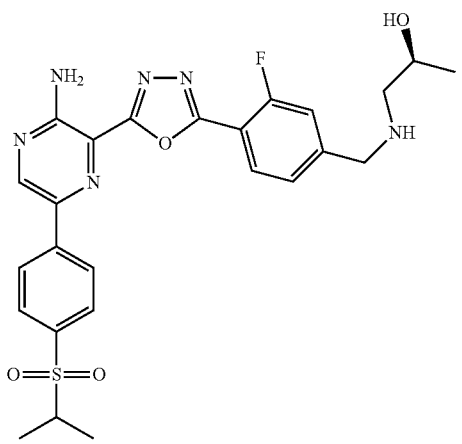 [SMILES: CC(C)S(=O)(=O)c1ccc(-c2cnc(N)c(-c3nnc(-c4ccc(CNC[C@H](C)O)cc4F)o3)n2)cc1]
IA-334

TABLE IA-3-continued
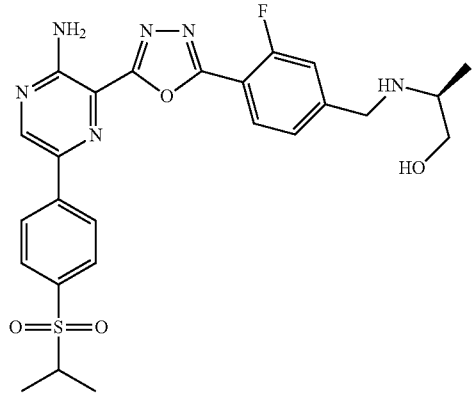 [SMILES: CC(C)S(=O)(=O)c1ccc(-c2cnc(N)c(-c3nnc(-c4ccc(CN[C@@H](C)CO)cc4F)o3)n2)cc1]
IA-335
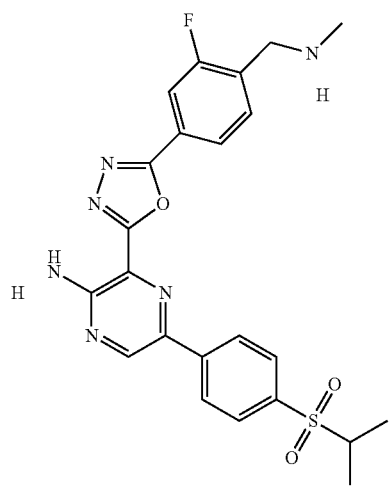
IA-336
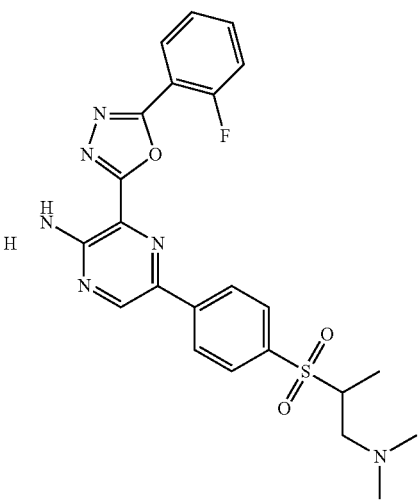
IA-337
TABLE IA-3-continued
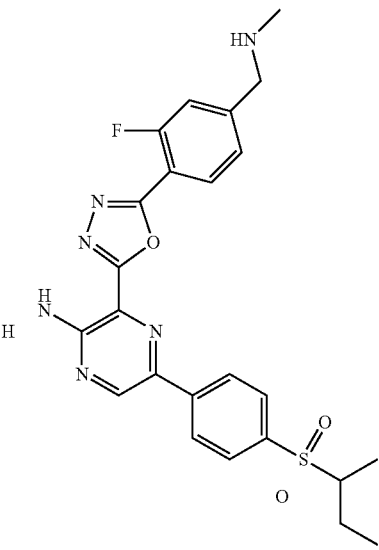
IA-338
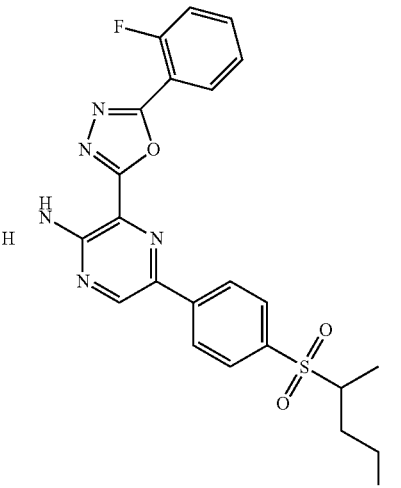
IA-339
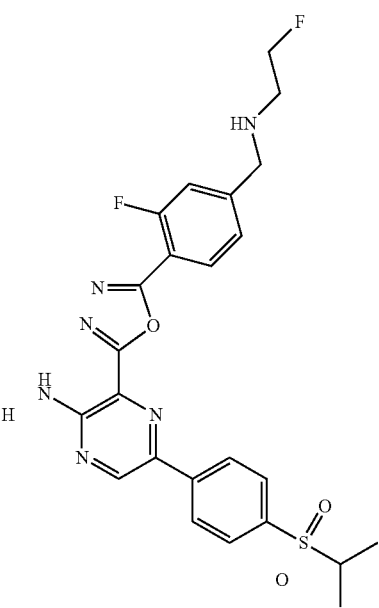
IA-340

TABLE IA-3-continued
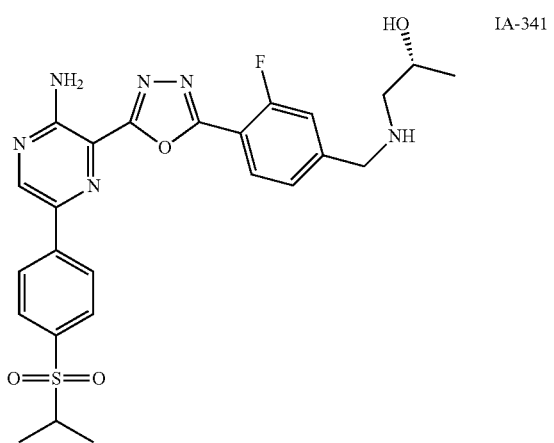
IA-341
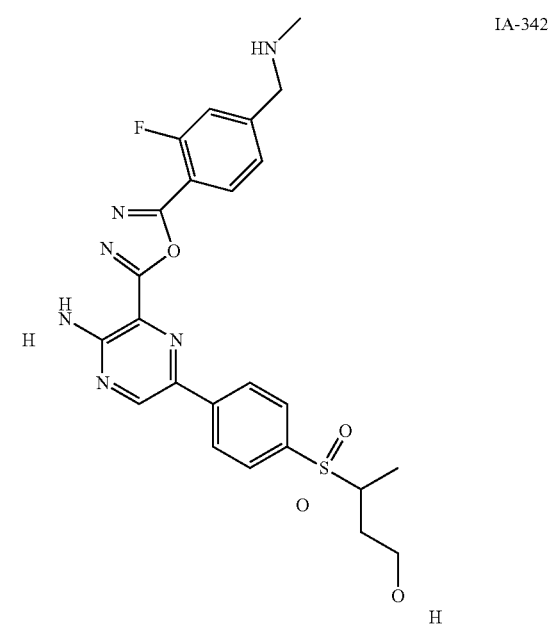
IA-342
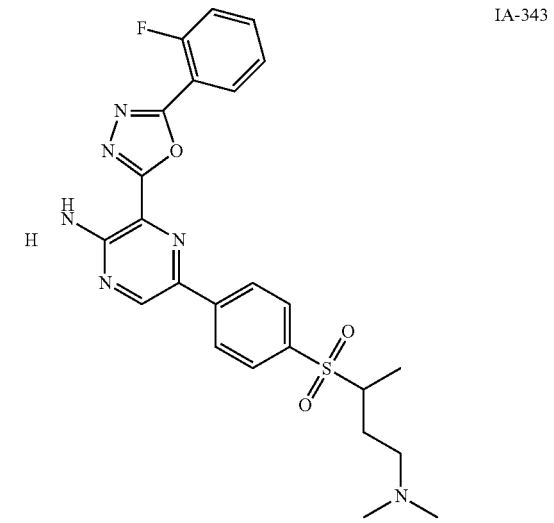
IA-343
TABLE IA-3-continued
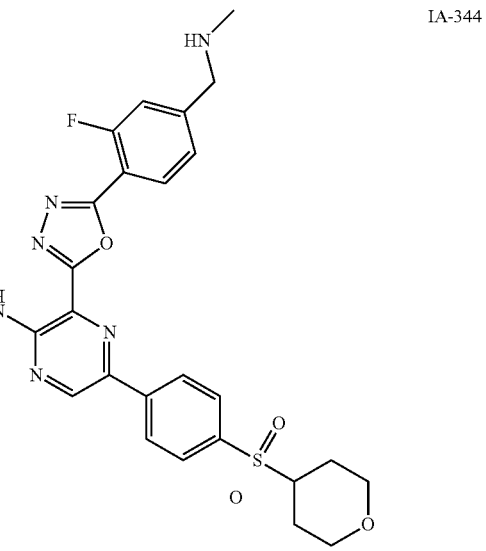
IA-344
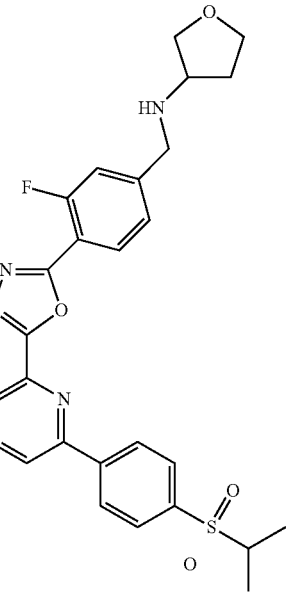
IA-345

TABLE IA-3-continued
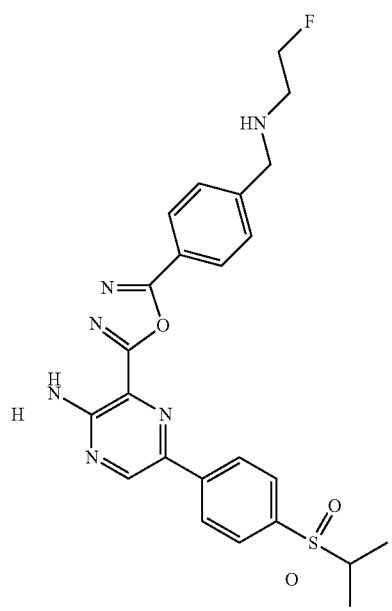
IA-346
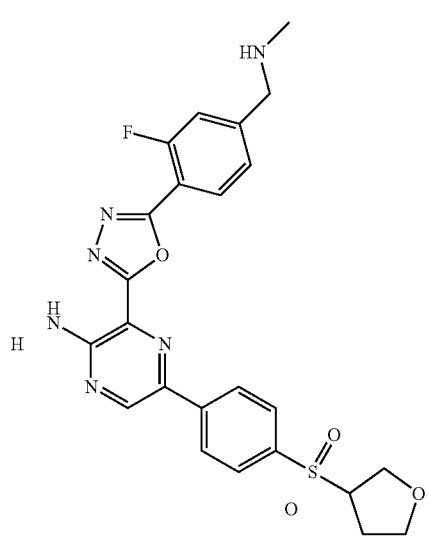
IA-347
TABLE IA-3-continued
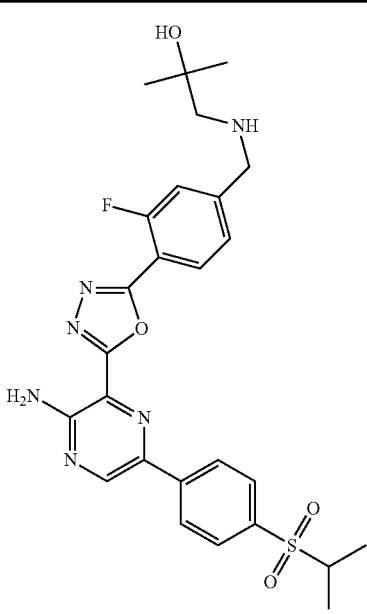
IA-348
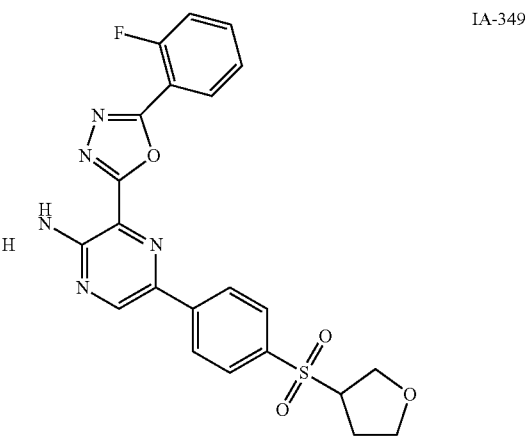
IA-349
TABLE IVA
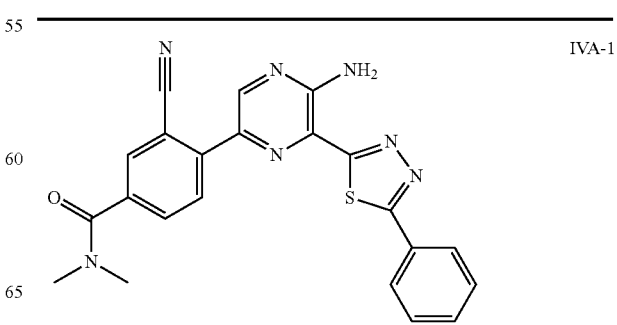
IVA-1

TABLE IVA-continued

IVA-2

IVA-3

TABLE IA-4

(part 1)

| Cmpd # | Name |
|---|---|
| P1 | 3-(5-(4-((2-fluoroethylamino)methyl)phenyl)-1,3,4-oxadiazol-2-yl)-5-(4-(tetrahydrofuran-3-ylsulfonyl)phenyl)pyrazin-2-amine |
| P2 | 3-(5-(4-((2-fluoropropylamino)methyl)phenyl)-1,3,4-oxadiazol-2-yl)-5-(4-(tetrahydrofuran-3-ylsulfonyl)phenyl)pyrazin-2-amine |
| P3 | 3-(5-(4-((1-fluoropropan-2-ylamino)methyl)phenyl)-1,3,4-oxadiazol-2-yl)-5-(4-(tetrahydrofuran-3-ylsulfonyl)phenyl)pyrazin-2-amine |
| P4 | 3-(5-(2-fluoro-4-((2-fluoroethylamino)methyl)phenyl)-1,3,4-oxadiazol-2-yl)-5-(4-(tetrahydrofuran-3-ylsulfonyl)phenyl)pyrazin-2-amine |
| P5 | 3-(5-(2-fluoro-4-((2-fluoropropylamino)methyl)phenyl)-1,3,4-oxadiazol-2-yl)-5-(4-(tetrahydrofuran-3-ylsulfonyl)phenyl)pyrazin-2-amine |
| P6 | 3-(5-(2-fluoro-4-((1-fluoropropan-2-ylamino)methyl)phenyl)-1,3,4-oxadiazol-2-yl)-5-(4-(tetrahydrofuran-3-ylsulfonyl)phenyl)pyrazin-2-amine |
| P7 | 3-(5-(2-fluoro-4-(((R)-tetrahydrofuran-3-ylamino)methyl)phenyl)-1,3,4-oxadiazol-2-yl)-5-(4-(tetrahydrofuran-3-ylsulfonyl)phenyl)pyrazin-2-amine |
| P8 | 3-(5-(2-fluoro-4-(((S)-tetrahydrofuran-3-ylamino)methyl)phenyl)-1,3,4-oxadiazol-2-yl)-5-(4-(tetrahydrofuran-3-ylsulfonyl)phenyl)pyrazin-2-amine |
| P9 | 3-(5-(4-(((S)-tetrahydrofuran-3-ylamino)methyl)phenyl)-1,3,4-oxadiazol-2-yl)-5-(4-(tetrahydrofuran-3-ylsulfonyl)phenyl)pyrazin-2-amine |
| P10 | 3-(5-(4-(((R)-tetrahydrofuran-3-ylamino)methyl)phenyl)-1,3,4-oxadiazol-2-yl)-5-(4-(tetrahydrofuran-3-ylsulfonyl)phenyl)pyrazin-2-amine |
| P11 | 5-(3-chloro-4-(tetrahydrofuran-3-ylsulfonyl)phenyl)-3-(5-(4-(((R)-tetrahydrofuran-3-ylamino)methyl)phenyl)-1,3,4-oxadiazol-2-yl)pyrazin-2-amine |
| P12 | 5-(3-chloro-4-(tetrahydrofuran-3-ylsulfonyl)phenyl)-3-(5-(2-fluoro-4-(((R)-tetrahydrofuran-3-ylamino)methyl)phenyl)-1,3,4-oxadiazol-2-yl)pyrazin-2-amine |
| P13 | (R)-5-(4-(tetrahydro-2H-pyran-4-ylsulfonyl)phenyl)-3-(5-(4-((tetrahydrofuran-3-ylamino)methyl)phenyl)-1,3,4-oxadiazol-2-yl)pyrazin-2-amine |

TABLE IA-4-continued (part 1)

| Cmpd # | Name |
|---|---|
| P14 | (S)-5-(4-(tetrahydro-2H-pyran-4-ylsulfonyl)phenyl)-3-(5-(4-((tetrahydrofuran-3-ylamino)methyl)phenyl)-1,3,4-oxadiazol-2-yl)pyrazin-2-amine |
| P15 | 3-(5-(4-((ethylamino)methyl)phenyl)-1,3,4-oxadiazol-2-yl)-5-(4-(tetrahydro-2H-pyran-4-ylsulfonyl)phenyl)pyrazin-2-amine |
| P16 | (R)-3-(5-(2-fluoro-4-((tetrahydrofuran-3-ylamino)methyl)phenyl)-1,3,4-oxadiazol-2-yl)-5-(4-(tetrahydro-2H-pyran-4-ylsulfonyl)phenyl)pyrazin-2-amine |
| P17 | (S)-3-(5-(2-fluoro-4-((tetrahydrofuran-3-ylamino)methyl)phenyl)-1,3,4-oxadiazol-2-yl)-5-(4-(tetrahydro-2H-pyran-4-ylsulfonyl)phenyl)pyrazin-2-amine |
| P18 | 3-(5-(4-((ethylamino)methyl)-2-fluorophenyl)-1,3,4-oxadiazol-2-yl)-5-(4-(tetrahydro-2H-pyran-4-ylsulfonyl)phenyl)pyrazin-2-amine |
| P19 | 3-(5-(2-fluoro-4-((2-fluoroethylamino)methyl)phenyl)-1,3,4-oxadiazol-2-yl)-5-(4-(tetrahydro-2H-pyran-4-ylsulfonyl)phenyl)pyrazin-2-amine |
| P20 | 3-(5-(2-fluoro-4-((2-fluoropropylamino)methyl)phenyl)-1,3,4-oxadiazol-2-yl)-5-(4-(tetrahydro-2H-pyran-4-ylsulfonyl)phenyl)pyrazin-2-amine |
| P21 | 3-(5-(2-fluoro-4-((1-fluoropropan-2-ylamino)methyl)phenyl)-1,3,4-oxadiazol-2-yl)-5-(4-(tetrahydro-2H-pyran-4-ylsulfonyl)phenyl)pyrazin-2-amine |
| P22 | 3-(5-(4-((2-fluoroethylamino)methyl)phenyl)-1,3,4-oxadiazol-2-yl)-5-(4-(tetrahydro-2H-pyran-4-ylsulfonyl)phenyl)pyrazin-2-amine |
| P23 | 3-(5-(4-((2-fluoropropylamino)methyl)phenyl)-1,3,4-oxadiazol-2-yl)-5-(4-(tetrahydro-2H-pyran-4-ylsulfonyl)phenyl)pyrazin-2-amine |
| P24 | 3-(5-(4-((1-fluoropropan-2-ylamino)methyl)phenyl)-1,3,4-oxadiazol-2-yl)-5-(4-(tetrahydro-2H-pyran-4-ylsulfonyl)phenyl)pyrazin-2-amine |
| P25 | 5-(4-(sec-butylsulfonyl)phenyl)-3-(5-(4-((2-fluoroethylamino)methyl)phenyl)-1,3,4-oxadiazol-2-yl)pyrazin-2-amine |
| P26 | 5-(4-(sec-butylsulfonyl)phenyl)-3-(5-(4-((2-fluoropropylamino)methyl)phenyl)-1,3,4-oxadiazol-2-yl)pyrazin-2-amine |
| P27 | 5-(4-(sec-butylsulfonyl)phenyl)-3-(5-(4-((1-fluoropropan-2-ylamino)methyl)phenyl)-1,3,4-oxadiazol-2-yl)pyrazin-2-amine |
| P28 | 5-(4-(sec-butylsulfonyl)phenyl)-3-(5-(2-fluoro-4-((2-fluoroethylamino)methyl)phenyl)-1,3,4-oxadiazol-2-yl)pyrazin-2-amine |
| P29 | 5-(4-(sec-butylsulfonyl)phenyl)-3-(5-(2-fluoro-4-((2-fluoropropylamino)methyl)phenyl)-1,3,4-oxadiazol-2-yl)pyrazin-2-amine |
| P30 | 5-(4-(sec-butylsulfonyl)phenyl)-3-(5-(2-fluoro-4-((1-fluoropropan-2-ylamino)methyl)phenyl)-1,3,4-oxadiazol-2-yl)pyrazin-2-amine |
| P31 | 5-(4-(sec-butylsulfonyl)phenyl)-3-(5-(2-fluoro-4-(((R)-tetrahydrofuran-3-ylamino)methyl)phenyl)-1,3,4-oxadiazol-2-yl)pyrazin-2-amine |
| P32 | 5-(4-(sec-butylsulfonyl)phenyl)-3-(5-(2-fluoro-4-(((S)-tetrahydrofuran-3-ylamino)methyl)phenyl)-1,3,4-oxadiazol-2-yl)pyrazin-2-amine |
| P33 | 5-(4-(sec-butylsulfonyl)phenyl)-3-(5-(2-fluoro-4-(((R)-2-fluoropropylamino)methyl)phenyl)-1,3,4-oxadiazol-2-yl)pyrazin-2-amine |
| P34 | 5-(4-(sec-butylsulfonyl)phenyl)-3-(5-(4-(((R)-tetrahydrofuran-3-ylamino)methyl)phenyl)-1,3,4-oxadiazol-2-yl)pyrazin-2-amine |
| P35 | 5-(4-(sec-butylsulfonyl)phenyl)-3-(5-(4-(((S)-tetrahydrofuran-3-ylamino)methyl)phenyl)-1,3,4-oxadiazol-2-yl)pyrazin-2-amine |
| P36 | 5-(4-(sec-butylsulfonyl)phenyl)-3-(5-(4-(((R)-2-fluoropropylamino)methyl)phenyl)-1,3,4-oxadiazol-2-yl)pyrazin-2-amine |
| P37 | (R)-5-(4-(isopropylsulfonyl)phenyl)-3-(5-(4-((tetrahydrofuran-3-ylamino)methyl)phenyl)-1,3,4-oxadiazol-2-yl)pyrazin-2-amine |
| P38 | (S)-5-(4-(isopropylsulfonyl)phenyl)-3-(5-(4-((tetrahydrofuran-3-ylamino)methyl)phenyl)-1,3,4-oxadiazol-2-yl)pyrazin-2-amine |
| P39 | (R)-3-(5-(4-((2-fluoropropylamino)methyl)phenyl)-1,3,4-oxadiazol-2-yl)-5-(4-(isopropylsulfonyl)phenyl)pyrazin-2-amine |
| P40 | (R)-3-(5-(2-fluoro-4-((tetrahydrofuran-3-ylamino)methyl)phenyl)-1,3,4-oxadiazol-2-yl)-5-(4-(isopropylsulfonyl)phenyl)pyrazin-2-amine |
| P41 | (S)-3-(5-(2-fluoro-4-((tetrahydrofuran-3-ylamino)methyl)phenyl)-1,3,4-oxadiazol-2-yl)-5-(4-(isopropylsulfonyl)phenyl)pyrazin-2-amine |
| P42 | (R)-3-(5-(2-fluoro-4-((2-fluoropropylamino)methyl)phenyl)-1,3,4-oxadiazol-2-yl)-5-(4-(isopropylsulfonyl)phenyl)pyrazin-2-amine |
| P43 | 3-(5-(2-fluoro-4-((2-fluoroethylamino)methyl)phenyl)-1,3,4-oxadiazol-2-yl)-5-(4-(isopropylsulfonyl)phenyl)pyrazin-2-amine |
| P44 | 3-(5-(2-fluoro-4-((2-fluoropropylamino)methyl)phenyl)-1,3,4-oxadiazol-2-yl)-5-(4-(isopropylsulfonyl)phenyl)pyrazin-2-amine |
| P45 | 3-(5-(2-fluoro-4-((1-fluoropropan-2-ylamino)methyl)phenyl)-1,3,4-oxadiazol-2-yl)-5-(4-(isopropylsulfonyl)phenyl)pyrazin-2-amine |
| P46 | 5-(3-chloro-4-(isopropylsulfonyl)phenyl)-3-(5-(4-((2-fluoroethylamino)methyl)phenyl)-1,3,4-oxadiazol-2-yl)pyrazin-2-amine |
| P47 | 3-(5-(4-((2-fluoropropylamino)methyl)phenyl)-1,3,4-oxadiazol-2-yl)-5-(4-(isopropylsulfonyl)phenyl)pyrazin-2-amine |
| P48 | 3-(5-(4-((1-fluoropropan-2-ylamino)methyl)phenyl)-1,3,4-oxadiazol-2-yl)-5-(4-(isopropylsulfonyl)phenyl)pyrazin-2-amine |
| P49 | 5-(4-(4-fluorobutan-2-ylsulfonyl)phenyl)-3-(5-(4-((2-fluoroethylamino)methyl)phenyl)-1,3,4-oxadiazol-2-yl)pyrazin-2-amine |
| P50 | 5-(4-(4-fluorobutan-2-ylsulfonyl)phenyl)-3-(5-(4-((2-fluoropropylamino)methyl)phenyl)-1,3,4-oxadiazol-2-yl)pyrazin-2-amine |

TABLE IA-4-continued (part 1)

| Cmpd # | Name |
| --- | --- |
| P51 | 5-(4-(4-fluorobutan-2-ylsulfonyl)phenyl)-3-(5-(4-((1-fluoropropan-2-ylamino)methyl)phenyl)-1,3,4-oxadiazol-2-yl)pyrazin-2-amine |
| P52 | 3-(5-(2-fluoro-4-((2-fluoroethylamino)methyl)phenyl)-1,3,4-oxadiazol-2-yl)-5-(4-(4-fluorobutan-2-ylsulfonyl)phenyl)pyrazin-2-amine |
| P53 | 3-(5-(2-fluoro-4-((2-fluoropropylamino)methyl)phenyl)-1,3,4-oxadiazol-2-yl)-5-(4-(4-fluorobutan-2-ylsulfonyl)phenyl)pyrazin-2-amine |
| P54 | 3-(5-(2-fluoro-4-((1-fluoropropan-2-ylamino)methyl)phenyl)-1,3,4-oxadiazol-2-yl)-5-(4-(4-fluorobutan-2-ylsulfonyl)phenyl)pyrazin-2-amine |
| P55 | 3-(5-(2-fluoro-4-(((R)-tetrahydrofuran-3-ylamino)methyl)phenyl)-1,3,4-oxadiazol-2-yl)-5-(4-(4-fluorobutan-2-ylsulfonyl)phenyl)pyrazin-2-amine |
| P56 | 3-(5-(2-fluoro-4-(((S)-tetrahydrofuran-3-ylamino)methyl)phenyl)-1,3,4-oxadiazol-2-yl)-5-(4-(4-fluorobutan-2-ylsulfonyl)phenyl)pyrazin-2-amine |
| P57 | 3-(5-(2-fluoro-4-((methylamino)methyl)phenyl)-1,3,4-oxadiazol-2-yl)-5-(4-(4-fluorobutan-2-ylsulfonyl)phenyl)pyrazin-2-amine |
| P58 | 5-(4-(4-fluorobutan-2-ylsulfonyl)phenyl)-3-(5-(4-(((R)-tetrahydrofuran-3-ylamino)methyl)phenyl)-1,3,4-oxadiazol-2-yl)pyrazin-2-amine |
| P59 | 5-(4-(4-fluorobutan-2-ylsulfonyl)phenyl)-3-(5-(4-(((S)-tetrahydrofuran-3-ylamino)methyl)phenyl)-1,3,4-oxadiazol-2-yl)pyrazin-2-amine |
| P60 | 5-(4-(4-fluorobutan-2-ylsulfonyl)phenyl)-3-(5-(4-((methylamino)methyl)phenyl)-1,3,4-oxadiazol-2-yl)pyrazin-2-amine |
| P61 | 3-(4-(5-amino-6-(5-(4-(((R)-tetrahydrofuran-3-ylamino)methyl)phenyl)-1,3,4-oxadiazol-2-yl)pyrazin-2-yl)phenylsulfonyl)butan-1-ol |
| P62 | 3-(4-(5-amino-6-(5-(4-(((S)-tetrahydrofuran-3-ylamino)methyl)phenyl)-1,3,4-oxadiazol-2-yl)pyrazin-2-yl)phenylsulfonyl)butan-1-ol |
| P63 | 3-(4-(5-amino-6-(5-(4-((methylamino)methyl)phenyl)-1,3,4-oxadiazol-2-yl)pyrazin-2-yl)-2-fluorophenylsulfonyl)butan-1-ol |
| P64 | 3-(4-(5-amino-6-(5-(2-fluoro-4-(((R)-tetrahydrofuran-3-ylamino)methyl)phenyl)-1,3,4-oxadiazol-2-yl)pyrazin-2-yl)phenylsulfonyl)butan-1-ol |
| P65 | 3-(4-(5-amino-6-(5-(2-fluoro-4-(((S)-tetrahydrofuran-3-ylamino)methyl)phenyl)-1,3,4-oxadiazol-2-yl)pyrazin-2-yl)phenylsulfonyl)butan-1-ol |
| P66 | 3-(4-(5-amino-6-(5-(2-fluoro-4-((methylamino)methyl)phenyl)-1,3,4-oxadiazol-2-yl)pyrazin-2-yl)-2-fluorophenylsulfonyl)butan-1-ol |
| P67 | 3-(4-(5-amino-6-(5-(2-fluoro-4-((2-fluoroethylamino)methyl)phenyl)-1,3,4-oxadiazol-2-yl)pyrazin-2-yl)phenylsulfonyl)butan-1-ol |
| P68 | 3-(4-(5-amino-6-(5-(2-fluoro-4-((2-fluoropropylamino)methyl)phenyl)-1,3,4-oxadiazol-2-yl)pyrazin-2-yl)phenylsulfonyl)butan-1-ol |
| P69 | 3-(4-(5-amino-6-(5-(2-fluoro-4-((1-fluoropropan-2-ylamino)methyl)phenyl)-1,3,4-oxadiazol-2-yl)pyrazin-2-yl)phenylsulfonyl)butan-1-ol |
| P70 | 3-(4-(5-amino-6-(5-(4-((2-fluoroethylamino)methyl)phenyl)-1,3,4-oxadiazol-2-yl)pyrazin-2-yl)phenylsulfonyl)butan-1-ol |
| P71 | 3-(4-(5-amino-6-(5-(4-((2-fluoropropylamino)methyl)phenyl)-1,3,4-oxadiazol-2-yl)pyrazin-2-yl)phenylsulfonyl)butan-1-ol |
| P72 | 3-(4-(5-amino-6-(5-(4-((1-fluoropropan-2-ylamino)methyl)phenyl)-1,3,4-oxadiazol-2-yl)pyrazin-2-yl)phenylsulfonyl)butan-1-ol |
| P73 | 3-(3-(4-((2-fluoroethylamino)methyl)phenyl)isoxazol-5-yl)-5-(4-(tetrahydrofuran-3-ylsulfonyl)phenyl)pyrazin-2-amine |
| P74 | 3-(3-(4-((2-fluoropropylamino)methyl)phenyl)isoxazol-5-yl)-5-(4-(tetrahydrofuran-3-ylsulfonyl)phenyl)pyrazin-2-amine |
| P75 | 3-(3-(4-((1-fluoropropan-2-ylamino)methyl)phenyl)isoxazol-5-yl)-5-(4-(tetrahydrofuran-3-ylsulfonyl)phenyl)pyrazin-2-amine |
| P76 | 3-(3-(2-fluoro-4-((2-fluoroethylamino)methyl)phenyl)isoxazol-5-yl)-5-(4-(tetrahydrofuran-3-ylsulfonyl)phenyl)pyrazin-2-amine |
| P77 | 3-(3-(2-fluoro-4-((2-fluoropropylamino)methyl)phenyl)isoxazol-5-yl)-5-(4-(tetrahydrofuran-3-ylsulfonyl)phenyl)pyrazin-2-amine |
| P78 | 3-(3-(2-fluoro-4-((1-fluoropropan-2-ylamino)methyl)phenyl)isoxazol-5-yl)-5-(4-(tetrahydrofuran-3-ylsulfonyl)phenyl)pyrazin-2-amine |
| P79 | 3-(3-(2-fluoro-4-(((S)-tetrahydrofuran-2-ylamino)methyl)phenyl)isoxazol-5-yl)-5-(4-(tetrahydrofuran-3-ylsulfonyl)phenyl)pyrazin-2-amine |
| P80 | 3-(3-(2-fluoro-4-(((S)-tetrahydrofuran-3-ylamino)methyl)phenyl)isoxazol-5-yl)-5-(4-(tetrahydrofuran-3-ylsulfonyl)phenyl)pyrazin-2-amine |
| P81 | 3-(3-(4-((ethylamino)methyl)-2-fluorophenyl)isoxazol-5-yl)-5-(4-(tetrahydrofuran-3-ylsulfonyl)phenyl)pyrazin-2-amine |
| P82 | 3-(3-(4-(((S)-tetrahydrofuran-2-ylamino)methyl)phenyl)isoxazol-5-yl)-5-(4-(tetrahydrofuran-3-ylsulfonyl)phenyl)pyrazin-2-amine |
| P83 | 3-(3-(4-(((S)-tetrahydrofuran-3-ylamino)methyl)phenyl)isoxazol-5-yl)-5-(4-(tetrahydrofuran-3-ylsulfonyl)phenyl)pyrazin-2-amine |
| P84 | 3-(3-(4-((methylamino)methyl)phenyl)isoxazol-5-yl)-5-(4-(tetrahydrofuran-3-ylsulfonyl)phenyl)pyrazin-2-amine |
| P85 | (S)-5-(4-(tetrahydro-2H-pyran-4-ylsulfonyl)phenyl)-3-(3-(4-((tetrahydrofuran-2-ylamino)methyl)phenyl)isoxazol-5-yl)pyrazin-2-amine |
| P86 | (S)-5-(4-(tetrahydro-2H-pyran-4-ylsulfonyl)phenyl)-3-(3-(4-((tetrahydrofuran-3-ylamino)methyl)phenyl)isoxazol-5-yl)pyrazin-2-amine |
| P87 | 3-(3-(4-((methylamino)methyl)phenyl)isoxazol-5-yl)-5-(4-(tetrahydro-2H-pyran-4-ylsulfonyl)phenyl)pyrazin-2-amine |

TABLE IA-4-continued (part 1)

| Cmpd # | Name |
|---|---|
| P88 | (S)-3-(3-(2-fluoro-4-((tetrahydrofuran-2-ylamino)methyl)phenyl)isoxazol-5-yl)-5-(4-(tetrahydro-2H-pyran-4-ylsulfonyl)phenyl)pyrazin-2-amine |
| P89 | (S)-3-(3-(2-fluoro-4-((tetrahydrofuran-3-ylamino)methyl)phenyl)isoxazol-5-yl)-5-(4-(tetrahydro-2H-pyran-4-ylsulfonyl)phenyl)pyrazin-2-amine |
| P90 | 3-(3-(2-fluoro-4-((methylamino)methyl)phenyl)isoxazol-5-yl)-5-(4-(tetrahydro-2H-pyran-4-ylsulfonyl)phenyl)pyrazin-2-amine |
| P91 | 3-(3-(2-fluoro-4-((fluoromethylamino)methyl)phenyl)isoxazol-5-yl)-5-(4-(tetrahydro-2H-pyran-4-ylsulfonyl)phenyl)pyrazin-2-amine |
| P92 | 3-(3-(2-fluoro-4-((2-fluoropropylamino)methyl)phenyl)isoxazol-5-yl)-5-(4-(tetrahydro-2H-pyran-4-ylsulfonyl)phenyl)pyrazin-2-amine |
| P93 | 3-(3-(2-fluoro-4-((1-fluoropropan-2-ylamino)methyl)phenyl)isoxazol-5-yl)-5-(4-(tetrahydro-2H-pyran-4-ylsulfonyl)phenyl)pyrazin-2-amine |
| P94 | 3-(3-(4-((fluoromethylamino)methyl)phenyl)isoxazol-5-yl)-5-(4-(tetrahydro-2H-pyran-4-ylsulfonyl)phenyl)pyrazin-2-amine |
| P95 | 3-(3-(4-((2-fluoropropylamino)methyl)phenyl)isoxazol-5-yl)-5-(4-(tetrahydro-2H-pyran-4-ylsulfonyl)phenyl)pyrazin-2-amine |
| P96 | 3-(3-(4-((1-fluoropropan-2-ylamino)methyl)phenyl)isoxazol-5-yl)-5-(4-(tetrahydro-2H-pyran-4-ylsulfonyl)phenyl)pyrazin-2-amine |
| P97 | 5-(4-(sec-butylsulfonyl)phenyl)-3-(3-(4-((fluoromethylamino)methyl)phenyl)isoxazol-5-yl)pyrazin-2-amine |
| P98 | 5-(4-(sec-butylsulfonyl)phenyl)-3-(3-(4-((2-fluoropropylamino)methyl)phenyl)isoxazol-5-yl)pyrazin-2-amine |
| P99 | 5-(4-(sec-butylsulfonyl)phenyl)-3-(3-(4-((1-fluoropropan-2-ylamino)methyl)phenyl)isoxazol-5-yl)pyrazin-2-amine |
| P100 | 5-(4-(sec-butylsulfonyl)phenyl)-3-(3-(2-fluoro-4-((fluoromethylamino)methyl)phenyl)isoxazol-5-yl)pyrazin-2-amine |
| P101 | 5-(4-(sec-butylsulfonyl)phenyl)-3-(3-(2-fluoro-4-((2-fluoropropylamino)methyl)phenyl)isoxazol-5-yl)pyrazin-2-amine |
| P102 | 5-(4-(sec-butylsulfonyl)phenyl)-3-(3-(2-fluoro-4-((1-fluoropropan-2-ylamino)methyl)phenyl)isoxazol-5-yl)pyrazin-2-amine |
| P103 | 5-(4-(sec-butylsulfonyl)phenyl)-3-(3-(2-fluoro-4-(((R)-tetrahydrofuran-3-ylamino)methyl)phenyl)isoxazol-5-yl)pyrazin-2-amine |
| P104 | 5-(4-(sec-butylsulfonyl)phenyl)-3-(3-(2-fluoro-4-(((S)-tetrahydrofuran-3-ylamino)methyl)phenyl)isoxazol-5-yl)pyrazin-2-amine |
| P105 | 5-(4-(sec-butylsulfonyl)phenyl)-3-(3-(2-fluoro-4-((methylamino)methyl)phenyl)isoxazol-5-yl)pyrazin-2-amine |
| P106 | 5-(4-(sec-butylsulfonyl)phenyl)-3-(3-(4-(((R)-tetrahydrofuran-3-ylamino)methyl)phenyl)isoxazol-5-yl)pyrazin-2-amine |
| P107 | 5-(4-(sec-butylsulfonyl)phenyl)-3-(3-(4-(((S)-tetrahydrofuran-3-ylamino)methyl)phenyl)isoxazol-5-yl)pyrazin-2-amine |
| P108 | 5-(4-(sec-butylsulfonyl)phenyl)-3-(3-(4-((methylamino)methyl)phenyl)isoxazol-5-yl)pyrazin-2-amine |
| P109 | (R)-5-(4-(isopropylsulfonyl)phenyl)-3-(3-(4-((tetrahydrofuran-3-ylamino)methyl)phenyl)isoxazol-5-yl)pyrazin-2-amine |
| P110 | (S)-5-(4-(isopropylsulfonyl)phenyl)-3-(3-(4-((tetrahydrofuran-3-ylamino)methyl)phenyl)isoxazol-5-yl)pyrazin-2-amine |
| P111 | 5-(3-chloro-4-(isopropylsulfonyl)phenyl)-3-(3-(4-((methylamino)methyl)phenyl)isoxazol-5-yl)pyrazin-2-amine |
| P112 | (R)-3-(3-(2-fluoro-4-((tetrahydrofuran-3-ylamino)methyl)phenyl)isoxazol-5-yl)-5-(4-(isopropylsulfonyl)phenyl)pyrazin-2-amine |
| P113 | (S)-3-(3-(2-fluoro-4-((tetrahydrofuran-3-ylamino)methyl)phenyl)isoxazol-5-yl)-5-(4-(isopropylsulfonyl)phenyl)pyrazin-2-amine |
| P114 | 3-(3-(2-fluoro-4-((methylamino)methyl)phenyl)isoxazol-5-yl)-5-(4-(isopropylsulfonyl)phenyl)pyrazin-2-amine |
| P115 | 3-(3-(2-fluoro-4-((2-fluoroethylamino)methyl)phenyl)isoxazol-5-yl)-5-(4-(isopropylsulfonyl)phenyl)pyrazin-2-amine |
| P116 | 3-(3-(2-fluoro-4-((1-fluoropropan-2-ylamino)methyl)phenyl)isoxazol-5-yl)-5-(4-(isopropylsulfonyl)phenyl)pyrazin-2-amine |
| P117 | 3-(3-(2-fluoro-4-((2-fluoropropylamino)methyl)phenyl)isoxazol-5-yl)-5-(4-(isopropylsulfonyl)phenyl)pyrazin-2-amine |
| P118 | 3-(3-(4-((2-fluoroethylamino)methyl)phenyl)isoxazol-5-yl)-5-(4-(isopropylsulfonyl)phenyl)pyrazin-2-amine |
| P119 | 3-(3-(4-((1-fluoropropan-2-ylamino)methyl)phenyl)isoxazol-5-yl)-5-(4-(isopropylsulfonyl)phenyl)pyrazin-2-amine |
| P120 | 3-(3-(4-((2-fluoropropylamino)methyl)phenyl)isoxazol-5-yl)-5-(4-(isopropylsulfonyl)phenyl)pyrazin-2-amine |
| P121 | 5-(4-(4-fluorobutan-2-ylsulfonyl)phenyl)-3-(3-(4-((2-fluoroethylamino)methyl)phenyl)isoxazol-5-yl)pyrazin-2-amine |
| P122 | 5-(4-(4-fluorobutan-2-ylsulfonyl)phenyl)-3-(3-(4-((1-fluoropropan-2-ylamino)methyl)phenyl)isoxazol-5-yl)pyrazin-2-amine |
| P123 | 5-(4-(4-fluorobutan-2-ylsulfonyl)phenyl)-3-(3-(4-((2-fluoropropylamino)methyl)phenyl)isoxazol-5-yl)pyrazin-2-amine |
| P124 | 3-(3-(2-fluoro-4-((2-fluoroethylamino)methyl)phenyl)isoxazol-5-yl)-5-(4-(4-fluorobutan-2-ylsulfonyl)phenyl)pyrazin-2-amine |

TABLE IA-4-continued (part 1)

| Cmpd # | Name |
|---|---|
| P125 | 3-(3-(2-fluoro-4-((1-fluoropropan-2-ylamino)methyl)phenyl)isoxazol-5-yl)-5-(4-(4-fluorobutan-2-ylsulfonyl)phenyl)pyrazin-2-amine |
| P126 | 3-(3-(2-fluoro-4-((2-fluoropropylamino)methyl)phenyl)isoxazol-5-yl)-5-(4-(4-fluorobutan-2-ylsulfonyl)phenyl)pyrazin-2-amine |
| P127 | 3-(3-(2-fluoro-4-(((R)-tetrahydrofuran-3-ylamino)methyl)phenyl)isoxazol-5-yl)-5-(4-(4-fluorobutan-2-ylsulfonyl)phenyl)pyrazin-2-amine |
| P128 | 3-(3-(2-fluoro-4-(((S)-tetrahydrofuran-3-ylamino)methyl)phenyl)isoxazol-5-yl)-5-(4-(4-fluorobutan-2-ylsulfonyl)phenyl)pyrazin-2-amine |
| P129 | 3-(3-(2-fluoro-4-((methylamino)methyl)phenyl)isoxazol-5-yl)-5-(4-(4-fluorobutan-2-ylsulfonyl)phenyl)pyrazin-2-amine |
| P130 | 5-(4-(4-fluorobutan-2-ylsulfonyl)phenyl)-3-(3-(4-(((R)-tetrahydrofuran-3-ylamino)methyl)phenyl)isoxazol-5-yl)pyrazin-2-amine |
| P131 | 5-(4-(4-fluorobutan-2-ylsulfonyl)phenyl)-3-(3-(4-(((S)-tetrahydrofuran-3-ylamino)methyl)phenyl)isoxazol-5-yl)pyrazin-2-amine |
| P132 | 5-(4-(4-fluorobutan-2-ylsulfonyl)phenyl)-3-(3-(4-((methylamino)methyl)phenyl)isoxazol-5-yl)pyrazin-2-amine |
| P133 | 3-(4-(5-amino-6-(3-(4-(((R)-tetrahydrofuran-3-ylamino)methyl)phenyl)isoxazol-5-yl)pyrazin-2-yl)phenylsulfonyl)butan-1-ol |
| P134 | 3-(4-(5-amino-6-(3-(4-(((S)-tetrahydrofuran-3-ylamino)methyl)phenyl)isoxazol-5-yl)pyrazin-2-yl)phenylsulfonyl)butan-1-ol |
| P135 | 3-(4-(5-amino-6-(3-(4-((methylamino)methyl)phenyl)isoxazol-5-yl)pyrazin-2-yl)phenylsulfonyl)butan-1-ol |
| P136 | 3-(4-(5-amino-6-(3-(2-fluoro-4-(((R)-tetrahydrofuran-3-ylamino)methyl)phenyl)isoxazol-5-yl)pyrazin-2-yl)phenylsulfonyl)butan-1-ol |
| P137 | 3-(4-(5-amino-6-(3-(2-fluoro-4-(((S)-tetrahydrofuran-3-ylamino)methyl)phenyl)isoxazol-5-yl)pyrazin-2-yl)phenylsulfonyl)butan-1-ol |
| P138 | 3-(4-(5-amino-6-(3-(2-fluoro-4-((methylamino)methyl)phenyl)isoxazol-5-yl)pyrazin-2-yl)phenylsulfonyl)butan-1-ol |
| P139 | 3-(4-(5-amino-6-(3-(2-fluoro-4-((2-fluoroethylamino)methyl)phenyl)isoxazol-5-yl)pyrazin-2-yl)phenylsulfonyl)butan-1-ol |
| P140 | 3-(4-(5-amino-6-(3-(2-fluoro-4-((1-fluoropropan-2-ylamino)methyl)phenyl)isoxazol-5-yl)pyrazin-2-yl)phenylsulfonyl)butan-1-ol |
| P141 | 3-(4-(5-amino-6-(3-(2-fluoro-4-((2-fluoropropylamino)methyl)phenyl)isoxazol-5-yl)pyrazin-2-yl)phenylsulfonyl)butan-1-ol |
| P142 | 3-(4-(5-amino-6-(3-(4-((2-fluoroethylamino)methyl)phenyl)isoxazol-5-yl)pyrazin-2-yl)phenylsulfonyl)butan-1-ol |
| P143 | 3-(4-(5-amino-6-(3-(4-((1-fluoropropan-2-ylamino)methyl)phenyl)isoxazol-5-yl)pyrazin-2-yl)phenylsulfonyl)butan-1-ol |
| P144 | 3-(4-(5-amino-6-(3-(4-((2-fluoropropylamino)methyl)phenyl)isoxazol-5-yl)pyrazin-2-yl)phenylsulfonyl)butan-1-ol |
| P145 | 3-(3-(4-(1-amino-2,2-difluoroethyl)phenyl)isoxazol-5-yl)-5-(4-(sec-butylsulfonyl)phenyl)pyrazin-2-amine |
| P146 | 3-(5-(4-(1-amino-2,2-difluoroethyl)phenyl)-1,3,4-oxadiazol-2-yl)-5-(4-(isopropylsulfonyl)phenyl)pyrazin-2-amine |
| P147 | 3-(3-(4-(1-amino-2,2-difluoroethyl)-2-fluorophenyl)isoxazol-5-yl)-5-(4-(tetrahydrofuran-3-ylsulfonyl)phenyl)pyrazin-2-amine |
| P148 | 3-(3-(4-(1-amino-2-fluoroethyl)phenyl)isoxazol-5-yl)-5-(4-(sec-butylsulfonyl)phenyl)pyrazin-2-amine |
| P149 | 3-(5-(4-(1-amino-2-fluoroethyl)phenyl)-1,3,4-oxadiazol-2-yl)-5-(4-(isopropylsulfonyl)phenyl)pyrazin-2-amine |
| P150 | 3-(3-(4-(1-amino-2-fluoroethyl)-2-fluorophenyl)isoxazol-5-yl)-5-(4-(tetrahydrofuran-3-ylsulfonyl)phenyl)pyrazin-2-amine |

TABLE IA-4

(part 2)

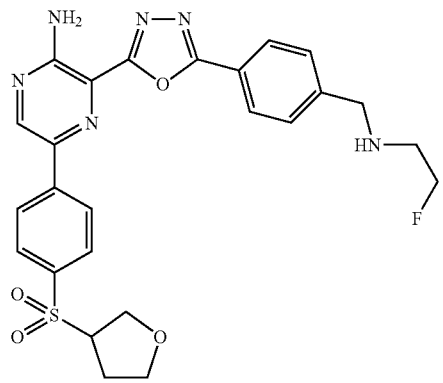 [SMILES: Nc1ncc(-c2ccc(S(=O)(=O)C3CCOC3)cc2)nc1-c1nnc(-c2ccc(CNCCF)cc2)o1]

P1

TABLE IA-4-continued

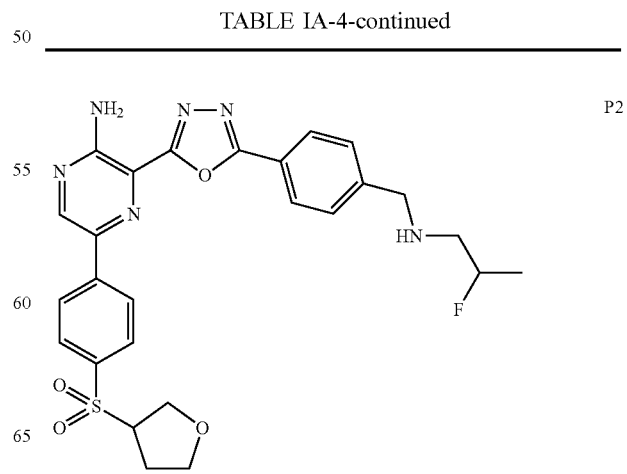

P2

TABLE IA-4-continued
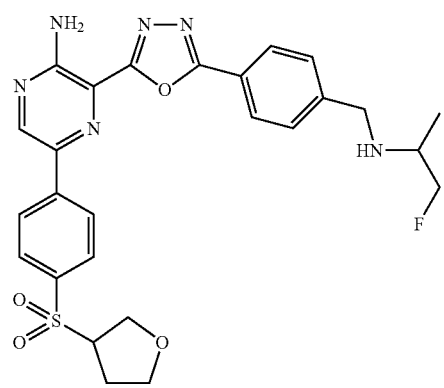 [SMILES: CC(CF)NCc1ccc(-c2nnc(-c3nc(-c4ccc(S(=O)(=O)C5CCOC5)cc4)cnc3N)o2)cc1]
P3
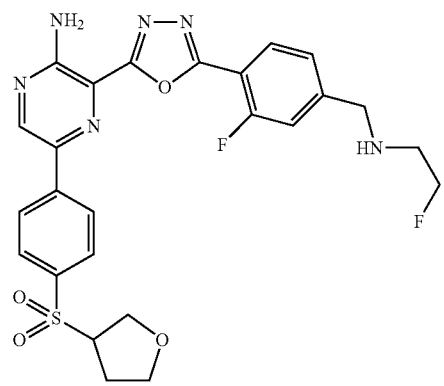 [SMILES: Nc1ncc(-c2ccc(S(=O)(=O)C3CCOC3)cc2)nc1-c1nnc(-c2ccc(CNCCF)cc2F)o1]
P4
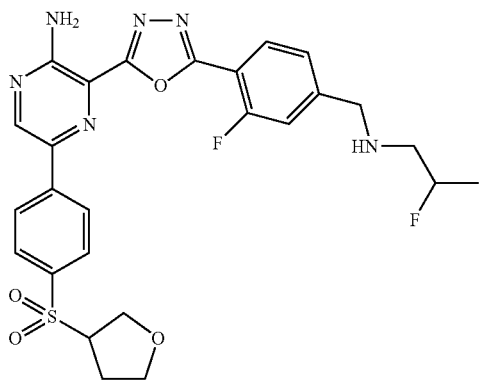 [SMILES: CC(F)CNCc1ccc(-c2nnc(-c3nc(-c4ccc(S(=O)(=O)C5CCOC5)cc4)cnc3N)o2)c(F)c1]
P5
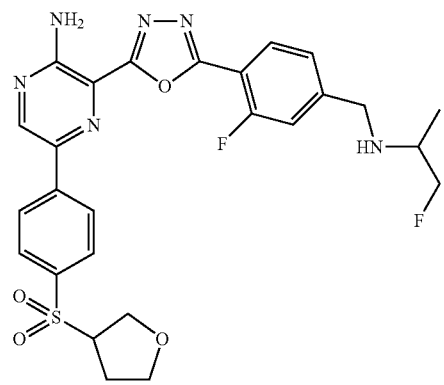 [SMILES: CC(CF)NCc1ccc(-c2nnc(-c3nc(-c4ccc(S(=O)(=O)C5CCOC5)cc4)cnc3N)o2)c(F)c1]
P6
TABLE IA-4-continued
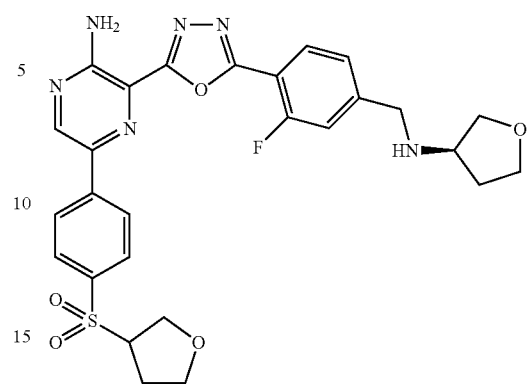
P7
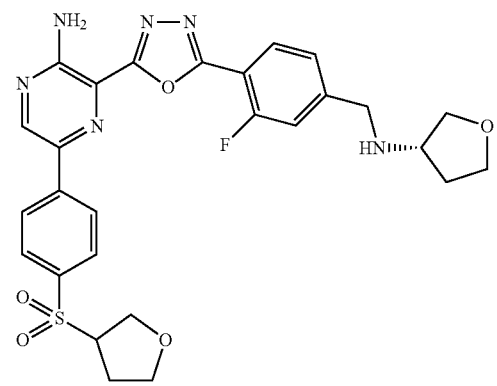 [SMILES: Nc1ncc(-c2ccc(S(=O)(=O)C3CCOC3)cc2)nc1-c1nnc(-c2ccc(CN[C@H]3CCOC3)cc2F)o1]
P8
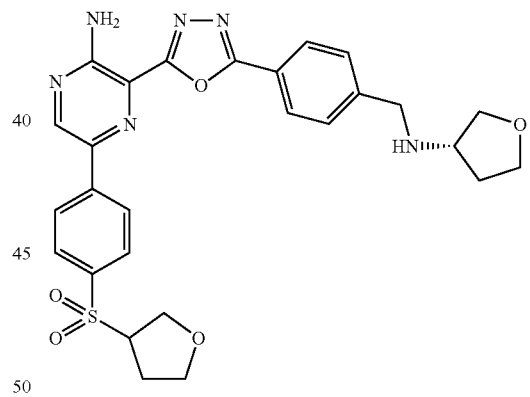
P9
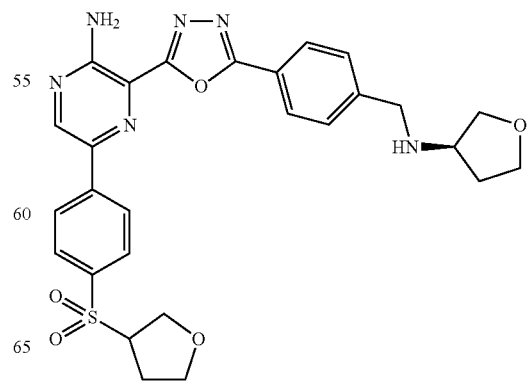
P10

TABLE IA-4-continued
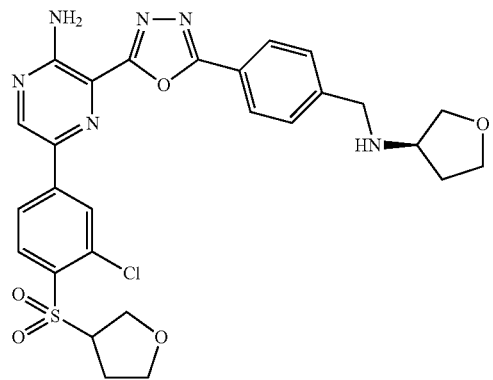 [SMILES: Nc1ncc(-c2ccc(S(=O)(=O)C3CCOC3)c(Cl)c2)nc1-c1nnc(-c2ccc(CN[C@@H]3CCOC3)cc2)o1] P11
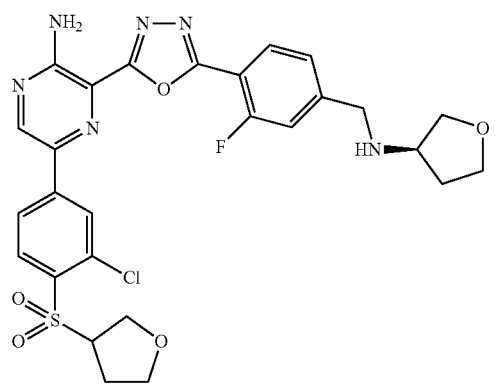 [SMILES: Nc1ncc(-c2ccc(S(=O)(=O)C3CCOC3)c(Cl)c2)nc1-c1nnc(-c2ccc(CN[C@@H]3CCOC3)cc2F)o1] P12
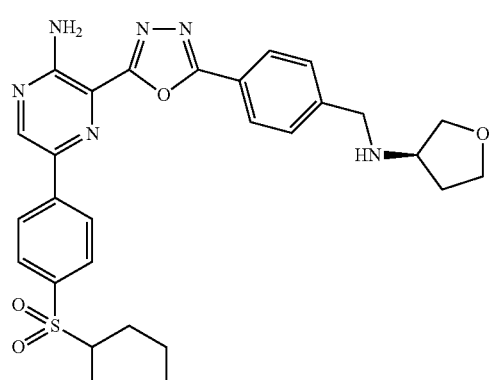 P13
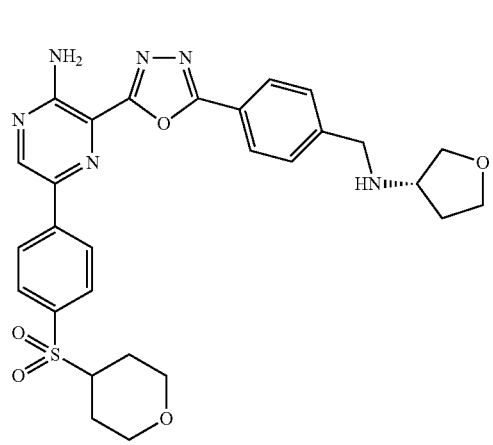 [SMILES: Nc1ncc(-c2ccc(S(=O)(=O)C3CCOCC3)cc2)nc1-c1nnc(-c2ccc(CN[C@H]3CCOC3)cc2)o1] P14
TABLE IA-4-continued
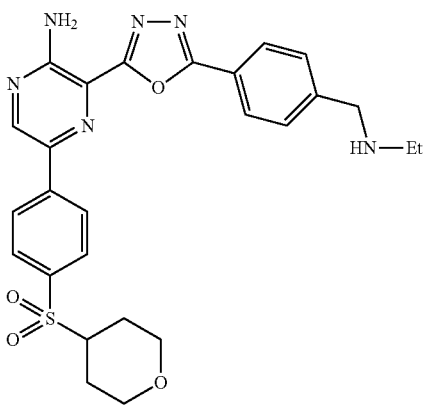 [SMILES: CCNCc1ccc(-c2nnc(-c3nc(-c4ccc(S(=O)(=O)C5CCOCC5)cc4)cnc3N)o2)cc1] P15
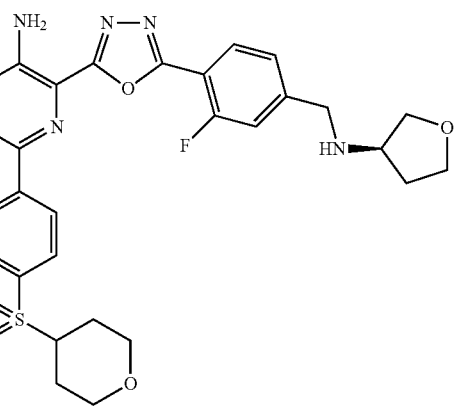 P16
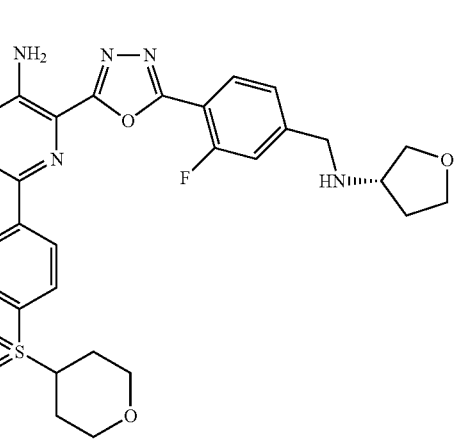 P17
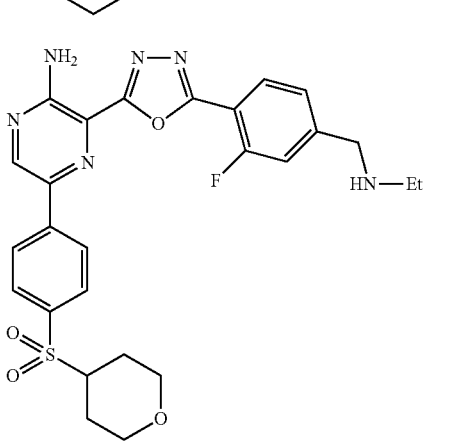 P18

TABLE IA-4-continued
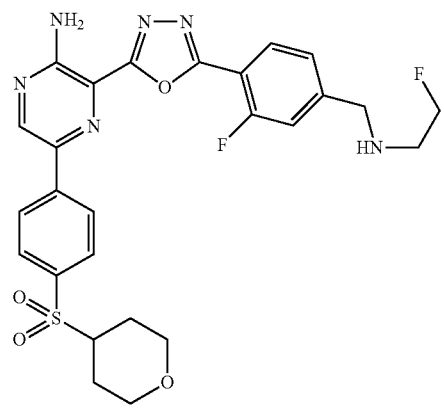 [SMILES: Nc1ncc(-c2ccc(S(=O)(=O)C3CCOCC3)cc2)nc1-c1nnc(-c2ccc(CNCCF)cc2F)o1] P19
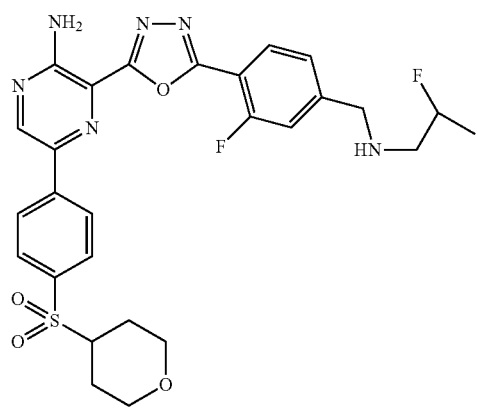 [SMILES: CC(F)CNCc1ccc(-c2nnc(-c3nc(-c4ccc(S(=O)(=O)C5CCOCC5)cc4)cnc3N)o2)c(F)c1] P20
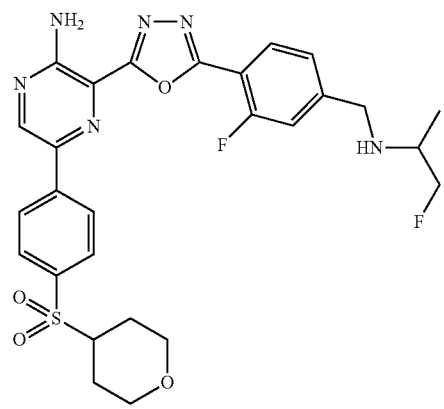 [SMILES: CC(CF)NCc1ccc(-c2nnc(-c3nc(-c4ccc(S(=O)(=O)C5CCOCC5)cc4)cnc3N)o2)c(F)c1] P21
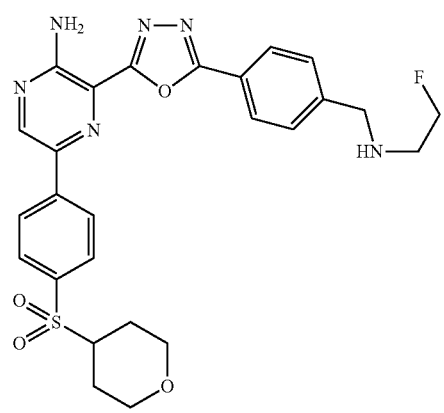 [SMILES: Nc1ncc(-c2ccc(S(=O)(=O)C3CCOCC3)cc2)nc1-c1nnc(-c2ccc(CNCCF)cc2)o1] P22
TABLE IA-4-continued
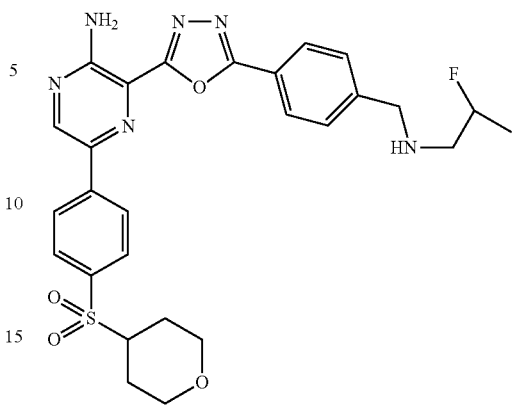 P23
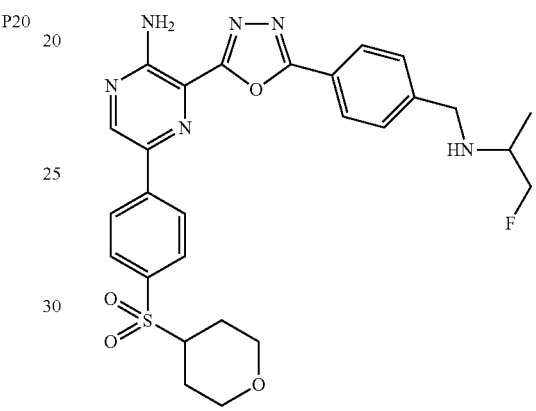 P24
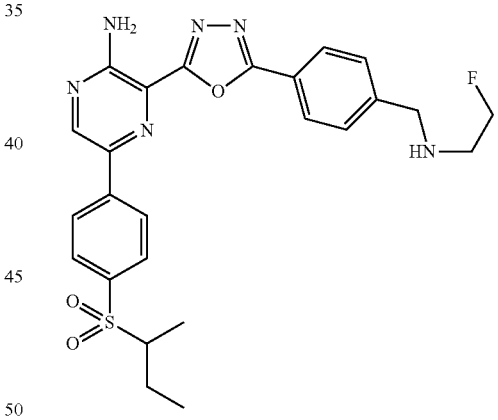 P25
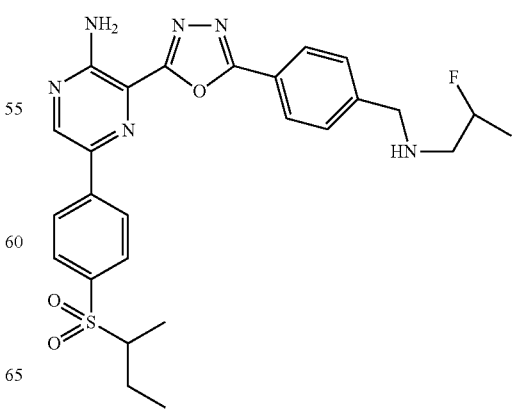 P26

157
TABLE IA-4-continued
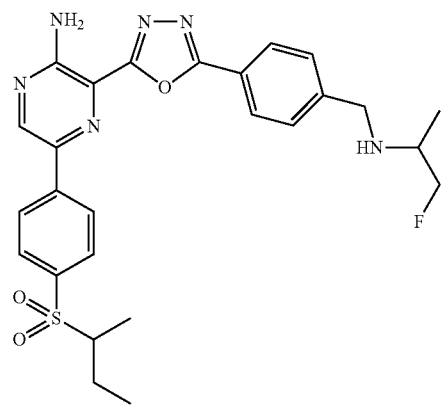 [SMILES: CCC(C)S(=O)(=O)c1ccc(-c2cnc(N)c(-c3nnc(-c4ccc(CNC(C)CF)cc4)o3)n2)cc1]
P27
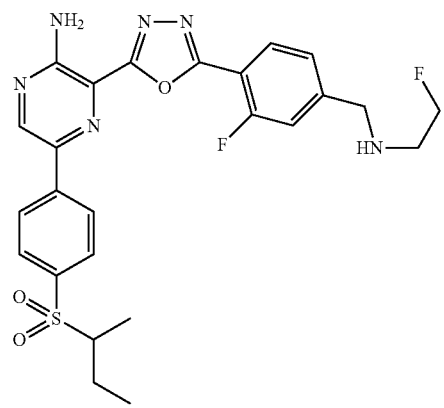 [SMILES: CCC(C)S(=O)(=O)c1ccc(-c2cnc(N)c(-c3nnc(-c4ccc(CNCCF)cc4F)o3)n2)cc1]
P28
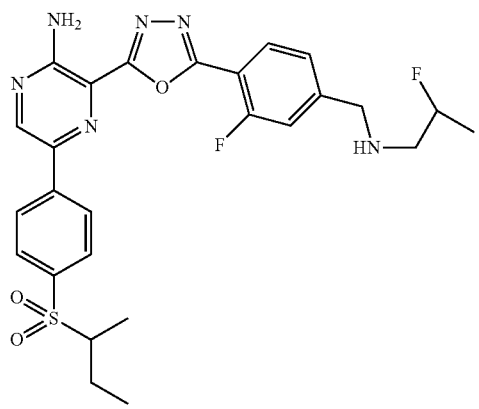 [SMILES: CCC(C)S(=O)(=O)c1ccc(-c2cnc(N)c(-c3nnc(-c4ccc(CNCC(C)F)cc4F)o3)n2)cc1]
P29
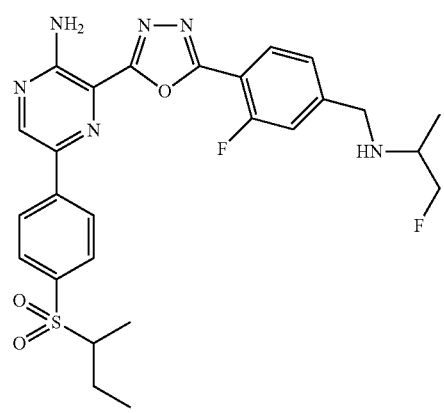 [SMILES: CCC(C)S(=O)(=O)c1ccc(-c2cnc(N)c(-c3nnc(-c4ccc(CNC(C)CF)cc4F)o3)n2)cc1]
P30
158
TABLE IA-4-continued
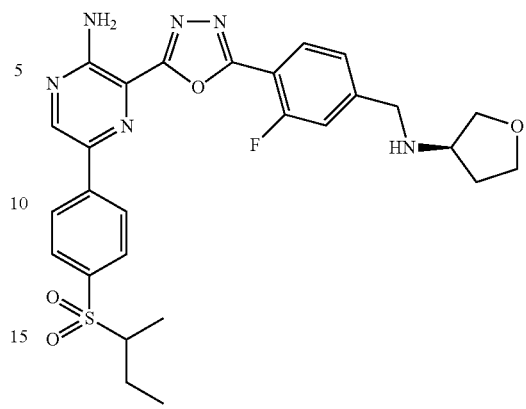
P31
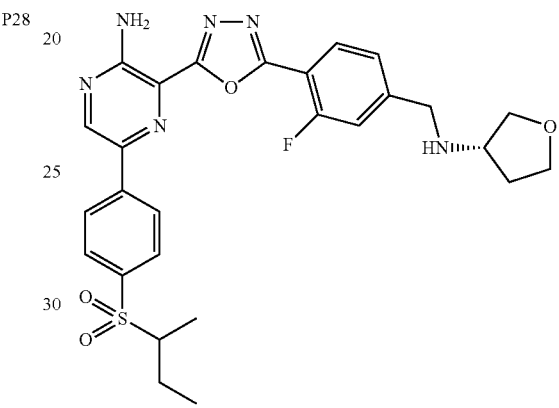
P32
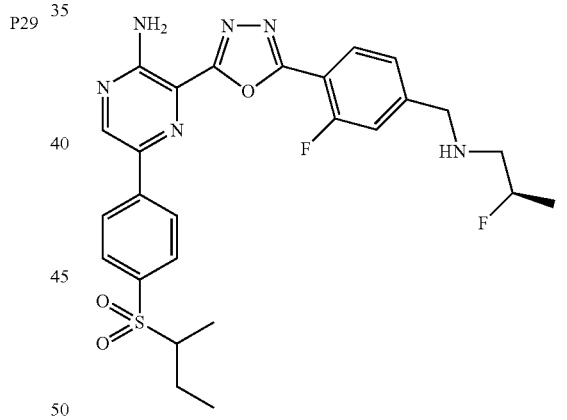
P33
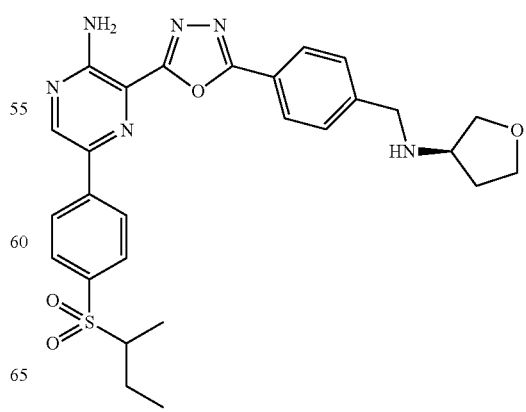
P34

TABLE IA-4-continued
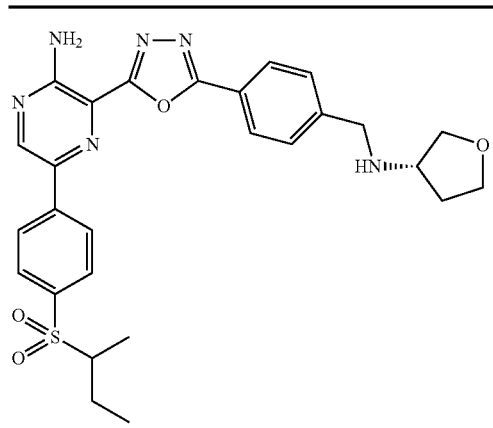
P35
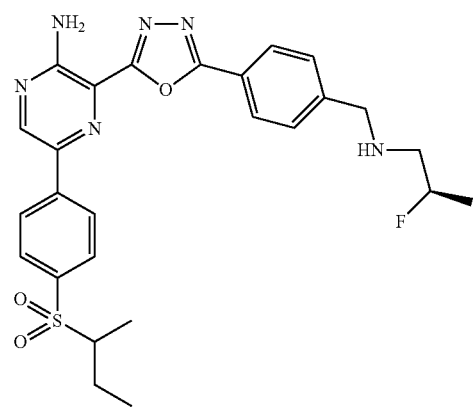 [SMILES: CCC(C)S(=O)(=O)c1ccc(-c2cnc(N)c(-c3nnc(-c4ccc(CNC[C@@H](C)F)cc4)o3)n2)cc1]
P36
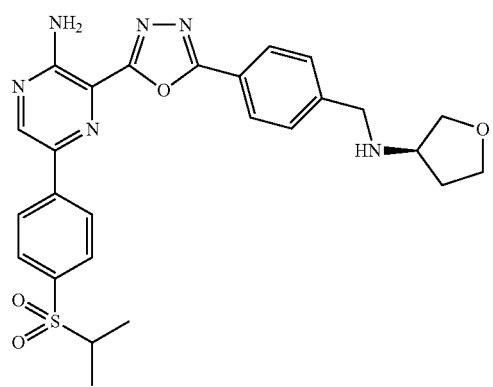 [SMILES: CC(C)S(=O)(=O)c1ccc(-c2cnc(N)c(-c3nnc(-c4ccc(CN[C@@H]5CCOC5)cc4)o3)n2)cc1]
P37
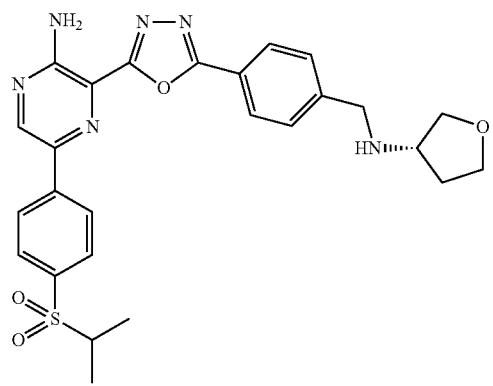 [SMILES: CC(C)S(=O)(=O)c1ccc(-c2cnc(N)c(-c3nnc(-c4ccc(CN[C@H]5CCOC5)cc4)o3)n2)cc1]
P38
TABLE IA-4-continued
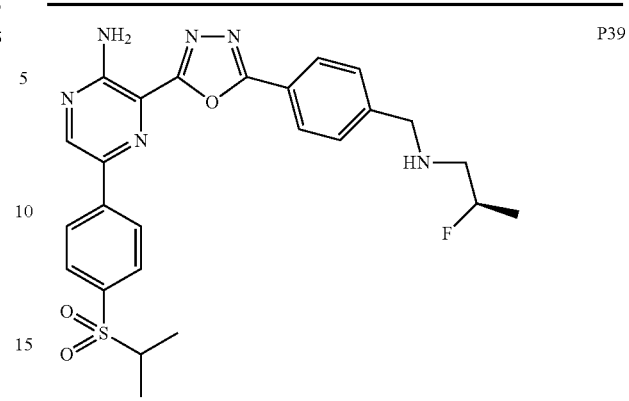
P39
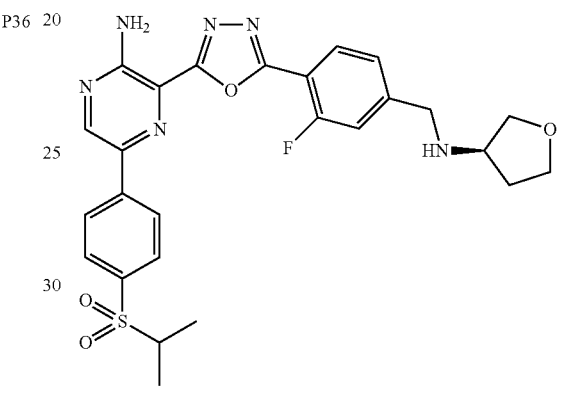
P40
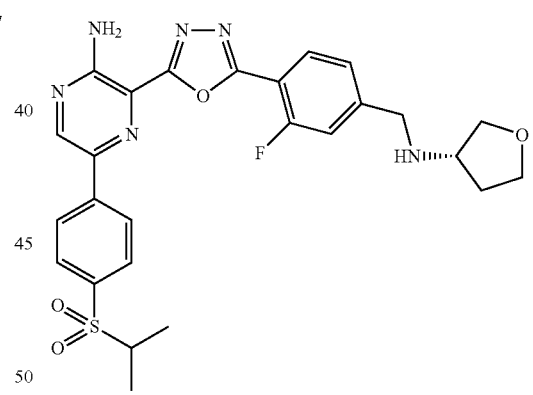
P41
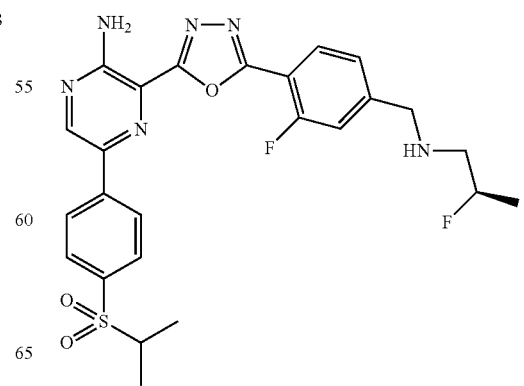
P42

TABLE IA-4-continued
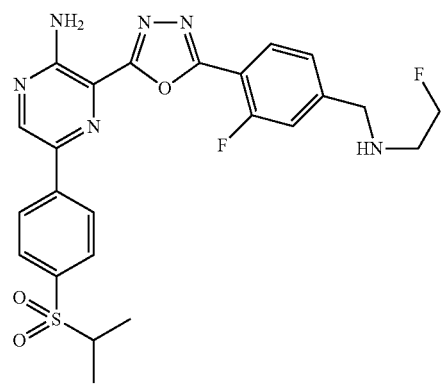 [SMILES: CC(C)S(=O)(=O)c1ccc(-c2cnc(N)c(-c3nnc(-c4ccc(CNCCF)cc4F)o3)n2)cc1]
P43
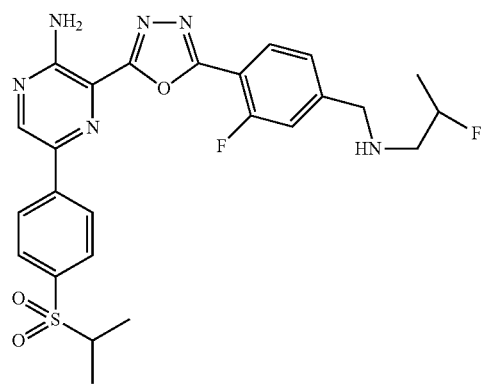 [SMILES: CC(F)CNCc1ccc(-c2nnc(-c3nc(-c4ccc(S(=O)(=O)C(C)C)cc4)cnc3N)o2)c(F)c1]
P44
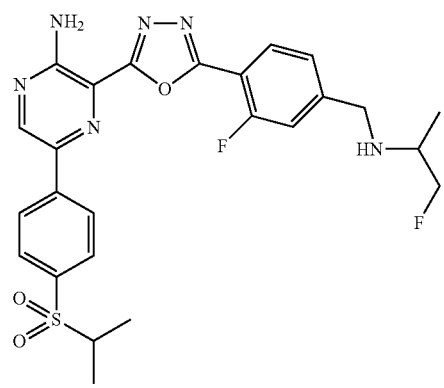 [SMILES: CC(CF)NCc1ccc(-c2nnc(-c3nc(-c4ccc(S(=O)(=O)C(C)C)cc4)cnc3N)o2)c(F)c1]
P45
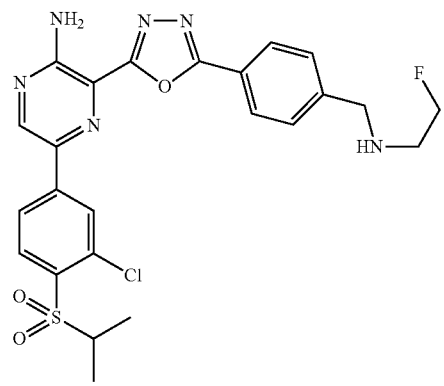 [SMILES: CC(C)S(=O)(=O)c1ccc(-c2cnc(N)c(-c3nnc(-c4ccc(CNCCF)cc4)o3)n2)cc1Cl]
P46
TABLE IA-4-continued
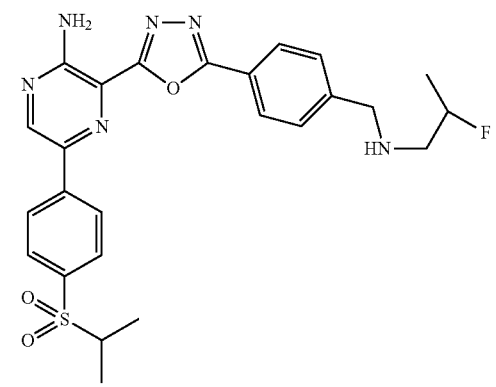 [SMILES: CC(F)CNCc1ccc(-c2nnc(-c3nc(-c4ccc(S(=O)(=O)C(C)C)cc4)cnc3N)o2)cc1]
P47
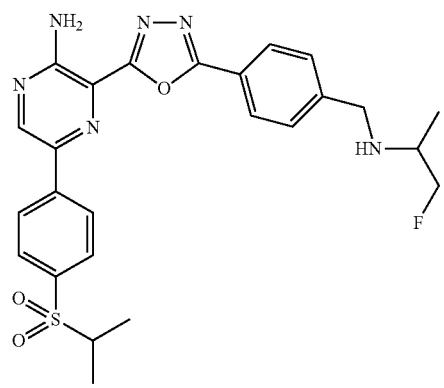 [SMILES: CC(CF)NCc1ccc(-c2nnc(-c3nc(-c4ccc(S(=O)(=O)C(C)C)cc4)cnc3N)o2)cc1]
P48
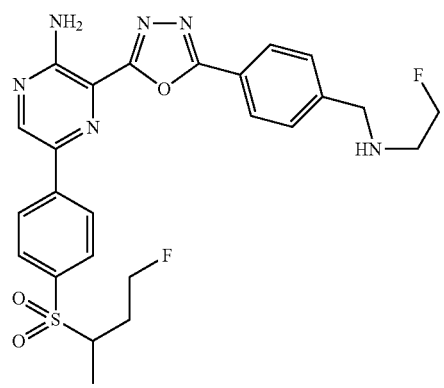 [SMILES: CC(CCF)S(=O)(=O)c1ccc(-c2cnc(N)c(-c3nnc(-c4ccc(CNCCF)cc4)o3)n2)cc1]
P49
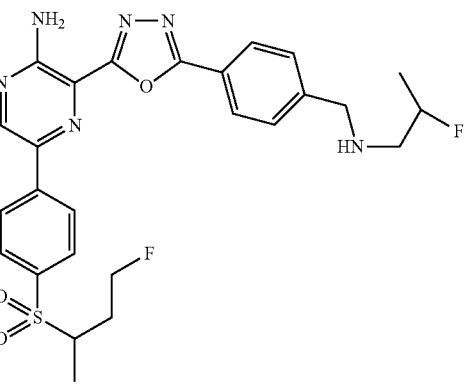
P50

TABLE IA-4-continued
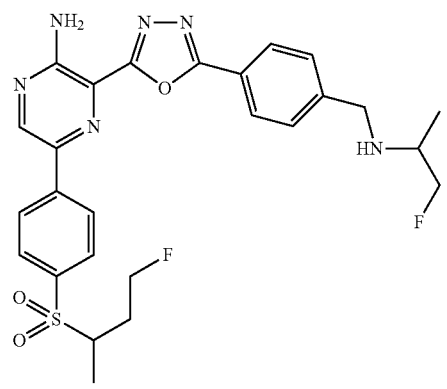 [SMILES: CC(CF)NCc1ccc(-c2nnc(-c3nc(-c4ccc(S(=O)(=O)C(C)CCF)cc4)cnc3N)o2)cc1] P51
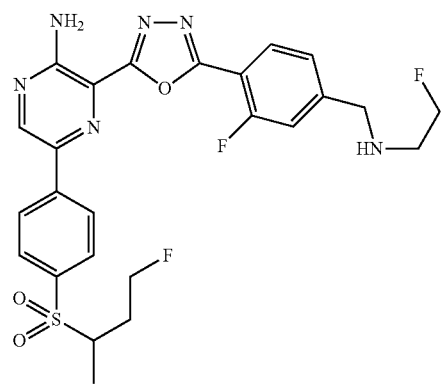 [SMILES: CC(CCF)S(=O)(=O)c1ccc(-c2cnc(N)c(-c3nnc(-c4ccc(CNCCF)cc4F)o3)n2)cc1] P52
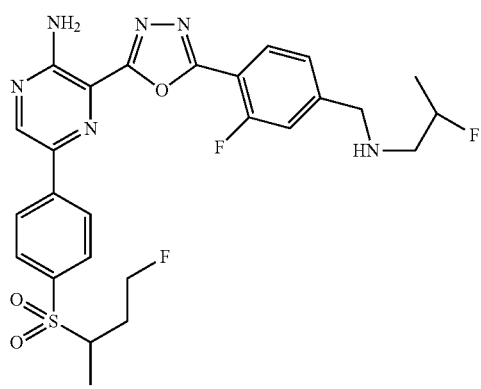 [SMILES: CC(F)CNCc1ccc(-c2nnc(-c3nc(-c4ccc(S(=O)(=O)C(C)CCF)cc4)cnc3N)o2)c(F)c1] P53
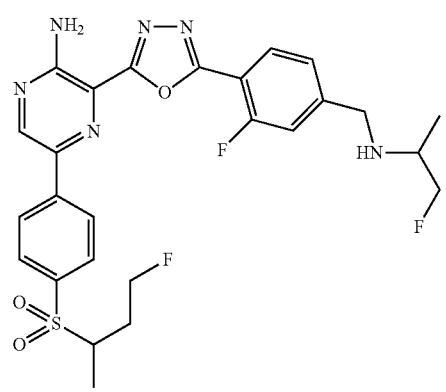 [SMILES: CC(CF)NCc1ccc(-c2nnc(-c3nc(-c4ccc(S(=O)(=O)C(C)CCF)cc4)cnc3N)o2)c(F)c1] P54
TABLE IA-4-continued
 P55
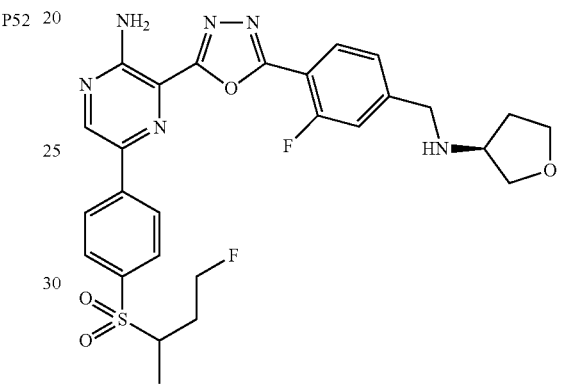 P56
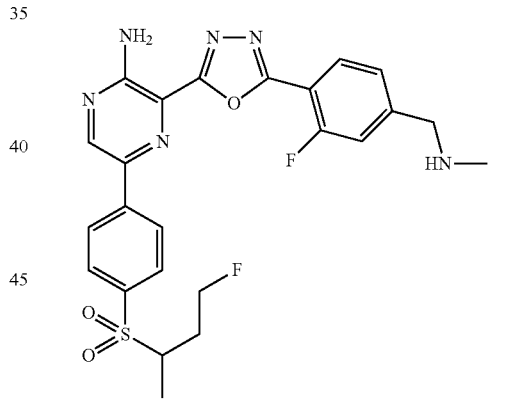 P57
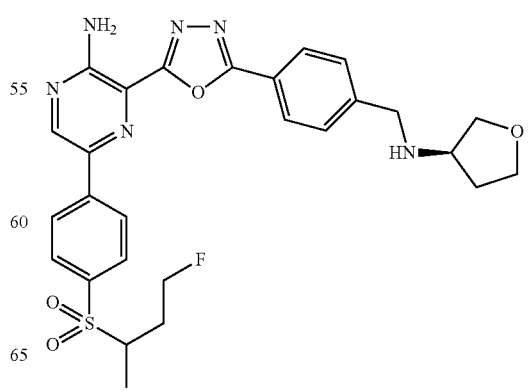 P58

TABLE IA-4-continued
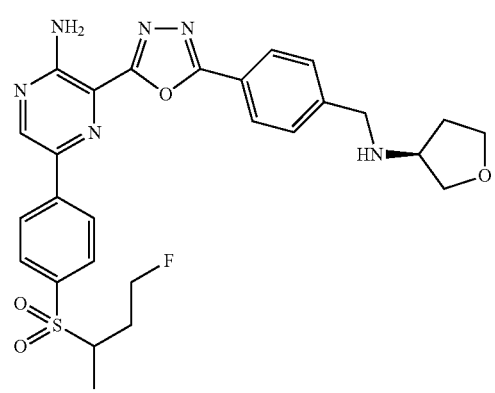 [SMILES: CC(CCF)S(=O)(=O)c1ccc(-c2cnc(N)c(-c3nnc(-c4ccc(CN[C@H]5CCOC5)cc4)o3)n2)cc1] P59
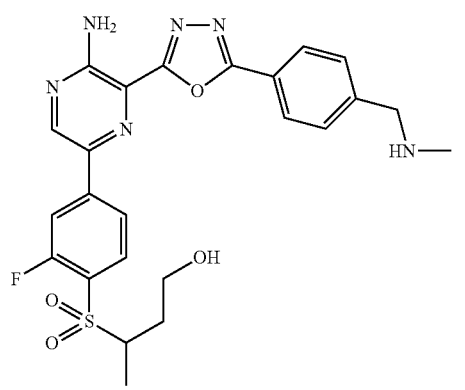 P63
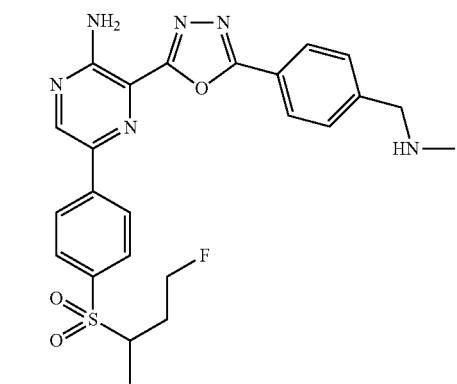 [SMILES: CNCc1ccc(-c2nnc(-c3nc(-c4ccc(S(=O)(=O)C(C)CCF)cc4)cnc3N)o2)cc1] P60
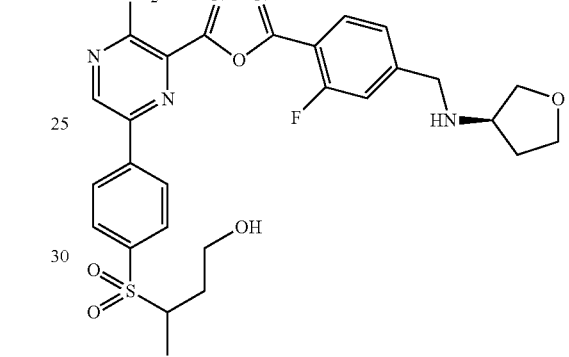 P64
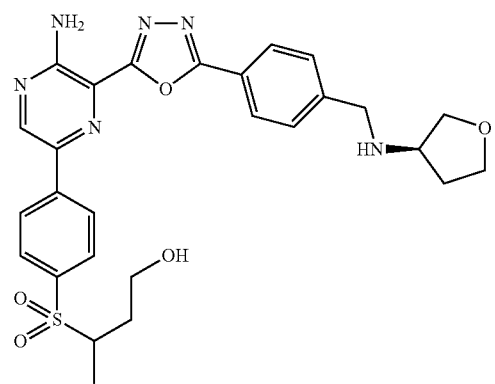 [SMILES: CC(CCO)S(=O)(=O)c1ccc(-c2cnc(N)c(-c3nnc(-c4ccc(CN[C@@H]5CCOC5)cc4)o3)n2)cc1] P61
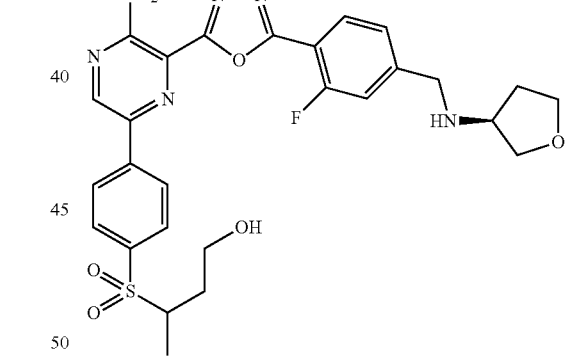 P65
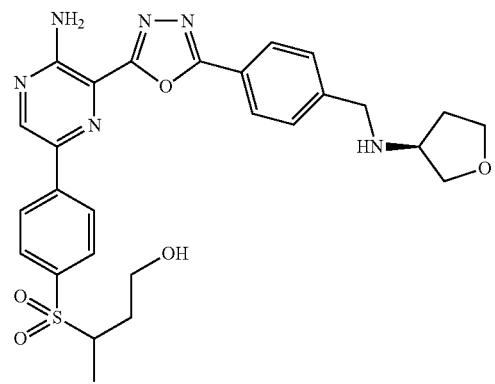 [SMILES: CC(CCO)S(=O)(=O)c1ccc(-c2cnc(N)c(-c3nnc(-c4ccc(CN[C@H]5CCOC5)cc4)o3)n2)cc1] P62
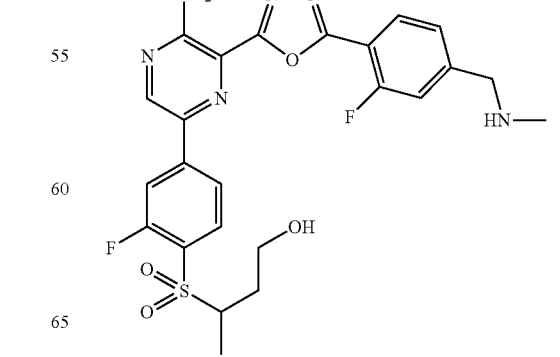 P66

TABLE IA-4-continued
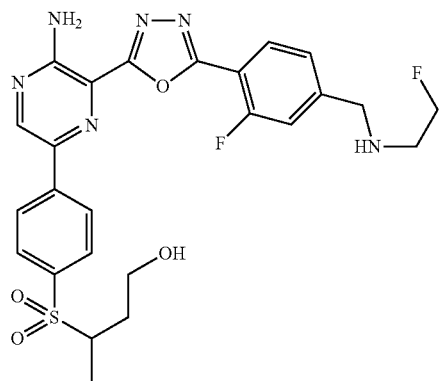 [SMILES: CC(CCO)S(=O)(=O)c1ccc(-c2cnc(N)c(-c3nnc(-c4ccc(CNCCF)cc4F)o3)n2)cc1] P67
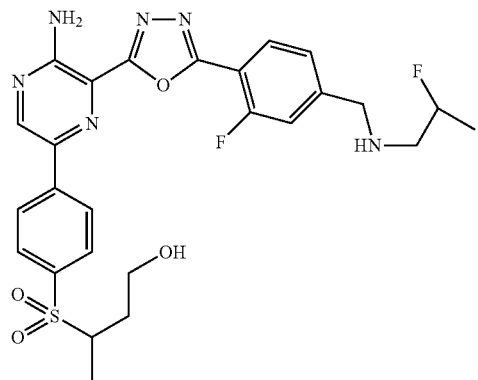 [SMILES: CC(F)CNCc1ccc(-c2nnc(-c3nc(-c4ccc(S(=O)(=O)C(C)CCO)cc4)cnc3N)o2)c(F)c1] P68
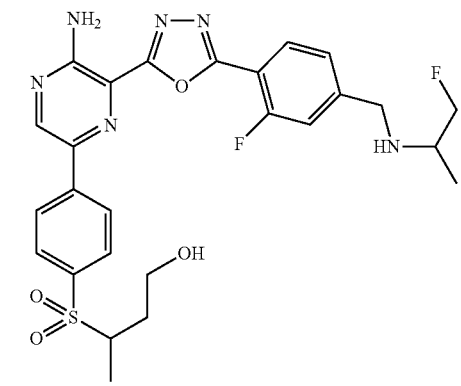 [SMILES: CC(CF)NCc1ccc(-c2nnc(-c3nc(-c4ccc(S(=O)(=O)C(C)CCO)cc4)cnc3N)o2)c(F)c1] P69
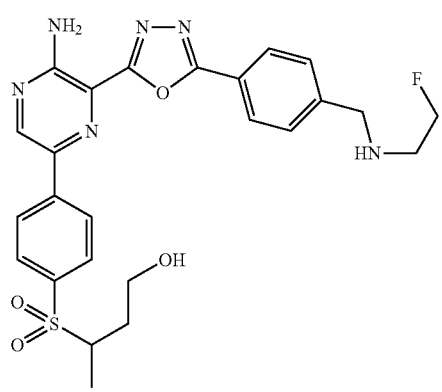 [SMILES: CC(CCO)S(=O)(=O)c1ccc(-c2cnc(N)c(-c3nnc(-c4ccc(CNCCF)cc4)o3)n2)cc1] P70
TABLE IA-4-continued
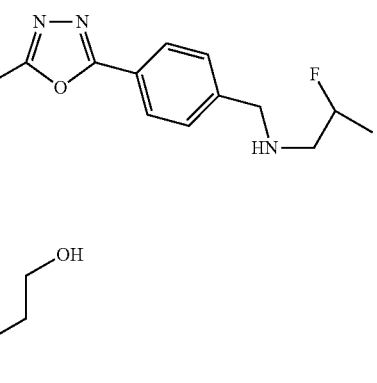 P71
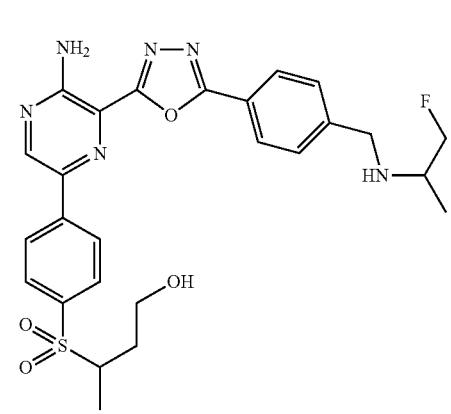 [SMILES: CC(CF)NCc1ccc(-c2nnc(-c3nc(-c4ccc(S(=O)(=O)C(C)CCO)cc4)cnc3N)o2)cc1] P72
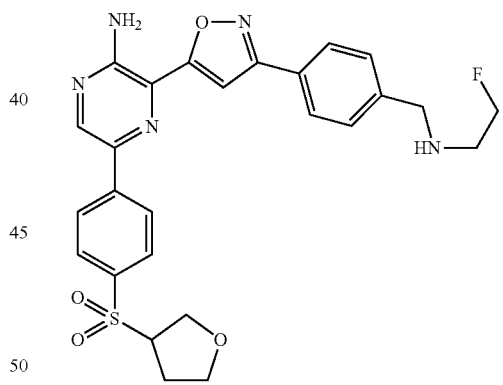 P73
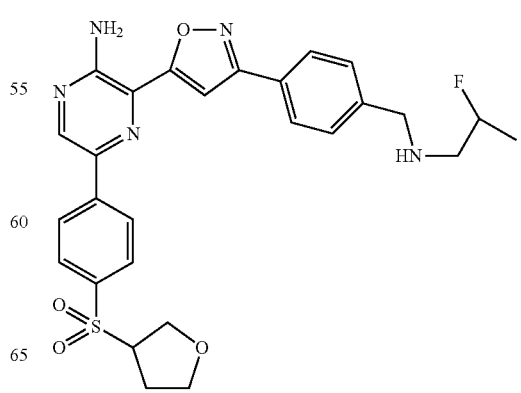 P74

TABLE IA-4-continued
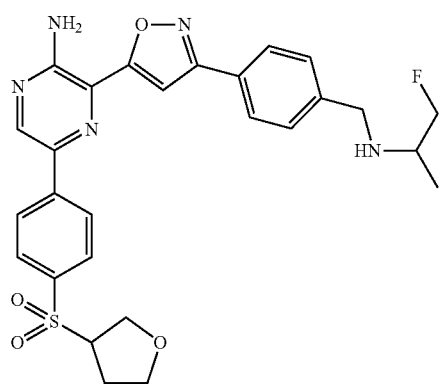 [SMILES: CC(CF)NCc1ccc(-c2cc(-c3nc(-c4ccc(S(=O)(=O)C5CCOC5)cc4)cnc3N)on2)cc1] P75
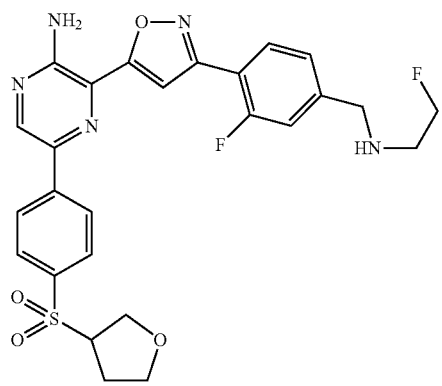 [SMILES: Nc1ncc(-c2ccc(S(=O)(=O)C3CCOC3)cc2)nc1-c1cc(-c2ccc(CNCCF)cc2F)no1] P76
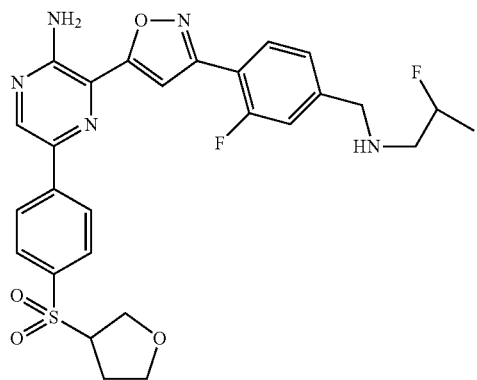 [SMILES: CC(F)CNCc1ccc(-c2cc(-c3nc(-c4ccc(S(=O)(=O)C5CCOC5)cc4)cnc3N)on2)c(F)c1] P77
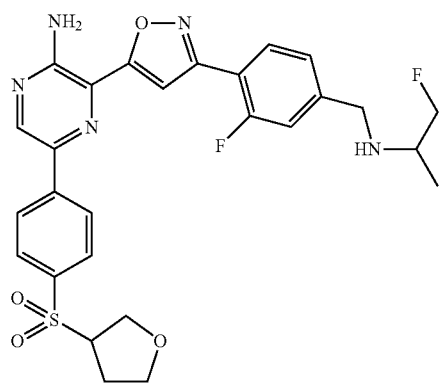 [SMILES: CC(CF)NCc1ccc(-c2cc(-c3nc(-c4ccc(S(=O)(=O)C5CCOC5)cc4)cnc3N)on2)c(F)c1] P78
TABLE IA-4-continued
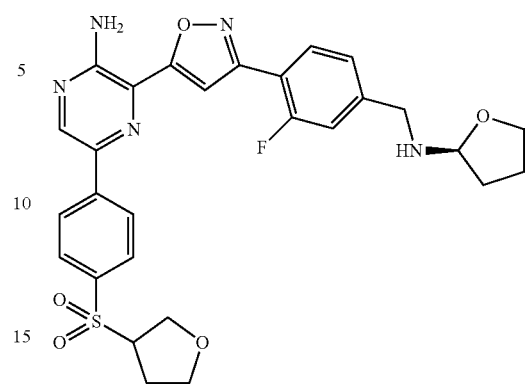 P79
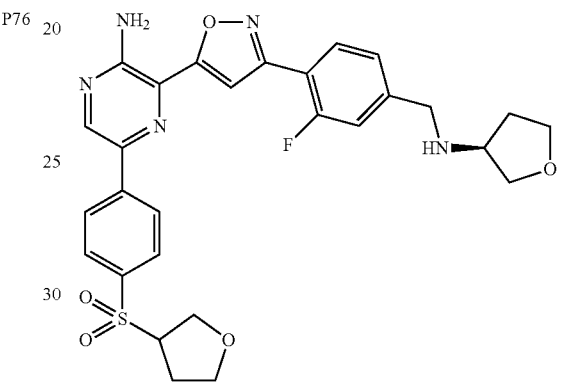 P80
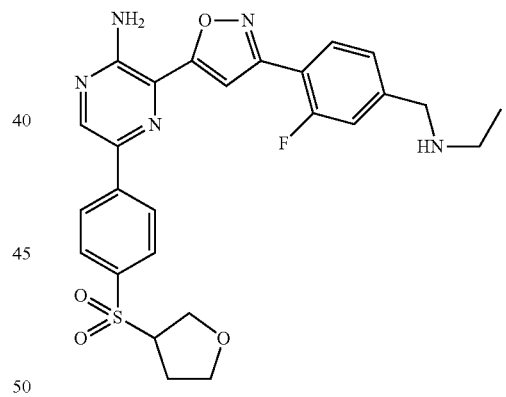 P81
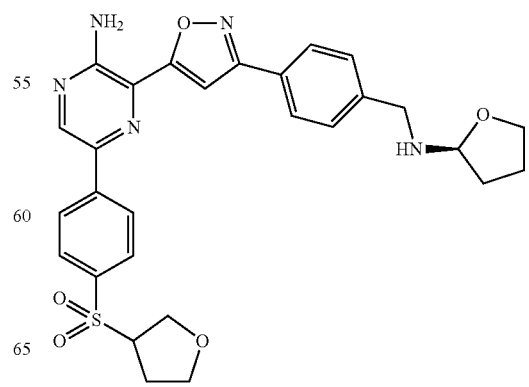 P82

TABLE IA-4-continued
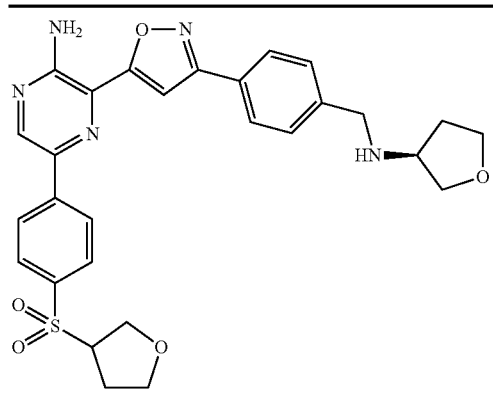
P83
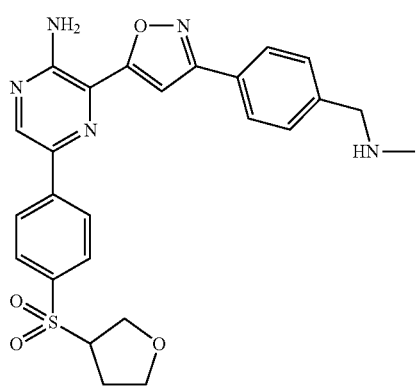 [SMILES: CNCc1ccc(-c2cc(-c3nc(-c4ccc(S(=O)(=O)C5CCOC5)cc4)cnc3N)on2)cc1]
P84
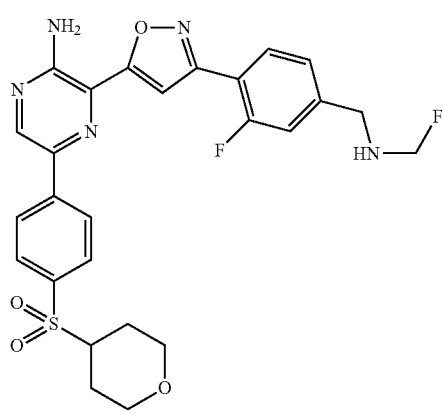 [SMILES: Nc1ncc(-c2ccc(S(=O)(=O)C3CCOCC3)cc2)nc1-c1cc(-c2ccc(CNCF)cc2F)no1]
P85
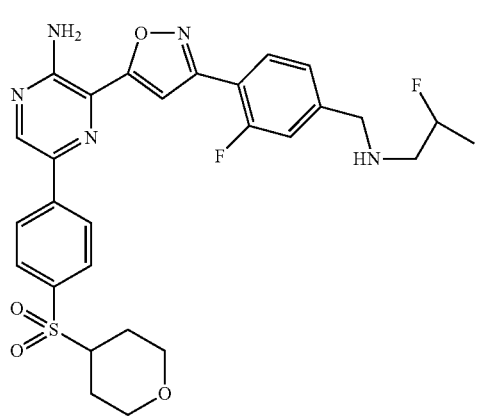 [SMILES: CC(F)CNCc1ccc(-c2cc(-c3nc(-c4ccc(S(=O)(=O)C5CCOCC5)cc4)cnc3N)on2)c(F)c1]
P86
TABLE IA-4-continued
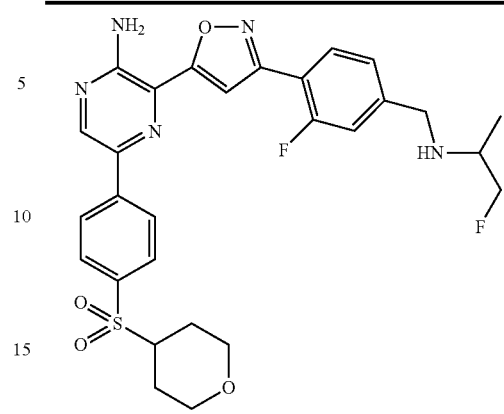
P87
P88
P89
P90

TABLE IA-4-continued
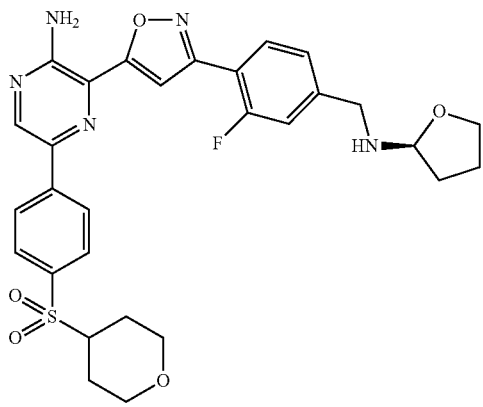 [SMILES: Nc1ncc(-c2ccc(S(=O)(=O)C3CCOCC3)cc2)nc1-c1cc(-c2ccc(CN[C@@H]3CCCO3)cc2F)no1]
P91
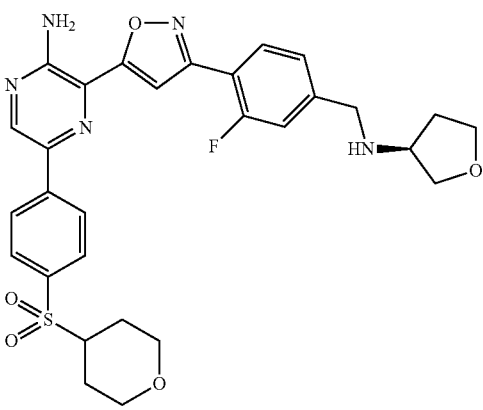 [SMILES: Nc1ncc(-c2ccc(S(=O)(=O)C3CCOCC3)cc2)nc1-c1cc(-c2ccc(CN[C@H]3CCOC3)cc2F)no1]
P92
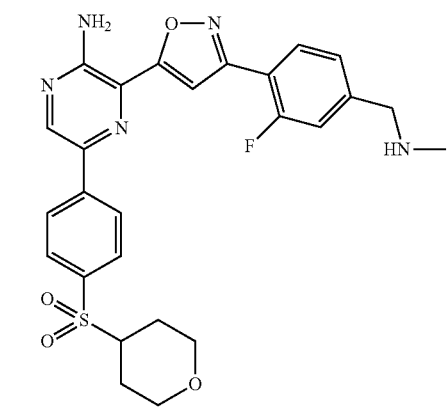 [SMILES: CNCc1ccc(-c2cc(-c3nc(-c4ccc(S(=O)(=O)C5CCOCC5)cc4)cnc3N)on2)c(F)c1]
P93
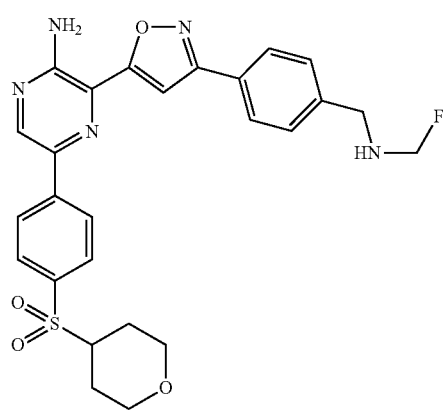 [SMILES: Nc1ncc(-c2ccc(S(=O)(=O)C3CCOCC3)cc2)nc1-c1cc(-c2ccc(CNCF)cc2)no1]
P94
TABLE IA-4-continued
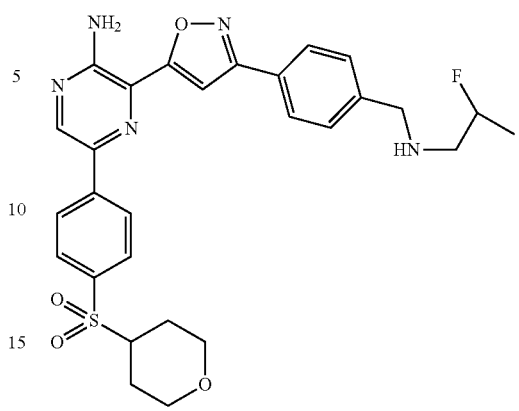
P95
P96
P97
P98

TABLE IA-4-continued
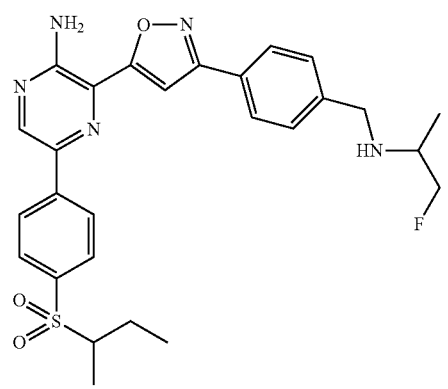 [SMILES: CCC(C)S(=O)(=O)c1ccc(-c2cnc(N)c(-c3cc(-c4ccc(CNC(C)CF)cc4)no3)n2)cc1]
P99
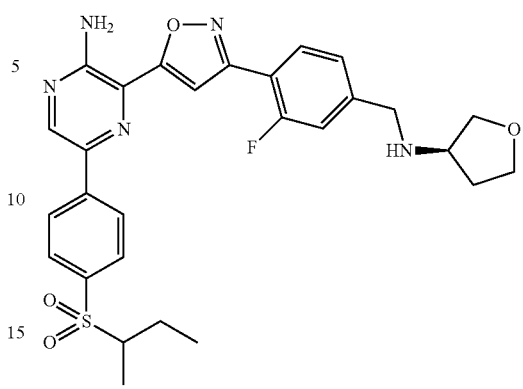
P103
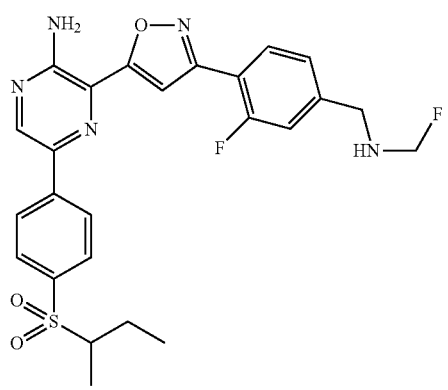 [SMILES: CCC(C)S(=O)(=O)c1ccc(-c2cnc(N)c(-c3cc(-c4ccc(CNCF)cc4F)no3)n2)cc1]
P100
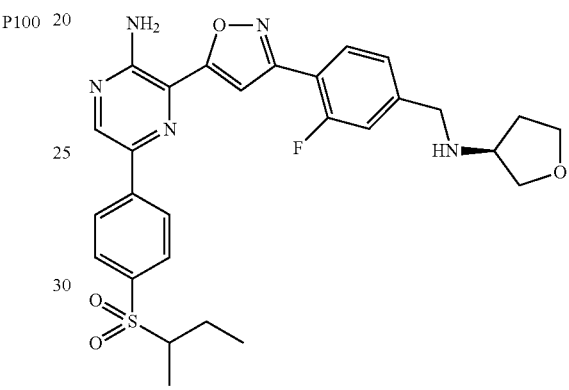
P104
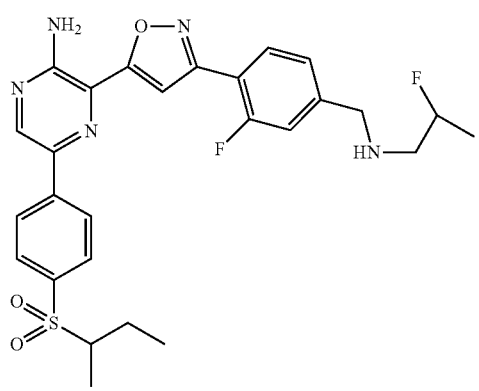 [SMILES: CCC(C)S(=O)(=O)c1ccc(-c2cnc(N)c(-c3cc(-c4ccc(CNCC(C)F)cc4F)no3)n2)cc1]
P101
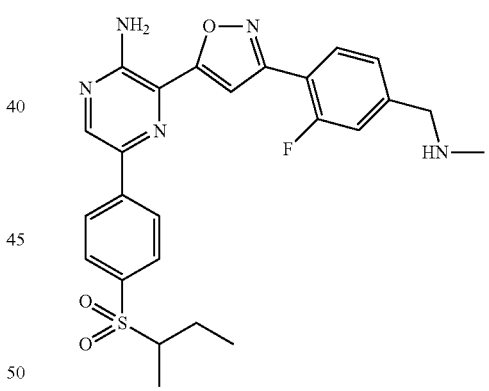
P105
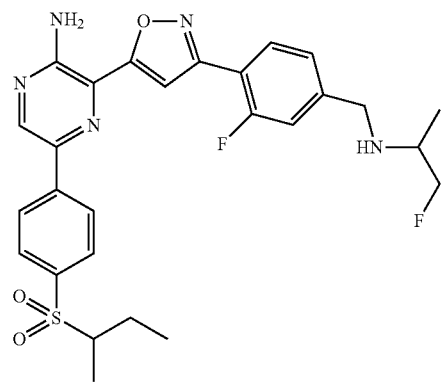 [SMILES: CCC(C)S(=O)(=O)c1ccc(-c2cnc(N)c(-c3cc(-c4ccc(CNC(C)CF)cc4F)no3)n2)cc1]
P102
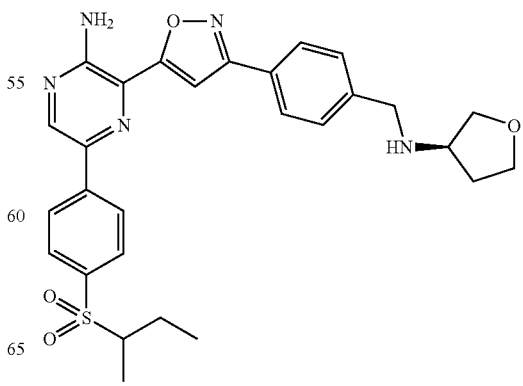
P106

TABLE IA-4-continued
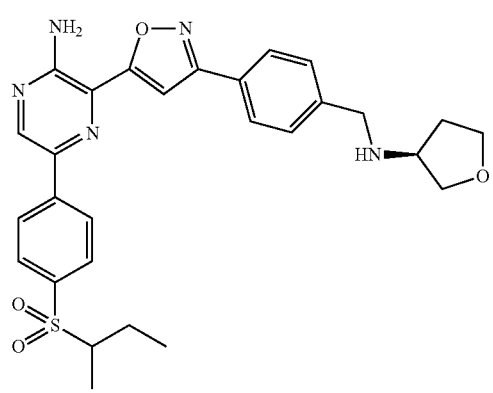 [SMILES: CCC(C)S(=O)(=O)c1ccc(-c2cnc(N)c(-c3cc(-c4ccc(CN[C@H]5CCOC5)cc4)no3)n2)cc1] P107
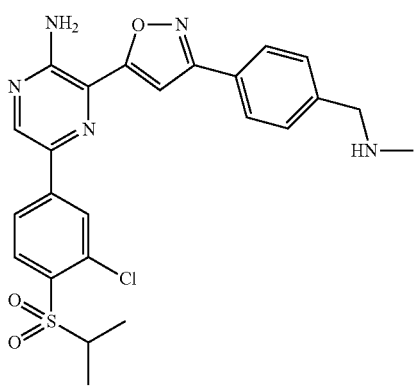 P111
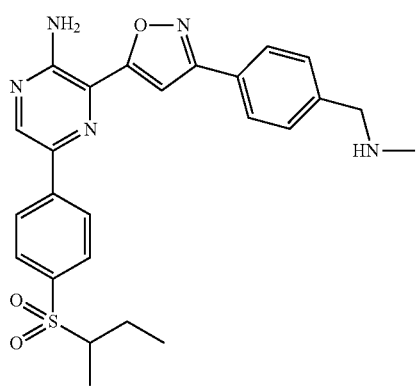 [SMILES: CCC(C)S(=O)(=O)c1ccc(-c2cnc(N)c(-c3cc(-c4ccc(CNC)cc4)no3)n2)cc1] P108
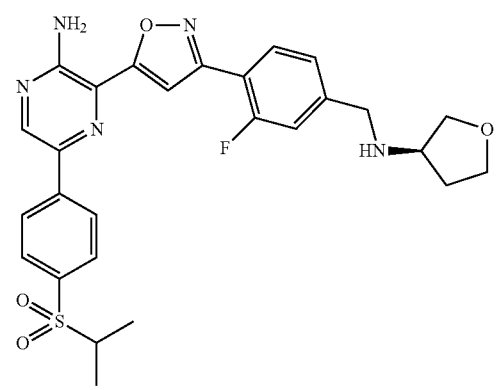 P112
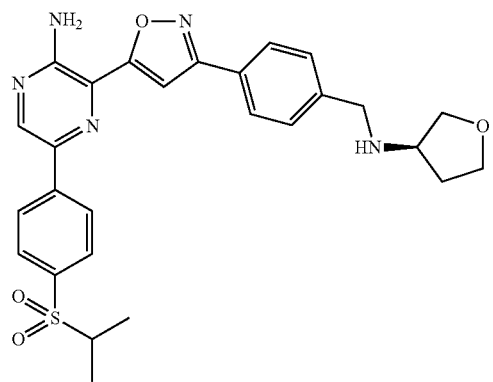 [SMILES: CC(C)S(=O)(=O)c1ccc(-c2cnc(N)c(-c3cc(-c4ccc(CN[C@@H]5CCOC5)cc4)no3)n2)cc1] P109
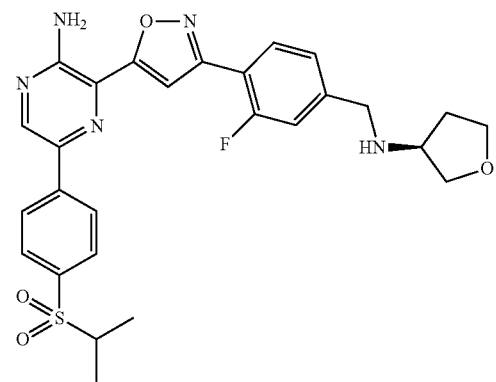 P113
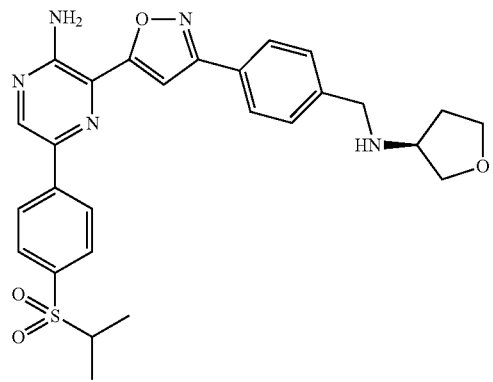 [SMILES: CC(C)S(=O)(=O)c1ccc(-c2cnc(N)c(-c3cc(-c4ccc(CN[C@H]5CCOC5)cc4)no3)n2)cc1] P110
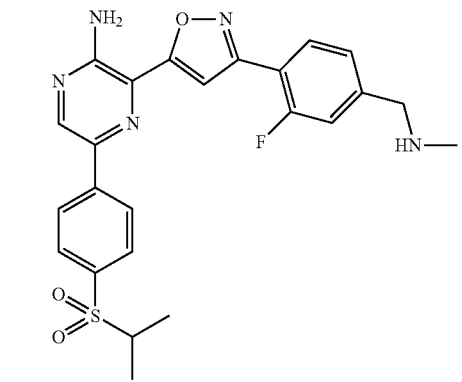 [SMILES: CNCc1ccc(-c2cc(-c3nc(-c4ccc(S(=O)(=O)C(C)C)cc4)cnc3N)on2)c(F)c1] P114

TABLE IA-4-continued
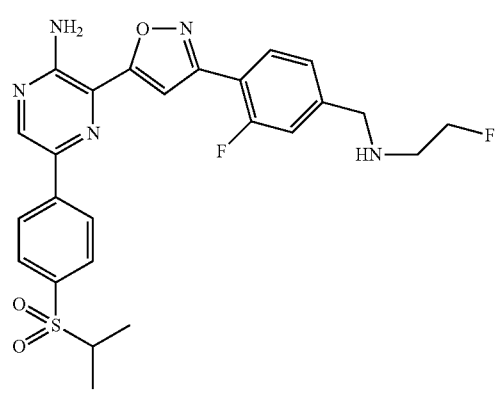 [SMILES: CC(C)S(=O)(=O)c1ccc(-c2cnc(N)c(-c3cc(-c4ccc(CNCCF)cc4F)no3)n2)cc1]
P115
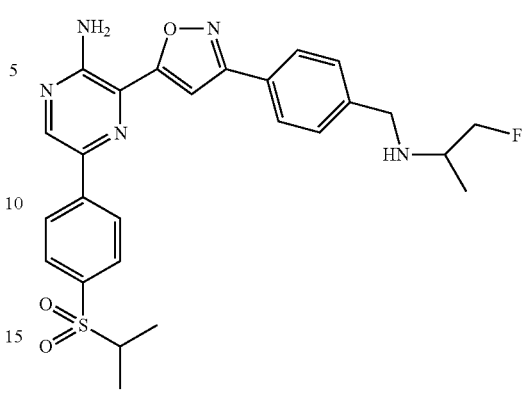
P119
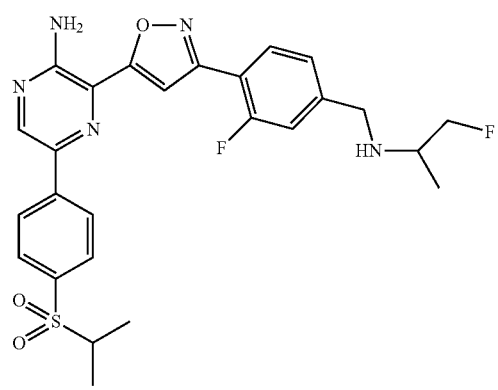 [SMILES: CC(CF)NCc1ccc(-c2cc(-c3nc(-c4ccc(S(=O)(=O)C(C)C)cc4)cnc3N)on2)c(F)c1]
P116
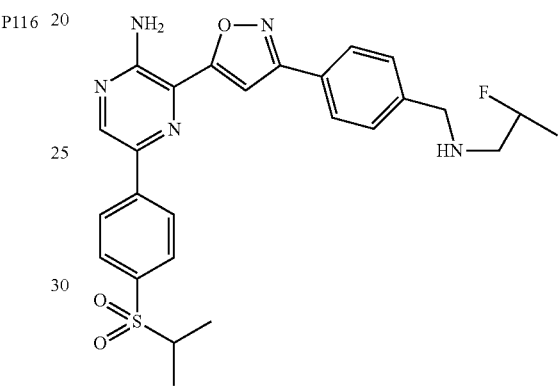
P120
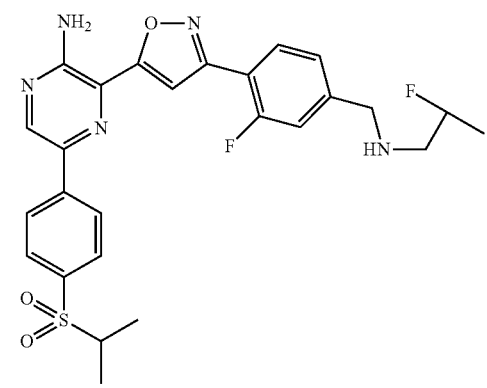 [SMILES: CC(F)CNCc1ccc(-c2cc(-c3nc(-c4ccc(S(=O)(=O)C(C)C)cc4)cnc3N)on2)c(F)c1]
P117
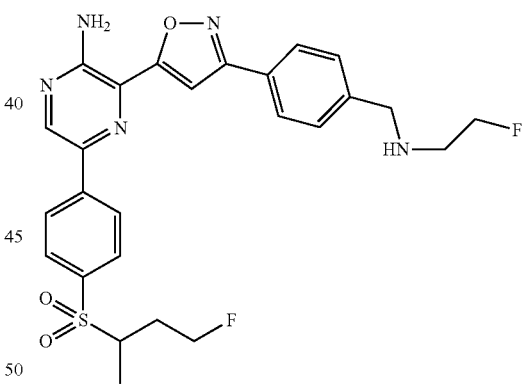
P121
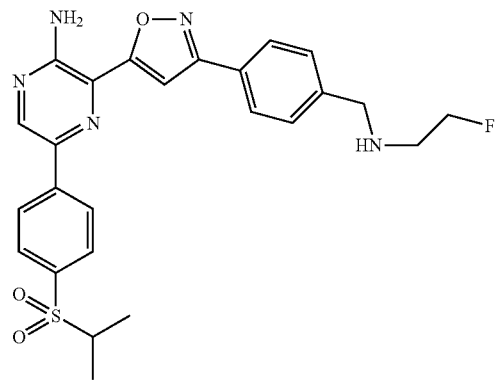 [SMILES: CC(C)S(=O)(=O)c1ccc(-c2cnc(N)c(-c3cc(-c4ccc(CNCCF)cc4)no3)n2)cc1]
P118
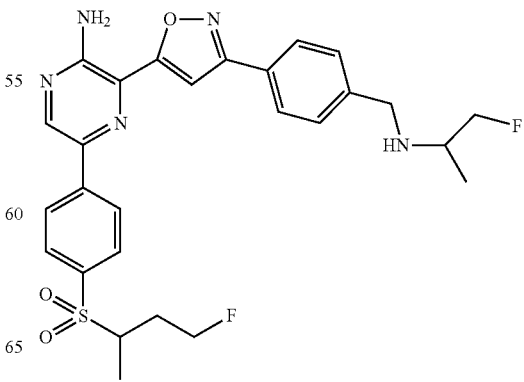
P122

TABLE IA-4-continued
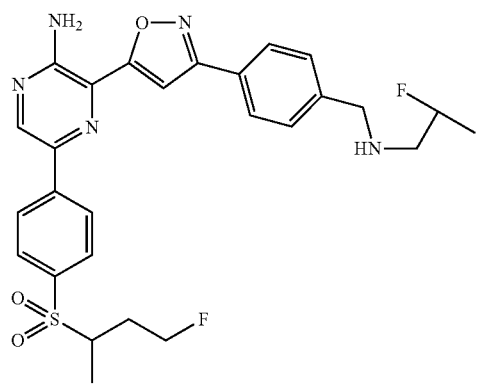 [SMILES: CC(F)CNCc1ccc(-c2cc(-c3nc(-c4ccc(S(=O)(=O)C(C)CCF)cc4)cnc3N)on2)cc1] P123
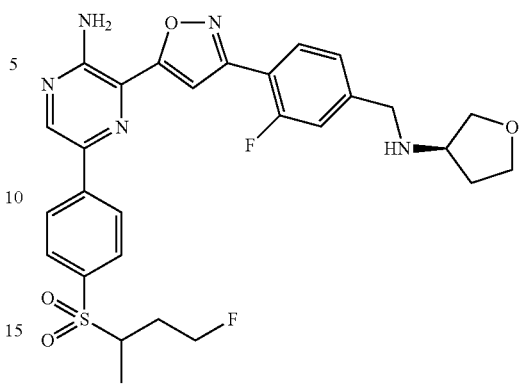 P127
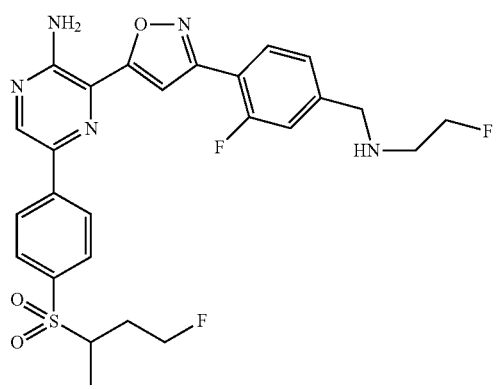 [SMILES: CC(CCF)S(=O)(=O)c1ccc(-c2cnc(N)c(-c3cc(-c4ccc(CNCCF)cc4F)no3)n2)cc1] P124
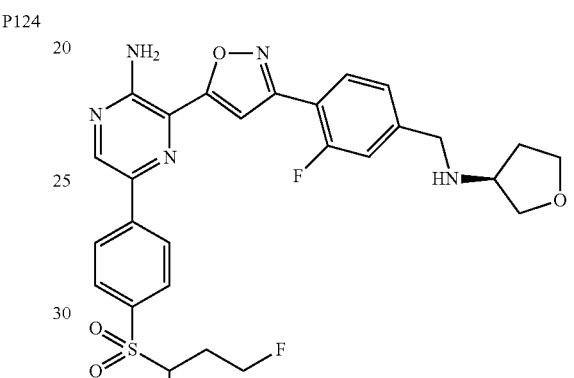 P128
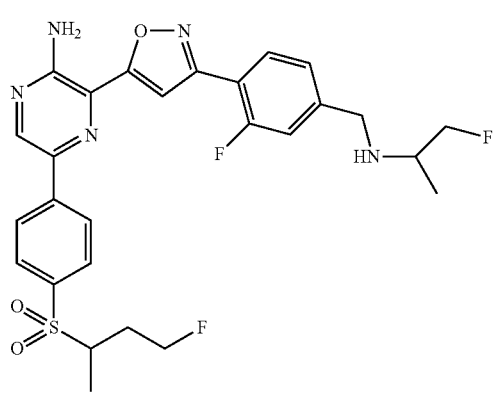 [SMILES: CC(CF)NCc1ccc(-c2cc(-c3nc(-c4ccc(S(=O)(=O)C(C)CCF)cc4)cnc3N)on2)c(F)c1] P125
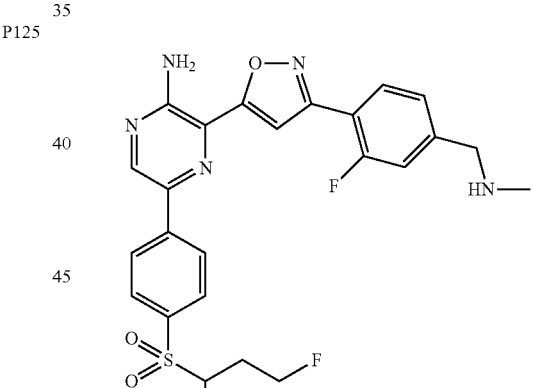 P129
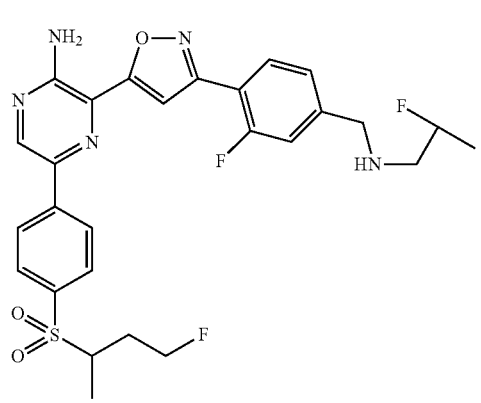 [SMILES: CC(F)CNCc1ccc(-c2cc(-c3nc(-c4ccc(S(=O)(=O)C(C)CCF)cc4)cnc3N)on2)c(F)c1] P126
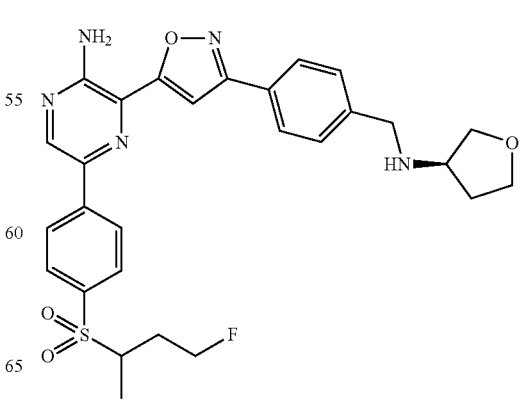 P130

TABLE IA-4-continued
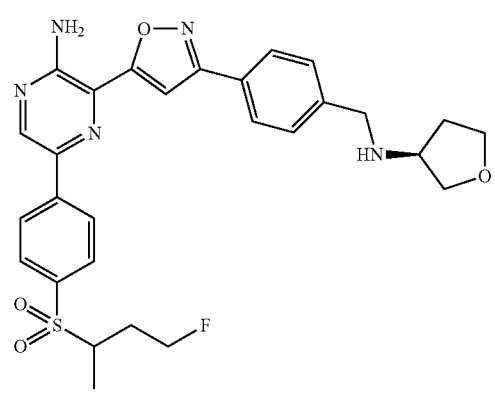 [SMILES: CC(CCF)S(=O)(=O)c1ccc(-c2cnc(N)c(-c3cc(-c4ccc(CN[C@H]5CCOC5)cc4)no3)n2)cc1]
P131
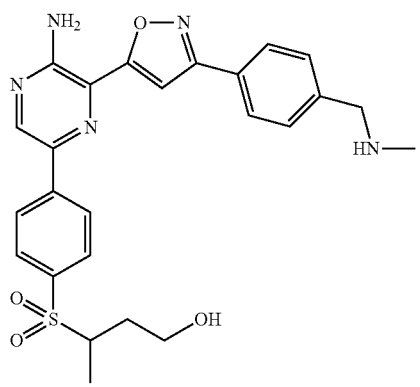
P135
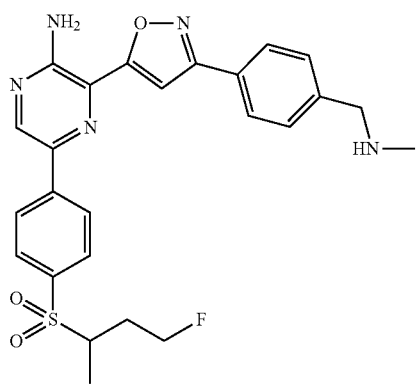 [SMILES: CNCc1ccc(-c2cc(-c3nc(-c4ccc(S(=O)(=O)C(C)CCF)cc4)cnc3N)on2)cc1]
P132
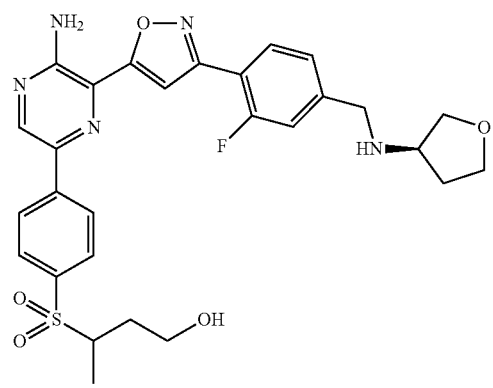
P136
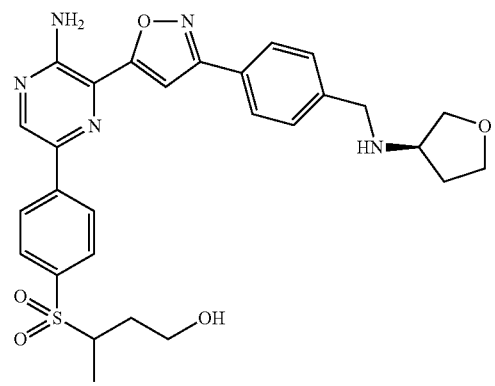 [SMILES: CC(CCO)S(=O)(=O)c1ccc(-c2cnc(N)c(-c3cc(-c4ccc(CN[C@@H]5CCOC5)cc4)no3)n2)cc1]
P133
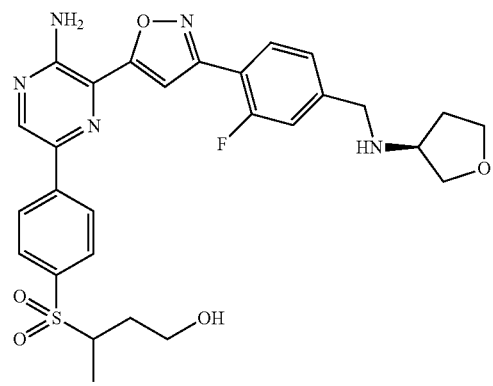
P137
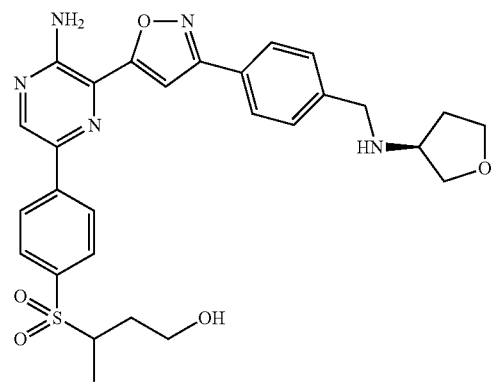 [SMILES: CC(CCO)S(=O)(=O)c1ccc(-c2cnc(N)c(-c3cc(-c4ccc(CN[C@H]5CCOC5)cc4)no3)n2)cc1]
P134
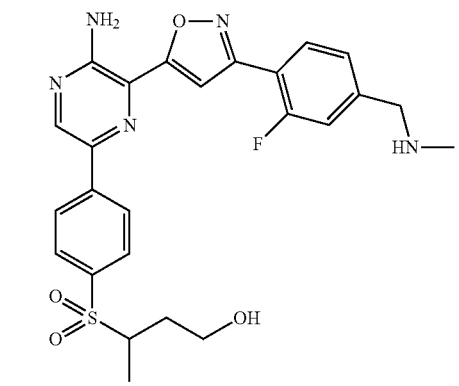 [SMILES: CNCc1ccc(-c2cc(-c3nc(-c4ccc(S(=O)(=O)C(C)CCO)cc4)cnc3N)on2)c(F)c1]
P138

TABLE IA-4-continued
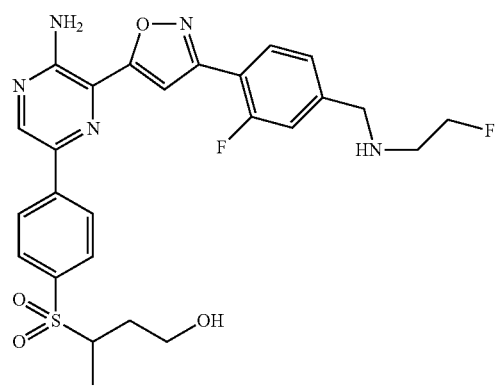 [SMILES: CC(CCO)S(=O)(=O)c1ccc(-c2cnc(N)c(-c3cc(-c4ccc(CNCCF)cc4F)no3)n2)cc1] P139
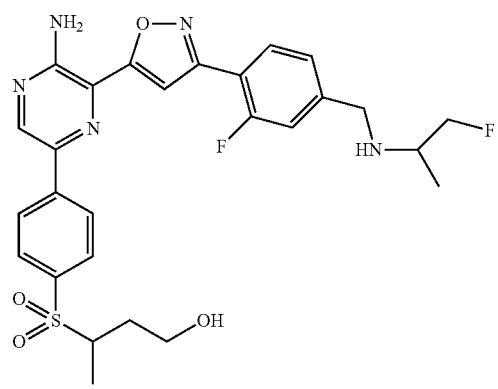 [SMILES: CC(CF)NCc1ccc(-c2cc(-c3nc(-c4ccc(S(=O)(=O)C(C)CCO)cc4)cnc3N)on2)c(F)c1] P140
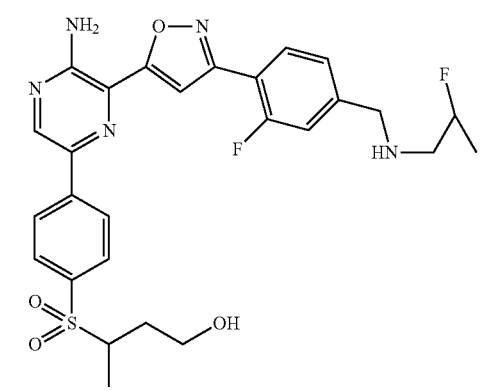 [SMILES: CC(F)CNCc1ccc(-c2cc(-c3nc(-c4ccc(S(=O)(=O)C(C)CCO)cc4)cnc3N)on2)c(F)c1] P141
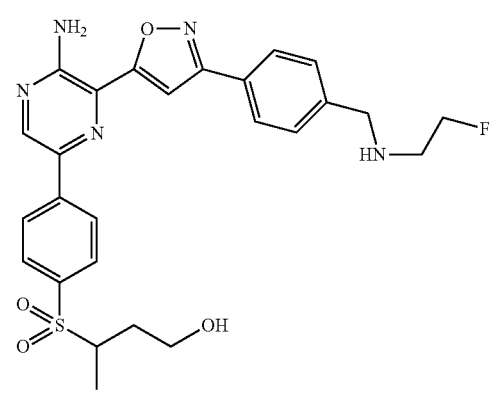 [SMILES: CC(CCO)S(=O)(=O)c1ccc(-c2cnc(N)c(-c3cc(-c4ccc(CNCCF)cc4)no3)n2)cc1] P142
TABLE IA-4-continued
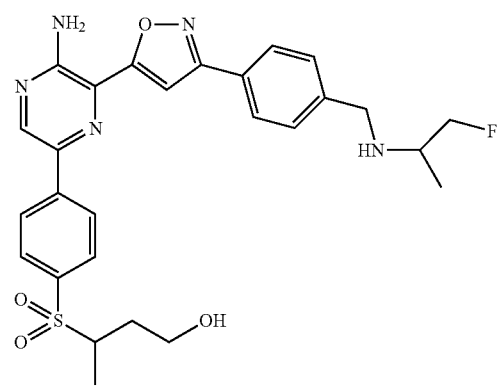 [SMILES: CC(CF)NCc1ccc(-c2cc(-c3nc(-c4ccc(S(=O)(=O)C(C)CCO)cc4)cnc3N)on2)cc1] P143
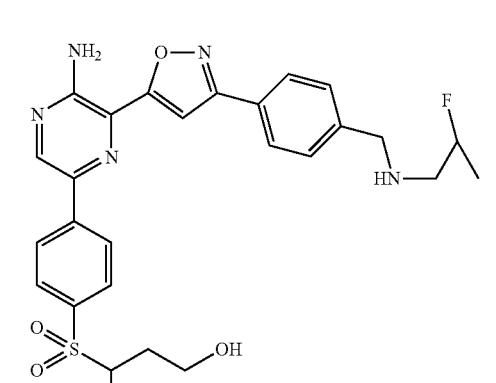 P144
P145
P146
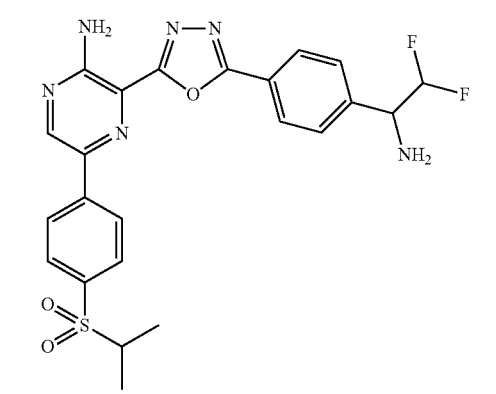 [SMILES: CC(C)S(=O)(=O)c1ccc(-c2cnc(N)c(-c3nnc(-c4ccc(C(N)C(F)F)cc4)o3)n2)cc1]

TABLE IA-4-continued

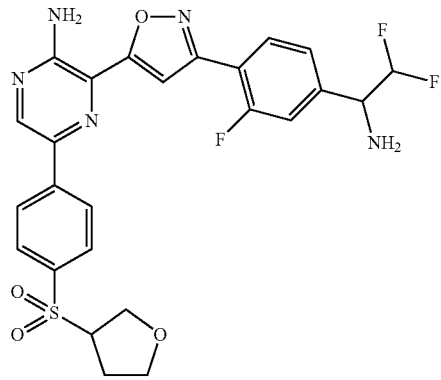 [SMILES: Nc1ncc(-c2ccc(S(=O)(=O)C3CCOC3)cc2)nc1-c1cc(-c2ccc(C(N)C(F)F)cc2F)no1]

P147

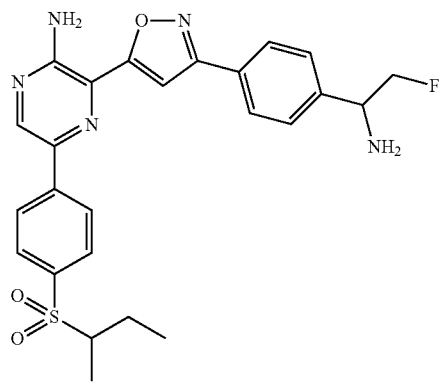 [SMILES: CCC(C)S(=O)(=O)c1ccc(-c2cnc(N)c(-c3cc(-c4ccc(C(N)CF)cc4)no3)n2)cc1]

P148

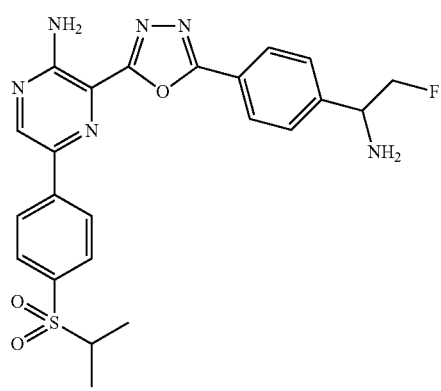 [SMILES: CC(C)S(=O)(=O)c1ccc(-c2cnc(N)c(-c3nnc(-c4ccc(C(N)CF)cc4)o3)n2)cc1]

P149

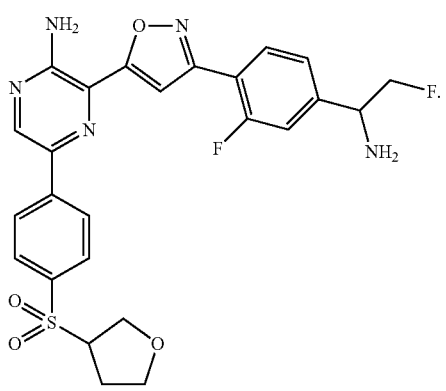 [SMILES: Nc1ncc(-c2ccc(S(=O)(=O)C3CCOC3)cc2)nc1-c1cc(-c2ccc(C(N)CF)cc2F)no1]

P150

Another aspect provides a compound of formula II,

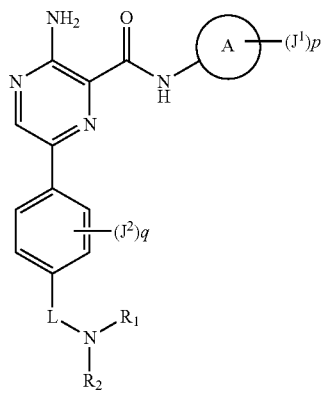

II or a pharmaceutically acceptable salt thereof; wherein

Ring A is a 5-6 membered monocyclic aromatic ring containing 0-2 heteroatoms selected from N, O, or S; Ring A is optionally fused to a 5-6 membered aromatic ring containing 0-2 heteroatoms selected from N, O, or S;

L is —C(O)—;

$R^1$ is $C_1$-$C_6$alkyl;

$R^2$ is —($C_2$-$C_6$alkyl)-Z or a 4-8 membered heterocyclic ring containing 0-2 nitrogen atoms; wherein said ring is bonded via a carbon atom and is optionally substituted with one occurrence of $J^Z$;

or $R^1$ and $R^2$, taken together with the atom to which they are bound, form a 4-8 membered heterocyclic ring containing 1-2 nitrogen atoms; wherein said heterocyclic ring is optionally substituted with one occurrence of $J^{Z1}$;

$J^{Z1}$ is —(X)$_t$—CN, $C_1$-$C_6$alkyl or —(X)$_t$—Z;

X is $C_1$-$C_4$alkyl;

each t, p, and r is independently 0 or 1;

Z is —$NR^3R^4$;

$R^3$ is H or $C_1$-$C_2$alkyl;

$R^4$ is H or $C_1$-$C_6$alkyl;

or $R^3$ and $R^4$, taken together with the atom to which they are bound, form a 4-8 membered heterocyclic ring containing 1-2 nitrogen atoms; wherein said ring is optionally substituted with one occurrence of $J^Z$;

each $J^Z$ and $J^1$ is independently $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO_2$ ($C_{1-4}aliphatic$), O(halo-$C_{1-4}aliphatic$), or halo$C_{1-4}aliphatic$;

$J^2$ is halo, $C_1$-$C_2$alkyl optionally substituted with 1-3 fluoro, or CN;

q is 0, 1, or 2.

In some embodiments, when Ring A is

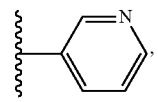

and $R^1$ is H; then $R^2$ is not

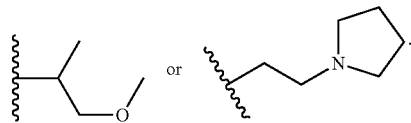

In some embodiments, Ring A is a 6-membered ring not fused to another ring. In other embodiments, Ring A is phenyl, pyridyl, or pyrimidyl. In yet other embodiments, Ring A is phenyl.

In some embodiments, $R^1$ and $R^2$, taken together with the atom to which they are bound, form a 4-8 membered heterocyclic ring containing 1-2 nitrogen atoms. In some embodiments, said heterocyclic ring is selected from pyrrolidinyl, piperidinyl, piperazinyl, azepanyl, or 1,4-diazepanyl. In other embodiments, said heterocyclic ring is selected from

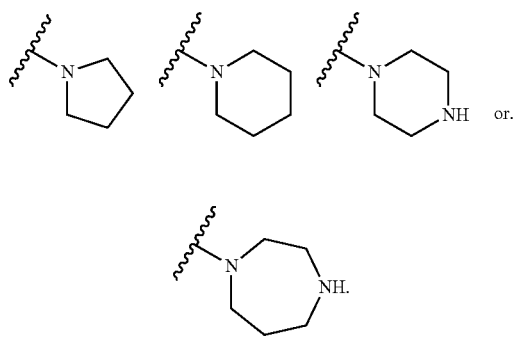

In yet other embodiments, the ring formed by $R^1$ and $R^2$ is optionally substituted with $CH_2$pyrrolidinyl, $C_{1-4}$alkyl, $N(C_{1-4}$alkyl$)_2$, or $CH_2CH_2CN$.

In some embodiments, t is 1. In other embodiments, t is 0.

In other embodiments, $R^1$ is H or $C_1$-$C_6$alkyl; and $R^2$ is —($C_2$-$C_6$alkyl)-Z.

In some embodiments, Z is —$NR^3R^4$, wherein $R^3$ and $R^4$ are both $C_1$-$C_2$alkyl. In other embodiments, $R^3$ and $R^4$, taken together with the atom to which they are bound, form a ring selected from pyrrolidinyl, piperidinyl, piperazinyl, azepanyl, or 1,4-diazepanyl. In some embodiments, said ring is pyrrolidinyl or piperidinyl.

In some embodiments, said ring is optionally substituted with one $J^Z$. In some embodiments, $J^Z$ is $C_{1-4}$alkyl or $N(C_{1-4}$alkyl$)_2$.

In one embodiment, p is 0, q is 0, and -L-$NR^1R^2$ is C(O)pyrrolidinyl, C(O)piperidinyl, C(O)piperazinyl, C(O)azepanyl, C(O)1,4-diazepanyl, $CON(CH_3)CH_2CH_2N(CH_3)_2$, wherein said pyrrolidinyl, piperidinyl, piperazinyl, azepanyl, or 1,4-diazepanyl is optionally substituted with $CH_2$pyrrolidinyl, $C_{1-4}$alkyl, $N(C_{1-4}$alkyl$)_2$, or $CH_2CH_2CN$.

Another embodiment provides a compound selected from Table II.

TABLE II

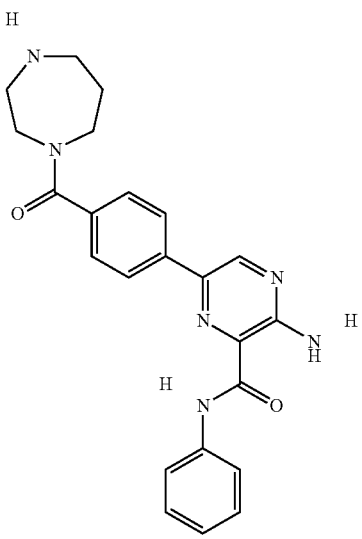

II-1

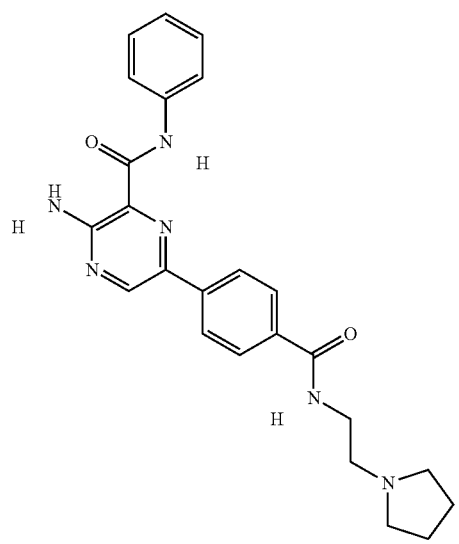

II-2

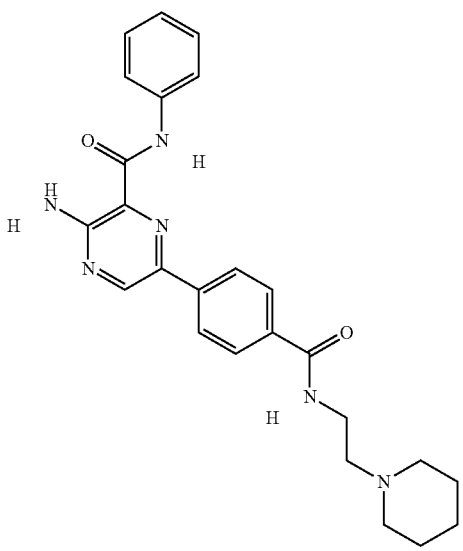

II-3

TABLE II-continued
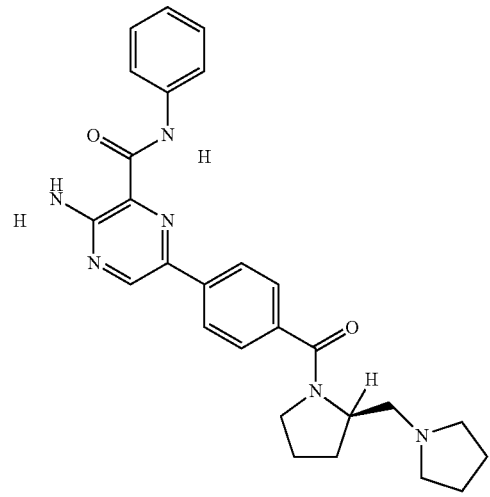
II-4
II-5
II-6
TABLE II-continued
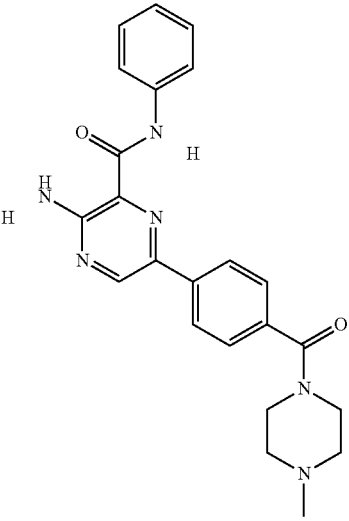
II-7
II-8
II-9

TABLE II-continued

II-10

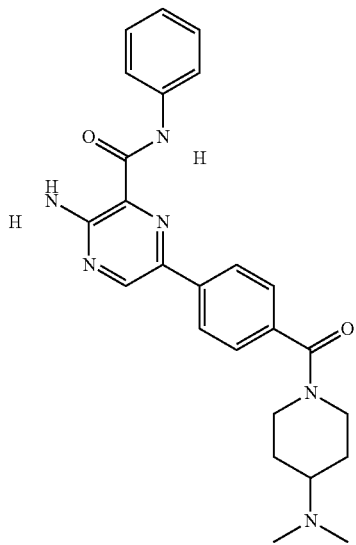

II-11

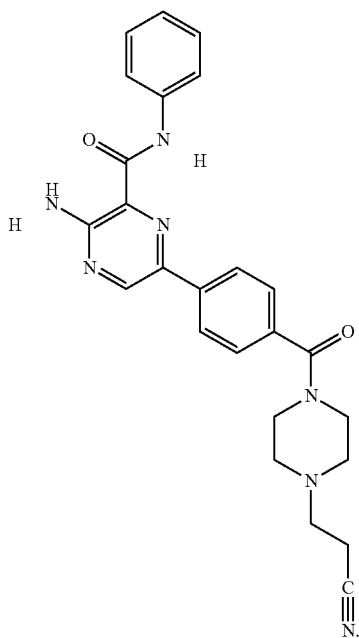

Another aspect provides a compound of formula III:

III

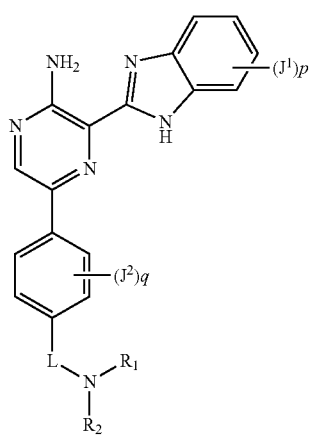

or a pharmaceutically acceptable salt thereof; wherein
L is —C(O)— or —SO$_2$—;
R$^1$ is H, or C$_1$-C$_6$alkyl;
R$^2$ is —(C$_2$-C$_6$alkyl)-Z or a 4-8 membered heterocyclic ring containing 0-2 nitrogen atoms; wherein said ring is bonded via a carbon atom and is optionally substituted with one occurrence of J$^Z$;
or R$^1$ and R$^2$, taken together with the atom to which they are bound, form a 4-8 membered heterocyclic ring containing 1-2 nitrogen atoms; wherein said heterocyclic ring is optionally substituted with one occurrence of J$^{Z1}$;
J$^{Z1}$ is —(X)$_t$—CN, C$_1$-C$_6$alkyl or —(X)$_t$—Z;
X is C$_1$-C$_4$alkyl;
each t, p, and r is independently 0 or 1;
Z is —NR$^3$R$^4$;
R$^3$ is H or C$_1$-C$_2$alkyl;
R$^4$ is H or C$_1$-C$_6$alkyl;
or R$^3$ and R$^4$, taken together with the atom to which they are bound, form a 4-8 membered heterocyclic ring containing 1-2 nitrogen atoms; wherein said ring is optionally substituted with one occurrence of J$^Z$;
each J$^Z$ and J$^1$ is independently NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO(C$_{1-4}$aliphatic), CO$_2$(C$_{1-4}$aliphatic), O(haloC$_{1-4}$ aliphatic), or haloC$_{1-4}$aliphatic;
J$^2$ is halo, C$_1$-C$_2$alkyl optionally substituted with 1-3 fluoro, or CN;
q is 0, 1, or 2.

III-i

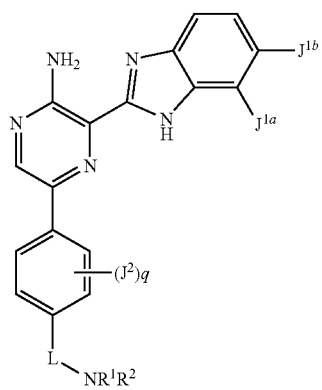

In some embodiments, J$^1$ is J$^{1a}$ or J$^{1b}$ as depicted in Formula III-i.
In some embodiments, when L is —C(O)—, q is 0, J$^{1a}$ is H, and J$^{1b}$ is H or F; then:
when R$^1$ is H; then R$^2$ is not —(C$_{1-4}$alkyl)-N(CH$_3$)$_2$; or R$^1$ and R$^2$ taken together are not

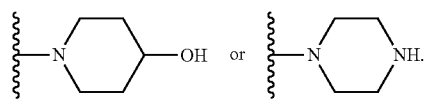

In some embodiments, R$^1$ and R$^2$, taken together with the atom to which they are bound, form a 4-8 membered heterocyclic ring containing 1-2 nitrogen atoms. In some embodiments, said heterocyclic ring is selected from pyrrolidinyl, piperidinyl, piperazinyl, azepanyl, or 1,4-diazepanyl. In other embodiments, said heterocyclic ring is selected from

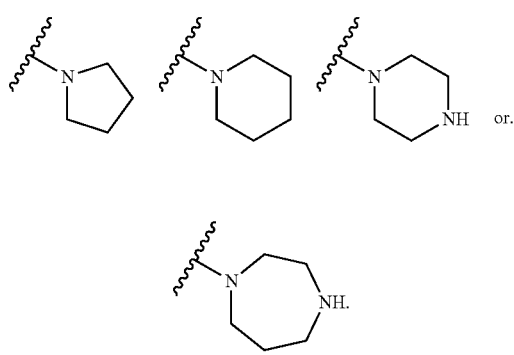

In some embodiments, t is 1. In other embodiments, t is 0.

In other embodiments, $R^1$ is H or $C_1$-$C_6$alkyl; and $R^2$ is —($C_2$-$C_6$alkyl)-Z. In some embodiments, Z is —$NR^3R^4$, wherein $R^3$ and $R^4$ are both $C_1$-$C_2$alkyl. In other embodiments, $R^3$ and $R^4$, taken together with the atom to which they are bound, form a ring selected from pyrrolidinyl, piperidinyl, piperazinyl, azepanyl, or 1,4-diazepanyl. In some embodiments, said ring is pyrrolidinyl or piperidinyl.

In some embodiments, said ring is optionally substituted with one $J^Z$. In some embodiments, $J^Z$ is $C_{1-4}$alkyl or $N(C_{1-4}alkyl)_2$.

In one embodiment, p is 0, q is 0, and -L-$NR^1R^2$ is C(O)pyrrolidinyl, C(O)piperidinyl, C(O)piperazinyl, C(O)azepanyl, C(O)1,4-diazepanyl, C(O)NH-piperidinyl, C(O)NHCH$_2$CH$_2$-pyrrolidinyl, C(O)NHCH$_2$CH$_2$-piperidinyl, CON(CH$_3$)CH$_2$CH$_2$N(CH$_3$)$_2$, wherein said pyrrolidinyl, piperidinyl, piperazinyl, azepanyl, or 1,4-diazepanyl is optionally substituted with $C_{1-4}$alkyl or $N(C_{1-4}alkyl)_2$.

Another embodiment provides a compound selected from Table III:

TABLE III

| Compound No. | $NR^1R^2$ | $J^1$ |
|---|---|---|
| III-1 | [1,4-diazepan-1-yl] | CH$_3$ |
| III-2 | [4-(dimethylamino)piperidin-1-yl] | CH$_3$ |
| III-3 | [piperazin-1-yl] | CH$_3$ |
| III-4 | [4-methylpiperazin-1-yl] | CH$_3$ |
| III-5 | [4-methyl-1,4-diazepan-1-yl] | CH$_3$ |
| III-6 | [NH-CH$_2$CH$_2$-pyrrolidin-1-yl] | H |

Another aspect provides a compound selected from Table III-2:

TABLE III-2

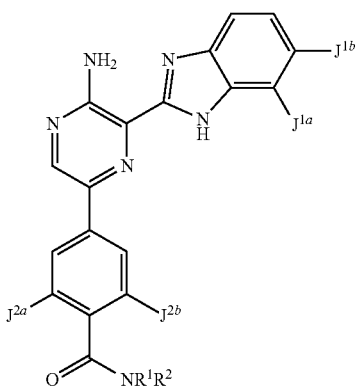

| Compound No. | NR¹R² | J¹ᵇ | J¹ᵃ | J²ᵃ | J²ᵇ |
|---|---|---|---|---|---|
| III-7 | homopiperazinyl (HN-CH₂CH₂CH₂-N) | H | CH₃ | H | H |
| III-8 | piperazinyl (HN-N) | H | H | H | H |
| III-9 | (S)-3-(dimethylamino)pyrrolidinyl | H | CH₃ | H | H |
| III-10 | 4-Boc-homopiperazinyl | H | F | H | H |
| III-11 | homopiperazinyl | OCH₃ | H | H | H |
| III-12 | piperazinyl | H | H | F | H |
| III-13 | (S)-3-(dimethylamino)pyrrolidinyl | H | CH₃ | H | F |
| III-14 | homopiperazinyl | H | F | H | H |

TABLE III-2-continued

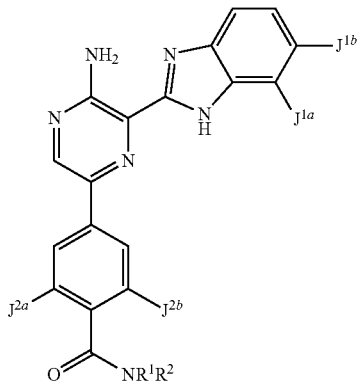

| Compound No. | NR¹R² | J¹ᵇ | J¹ᵃ | J²ᵃ | J²ᵇ |
|---|---|---|---|---|---|
| III-15 | 4-(dimethylamino)piperidinyl | H | H | H | H |
| III-16 | piperazinyl | H | CH₃ | H | H |
| III-17 | (S)-3-(dimethylamino)pyrrolidinyl | OCH₃ | H | H | H |
| III-18 | 4-(dimethylamino)piperidinyl | H | F | H | H |
| III-19 | 4-(dimethylamino)piperidinyl | H | H | F | H |
| III-20 | piperazinyl | H | CH₃ | H | F |
| III-21 | homomorpholinyl | H | F | H | H |
| III-22 | (S)-3-(dimethylamino)pyrrolidinyl | H | F | H | H |

TABLE III-2-continued

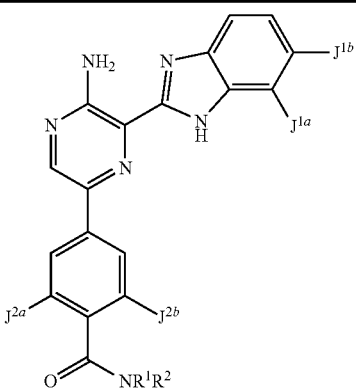

| Compound No. | NR¹R² | J^{1b} | J^{1a} | J^{2a} | J^{2b} |
|---|---|---|---|---|---|
| III-23 | 4-(dimethylamino)piperidin-1-yl | H | CH$_3$ | H | H |
| III-24 | piperazin-1-yl | OCH$_3$ | H | H | H |
| III-25 | 1,4-diazepan-1-yl | H | CH$_3$ | H | F |
| III-26 | piperazin-1-yl | H | F | H | H |
| III-27 | 4-(dimethylamino)piperidin-1-yl | H | CH$_3$ | H | F |
| III-28 | piperazin-1-yl | CF$_3$ | H | H | H |
| III-29 | 1,4-diazepan-1-yl | CF$_3$ | H | H | H |
| III-30 | 1,4-diazepan-1-yl | H | H | H | H |
| III-31 | 4-(dimethylamino)piperidin-1-yl | OCH$_3$ | H | H | H |

TABLE III-2-continued

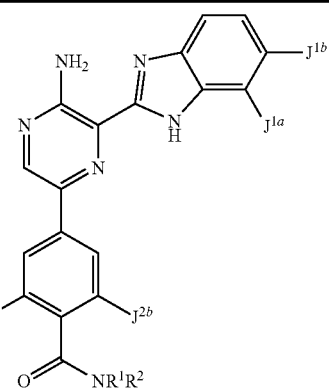

| Compound No. | NR¹R² | J^{1b} | J^{1a} | J^{2a} | J^{2b} |
|---|---|---|---|---|---|
| III-32 | (3S)-3-(dimethylamino)pyrrolidin-1-yl | H | H | H | H |
| III-33 | 1,4-diazepan-1-yl | H | H | F | H |
| III-34 | 4-(dimethylamino)piperidin-1-yl | CF$_3$ | H | H | H |
| III-35 | (3S)-3-(dimethylamino)pyrrolidin-1-yl | H | H | F | H. |

Another aspect provides a compound of Formula V:

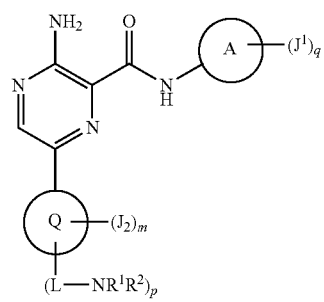

V or a pharmaceutically acceptable salt thereof:
wherein
Ring A is a 8-9 membered bicyclic heteroaryl ring having 1-4 heteroatoms selected from the group consisting of oxygen, nitrogen, and sulfur;
Q is a 5-6 membered monocyclic aromatic ring containing 0-3 heteroatoms independently selected from the group consisting of nitrogen, oxygen, and sulfur;

L is C₁₋₄alkyl chain wherein up to two methylene units of the alkyl chain are optionally replaced with O, NR⁶, S, —C(O)—, —SO—, or —SO₂—;

R¹ is H or C₁-C₆alkyl;

R² is H, C₁-C₆alkyl, —(C₂-C₆alkyl)-Z, or a 3-8 membered cyclic ring containing 0-2 nitrogen atoms; wherein said ring is bonded via a carbon atom and is optionally substituted with one occurrence of J^Z;

or R¹ and R², taken together with the atom to which they are bound, form a 3-8 membered monocyclic or 8-9 membered bicyclic heterocyclic ring containing 1-2 heteroatoms selected the group consisting of oxygen, nitrogen, and sulfur; wherein said heterocyclic ring is optionally substituted with one occurrence of J^Z1;

J^Z1 is —(X)ₜ—CN, C₁-C₆alkyl or —(X)ᵣ—Z¹;

X is C₁₋₄alkyl;

Z is —NR³R⁴;

R³ is H or C₁-C₂alkyl;

R⁴ is H or C₁-C₆alkyl;

or R³ and R⁴, taken together with the atom to which they are bound, form a 4-8 membered heterocyclic ring containing 1-2 nitrogen atoms; wherein said ring is optionally substituted with one occurrence of J^Z;

Z¹ is —NR⁵R⁶;

R⁵ is H or C₁-C₂alkyl;

R⁶ is H or C₁-C₆alkyl;

or R⁵ and R⁶, taken together with the atom to which they are bound, form a 4-8 membered heterocyclic ring containing 1-2 nitrogen atoms; wherein said ring is optionally substituted with one occurrence of J^Z1;

J¹ is halo, CN, or a C₁₋₆aliphatic group wherein up to 2 methylene units are optionally replaced with O, NR″, C(O), S, S(O), or S(O)₂; said C₁₋₆aliphatic group is optionally substituted with 1-3 fluoro or CN;

J² is halo; CN; or a C₁₋₆aliphatic group wherein up to 2 methylene units are optionally replaced with O, NR″, C(O), S, S(O), or S(O)₂; said C₁₋₆aliphatic group is optionally substituted with 1-3 fluoro or CN;

each J^Z and J^Z1 is independently NH₂, NH(C₁₋₄aliphatic), N(C₁₋₄aliphatic)₂, halogen, C₁₋₄aliphatic, OH, O(C₁₋₄aliphatic), NO₂, CN, CO₂H, CO(C₁₋₄aliphatic), CO₂(C₁₋₄aliphatic), O(haloC₁₋₄ aliphatic), or haloC₁₋₄aliphatic;

each q and m is independently 0, 1, or 2;

each t, p, and r is independently 0 or 1.

According to one embodiment, Ring A is a 9-membered ring. In some embodiments, Ring A is a 5-6 bicyclic ring system. A 5-6 bicyclic system is a five-membered ring fused to a six membered ring as shown below.

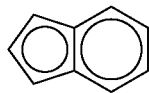

Examples of 5-6 bicyclic systems include, but are not limited to, benzimidazolyl, benzoxazolyl, indazolyl, pyrrolopyridinyl, pyrrolopyrimidinyl, pyrrolopyrazinyl, benzothiazolyl, benzothiophenyl, indolyl, benzofuranyl, benzotriazolyl, and azaindolyl.

In some embodiments, Ring A has 1-2 heteroatoms. In some embodiments, Ring A is benzimidazolyl, benzoxazolyl, indazolyl, benzothiazolyl, indolyl, benzotriazolyl, or azaindolyl.

According to another embodiment, Ring Q is phenyl or pyridyl. In some embodiment, Q is phenyl.

In some embodiments, p is 1 and Ring Q is substituted in the para position with L-NR¹R² as shown in formula V-a:

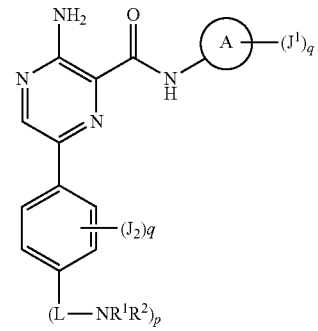

V-a

In some embodiments, L is C(O) or S(O)₂. In other embodiments, R¹ and R² are both C₁₋₄alkyl. In yet other embodiments, R¹ and R², taken together with the atom to which they are bound, form a 4-7 membered heterocyclic ring containing 1-2 nitrogen atoms. In some embodiments, said heterocyclic ring is selected from the group consisting of pyrrolidinyl, piperidinyl, piperazinyl, azepanyl, and 1,4-diazepanyl. In some embodiments, said heterocyclyl is 1,4-diazepanyl.

In other embodiments, Ring Q is pyridyl.

In some embodiments, p is 0. In other embodiments, q is 1 and J² is CN.

Another embodiment provides a compound selected from Table V:

TABLE V

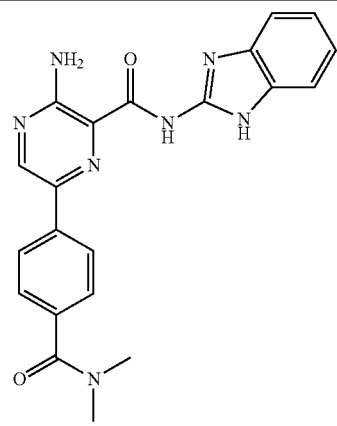

V-1

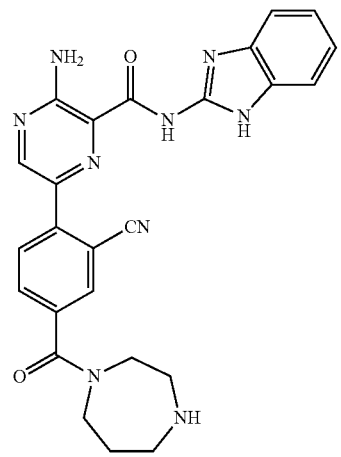 [SMILES: N#Cc1cc(C(=O)N2CCCNCC2)ccc1-c1cnc(N)c(C(=O)Nc2nc3ccccc3[nH]2)n1]

V-2

TABLE V-continued
V-3
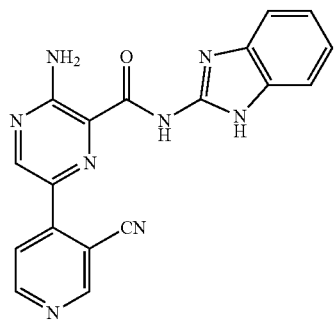 [SMILES: N#Cc1cnccc1-c1cnc(N)c(C(=O)Nc2nc3ccccc3[nH]2)n1]
V-4
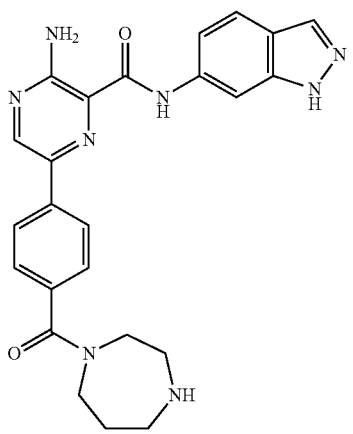 [SMILES: Nc1ncc(-c2ccc(C(=O)N3CCCNCC3)cc2)nc1C(=O)Nc1ccc2cn[nH]c2c1]
V-5
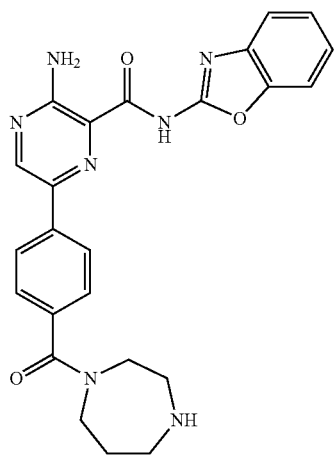 [SMILES: Nc1ncc(-c2ccc(C(=O)N3CCCNCC3)cc2)nc1C(=O)Nc1nc2ccccc2o1]
V-6
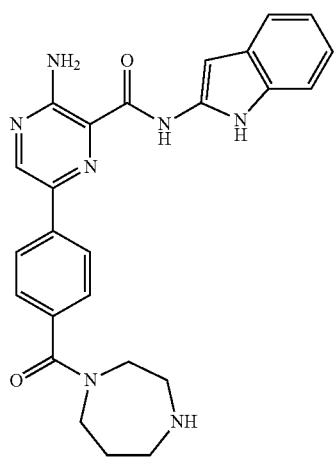 [SMILES: Nc1ncc(-c2ccc(C(=O)N3CCCNCC3)cc2)nc1C(=O)Nc1cc2ccccc2[nH]1]
TABLE V-continued
V-7
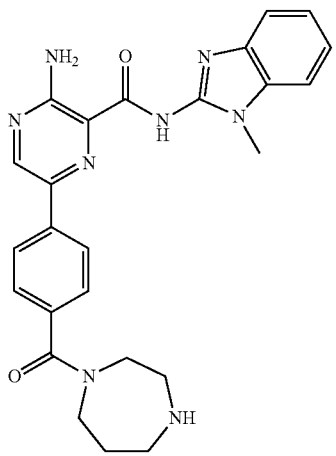 [SMILES: Cn1c(NC(=O)c2nc(-c3ccc(C(=O)N4CCCNCC4)cc3)cnc2N)nc2ccccc21]
V-8
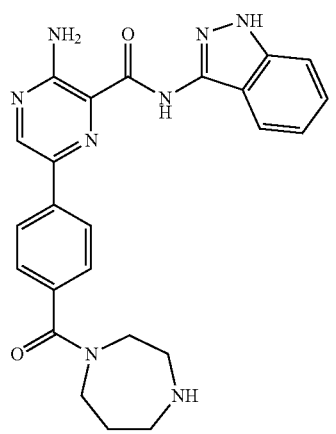 [SMILES: Nc1ncc(-c2ccc(C(=O)N3CCCNCC3)cc2)nc1C(=O)Nc1n[nH]c2ccccc12]
V-9
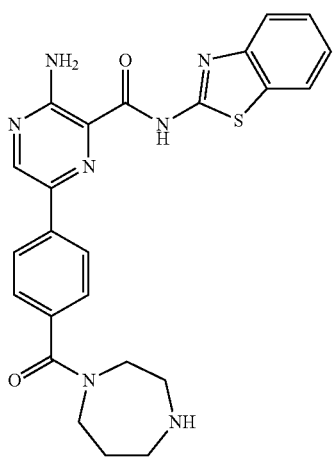 [SMILES: Nc1ncc(-c2ccc(C(=O)N3CCCNCC3)cc2)nc1C(=O)Nc1nc2ccccc2s1]

TABLE V-continued
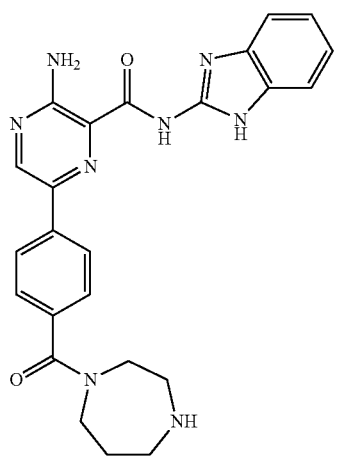 [SMILES: Nc1ncc(-c2ccc(C(=O)N3CCCNCC3)cc2)nc1C(=O)Nc1nc2ccccc2[nH]1]
V-10
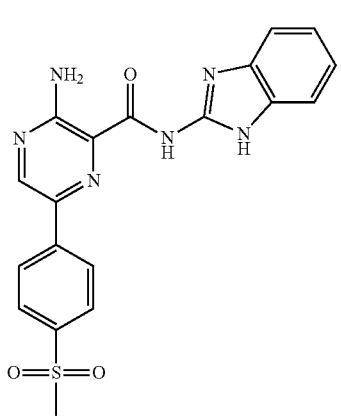 [SMILES: CS(=O)(=O)c1ccc(-c2cnc(N)c(C(=O)Nc3nc4ccccc4[nH]3)n2)cc1]
V-11
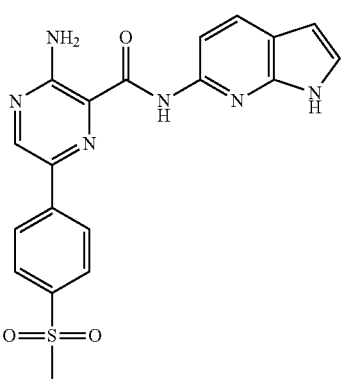 [SMILES: CS(=O)(=O)c1ccc(-c2cnc(N)c(C(=O)Nc3ccc4cc[nH]c4n3)n2)cc1]
V-12
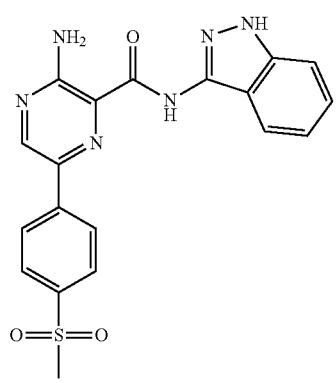 [SMILES: CS(=O)(=O)c1ccc(-c2cnc(N)c(C(=O)Nc3n[nH]c4ccccc34)n2)cc1]
V-13
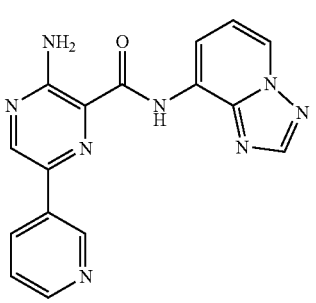 [SMILES: Nc1ncc(-c2cccnc2)nc1C(=O)Nc1cccn2ncnc12]
V-14
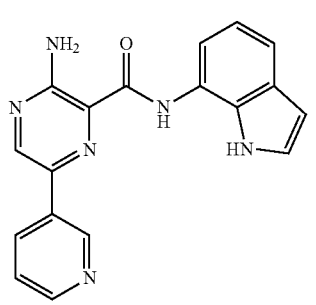 [SMILES: Nc1ncc(-c2cccnc2)nc1C(=O)Nc1cccc2cc[nH]c12]
V-15
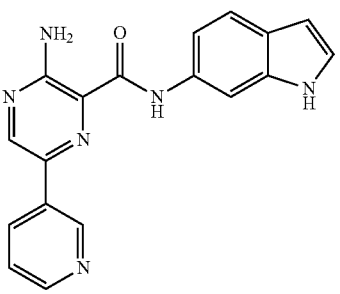 [SMILES: Nc1ncc(-c2cccnc2)nc1C(=O)Nc1ccc2cc[nH]c2c1]
V-16
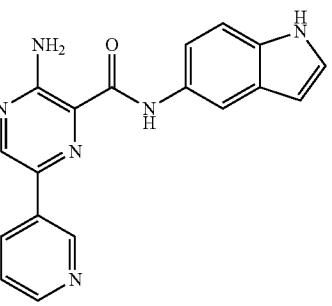
V-17

TABLE V-2

| Compound No. | Ring A | J² | NR¹R² |
|---|---|---|---|
| V-18 | 1H-indazol-3-yl | H | SO₂CH₃ |
| V-19 | 7-azaindol-2-yl (1H-pyrrolo[2,3-b]pyridin-6-yl) | H | SO₂CH₃ |
| V-20 | 1H-benzimidazol-2-yl | H | SO₂CH₃ |
| V-21 | 1H-benzimidazol-2-yl | H | CON(CH₃)₂ |
| V-22 | benzothiazol-2-yl | H | 1,4-diazepan-1-yl carbonyl |
| V-23 | 1H-indazol-3-yl | H | 1,4-diazepan-1-yl carbonyl |
| V-24 | 1H-benzimidazol-2-yl | H | 1,4-diazepan-1-yl carbonyl |
| V-25 | 1-methylbenzimidazol-2-yl | H | 1,4-diazepan-1-yl carbonyl |
| V-26 | 1H-indol-2-yl | H | 1,4-diazepan-1-yl carbonyl |
| V-27 | benzoxazol-2-yl | H | 1,4-diazepan-1-yl carbonyl |
| V-28 | 1H-indazol-6-yl | H | 1,4-diazepan-1-yl carbonyl |
| V-29 | 1H-benzimidazol-2-yl | CN | 1,4-diazepan-1-yl carbonyl or |

V-30: 3-amino-N-(1H-benzimidazol-2-yl)-6-(3-cyanopyridin-4-yl)pyrazine-2-carboxamide Another embodiment provides a compound of formula VI:

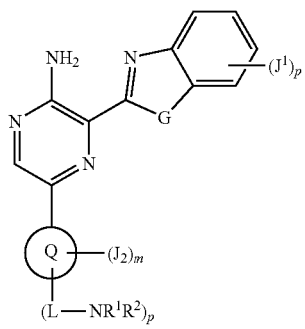

or a pharmaceutically acceptable salt thereof; wherein
Q is a 5-6 membered monocyclic aromatic ring containing 0-4 heteroatoms independently selected from nitrogen, oxygen, or sulfur; or an 8-10 membered bicyclic aromatic ring containing 0-6 heteroatoms independently selected from nitrogen, oxygen, or sulfur;

L is —C(O)— or —SO$_2$—;

G is S or O;

$R^1$ is H, or $C_1$-$C_6$alkyl;

$R^2$ is —($C_2$-$C_6$alkyl)-Z or a 4-8 membered heterocyclic ring containing 0-2 nitrogen atoms; wherein said ring is bonded via a carbon atom and is optionally substituted with one occurrence of $J^Z$;

or $R^1$ and $R^2$, taken together with the atom to which they are bound, form a 4-8 membered heterocyclic ring containing 1-2 nitrogen atoms; wherein said heterocyclic ring is optionally substituted with one occurrence of $J^{Z1}$;

$J^{Z1}$ is 1 (X)$_r$—CN, $C_1$-$C_6$alkyl or —(X)$_r$—Z;

X is $C_1$-$C_4$alkyl;

each t, p, and r is independently 0 or 1;

Z is —NR$^3$R$^4$;

$R^3$ is H or $C_1$-$C_2$alkyl;

$R^4$ is H or $C_1$-$C_6$alkyl;

or $R^3$ and $R^4$, taken together with the atom to which they are bound, form a 4-8 membered heterocyclic ring containing 1-2 nitrogen atoms; wherein said ring is optionally substituted with one occurrence of $J^Z$;

each $J^Z$ and $J^1$ is independently NH$_2$, NH($C_{1-4}$aliphatic), N($C_{1-4}$aliphatic)$_2$, halogen, $C_{1-4}$aliphatic, OH, O($C_{1-4}$aliphatic), NO$_2$, CN, CO$_2$H, CO($C_{1-4}$aliphatic), CO$_2$($C_{1-4}$aliphatic), O(halo$C_{1-4}$aliphatic), or halo$C_{1-4}$aliphatic;

$J^2$ is halo, $C_1$-$C_2$alkyl optionally substituted with 1-3 fluoro, or CN;

q is 0, 1, or 2;

p is 0 or 1.

According to one aspect of the invention, p is 1. In some embodiments, Q is phenyl. In other embodiments, L is —C(O)—. In some embodiments, $R^1$ and $R^2$, taken together with the atom to which they are bound, form a 4-8 membered heterocyclic ring containing 1-2 nitrogen atoms. In some embodiments, the heterocyclic ring formed by $R^1$ and $R^2$ is selected from pyrrolidinyl, piperidinyl, piperazinyl, azepanyl, or 1,4-diazepanyl. In other embodiments, said heterocyclyl is

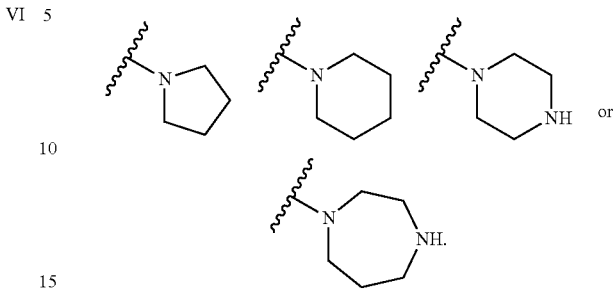

According to another aspect of the invention, p is 0, q is 0, and -L-NR$^1$R$^2$ is C(O)1,4-diazepanyl.

Another embodiment provides a compound selected from Table VI:

TABLE VI

| Compound No. | NR$^1$R$^2$ | G |
|---|---|---|
| VI-1 | ![homopiperazine-NH] | S |
| VI-2 | ![homopiperazine-NH] | O |
| VI-3 | ![homopiperazine-NBOC] | S |

Another embodiment provides a compound of formula VII,

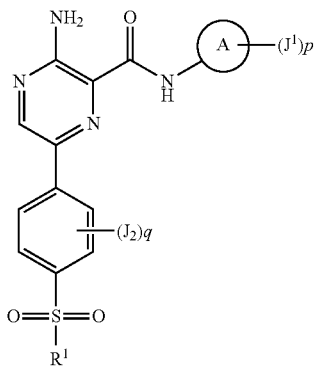

or a pharmaceutically acceptable salt thereof; wherein

Ring A is a 5-6 membered monocyclic aryl or heteroaryl ring having 0-3 heteroatoms independently selected from nitrogen, oxygen, or sulfur, wherein said ring is optionally substituted with $J^1$;

$R^1$ is $C_1$-$C_6$alkyl;

$J^1$ is a $C_{1-6}$ alkyl chain wherein 1-2 methylene units are optionally replaced with O, NR*, S, or C(O); $J^1$ is optionally substituted with 1-3 occurrences of halo;

R* is H or $C_{1-4}$alkyl;

$J^2$ is halo, $C_1$-$C_2$alkyl optionally substituted with 1-3 fluoro, or CN;

Each p and q is independently 0, 1, or 2.

According to one aspect of the invention, Ring A is a 5-6 membered heteroaryl having 1-3 heteroatoms independently selected from nitrogen, oxygen, or sulfur. In some embodiments, Ring A is pyridinyl, pyrimidyl, pyrazinyl, triazinyl, pyrrolyl, pyrazolyl, triazolyl, thienyl, thiazolyl, thiadiazolyl, furanyl, oxazolyl, or oxadiaozolyl. In other embodiments, Ring A is pyridinyl, pyrazolyl, thiadiazolyl, or thiazolyl wherein Ring A is optionally substituted with halo or $C_{1-4}$alkyl. In some embodiments, Ring A is phenyl. In some embodiments, said phenyl is substituted with one occurrence of $J^1$.

In some embodiments, $J^1$ is a $C_{1-6}$ alkyl chain wherein 1 methylene unit is replaced with N or O. In other embodiments, $J^1$ is O($C_{1-4}$alkyl) or —($C_{1-4}$alkyl)NH($C_{1-4}$alkyl). In yet other embodiments, $J^1$ is —($C_{1-4}$alkyl)NH($C_{1-4}$alkyl).

Another embodiment provides a compound selected from the following:

TABLE VII

| Compound No. | R1 |  |
|---|---|---|
| VII-1 | CH₃ | 2-methoxypyridin-3-yl |
| VII-2 | CH₃ | 2-methylpyridin-4-yl |
| VII-3 | CH₃ | 1,3-dimethyl-1H-pyrazol-5-yl |
| VII-4 | CH₃ | 6-ethylpyridin-2-yl |
| VII-5 | CH₃ | 6-methylpyridin-2-yl |

TABLE VII-continued

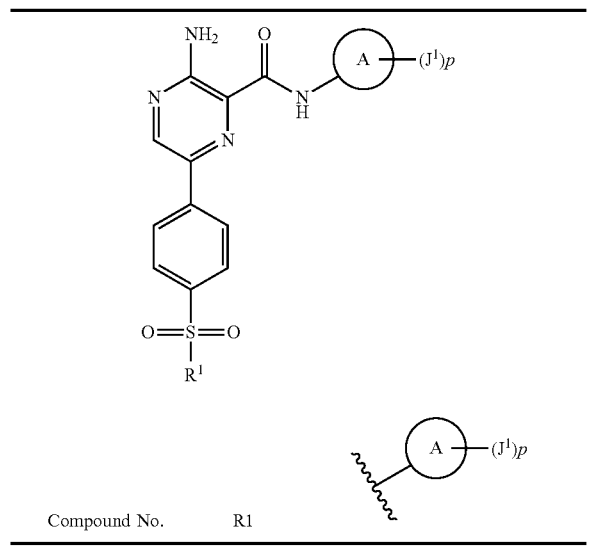

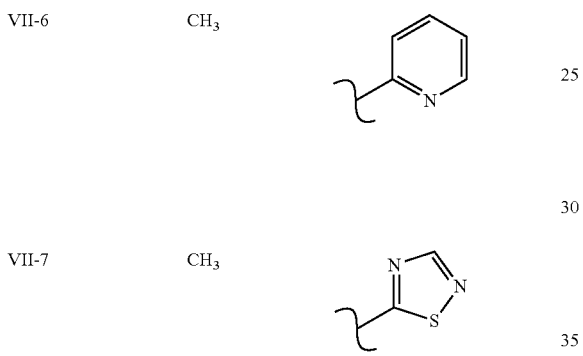

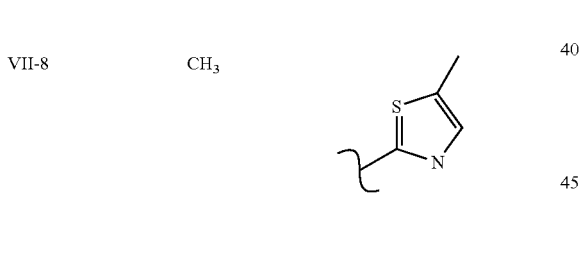

| Compound No. | R1 | |
|---|---|---|
| VII-6 | CH$_3$ | (2-pyridyl) |
| VII-7 | CH$_3$ | (1,3,4-thiadiazol-2-yl) |
| VII-8 | CH$_3$ | (4-methylthiazol-2-yl) |
| VII-9 | CH$_3$ | (4-methoxypyridin-3-yl) |
| VII-10 | CH$_3$ | (4-(N-methylaminomethyl)phenyl) |

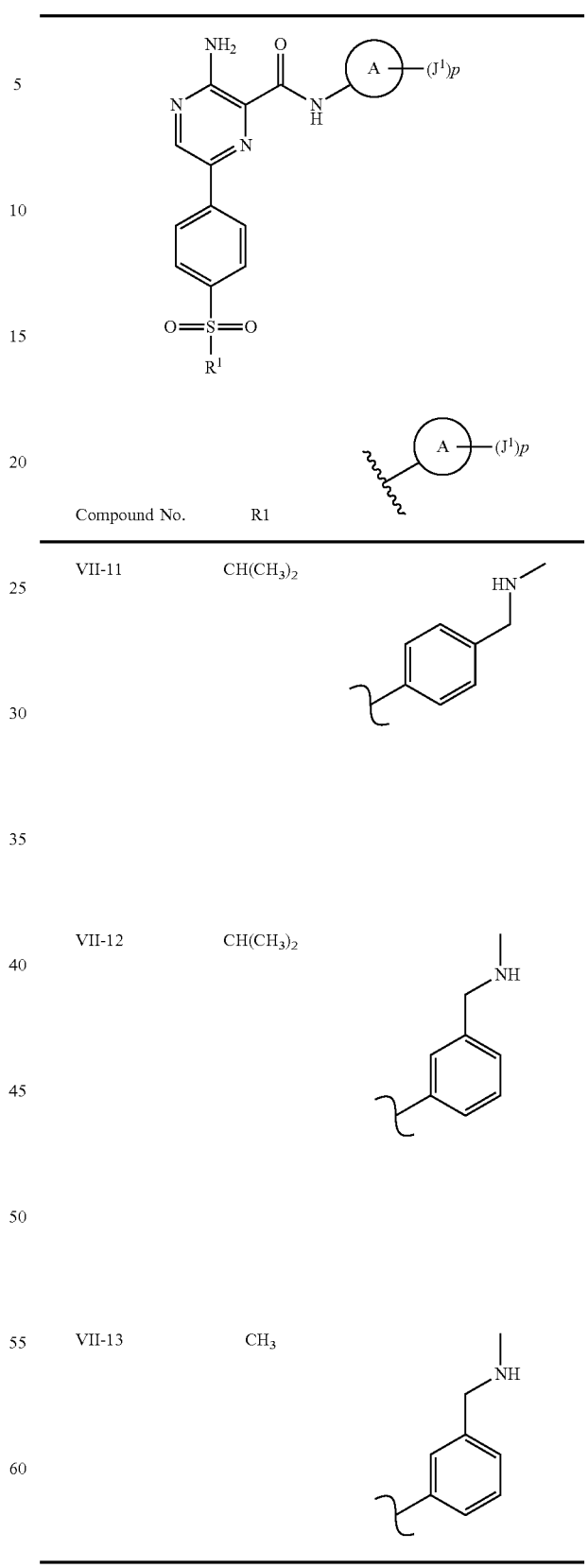

| Compound No. | R1 | |
|---|---|---|
| VII-11 | CH(CH$_3$)$_2$ | (4-(N-methylaminomethyl)phenyl) |
| VII-12 | CH(CH$_3$)$_2$ | (3-(N-methylaminomethyl)phenyl) |
| VII-13 | CH$_3$ | (3-(N-methylaminomethyl)phenyl) |

Another embodiment provides a compound selected from Table 1.

TABLE I
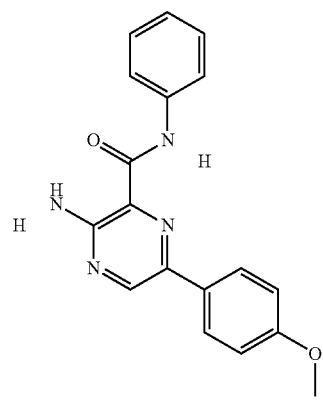
I-1
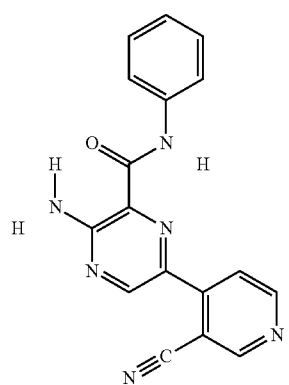
I-2
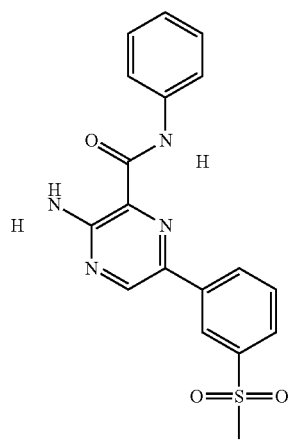
I-3
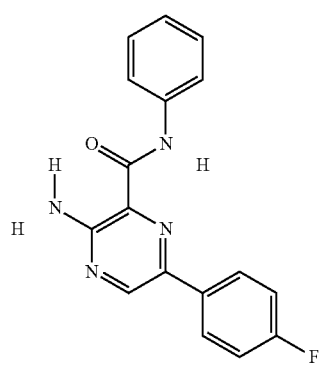
I-4

TABLE I-continued
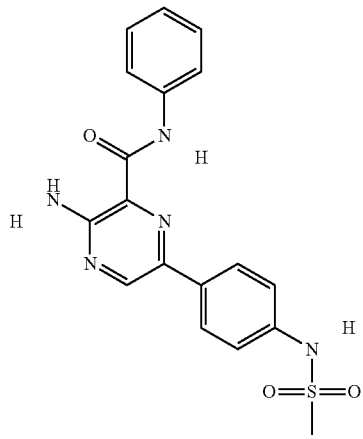
I-5
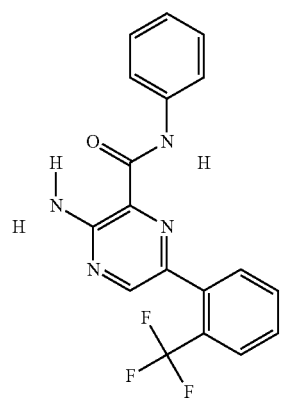
I-6
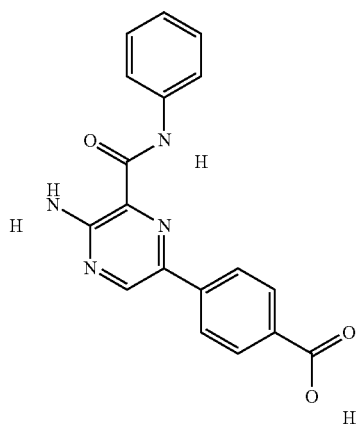
I-7

TABLE I-continued
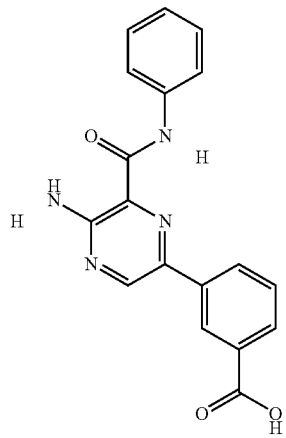
I-8
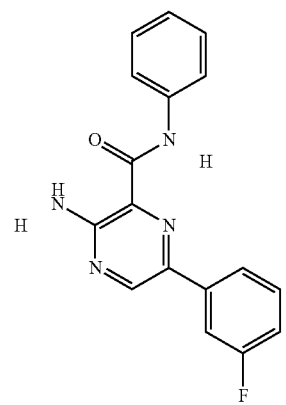
I-9
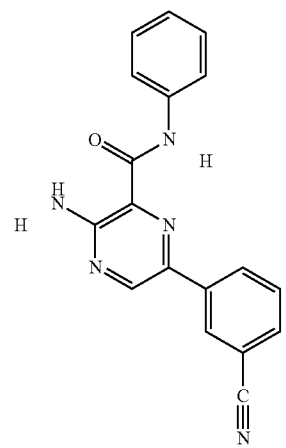
I-10
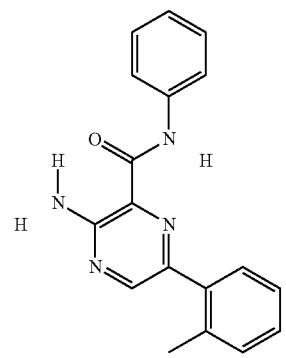
I-11

TABLE I-continued
I-12
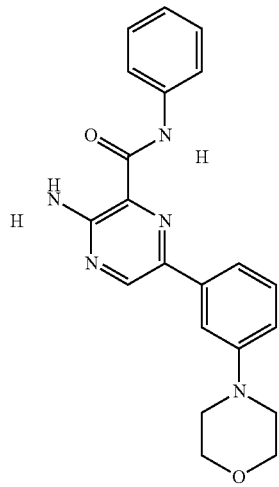
I-13
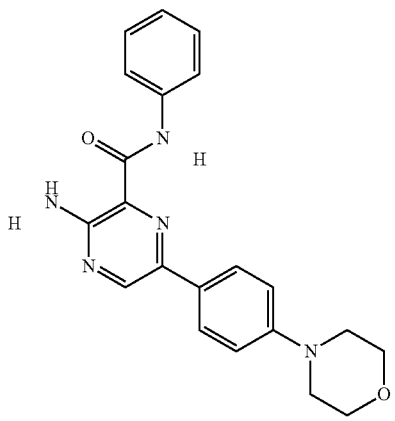
I-14
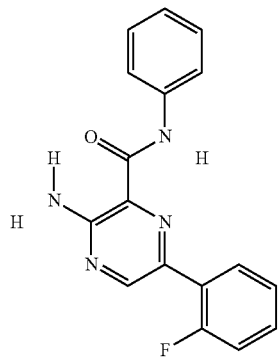
I-15
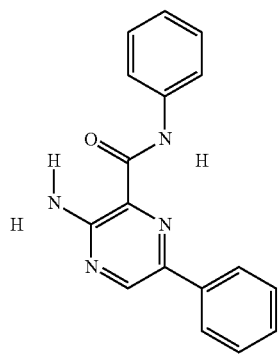

TABLE I-continued
I-16
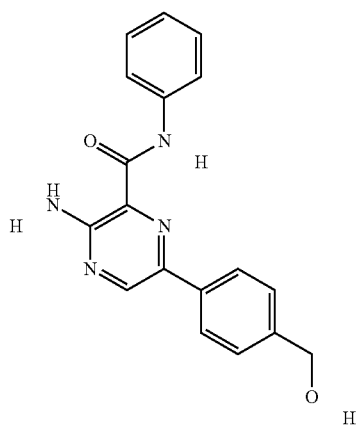
I-17
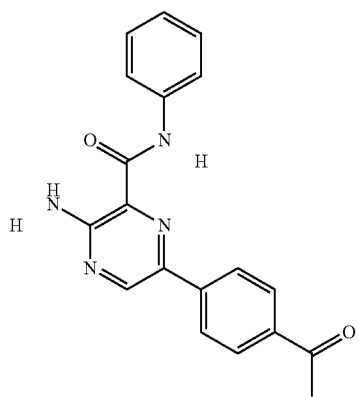
I-18
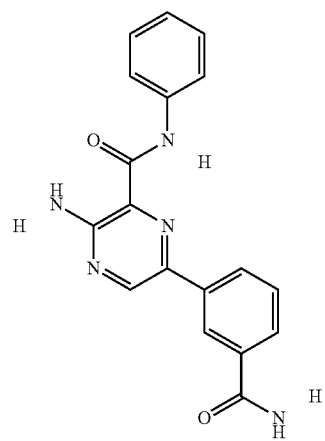

TABLE I-continued
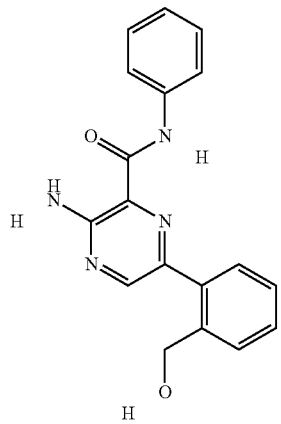
I-19
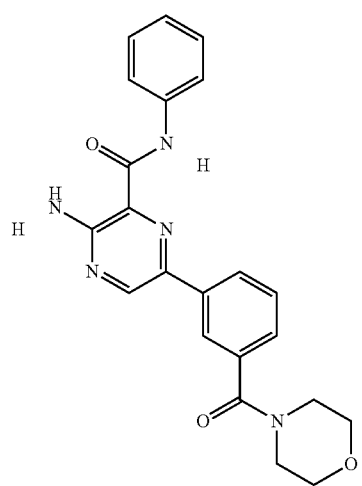
I-20
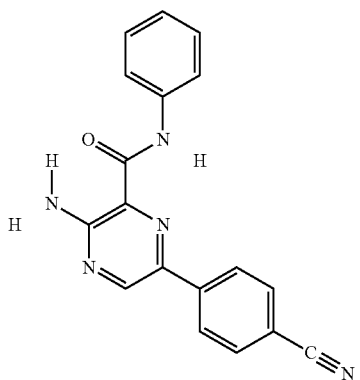
I-21

TABLE I-continued
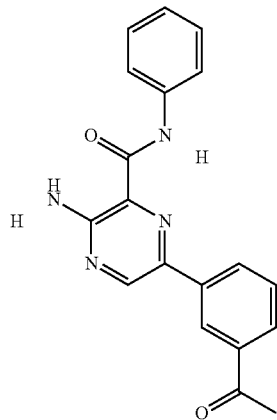
I-22
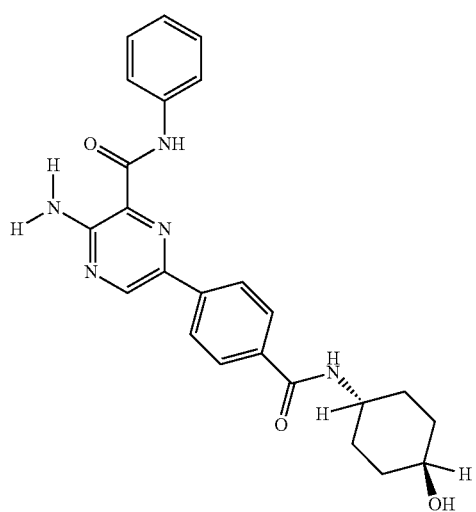 [SMILES: Nc1ncc(-c2ccc(C(=O)N[C@H]3CC[C@H](O)CC3)cc2)nc1C(=O)Nc1ccccc1]
I-23
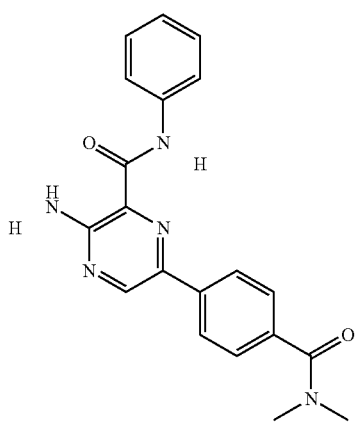
I-24

TABLE I-continued
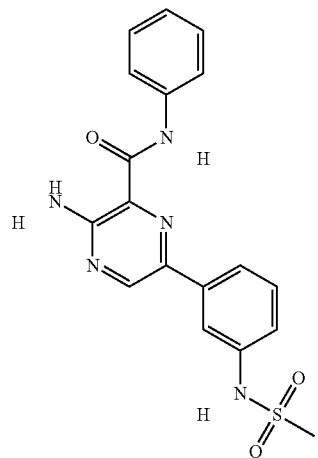
I-25
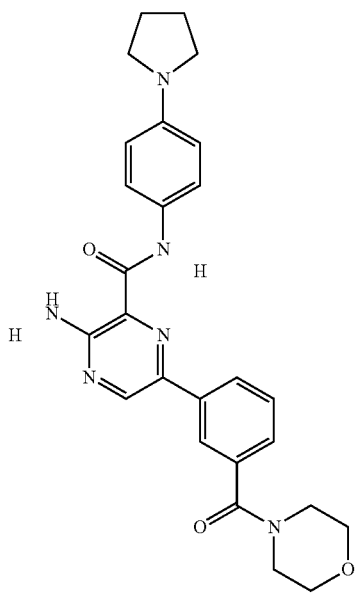
I-26
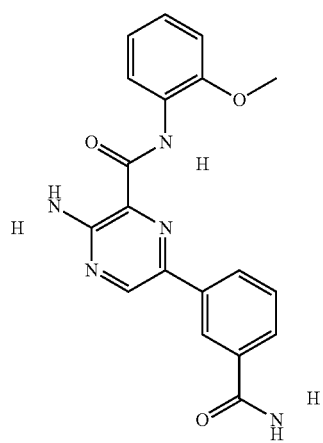
I-27

TABLE I-continued
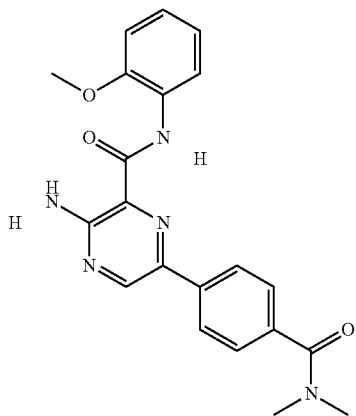
I-28
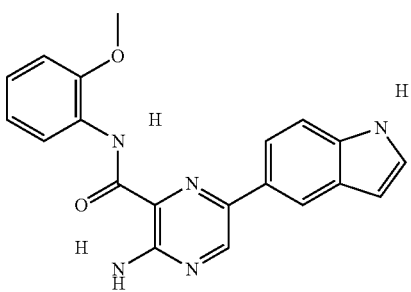
I-29
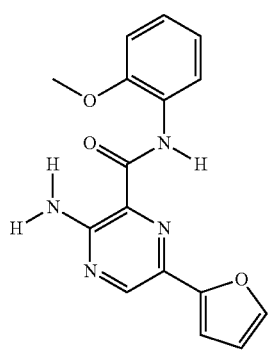 [SMILES: COc1ccccc1NC(=O)c1nc(-c2ccco2)cnc1N]
I-30
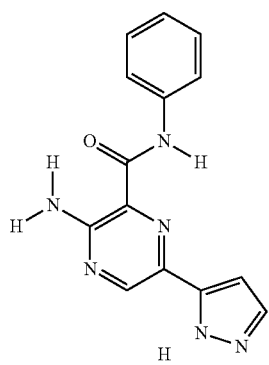
I-31

TABLE I-continued
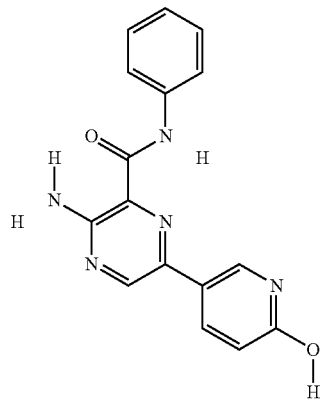
I-32
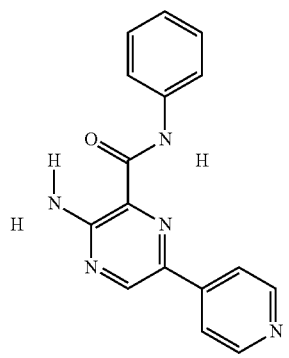
I-33
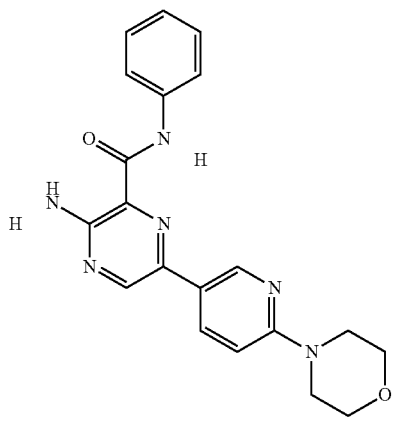
I-34
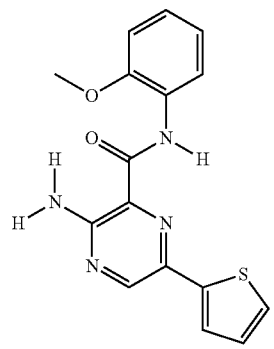 [SMILES: COc1ccccc1NC(=O)c1nc(-c2cccs2)cnc1N]
I-35

TABLE I-continued
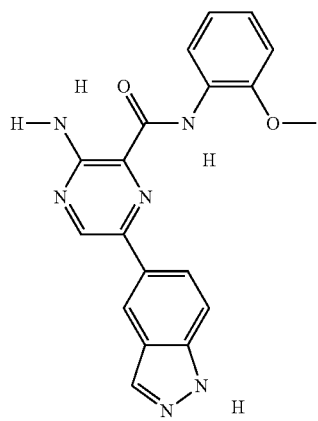
I-36
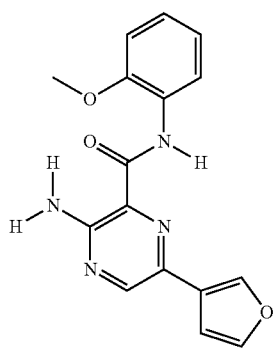 [SMILES: COc1ccccc1NC(=O)c1nc(-c2ccoc2)cnc1N]
I-37
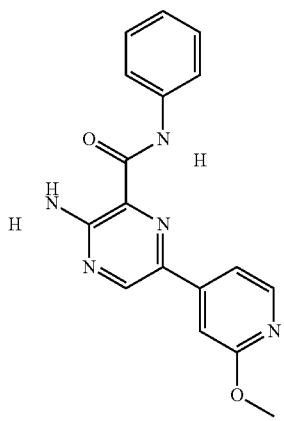
I-38
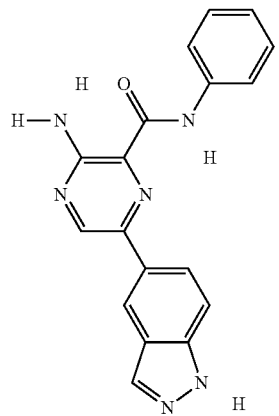
I-39

TABLE I-continued
I-40
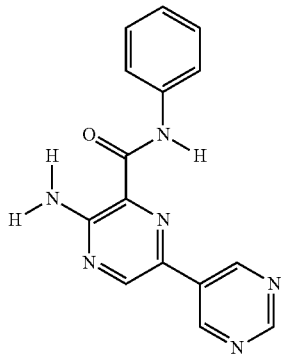 [SMILES: Nc1ncc(-c2cncnc2)nc1C(=O)Nc1ccccc1]
I-41
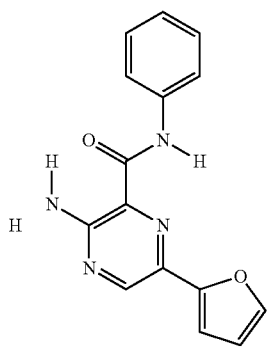
I-42
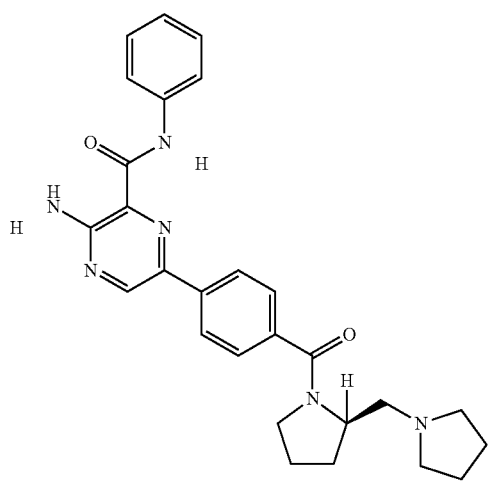

TABLE I-continued
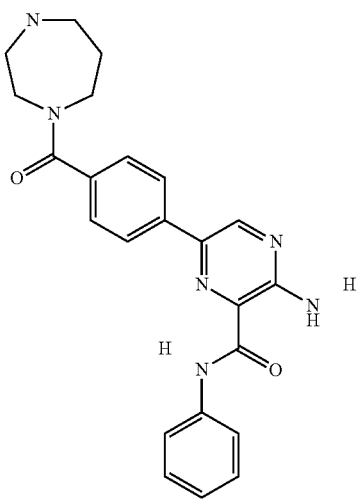
I-43
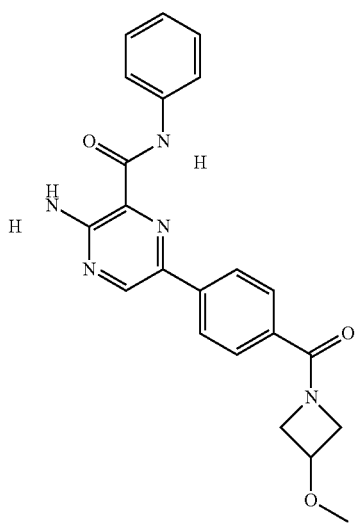
I-44
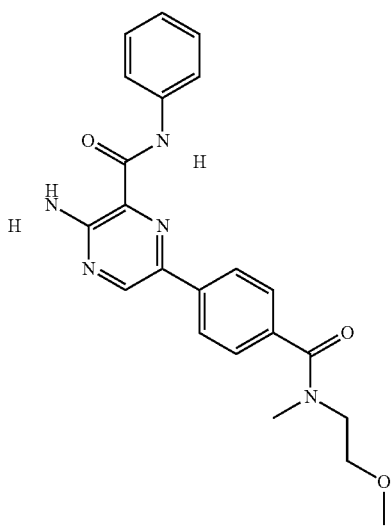
I-45

TABLE I-continued
I-46
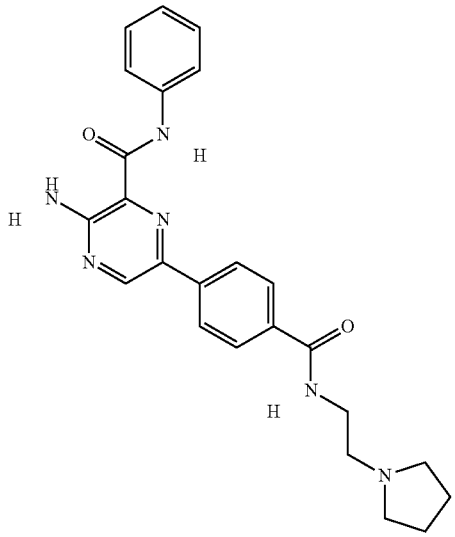
I-47
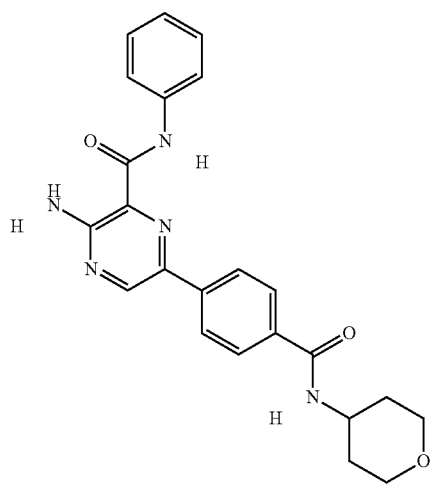
I-48
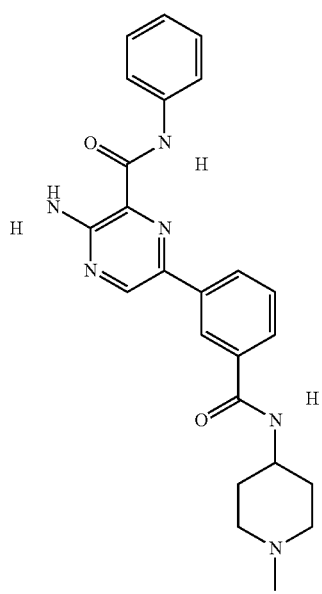

TABLE I-continued
I-49
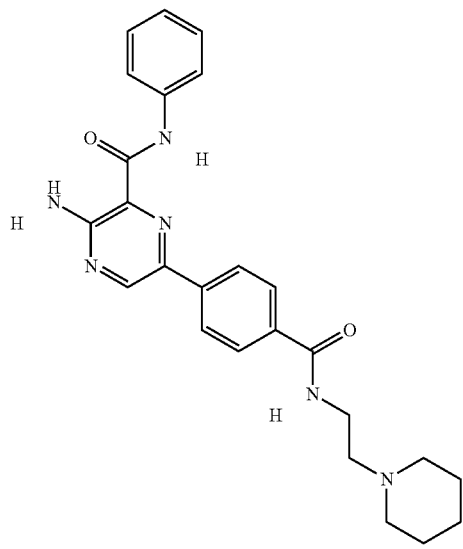
I-50
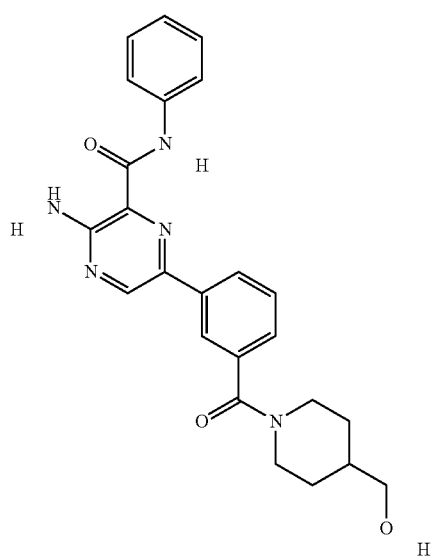
I-51
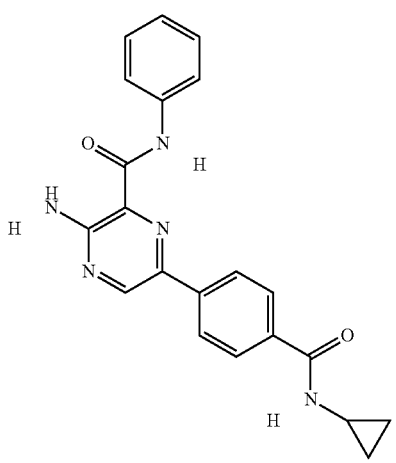

TABLE I-continued
I-52
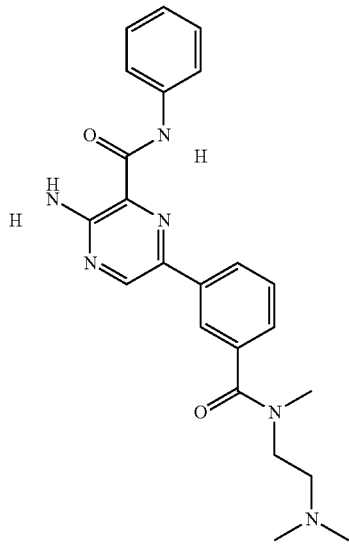
I-53
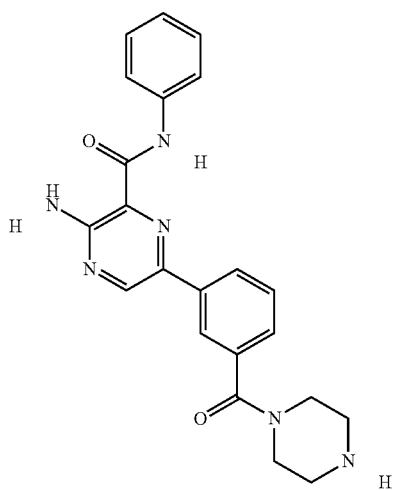
I-54
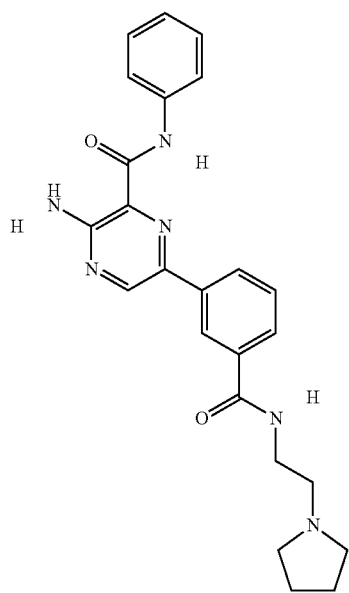

TABLE I-continued
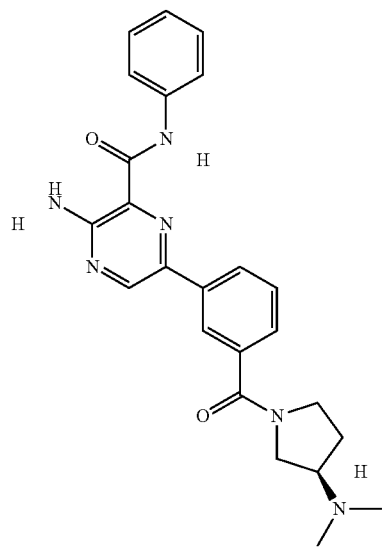
I-55
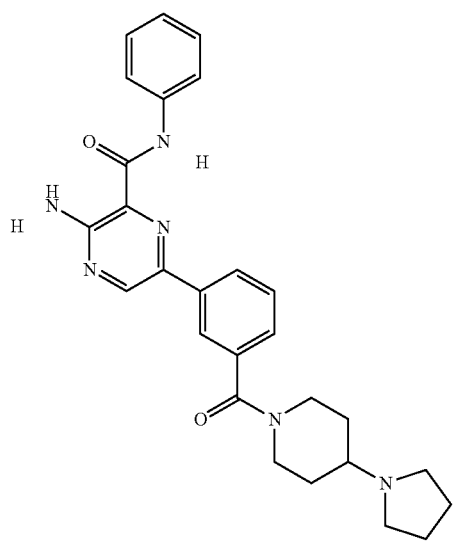
I-56
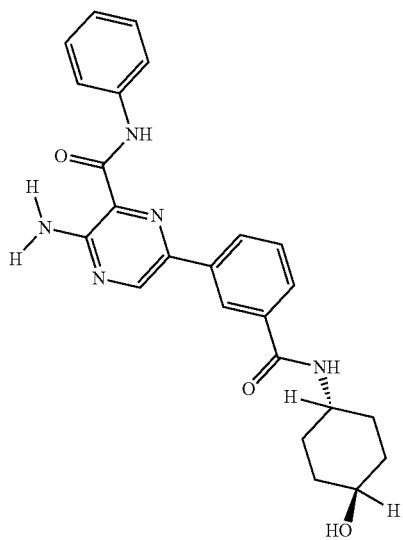 [SMILES: Nc1ncc(-c2cccc(C(=O)N[C@H]3CC[C@H](O)CC3)c2)nc1C(=O)Nc1ccccc1]
I-57

TABLE I-continued
I-58
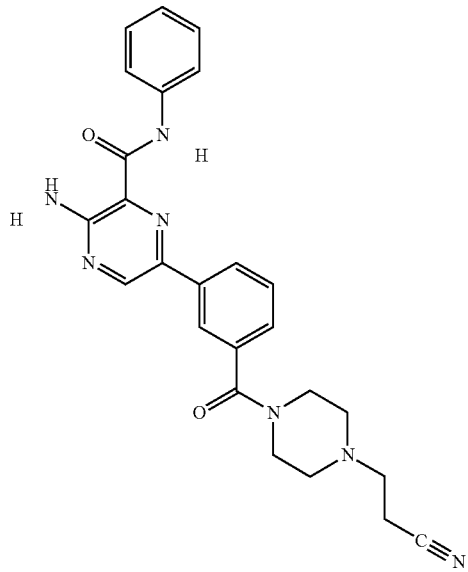
I-59
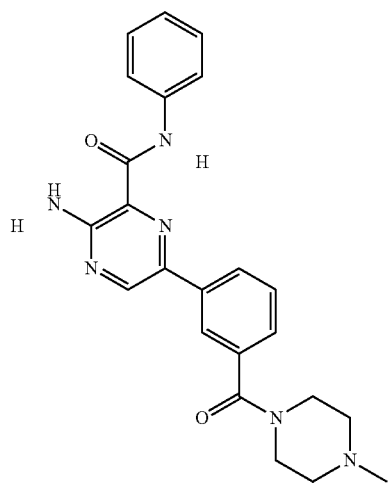
I-60
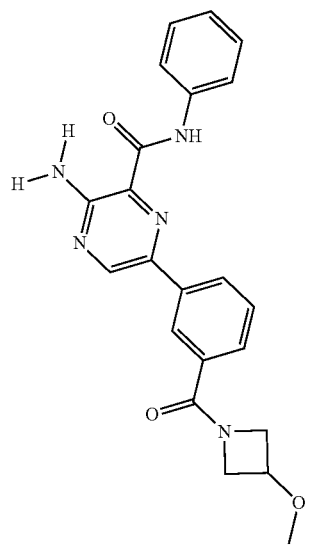 [SMILES: COC1CN(C(=O)c2cccc(-c3cnc(N)c(C(=O)Nc4ccccc4)n3)c2)C1]

TABLE I-continued
I-61
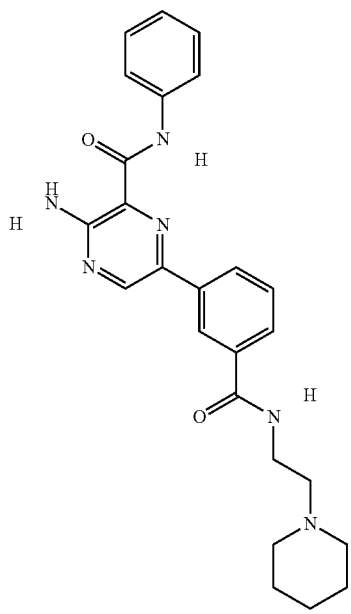
I-62
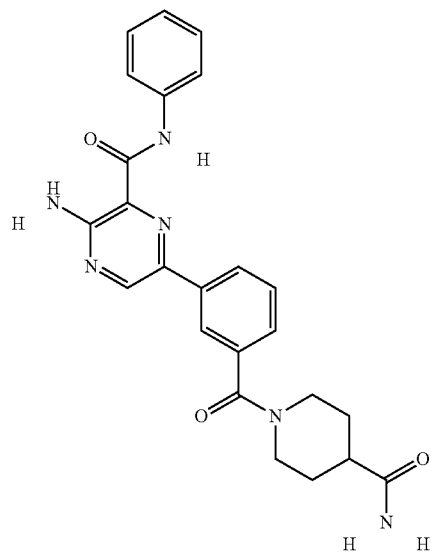
I-63
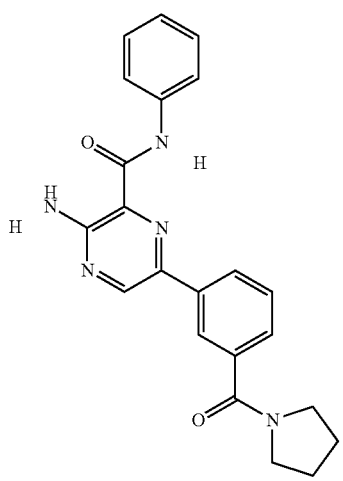

US 9,701,674 B2
253 254
TABLE I-continued
I-64
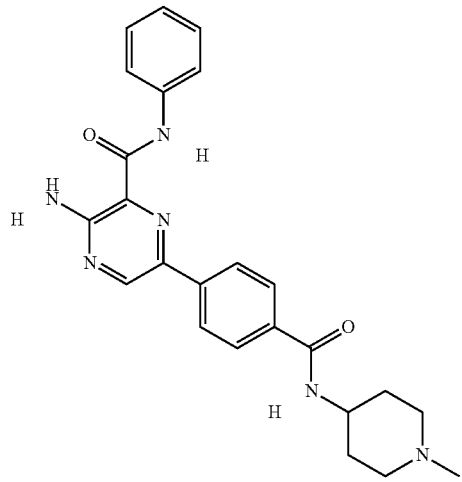
I-65
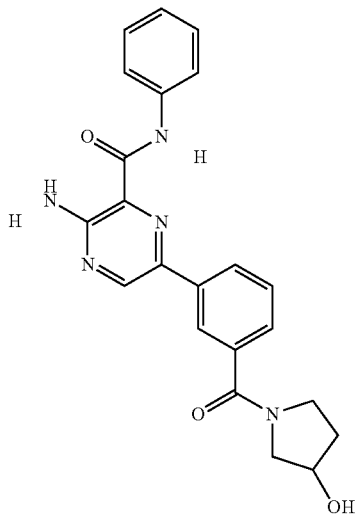
I-66
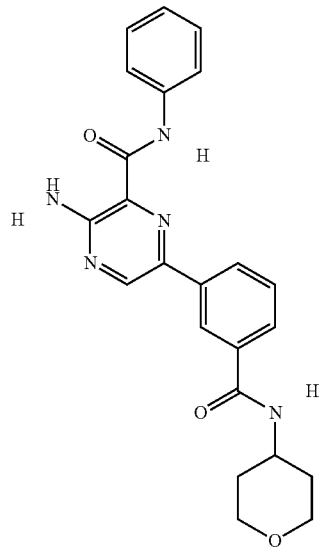

TABLE I-continued
I-67
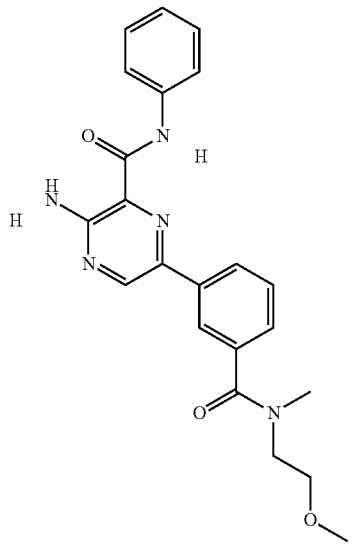
I-68
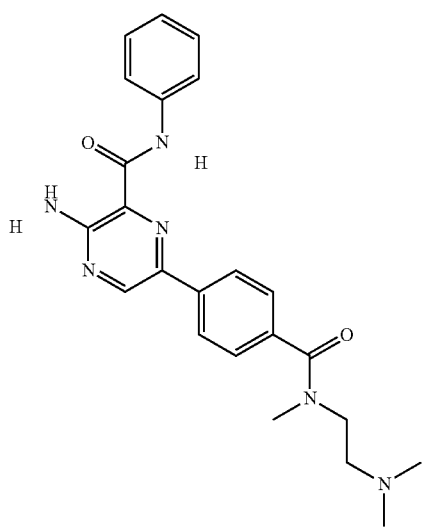
I-69
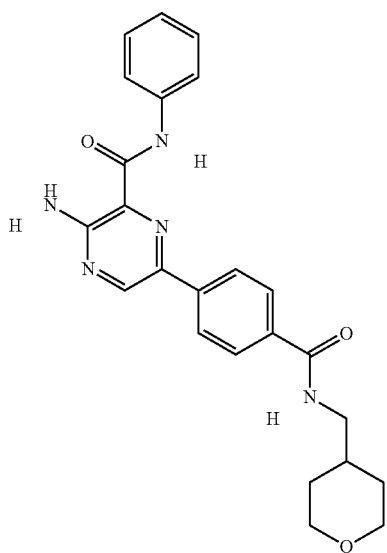

TABLE I-continued
I-70
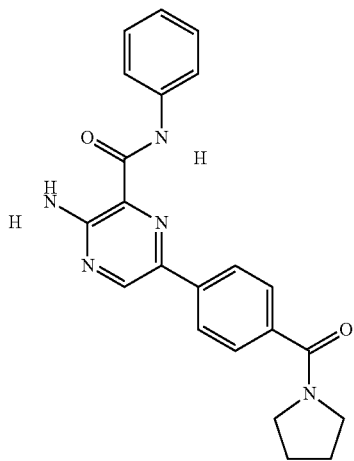
I-71
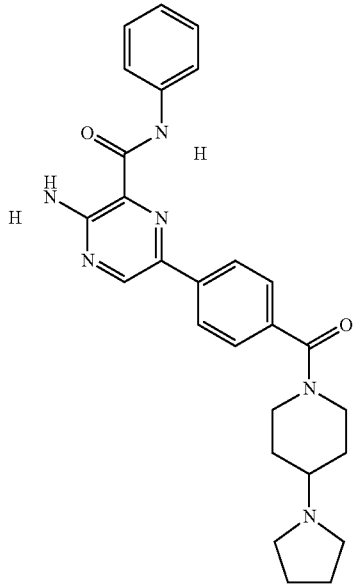
I-72
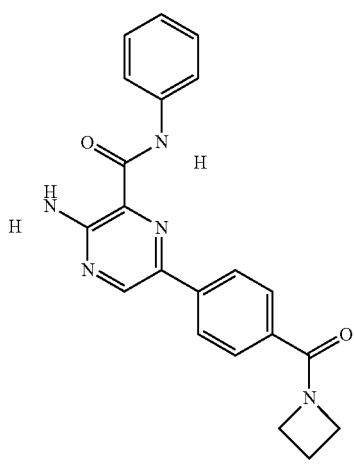

TABLE I-continued
I-73
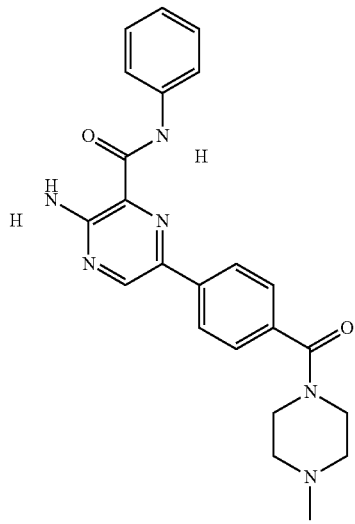
I-74
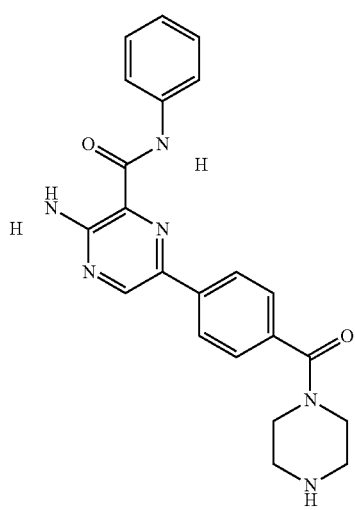
I-75
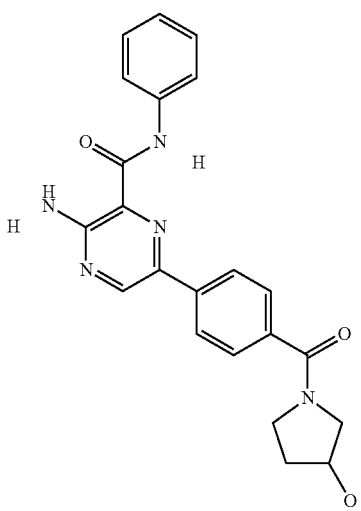

TABLE I-continued
I-76
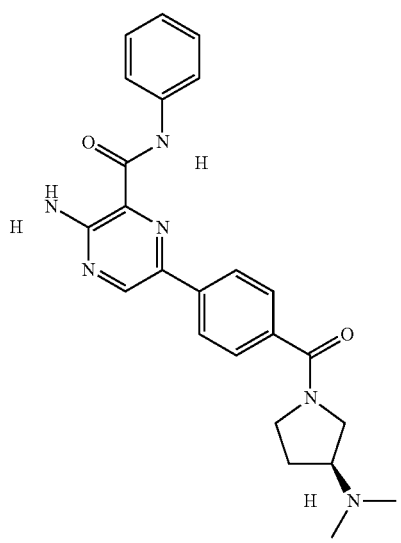
I-77
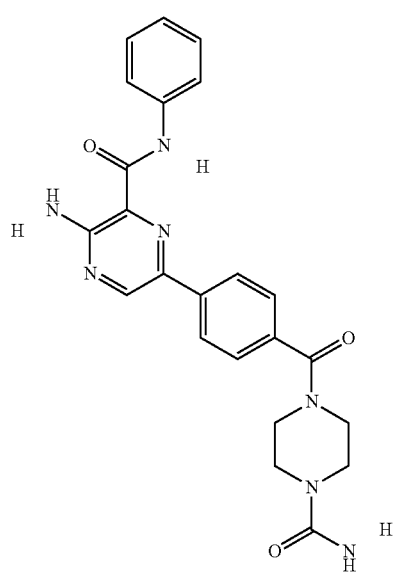
I-78
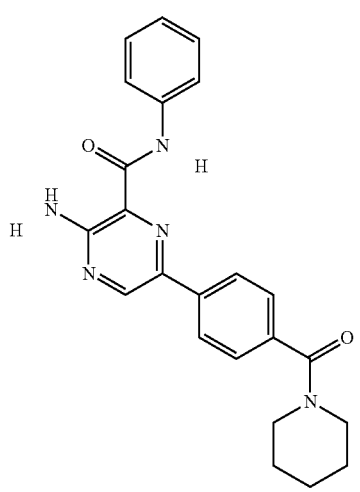

TABLE I-continued
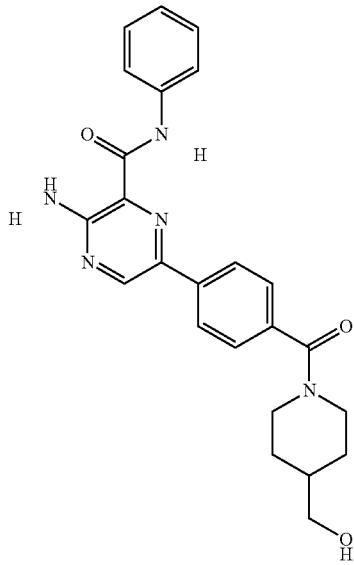
I-79
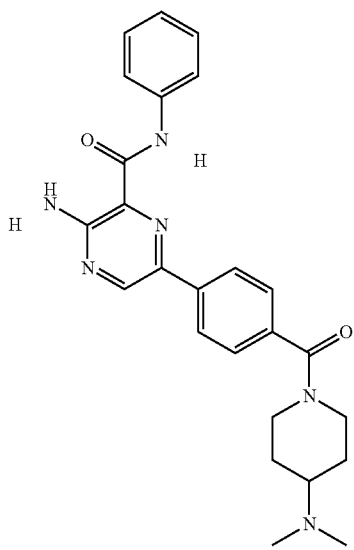
I-80

TABLE I-continued
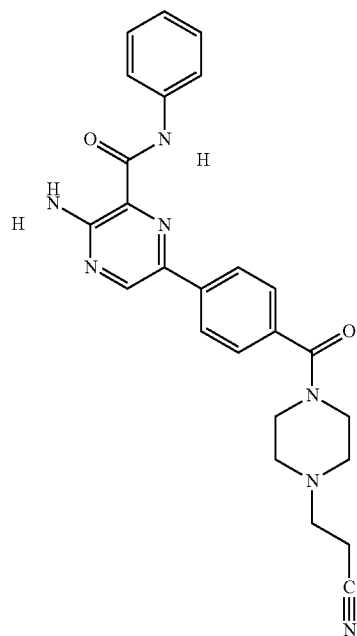
I-81
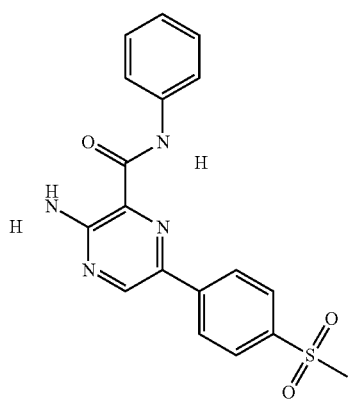
I-82
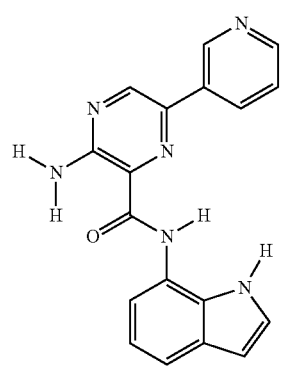 [SMILES: Nc1ncc(-c2cccnc2)nc1C(=O)Nc1cccc2cc[nH]c12]
I-83

TABLE I-continued
I-84
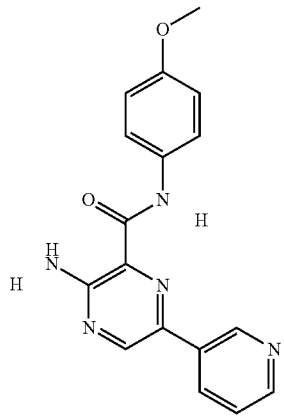
I-85
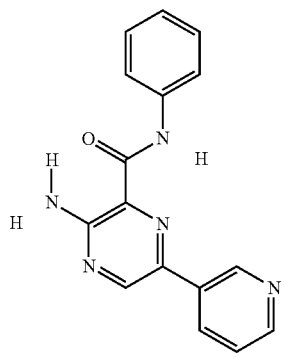
I-86
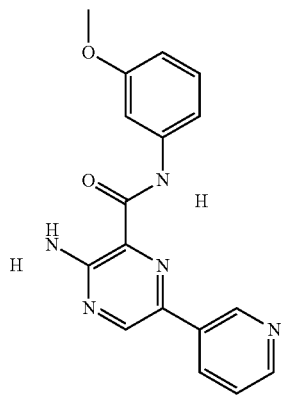
I-87
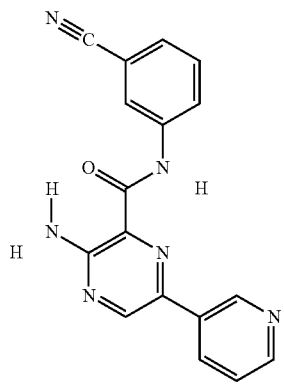

TABLE I-continued
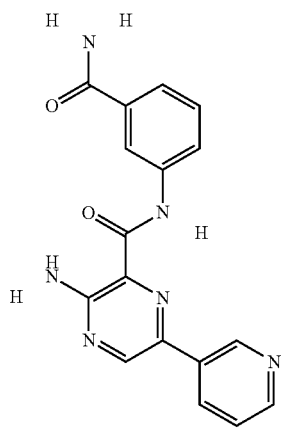
I-88
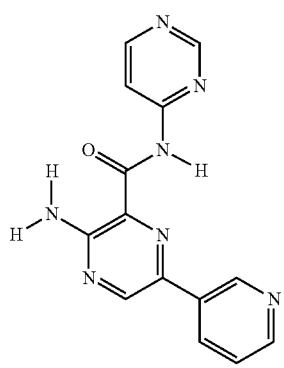 [SMILES: Nc1ncc(-c2cccnc2)nc1C(=O)Nc1ccncn1]
I-89
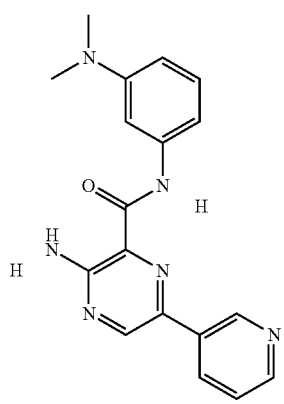
I-90
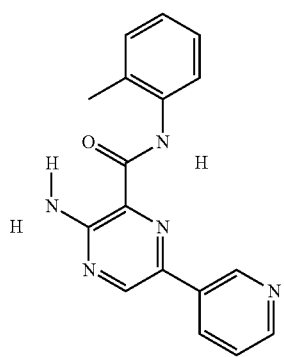
I-91

TABLE I-continued
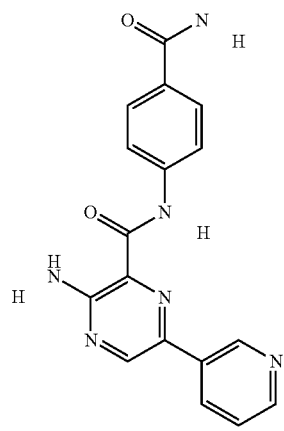
I-92
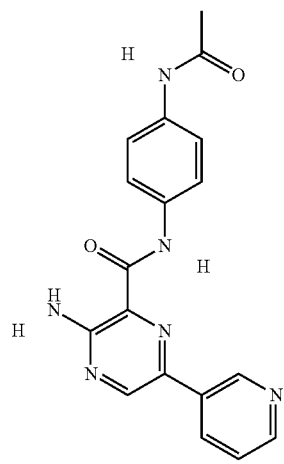
I-93
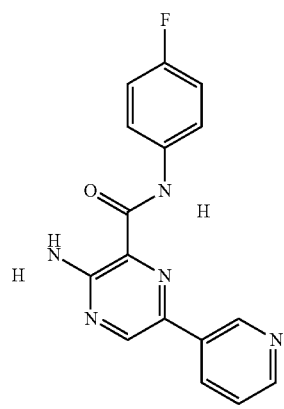
I-94

TABLE I-continued
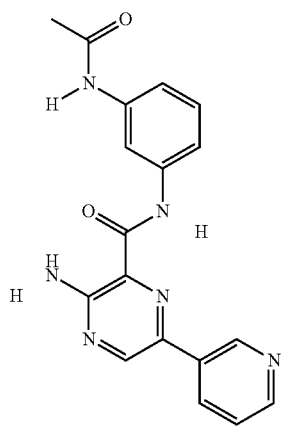
I-95
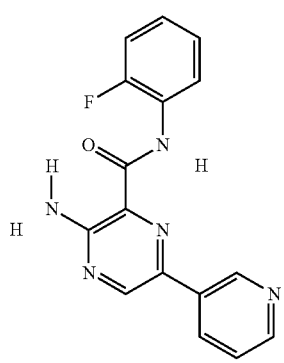
I-96
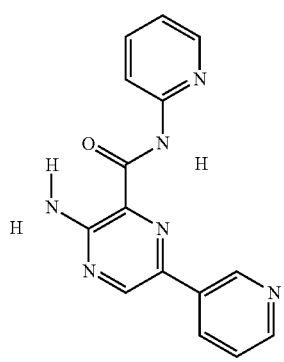
I-97
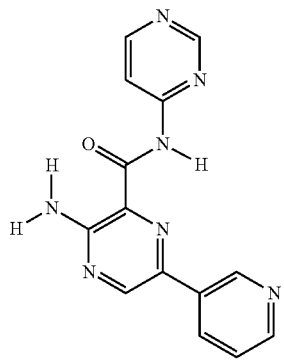 [SMILES: Nc1ncc(-c2cccnc2)nc1C(=O)Nc1ccncn1]
I-98

TABLE I-continued
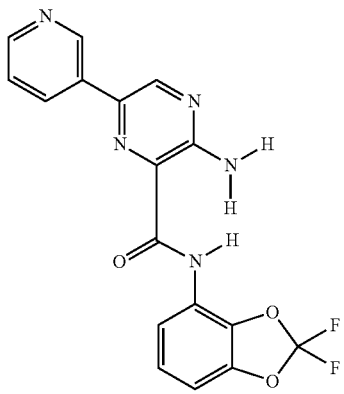 [SMILES: Nc1ncc(-c2cccnc2)nc1C(=O)Nc1cccc2c1OC(F)(F)O2]
I-99
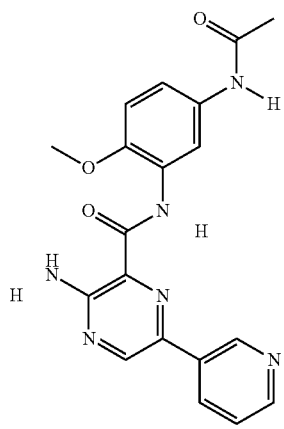
I-100
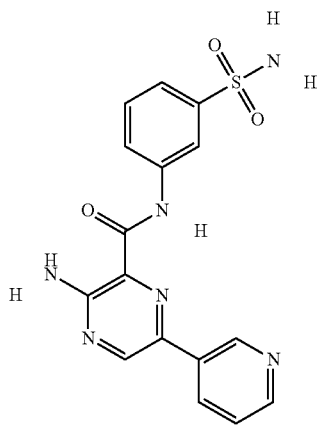
I-101
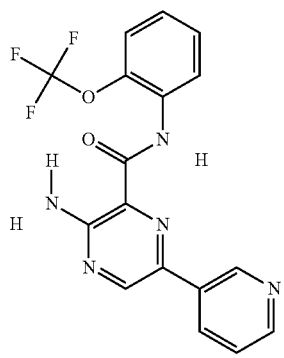
I-102

TABLE I-continued
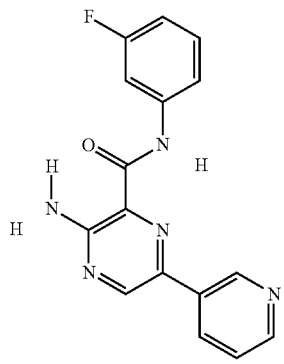
I-103
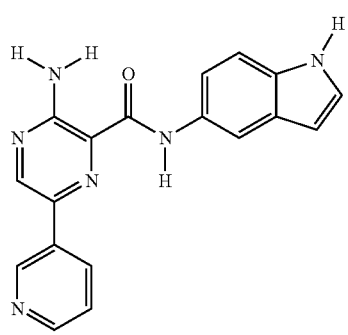 [SMILES: Nc1ncc(-c2cccnc2)nc1C(=O)Nc1ccc2[nH]ccc2c1]
I-104
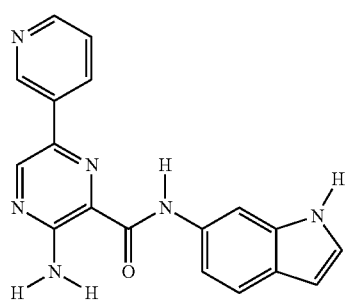 [SMILES: Nc1ncc(-c2cccnc2)nc1C(=O)Nc1ccc2cc[nH]c2c1]
I-105
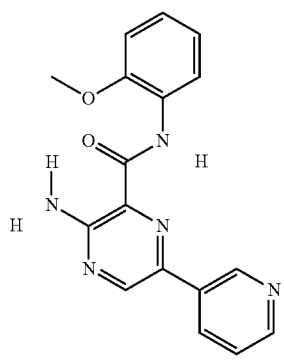
I-106

TABLE I-continued
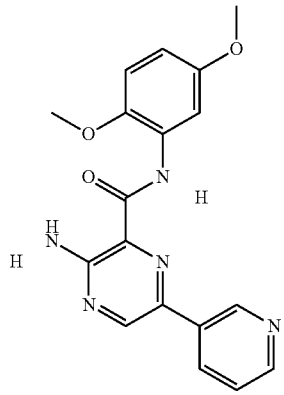
I-107
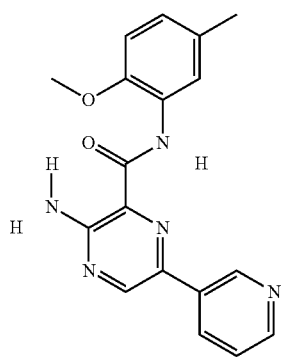
I-108
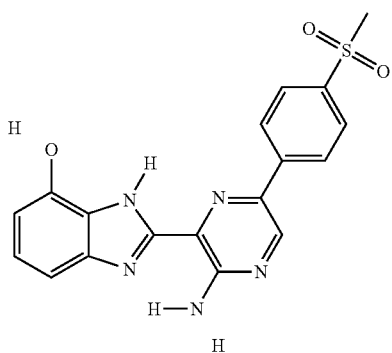
I-109
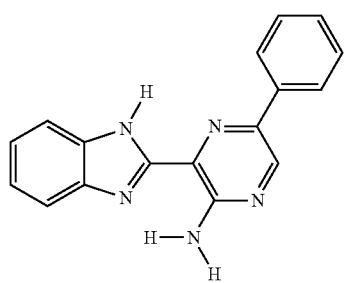 [SMILES: Nc1ncc(-c2ccccc2)nc1-c1nc2ccccc2[nH]1]
I-110

TABLE I-continued
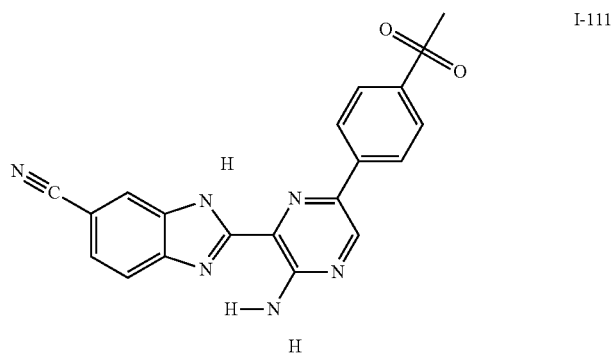
I-111
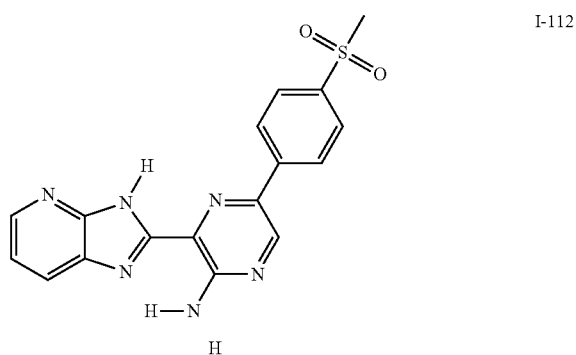
I-112
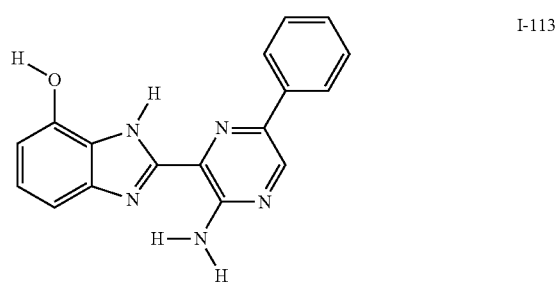
I-113
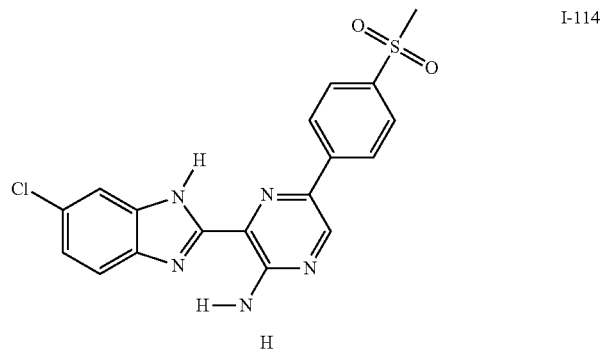
I-114

TABLE I-continued
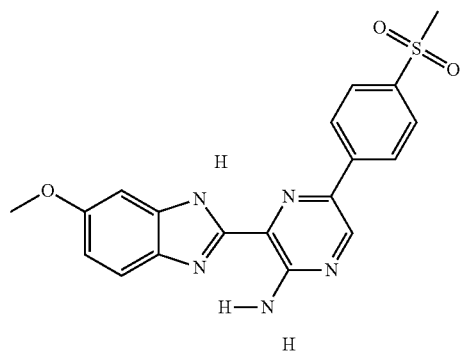
I-115
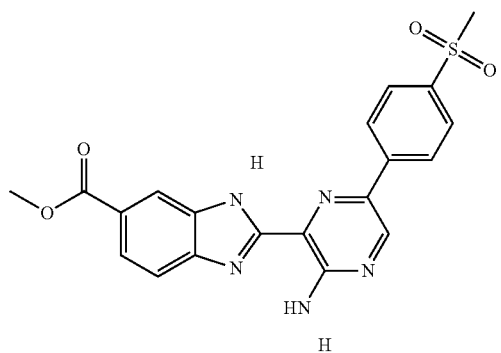
I-116
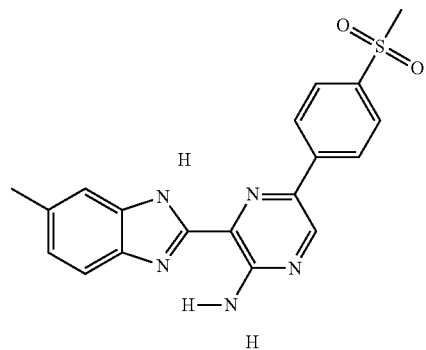
I-117
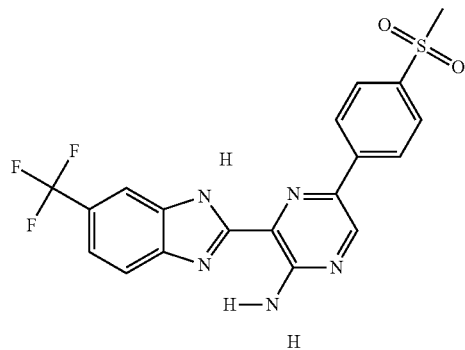
I-118

TABLE I-continued
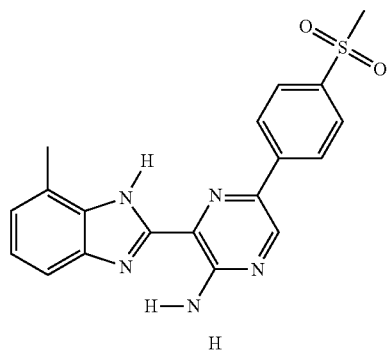
I-119
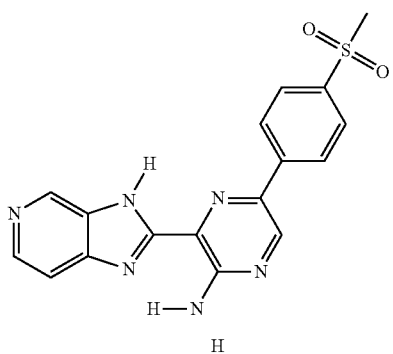
I-120
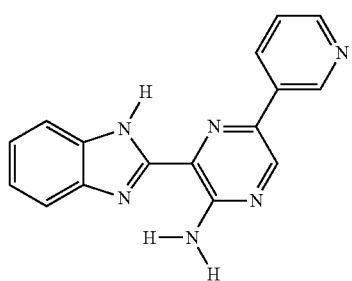 [SMILES: Nc1ncc(-c2cccnc2)nc1-c1nc2ccccc2[nH]1]
I-121
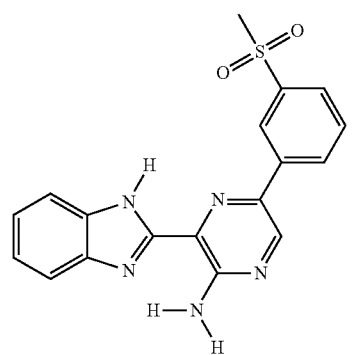 [SMILES: CS(=O)(=O)c1cccc(-c2cnc(N)c(-c3nc4ccccc4[nH]3)n2)c1]
I-122

TABLE I-continued
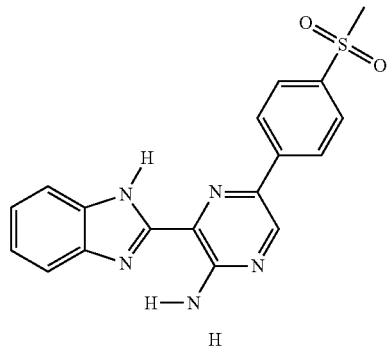
I-123
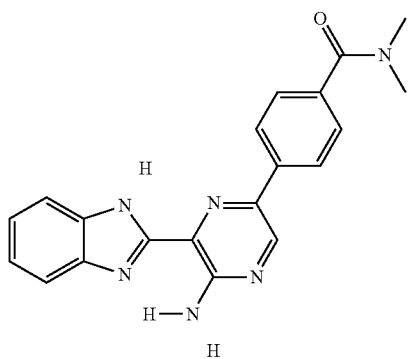
I-124
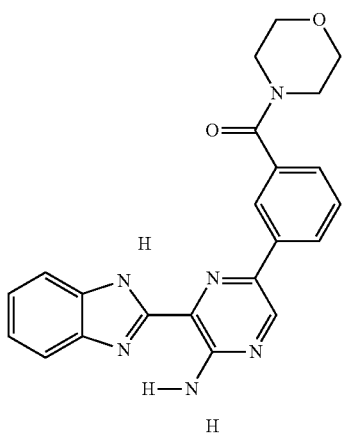
I-125
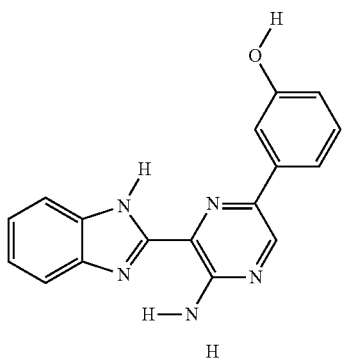
I-126

TABLE I-continued
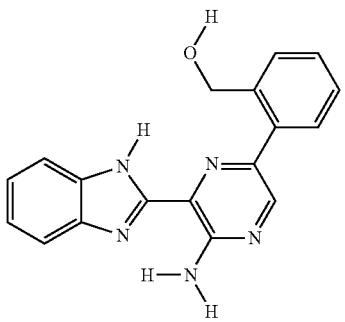 [SMILES: Nc1ncc(-c2ccccc2CO)nc1-c1nc2ccccc2[nH]1]
I-127
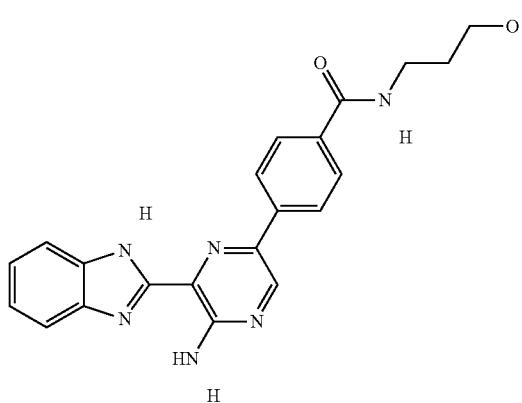
I-128
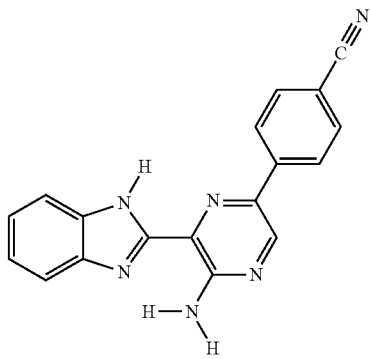 [SMILES: N#Cc1ccc(-c2cnc(N)c(-c3nc4ccccc4[nH]3)n2)cc1]
I-129
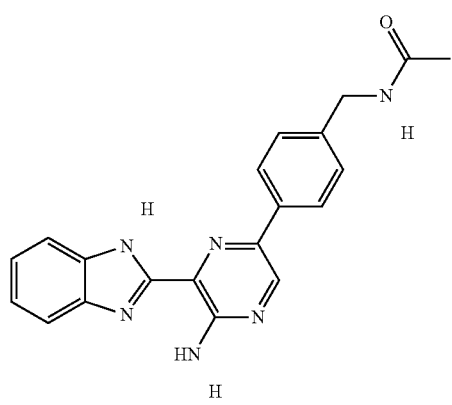
I-130

TABLE I-continued
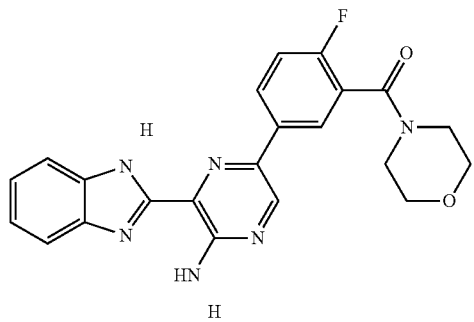
I-131
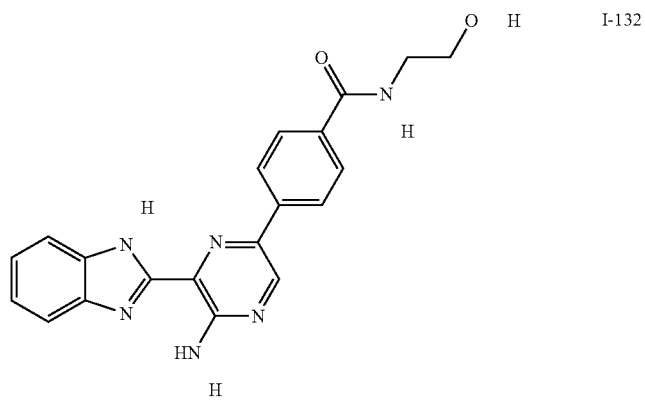
I-132
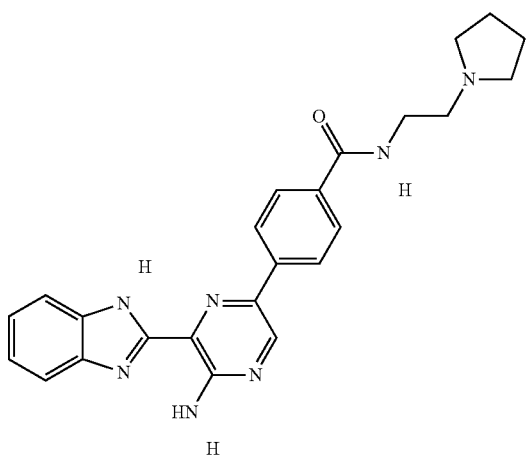
I-133
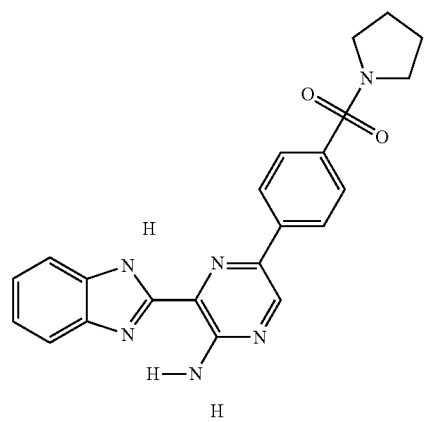
I-134

TABLE I-continued
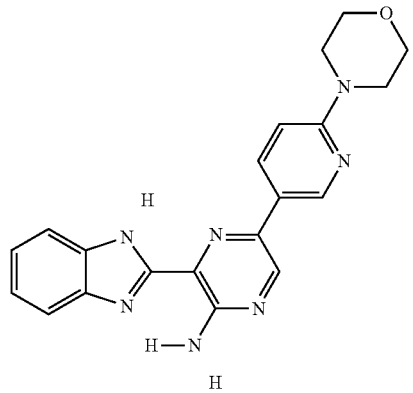
I-135
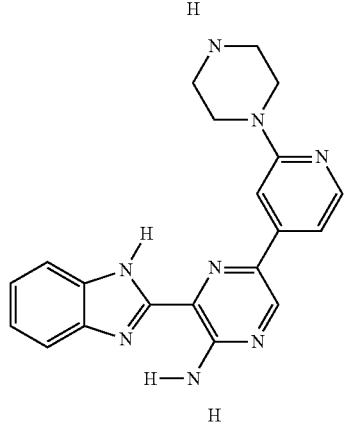
I-136
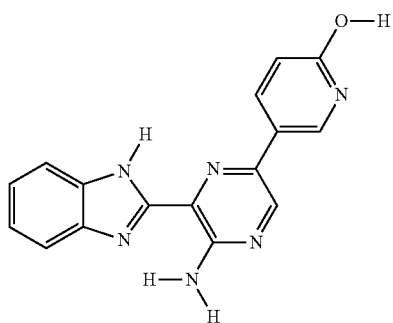 [SMILES: Nc1ncc(-c2ccc(O)nc2)nc1-c1nc2ccccc2[nH]1]
I-137
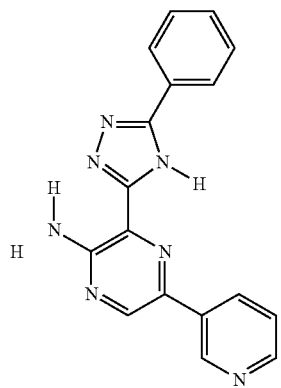
I-138

TABLE I-continued
| | |
|---|---|
| 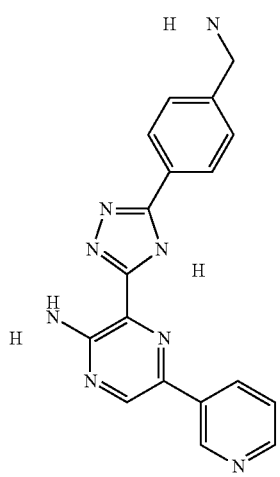 | I-139 |
| 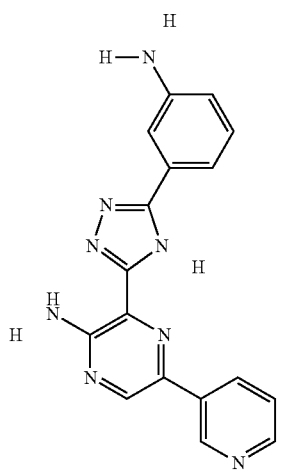 | I-140 |
| 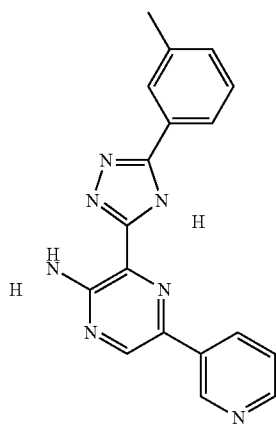 | I-141 |

TABLE I-continued
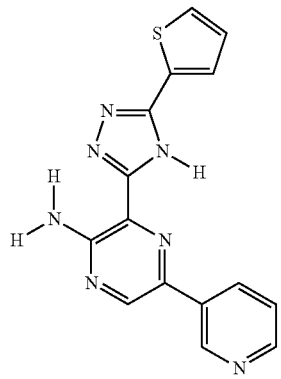 [SMILES: Nc1ncc(-c2cccnc2)nc1-c1nnc(-c2cccs2)[nH]1]
I-142
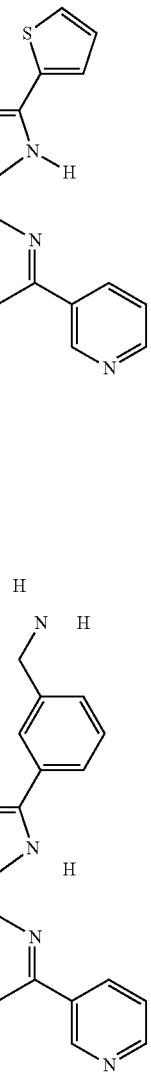
I-143
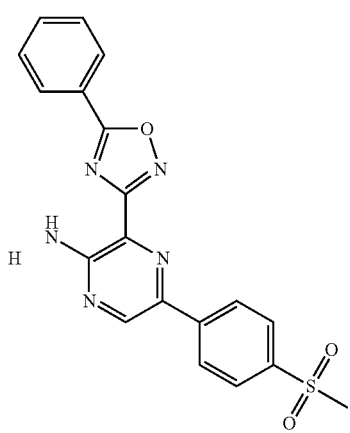
I-144

TABLE I-continued
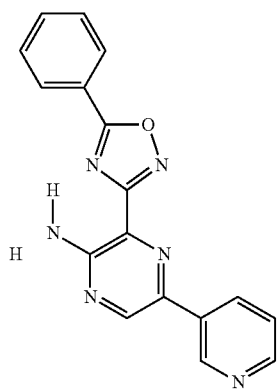
I-145
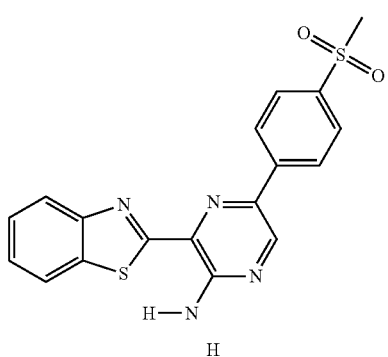
I-146
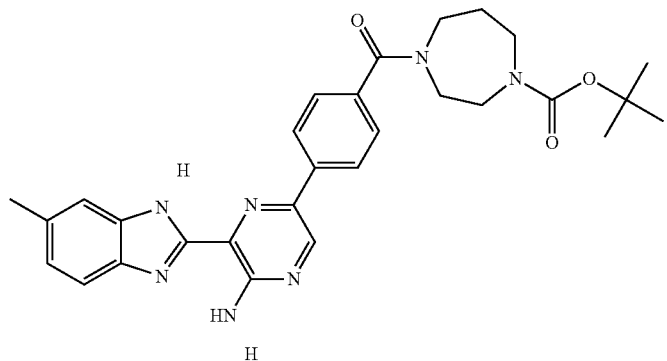
I-147
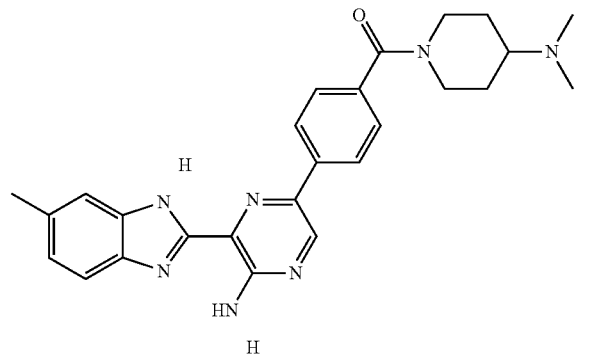
I-148

TABLE I-continued
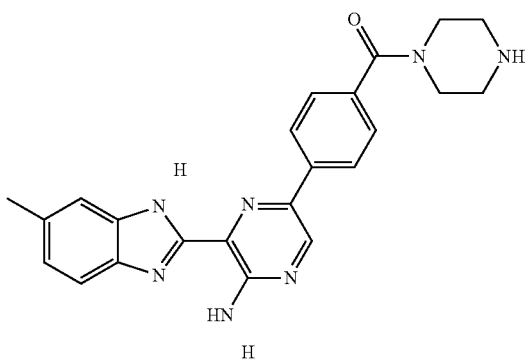
I-149
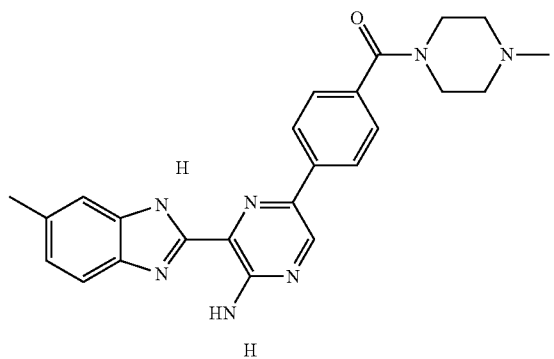
I-150
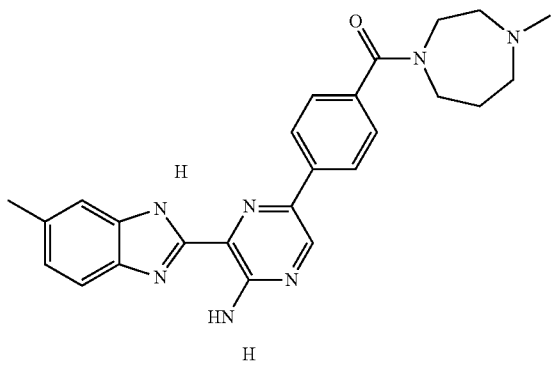
I-151
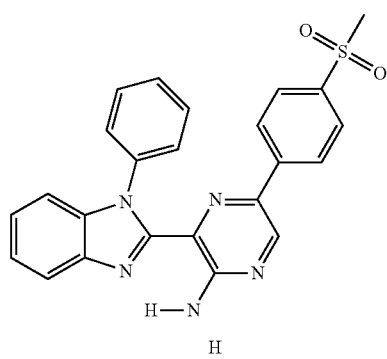
I-152

TABLE I-continued

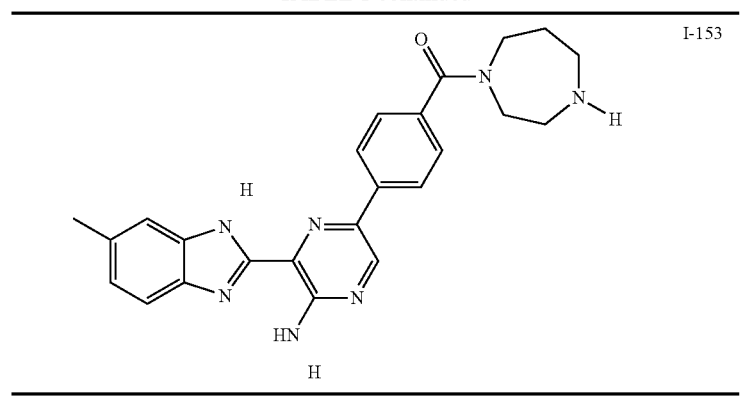

I-153

In some embodiments, the variables are as depicted in the compounds of the disclosure including compounds in the tables above.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, J$^1$ can be bonded to any position on the pyridyl ring. For bicyclic rings, a bond drawn through both rings indicates that the substituent can be bonded from any position of the bicyclic ring. In example 11 below, for instance, J$^1$ can be bonded to the 5-membered ring (on the nitrogen atom, for instance), and to the 6-membered ring.

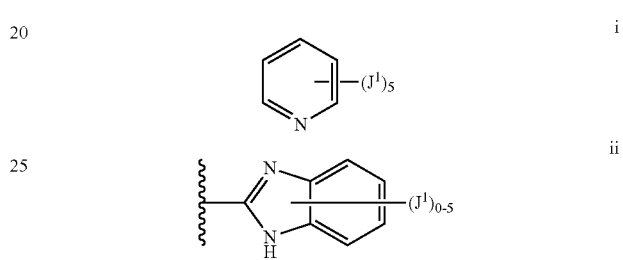

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —CF$_3$ and —CF$_2$CF$_3$.

The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

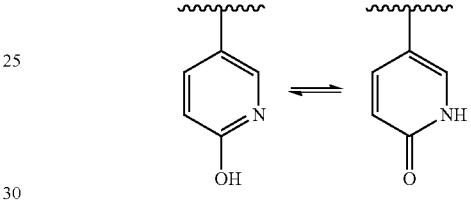

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —SO$_2$—. These atoms or groups can be combined to form larger groups. Examples of such larger groups include, but are not limited to, —OC(O)—, —C(O) CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is, for example, H or C$_{1-6}$aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —CH$_2$CH═N—CH$_3$. In some cases, especially on the terminal end, an optional replacement can be bonded to the aliphatic group via a triple bond. One example of this would be CH$_2$CH$_2$CH$_2$C≡N. It should be understood that in this situation, the terminal nitrogen is not bonded to another atom.

It should also be understood that, the term "methylene unit" can also refer to branched or substituted methylene units. For example, in an isopropyl moiety [—CH(CH$_3$)$_2$], a nitrogen atom (e.g. NR) replacing the first recited "methylene unit" would result in dimethylamine [—N(CH$_3$)$_2$]. In instances such as these, one of skill in the art would understand that the nitrogen atom will not have any additional atoms bonded to it, and the "R" from "NR" would be absent in this case.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a C$_3$ aliphatic can be optionally replaced by 2 nitrogen atoms to form —C—N≡N. The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —CH$_2$CH$_2$CH$_3$ were optionally replaced with —O—, the resulting compound could be —OCH$_2$CH$_3$, —CH$_2$OCH$_3$, or —CH$_2$CH$_2$OH. It should be understood that if the terminal atom does not contain any free valence electrons, then a hydrogen atom is not required at the terminal end (e.g., —CH$_2$CH$_2$CH═O or —CH$_2$CH$_2$C≡N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

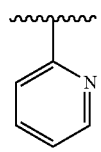

also represents

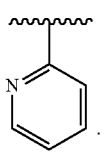

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays.

Pharmaceutically Acceptable Salts

The compounds of this invention can exist in free form for treatment, or where appropriate, as a pharmaceutically acceptable salt.

A "pharmaceutically acceptable salt" means any nontoxic salt of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of the ATR protein kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Base addition salts can be prepared by 1) reacting the purified compound in its acid form with a suitable organic or inorganic base and 2) isolating the salt thus formed. Salts derived from appropriate bases include alkali metal (e.g., sodium, lithium, and potassium), alkaline earth metal (e.g., magnesium and calcium), ammonium and N⁺(C₁₋₄alkyl)₄ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

ABBREVIATIONS

The following abbreviations are used:
DMSO dimethyl sulfoxide
ATP adenosine triphosphate
¹HNMR proton nuclear magnetic resonance
HPLC high performance liquid chromatography
LCMS liquid chromatography-mass spectrometry
TLC thin layer chromatography
Rt retention time
Compound Uses One aspect of this invention provides a compound for use in inhibiting ATR kinase. These compounds have formula I:

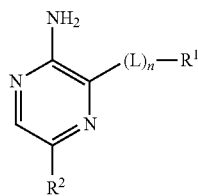

I

Or an acceptable salt thereof;
wherein
R¹ is a 5-6 membered monocyclic aryl or heteroaryl ring having 0-4 heteroatoms independently selected from nitrogen, oxygen, or sulfur, wherein said monocyclic aryl or heteroaryl ring is optionally fused to another ring to form an 8-10 membered bicyclic aryl or heteroaryl ring having 0-6 heteroatoms independently selected from nitrogen, oxygen, or sulfur; each R¹ is optionally substituted with 1-5 J¹ groups;
R² is a 5-6 membered monocyclic aryl or heteroaryl ring having 0-3 heteroatoms independently selected from nitrogen, oxygen, or sulfur, wherein said monocyclic aryl or heteroaryl ring is optionally fused to another ring to form an 8-10 membered bicyclic aryl or heteroaryl ring having 0-4 heteroatoms independently selected from nitrogen, oxygen, or sulfur; each R² is optionally substituted with 1-5 J² groups;
L is —C(O)NH— or —C(O)N(C₁₋₆alkyl)-;
n is 0 or 1;
Each J¹ and J² is independently halo, —CN, —NO₂, —V¹—R, or —(V²)$_m$-Q;
V¹ is a C₁₋₁₀aliphatic chain wherein 0-3 methylene units are optionally and independently replaced with O, NR", S, C(O), S(O), or S(O)₂; V¹ is optionally substituted with 1-6 occurrences of J$^{V1}$;

V² is a C₁₋₁₀aliphatic chain wherein 0-3 methylene units are optionally and independently replaced with O, NR", S, C(O), S(O), or S(O)₂; V² is optionally substituted with 1-6 occurrences of J$^{V2}$;
m is 0 or 1;
Q is a 3-8 membered saturated or unsaturated monocyclic ring having 0-4 heteroatoms independently selected from nitrogen, oxygen, or sulfur, or a 9-10 membered saturated or unsaturated bicyclic ring having 0-6 heteroatoms independently selected from nitrogen, oxygen, or sulfur; each Q is optionally substituted with 0-5 J$^Q$;
each J$^{V1}$ or J$^{V2}$ is independently halogen, CN, NH₂, NO₂, C₁₋₄aliphatic, NH(C₁₋₄aliphatic), N(C₁₋₄aliphatic)₂, OH, O(C₁₋₄aliphatic), CO₂H, CO₂(C₁₋₄aliphatic), C(O)NH₂, C(O)NH(C₁₋₄aliphatic), C(O)N(C₁₋₄aliphatic)₂, NHCO (C₁₋₄aliphatic), N(C₁₋₄aliphatic)CO(C₁₋₄aliphatic), SO₂(C₁₋₄aliphatic), NHSO₂(C₁₋₄aliphatic), or N(C₁₋₄aliphatic)SO₂(C₁₋₄aliphatic), wherein said C₁₋₄aliphatic is optionally substituted with halo;
R is H or C₁₋₆aliphatic wherein said C₁₋₆aliphatic is optionally substituted with 1-4 occurrences of NH₂, NH(C₁₋₄aliphatic), N(C₁₋₄aliphatic)₂, halogen, C₁₋₄aliphatic, OH, O(C₁₋₄aliphatic), NO₂, CN, CO₂H, CO₂(C₁₋₄aliphatic), CO(C₁₋₄aliphatic), O(haloC₁₋₄aliphatic), or haloC₁₋₄aliphatic;
each J$^Q$ is independently halo, oxo, CN, NO₂, X—R, or —(X)$_p$-Q⁴;
p is 0 or 1;
X is C₁₋₁₀aliphatic; wherein 1-3 methylene units of said C₁₋₆aliphatic are optionally replaced with —NR, —O—, —S—, C(O), S(O)₂, or S(O); wherein X is optionally and independently substituted with 1-4 occurrences of NH₂, NH(C₁₋₄aliphatic), N(C₁₋₄aliphatic)₂, halogen, C₁₋₄aliphatic, OH, O(C₁₋₄aliphatic), NO₂, CN, CO(C₁₋₄aliphatic), CO₂H, CO₂(C₁₋₄aliphatic), C(O)NH₂, C(O)NH(C₁₋₄aliphatic), C(O)N(C₁₋₄aliphatic)₂, SO(C₁₋₄aliphatic), SO₂(C₁₋₄aliphatic), SO₂NH(C₁₋₄aliphatic), SO₂N(C₁₋₄aliphatic)₂, NHC(O)(C₁₋₄aliphatic), N(C₁₋₄aliphatic)C(O)(C₁₋₄aliphatic), wherein said C₁₋₄aliphatic is optionally substituted with 1-3 occurrences of halo;
Q⁴ is a 3-8 membered saturated or unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each Q⁴ is optionally substituted with 1-5 J$^{Q4}$;
J$^{Q4}$ is halo, CN, or C₁₋₄alkyl wherein up to 2 methylene units are optionally replaced with O, NR*, S, C(O), S(O), or S(O)₂;
R is H or C₁₋₄alkyl wherein said C₁₋₄alkyl is optionally substituted with 1-4 halo;
R', R", and R* are each independently H, C₁₋₄alkyl, or is absent; wherein said C₁₋₄alkyl is optionally substituted with 1-4 halo.

In one embodiment, R¹ is a 5-6 membered monocyclic aryl or heteroaryl ring having 0-3 heteroatoms independently selected from nitrogen, oxygen, or sulfur, wherein said monocyclic aryl or heteroaryl ring is optionally fused to another ring to form an 8-10 membered bicyclic aryl or heteroaryl ring having 0-4 heteroatoms independently selected from nitrogen, oxygen, or sulfur; each R¹ is optionally substituted with 1-5 J¹ groups;
R² is a 5-6 membered monocyclic aryl or heteroaryl ring having 0-3 heteroatoms independently selected from nitrogen, oxygen, or sulfur, wherein said monocyclic aryl or heteroaryl ring is optionally fused to another ring to form an 8-10 membered bicyclic aryl or heteroaryl ring having 0-4 heteroatoms independently selected from nitrogen, oxygen, or sulfur; each $R^2$ is optionally substituted with 1-5 $J^2$ groups;

each $J^{V1}$ or $J^{V2}$ is independently $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO_2(C_{1-4}aliphatic)$, $CO(C_{1-4}aliphatic)$, $O(haloC_{1-4}aliphatic)$, or $haloC_{1-4}aliphatic$;

each $J^Q$ is independently halogen, $NO_2$, CN, or $C_{1-6}aliphatic$ wherein up to 1 methylene unit is optionally replaced with NR', O, S, CO, $CO_2$, CONR', SO, $SO_2$, $SO_2NR'$, OCO, NR'CO, NR'COO, NR'SO, $NR'SO_2$, $NR'SO_2NR'$, OCONR', or NR'CONR'; wherein said $C_{1-6}aliphatic$ is optionally substituted with 1-4 substituents selected from $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO_2$ $(C_{1-4}aliphatic)$, $CO(C_{1-4}aliphatic)$, $O(haloC_{1-4}aliphatic)$, or $haloC_{1-4}aliphatic$.

In some embodiments, $R^2$ is substituted with one or two occurrences of $J^2$. In other embodiments, In some embodiments, $R^2$ is a 5-6 membered monocyclic aromatic ring. In some embodiments, $R^2$ is a 6-membered aromatic ring. In other embodiments, $R^2$ is phenyl or pyridyl. In yet other embodiments, $R^2$ is phenyl.

$R^2$ is optionally substituted with 1-5 $J^2$ groups. In some embodiments, 1-3 $J^2$ groups, and in other embodiments, 1-2 $J^2$ groups. In yet another embodiment, $R^2$ is substituted with 0 or 1 occurrences of $J^2$. In some embodiments, $J^2$ is $-(V^2)_m$-Q or $V^1$—R; wherein each $V^1$ and $V^2$ is independently a $C_{1-6}aliphatic$ chain wherein 0-3 methylene units are optionally replaced with O, NR', S, C(O), S(O), or $S(O)_2$; wherein the first or second methylene group away from the point of attachment is replaced with C(O), S(O), or $S(O)_2$, S or O;

m is 1;

R is H; and

Q is a 5-7 membered monocyclic ring containing 0-2 heteroatoms selected from oxygen, nitrogen, or sulfur; wherein said Q is optionally substituted with 1-3 occurrences of halogen, $C_{1-3}$ alkyl, CN, OH, $O(C_{1-3}alkyl)$, $NH_2$, $NH(C_{1-3}alkyl)$, $N(C_{1-3}alkyl)_2$, or $CO(C_{1-3}alkyl)$.

In some embodiments, Q is a 5-6 membered monocyclic ring.

Another to another embodiment, n is 0.

In some embodiments, n is 0 and $R^1$ is a 5-6 membered monocyclic aromatic ring having 1-4 heteroatoms independently selected from nitrogen, oxygen, or sulfur, or a 9-10 membered bicyclic aromatic ring having 1-6 heteroatoms independently selected from nitrogen, oxygen, or sulfur; wherein each $R^1$ is optionally substituted with 1-5 $J^1$ groups.

In some embodiments, $R^1$ is benzothiazole, oxadiazole, benzoxazole, triazole, thiadiazole, or isoxazole. In other embodiments, $R^1$ is benzimidazole, benzothioazole, oxadiazole, isoxazole, or triazole. In some embodiments, $R^1$ is benzimidazole. In other embodiments, $R^1$ is isoxazole.

$R^1$ is optionally substituted with 1-5 $J^1$ groups. In some embodiments, 1-3 $J^1$ groups, and in other embodiments, 1-2 $J^1$ groups. In some embodiments, $J^1$ is halo, CN, $NO_2$, or $-V^1$—R. In other embodiments, $J^1$ is halo, CN, $C_{1-6}alkyl$, OR, SR, NR"R, C(O)R, C(O)OR, C(O)NR"R, $S(O)_2R$, or S(O)R. In yet other embodiments, $J^1$ is phenyl optionally substituted with $NH_2$, $C_{1-4}alkyl$, thiophene, or $CH_2NH_2$.

In some embodiments, $R^2$ is a 5-6 membered monocyclic aromatic ring. In some embodiments, $R^2$ is a 6-membered aromatic ring. In other embodiments, $R^2$ is phenyl or pyridyl. In yet other embodiments, $R^2$ is phenyl.

In another embodiment, $J^2$ is $-V^1$—R or $-(V^2)_m$-Q; wherein $V^1$ and $V^2$ are O, NR", —CO—, or $-SO_2-$; Q is a 5-6 membered heterocyclic ring containing 1-2 heteroatoms selected from N or O; and $J^{V1}$ and $J^{V2}$ are halo. In another embodiment, $J^2$ is $SO_2CH_3$, morpholinyl, $CH_2OH$, C(O)-(morpholinyl), $C(O)NH(C_{1-4}alkyl)OH$, piperazinyl, CN, $CH_2NHC(O)CH_3$, halo, $C(O)NH(C_{1-4}alkyl)pyrrolidinyl$, or $SO_2(pyrrolidinyl)$.

In some embodiments, $R^2$ is phenyl or pyridyl.

In some embodiments, $J^2$ is $SO_2(C_{1-4}alkyl)$.

In one embodiment, n is 0;

$R^1$ is benzimidazole, benzothiazole, benzoxazole, oxadiazole, isoxazole, thiadiazole, or triazole;

$J^1$ is halo, CN, $NO_2$, or $-V^1$—R;

$R^2$ is phenyl or pyridyl;

$J^2$ is $-(V^2)_m$-Q or $-V^1$—R;

m is 1;

$V^1$ and $V^2$ are $-SO_2-$, —O—, —NR—, or —CO—;

Q is a 5-6 membered heterocyclic ring containing 1-2 heteroatoms selected from nitrogen or oxygen; and R is H or $C_{1-6}alkyl$ wherein said $C_{1-6}alkyl$ is optionally substituted with 1-4 halo.

According to another embodiment, n is 1.

In some embodiments, $R^1$ is phenyl, pyridyl, pyrimidyl, pyrazinyl, piperonyl, indolyl, benzimidazolyl, indazolyl, benzothiazolyl, benzothiophenyl (i.e. benzothienyl), benzoxazolyl, pyrrolopyrimidinyl, pyrrolopyridinyl, azaindazolyl, or azaindolyl. In other embodiments, $R^1$ is phenyl, pyridyl, pyrimidyl, piperonyl, or indole. In yet other embodiments, $R^1$ is phenyl.

$R^1$ is optionally substituted with 1-5 $J^1$ groups. In some embodiments, 1-3 $J^1$ groups, and in other embodiments, 1-2 $J^1$ groups. In some embodiments, $J^1$ is $C_{1-6}alkyl$, CN, halo, OR, NR"R, SR, COR, $CO_2R$, CONR"R, SOR, $SO_2R$, $S(O)_2NR"R$, OCOR, NRC(O)R, NRCOOR, NRSOR, $NRSO_2R$, $NRSO_2NR"R$, OCONR"R, or NRCONR"R; 4-6 membered fully saturated monocyclic ring containing 0-2 heteroatoms selected from oxygen, nitrogen, or sulfur. In other embodiments, $J^1$ is $C_{1-6}alkyl$, CN, halo, OR, NR"R, CONR"R, $S(O)_2NR"R$, NC(O)R, or pyrrolidinyl.

In some embodiments, $R^2$ is phenyl, pyridyl, pyrimidyl, indole, furanyl, pyrazole, thiophene, tetrahydropyran, or indazole. $R^2$ is optionally substituted with 1-5 $J^2$ groups. In some embodiments, 1-3 $J^2$ groups, and in other embodiments, 1-2 $J^2$ groups. In some embodiments, $J^2$ is halo, CN, NR"R, $C_{1-6}alkyl$, OR, $SO_2R$, $NHSO_2R$, COOR, CONR"R, morpholinyl, $-V^1$—R, or $-(V^2)_m$-Q, wherein $V^1$ and $V^2$ are CO, —CONR"—, —CONR"—$(C_{1-4}alkyl)$-, —CONR"—$(C_{1-4}alkyl)$-$OCH_2$—, —CONR"—$(C_{1-4}alkyl)$-$N(CH_3)$—, R is H or $C_{1-4}alkyl$; and Q is 1,4-diazepanyl, azetidinyl optionally substituted with OMe, piperidinyl optionally substituted with $C_{1-4}alkyl$, 4-$CH_2OH$, $CONH_2$, pyrrolidinyl, OH, or $CH_2$-pyrrolidinyl; piperazinyl optionally substituted with $CH_2CH_2CN$, $CH_3$, $COCH_3$, pyrrolidinyl optionally substituted with dimethylamino, tetrahydropyran, $C_{3-10}cyclolkyl$ optionally substituted with OH.

In other embodiments, $J^2$ is $SO_2CH_3$, $NHSO_2CH_3$, CN, OH, $OCH_3$, F, $N(CH_3)_2$, $NHSO_2CH_3$, $CF_3$, $C_{1-6}alkyl$, CO(1,4-diazepanyl), COOH, $CONH_2$, $CON(CH_3)_2$, CO(azetidinyl), $CON(CH_3)(C_{1-4}alkyl)OCH_3$, $CONH(C_{1-4}alkyl)piperazinyl$, $CONH(C_{1-4}alkyl)piperidinyl$, CONH-tetrahydropyran, CON(methylpiperidinyl), CO(piperidinyl), CONH-cyclopropyl, CO(morpholinyl), $CON(CH_3)$—$(C_{1-4}alkyl)$-$N(CH_3)_2$, CO(piperazinyl), CONH—

($C_{1-4}$alkyl)-pyrrolidinyl, CONH—($C_{1-4}$alkyl)-piperidinyl, CONH—($C_{1-4}$alkyl)-tetrahydropyranyl, morpholinyl, CO(pyrrolidinyl), CO(piperidinyl), CO(pyrrolidinyl), $CH_2$-pyrrolidinyl, or CONH(cyclohexyl), wherein said $J^2$ is optionally substituted with $C_{1-4}$alkyl, $CONH_2$, pyrrolidinyl, OH, O($C_{1-4}$alkyl), $NH_2$, NH($C_{1-4}$alkyl), N($C_{1-4}$alkyl)$_2$, —($C_{1-4}$alkyl)-CN, —($C_{1-4}$alkyl)-OH, —($C_{1-4}$alkyl)-N($C_{1-4}$alkyl)$_2$, or CO($C_{1-4}$alkyl).

In some embodiments, n is 1;

$R^1$ is phenyl;

$R^2$ is phenyl, pyridyl, indole, furanyl, pyrazole, thiophene, tetrahydropyran, or indazole;

$J^2$ is halo, CN, NR"R, $C_{1-6}$alkyl, OR, $SO_2R$, $NHSO_2R$, COOR, CONR"R, morpholinyl, —$V^1$—R, or —$(V^2)_m$-Q, wherein m is 1;

$V^1$ and $V^2$ are CO, —CONR—, —CONR—($C_{1-4}$alkyl)-, —CONR—($C_{1-4}$alkyl)-$OCH_{2-5}$ or —CONR—($C_{1-4}$alkyl)-N($CH_3$)—;

R is H or $C_{1-4}$alkyl; and

Q is 1,4-diazepanyl, azetidinyl optionally substituted with OMe, piperidinyl optionally substituted with $C_{1-4}$alkyl, 4-$CH_2OH$, $CONH_2$, pyrrolidinyl, OH, or $CH_2$-pyrrolidinyl; piperazinyl optionally substituted with $CH_2CH_2CN$, $CH_3$, $COCH_3$, pyrrolidinyl optionally substituted with dimethylamino, tetrahydropyran, $C_{3-10}$cycloalkyl optionally substituted with OH; and $J^1$ is $C_{1-6}$alkyl, CN, halo, OR, NR"R, SR, COR, $CO_2R$, CONR"R, SOR, $SO_2R$, $S(O)_2NR"R$, OCOR, NRC(O)R, NRCOOR, NRSOR, $NRSO_2R$, $NRSO_2NR"R$, OCONR"R, or NRCONR"R; 4-6 membered fully saturated monocyclic ring containing 0-2 heteroatoms selected from oxygen, nitrogen, or sulfur.

In other embodiments, n is 0;

$R^1$ is benzimidazole, benzothioazole, oxadiazole, isoxazole, or triazole;

$J^1$ is halo, CN, $NO_2$, or —$V^1$—R;

$R^2$ is phenyl or pyridyl;

$J^2$ is —$(V^2)_m$-Q or —$V^1$—R;

m is 1;

$V^1$ and $V^2$ are —$SO_2$—, —O—, —NR"—, or —CO—;

Q is a 5-6 membered heterocyclic ring containing 1-2 heteroatoms selected from nitrogen or oxygen; and R is H or $C_{1-6}$alkyl wherein said $C_{1-6}$alkyl is optionally substituted with 1-4 halo.

In yet other embodiments, the compound is selected from Table 1 (above).

One aspect of this invention provides compounds that are inhibitors of ATR kinase, and thus are useful for treating or lessening the severity of a disease, condition, or disorder where ATR is implicated in the disease, condition, or disorder.

Another aspect of this invention provides compounds that are useful for the treatment of diseases, disorders, and conditions characterized by excessive or abnormal cell proliferation. Such diseases include, a proliferative or hyperproliferative disease. Examples of proliferative and hyperproliferative diseases include, without limitation, cancer and myeloproliferative disorders.

In some embodiments, said compounds are selected from the group consisting of a compound of formula I, II, III, IV, IA, IIA, IIIA, IVA, IA-i, IA-ii, IA-iii, V, VI, and VII.

The term "cancer" includes, but is not limited to the following cancers. Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; [note to scientist: do we want to added "undifferentiated thyroid cancer"?—from original] medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

Thus, the term "cancerous cell" as provided herein, includes a cell afflicted by any one of the above-identified conditions. In some embodiments, the cancer is selected from colorectal, thyroid, or breast cancer.

The term "myeloproliferative disorders", includes disorders such as polycythemia vera, thrombocythemia, myeloid metaplasia with myelofibrosis, hypereosinophilic syndrome, juvenile myelomonocytic leukemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Pharmaceutically Acceptable Derivatives or Prodrugs

In addition to the compounds of this invention, pharmaceutically acceptable derivatives or prodrugs of the compounds of this invention may also be employed in compositions to treat or prevent the herein identified disorders.

The compounds of this invention can also exist as pharmaceutically acceptable derivatives.

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" means any pharmaceutically acceptable ester, salt of an ester or other derivative or salt thereof of a compound, of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutical Compositions

The present invention also provides compounds and compositions that are useful as inhibitors of ATR kinase.

One aspect of this invention provides pharmaceutically acceptable compositions that comprise any of the compounds as described herein, and optionally comprise a pharmaceutically acceptable carrier, adjuvant or vehicle.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Combination Therapies

Another aspect of this invention is directed towards a method of treating cancer in a subject in need thereof, comprising administration of a compound of this invention or a pharmaceutically acceptable salt thereof, and an additional therapeutic agent. In some embodiments, said method comprises the sequential or co-administration of the compound or a pharmaceutically acceptable salt thereof, and the additional therapeutic agent.

In some embodiments, said additional therapeutic agent is an anti-cancer agent. In other embodiments, said additional therapeutic agent is a DNA-damaging agent. In yet other embodiments, said additional therapeutic agent is selected from radiation therapy, chemotherapy, or other agents typically used in combination with radiation therapy or chemotherapy, such as radiosensitizers and chemosensitizers.

As would be known by one of skill in the art, radiosensitizers are agents that can be used in combination with radiation therapy. Radiosensitizers work in various different ways, including, but not limited to, making cancer cells more sensitive to radiation therapy, working in synergy with radiation therapy to provide an improved synergistic effect, acting additively with radiation therapy, or protecting surrounding healthy cells from damage caused by radiation therapy. Likewise chemosensitizers are agents that can be used in combination with chemotherapy. Similarly, chemosensitizers work in various different ways, including, but not limited to, making cancer cells more sensitive to chemotherapy, working in synergy with chemotherapy to provide an improved synergistic effect, acting additively to chemotherapy, or protecting surrounding healthy cells from damage caused by chemotherapy.

Examples of DNA-damaging agents that may be used in combination with compounds of this invention include, but are not limited to Platinating agents, such as Carboplatin, Nedaplatin, Satraplatin and other derivatives; Topo I inhibitors, such as Topotecan, irinotecan/SN38, rubitecan and other derivatives; Antimetabolites, such as Folic family (Methotrexate, Pemetrexed and relatives); Purine antagonists and Pyrimidine antagonists (Thioguanine, Fludarabine, Cladribine, Cytarabine, Gemcitabine, 6-Mercaptopurine, 5-Fluorouracil (5FU) and relatives); Alkylating agents, such as Nitrogen mustards (Cyclophosphamide, Melphalan, Chlorambucil, mechlorethamine, Ifosfamide and relatives); nitrosoureas (eg Carmustine); Triazenes (Dacarbazine, temozolomide); Alkyl sulphonates (eg Busulfan); Procarbazine and Aziridines; Antibiotics, such as Hydroxyurea, Anthracyclines (doxorubicin, daunorubicin, epirubicin and other derivatives); Anthracenediones (Mitoxantrone and relatives); Streptomyces family (Bleomycin, Mitomycin C, actinomycin); and Ultraviolet light.

Other therapies or anticancer agents that may be used in combination with the inventive agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, the DNA damaging agents listed herein, spindle poisons (Vinblastine, Vincristine, Vinorelbine, Paclitaxel), podophyllotoxins (Etoposide, Irinotecan, Topotecan), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide.

A compound of the instant invention may also be useful for treating cancer in combination with any of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Compositions for Administration into a Subject

The ATR kinase inhibitors or pharmaceutical salts thereof may be formulated into pharmaceutical compositions for administration to animals or humans. These pharmaceutical compositions, which comprise an amount of the ATR inhibitor effective to treat or prevent the diseases or conditions described herein and a pharmaceutically acceptable carrier, are another embodiment of the present invention.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In some embodiments, these compositions optionally further comprise one or more additional therapeutic agents. For example, chemotherapeutic agents or other anti-proliferative agents may be combined with the compounds of this invention to treat proliferative diseases and cancer. Examples of known agents with which these compositions can be combined are listed above under the "Combination Therapies" section and also throughout the specification. Some embodiments provide a simultaneous, separate or sequential use of a combined preparation.

Modes of Administration and Dosage Forms

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intra-hepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

Administering with Another Agent

Depending upon the particular protein kinase-mediated conditions to be treated or prevented, additional drugs, which are normally administered to treat or prevent that condition, may be administered together with the compounds of this invention.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

Another aspect of this invention is directed towards a method of treating cancer in a subject in need thereof, comprising the sequential or co-administration of a compound of this invention or a pharmaceutically acceptable salt thereof, and an anti-cancer agent. In some embodiments, said anti-cancer agent is selected from Platinating agents, such as Cisplatin, Oxaliplatin, Carboplatin, Nedaplatin, or Satraplatin and other derivatives; Topo I inhibitors, such as Camptothecin, Topotecan, irinotecan/SN38, rubitecan and other derivatives; Antimetabolites, such as Folic family (Methotrexate, Pemetrexed and relatives); Purine family (Thioguanine, Fludarabine, Cladribine, 6-Mercaptopurine and relatives); Pyrimidine family (Cytarabine, Gemcitabine, 5-Fluorouracil and relatives); Alkylating agents, such as Nitrogen mustards (Cyclophosphamide, Melphalan, Chlorambucil, mechlorethamine, Ifosfamide, and relatives); nitrosoureas (e.g. Carmustine); Triazenes (Dacarbazine, temozolomide); Alkyl sulphonates (e.g. Busulfan); Procarbazine and Aziridines; Antibiotics, such as Hydroxyurea; Anthracyclines (doxorubicin, daunorubicin, epirubicin and other derivatives); Anthracenediones (Mitoxantrone and relatives); Streptomyces family (Bleomycin, Mitomycin C, actinomycin) and Ultraviolet light.

Biological Samples

As inhibitors of ATR kinase, the compounds and compositions of this invention are also useful in biological samples. One aspect of the invention relates to inhibiting ATR kinase activity in a biological sample, which method comprises contacting said biological sample with a compound described herein or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. The term "compounds described herein" includes compounds of formula I, II, III, IV, IA, IIA, IIIA, IVA, IA-i, IA-ii, IA-iii, V, VI, and VII.

Inhibition of ATR kinase activity in a biological sample is useful for a variety of purposes that are known to one of skill in the art. Examples of such purposes include, but are not limited to, blood transfusion, organ-transplantation, and biological specimen storage.

Study of Protein Kinases

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of ATR is set forth in the Examples below.

Another aspect of the invention provides a method for modulating enzyme activity by contacting a compound described herein with ATR kinase.

Methods of Treatment

In one aspect, the present invention provides a method for treating or lessening the severity of a disease, condition, or disorder where ATR kinase is implicated in the disease state. In another aspect, the present invention provides a method for treating or lessening the severity of an ATR kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the ATR kinase. Another aspect provides a method for treating or lessening the severity of a kinase disease, condition, or disorder by inhibiting enzymatic activity of ATR kinase with an ATR kinase inhibitor.

One aspect of the invention relates to a method of inhibiting ATR kinase activity in a patient, which method comprises administering to the patient a compound described herein, or a composition comprising said compound. In some embodiments, said method is used to treat or prevent a condition selected from proliferative and hyperproliferative diseases, such as cancer.

Another aspect of this invention provides a method for treating, preventing, or lessening the severity of proliferative or hyperproliferative diseases comprising administering an effective amount of a compound, or a pharmaceutically acceptable composition comprising a compound, to a subject in need thereof. In some embodiments, said subject is a patient. The term "patient", as used herein, means an animal, preferably a human.

In some embodiments, said method is used to treat or prevent cancer. In some embodiments, said method is used to treat or prevent a type of cancer with solid tumors. In yet another embodiment, said cancer is selected from the following cancers: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma;

and Adrenal glands: neuroblastoma.

In some embodiments, the cancer is selected from the cancers described herein. In some embodiments, said cancer is lung cancer, head and neck cancer, pancreatic cancer, gastric cancer, or brain cancer.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

One aspect provides a method for inhibiting ATR in a patient comprising administering a compound described herein as described herein. Another embodiment provides a method of treating cancer comprising administering to a patient a compound described herein, wherein the variables are as defined herein.

Some embodiments comprising administering to said patient an additional therapeutic agent selected from a DNA-damaging agent; wherein said additional therapeutic agent is appropriate for the disease being treated; and said additional therapeutic agent is administered together with said compound as a single dosage form or separately from said compound as part of a multiple dosage form.

In some embodiments, said DNA-damaging agent is selected from ionizing radiation, radiomimetic neocarzinostatin, a platinating agent, a Topo I inhibitor, a Topo II inhibitor, an antimetabolite, an alkylating agent, an alkyl sulphonates, an antimetabolite, or an antibiotic. In other embodiments, said DNA-damaging agent is selected from ionizing radiation, a platinating agent, a Topo I inhibitor, a Topo II inhibitor, or an antibiotic.

Examples of Platinating agents include Cisplatin, Oxaliplatin, Carboplatin, Nedaplatin, Satraplatin and other derivatives. Other platinating agents include Lobaplatin, and Triplatin. Other platinating agents include Tetranitrate, Picoplatin, Satraplatin, ProLindac and Aroplatin.

Examples of Topo I inhibitor include Camptothecin, Topotecan, irinotecan/SN38, rubitecan and other derivatives. Other Topo I inhibitors include Belotecan.

Examples of Topo II inhibitors include Etoposide, Daunorubicin, Doxorubicin, Aclarubicin, Epirubicin, Idarubicin, Amrubicin, Pirarubicin, Valrubicin, Zorubicin and Teniposide.

Examples of Antimetabolites include members of the Folic family, Purine family (purine antagonists), or Pyrimidine family (pyrimidine antagonists). Examples of the Folic family include methotrexate, pemetrexed and relatives; examples of the Purine family include Thioguanine, Fludarabine, Cladribine, 6-Mercaptopurine, and relatives; examples of the Pyrimidine family include Cytarabine, gemcitabine, 5-Fluorouracil (5FU) and relatives.

Some other specific examples of antimetabolites include Aminopterin, Methotrexate, Pemetrexed, Raltitrexed, Pentostatin, Cladribine, Clofarabine, Fludarabine, Thioguanine, Mercaptopurine, Fluorouracil, Capecitabine, Tegafur, Carmofur, Floxuridine, Cytarabine, Gemcitabine, Azacitidine and Hydroxyurea.

Examples of alkylating agents include Nitrogen mustards, Triazenes, alkyl sulphonates, Procarbazine and Aziridines. Examples of Nitrogen mustards include Cyclophosphamide, Melphalan, Chlorambucil and relatives; examples of nitrosoureas include Carmustine; examples of triazenes include Dacarbazine and temozolomide; examples of alkyl sulphonates include Busulfan.

Other specific examples of alkylating agents include Mechlorethamine, Cyclophosphamide, Ifosfamide, Trofosfamide, Chlorambucil, Melphalan, Prednimustine, Bendamustine, Uramustine, Estramustine, Carmustine, Lomustine, Semustine, Fotemustine, Nimustine, Ranimustine, Streptozocin, Busulfan, Mannosulfan, Treosulfan, Carboquone, ThioTEPA, Triaziquone, Triethylenemelamine, Procarbazine, Dacarbazine, Temozolomide, Altretamine, Mitobronitol, Actinomycin, Bleomycin, Mitomycin and Plicamycin.

Examples of antibiotics include Mitomycin, Hydroxyurea; Anthracyclines, Anthracenediones, Streptomyces family. Examples of Anthracyclines include doxorubicin, daunorubicin, epirubicin and other derivatives; examples of Anthracenediones include Mitoxantrone and relatives; examples of Streptomyces family include Bleomycin, Mitomycin C, and actinomycin.

In certain embodiments, said platinating agent is Cisplatin or Oxaliplatin; said Topo I inhibitor is Camptothecin; said Topo II inhibitor is Etoposide; and said antibiotic is Mitomycin. In other embodiments, said platinating agent is selected from Cisplatin, Oxaliplatin, Carboplatin, Nedaplatin, or Satraplatin; said Topo I inhibitor is selected from Camptothecin, Topotecan, irinotecan/SN38, rubitecan; said Topo II inhibitor is selected from Etoposide; said antimetabolite is selected from a member of the Folic Family, the Purine Family, or the Pyrimidine Family; said alkylating agent is selected from nitrogen mustards, nitrosoureas, triazenes, alkyl sulfonates, Procarbazine, or aziridines; and said antibiotic is selected from Hydroxyurea, Anthracyclines, Anthracenediones, or Streptomyces family.

Another embodiment provides a method of promoting cell death in cancer cells comprising administering to a patient a compound described herein, or a composition comprising said compound.

Yet another embodiment provides a method of preventing cell repair of DNA damage in cancer cells comprising administering to a patient a compound described herein, or a composition comprising said compound. Yet another embodiment provides a method of preventing cell repair caused by of DNA damage in cancer cells comprising administering to a patient a compound of formula I, or composition comprising said compound.

Another embodiment provides a method of sensitizing cells to DNA damaging agents comprising administering to a patient a compound described herein, or a composition comprising said compound.

In some embodiments, the method is used on a cancer cell having defects in the ATM signaling cascade. In some embodiments, said defect is altered expression or activity of one or more of the following: ATM, p53, CHK2, MRE11, RAD50, NBS1, 53BP1, MDC1 or H2AX. In another embodiment, the cell is a cancer cell expressing DNA damaging oncogenes. In some embodiments, said cancer cell has altered expression or activity of one or more of the following: K-Ras, N-Ras, H-Ras, Raf, Myc, Mos, E2F, Cdc25A, CDC4, CDK2, Cyclin E, Cyclin A and Rb.

Yet another embodiment provides use of a compound described herein as a radio-sensitizer or a chemo-sensitizer.

Yet other embodiment provides use of a compound of formula I as a single agent (monotherapy) for treating cancer. In some embodiments, the compounds of formula I are used for treating patients having cancer with a DNA-damage response (DDR) defect. In other embodiments, said defect is a mutation or loss of ATM, p53, CHK2, MRE11, RAD50, NBS1, 53BP1, MDC1, or H2AX.

SCHEMES

The compounds of the disclosure may be prepared in light of the specification using steps generally known to those of ordinary skill in the art. Those compounds may be analyzed by known methods, including but not limited to LCMS (liquid chromatography mass spectrometry) and NMR (nuclear magnetic resonance). Below are a set of generic schemes that illustrate generally how to prepare the compounds of the present disclosure.

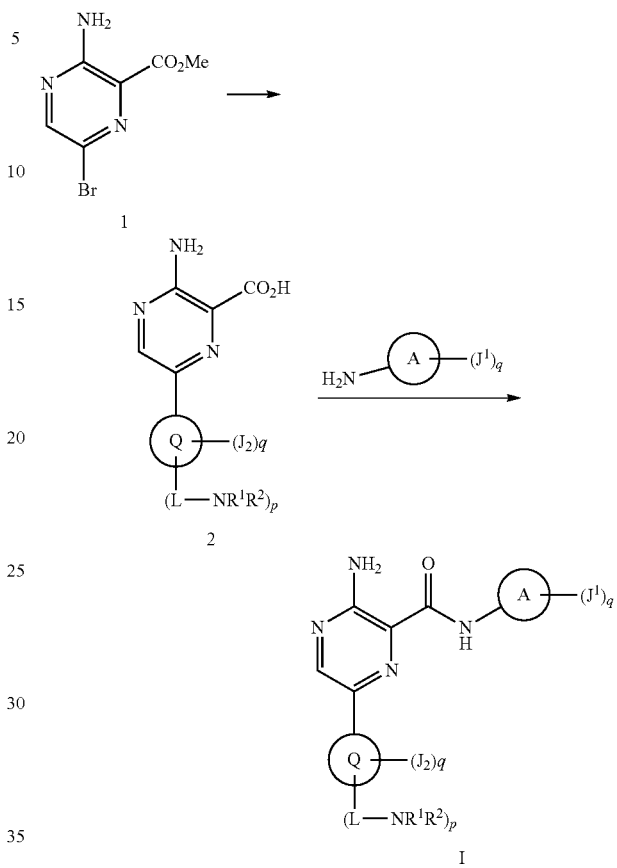

Scheme I-A1: Preparation of Compounds wherein —L—$R^1$ is an Aromatic Amide

Cyclic amides compounds of the present disclosure wherein -L-$R^1$ is an aromatic amide can be prepared according to methods similar to the one depicted in Scheme I-A1: Commercially available ester 1 is reacted with a boronic acid under Suzuki conditions to give intermediate 2. The carboxylic acid group is engaged in a coupling reaction with an amine to lead to cyclic amide compounds of the Formula I.

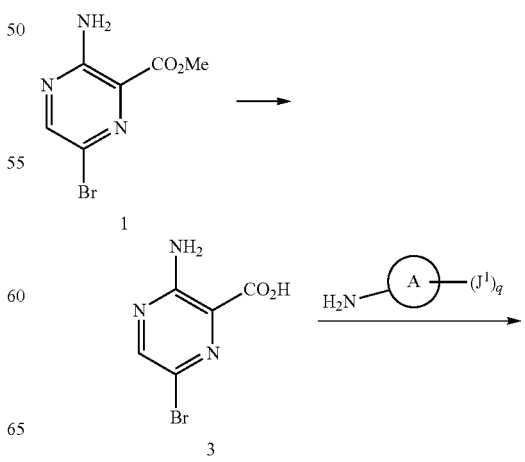

Scheme I-A2: Preparation of Compounds wherein —L—$R^1$ is an Aromatic Amide

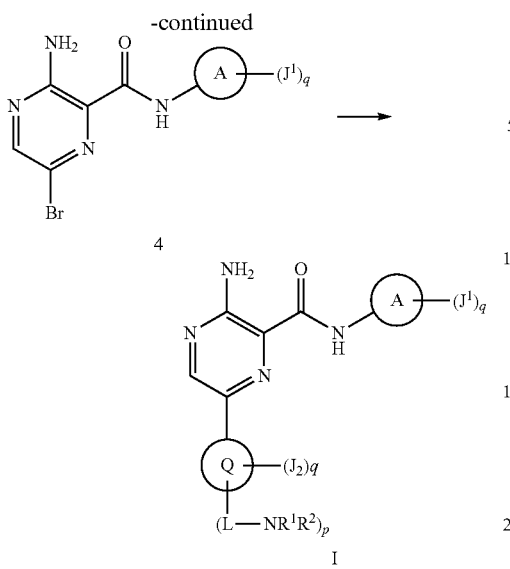

Alternatively, compounds of the present disclosure wherein -L-R¹ is an aromatic amide can be prepared according to methods similar to the one depicted in Scheme I-A2, a variation of the synthetic sequence depicted in scheme I-A1 which consists in starting from methyl ester 1. Ester 1 is transformed into carboxylic acid 3 which is engaged in a coupling reaction with an amine to give amide 4. This is reacted with a boronic acid under Suzuki conditions to lead to compounds of formula I.

Scheme I-B1: preparation of compounds where Ring A is a 1,3,4-oxadiazole

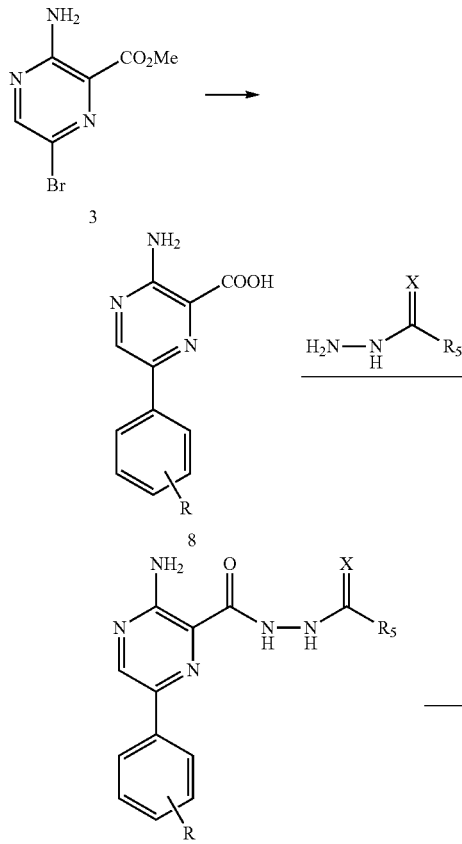

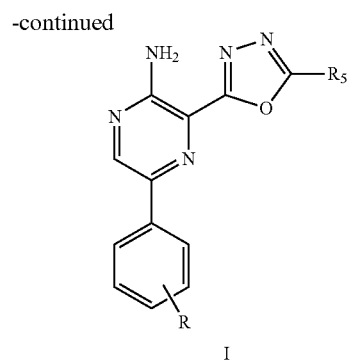

wherein R is $-(L-NR^1R^2)_p$ or $-(J_2)_q$

Compounds of the present disclosure where Ring A is a 1,3,4-oxadiazole can be prepared according to methods similar to the one depicted in Scheme I-B1: methyl ester 3 is reacted with a boronic acid under Suzuki conditions to give intermediate 8. The carboxylic acid in 8 is then engaged into a coupling reaction with an hydrazide (X=O) or thiohydrazide (X=S) to form 9. Finally, the acylhydrazide in 9 undergoes a cyclodehydration to lead to compounds of the present disclosure (formula I in Scheme I-B1). Transformation of intermediate 8 into compounds of formula I has also been performed in a one-pot procedure using reagents serving two purposes (coupling and cyclodehydration).

Scheme I-B2: preparation of compounds where Ring A is a 1,3,4-oxadiazole

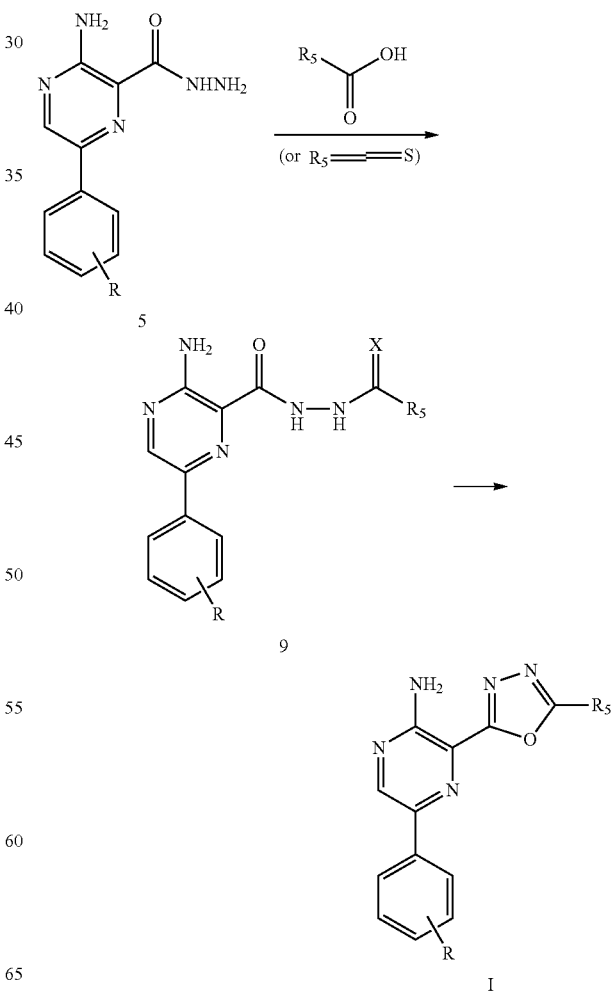

wherein R is $-(L-NR^1R^2)_p$ or $-(J_2)_q$

Alternatively, compounds of the present disclosure where Ring A is a 1,3,4-oxadiazole can be prepared according to methods similar to the one depicted in Scheme I-B2, a variation of the synthetic sequence depicted in scheme I-B1. The hydrazide 5 is engaged in a coupling reaction with a carboxylic acid functional group to form intermediate 9 (X=O). As in scheme I-B1 the acylhydrazide then undergoes a cyclodehydration to lead to compounds of formula I. When R5 is a moiety bound to the oxadiazole ring through a C—N bond, then an thioisocyanate can be used to generate intermediate 9 (X=S); the thioacylhydrazide then undergoes a cyclodehydration to lead to compounds of formula I.

Scheme I-B3: preparation of compounds where Ring A is a 1,3,4-oxadiazole

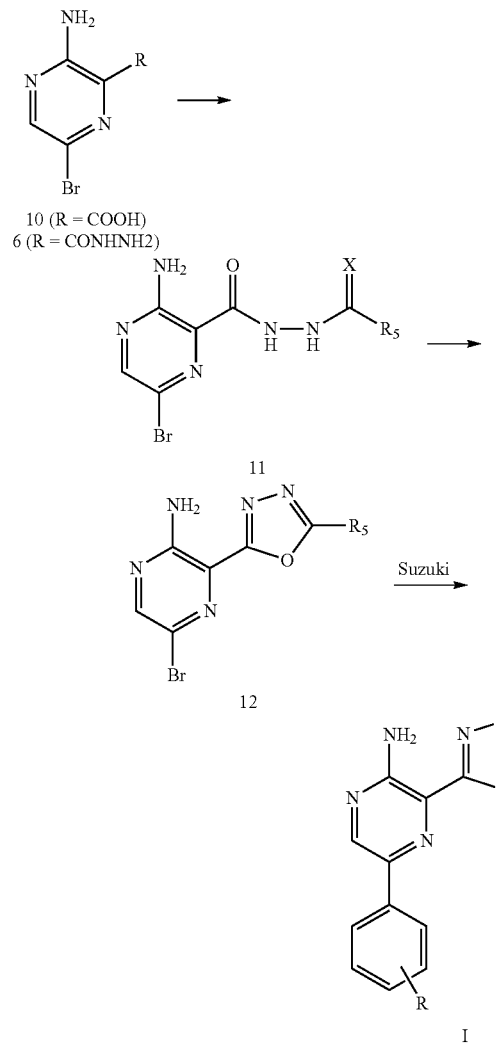

wherein R is -(L-NR$^1$R$^2$)$_p$ or -(J$_2$)$_q$

Alternatively, compounds of the present disclosure where Ring A is 1,3,4-oxadiazole can be prepared according to methods similar to the one depicted in Scheme I-B3:

the R functional group in 10 or 6 (acid and hydrazide respectively, both prepared from methyl ester 3 through hydrolysis and hydrazinolysis respectively) are engaged into coupling with a suitable partner (R$_5$CXNHNH$_2$ when starting from 10; R$_5$COOH/R$_5$=S when starting from 6) to form acylhydrazide intermediate H. Subsequent cyclodehydration leads to the compound 12 where the 1,3,4-oxadiazole ring has been constructed. Transformation of starting point 10 or 6 into intermediate 12 has also been performed in a one-pot procedure using reagents serving two purposes (coupling and cyclodehydration). The bromo handle in oxadiazole 12 is then reacted with a boronic acid under Suzuki conditions to give compounds of formula I. When R group in I contains a carboxylic acid moiety, it can be further transformed (eg into an amide) using conditions known in the art.

Scheme I-C1: preparation of compounds where Ring A is a 1,2,4-oxadiazole

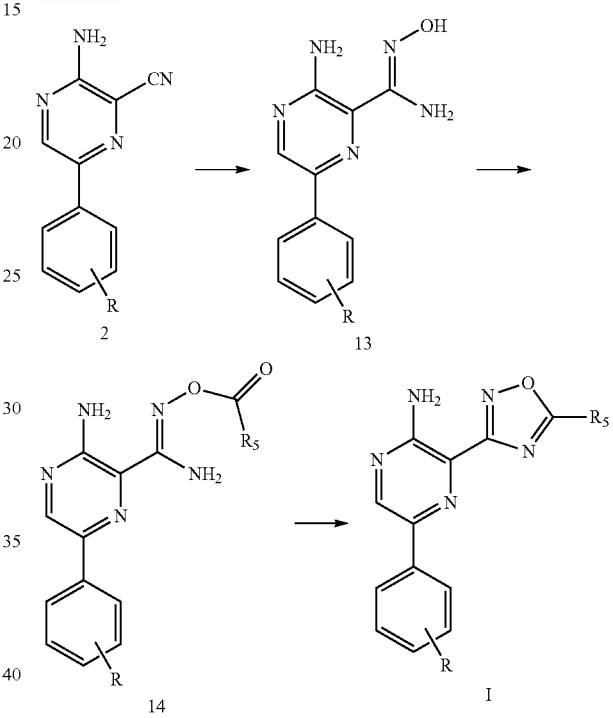

wherein R is -(L-NR$^1$R$^2$)$_p$ or -(J$_2$)$_q$

Compounds of the present disclosure where Ring A is a 1,2,4-oxadiazole can be prepared according to methods similar to the one depicted in Scheme I-C1: nitrile 2 reacts with hydroxylamine to give intermediate 13. The hydroxy group in 13 reacts with acid chlorides to lead to intermediate 14 which undergoes cyclodehydration to afford compounds of formula I.

Scheme I-C2: preparation of compounds where Ring A is a 1,2,4- oxadiazole

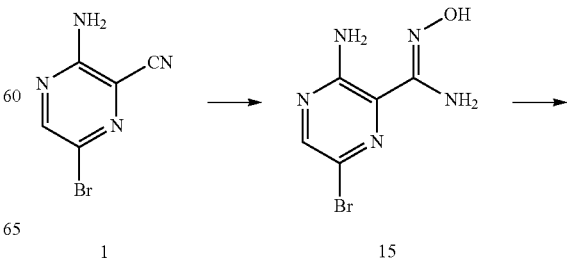

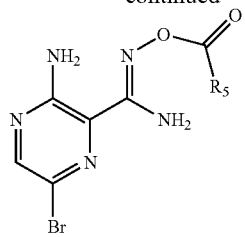

16

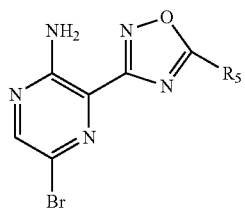

17

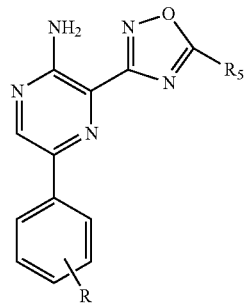

I wherein R is -(L-NR$^1$R$^2$)$_p$ or -(J$_2$)$_q$

Alternatively, compounds of the present disclosure where Ring A is a 1,2,4-oxadiazole can be prepared according to methods similar to the one depicted in Scheme I-C2: Commercially available nitrile 1 reacts with hydroxylamine to give intermediate 15. The hydroxy group in 15 reacts with acid chlorides to lead to intermediate 16 which undergoes cyclodehydration to afford intermediate 17. The bromo handle in 17 is then used to perform a Suzuki reaction with a boronic acid coupling partner to give compounds of formula I. When R group in I contains a carboxylic acid moiety, it can be further transformed (eg into an amide) using conditions known in the art.

Scheme I-D1: preparation of compounds where Ring A is a 1,3,4-thiadiazole

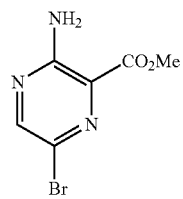

3

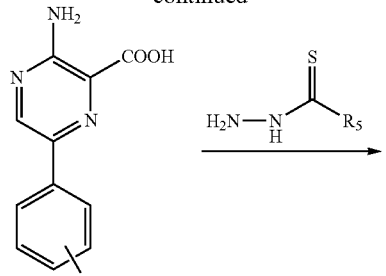

8

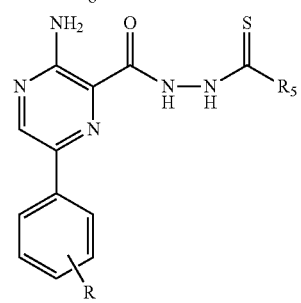

18

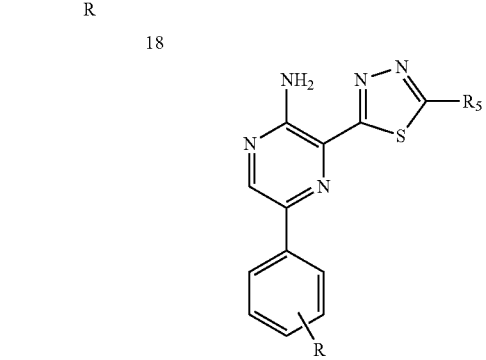

I wherein R is -(L-NR$^1$R$^2$)$_p$ or -(J$_2$)$_q$

Compounds of the present disclosure where Ring A is a 1,3,4-thiadiazole can be prepared according to methods similar to the one depicted in Scheme I-D1: methyl ester 3 is reacted with a boronic acid under Suzuki conditions to give intermediate 8. The carboxylic acid in 8 is then engaged into a coupling reaction with a thiohydrazide to form 18. Finally, the thioacylhydrazide in 18 undergoes a cyclodehydration to lead to compounds of formula I. Transformation of intermediate 8 into compounds of formula I can be performed in a one-pot procedure using reagents serving two purposes (coupling and cyclodehydration)

Scheme I-D2: preparation of compounds where Ring A is a 1,3,4-thiadiazole

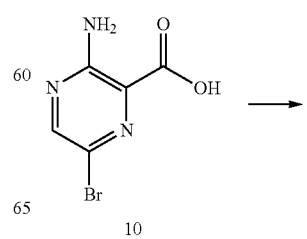

10

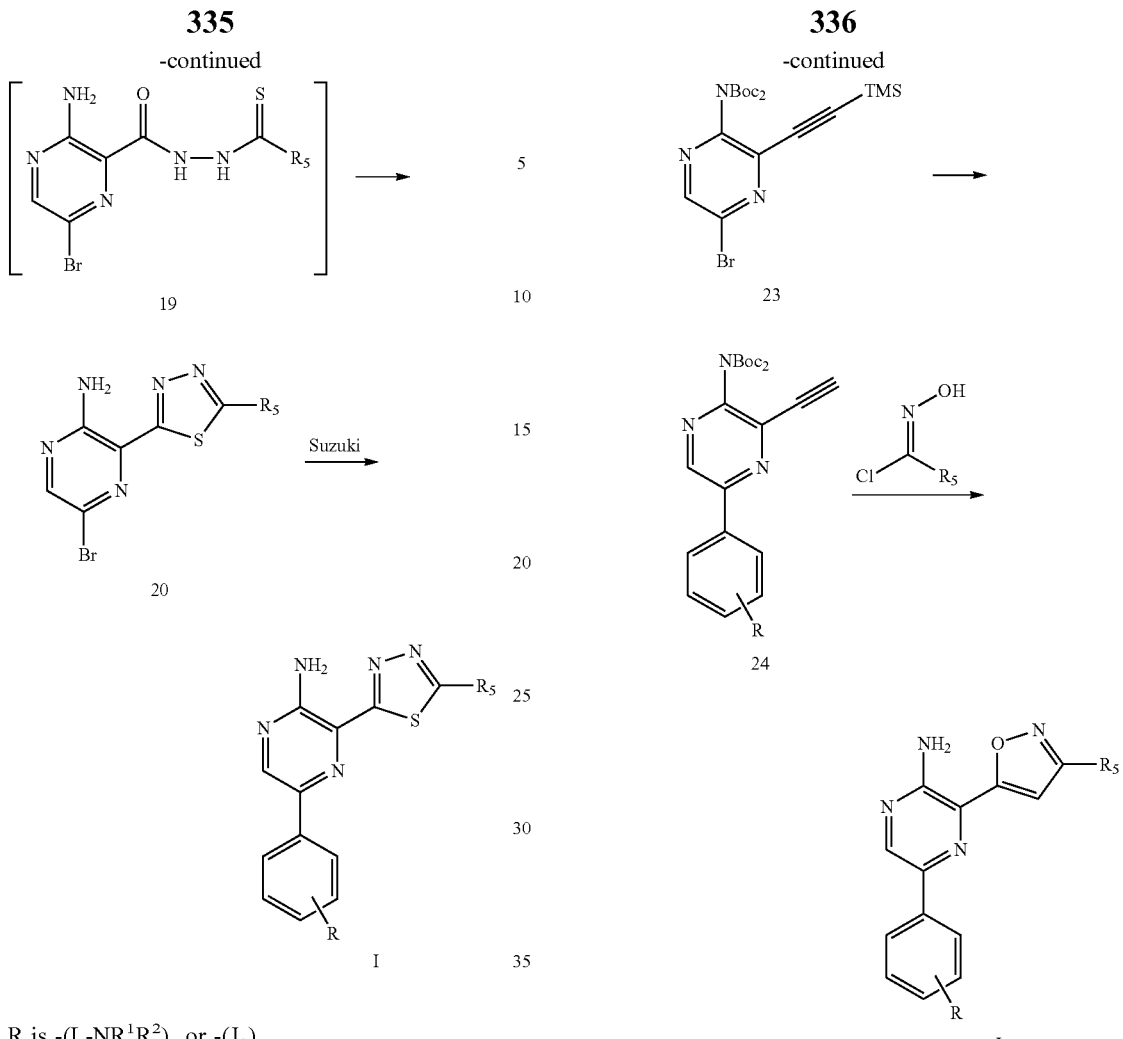

wherein R is -(L-NR$^1$R$^2$)$_p$ or -(J$_2$)$_q$

Alternatively, compounds of the present disclosure where Ring A is 1,3,4-thiadiazole can be prepared according to methods similar to the one depicted in Scheme I-D2: the acid functional group in 10 is engaged into coupling with a suitable partner (R$_5$CSNHNH$_2$) to form the thioacylhydrazide intermediate 19. Subsequent cyclodehydration leads to the compound 20 where the 1,3,4-thiadiazole ring has been constructed. Transformation of starting point 10 into 20 has been performed in a one-pot procedure using reagents serving two purposes (coupling and cyclodehydration). The bromo handle in thiadiazole 20 is then reacted with a boronic acid under Suzuki conditions to give compounds of formula I. When R group in I contains a carboxylic acid moiety, it can be further transformed (eg into an amide) using conditions known in the art.

wherein R is -(L-NR$^1$R$^2$)$_p$ or -(J$_2$)$_q$

Compounds of the present disclosure where Ring A is an isoxazole can be prepared according to methods similar to the one depicted in Scheme I-E1: Commercially available 2-amino-3,5-dibromo pyrazine 21 undergoes a Sonogashira coupling with TMS-acetylene to give intermediate 22, the amino group of which can be fully protected as the diBoc species 23. A Suzuki coupling with the remaining bromo handle, with concommitent TMS deprotection affords intermediate 24. The alkyne 24 finally reacts in a cyclocondensation with N-hydroxyaroyl chloride to furnish compounds of Formula I.

Scheme I-E1: preparation of compounds where Ring A is an isoxazole

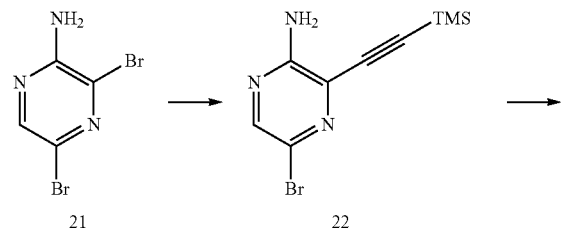

Scheme I-E2: preparation of compounds where Ring A is an isoxazole

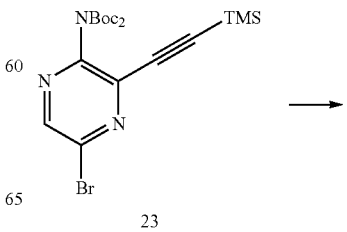

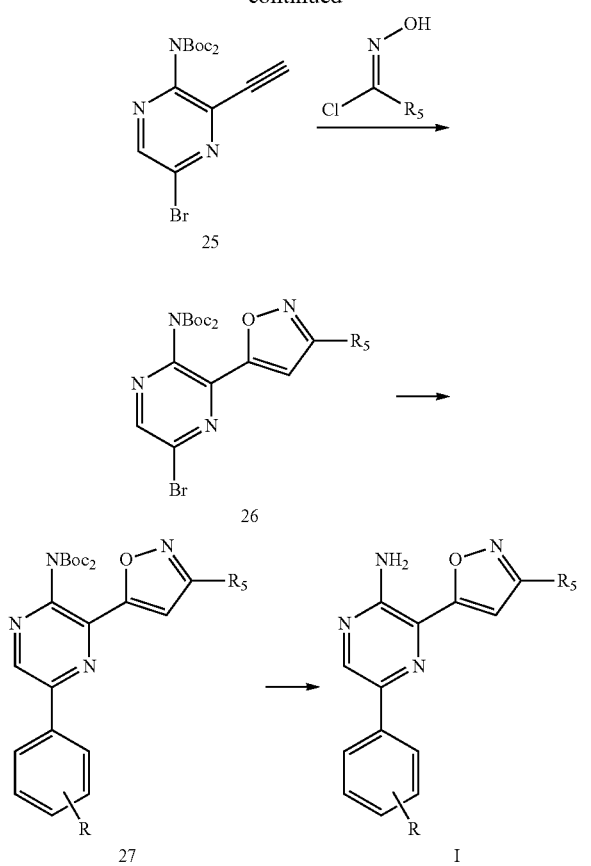

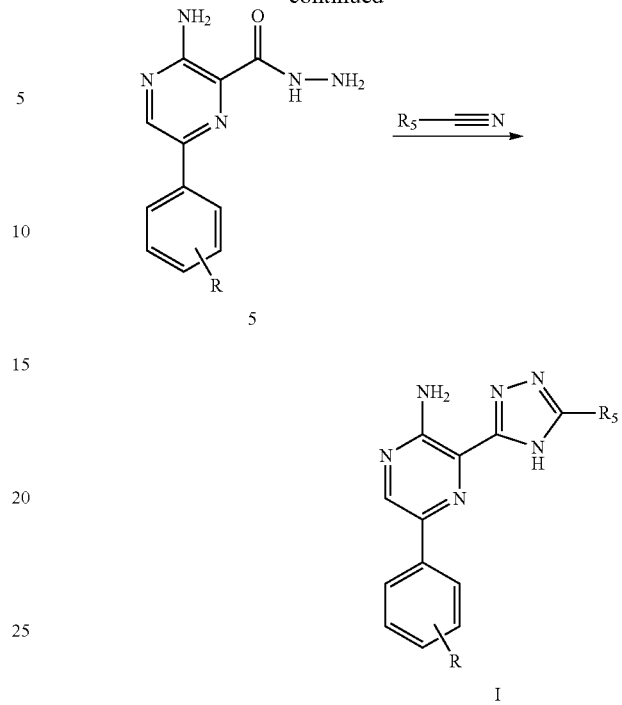

wherein R is -(L-NR$^1$R$^2$)$_p$ or -(J$_2$)$_q$

Alternatively, compounds of the present disclosure where Ring A is an isoxazole can be prepared according to methods similar to the one depicted in Scheme I-E2: The TMS-protected intermediate 23, described in scheme I-E1 can be deprotected to reveal the alkyne compound 25. The alkyne 25 reacts in a cyclocondensation with N-hydroxyaroyl chloride to furnish intermediate 26 where the isoxazole ring has been constructed. The bromo handle in isoxazole 26 is then reacted with a boronic acid under Suzuki conditions to give compounds 27. A final deprotection of N-protecting groups in 27 can reveal compounds of Formula I. When R group in I contains a carboxylic acid moiety, it can be further transformed (eg into an amide) using conditions known in the art.

wherein R is -(L-NR$^1$R$^2$)$_p$ or -(J$_2$)$_q$

Alternatively, compounds of the present disclosure where Ring A is a 1,2,4-triazole can be prepared according to methods similar to the one depicted in Scheme I-F1 starting from methyl ester 3. Ester 3 is reacted with a boronic acid under Suzuki conditions to give intermediate 4. When R group contains a carboxylic acid moiety, it can be further transformed at this stage (eg into an amide) using conditions known in the art. The methyl ester group in 4 is then transformed into an hydrazide by reaction with hydrazine to give 5. Finally, the hydrazide group in 5 is engaged in a coupling reaction with a nitrile and subsequently undergoes a cyclodehydration to lead to compounds of formula I.

Scheme I-F2: preparation of compounds where Ring A is a 1,2,4-triazole

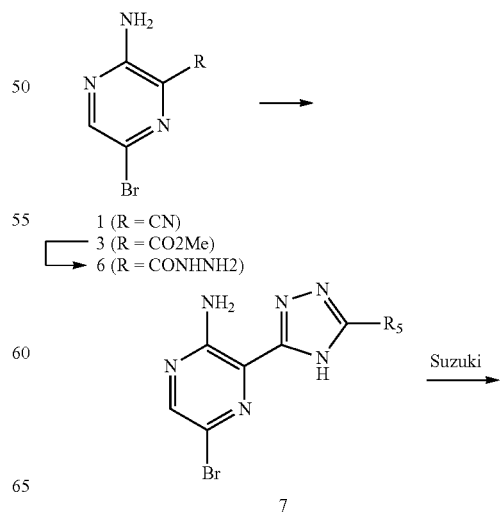

Scheme I-F1: preparation of compounds where Ring A is a 1,2,4-triazole

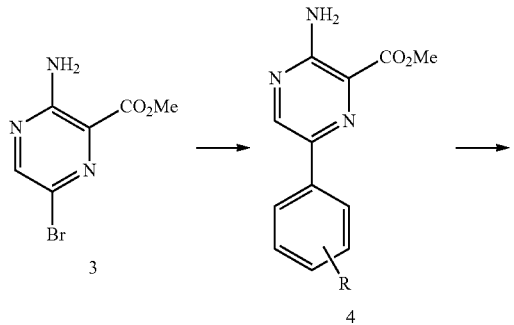

-continued

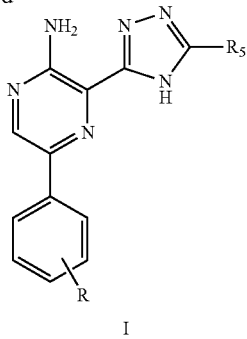

I wherein R is -(L-NR$^1$R$^2$)$_p$ or -(J$_2$)$_q$

Alternatively, compounds of the present disclosure where Ring A is a 1,2,4-triazole can be prepared according to methods similar to the one depicted in Scheme I-F2: the R functional group in 1 or 3 (nitrile and methyl ester respectively) are engaged into coupling (after appropriate transformation of 3 into hydrazide 6) with a suitable coupling partner (R$_5$CONHNH$_2$ when starting from 1; R$_5$CN if using 6). Subsequent cyclodehydration leads to the intermediate 7 where the 1,2,4-triazole ring has been constructed. The bromo handle in triazole 7 is then reacted with a boronic acid under Suzuki conditions to give compounds of formula I. When R group in I contains a carboxylic acid moiety, it can be further transformed (eg into an amide) using conditions known in the art.

Scheme I-G1: preparation of compounds where Ring A is a benzoxazole

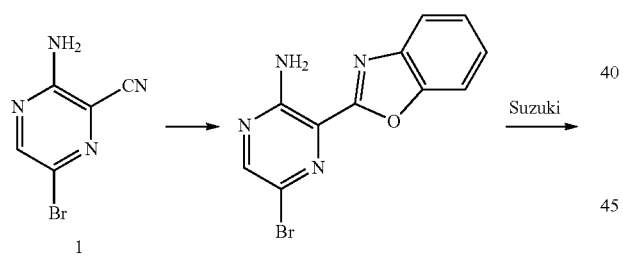

VI wherein R is -(L-NR$^1$R$^2$)$_p$ or -(J$_2$)$_q$

Benzoxazole compounds of Formula VI can be prepared according to methods similar to the one depicted in Scheme I-G1: Commercially available nitrile 1 is reacted with a amino phenol to give the benzoxazole which is then reacted with a boronic acid under Suzuki conditions to give compounds of the formula VI.

Scheme I-H1: preparation of compounds where Ring A is a benzothiazole

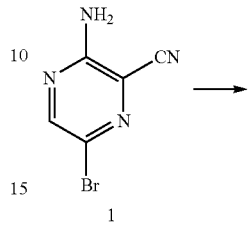

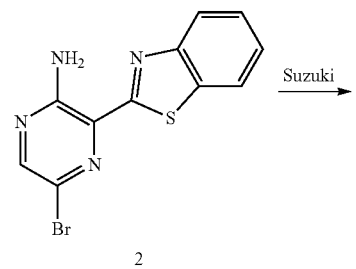

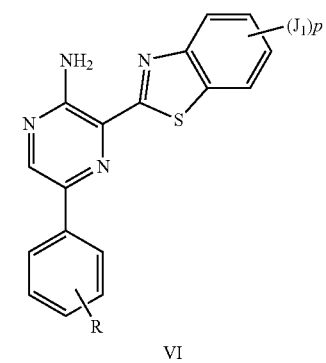

VI wherein R is -(L-NR$^1$R$^2$)$_p$ or -(J$_2$)$_q$

Benzothiazole compounds of Formula VI can be prepared according to methods similar to the one depicted in Scheme I-H1: Commercially available nitrile 1 is reacted with a aminobenzenethiol to give the benzothiazole which is then reacted with a boronic acid under Suzuki conditions to give compounds of the formula VI.

Scheme I-H2: preparation of compounds where benzothiazole

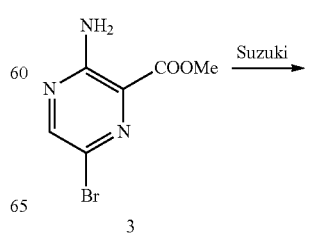

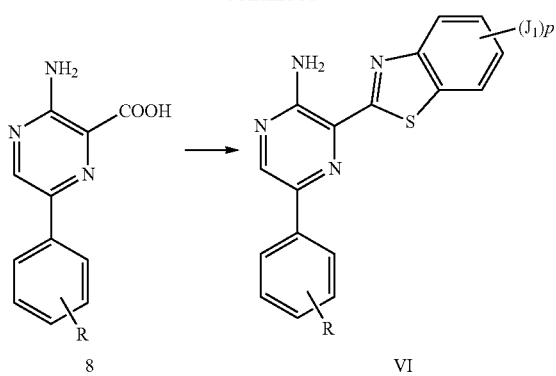

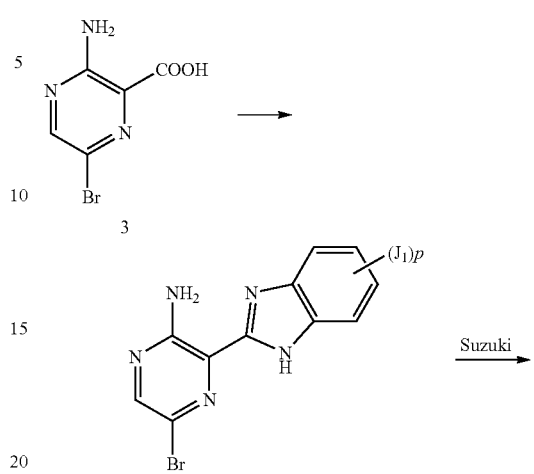

wherein R is -(L-NR$^1$R$^2$)$_p$ or -(J$_2$)$_q$

Alternatively, benzothiazole compounds of Formula VI can be prepared according to Scheme I-H2; methyl ester 3 is reacted with a boronic acid under Suzuki conditions to give intermediate 8. Cyclisation of intermediate 8 with an amino benzenethiol will lead to compounds of the formula VI.

Scheme I-I1: preparation of compounds where Ring A is an imidazole

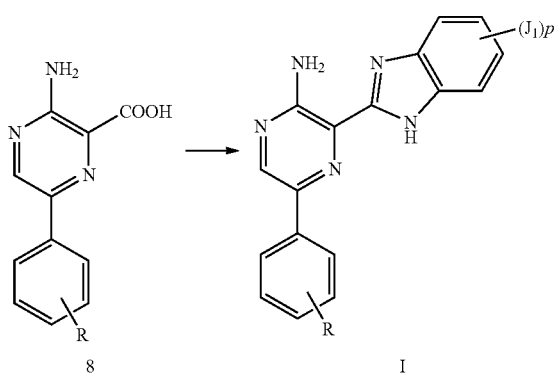

wherein R is -(L-NR$^1$R$^2$)$_p$ or -(J$_2$)$_q$

Benzimidazole compounds of Formula I can be prepared according to methods similar to the one depicted in Scheme I-I1: methyl ester 3 is reacted with a boronic acid under Suzuki conditions to give intermediate 8. Cyclisation of intermediate 8 with a benzene 1,2-diamine will lead to compounds of the formula I Scheme I-I2: preparation of compounds where Ring A is an imidazole

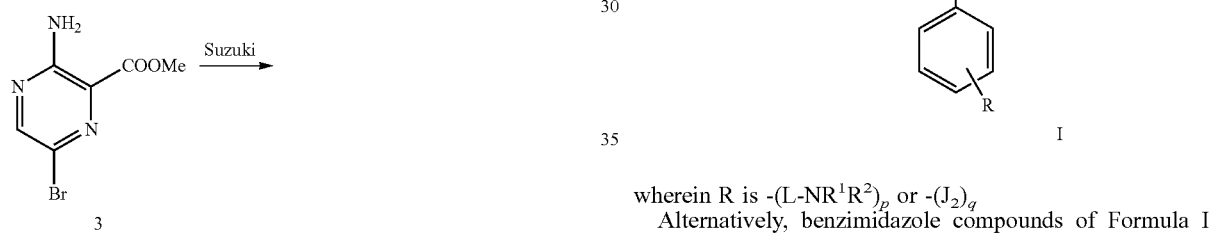

wherein R is -(L-NR$^1$R$^2$)$_p$ or -(J$_2$)$_q$

Alternatively, benzimidazole compounds of Formula I can be prepared according to methods similar to the one depicted in Scheme I-12: Reaction of the acid functional group of 3 is reacted with a benzene 1,2-diamine to give the benzimidazole intermediate 9. Intermediate 9 is then reacted with a boronic acid under Suzuki conditions to give compounds of the formula I.

EXAMPLES

It should be understood that the specific conditions shown below are only examples, and are not meant to limit the scope of the conditions that can be used for making, analyzing, or testing the compounds of the disclosure. Instead, this invention also includes conditions known to those skilled in that art for making, analyzing, and testing the compounds of the disclosure.

HPLC Methods

As used herein, the term "Rt(min)" refers to the HPLC retention time, in minutes, associated with the compound. Unless otherwise indicated, the HPLC method utilized to obtain the reported retention time is as follows:

Column: ACE C8 column, 4.6×150 mm
Gradient: 0-100% acetonitrile+methanol 60:40 (20 mM Tris phosphate)
Flow rate: 1.5 mL/minute
Detection: 225 nm.

HNMR Methods

1H-NMR spectra were recorded at 400 MHz using a Bruker DPX 400 instrument.

Mass Spectrometry Methods

Mass spec. samples were analyzed on a MicroMass Quattro Micro mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture, column gradient conditions are 5%-100% acetonitrile-methanol over 3.5 mins gradient time and 5 mins run time on an ACE C8 3.0×75 mm column. Flow rate is 1.2 ml/min.

The following compounds were prepared and analyzed as follows.

Example 1

3-amino-6-(4-methoxyphenyl)-N-phenylpyrazine-2-carboxamide (Compound I-1)

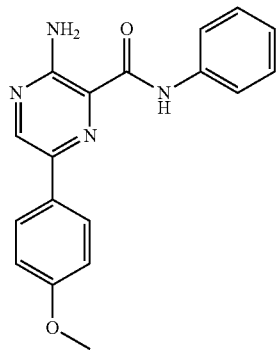 [SMILES: COc1ccc(-c2cnc(N)c(C(=O)Nc3ccccc3)n2)cc1]

SCHEME A

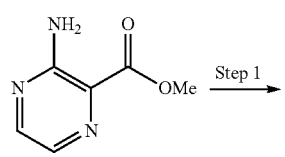 Step 1

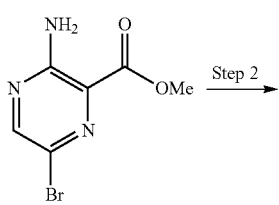 Step 2

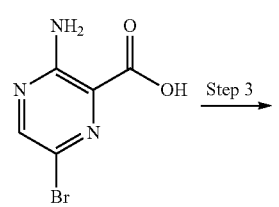 Step 3

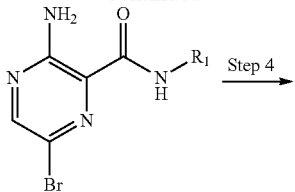 Step 4

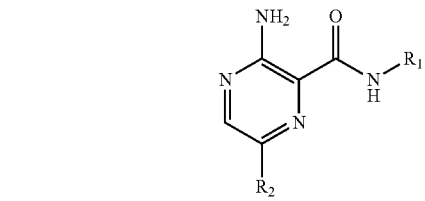

Method A

Step 1: Methyl 3-amino-6-bromopyrazine-2-carboxylate

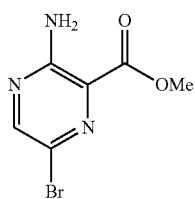 [SMILES: COC(=O)c1nc(Br)cnc1N]

A mixture of methyl 3-aminopyrazine-2-carboxylate (8.35 g, 54.53 mmol) and N-bromo-succinimide (9.705 g, 54.53 mmol) was stirred in MeCN (100 mL) at room temp overnight. The resultant precipitate was filtered, washed with MeCN and dried to give the desired product as a yellow solid (11.68 g, 92% Yield)

$^1$H NMR (400.0 MHz, DMSO) 3.85 (s, 3H), 7.55 (br s, 2H) and 8.42 (s, 1H) ppm; MS (ES$^+$) 233

Step 2: 3-amino-6-bromopyrazine-2-carboxylic Acid

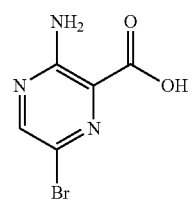 [SMILES: Nc1ncc(Br)nc1C(=O)O]

A mixture of methyl 3-amino-6-bromo-pyrazine-2-carboxylate (5.11 g, 22.02 mmol) and lithium hydroxide (2.637 g, 110.1 mmol) in MeOH (20 mL) and H2O (20 mL) was heated to 90° C. for 2 hours. The reaction mixture was allowed to cool and neutralised with HCl and the resultant precipitate collected by filtration. Taken on to the next step without further purification (4.80 g, 99% Yield).

Step 3:
3-amino-6-bromo-N-phenylpyrazine-2-carboxamide

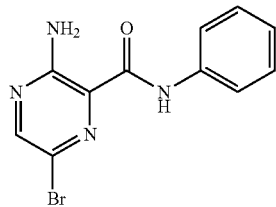 [SMILES: Nc1ncc(Br)nc1C(=O)Nc1ccccc1]

A mixture of 3-amino-6-bromo-pyrazine-2-carboxylic acid (3.5 g, 16.05 mmol), 1,1'-carbonyldiimidazole (5.205 g, 32.10 mmol), DIPEA (2.282 g, 3.075 mL, 17.66 mmol) and DMAP (98.04 mg, 0.8025 mmol) were combined in DMSO (131.2 mL) and stirred for 30 min. Aniline (1.495 g, 1.463 mL, 16.05 mmol) was then added and the resulting solution stirred at RT for 18 hours. After this time water was added and the product collected by filtration to give a brown powder (3.5 g, 74% Yield).

1H NMR (400.0 MHz, DMSO) d 7.04 (1H, m), 7.29 (2H, m), 7.72 (4H, m), 8.36 (1H, s), 10.22 (NH$_2$) ppm; MS (ES$^+$) 295.

Step 4: 3-amino-6-(4-methoxyphenyl)-N-phenylpyrazine-2-carboxamide (Compound I-1)

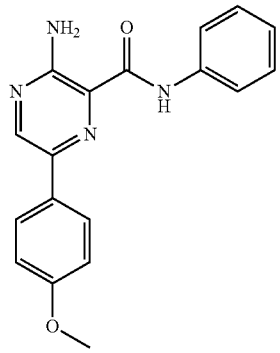 [SMILES: COc1ccc(-c2cnc(N)c(C(=O)Nc3ccccc3)n2)cc1]

A Greenhouse tube was charged with 4-Methoxyphenylboronic acid (31.4 mg, 0.207 mmol) and treated with a solution of dichloropalladium; triphenylphosphane (4.84 mg, 0.0069 mmol) and 3-amino-6-bromo-N-phenyl-pyrazine-2-carboxamide (40.45 mg, 0.138 mmol) in DMF (0.81 mL) followed by Na$_2$CO$_3$ (2M solution, 207 uL, 0.414 mmol). The mixture was flushed with nitrogen and heated to 88° C. for 18 hours. After this time the reaction was filtered to remove inorganics and the resultant residue was purified by reverse phase preparative HPLC [Waters Sunfire C18, 10 uM, 100 A column, gradient 10%-95% B (solvent A: 0.05% TFA in water, solvent B: CH3CN over 16 minutes at 25 mL/min]. The fractions were freeze-dried to give the title compound as a solid (18.56 mg, 38% Yield). MS (ES$^+$) 321

Compounds I-1 to I-41 were prepared using Method A.

Compound I-2 3-amino-6-(3-cyanopyridin-4-yl)-N-phenylpyrazine-2-carboxamide 1H NMR (400.0 MHz, DMSO) d 7.17 (t, J=7.3 Hz, 1H), 7.39-7.43 (m, 2H), 7.81-7.83 (m, 2H), 8.30 (d, J=5.4 Hz, 2H), 8.40 (s, 1H), 8.91 (d, J=5.5 Hz, 1H), 9.13 (s, 1H), 9.17 (s, 1H) and 10.16 (s, 1H) ppm; MS (ES$^+$) 317

Compound I-3 3-amino-N-phenyl-6-(4-(2-(piperidin-1-yl)ethylcarbamoyl)phenyl)pyrazine-2-carboxamide 1H NMR (400.0 MHz, DMSO) d 3.35 (s, 3H), 7.17 (t, J=7.4 Hz, 1H), 7.43-7.39 (m, 2H), 7.78 (t, J=7.8 Hz, 2H), 7.82 (d, J=7.7 Hz, 2H), 7.92-7.94 (m, 1H), 8.60-8.66 (m, 2H), 9.05 (s, 1H) and 10.50 (s, 1H) ppm; MS (ES$^+$) 369.

Compound I-4 3-amino-6-(4-fluorophenyl)-N-phenylpyrazine-2-carboxamide 1H NMR (400.0 MHz, DMSO) d 7.16 (t, J=7.3 Hz, 1H), 7.32 (t, J=8.9 Hz, 2H), 7.38-7.42 (m, 2H), 7.69 (s, 2H), 7.81-7.83 (m, 2H), 8.28-8.31 (m, 2H), 8.92 (s, 1H), 10.42 (s, 1H) ppm; MS (ES$^+$) 309

Compound I-5 3-amino-6-(4-(methylsulfonamido)phenyl)-N-phenylpyrazine-2-carboxamide 1H NMR (400.0 MHz, DMSO) d 7.16 (t, J=7.4 Hz, 1H), 7.33 (d, J=8.7 Hz, 2H), 7.38-7.42 (m, 2H), 7.65 (s, 2H), 7.83 (d, J=7.6 Hz, 2H), 8.21 (d, J=8.7 Hz, 2H), 8.90 (s, 1H), 9.92 (s, 1H), 10.37 (s, 1H) ppm; MS (ES$^+$) 384

Compound I-6 3-amino-N-phenyl-6-(2-(trifluoromethyl)phenyl)pyrazine-2-carboxamide 1H NMR (400.0 MHz, DMSO) d 7.11-7.16 (m, 1H), 7.36-7.40 (m, 2H), 7.69-7.72 (m, 3H), 7.80-7.84 (m, 4H), 7.93 (d, J=7.8 Hz, 1H), 8.52 (s, 1H), 10.12 (s, 1H) ppm; MS (ES$^+$) 359

Compound I-7 4-(5-amino-6-(phenylcarbamoyl)pyrazin-2-yl)benzoic acid 1H NMR (400 MHz, DMSO) 7.17 (1H, t), 7.41 (2H, t), 7.83 (4H, d), 8.03 (2H, d), 8.37 (2H, d), 9.01 (1H, s), 10.45 (1H, s), 13.03 (1H, br s) ppm; MS (ES$^+$) 335

Compound I-8 3-(5-amino-6-(phenylcarbamoyl)pyrazin-2-yl)benzoic acid 1H NMR (400 MHz, DMSO) 7.16 (1H, t), 7.38-7.42 (3H, m), 7.64 (2H, br s), 7.81 (2H, d), 7.88 (1H, d), 8.17 (1H, d), 8.46 (1H, d), 8.85 (1H, s), 10.39 (1H, s) ppm; MS (ES$^+$) 335

Compound I-9 3-amino-6-(3-fluorophenyl)-N-phenylpyrazine-2-carboxamide 1H NMR (400.0 MHz, DMSO) d 7.15-7.25 (m, 2H), 7.40 (dd, J=1.7, 15.9 Hz, 1H), 7.41 (s, 1H), 7.52 (td, J=8.0, 4.7 Hz, 1H), 7.80-7.82 (m, 4H), 8.06 (d, J=8.0 Hz, 8.17-8.20 (m, 1H), 8.97 (s, 1H), 10.46 (s, 1H) ppm; MS (ES$^+$) 309

Compound I-10 3-amino-6-(3-cyanophenyl)-N-phenylpyrazine-2-carboxamide MS (ES$^+$) 316

Compound I-11 3-amino-N-phenyl-6-o-tolylpyrazine-2-carboxamide MS (ES$^+$) 305

Compound I-12 3-amino-6-(3-morpholinophenyl)-N-phenylpyrazine-2-carboxamide; MS (ES+) 376

Compound I-13 3-amino-6-(4-morpholinophenyl)-N-phenylpyrazine-2-carboxamide MS (ES+) 376

Compound I-14 3-amino-6-(2-fluorophenyl)-N-phenylpyrazine-2-carboxamide MS (ES$^+$) 309

Compound I-15 3-amino-N,6-diphenylpyrazine-2-carboxamide; MS (ES$^+$) 291

Compound I-16 3-amino-6-(4-(hydroxymethyl)phenyl)-N-phenylpyrazine-2-carboxamide; MS (ES+) 321

Compound I-17 6-(4-acetylphenyl)-3-amino-N-phenylpyrazine-2-carboxamide MS (ES$^+$) 333

Compound I-18 3-amino-6-(3-carbamoylphenyl)-N-phenylpyrazine-2-carboxamide; MS (ES+) 334

Compound I-19 3-amino-6-(2-(hydroxymethyl)phenyl)-N-phenylpyrazine-2-carboxamide; MS (ES+) 321

Compound I-20 3-amino-6-(3-(morpholine-4-carbonyl)phenyl)-N-phenylpyrazine-2-carboxamide; MS (ES+) 404

Compound I-21 3-amino-6-(4-cyanophenyl)-N-phenylpyrazine-2-carboxamide MS (ES$^+$) 316

Compound I-22 6-(3-acetylphenyl)-3-amino-N-phenylpyrazine-2-carboxamide MS (ES$^+$) 333

Compound I-23 3-amino-6-(4-(2-(4-hydroxypiperidin-1-yl)acetyl)phenyl)-N-phenylpyrazine-2-carboxamide; MS (ES+) 432

Compound I-24 3-amino-6-(4-(dimethylcarbamoyl)phenyl)-N-phenylpyrazine-2-carboxamide; MS (ES+) 362

Compound I-25 3-amino-6-(3-(methylsolfonamido)phenyl)-N-phenylpyrazine-2-carboxamide; MS (ES+) 384

Compound I-26 3-amino-6-(3-(morpholine-4-carbonyl)phenyl)-N-(4-(pyrrolidin-1-yl)phenyl)pyrazine-2-carboxamide; MS (ES+) 473

Compound I-27 3-amino-6-(3-carbamoylphenyl)-N-(2-methoxyphenyl)pyrazine-2-carboxamide; MS (ES+) 364

Compound I-28 3-amino-6-(4-(dimethylcarbamoyl)phenyl)-N-(2-methoxyphenyl)pyrazine-2-carboxamide; MS (ES+) 392

Compound I-29 3-amino-6-(1H-indol-5-yl)-N-(2-methoxyphenyl)pyrazine-2-carboxamide 1H NMR (400.0 MHz, DMSO) d 4.03 (s, 3H), 6.55 (d, J=1.9 Hz, 1H), 7.03-7.05 (m, 1H), 7.13-7.19 (m, 2H), 7.43 (t, J=2.7 Hz, 1H), 7.55 (d, J=8.6 Hz, 2H), 7.87 (dd, J=1.6, 8.6 Hz, 1H), 8.31 (s, 1H), 8.39 (dd, J=1.4, 7.9 Hz, 1H), 8.99 (s, 1H), 10.85 (s, 1H) and 11.27 (s, 1H) ppm; MS (ES$^+$) 360

Compound I-30 3-amino-6-(furan-2-yl)-N-(2-methoxyphenyl)pyrazine-2-carboxamide 1H NMR (400.0 MHz, DMSO) d 3.98 (s, 3H), 6.56 (s, 1H), 6.69 (s, 1H), 7.00-7.03 (m, 2H), 7.15 (s, 1H), 7.86 (br s, 2H), 7.86 (s, 1H), 8.32 (d, 1H), 8.72 (s, 1H) and 10.51 (s, 1H) ppm; MS (ES$^+$) 311

Compound I-31 3-amino-N-phenyl-6-(1H-pyrazol-5-yl)pyrazine-2-carboxamide 1H NMR (400.0 MHz, DMSO) d 6.98 (d, J=10.5 Hz, 1H), 7.18 (t, J=7.4 Hz, 1H), 7.40-7.44 (m, 2H), 7.67 (s, 3H), 7.81 (d, J=7.7 Hz, 2H), 8.83 (s, 1H), 10.54 (s, 1H) and 13.80 (s, 1H) ppm; MS (ES$^+$) 281

Compound I-32 3-amino-6-(6-hydroxypyridin-3-yl)-N-phenylpyrazine-2-carboxamide 1H NMR (400.0 MHz, DMSO) d 6.45 (d, J=9.6 Hz, 1H), 7.14-7.18 (m, 1H), 7.38-7.42 (m, 2H), 7.58 (s, 2H), 7.78-7.80 (m, 2H), 8.31 (d, J=2.5 Hz, 1H), 8.39 (dd, J=2.6, 9.6 Hz, 1H), 8.79 (s, 1H), 10.42 (s, 1H) and 12.00 (s, 1H) ppm; MS (ES$^+$) 308

Compound I-33 3-amino-N-phenyl-6-(pyridin-4-yl)pyrazine-2-carboxamide 1H NMR (400.0 MHz, DMSO) d 7.18 (t, J=7.5 Hz, 1H), 7.41 (dd, J=1.8, 14.1 Hz, 2H), 7.82 (dd, J=0.8, 8.4 Hz, 2H), 7.90 (s, 2H), 8.25 (dd, J=1.6, 4.6 Hz, 2H), 8.67 (dd, J=1.4, 4.8 Hz, 2H), 9.07 (s, 1H) and 10.48 (s, 1H) ppm; MS (ES$^+$) 292

Compound I-34 3-amino-6-(6-morpholinopyridin-3-yl)-N-phenylpyrazine-2-carboxamide; MS (ES+) 377

Compound I-35 3-amino-N-(2-methoxyphenyl)-6-(thiophen-2-yl)pyrazine-2-carboxamide; MS (ES+) 327

Compound I-36 3-amino-6-(1H-indazol-5-yl)-N-(2-methoxyphenyl)pyrazine-2-carboxamide; MS (ES+) 361

Compound I-37 3-amino-6-(furan-3-yl)-N-(2-methoxyphenyl)pyrazine-2-carboxamide; MS (ES+) 311

Compound I-38 3-amino-6-(2-methoxypyridin-4-yl)-N-phenylpyrazine-2-carboxamide; MS (ES+) 322

Compound I-39 3-amino-6-(1H-indazol-5-yl)-N-phenylpyrazine-2-carboxamide MS (ES$^+$) 331

Compound I-40 3-amino-N-phenyl-6-(pyrimidin-5-yl)pyrazine-2-carboxamide MS (ES$^+$) 293

Compound I-41 3-amino-6-(furan-2-yl)-N-phenylpyrazine-2-carboxamide MS (ES$^+$) 281

Example 2

(R)-3-amino-N-phenyl-6-(4-(2-(pyrrolidin-1-ylmethyl)pyrrolidine-1-carbonyl)phenyl)pyrazine-2-carboxamide (Compound I-42)

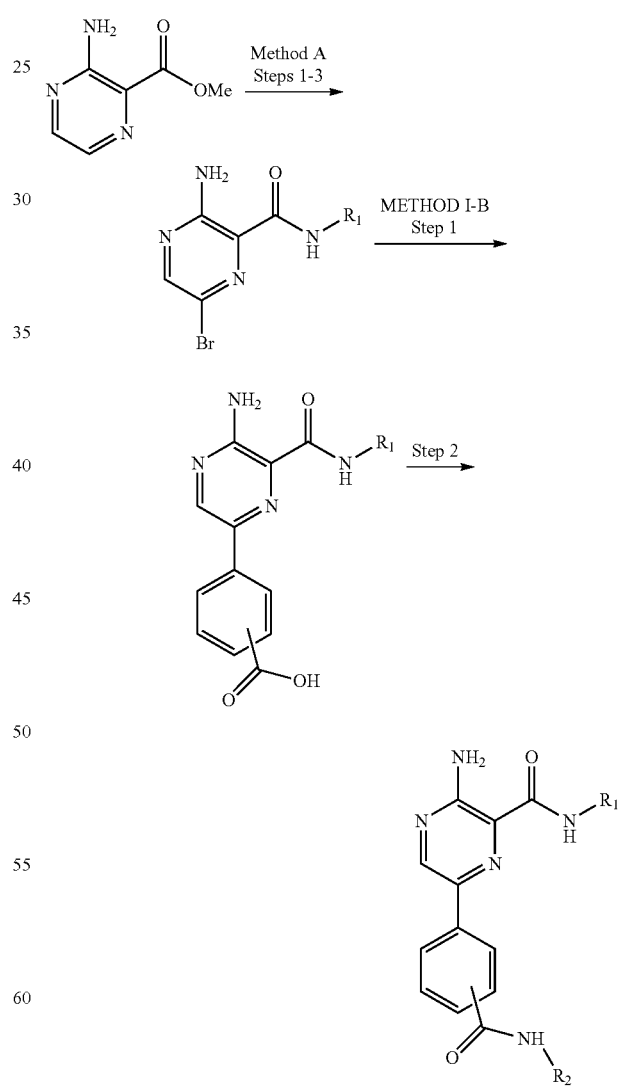

Compound I-42 was prepared by using Method A, Steps 1-3 followed by Method I-B, Steps 1-2.

Method I-B

Step 1:
3-(5-amino-6-(phenylcarbamoyl)pyrazin-2-yl)benzoic Acid

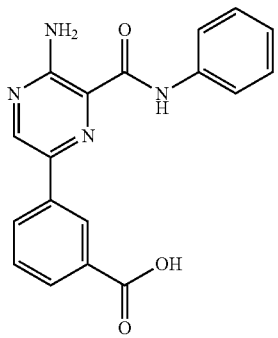 [SMILES: Nc1ncc(-c2cccc(C(=O)O)c2)nc1C(=O)Nc1ccccc1]

A mixture of 3-amino-6-bromo-N-phenyl-pyrazine-2-carboxamide (2.5 g, 8.529 mmol), 3-boronobenzoic acid (1.415 g, 8.527 mmol) and $Na_2CO_3$ (1.808 g, 17.06 mmol) was suspended in MeCN (40 mL)/water (40 mL). The mixture was degassed (5×$N_2$ vacuum cycles) and Pd(PPh$_3$)$_4$ (985.6 mg, 0.8529 mmol) added. The mixture was degassed again and heated to 90° C. After 2 hours, the mixture was allowed to cool and concentrated to half its original volume. The resulting yellow precipitate was collected and washed with DCM and water (3.05 g, 86% Yield). 1H NMR (400 MHz, DMSO) d 7.16 (1H, t), 7.38-7.42 (3H, m), 7.64 (2H, br s), 7.81 (2H, d), 7.88 (1H, d), 8.17 (1H, d), 8.46 (1H, d), 8.85 (1H, s), 10.39 (1H, s) ppm; MS (ES$^+$) 335

Step 2: (R)-3-amino-N-phenyl-6-(4-(2-(pyrrolidin-1-ylmethyl)pyrrolidine-1-carbonyl)phenyl)pyrazine-2-carboxamide

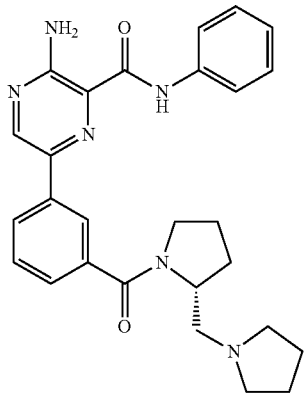 [SMILES: Nc1ncc(-c2cccc(C(=O)N3CCC[C@@H]3CN3CCCC3)c2)nc1C(=O)Nc1ccccc1]

1-[[(2R)-pyrrolidin-2-yl]methyl]pyrrolidine (69.23 mg, 0.449 mmol) was weighed into a greenhouse tube and treated with a solution of 3-(5-amino-6-(phenylcarbamoyl)pyrazin-2-yl)benzoic acid (50 mg, 0.150 mmol), CDI (48.51 mg, 0.299 mmol) and DMAP (1.82 mg, 0.015 mmol) in DMSO (1 mL of a stock solution). DIPEA (78.2 uL, 0.449 mmol) was then added and the mixture stirred at 38° C. for 6 hours. The reaction mixture was filtered and the resultant residue was purified by reverse phase preparative HPLC [Waters Sunfire C18, 10 uM, 100 A column, gradient 10%-95% B (solvent A: 0.05% TFA in water, solvent B: CH3CN) over 16 minutes at 25 mL/min]. The fractions were freeze-dried to give the title compound as a solid (51.87 mg, 73% Yield). (ES$^+$) 471

Compounds I-42 to I-81 were prepared using Method A, Steps 1-3 followed by Method I-B, Steps 1-2.

Compound I-43 6-(4-(1,4-diazepane-1-carbonyl)phenyl)-3-amino-N-phenylpyrazine-2-carboxamide 1H NMR (400.0 MHz, DMSO) 1.44-1.47 (m, 1H), 1.53-1.58 (m, 1H), 2.57-2.61 (m, 1H), 2.62-2.69 (m, 2H), 2.74-2.80 (m, 1H), 3.15-3.20 (m, 2H), 3.40-3.46 (m, 2H), 6.91-6.96 (m, 1H), 7.15-7.19 (m, 2H), 7.23-7.28 (m, 2H), 7.51 (br s, 2H), 7.58-7.60 (m, 2H), 8.05-8.08 (m, 2H), 8.74 (s, 1H) and 10.20 (s, 1H) ppm; MS (ES$^+$) 417

Compound I-44 3-amino-6-(4-(3-methoxyazetidine-1-carbonyl)phenyl)-N-phenylpyrazine-2-carboxamide 1H NMR (400 MHz, DMSO) 3.22 (3H, s), 3.87 (1H, br dd), 4.18 (1H, br d), 4.23-4.29 (2H, br dd), 4.47-4.49 (1H, m), 7.17 (1H, t), 7.40 (2H, t), 7.75 (2H, d), 7.79 (2H, br s), 7.83 (2H, d), 8.29 (2H, d), 9.00 (1H, s), 10.44 (1H, s) ppm; MS (ES$^+$) 404

Compound I-45 3-amino-6-(4-((2-methoxyethyl)(methyl)carbamoyl)phenyl)-N-phenylpyrazine-2-carboxamide 1H NMR (400 MHz, DMSO) 3.00 (3H, br s), 3.45 (3H, br s), 3.61 (2H, br d), 7.17 (1H, t), 7.41 (2H, t), 7.49 (2H, d), 7.76 (2H, br s), 7.84 (2H, d), 8.29 (1H, d), 8.97 (1H, s), 10.44 (1H, s) ppm; MS (ES') 406

Compound I-46 3-amino-N-phenyl-6-(4-(2-(pyrrolidin-1-yl)ethylcarbamoyl)phenyl)pyrazine-2-carboxamide 1H NMR (400 MHz, DMSO) 1.80 (4H, br s), 3.51 (2H, br s), 7.18 (1H, t), 7.41 (2H, t), 7.81-7.85 (4H, m), 7.95 (2H, d), 8.35 (2H, d), 8.65 (1H, br s), 9.02 (1H, s), 10.44 (1H, s) ppm; MS (ES$^+$) 431

Compound I-47 3-amino-N-phenyl-6-(4-(tetrahydro-2H-pyran-4-ylcarbamoyl)phenyl)pyrazine-2-carboxamide 1H NMR (400 MHz, DMSO) 1.56-1.67 (2H, m), 1.75-1.80 (2H, m), 3.29-3.44 (2H, m), 3.88-3.92 (2H, m), 4.00-4.07 (1H, m), 7.15 (1H, t), 7.41 (2H, t), 7.79 (2H, br s), 7.82 (2H, d), 7.97 (2H, d), 8.33 (2H, d), 8.40 (1H, d), 9.01 (1H, s), 10.44 (1H, s) ppm; MS (ES$^+$) 418

Compound I-48 3-amino-6-(3-(1-methylpiperidin-4-ylcarbamoyl)phenyl)-N-phenylpyrazine-2-carboxamide 1H NMR (400 MHz, DMSO) 1.55-1.64 (2H, m), 1.76-1.81 (2H, m), 1.93 (2H, t), 2.16 (3H, s), 2.75 (2H, br d), 3.72-3.76 (1H, m), 7.12 (1H, t), 7.36 (2H, t), 7.54 (1H, t), 7.72 (2H, br s), 7.78-7.83 (3H, m), 8.37 (2H, dd), 8.55 (1H, s), 8.98 (1H, s), 10.44 (1H, s) ppm; MS (ES$^+$) 431

Compound I-49 3-amino-6-(4-(2-(piperidin-1-yl)ethylcarbamoyl)phenyl)-N-phenylpyrazine-2-carboxamide 1H NMR (400 MHz, DMSO) 1.30-1.40 (2H, m), 1.46-1.53 (4H, m), 2.33 (4H, m), 2.45 (2H, t), 3.37-3.44 (2H, m), 7.16 (1H, t), 7.41 (2H, t), 7.79 (2H, br s), 7.81 (2H, d), 7.95 (2H, d), 8.34 (2H, d), 8.48 (1H, t), 9.00 (1H, s), 10.45 (1H, s) ppm; MS (ES$^+$) 445

Compound I-50 3-amino-6-(3-(4-(hydroxymethyl)piperidine-1-carbonyl)phenyl)-N-phenylpyrazine-2-carboxamide 1H NMR (400 MHz, DMSO) 1.10-1.22 (3H, m), 1.65 (2H, br s), 1.79 (1H, br d), 2.77 (1H, br t), 3.05 (1H, br t), 3.27 (2H, d), 3.64 (1H, br d), 4.52 (1H, br s), 7.17 (1H, t), 7.38-7.42 (3H, m), 7.55 (1H, t), 7.73 (2H, brs), 7.80 (2H, d), 8.19 (1H, s), 8.29 (1H, d), 8.96 (1H, s), 10.45 (1H, s) ppm; MS (ES$^+$) 432

Compound I-51 3-amino-6-(4-(cyclopropylcarbamoyl)phenyl)-N-phenylpyrazine-2-carboxamide 1H NMR (400 MHz, DMSO) 0.59-0.67 (2H, m), 0.69-0.74 (2H, m), 2.84-

2.91 (1H, m), 7.17 (1H, t), 7.21 (2H, t), 7.79 (2H, br s), 7.81 (2H, d), 7.95 (2H, d), 8.39 (2H, d), 8.53 (1H, d), 8.97 1H, s), 10.46 (1H, s) ppm; MS (ES+) 374

Compound I-52 3-amino-6-(3-((2-(dimethylamino)ethyl)(methyl)carbamoyl)phenyl)-N-phenylpyrazine-2-carboxamide; MS (ES+) 419

Compound I-53 3-amino-N-phenyl-6-(3-(piperazine-1-carbonyl)phenyl)pyrazine-2-carboxamide; MS (ES+) 403

Compound I-54 3-amino-N-phenyl-6-(3-(2-(pyrrolidin-1-yl)ethylcarbamoyl)phenyl)pyrazine-2-carboxamide; MS (ES+) 431

Compound I-55 3-amino-6-(3-(3-(dimethylamino)pyrrolidine-1-carbonyl)phenyl)-N-phenylpyrazine-2-carboxamide; MS (ES+) 431

Compound I-56 3-amino-N-phenyl-6-(3-(4-(pyrrolidin-1-yl)piperidine-1-carbonyl)phenyl)pyrazine-2-carboxamide; MS (ES+) 471

Compound I-57 3-amino-6-(3-(4-hydroxycyclohexylcarbamoyl)phenyl)-N-phenylpyrazine-2-carboxamide; MS (ES+) 432

Compound I-58 3-amino-6-(3-(4-(2-cyanoethyl)piperazine-1-carbonyl)phenyl)-N-phenylpyrazine-2-carboxamide; MS (ES+) 456

Compound I-59 3-amino-6-(3-(4-methylpiperazine-1-carbonyl)phenyl)-N-phenylpyrazine-2-carboxamide; MS (ES+) 417

Compound I-60 3-amino-6-(3-(3-methoxyazetidine-1-carbonyl)phenyl)-N-phenylpyrazine-2-carboxamide; MS (ES+) 404

Compound I-61 3-amino-N-phenyl-6-(3-(2-(piperidin-1-yl)ethylcarbamoyl)phenyl)pyrazine-2-carboxamide; MS (ES+) 445

Compound I-62 3-amino-6-(3-(4-carbamoylpiperidine-1-carbonyl)phenyl)-N-phenylpyrazine-2-carboxamide; MS (ES+) 445

Compound I-63 3-amino-N-phenyl-6-(3-(pyrrolidine-1-carbonyl)phenyl)pyrazine-2-carboxamide; MS (ES+) 388

Compound I-64 3-amino-6-(4-(1-methylpiperidin-4-ylcarbamoyl)phenyl)-N-phenylpyrazine-2-carboxamide; MS (ES+) 431

Compound I-65 3-amino-6-(3-(3-hydroxypyrrolidine-1-carbonyl)phenyl)-N-phenylpyrazine-2-carboxamide; MS (ES+) 404

Compound I-66 3-amino-N-phenyl-6-(3-(tetrahydro-2H-pyran-4-ylcarbamoyl)phenyl)pyrazine-2-carboxamide; MS (ES+) 418

Compound I-67 3-amino-6-(3-((2-methoxyethyl)(methyl)carbamoyl)phenyl)-N-phenylpyrazine-2-carboxamide; MS (ES+) 406

Compound I-68 3-amino-6-(4-((2-(dimethylamino)ethyl)(methyl)carbamoyl)phenyl)-N-phenylpyrazine-2-carboxamide; MS (ES+) 419

Compound I-69 3-amino-N-phenyl-6-(4-((tetrahydro-2H-pyran-4-yl)methylcarbamoyl)phenyl)pyrazine-2-carboxamide; MS (ES+) 432

Compound I-70 3-amino-N-phenyl-6-(4-(pyrrolidine-1-carbonyl)phenyl)pyrazine-2-carboxamide; MS (ES+) 388

Compound I-71 3-amino-N-phenyl-6-(4-(4-(pyrrolidin-1-yl)piperidine-1-carbonyl)phenyl)pyrazine-2-carboxamide; MS (ES+) 471

Compound I-72 3-amino-6-(4-(azetidine-1-carbonyl)phenyl)-N-phenylpyrazine-2-carboxamide; MS (ES+) 374

Compound I-73 3-amino-6-(4-(4-methylpiperazine-1-carbonyl)phenyl)-N-phenylpyrazine-2-carboxamide; MS (ES+) 417

Compound I-74 3-amino-N-phenyl-6-(4-(piperazine-1-carbonyl)phenyl)pyrazine-2-carboxamide; MS (ES+) 403

Compound I-75 3-amino-6-(4-(3-hydroxypyrrolidine-1-carbonyl)phenyl)-N-phenylpyrazine-2-carboxamide; MS (ES+) 404

Compound I-76 3-amino-6-(4-(3-(dimethylamino)pyrrolidine-1-carbonyl)phenyl)-N-phenylpyrazine-2-carboxamide; MS (ES+) 431

Compound I-77 3-amino-6-(4-(4-carbamoylpiperidine-1-carbonyl)phenyl)-N-phenylpyrazine-2-carboxamide; MS (ES+) 445

Compound I-78 3-amino-N-phenyl-6-(4-(piperidine-1-carbonyl)phenyl)pyrazine-2-carboxamide; MS (ES+) 402

Compound I-79 3-amino-6-(4-(4-(hydroxymethyl)piperidine-1-carbonyl)phenyl)-N-phenylpyrazine-2-carboxamide; MS (ES+) 432

Compound I-80 3-amino-6-(4-(4-(dimethylamino)piperidine-1-carbonyl)phenyl)-N-phenylpyrazine-2-carboxamide; MS (ES+) 445

Compound I-81 3-amino-6-(4-(4-(2-cyanoethyl)piperazine-1-carbonyl)phenyl)-N-phenylpyrazine-2-carboxamide; MS (ES+) 456

Example 3

3-amino-6-(4-(methylsulfonyl)phenyl)-N-phenylpyrazine-2-carboxamide (Compound I-82)

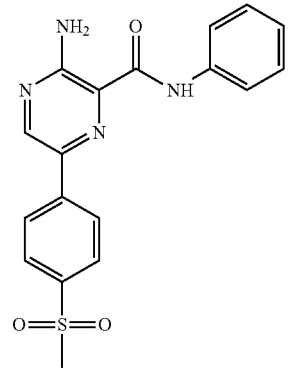 [SMILES: CS(=O)(=O)c1ccc(-c2cnc(N)c(C(=O)Nc3ccccc3)n2)cc1]

SCHEME C

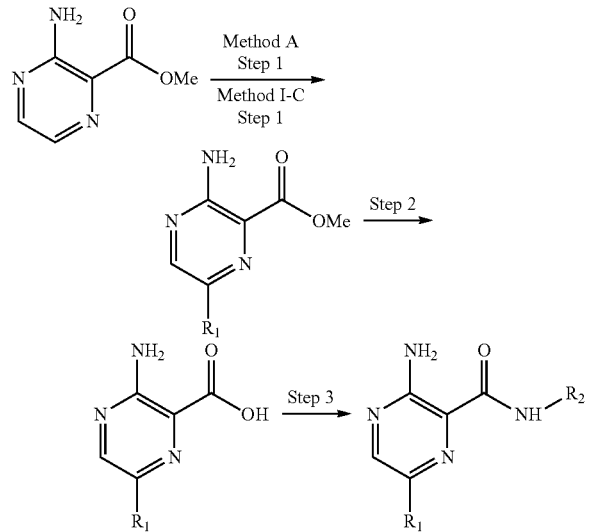

Compound I-82 was prepared using Method A, Step 1 followed by Method I-C, Steps 1-3

Method I-C

Step 1: Methyl 3-amino-6-(4-(methylsulfonyl)phenyl)pyrazine-2-carboxylate

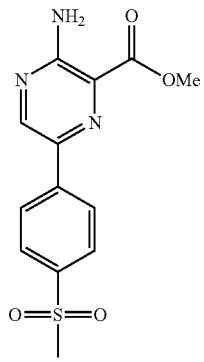 [SMILES: COC(=O)c1nc(-c2ccc(S(C)(=O)=O)cc2)cnc1N]

A mixture of methyl 3-amino-6-bromo-pyrazine-2-carboxylate (1.5 g, 6.465 mmol), (4-methylsulfonylphenyl)boronic acid (1.552 g, 7.758 mmol), bis(triphenylphosphine)palladium(II)dichloride (226.9 mg, 0.3233 mmol), and $Na_2CO_3$ (9.700 mL of 2 M, 19.40 mmol) in DME (18.75 mL) were heated in the microwave at 110° C. for 1 hour. The resultant mixture was diluted with EtOAc and washed with water. The organic phase was dried over magnesium sulfate, filtered and concentrated in vacuo. The residue was purified on silica gel by flash column chromatography (50% EtOAc/hexanes) to afford the title compound (600 mg, 53% Yield).

1H NMR (400 MHz, DMSO) 3.25 (3H, s), 3.92 (3H, s), 7.61 (2H, br s), 8.00 (2H, m), 8.26 (2H, m), 9.03 (H, s) ppm; MS (ES$^+$) 308

Step 2: 3-amino-6-(4-(methylsulfonyl)phenyl)pyrazine-2-carboxylic Acid

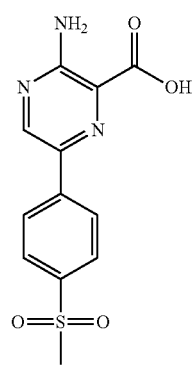 [SMILES: CS(=O)(=O)c1ccc(-c2cnc(N)c(C(=O)O)n2)cc1]

A mixture of methyl 3-amino-6-(4-(methylsulfonyl)phenyl)pyrazine-2-carboxylate (3.50 g, 11.39 mmol) and LiOH (1.364 g, 56.95 mmol) was dissolved in Methanol (14 mL) and water (14 ml) and allowed to heat at 90° C. for 2 hours. The reaction mixture was allowed to cool and neutralized with 1M HCl. The resultant precipitate was collected by filtration to afford the pure product as a yellow solid (3.32 g, 99% Yield). MS (ES$^+$) 293

Step 3: 3-amino-6-(4-(methylsulfonyl)phenyl)-N-phenylpyrazine-2-carboxamide (Compound I-82)

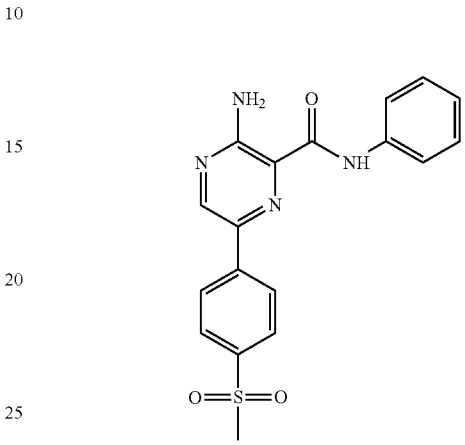

A mixture of 3-amino-6-(4-methylsulfonylphenyl)pyrazine-2-carboxylic acid (1.5 g, 5.114 mmol), diethoxyphosphorylformonitrile (926.8 mg, 849.5 µL, 5.114 mmol), aniline (476.2 mg, 465.9 µL, 5.114 mmol) and triethylamine (1.035 g, 1.426 mL, 10.23 mmol) were stirred in DME (18.75 mL) at 120° C. for 18 hours. After this time water was added and the resultant solid collected by filtration. The solid was triturated with acetone and dried to give the desired product (1.335 g, 71% Yield). 1H NMR (400.0 MHz, DMSO) d 3.28 (s, 3H), 7.18 (t, J=7.3 Hz, 1H), 7.41 (t, J=7.8 Hz, 2H), 7.82 (d, J=7.9 Hz, 2H), 7.89 (s, 2H), 8.01 (d, J=8.4 Hz, 2H), 8.51 (d, J=8.4 Hz, 2H), 9.04 (s, 1H) and 10.47 (s, 1H) ppm; MS (ES$^+$) 369

Compounds I-82 to I-108 were all prepared using Method A, Step 1 followed by Method I-C, Steps 1-3.

Compound I-82 3-amino-6-(4-(methylsulfonyl)phenyl)-N-phenylpyrazine-2-carboxamide 1H NMR (400.0 MHz, DMSO) d 3.28 (s, 3H), 7.18 (t, J=7.4 Hz, 1H), 7.43-7.39 (m, 2H), 7.83-7.81 (m, 2H), 7.89 (s, 2H), 8.01 (dd, J=1.6, 7.0 Hz, 2H), 8.51 (d, J=8.5 Hz, 2H), 9.04 (s, 1H) and 10.46 (s, 1H) ppm; MS (ES$^+$) 369.

Compound I-83 3-amino-N-(1H-indol-7-yl)-6-(pyridin-3-yl)pyrazine-2-carboxamide 1H NMR (400.0 MHz, DMSO) d 6.50 (dd, J=2.0, 2.9 Hz, 1H), 7.04 (t, J=7.7 Hz, 1H), 7.21 (d, J=7.4 Hz, 1H), 7.35 (t, J=2.8 Hz, 1H), 7.50 (d, J=7.8 Hz, 1H), 7.79 (dd, J=5.2, 8.0 Hz, 3H), 8.73 (dd, J=1.2, 5.2 Hz, 1H), 9.03 (d, J=8.2 Hz, 1H), 9.09 (s, 1H), 9.65 (d, J=1.9 Hz, 1H), 10.67 (s, 1H) and 11.00 (s, 1H) ppm; MS (ES$^+$) 331

Compound I-84 3-amino-N-(4-methoxyphenyl)-6-(pyridin-3-yl)pyrazine-2-carboxamide 1H NMR (400.0 MHz, DMSO) d 3.76 (s, 3H), 6.98 (dd, J=2.1, 6.9 Hz, 2H), 7.69 (dd, J=2.1, 6.9 Hz, 2H), 7.84 (dd, J=5.2, 8.1 Hz, 3H), 8.76 (dd, J=1.2, 5.2 Hz, 1H), 9.01-9.06 (m, 2H), 9.62 (d, J=1.9 Hz, 1H) and 10.46 (s, 1H) ppm; MS (ES$^+$) 322

Compound I-85 3-amino-N-phenyl-6-(pyridin-3-yl)pyrazine-2-carboxamide 1H NMR (400.0 MHz, DMSO) d 7.17 (t, 1H), 7.49 (t, 2H), 7.68 (t, 1H), 7.82 (d, 2H), 7.87 (br s, 2H), 8.68 (d, 1H), 8.81 (d, 1H), 9.12 (s, 1H), 9.51 (s, 1H) and 10.48 (s, 1H) ppm; MS (ES+) 292

Compound I-86 3-amino-N-(3-methoxyphenyl)-6-(pyridin-3-yl)pyrazine-2-carboxamide 1H NMR (400 MHz, DMSO) d 3.79 (3H, s), 6.74 (1H, dd), 7.30 (1H, t), 7.44 (1H, d), 7.50-7.52 (2H, m), 7.8 (2H, br s), 8.59-8.62 (2H, m), 9.00 (1H, s), 9.44 (1H, s) and 10.42 (1H, s) ppm; MS (ES+) 322

Compound I-87 3-amino-N-(3-cyanophenyl)-6-(pyridin-3-yl)pyrazine-2-carboxamide; MS (ES+) 317

Compound I-88 3-amino-N-(3-carbamoylphenyl)-6-(pyridin-3-yl)pyrazine-2-carboxamide; MS (ES+) 335

Compound I-89 3-amino-6-(pyridin-3-yl)-N-(pyrimidin-4-yl)pyrazine-2-carboxamide; MS (ES+) 294

Compound I-90 3-amino-N-(3-(dimethylamino)phenyl)-6-(pyridin-3-yl)pyrazine-2-carboxamide; MS (ES+) 335

Compound I-91 3-amino-6-(pyridin-3-yl)-N-o-tolylpyrazine-2-carboxamide MS (ES+) 306

Compound I-92 3-amino-N-(4-carbamoylphenyl)-6-(pyridin-3-yl)pyrazine-2-carboxamide; MS (ES+) 335

Compound I-93 3-amino-N-(4-ethanamidophenyl)-6-(pyridin-3-yl)pyrazine-2-carboxamide; MS (ES+) 349

Compound I-94 3-amino-N-(4-fluorophenyl)-6-(pyridin-3-yl)pyrazine-2-carboxamide; MS (ES+) 310

Compound I-95 3-amino-N-(3-ethanamidophenyl)-6-(pyridin-3-yl)pyrazine-2-carboxamide; MS (ES+) 349

Compound I-96 3-amino-N-(2-fluorophenyl)-6-(pyridin-3-yl)pyrazine-2-carboxamide; MS (ES+) 310

Compound I-97 3-amino-N-(pyridin-2-yl)-6-(pyridin-3-yl)pyrazine-2-carboxamide; MS (ES+) 293

Compound I-98 3-amino-6-(pyridin-3-yl)-N-(pyridin-4-yl)pyrazine-2-carboxamide; MS (ES+) 293

Compound I-99 3-amino-N-(2,2-difluorobenzo[d][1,3]dioxol-4-yl)-6-(pyridin-3-yl)pyrazine-2-carboxamide; MS (ES+) 372

Compound I-100 3-amino-N-(5-ethanamido-2-methoxyphenyl)-6-(pyridin-3-yl)pyrazine-2-carboxamide; MS (ES+) 379

Compound I-101 3-amino-6-(pyridin-3-yl)-N-(3-sulfamoylphenyl)pyrazine-2-carboxamide; MS (ES+) 371

Compound I-102 3-amino-6-(pyridin-3-yl)-N-(2-(trifluoromethoxy)phenyl)pyrazine-2-carboxamide; MS (ES+) 376

Compound I-103 3-amino-N-(3-fluorophenyl)-6-(pyridin-3-yl)pyrazine-2-carboxamide; MS (ES+) 310

Compound I-104 3-amino-N-(1H-indol-5-yl)-6-(pyridin-3-yl)pyrazine-2-carboxamide; MS (ES+) 331

Compound I-105 3-amino-N-(1H-indol-6-yl)-6-(pyridin-3-yl)pyrazine-2-carboxamide; MS (ES+) 331

Compound I-106 3-amino-N-(2-methoxyphenyl)-6-(pyridin-3-yl)pyrazine-2-carboxamide; MS (ES+) 322

Compound I-107 3-amino-N-(2,5-dimethoxyphenyl)-6-(pyridin-3-yl)pyrazine-2-carboxamide; MS (ES+) 352

Compound I-108 3-amino-N-(2-methoxy-5-methylphenyl)-6-(pyridin-3-yl)pyrazine-2-carboxamide; MS (ES+) 336

Example 4

2-(3-amino-6-(4-(methylsulfonyl)phenyl)pyrazin-2-yl)-1H-benzo[d]imidazol-7-ol (Compound I-109)

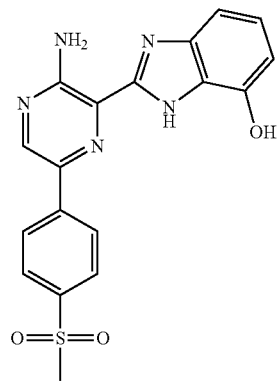 [SMILES: CS(=O)(=O)c1ccc(-c2cnc(N)c(-c3nc4cccc(O)c4[nH]3)n2)cc1]

SCHEME D

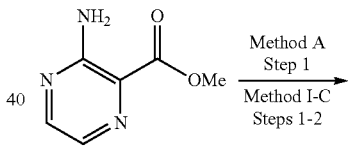

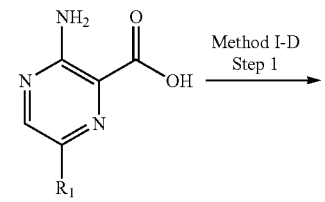

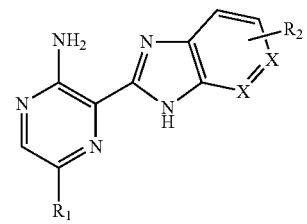

Compound I-109 was prepared using Method A, Step 1 followed by Method I-C, Steps 1-2 followed by Method I-D, Step 1.

Method I-D

Step 1: 2-(3-amino-6-(4-(methylsulfonyl)phenyl) pyrazin-2-yl)-1H-benzo[d]imidazol-7-ol

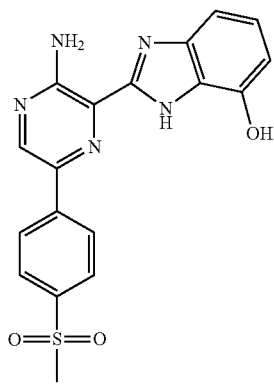 [SMILES: CS(=O)(=O)c1ccc(-c2cnc(N)c(-c3nc4cccc(O)c4[nH]3)n2)cc1]

A mixture of 3-amino-6-(4-methylsulfonylphenyl)pyrazine-2-carboxylic acid (120 mg, 0.4091 mmol), diethoxyphosphorylformonitrile (73.40 mg, 0.4500 mmol), triethylamine (124.2 mg, 171.1 μL, 1.227 mmol) and 2,3-diaminophenol (50.79 mg, 0.4091 mmol) in DME (5 mL) was heated in the microwave at 170° C. for 1 hour. The mixture was diluted with EtOAc, washed with water and brine and concentrated in vacuo The residue was then dissolved in DCM and triturated with ether to give the desired product as a yellow solid (115 mg, 74% Yield). 1H NMR (400 MHz, DMSO) 3.6 (3H, s), 6.65 (1H, d), 7.1-7.18 (2H, m), 8.0-8.1 (4H, m), 8.6 (2H, d), 8.9 (1H, s), 9.05 (1H, br s), 9.9 (1H, s), 12.9 (1H, b rs) ppm; MS (ES+) 382

Compounds I-109 to I-121 were prepared using Method A, Step 1 followed by Method I-C, Steps 1-2 followed by Method I-D, Step 1.

Compound I-110 3-(1H-benzo[d]imidazol-2-yl)-5-phenylpyrazin-2-amine 1H NMR (400 MHz, CDCl3) 1.5 (2H, br s), 7.35-7.7 (3H, m), 7.5-7.67 (3H, m), 7.87 (1H, d), 8.02 (1H, d), 8.62 (1H, s), 10.45 (1H, s) ppm; MS (ES+) 288

Compound I-111 2-(3-amino-6-(4-(methylsulfonyl)phenyl)pyrazin-2-yl)-1H-benzo[d]imidazole-6-carbonitrile 1H NMR (400 MHz, DMSO) 3.3 (3H, s), 7.7-7.85 (2H, m), 8.05 (2H, d), 8.43 (1H, s), 8.55 (2H, s), 9.05 (1H, s), 13.55 (1H, br s) ppm; MS (ES+) 389

Compound I-112 3-(3H-imidazo[4,5-b]pyridin-2-yl)-5-(4-(methylsulfonyl)phenyl)pyrazin-2-amine 1H NMR (400 MHz, CDCl3) 3.05-3.1 (3H, m), 7.4-7.5 (2H, m), 7.95-8.05 (2H, m), 8.3-8.42 (3H, m), 8.8 (1H, m) ppm; MS (ES+) 367

Compound I-113 2-(3-amino-6-phenylpyrazin-2-yl)-1H-benzo[d]imidazol-7-ol 1H NMR (400 MHz, DMSO) 6.63 (1H, d), 7.05-7.15 (2H, m), 7.4-7.44 (1H, m), 7.5-7.53 (3H, m), 8.3 (1H, d), 8.75 (2H, s), 9.95 (1H, s), 12.9 (1H, s) ppm; MS (ES+) 304

Compound I-114 3-(6-chloro-1H-benzo[d]imidazol-2-yl)-5-(4-(methylsulfonyl)phenyl)pyrazin-2-amine 1H NMR (400 MHz, DMSO) 3.35 (3H, s), 7.25-7.35 (1H, m), 7.58-7.62 (1H, m), 7.75-7.85 (1H, m), 7.95-8.0 (2H, m), 8.45-8.52 (2H, m), 8.65-8.8 (1H, br s), 8.92-8.94 (1H, m), 13.2-13.26 (1H, m) ppm; MS (ES+) 400

Compound I-115 3-(6-methoxy-1H-benzo[d]imidazol-2-yl)-5-(4-(methylsulfonyl)phenyl)pyrazin-2-amine 1H NMR (400 MHz, DMSO) 3.3 (3H, s), 3.85 (3H, s), 6.9-6.93 (1H, m), 7.1-7.3 (1H, m), 7.6-7.7 (1H, m), 8.05 (2H, d), 8.6 (2H, d), 8.95 (1H, s), 13.1 (1H, br s) ppm; MS (ES+) 396

Compound I-116 methyl 2-(3-amino-6-(4-(methylsulfonyl)phenyl)pyrazin-2-yl)-1H-benzo[d]imidazole-6-carboxylate 1H NMR (400 MHz, DMSO) 3.28-3.32 (3H, m), 3.9-3.95 (3H, m), 7.7-7.75 (1H, m), 7.9-7.92 (1H, m), 8.0-8.1 (3H, m), 8.3 (0.5H, s), 8.42 (0.5H, s), 8.52-8.6 (2H, m), 8.7 (1H, br s), 9.0-9.03 (1H, m), 13.4-13.48 (1H, m) ppm; MS (ES+) 424

Compound I-117 3-(6-methyl-1H-benzo[d]imidazol-2-yl)-5-(4-(methylsulfonyl)phenyl)pyrazin-2-amine; 1H NMR (400 MHz, DMSO) 2.5 (3H, s), 3.35 (3H, s), 7.05-7.1 (1H, m), 7.4-7.7 (1H, m), 8.03 (2H, d), 8.57 (1H, d), 8.95 (1H, s), 12.95-13.05 (1H, m) ppm; MS (ES+) 380

Compound I-118 5-(4-(methylsulfonyl)phenyl)-3-(6-(trifluoromethyl)-1H-benzo[d]imidazol-2-yl)pyrazin-2-amine; 1H NMR (400 MHz, DMSO) 3.3 (3H, s), 3.85 (3H, s), 6.9-6.93 (1H, m), 7.1-7.3 (1H, m), 7.6-7.7 (1H, m), 8.05 (2H, d), 8.6 (2H, d), 8.95 (1H, s), 13.1 (1H, br s) ppm; MS (ES+) 434

Compound I-119 3-(7-methyl-1H-benzo[d]imidazol-2-yl)-5-(4-(methylsulfonyl)phenyl)pyrazin-2-amine; 1H NMR (400 MHz, DMSO) 2.6-2.7 (3H, m), 3.3 (3H, s), 7.1-7.25 (2H, m), 7.47 (1H, d), 8.0-8.1 (3H, m), 8.6 (1H, d), 8.95 (1H, s), 9.05 (1H, br s), 12.7 (0.2H, br s), 13.1 (1H, br s) ppm; MS (ES+) 380

Compound I-120 3-(3H-imidazo[4,5-c]pyridin-2-yl)-5-(4-(methylsulfonyl)phenyl)pyrazin-2-amine; 1H NMR (400 MHz, DMSO) 3.13 (3H, s), 7.4-7.45 (1H, m), 7.5-7.6 (1H, m), 7.8-7.85 (2H, m), 8.2-8.25 (1H, m), 8.35-8.4 (2H, m), 8.7-8.75 (1H, m), 8.9 (1H, s), 13.25-13.35 (1H, m) ppm; MS (ES+) 367

Compound I-121 3-(1H-benzo[d]imidazol-2-yl)-5-(pyridin-3-yl)pyrazin-2-amine 1H NMR (400 MHz, CDCl3) 7.25-7.35 (3H, m), 7.35-7.4 (1H, m), 7.52 (1H, d), 7.78 (1H, d), 8.17 (1H, d), 8.55 (1H, s), 8.59-8.62 (1H, m), 9.17-9.19 (1H, m) ppm; MS (ES+) 289

Example 5

3-(1H-benzo[d]imidazol-2-yl)-5-(3-(methylsulfonyl)phenyl)pyrazin-2-amine (Compound I-122)

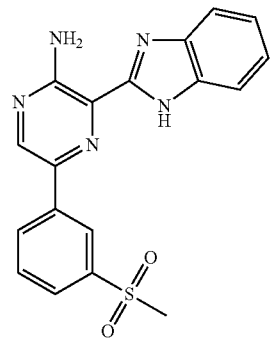 [SMILES: CS(=O)(=O)c1cccc(-c2cnc(N)c(-c3nc4ccccc4[nH]3)n2)c1]

SCHEME E

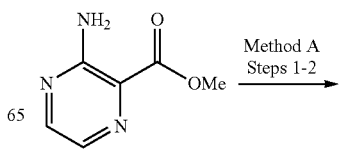

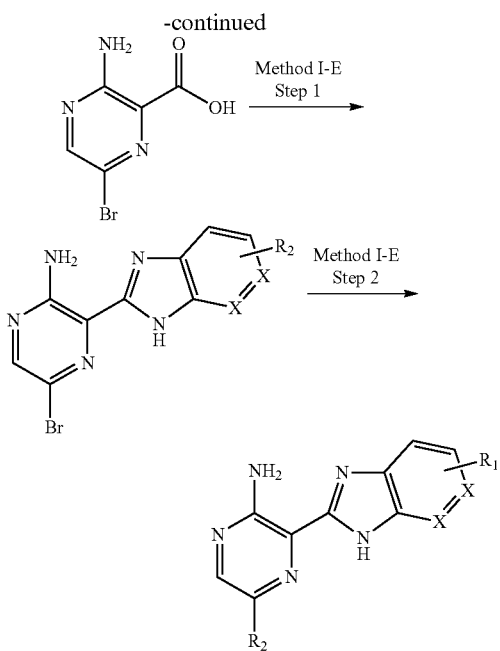

Compound 122 was prepared using Method A, Steps 1-2 followed by Method I-E, Steps 1-2.

Method I-E

Step 1: 3-(1H-benzo[d]imidazol-2-yl)-5-bromopyrazin-2-amine

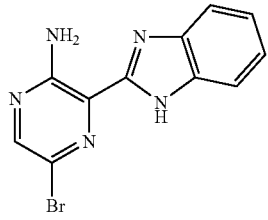 [SMILES: Nc1ncc(Br)nc1-c1nc2ccccc2[nH]1]

A mixture of 3-amino-6-bromo-pyrazine-2-carboxylic acid (10 g, 45.87 mmol), benzene-1,2-diamine (5.45 g, 50.46 mmol), diethoxyphosphorylformonitrile (8.23 g, 50.46 mmol) and triethylamine (12.79 mL, 91.74 mmol) in DME (30 mL) was heated in the microwave at 170° C. for 40 minutes. The mixture was allowed to cool and water was added. The resultant dark-coloured precipitate was dissolved in EtOAc and stirred with charcoal for 30 minutes. After filtering through celite, the filtrate was concentrated in vacuo to give the product as a yellow solid (8.04 g, 60% Yield). 1H NMR (400 MHz, DMSO) 7.22-7.32 (2H, m), 7.55 (1H, d), 7.75 (1H, d), 7.8 (1 h, br s), 8.8 (1H, br s), 13.1 (1H, s); MS (ES$^+$) 291

Step 2: 3-(1H-benzo[d]imidazol-2-yl)-5-(3-(methylsulfonyl)phenyl)pyrazin-2-amine A mixture of 3-(1H-benzimidazol-2-yl)-5-bromopyrazin-2-amine (50 mg, 0.1723 mmol), 3-methylsulfonylphenyl)boronic acid (34.46 mg, 0.1723 mmol), dichloropalladium; triphenylphosphane (6.047 mg, 0.008615 mmol) and disodium carbonate (258.5 μL of 2 M, 0.5169 mmol) in DME (625.0 μL) was heated in the microwave at 110° C. for 1 hour and then at 150° C. for 3 hours. The mixture was diluted with EtOAc and washed with water. The organic layer was separated, dried (MgSO$_4$) and concentrated in vacuo. The residue was purified by reverse phase preparative HPLC [Waters Sunfire C18, 10 uM, 100 A column, gradient 10%-95% B (solvent A: 0.05% TFA in water, solvent B: CH$_3$CN) over 16 minutes at 25 mL/min]. The fractions were freeze-dried to give the title compound as a solid (37.7 mg, 60% Yield). 1H NMR (400 MHz, CDCl$_3$) 3.2 (3H, s), 7.3-7.45 (2H, m), 7.65 (1H, d), 7.75 (1H, t), 7.85 (1H, d), 8.0 (1H, d), 8.23 (1H, d), 8.65 (2H, s), 10.55 (1H, s); MS (ES$^+$) 366

Compounds I-122 to I-137 were prepared was prepared using Method A, Steps 1-2 followed by Method I-E, Steps 1-2.

Compound I-123 3-(1H-benzo[d]imidazol-2-yl)-5-(4-(methylsulfonyl)phenyl)pyrazin-2-amine 1H NMR (400 MHz, DMSO) 3.4 (3H, s), 5.75 (2H, s), 7.2-7.38 (2H, m), 7.65 (1H, d), 7.8 (1H, d), 8.05 (1H, d), 8.55 (1H, d), 8.95 (2H, s), 13.3 (1H, s) ppm; MS (ES$^+$) 366

Compound I-124 4-(5-amino-6-(1H-benzo[d]imidazol-2-yl)pyrazin-2-yl)-N,N-dimethylbenzamide 1H NMR (400 MHz, DMSO) d 2.99 (s, 3H), 3.02 (s, 3H), 7.31 (dd, J=3.0, 6.0 Hz, 2H), 7.54 (d, J=8.4 Hz, 2H), 7.72 (s, 2H), 8.35 (d, J=8.4 Hz, 2H) and 8.86 (s, 1H) ppm; MS (ES$^+$) 359

Compound I-125 (3-(5-amino-6-(1H-benzo[d]imidazol-2-yl)pyrazin-2-yl)phenyl) (morpholino)methanone; MS (ES+) 401

Compound I-126 3-(5-amino-6-(1H-benzo[d]imidazol-2-yl)pyrazin-2-yl)phenol MS (ES$^+$) 304

Compound I-127 (2-(5-amino-6-(1H-benzo[d]imidazol-2-yl)pyrazin-2-yl)phenyl)methanol 1H NMR (400.0 MHz, DMSO) d 4.72 (s, 2H), 7.27 (q, J=3.0 Hz, 2H), 7.38-7.47 (m, 2H), 7.55-7.67 (m, 5H) and 8.37 (s, 1H) ppm; MS (ES$^+$) 318

Compound I-128 4-(5-amino-6-(1H-benzo[d]imidazol-2-yl)pyrazin-2-yl)-N-(3-hydroxypropyl)benzamide; MS (ES+) 389

Compound I-129 4-(5-amino-6-(1H-benzo[d]imidazol-2-yl)pyrazin-2-yl)benzonitrile; MS (ES+) 313

Compound I-130 N-(4-(5-amino-6-(1H-benzo[d]imidazol-2-yl)pyrazin-2-yl)benzyl)ethanamide; MS (ES+) 359

Compound I-131 (5-(5-amino-6-(1H-benzo[d]imidazol-2-yl)pyrazin-2-yl)-2-fluorophenyl) (morpholino)methanone; MS (ES$^+$) 419

Compound I-132 4-(5-amino-6-(1H-benzo[d]imidazol-2-yl)pyrazin-2-yl)-N-(2-hydroxyethyl)benzamide; MS (ES+) 375

Compound I-133 4-(5-amino-6-(1H-benzo[d]imidazol-2-yl)pyrazin-2-yl)-N-(2-(pyrrolidin-1-yl)ethyl)benzamide; MS (ES+) 428

Compound I-134 3-(1H-benzo[d]imidazol-2-yl)-5-(4-(pyrrolidin-1-ylsulfonyl)phenyl)pyrazin-2-amine; MS (ES+) 421

Compound I-135 3-(1H-benzo[d]imidazol-2-yl)-5-(6-morpholinopyridin-3-yl)pyrazin-2-amine; 1H NMR (400.0 MHz, DMSO) d 3.57-3.59 (m, 4H), 3.75-3.77 (m, 4H), 7.07 (d, J=9.1 Hz, 1H), 7.28-7.32 (m, 2H), 7.71 (s, 2H), 8.53 (d, J=8.2 Hz, 1H), 8.77 (s, 1H) and 9.03 (d, J=2.0 Hz, 1H) ppm; MS (ES$^+$) 374

Compound I-136 3-(1H-benzo[d]imidazol-2-yl)-5-(2-(piperazin-1-yl)pyridin-4-yl)pyrazin-2-amine; MS (ES+) 373

361

Compound I-137 5-(5-amino-6-(1H-benzo[d]imidazol-2-yl)pyrazin-2-yl)pyridin-2-ol; MS (ES+) 305

Example 6

3-(5-phenyl-4H-1,2,4-triazol-3-yl)-5-(pyridin-3-yl)pyrazin-2-amine (Compound I-138)

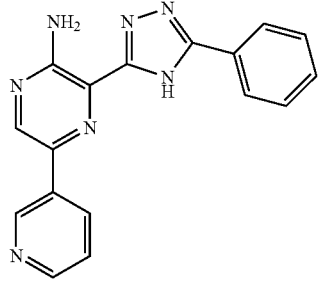 [SMILES: Nc1ncc(-c2cccnc2)nc1-c1nnc(-c2ccccc2)[nH]1]

SCHEME F

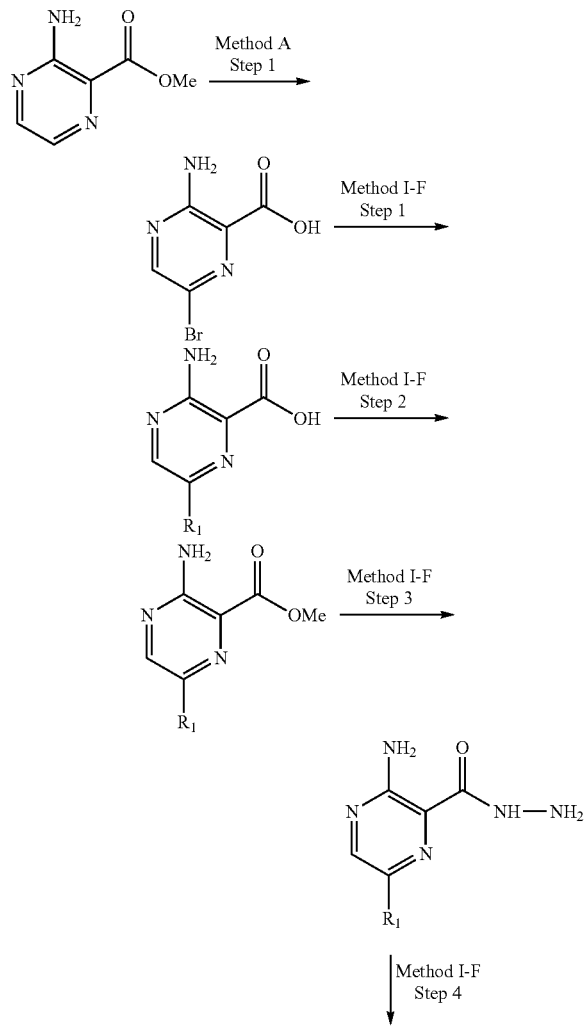

362

-continued

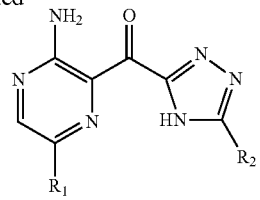

Compound 138 was prepared using Method A, Step 1 followed by Method I-F, Steps 1-4.

Method I-F

Step 1:
3-amino-6-(pyridin-3-yl)pyrazine-2-carboxylic Acid

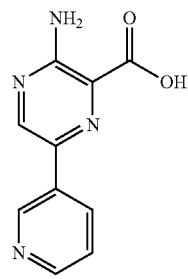 [SMILES: Nc1ncc(-c2cccnc2)nc1C(=O)O]

A mixture of methyl 3-amino-6-bromo-pyrazine-2-carboxylate (8 g, 34.48 mmol), diethyl-(3-pyridyl)borane (6.084 g, 41.38 mmol), dichloropalladium; triphenylphosphane (1.210 g, 1.724 mmol) and disodium carbonate (51.70 mL of 2 M, 103.4 mmol) in DME (100 mL) were heated overnight at 80° C. The reaction mixture was cooled and EtOAc was added. The resultant precipitate was collected, treated with water and the resultant suspension heated and filtered hot. The solution was then allowed to cool and acidified with AcOH to approx pH 5. The precipitate was collected, washed with MeOH and dried to yield the product as a yellow powder (6.22 g, 83% Yield). 1H NMR (400.0 MHz, DMSO) d 7.49 (dd, J=4.8, 7.4 Hz, 1H), 7.60 (s, 2H), 8.44 (d, J=7.6 Hz, 1H), 8.57 (d, J=3.7 Hz, 1H), 8.97 (s, 1H) and 9.27 (s, 1H) ppm; MS (ES+) 217

Step 2: Methyl
3-amino-6-(pyridin-3-yl)pyrazine-2-carboxylate

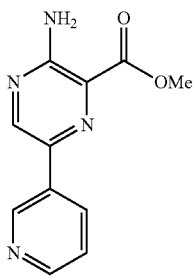 [SMILES: COC(=O)c1nc(-c2cccnc2)cnc1N]

To 3-amino-6-(3-pyridyl)pyrazine-2-carboxylic acid (2 g, 9.251 mmol) in MeOH (50 mL) was added conc. H$_2$SO$_4$ (907.3 mg, 493.1 μL, 9.251 mmol) and the mixture heated to reflux for 2 hours. The solvent was removed in vacuo and the mixture neutralised with aq. Na$_2$CO$_3$. The resulting brown solid was collected by filtration and dried (2.08 g, 97% Yield). MS (ES$^+$) 231

Step 3:
3-amino-6-(pyridin-3-yl)pyrazine-2-carbohydrazide

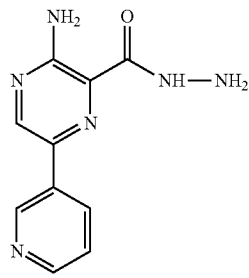 [SMILES: NNC(=O)c1nc(-c2cccnc2)cnc1N]

A mixture of methyl 3-amino-6-(3-pyridyl)pyrazine-2-carboxylate (2 g, 8.687 mmol) was heated in Hydrazine (1.392 g, 1.363 mL, 43.43 mmol) with a minimal amount of MeOH (5 mL) added at 80° C. for 2 hours. Water was added and the product collected by filtration, washed with methanol and dried to furnish the product as a brown solid (1.17 g, 58% Yield). 1H NMR (400.0 MHz, DMSO) d 4.52 (br s, 2H), 7.43 (m, 1H), 7.71 (s, 2H), 8.54 (2H, m), 8.90 (1H, s), 9.39 (1H, s), 10.16 (1H, s) ppm; MS (ES$^+$) 231

Step 4: 3-(5-phenyl-4H-1,2,4-triazol-3-yl)-5-(pyridin-3-yl)pyrazin-2-amine (Compound 138)

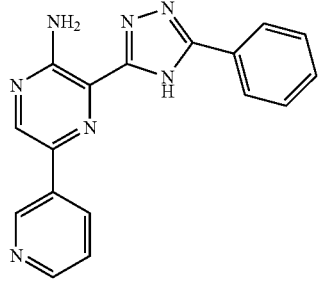 [SMILES: Nc1ncc(-c2cccnc2)nc1-c1nnc(-c2ccccc2)[nH]1]

A mixture of 3-amino-6-(3-pyridyl)pyrazine-2-carbohydrazide (40 mg, 0.173 mmol), benzamidine hydrochloride (27.2 mg, 0.173 mmol) and sodium ethanolate (11.82 mg, 0.173 mmol) were added to a 5 mL microwave vial in DMF (1 mL). The reaction mixture was heated in the microwave at 200° C. for 20 min. The mixture was concentrated in vacuo and the residue purified by reverse phase preparative HPLC [Waters Sunfire C18, 10 uM, 100 A column, gradient 10%-95% B (solvent A: 0.05% TFA in water, solvent B: CH$_3$CN over 16 minutes at 25 mL/min]. The fractions were freeze-dried to give the title compound as a solid (12.5 mg, 20% Yield). 1H NMR (500 MHz, DMSO) d 7.5 (m, 3H), 7.66 (m, 1H), 7.94 (br s, 2H), 8.16 (m, 2H), 8.66 (s, 1H), 8.79 (br s, 1H), 8.96 (s, 1H), 9.52 (s, 1H) and 14.94 (s, 1H) ppm; MS (ES$^+$) 316

Compounds I-138 to I-143 were prepared using Method A, Step 1 followed by Method I-F, Steps 1-4

Compound I-139: 3-(5-(4-(aminomethyl)phenyl)-4H-1,2,4-triazol-3-yl)-5-(pyridin-3-yl)pyrazin-2-amine; MS (ES+) 345

Compound I-140 3-(5-(3-aminophenyl)-4H-1,2,4-triazol-3-yl)-5-(pyridin-3-yl)pyrazin-2-amine; 1H NMR (400.0 MHz, DMSO) d 6.98-7.03 (m, 1H), 7.39 (t, J=7.8 Hz, 1H), 7.74 (s, 2H), 7.82 (dd, J=5.2, 8.1 Hz, 1H), 8.06 (s, 2H), 8.74 (dd, J=1.3, 5.2 Hz, 1H), 8.96 (d, J=7.9 Hz, 1H), 9.02 (s, 1H), 9.60 (s, 1H) and 15.03 (br s, 1H) ppm; MS (ES$^+$) 331

Compound I-141 5-(pyridin-3-yl)-3-(5-m-tolyl-4H-1,2,4-triazol-3-yl)pyrazin-2-amine; MS (ES$^+$) 330

Compound I-142 5-(pyridin-3-yl)-3-(5-(thiophen-2-yl)-4H-1,2,4-triazol-3-yl)pyrazin-2-amine; 1H NMR (400.0 MHz, DMSO) d 7.22 (dd, J=3.8, 4.8 Hz, 1H), 7.68-7.73 (m, 2H), 7.81 (d, J=3.0 Hz, 1H), 7.95 (s, 2H), 8.69 (dd, J=1.2, 4.9 Hz, 1H), 8.84 (d, J=6.1 Hz, 1H), 8.99 (s, 1H), 9.55 (s, 1H) and 14.96 (s, 1H) ppm; MS (ES$^+$) 322

Compound I-143 3-(5-(3-(aminomethyl)phenyl)-4H-1,2,4-triazol-3-yl)-5-(pyridin-3-yl)pyrazin-2-amine; MS (ES+) 345

Example 7

5-(4-(methylsulfonyl)phenyl)-3-(5-phenyl-1,2,4-oxadiazol-3-yl)pyrazin-2-amine (Compound I-144) [there are Some Compounds from the PRV that are Repeated with New Number in the Table! Like this One!]

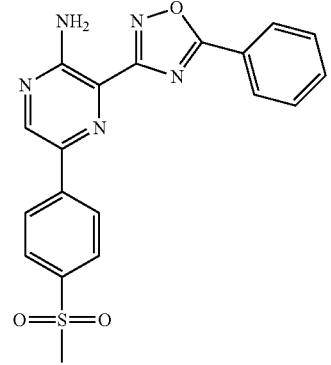 [SMILES: CS(=O)(=O)c1ccc(-c2cnc(N)c(-c3noc(-c4ccccc4)n3)n2)cc1]

SCHEME G

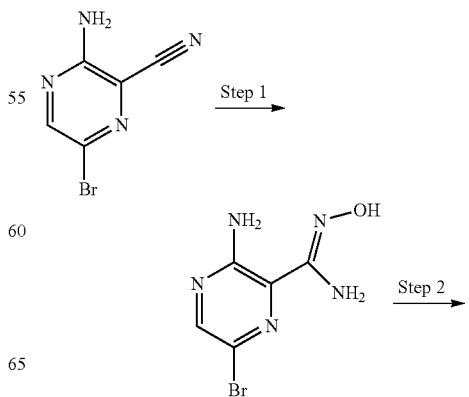

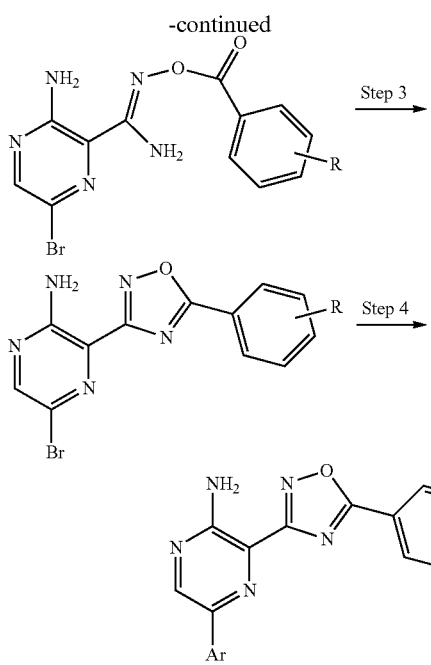

Method I-G

Step 1: 3-amino-6-bromo-N'-hydroxypyrazine-2-carboximidamide

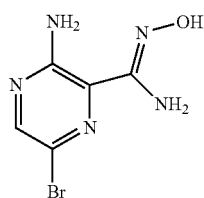 [SMILES: N/C(=N\O)c1nc(Br)cnc1N]

A solution of 3-amino-6-bromo-pyrazine-2-carbonitrile (1 g, 5.025 mmol) in MeOH (20 mL) was cooled to 0° C. and treated with hydroxylamine hydrochloride (349.2 mg, 5.025 mmol) and triethylamine (508.5 mg, 700.4 µL, 5.025 mmol) and the reaction allowed to warm to ambient temperature. After a period of 2 hours a precipitate was observed which was filtered off. The resultant filtrate was evaporated to dryness and triturated with MeOH to furnish further product as a beige solid (771 mg, 78% Yield).

1H NMR (400.0 MHz, DMSO) d 5.88 (s, 2H), 7.64 (br s, 2H), 8.14 (s, 1H) and 10.38 (s, 1H) ppm; MS (ES⁺) 233

Step 2: 3-amino-N'-(benzoyloxy)-6-bromopyrazine-2-carboximidamide

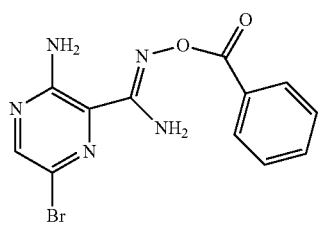 [SMILES: N/C(=N\OC(=O)c1ccccc1)c1nc(Br)cnc1N]

3-amino-6-bromo-N'-hydroxypyrazine-2-carboximidamide (770 mg, 3.318 mmol) was suspended in DCM (10 mL) and triethylamine (369.3 mg, 508.7 µL, 3.650 mmol) followed by benzoyl chloride (513.1 mg, 423.7 µL, 3.650 mmol) were added. After 1 hour, the solvent was removed in vacuo and the residue triturated with MeOH. The resultant filtrate was filtered off to furnish the product as an off-white solid (779 mg, 70% Yield).

1H NMR (400.0 MHz, DMSO) d 7.18 (br s, 2H), 7.55-7.59 (m, 2H), 7.69-7.73 (m, 1H), 7.89 (br s, 2H), 8.28-8.30 (m, 2H) and 8.32 (s, 1H) ppm; MS (ES⁺) 337

Step 3: 5-bromo-3-(5-phenyl-1,2,4-oxadiazol-3-yl)pyrazin-2-amine

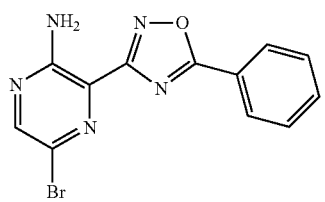 [SMILES: Nc1ncc(Br)nc1-c1noc(-c2ccccc2)n1]

A mixture of 3-amino-N'-(benzoyloxy)-6-bromopyrazine-2-carboximidamide (575 mg, 1.711 mmol) and polyphosphonic acid (2.300 mL) was heated at 70° C. for 3.5 hours. The resultant solution was diluted with water (20 mL), quenched with NaHCO₃ and the resultant product isolated by filtration (475 mg, 87% Yield) as a fawn solid.

1H NMR (400.0 MHz, DMSO) d 7.48 (br s, 2H), 7.67-7.71 (m, 2H), 7.76-7.78 (m, 1H), 8.26-8.28 (m, 2H) and 8.43 (s, 1H) ppm; MS (ES⁺) 319

Step 4: 5-(4-(methylsulfonyl)phenyl)-3-(5-phenyl-1,2,4-oxadiazol-3-yl)pyrazin-2-amine (Compound 144)

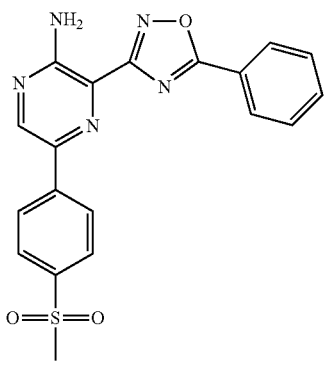 [SMILES: CS(=O)(=O)c1ccc(-c2cnc(N)c(-c3noc(-c4ccccc4)n3)n2)cc1]

A mixture of 5-bromo-3-(5-phenyl-1,2,4-oxadiazol-3-yl)pyrazin-2-amine (100 mg, 0.3143 mmol), (4-methylsulfonylphenyl)boronic acid (94.29 mg, 0.4714 mmol) and PdCl₂(PPh₃)₂ (11.03 mg, 0.01572 mmol) in DMF (2 mL) was treated with Na₂CO₃ (471.4 µL of 2 M, 0.9429 mmol) and the reaction placed under an atmosphere of nitrogen and heated at 110° C. in a sealed tube for 16 hours. The resultant precipitate was filtered, washed with water and dried under vacuum (83 mg, 67% Yield).

1H NMR (400.0 MHz, DMSO) d 3.27 (s, 3H), 7.58 (br s, 2H), 7.69-7.73 (m, 2H), 7.77-7.81 (m, 1H), 8.05 (d, J=8.5 Hz, 2H), 8.32 (dd, J=8.5, 18.0 Hz, 4H) and 9.04 (s, 1H) ppm; MS (ES⁺) 394

367

Compound IIA-1 was also prepared using Method I-G.

Compound IIA-1: 3-(5-phenyl-1,2,4-oxadiazol-3-yl)-5-(pyridin-3-yl)pyrazin-2-amine

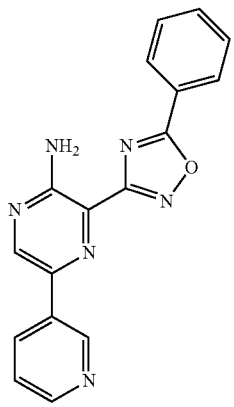 [SMILES: Nc1ncc(-c2cccnc2)nc1-c1noc(-c2ccccc2)n1]

1H NMR (400.0 MHz, DMSO) d 7.32 (br s, 2H), 7.38 (dd, J=4.3, 8.0 Hz, 1H), 7.52-7.56 (m, 2H), 7.59-7.64 (m, 1H), 8.12-8.14 (m, 2H), 8.24-8.27 (m, 1H), 8.44 (dd, J=1.6, 4.8 Hz, 1H), 8.82 (s, 1H) and 9.11 (d, J=1.8 Hz, 1H) ppm; MS (ES+) 317

Example 8

3-(benzo[d]thiazol-2-yl)-5-(4-(methylsulfonyl)phenyl)pyrazin-2-amine (Compound I-146)

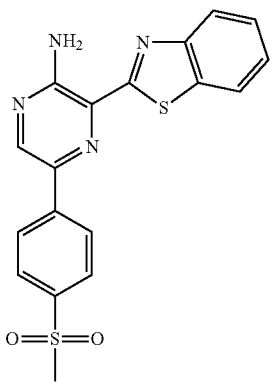 [SMILES: CS(=O)(=O)c1ccc(-c2cnc(N)c(-c3nc4ccccc4s3)n2)cc1]

SCHEME H

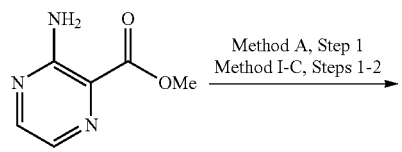
Method A, Step 1
Method I-C, Steps 1-2

368

-continued

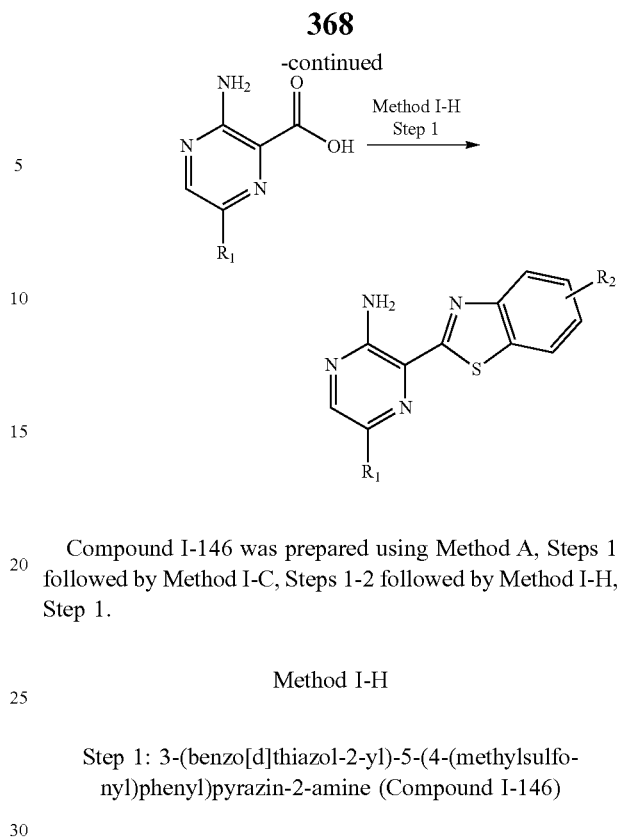

Compound I-146 was prepared using Method A, Steps 1 followed by Method I-C, Steps 1-2 followed by Method I-H, Step 1.

Method I-H

Step 1: 3-(benzo[d]thiazol-2-yl)-5-(4-(methylsulfonyl)phenyl)pyrazin-2-amine (Compound I-146)

3-amino-6-(4-methylsulfonylphenyl)pyrazine-2-carboxylic acid (350 mg, 1.193 mmol), was heated in thionyl chloride (4.258 g, 2.611 mL, 35.79 mmol) at 70° C. for 1 hour. The mixture was concentrated to dryness and washed several times with ether. The resultant acid chloride (150 mg, 0.458 mmol) was dissolved in acetonitrile, treated with 2-aminobenzothiol (172 mg, 1.374 mmol) and heated at 70° C. for 2 hours. The mixture was diluted with EtOAc and washed with sat. aq. Na$_2$CO$_3$, water and brine. The organic phase was dried over magnesium sulfate, filtered and concentrated in vacuo. The residue was purified on silica gel by flash column chromatography (30-70% EtOAc/hexanes) to afford the title compound as a yellow solid after trituration with DCM/diethyl ether (102 mg, 52% Yield); 1H NMR (400 MHz, CDCl$_3$) 3.3 (3H, s), 7.65-7.8 (2H, m), 8.2 (1H, d), 8.25-8.3 (3H, m), 8.45 (2H, d), 8.8 (1H, br s), 8.85 (1H, s) ppm; MS (ES+) 383

Example 9 tert-butyl 4-(4-(5-amino-6-(6-methyl-1H-benzo[d]imidazol-2-yl)pyrazin-2-yl)phenylcarbonyl)-1,4-diazepane-1-carboxylate (Compound I-147)

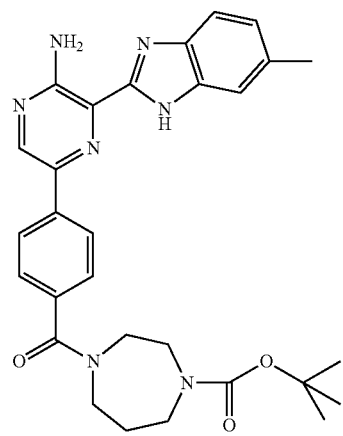 [SMILES: Cc1ccc2nc(-c3nc(-c4ccc(C(=O)N5CCCN(C(=O)OC(C)(C)C)CC5)cc4)cnc3N)[nH]c2c1]

Compound I-147 was prepared using Method A, Steps 1-2 followed by Method 1-E, Step 1 followed by Method I, Steps 1-2.

Method I

Step 1: 4-(5-amino-6-(6-methyl-1H-benzo[d]imidazol-2-yl)pyrazin-2-yl)benzoic Acid

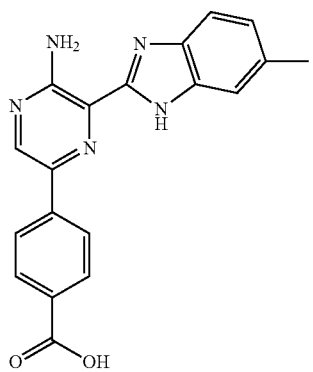 [SMILES: Cc1ccc2nc(-c3nc(-c4ccc(C(=O)O)cc4)cnc3N)[nH]c2c1]

5-bromo-3-(6-methyl-1H-benzimidazol-2-yl)pyrazin-2-amine (1.855 g, 6.099 mmol), 4-boronobenzoic acid (1.012

SCHEME I

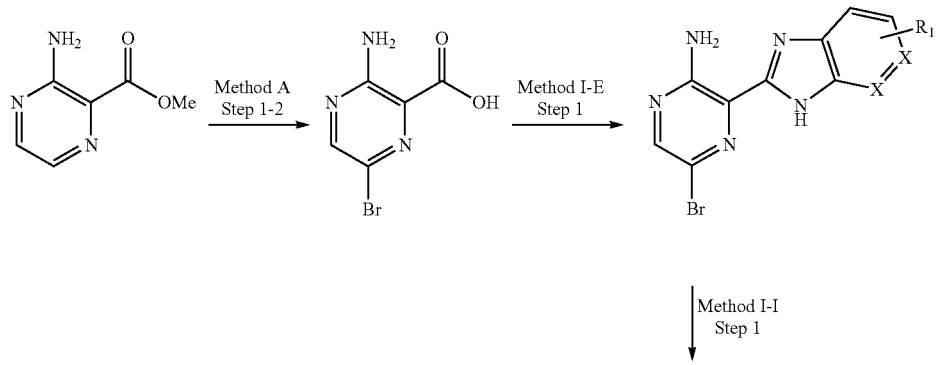

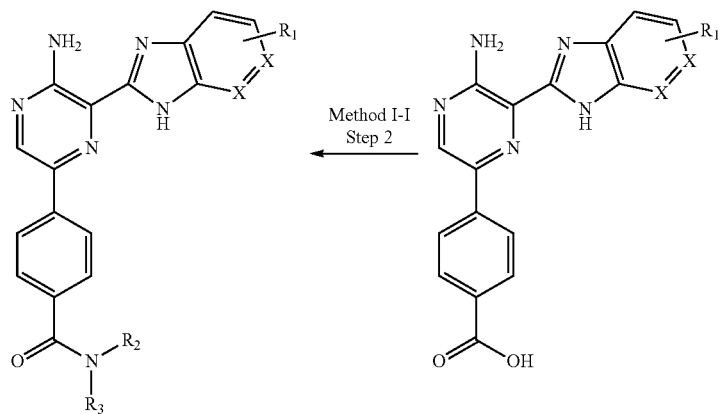

g, 6.099 mmol) and Na₂CO₃ (1.293 g, 12.20 mmol) suspended in MeCN (30 mL)/water (30 mL). The mixture was degassed (5×N₂ vacuum cycles) and Pd(PPh₃)₄ (704.8 mg, 0.6099 mmol) added. The mixture was degassed again and heated to 90° C. No sign of product was observed therefore 25 mL aliquots were heated in the microwave for 1 hour at 140° C. which led to product formation. The mixture was allowed to cool and washed with DCM (×2). The aqueous layer was acidified to pH4 (1M HCl) and the resulting precipitate collected, washed with water and dried overnight under vacuum to give the product as a bright yellow solid, (1.30 g, 62% Yield); MS (ES⁺) 346

Step 2: tert-butyl 4-(4-(5-amino-6-(6-methyl-1H-benzo[d]imidazol-2-yl)pyrazin-2-yl)phenylcarbonyl)-1,4-diazepane-1-carboxylate

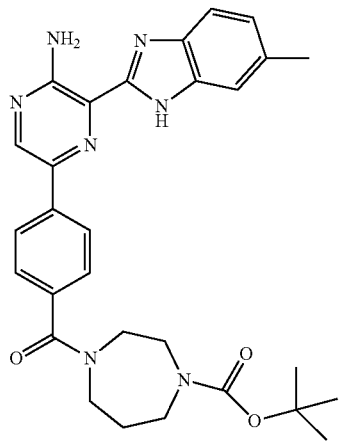 [SMILES: Cc1ccc2nc(-c3nc(-c4ccc(C(=O)N5CCCN(C(=O)OC(C)(C)C)CC5)cc4)cnc3N)[nH]c2c1]

To a solution of 4-[5-amino-6-(6-methyl-1H-benzimidazol-2-yl)pyrazin-2-yl]benzoic acid (108 mg, 0.3127 mmol) in DMSO (1 mL) were added tert-butyl 1,4-diazepane-1-carboxylate (187.9 mg, 0.9381 mmol), diethylcyanophosphonate (124.7 mg, 114.3 µL, 0.6879 mmol) and DIPEA (121.2 mg, 163.3 µL, 0.9381 mmol). The reaction mixture was heated at 80° C. overnight, allowed to cool and filtered and the resultant taken on to the next step without further purification (122 mg, 75% Yield).

1H NMR (400.0 MHz, DMSO) d 1.43 (s, 9H), 1.59 (s, 1H), 1.79 (s, 1H), 2.47 (s, 3H), 3.39-3.73 (m, 8H), 5.80 (br s, 2H), 7.13 (m, 1H), 7.44-7.49 (m, 3H), 7.61 (d, 1H), 8.32-8.37 (m, 3H) and 8.85 (s, 1H) ppm; MS (ES⁺) 528

Compounds I-147 to I-152 were all prepared using Method A, Steps 1-2 followed by Method I-E, Step 1 followed by Method I, Steps 1-2.

Compound 148 (4-(5-amino-6-(6-methyl-1H-benzo[d]imidazol-2-yl)pyrazin-2-yl)phenyl)(4-(dimethylamino)piperidin-1-yl)methanone 1H NMR (400.0 MHz, DMSO) d 12.9 (2H, d), 9.78 (1H, s), 8.86 (1H, s), 8.37 (2H, d), 8.24 (1H, br s), 7.61 (1H, d), 7.54 (2H, d), 7.49 (1H, s), 7.13 (1H, d), 4.05-5.00 (4H, m), 3.79 (1H, m), 3.47 (1H, m), 3.14 (1H, m), 2.79 (3H, s), 2.77 (3H, s), 2.47 (3H, s), 2.02 (2H, m), 1.63 (2H, m) ppm; MS (ES⁺) 456

Compound I-149 (4-(5-amino-6-(6-methyl-1H-benzo[d]imidazol-2-yl)pyrazin-2-yl)phenyl)(piperazin-1-yl)methanone; MS (ES+) 414

Compound I-150 (4-(5-amino-6-(6-methyl-1H-benzo[d]imidazol-2-yl)pyrazin-2-yl)phenyl)(4-methylpiperazin-1-yl)methanone 1H NMR (400.0 MHz, DMSO) d 12.96 (1H, br s), 10.16 (1H, s), 8.87 (1H, s), 8.40 (2H, d), 7.61-7.57 (3H, m), 7.49 (1H, s), 7.12 (1H, d), 5.2-3.81 (2H, m), 3.49-3.11 (6H, m), 2.85 (3H, s), 2.47 (3H, s) ppm; MS (ES⁺) 428

Compound I-151 (4-(5-amino-6-(6-methyl-1H-benzo[d]imidazol-2-yl)pyrazin-2-yl)phenyl)(4-methyl-1,4-diazepan-1-yl)methanone 1H NMR (400.0 MHz, CD₃OD) δ 8.56 (1H, s), 8.22 (2H, d), 7.55-7.46 (3H, m), 7.39 (1H, s), 7.05 (1H, d), 3.81-3.25 (10H, m), 2.90 (3H, s), 2.20 (3H, s), 2.21-2.07 (2H, m) ppm; MS (ES⁺) 442

Compound I-152 4-(5-amino-6-(1H-benzo[d]imidazol-2-yl)pyrazin-2-yl)-N-(2-(pyrrolidin-1-yl)ethyl)benzamide; MS (ES+) 428

Example 10

(4-(5-amino-6-(6-methyl-1H-benzo[d]imidazol-2-yl)pyrazin-2-yl)phenyl) (1,4-diazepan-1-yl)methanone (Compound I-153)

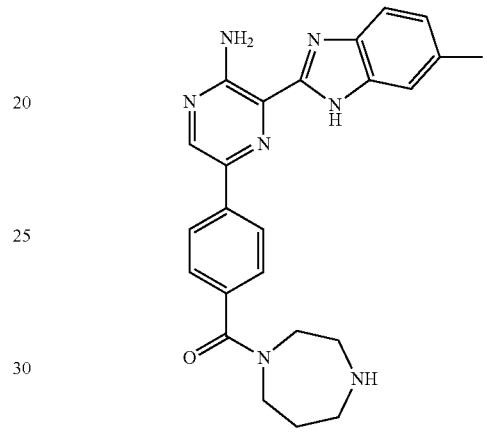

SCHEME I-J

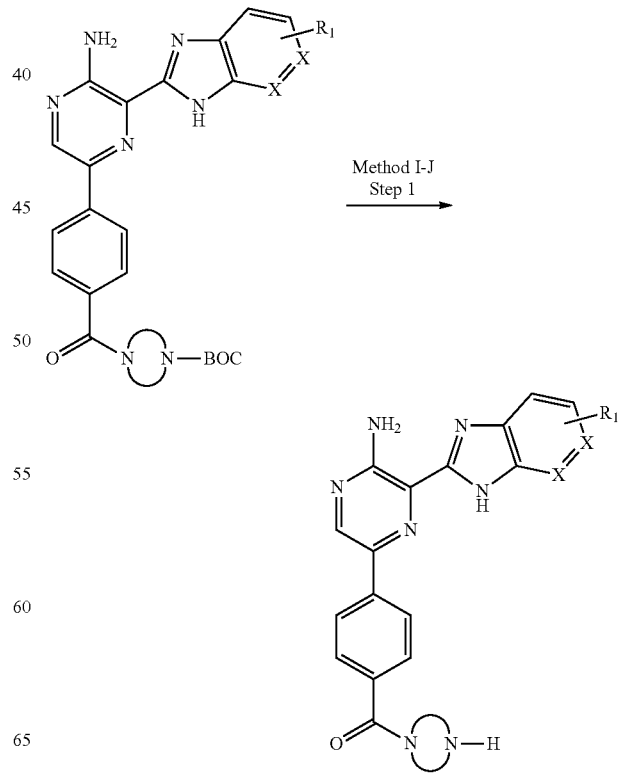

Method I-J
Step 1

Method I-J

Step 1: (4-(5-amino-6-(6-methyl-1H-benzo[d]imidazol-2-yl)pyrazin-2-yl)phenyl) (1,4-diazepan-1-yl) methanone

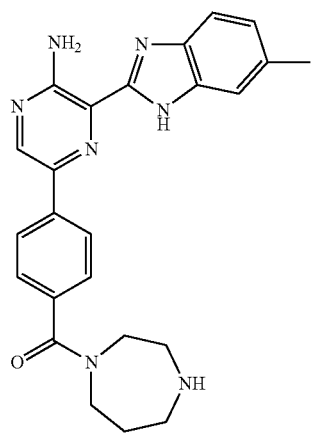 [SMILES: Cc1ccc2nc(-c3nc(-c4ccc(C(=O)N5CCCNCC5)cc4)cnc3N)[nH]c2c1]

tert-butyl 4-[4-[5-amino-6-(6-methyl-1H-benzimidazol-2-yl)pyrazin-2-yl]benzoyl]-1,4-diazepane-1-carboxylate (117 mg, 0.2218 mmol) was dissolved in DCM (3 mL) and the mixture was cooled to 0° C. TFA (3 mL, 38.94 mmol) was added and the reaction mixture was allowed to warm to room temperature and stirred for a further 2 hours. Solvents were evaporated and the residue was dissolved in a mixture of MeCN and water (5 mL/5 mL) and submitted to Genevac evaporation to yield the product (119 mg, 99% Yield). 1H NMR (400.0 MHz, CD$_3$OD) δ 2.18-2.04 (2H, m), 2.45 (3H, s), 3.33 (3H, m), 3.44 (2H, m), 3.63 (2H, m), 3.82 (1H, m), 3.96 (2H, m), 7.15 (1H, d), 7.45 (1H, s), 7.55 (2H, d), 7.58 (1H, s), 8.59 (2H, d), 8.59 (1H, s) ppm; MS (ES$^+$) 428

Example 11

3-amino-6-(4-(4-(dimethylamino)piperidine-1-carbonyl)phenyl)-N-phenylpyrazine-2-carboxamide (Compound II-10)

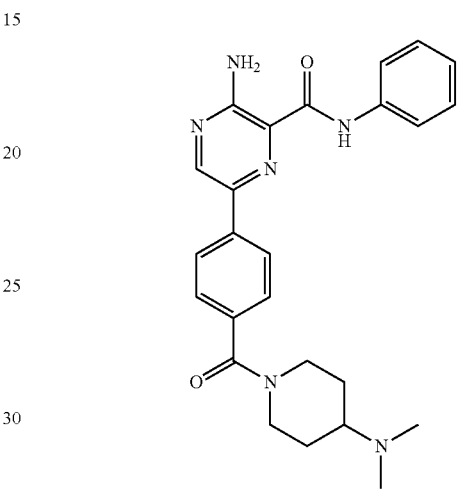

SCHEME II-A

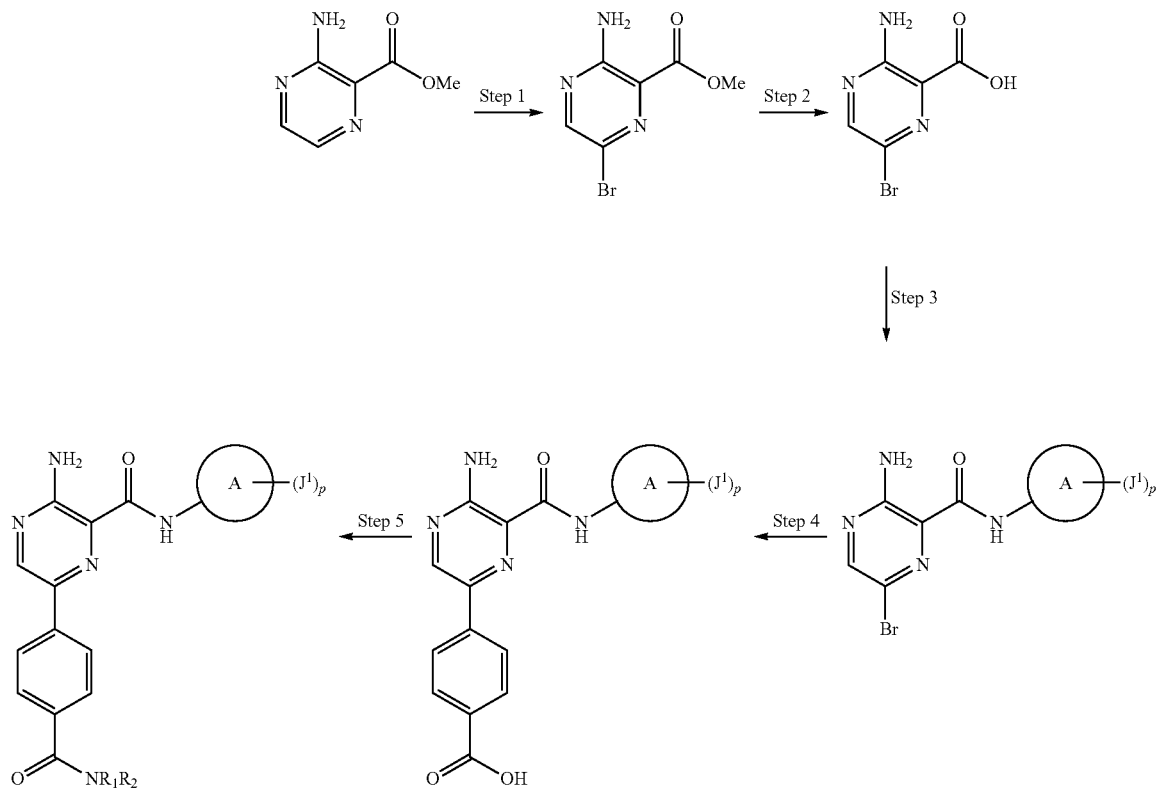

Method II-A: Step 1: Methyl 3-amino-6-bromopyrazine-2-carboxylate

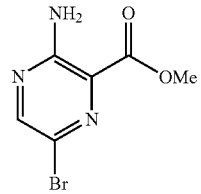 [SMILES: COC(=O)c1nc(Br)cnc1N]

A mixture of methyl 3-aminopyrazine-2-carboxylate (8.35 g, 54.53 mmol) and N-bromo-succinimide (9.705 g, 54.53 mmol) was stirred in MeCN (100 mL) at room temp overnight. The resultant precipitate was filtered, washed with MeCN and dried to give the desired product as a yellow solid (11.68 g, 92% Yield); 1H NMR (400.0 MHz, DMSO) 3.85 (s, 3H), 7.55 (br s, 2H) and 8.42 (s, 1H) ppm; MS (ES$^+$) 233

Step 2: 3-amino-6-bromopyrazine-2-carboxylic Acid

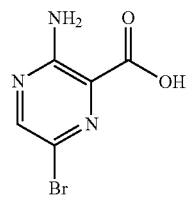

A mixture of methyl 3-amino-6-bromo-pyrazine-2-carboxylate (5.11 g, 22.02 mmol) and lithium hydroxide (2.637 g, 110.1 mmol) in MeOH (20 mL) and H2O (20 mL) was heated to 90° C. for 2 hours. The reaction mixture was allowed to cool and neutralised with HCl and the resultant precipitate collected by filtration. Taken on to the next step without further purification (4.80 g, 99% Yield).

Step 3: 3-amino-6-bromo-N-phenylpyrazine-2-carboxamide

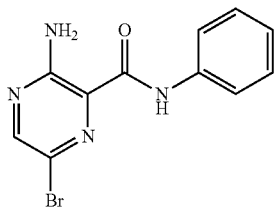 [SMILES: Nc1ncc(Br)nc1C(=O)Nc1ccccc1]

A mixture of 3-amino-6-bromo-pyrazine-2-carboxylic acid (3.5 g, 16.05 mmol), 1,1'-carbonyldiimidazole (5.205 g, 32.10 mmol), DIPEA (2.282 g, 3.075 mL, 17.66 mmol) and DMAP (98.04 mg, 0.8025 mmol) were combined in DMSO (131 mL) and stirred for 30 min. Aniline (1.495 g, 1.463 mL, 16.05 mmol) was then added and the resulting solution stirred at RT for 18 hours. After this time water was added and the product collected by filtration to give a brown powder (3.5 g, 74% Yield).

1H NMR (400.0 MHz, DMSO) d 7.04 (1H, m), 7.29 (2H, m), 7.72 (4H, m), 8.36 (1H, s), 10.22 (NH$_2$) ppm; MS (ES$^+$) 295.

Step 4: 4-(5-amino-6-(phenylcarbamoyl)pyrazin-2-yl)benzoic Acid

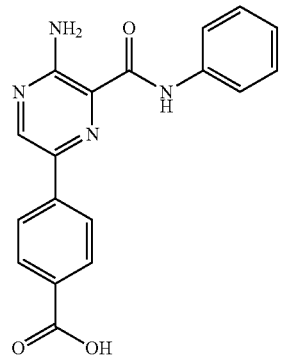 [SMILES: Nc1ncc(-c2ccc(C(=O)O)cc2)nc1C(=O)Nc1ccccc1]

A mixture of 3-amino-6-bromo-N-phenyl-pyrazine-2-carboxamide (3.62 g, 12.35 mmol), 4-boronobenzoic acid (2.049 g, 12.35 mmol) and Na$_2$CO$_3$ (2.618 g, 24.70 mmol) was suspended in MeCN (60 mL)/water (60 mL). The mixture was degassed (5×N$_2$ vacuum cycles) and Pd(PPh$_3$)$_4$ (1.427 g, 1.235 mmol) added. The mixture was degassed again and heated to 90° C. After 4 hours, the mixture was allowed to cool, concentrated to half its original volume and washed with DCM. The aqueous phase was acidified to pH4 (2M HCl) and the resulting precipitate collected, washed with water and dried overnight under vacuum to give the product as a bright yellow solid, (3.05 g, 69% Yield). 1H NMR (400 MHz, DMSO) d 7.17 (1H, t), 7.41 (2H, t), 7.83 (4H, d), 8.03 (2H, d), 8.37 (2H, d), 9.01 (1H, s), 10.45 (1H, s), 13.03 (1H, brs) ppm; MS (ES+) 335

Step 5: 3-amino-6-(4-(4-(dimethylamino)piperidine-1-carbonyl)phenyl)-N-phenylpyrazine-2-carboxamide

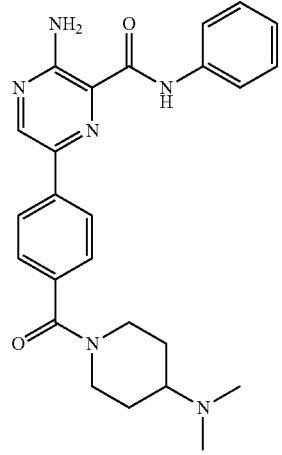 [SMILES: CN(C)C1CCN(C(=O)c2ccc(-c3cnc(N)c(C(=O)Nc4ccccc4)n3)cc2)CC1]

N,N-dimethylpiperidin-4-amine (57.54 mg, 0.449 mmol) was weighed into a greenhouse tube and treated with a solution of 4-(5-amino-6-(phenylcarbamoyl)pyrazin-2-yl) benzoic acid (50 mg, 0.150 mmol), CDI (48.51 mg, 0.299 mmol) and DMAP (1.82 mg, 0.015 mmol) in DMSO (1 mL of a stock solution). DIPEA (78.2 uL, 0.449 mmol) was then added and the mixture stirred at 38° C. for 6 hours. The reaction mixture was filtered and the resultant residue was purified by reverse phase preparative HPLC [Waters Sunfire C18, 10 uM, 100 A column, gradient 10%-95% B (solvent A: 0.05% TFA in water, solvent B: CH3CN) over 16 minutes at 25 mL/min]. The fractions were freeze-dried to give the title compound as a solid (54.65, 80% Yield). (ES+) 445

The following compounds were all prepared using the above sequence:

Compound II-1: 6-(4-(1,4-diazepane-1-carbonyl)phenyl)-3-amino-N-phenylpyrazine-2-carboxamide 1H NMR (400.0 MHz, DMSO) d 1.44-1.47 (m, 1H), 1.53-1.58 (m, 1H), 2.57-2.61 (m, 1H), 2.62-2.69 (m, 2H), 2.74-2.80 (m, 1H), 3.15-3.20 (m, 2H), 3.40-3.46 (m, 2H), 6.91-6.96 (m, 1H), 7.15-7.19 (m, 2H), 7.23-7.28 (m, 2H), 7.51 (br s, 2H), 7.58-7.60 (m, 2H), 8.05-8.08 (m, 2H), 8.74 (s, 1H) and 10.20 (s, 1H) ppm; (ES+) 417

Compound II-2: 3-amino-N-phenyl-6-(4-(2-(pyrrolidin-1-yl)ethylcarbamoyl)phenyl)pyrazine-2-carboxamide; 1H NMR (400 MHz, DMSO) d 1.80 (4H, vbrs), 3.51 (2H, brs), 7.18 (1H, t), 7.41 (2H, t), 7.81-7.85 (4H, m), 7.95 (2H, d), 8.35 (2H, d), 8.65 (1H, brs), 9.02 (1H, s), 10.44 (1H, s) ppm; (ES+) 431

Compound II-3: 3-amino-N-phenyl-6-(4-(2-(piperidin-1-yl)ethylcarbamoyl)phenyl)pyrazine-2-carboxamide 1H NMR (400 MHz, DMSO) d 1.30-2.40 (2H, m), 1.46-1.53 (4H, m), 2.33 (4H, m), 2.45 (2H, t), 3.37-3.44 (2H, m), 7.16 (1H, t), 7.41 (2H, t), 7.79 (2H, brs), 7.81 (2H, d), 7.95 (2H, d), 8.34 (2H, d), 8.48 (1H, t), 9.00 (1H, s), 10.45 (1H, s) ppm; (ES+) 445

Compound II-4: 3-amino-N-phenyl-6-(4-(2-(pyrrolidin-1-ylmethyl)pyrrolidine-1-carbonyl)phenyl)pyrazine-2-carboxamide (ES+) 471

Compound II-5: 3-amino-6-(4-((2-(dimethylamino)ethyl)(methyl)carbamoyl)phenyl)-N-phenylpyrazine-2-carboxamide; (ES+) 419

Compound II-6: 3-amino-N-phenyl-6-(4-(4-(pyrrolidin-1-yl)piperidine-1-carbonyl)phenyl)pyrazine-2-carboxamide (ES+) 471

Compound II-7: 3-amino-6-(4-(4-methylpiperazine-1-carbonyl)phenyl)-N-phenylpyrazine-2-carboxamide; (ES+) 417

Compound II-8: 3-amino-N-phenyl-6-(4-(piperazine-1-carbonyl)phenyl)pyrazine-2-carboxamide; (ES+) 403

Compound II-9: 3-amino-6-(4-(3-(dimethylamino)pyrrolidine-1-carbonyl)phenyl)-N-phenylpyrazine-2-carboxamide; (ES+) 431

Compound II-11: 3-amino-6-(4-(4-(2-cyanoethyl)piperazine-1-carbonyl)phenyl)-N-phenylpyrazine-2-carboxamide; (ES+) 456

Example 12

(4-(5-amino-6-(6-methyl-1H-benzo[d]imidazol-2-yl)pyrazin-2-yl)phenyl) (1,4-diazepan-1-yl)methanone (Compound III-1)

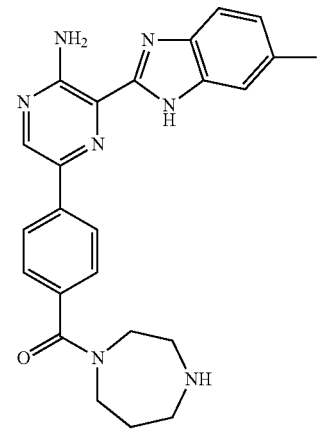 [SMILES: Cc1ccc2nc(-c3nc(-c4ccc(C(=O)N5CCCNCC5)cc4)cnc3N)[nH]c2c1]

SCHEME III-A

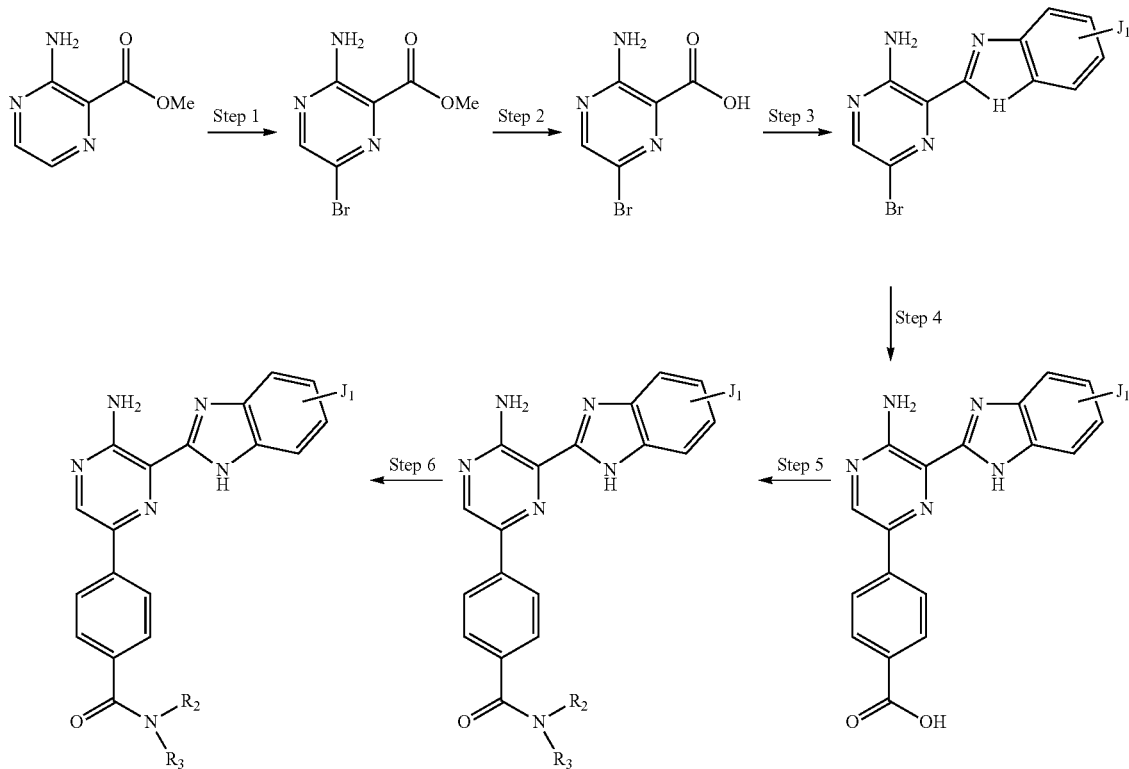

Method III-A

Step 1: Methyl 3-amino-6-bromopyrazine-2-carboxylate

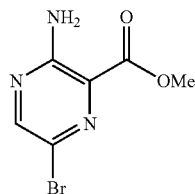 [SMILES: COC(=O)c1nc(Br)cnc1N]

A mixture of methyl 3-aminopyrazine-2-carboxylate (8.35 g, 54.53 mmol) and N-bromo-succinimide (9.705 g, 54.53 mmol) was stirred in MeCN (100 mL) at room temp overnight. The resultant precipitate was filtered, washed with MeCN and dried to give the desired product as a yellow solid (11.68 g, 92% Yield) 1H NMR (400.0 MHz, DMSO) 3.85 (s, 3H), 7.55 (br s, 2H) and 8.42 (s, 1H) ppm; MS (ES$^+$)

Step 2: 3-amino-6-bromopyrazine-2-carboxylic acid

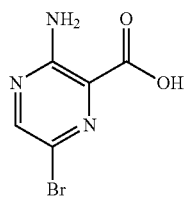

A mixture of methyl 3-amino-6-bromo-pyrazine-2-carboxylate (5.11 g, 22.02 mmol) and lithium hydroxide (2.637 g, 110.1 mmol) in MeOH (20 mL) and H2O (20 mL) was heated to 90° C. for 2 hours. The reaction mixture was allowed to cool and neutralised with HCl and the resultant precipitate collected by filtration. Taken on to the next step without further purification (4.80 g, 99% Yield).

Step 3: 5-bromo-3-(6-methyl-1H-benzo[d]imidazol-2-yl)pyrazin-2-amine

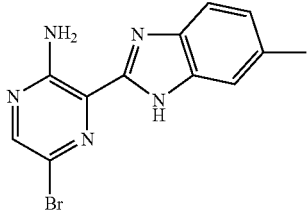 [SMILES: Cc1ccc2nc(-c3nc(Br)cnc3N)[nH]c2c1]

A mixture of 3-amino-6-bromo-pyrazine-2-carboxylic acid (5.52 g, 25.32 mmol), 4-methylbenzene-1,2-diamine (3.09 g, 25.32 mmol), diethoxyphosphorylformonitrile (4.54, 27.85 mmol) and triethylamine (7.06 mL, 50.64 mmol) in DME (30 mL) was heated in the microwave at 170° C. for 60 minutes. The mixture was diluted with Ethyl acetate, washed with water followed by aqueous NaHCO3 then brine. After drying over MgSO4, the mixture was decolourised with charcoal and filtered through silica gel. After concentration, the mixture was filtered to give gold coloured crystals (4.005 g, 52% Yield).

MS (ES$^+$) 305

Step 4: 4-(5-amino-6-(6-methyl-1H-benzo[d]imidazol-2-yl)pyrazin-2-yl)benzoic acid

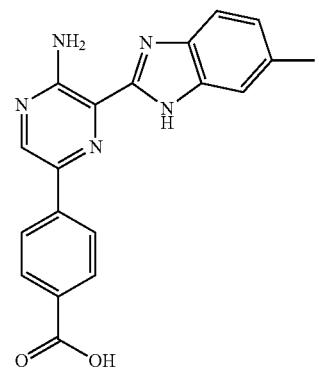 [SMILES: Cc1ccc2nc(-c3nc(-c4ccc(C(=O)O)cc4)cnc3N)[nH]c2c1]

5-bromo-3-(6-methyl-1H-benzimidazol-2-yl)pyrazin-2-amine (1.855 g, 6.099 mmol), 4-boronobenzoic acid (1.012 g, 6.099 mmol) and Na$_2$CO$_3$ (1.293 g, 12.20 mmol) suspended in MeCN (30 mL)/water (30 mL). The mixture was degassed (5×N$_2$ vacuum cycles) and Pd(PPh$_3$)$_4$ (704.8 mg, 0.6099 mmol) added. The mixture was degassed again and heated to 90° C. No sign of product was observed therefore 25 mL aliquots were heated in the microwave for 1 hour at 140° C. which led to product formation. The mixture was allowed to cool and washed with DCM (×2). The aqueous layer was acidified to pH4 (1M HCl) and the resulting precipitate collected, washed with water and dried overnight under vacuum to give the product as a bright yellow solid, (1.30 g, 62% Yield).

MS (ES$^+$) 346

Step 5: tert-butyl 4-(4-(5-amino-6-(6-methyl-1H-benzo[d]imidazol-2-yl)pyrazin-2-yl)phenylcarbonyl)-1,4-diazepane-1-carboxylate

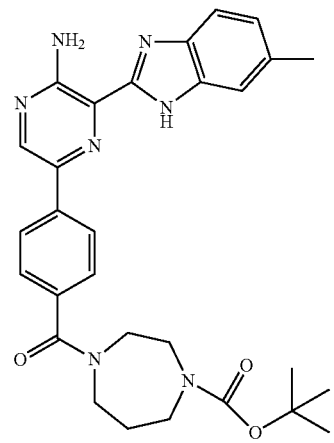 [SMILES: Cc1ccc2nc(-c3nc(-c4ccc(C(=O)N5CCCN(C(=O)OC(C)(C)C)CC5)cc4)cnc3N)[nH]c2c1]

To a solution of 4-[5-amino-6-(6-methyl-1H-benzimidazol-2-yl)pyrazin-2-yl]benzoic acid (108 mg, 0.3127 mmol)

in DMSO (1 mL) were added tert-butyl 1,4-diazepane-1-carboxylate (187.9 mg, 0.9381 mmol), diethylcyanophosphonate (124.7 mg, 114.3 μL, 0.6879 mmol) and DIPEA (121.2 mg, 163.3 μL, 0.9381 mmol). The reaction mixture was heated at 80° C. overnight, allowed to cool and filtered and the resultant taken on to the next step without further purification (122 mg, 75% Yield).

1H NMR (400.0 MHz, DMSO) d 1.43 (s, 9H), 1.59 (s, 1H), 1.79 (s, 1H), 2.47 (s, 3H), 3.39-3.73 (m, 8H), 5.80 (br s, 2H), 7.13 (m, 1H), 7.44-7.49 (m, 3H), 7.61 (d, 1H), 8.32-8.37 (m, 3H) and 8.85 (s, 1H) ppm; MS (ES$^+$) 528

Step 6: (4-(5-amino-6-(6-methyl-4H-benzo[d]imidazol-2-yl)pyrazin-2-yl)phenyl) (1,4-diazepan-1-yl)methanone (Compound III-1)

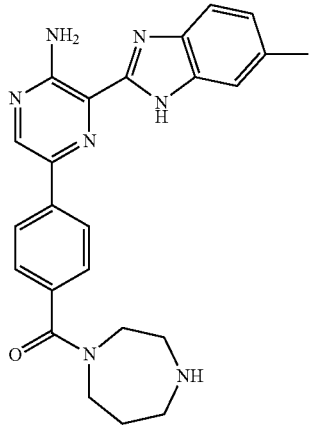 [SMILES: Cc1ccc2nc(-c3nc(-c4ccc(C(=O)N5CCCNCC5)cc4)cnc3N)[nH]c2c1]

tert-butyl 4-[4-[5-amino-6-(6-methyl-1H-benzimidazol-2-yl)pyrazin-2-yl]benzoyl]-1,4-diazepane-1-carboxylate (117 mg, 0.2218 mmol) was dissolved in DCM (3 mL) and the mixture was cooled to 0° C. TFA (3 mL, 38.94 mmol) was added and the reaction mixture was allowed to warm to room temperature and stirred for a further 2 hours. Solvents were evaporated and the residue was dissolved in a mixture of MeCN and water (5 mL/5 mL) and submitted to Genevac evaporation to yield the product (119 mg, 99% Yield). 1H NMR (400.0 MHz, CD$_3$OD) δ 2.18-2.04 (2H, m), 2.45 (3H, s), 3.33 (3H, m), 3.44 (2H, m), 3.63 (2H, m), 3.82 (1H, m), 3.96 (2H, m), 7.15 (1H, d), 7.45 (1H, s), 7.55 (2H, d), 7.58 (1H, s), 8.59 (2H, d), 8.59 (1H, s) ppm; MS (ES$^+$) 428

The following compounds were all prepared using the above sequence Step 1-5:

Compound III-2 (4-(5-amino-6-(6-methyl-1H-benzo[d]imidazol-2-yl)pyrazin-2-yl)phenyl)(4-(dimethylamino)piperidin-1-yl)methanone 1H NMR (400.0 MHz, DMSO) d 12.9 (2H, d), 9.78 (1H, s), 8.86 (1H, s), 8.37 (2H, d), 8.24 (1H, br s), 7.61 (1H, d), 7.54 (2H, d), 7.49 (1H, s), 7.13 (1H, d), 4.05-5.00 (4H, m), 3.79 (1H, m), 3.47 (1H, m), 3.14 (1H, m), 2.79 (3H, s), 2.77 (3H, s), 2.47 (3H, s), 2.02 (2H, m), 1.63 (2H, m) ppm; MS (ES$^+$) 456

Compound III-3: (4-(5-amino-6-(6-methyl-1H-benzo[d]imidazol-2-yl)pyrazin-2-yl)phenyl)(piperazin-1-yl)methanone; MS (ES+) 414

Compound III-4: (4-(5-amino-6-(6-methyl-1H-benzo[d]imidazol-2-yl)pyrazin-2-yl)phenyl)(4-methylpiperazin-1-yl)methanone 1H NMR (400.0 MHz, DMSO) d 12.96 (1H, br s), 10.16 (1H, s), 8.87 (1H, s), 8.40 (2H, d), 7.61-7.57 (3H, m), 7.49 (1H, s), 7.12 (1H, d), 5.2-3.81 (2H, m), 3.49-3.11 (6H, m), 2.85 (3H, s), 2.47 (3H, s) ppm; MS (ES$^+$) 428

Compound III-5: (4-(5-amino-6-(6-methyl-1H-benzo[d]imidazol-2-yl)pyrazin-2-yl)phenyl)(4-methyl-1,4-diazepan-1-yl)methanone 1H NMR (400.0 MHz, CD$_3$OD) δ 8.56 (1H, s), 8.22 (2H, d), 7.55-7.46 (3H, m), 7.39 (1H, s), 7.05 (1H, d), 3.81-3.25 (10H, m), 2.90 (3H, s), 2.20 (3H, s), 2.21-2.07 (2H, m) ppm; MS (ES$^+$) 442

Compound III-6: 4-(5-amino-6-(1H-benzo[d]imidazol-2-yl)pyrazin-2-yl)-N-(2-(pyrrolidin-1-yl)ethyl)benzamide: MS (ES$^+$) 428

Example 1A 4-(5-amino-6-(5-phenyl-1,3,4-oxadiazol-2-yl)pyrazin-2-yl)-N,N-dimethylbenzamide (Compound IA-23)

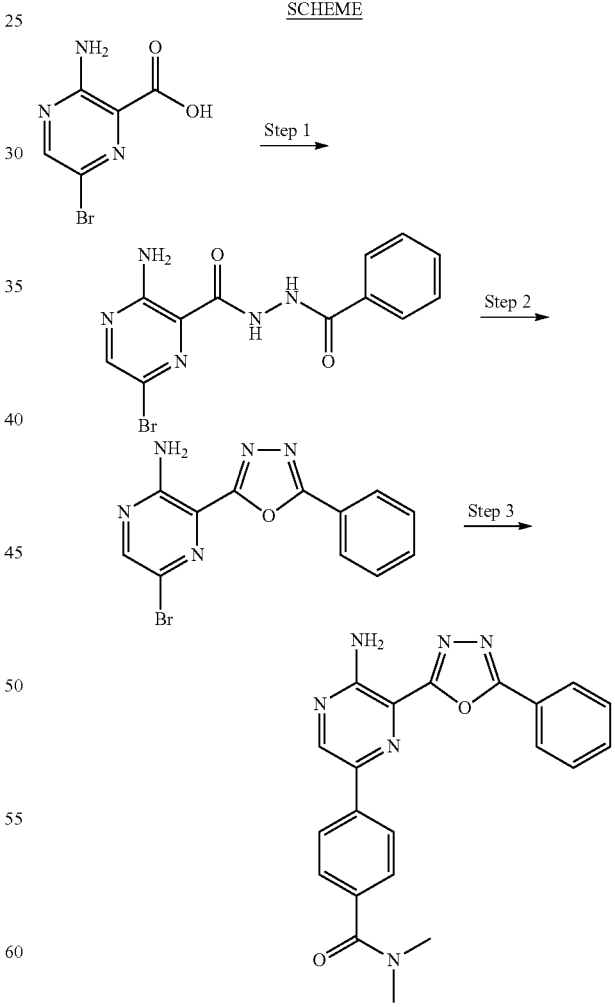

Compound IA-23

Compound IA-23 was prepared using Method IV-A, Steps 1-3

Method IV-A

Step 1: 3-amino-6-bromo-N'-(phenylcarbonyl)pyrazine-2-carbohydrazide

TBTU (22.09 g, 68.80 mmol) and triethylamine (4.642 g, 6.394 mL, 45.87 mmol) were added to a suspension of 3-amino-6-bromo-pyrazine-2-carboxylic acid (10 g, 45.87 mmol) and benzohydrazide (7.494 g, 55.04 mmol) in DMF (100.0 mL) and the resulting solution stirred at ambient temperature for 48 hours and then poured into water (400 mL) with vigorous stirring. This was allowed to stir for 30 minutes, filtered and washed with water. The moist solid was dissolved in hot EtOAc, dried (MgSO$_4$), filtered and concentrated in vacuo and the resultant solid dried under vacuum to give the desired product (11.34 g, 73% Yield). 1H NMR (400.0 MHz, DMSO) d 7.51 (2H, m), 7.61 (1H, m), 7.69 (2H, br s), 7.92 (2H, m), 8.44 (1H, s), 10.48 (1H, br s), 10.54 (1H, br s) ppm; MS (ES$^+$) 338.01

Step 2: 5-bromo-3-(5-phenyl-1,3,4-oxadiazol-2-yl)pyrazin-2-amine

Polyphosphoric acid (314 g) was heated to 100° C. and treated portionwise with 3-amino-N'-benzoyl-6-bromopyrazine-2-carbohydrazide (22.5 g, 66.94 mmol) over a period of 20 minutes. The reaction was allowed to stir at 110-120° C. for 6 hours and then allowed to cool and treated with ice/water and stirred. The resultant solid was filtered and washed with water. It was taken into EtOAc, washed with water and adjusted to pH 11 (NaOH solution) and then washed with brine, dried (MgSO$_4$) and concentrated in vacuo to give the desired product (13.25 g, 62% Yield). 1H NMR (400.0 MHz, DMSO) d 7.69 (3H, m), 7.86 (2H, br s), 8.16 (2H, m), 8.50 (1H, s) ppm; MS (ES$^+$) 319.89

Step 3: 4-(5-amino-6-(5-phenyl-1,3,4-oxadiazol-2-yl)pyrazin-2-yl)-N,N-dimethylbenzamide 5-bromo-3-(5-phenyl-1,3,4-oxadiazol-2-yl)pyrazin-2-amine (150 mg, 0.4715 mmol), [4-(dimethylcarbamoyl)phenyl]boronic acid (91.00 mg, 0.4715 mmol), sodium carbonate (99.95 mg, 0.9430 mmol) and palladium; triphenylphosphane (54.48 mg, 0.04715 mmol) in a mixture of acetonitrile (1.5 mL) and water (1.5 mL) was heated at 110° C. in the microwave for 30 minutes. The reaction was diluted with water and EtOAc and the layers separated. The combined organics were dried (MgSO$_4$), filtered and concentrated in vacuo. The residue was purified by column chromatography (ISCO Companion™, 12 g column, 0-100% EtOAc/Petroleum ether) to give the desired product (102.8 mg, 56% Yield). 1H NMR (400.0 MHz, DMSO) d 2.98 (6H, m), 7.55 (2H, m), 7.69-7.71 (3H, m), 7.83 (2H, br s), 8.17-8.20 (4H, m), 9.00 (1H, s) ppm; MS (ES$^+$) 387.13

The following compounds were all prepared using a method similar to the one described for Compound IA-23 above.

Compound IA-90 5-(4-isopropylsulfinylphenyl)-3-(5-phenyl-1,3,4-oxadiazol-2-yl)pyrazin-2-amine 1H NMR (400.0 MHz, DMSO) d 0.95 (d, 3H), 1.25 (d, 3H), 2.98-3.02 (m, 1H), 7.6-8.0 (m, 6H), 8.25 (d, 2H), 8.35 (d, 2H) and 9.05 (s, 1H) ppm; MS (ES$^+$) 406.2

Compound IA-112 5-[4-(azetidin-1-ylsulfonyl)phenyl]-3-(5-phenyl-1,3,4-oxadiazol-2-yl)pyrazin-2-amine 1H NMR (400.0 MHz, CDCl$_3$) d 2.0-2.2 (m, 2H), 3.0-3.2 (m, 2H), 3.83-3.9 (m, 4H), 7.6-7.7 (m, 3H), 8.05 (d, 2H), 8.25-8.3 (m, 4H) and 8.85 (s, 1H) ppm; MS (ES$^+$) 435.2

Compound IA-134 3-(5-phenyl-1,3,4-oxadiazol-2-yl)-5-(2-phenylphenyl)pyrazin-2-amine 1H NMR (400 MHz, DMSO) d 7.2-7.28 (2H, m), 7.3-7.35 (1H, m), 7.45-7.5 (1H, m), 7.55-7.6 (3H, m), 7.65-7.7 (3H, m), 7.75-7.8 (1H, m), 7.72 (1H, s) and 8.1-8.15 (2H, m) ppm; MS (ES$^+$) 392.3

Compound IA-184 5-(2-ethylsulfanylphenyl)-3-(5-phenyl-1,3,4-oxadiazol-2-yl)pyrazin-2-amine 1H NMR (400.0 MHz, CDCl$_3$) d 1.25 (t, 3H), 3.95 (q, 2H), 7.4-7.5 (m, 2H), 7.5-7.65 (m, 5H), 8.25 (d, 2H) and 8.6 (s, 1H) ppm; MS (ES$^+$) 376.2

Compound IA-207 5-(2-oxazol-5-ylphenyl)-3-(5-phenyl-1,3,4-oxadiazol-2-yl)pyrazin-2-amine 1H NMR (400.0 MHz, DMSO) d 7.6-7.8 (m, 9H), 8.1-8.13 (m, 2H), 8.15 (s, 1H) and 8.18 (s, 1H) ppm; MS (ES$^+$) 383.1

Compound IA-229 5-(2-isopropylsulfanylphenyl)-3-(5-phenyl-1,3,4-oxadiazol-2-yl)pyrazin-2-amine 1H NMR (400.0 MHz, CDCl$_3$) d 1.35 (d, 6H), 3.4-3.5 (m, 1H), 7.0 (br s, 2H), 7.4-7.45 (m, 2H), 7.5-7.65 (m, 5H), 8.2-8.25 (m, 2H) and 8.55 (s, 1H) ppm; MS (ES$^+$) 390.2

Example 2A

4-(5-amino-6-(5-(3-fluorophenyl)-1,3,4-oxadiazol-2-yl)pyrazin-2-yl)-N,N-dimethylbenzamide (Compound IA-40)

SCHEME

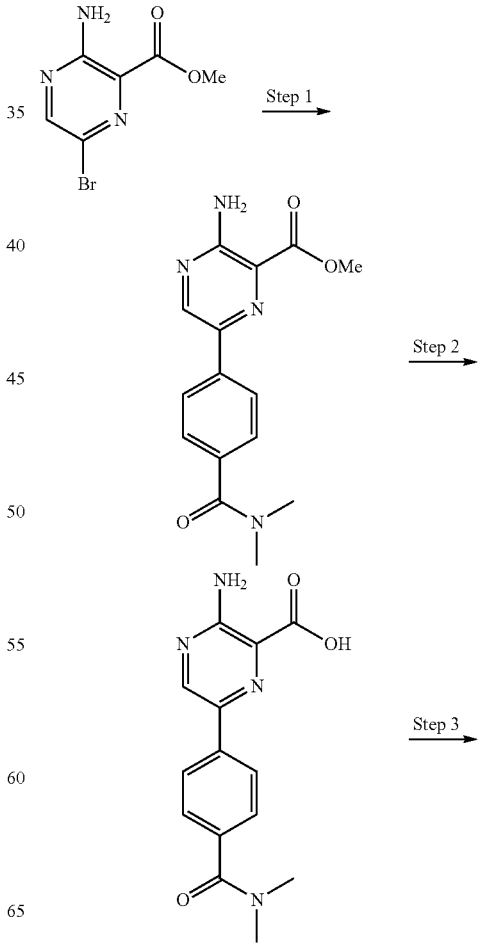

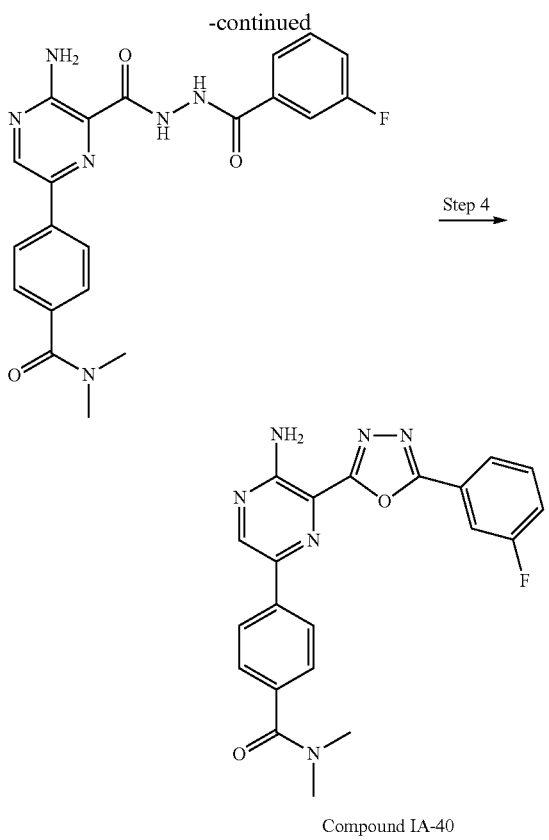

Compound IA-40

Compound IA-40 was prepared using Method IV-B, Steps 1-4

Method IV-B

Step 1: Methyl 3-amino-6-(4-(dimethylcarbamoyl)phenyl)pyrazine-2-carboxylate

Methyl 3-amino-6-bromo-pyrazine-2-carboxylate (625.1 mg, 2.694 mmol), [4-(dimethylcarbamoyl)phenyl]boronic acid (520 mg, 2.694 mmol), sodium carbonate (571.1 mg, 5.388 mmol) and palladium; triphenylphosphane (311.3 mg, 0.2694 mmol) in a mixture of acetonitrile (3 mL) and water (3 mL) was heated at 110° C. in the microwave for 30 minutes. The reaction was diluted with EtOAc and water and the layers separated. The aqueous later was extracted further with EtOAc (2×) and the combined organics dried (MgSO$_4$), filtered and concentrated in vacuo. The residue was purified by column chromatography (ISCO Companion™, 40 g column, 0-100% EtOAc/Petroleum ether) to give the desired product as a yellow solid (375 mg, 46% Yield). 1H NMR (400.0 MHz, DMSO) d 3.02 (3H, s), 3.15 (3H, s), 4.04 (3H, s), 7.54 (2H, m), 7.97 (2H, m), 8.71 (1H, s) ppm; MS (ES$^+$) 301.13

Step 2: 3-amino-6-(4-(dimethylcarbamoyl)phenyl)pyrazine-2-carboxylic Acid

To a solution of methyl 3-amino-6-[4-(dimethylcarbamoyl)phenyl]pyrazine-2-carboxylate (390 mg, 1.299 mmol) in MeOH (2.127 mL) was added a solution of NaOH (649.5 µL of 2 M, 1.299 mmol) in H$_2$O (2.127 mL). The resulting solution was heated to 60° C. for 2 hours and then allowed to cool and neutralised with HCl. The resultant precipitate was collected and washed with ether and dried (340 mg, 91% Yield). MS (ES$^+$) 287.08

Step 3: 4-(5-amino-6-(2-(3-fluorophenylcarbonyl)hydrazinecarbonyl)pyrazin-2-yl)-N,N-dimethylbenzamide 3-fluorobenzohydrazide (80.77 mg, 0.5240 mmol) was added to a solution of 3-amino-6-[4-(dimethylcarbamoyl)phenyl]pyrazine-2-carboxylic acid (150 mg, 0.5240 mmol), triethylamine (53.02 mg, 73.03 µL, 0.5240 mmol) and TBTU (252.4 mg, 0.7860 mmol) in DMF (3.000 mL) and the resulting solution stirred at RT for 2 hours. The reaction was diluted with EtOAc and water and the layers separated. The aqueous layer was extracted further with EtOAc (2×) and the combined organics washed with water (3×), dried (MgSO$_4$), filtered and concentrated to give the desired product as a yellow solid (172 mg, 78% Yield). MS (ES$^+$) 423.13

Step 4: 4-(5-amino-6-(5-(3-fluorophenyl)-1,3,4-oxadiazol-2-yl)pyrazin-2-yl)-N,N-dimethylbenzamide A suspension of 4-[5-amino-6-[[(3-fluorobenzoyl)amino]carbamoyl]pyrazin-2-yl]-N,N-dimethyl-benzamide (127 mg, 0.3007 mmol) in anhydrous acetonitrile (2.540 mL) cooled in an ice bath, was treated with DIPEA (116.6 mg, 157.1 µL, 0.9021 mmol) followed by dibromo(triphenyl)phosphorane (165.0 mg, 0.3909 mmol) portionwise. The reaction mixture was then placed under nitrogen and allowed to stir for 10 minutes. The resultant precipitate was isolated by filtration, washed with ether and dried to give the impure desired product. The material was purified further by reverse phase preparative HPLC [Waters Sunfire C18, 10 mM, 100 Å column, gradient 10%-95% B (solvent A: 0.05% TFA in water; solvent B: CH$_3$CN) over 16 minutes at 25 mL/min]. The fractions were collected, passed through a sodium bicarbonate cartridge and freeze-dried to give the title compound as a yellow solid (58.4 mg, 48% Yield). 1H NMR (400.0 MHz, DMSO) d 2.98 (6H, m), 7.55-7.61 (3H, m), 7.73-7.85 (3H, m), 7.96 (1H, m), 8.02 (1H, m), 8.19 (2H, m), 9.01 (1H, s) ppm; MS (ES$^+$) 405.16

The following compounds were all prepared using a method similar to the one described for Compound IA-40 above.

Compound IA-195 4-[5-amino-6-[5-(3-methoxyphenyl)-1,3,4-oxadiazol-2-yl]pyrazin-2-yl]-N,N-dimethyl-benzamide 1H NMR (400.0 MHz, DMSO) d 2.98 (m, 6H), 3.90 (s, 3H), 7.28 (m, 1H), 7.55-7.57 (m, 2H), 7.60-7.65 (m, 2H), 7.74 (m, 1H), 8.17 (m, 2H) and 9.00 (1H, s) ppm; MS (ES$^+$) 417.17

Compound IA-233 4-[5-amino-6-[5-[2-(trifluoromethyl)phenyl]-1,3,4-oxadiazol-2-yl]pyrazin-2-yl]-N,N-dimethyl-benzamide 1H NMR (400.0 MHz, DMSO) d 2.98 (m, 6H), 7.51 (m, 2H), 7.80 (br s, 1H), 7.93-8.01 (m, 2H), 8.09-8.14 (m, 3H), 8.19 (m, 1H) and 9.03 (s, 1H) ppm; MS (ES$^+$) 455.12

Example 3A

4-(5-amino-6-(5-(benzylamino)-1,3,4-oxadiazol-2-yl)pyrazin-2-yl)-N,N-dimethylbenzamide (Compound IA-55)

SCHEME

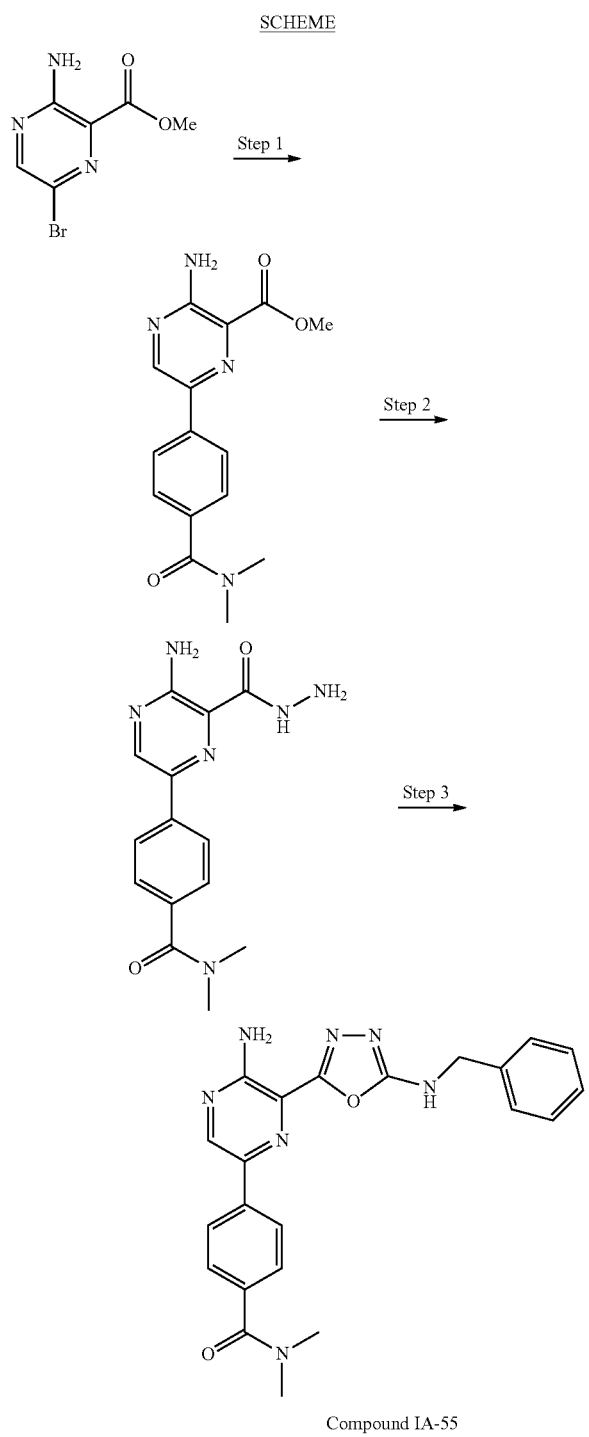

Compound IA-55

Compound IA-55 was prepared using Method IV-C, Steps 1-3

Method IV-C

Step 1: Methyl 3-amino-6-(4-(dimethylcarbamoyl)phenyl)pyrazine-2-carboxylate Methyl 3-amino-6-bromo-pyrazine-2-carboxylate (6.012 g, 25.91 mmol), [4-(dimethylcarbamoyl)phenyl]boronic acid (5 g, 25.91 mmol), sodium carbonate (5.492 g, 51.82 mmol) and Pd(PPh$_3$)$_4$ (2.994 g, 2.591 mmol) in a mixture of acetonitrile (28.85 mL) and water (28.85 mL) was heated at 110° C. The reaction mixture was allowed to cool and the residual solid filtered off. The filtrate was diluted with EtOAc and water and the layers separated. The aqueous layer was acidified to pH4 (by addition of 1M HCl) and then extracted with dichloromethane (3×), dried (MgSO$_4$), filtered and concentrated in vacuo to leave the product as a yellow solid. The ethyl acetate extracts were concentrated in vacuo and combined with the filtered solid. Preabsorbed onto silica and purified by column chromatography on silica using the companion eluting with ethyl acetate/petroleum ether (0-100% EtOAc). Product eluted with 100% EtOAc. Product fractions combined and conc in vacuo to leave a yellow solid (1.95 g, 50% Yield). 1H NMR (400.0 MHz, DMSO) d 3.02 (3H, s), 3.15 (3H, s), 4.04 (3H, s), 7.54 (2H, m), 7.97 (2H, m), 8.71 (1H, s) ppm; MS (ES$^+$) 301.13

Step 2: 4-(5-amino-6-(hydrazinecarbonyl)pyrazin-2-yl)-N,N-dimethylbenzamide

To a stirred solution of methyl 3-amino-6-[4-(dimethylcarbamoyl)phenyl]pyrazine-2-carboxylate (1.7011 g, 5.664 mmol) in EtOH (10.21 mL) was added hydrazine (726.1 mg, 711.2 μL, 22.66 mmol). The resultant solution was heated to reflux for 30 minutes and then allowed to cool to RT. The precipitate was filtered off and dried (1.47 g, 87% Yield). 1H NMR (400.0 MHz, DMSO) d 2.96 (s, 3H), 3.00 (s, 3H), 4.58 (d, J=4.4 Hz, 2H), 7.46 (d, J=8.4 Hz, 2H), 8.27-8.29 (m, 2H), 8.88 (s, 1H) and 10.09 (s, 1H) ppm; MS (ES$^+$) 301.13

Step 3: 4-(5-amino-6-(5-(benzylamino)-1,3,4-oxadiazol-2-yl)pyrazin-2-yl)-N,N-dimethylbenzamide A mixture of 4-(5-amino-6-(hydrazinecarbonyl)pyrazin-2-yl)-N,N-dimethylbenzamide (75 mg, 0.2497 mmol), isothiocyanatomethylbenzene (37.26 mg, 33.12 μL, 0.2497 mmol) and dry THF (1.500 mL) was stirred at RT for 4 hours. The reaction mixture was evaporated to dryness and treated with DCM followed by EDC (71.81 mg, 0.3746 mmol) and the resultant mixture allowed to stir at RT overnight. The reaction mixture was filtered and the resultant green precipitate dried under vacuum (78 mg, 73% Yield). 1H NMR (400.0 MHz, DMSO) d 2.96 (s, 3H), 3.00 (s, 3H), 4.50 (d, J=6.1 Hz, 2H), 7.29 (d, J=7.2 Hz, 1H), 7.35-7.42 (m, 4H), 7.51-7.53 (m, 2H), 7.65 (br s, 2H), 8.06 (dd, J=1.5, 6.9 Hz, 2H) and 8.81 (d, J=12.4 Hz, 2H) ppm; MS (ES$^+$) 416.2

The following compounds were all prepared using a method similar to the one described for Compound IA-55 above.

Compound IA-103 4-[5-amino-6-[5-(2-methoxyanilino)-1,3,4-oxadiazol-2-yl]pyrazin-2-yl]-N,N-dimethyl-benzamide 1H NMR (400.0 MHz, DMSO) d 3.03 (s, 3H), 3.07 (s, 3H), 3.94 (s, 3H), 7.07-7.10 (m, 1H), 7.15-7.17 (m, 2H), 7.59 (d, 2H), 7.75 (br s, 2H), 8.12-8.19 (m, 3H), 8.94 (s, 1H) and 10.17 (s, 1H) ppm; MS (ES$^+$) 432.16

389

Compound IA-129 4-[5-amino-6-[5-[[(1S)-1-(4-chlorophenyl)ethyl]amino]-1,3,4-oxadiazol-2-yl]pyrazin-2-yl]-N,N-dimethyl-benzamide 1H NMR (400.0 MHz, DMSO) d 1.50 (d, 3H), 2.96 (s, 3H), 3.01 (s, 3H), 4.83 (d, 1H), 7.40-7.47 (m, 4H), 7.51-7.54 (m, 4H), 8.06 (d, 2H), 8.81 (s, 1H) and 8.90 (br s, 1H) ppm; MS (ES+) 464.16

Compound IA-156 4-[5-amino-6-[5-(phenethylamino)-1,3,4-oxadiazol-2-yl]pyrazin-2-yl]-N,N-dimethyl-benzamide 1H NMR (400.0 MHz, DMSO) d 2.77 (s, 1H), 2.94 (t, 4H), 3.00 (s, 3H), 3.04 (s, 1H), 3.51-3.56 (m, 2H), 7.22-7.24 (m, 1H), 7.28-7.34 (m, 4H), 7.52 (d, 2H), 7.61 (s, 1H), 8.05-8.07 (m, 2H), 8.32 (t, 1H) and 8.81 (s, 1H) ppm; MS (ES+) 430.2

Compound IA-163 4-[5-amino-6-[5-(cyclohexylamino)-1,3,4-oxadiazol-2-yl]pyrazin-2-yl]-N,N-dimethyl-benzamide 1H NMR (400.0 MHz, DMSO) d 1.17-1.19 (m, 1H), 1.30-1.35 (m, 4H), 1.57-1.60 (m, 1H), 1.74-1.76 (m, 2H), 1.99 (s, 2H), 2.96 (s, 3H), 3.00 (s, 3H), 3.48 (br s, 1H), 7.52 (d, 2H), 7.62 (br s, 2H), 8.06 (d, 2H), 8.20 (d, 1H) and 8.81 (s, 1H) ppm; MS (ES+) 408.22

Compound IA-254 4-[5-amino-6-[5-(3-cyanoanilino)-1,3,4-oxadiazol-2-yl]pyrazin-2-yl]-N,N-dimethyl-benzamide 1H NMR (400.0 MHz, DMSO) d 2.97 (s, 3H), 3.01 (s, 3H), 7.54 (t, 3H), 7.63 (t, 1H), 7.75 (br s, 1H), 7.91 (dd, 2H), 8.09-8.13 (m, 3H), 8.91 (s, 1H) and 11.51 (s, 1H) ppm; MS (ES+) 427.15

Compound IA-278 4-[6-(5-acetamido-1,3,4-oxadiazol-2-yl)-5-amino-pyrazin-2-yl]-N,N-dimethyl-benzamide 1H NMR (400.0 MHz, DMSO) d 2.20 (s, 3H), 2.96 (s, 3H), 3.01 (s, 3H), 7.54 (d, 2H), 7.66 (br s, 2H), 8.08 (d, 2H), 8.92 (s, 1H) and 11.92 (s, 1H) ppm; MS (ES+) 368.13

Compound IA-287 4-[5-amino-6-(5-benzamido-1,3,4-oxadiazol-2-yl)pyrazin-2-yl]-N,N-dimethyl-benzamide 1H NMR (400.0 MHz, DMSO) d 2.96 (s, 3H), 3.00 (s, 3H), 3.31 (s, 1H), 7.52-7.61 (m, 4H), 7.69 (t, 2H), 8.06-8.12 (m, 4H), 8.95 (s, 1H) and 12.35 (br s, 1H) ppm; MS (ES+) 430.14

Example 4A (4-(5-amino-6-(5-phenyl-1,3,4-thiadiazol-2-yl)pyrazin-2-yl)phenyl)(1,4-diazepan-1-yl)methanone (Compound IA-68 or Compound IV-2)

SCHEME

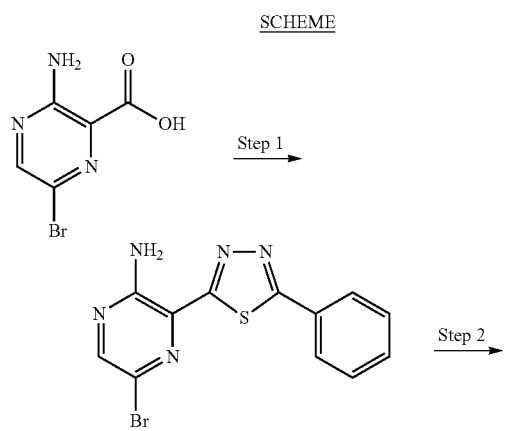

-continued

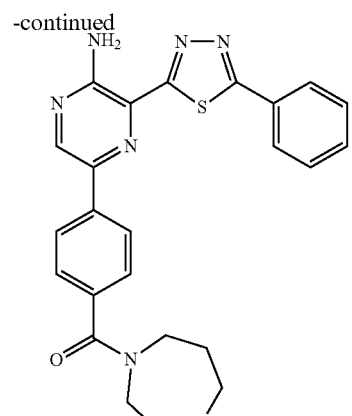

Compound IA-68

Compound IA-68 was prepared using Method IV-D, Steps 1-2.

Method IV-D

Step 1: 5-bromo-3-(5-phenyl-1,3,4-thiadiazol-2-yl)pyrazin-2-amine 3-amino-6-bromo-pyrazine-2-carboxylic acid (1.000 g, 4.588 mmol) and benzenecarbothiohydrazide (759.1 mg, 4.588 mmol) were suspended in acetonitrile (25.00 mL), cooled in an ice bath and then treated with dibromotriphenyl-phosphorane (4.453 g, 10.55 mmol) The reaction mixture was allowed to stir in an ice bath for 2 hours and then DIPEA (1.778 g, 2.396 mL, 13.76 mmol) was added slowly at 10° C. The reaction was left to stir at 0-10° C. for a further hour and the resultant precipitate was isolated by filtration, washed with a small amount of acetonitrile and dried (659 mg, 43% Yield). MS (ES+) 335.93

Step 2: (4-(5-amino-6-(5-phenyl-1,3,4-thiadiazol-2-yl)pyrazin-2-yl)phenyl)(1,4-diazepan-1-yl)methanone 5-bromo-3-(5-phenyl-1,3,4-thiadiazol-2-yl)pyrazin-2-amine (70 mg, 0.1257 mmol) and [4-(4-tert-butoxycarbonyl-1,4-diazepane-1-carbonyl)phenyl]boronic acid (43.77 mg, 0.1257 mmol) (60% pure) were taken into dioxane (700.1 µL), treated with Na2CO3 (125.7 µL of 2 M, 0.2514 mmol) and degassed/nitrogen flushed (5×). The reaction was then treated with palladium; triphenylphosphane (14.53 mg, 0.01257 mmol), degassed again and heated in the microwave at 140° C. for 30 minutes. The reaction was treated with EtOAc and brine, the organics separated, dried over MgSO4, filtered and concentrated under vacuum. The product was purified by column chromatography eluting 50% EtOAc/Petroleum ether followed by 10% MeOH/DCM to give the desired product which was dissolved in DCM (2.000 mL) and treating with TFA (2.960 g, 2.000 mL, 25.96 mmol). After stirring at RT for 30 minutes and concentration, the residue was purified by reverse phase preparative HPLC [Waters Sunfire C18, 10 mM, 100 Å column, gradient 10%-95% B (solvent A: 0.05% TFA in water; solvent B: CH$_3$CN) over 16 minutes at 25 mL/min]. The fractions were collected, passed through a sodium bicarbonate cartridge and freeze-dried to give the title compound (42 mg, 74% Yield). 1H NMR (400.0 MHz, DMSO) d 1.60 (1H, m), 1.77 (1H, m), 2.72-2.39 (4H, m, 3.40 (2H, m), 3.60-3.67 (2H, m), 7.52 (2H, d), 7.58-7.65 (3H, m), 7.99 (1H, m), 8.00 (2H, br s), 8.10-8.14 (3H, m), 8.95 (1H, s); MS (ES$^+$) 458.07

Example 5

4-(5-amino-6-(5-phenyl-1,2,4-oxadiazol-3-yl) pyrazin-2-yl)phenyl)(1,4-diazepan-1-yl)methanone (Compound IA-2)

Method IV-E

Step 1: 3-amino-6-bromo-N-hydroxypyrazine-2-carboximidamide

A mixture of 3-amino-6-bromo-pyrazine-2-carbonitrile (1 g, 5.025 mmol) was dissolved in MeOH (20.00 mL) and cooled to 0° C. Hydroxylamine hydrochloride (349.2 mg, 5.025 mmol) and triethylamine (508.5 mg, 700.4 μL, 5.025 mmol) were added and the reaction allowed to warm to ambient temperature. After 2 hours the resultant precipitate was filtered off and dried (898 mg, 77% Yield). MS (ES$^+$) 234.89

Step 2: 3-amino-6-bromo-N'-(phenylcarbonyloxy) pyrazine-2-carboximidamide 3-amino-6-bromo-N'-hydroxypyrazine-2-carboximidamide (890 mg, 3.836 mmol) was suspended in dichlo-

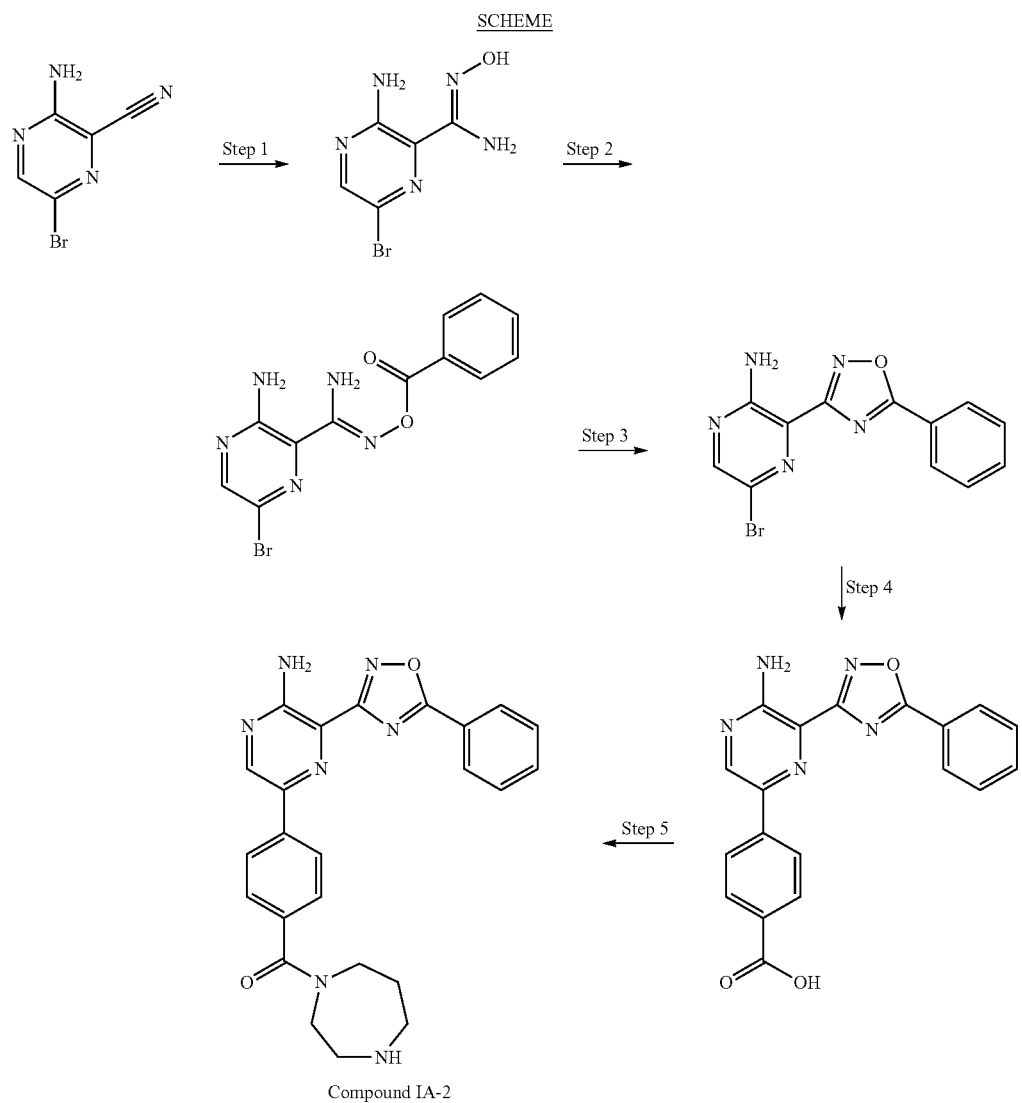

Compound IA-2

Compound IA-2 was prepared using Method IV-E, Steps 1-5.

romethane (11.56 mL) and treated with triethylamine (427.0 mg, 588.2 μL, 4.220 mmol) followed by benzoyl chloride (593.2 mg, 489.8 μL, 4.220 mmol) The reaction mixture was allowed to stir for 1 hour and concentrated in vacuo. The resultant residue was triturated with methanol to give the desired product as a pale beige solid (891 mg, 69% Yield). 1H NMR (400.0 MHz, DMSO) d 7.55 (2H, m), 7.65 (1H, m), 7.90 (2H, br s), 8.28 (2H, m), 8.33 (1H, s); MS (ES$^+$) 337.87

Step 3: 5-bromo-3-(5-phenyl-1,2,4-oxadiazol-3-yl)pyrazin-2-amine 3-amino-N'-(benzoyloxy)-6-bromopyrazine-2-carboximidamide (890 mg, 2.648 mmol) and polyphosphonic acid (3.560 mL) were mixed and the reaction heated to 70° C. Further polyphosphonic acid (8.900 mL) was added and the reaction allowed to stir for a further 3 hours at 70° C. The mixture was then allowed to cool to RT, diluted with water and neutralised by the portionwise addition of solid NaHCO$_3$. The resulting precipitate was isolated by filtration and dried (643 mg, 76% Yield). 1H NMR (400.0 MHz, DMSO) d 7.49 (2H, br s), 7.69 (2H, m), 7.77 (1H, m), 8.28 (2H, m), 8.43 (1H, s); MS (ES$^+$) 319.89

Step 4: 4-(5-amino-6-(5-phenyl-1,2,4-oxadiazol-3-yl)pyrazin-2-yl)benzoic acid 5-bromo-3-(5-phenyl-1,2,4-oxadiazol-3-yl)pyrazin-2-amine (200 mg, 0.6287 mmol) 4-carboxyphenylboronic acid (104.3 mg, 0.6287 mmol) and Na$_2$CO$_3$ (133.2 mg, 1.257 mmol) were suspended in MeCN (3.314 mL)/water (3.314 mL) and the mixture de-gassed (×5) and treated with Pd(PPh$_3$)$_4$ (72.65 mg, 0.06287 mmol). The reaction was de-gassed again and heated at 110° C. in the microwave for 30 minutes. The mixture was concentrated to half its original volume and washed with DCM. The aqueous phase was acidified to pH4 (2M HCl) and resulting precipitate collected, washed with water and dried under vacuum (172 mg, 76% Yield). 1H NMR (400.0 MHz, DMSO) d 7.41 (2H, br s), 7.69 (2H, m), 7.76 (1H, m), 7.98 (2H, m), 8.09 (2H, m), 8.29 (2H, m), 8.94 (1H, s); MS (ES$^+$) 360.98

Step 5: 4-(5-amino-6-(5-phenyl-1,2,4-oxadiazol-3-yl)pyrazin-2-yl)phenyl)(1,4-diazepan-1-yl)methanone A solution of 4-[5-amino-6-(5-phenyl-1,2,4-oxadiazol-3-yl)pyrazin-2-yl]benzoic acid (80 mg, 0.2226 mmol), CDI (72.19 mg, 0.4452 mmol), DIPEA (86.31 mg, 116.3 μL, 0.6678 mmol), DMAP (2.719 mg, 0.02226 mmol) in DMSO (1.370 mL) was treated with 1,4-diazepane (66.89 mg, 0.6678 mmol) and the resulting solution stirred at RT overnight. An additional equivalent of 1,4-diazepane (22.30 mg, 0.2226 mmol) was added and the reaction mixture allowed to stir for a further night. The reaction mixture was treated with water and the aqueous layer extracted with EtOAc. The layers were separated and the organics dried (MgSO$_4$), concentrated in vacuo and purified by reverse phase preparative HPLC [Waters Sunfire C18, 10 mM, 100 Å column, gradient 10%-95% B (solvent A: 0.05% TFA in water; solvent B: CH$_3$CN) over 16 minutes at 25 mL/min]. The fractions were collected and freeze-dried to give the title compound as a yellow solid (58.1 mg, 39% Yield). 1H NMR (400.0 MHz, DMSO) d 1.96-2.04 (2H, m), 3.25-3.85 (8H, m—with water signal), 7.47 (2H, br s), 7.60 (2H, m), 7.71 (2H, m), 7.79 (1H, m), 8.16 (2H, m), 8.29 (2H, m), 8.77 (2H, m), 8.97 (1H, s); MS (ES$^+$) 442.02

Example 6A 4-(5-amino-6-(3-phenylisoxazol-5-yl)pyrazin-2-yl)phenyl)(1,4-diazepan-1-yl)methanone (Compound IIA-3)

SCHEME

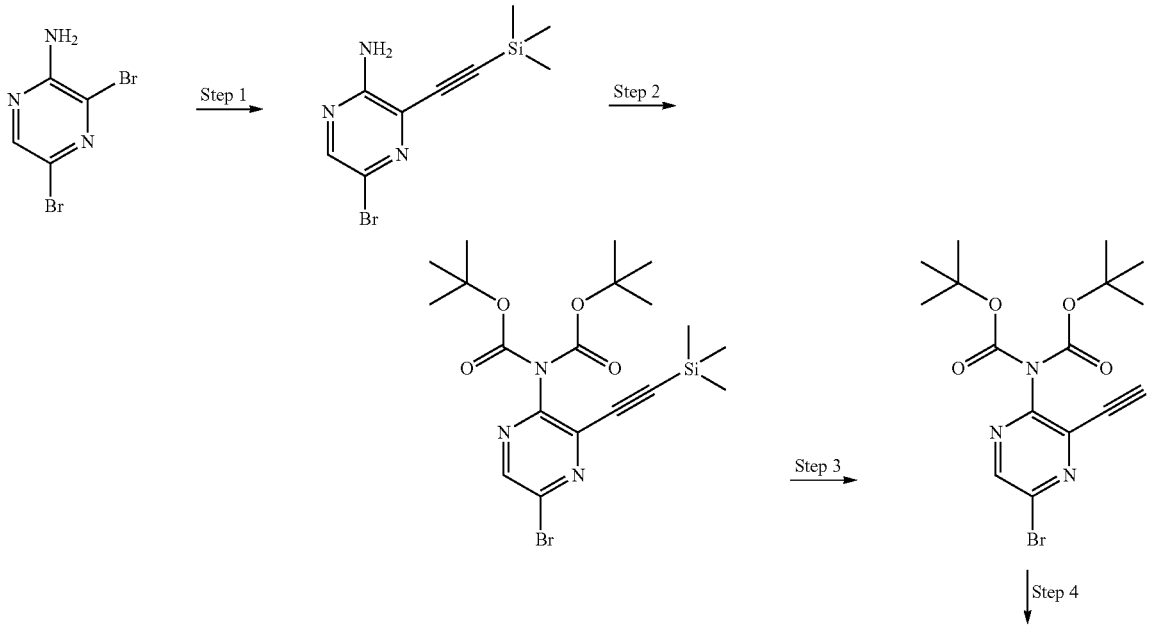

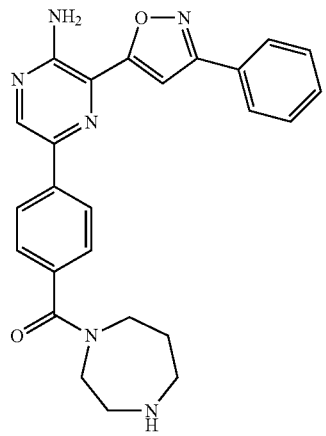

Compound IIA-3

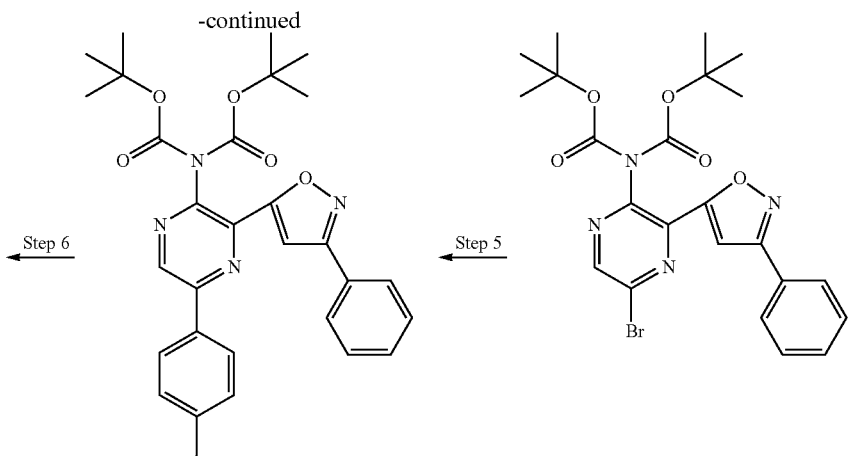

Compound IIA-3 was prepared using Method IV-F, Steps 1-6.

Method IV-F

Step 1:
5-bromo-3-((trimethylsilyl)ethynyl)pyrazin-2-amine (Trimethylsilyl)acetylene (1.845 g, 2.655 mL, 18.78 mmol) was added dropwise to a solution of 3,5-dibromopyrazin-2-amine (5 g, 19.77 mmol), triethylamine (10.00 g, 13.77 mL, 98.85 mmol), Copper(I) iodide (451.7 mg, 2.372 mmol) and Pd(PPh$_3$)$_4$ (1.142 g, 0.9885 mmol) in DMF (25.00 mL) and the resulting solution stirred at RT for 30 minutes. The reaction mixture was diluted with EtOAc and water and the layers separated. The aqueous layer was extracted further with EtOAc and the combined organics washed with water, dried (MgSO$_4$) and concentrated in vacuo. The residue was purified by column chromatography eluting with 15% EtOAc/Petroleum ether to give the product as a yellow solid (3.99 g, 75% Yield). 1H NMR (400.0 MHz, DMSO) d 0.30 (9H, s), 8.06 (1H, s); MS (ES$^+$) 271.82

Step 2: tert-butyl N-tert-butoxycarbonyl-N-[5-bromo-3-((trimethylsilyl)ethyynyl)pyrazin-2-yl]carbamate 5-bromo-3-(2-trimethylsilylethynyl)pyrazin-2-amine (2.85 g, 10.55 mmol) was dissolved in DCM (89.06 mL) and treated with BOC anhydride (6.908 g, 7.272 mL, 31.65 mmol) followed by DMAP (128.9 mg, 1.055 mmol). The reaction was allowed to stir at ambient temperature for 2 hours and then diluted with DCM and NaHCO$_3$ and the layers separated. The aqueous layer was extracted further with DCM, dried (MgSO$_4$), filtered and concentrated in vacuo. The resultant residue was purified by column chromatography eluting with dichloromethane to give the desired product as a colourless oil (4.95 g, 99% Yield). 1H NMR (400.0 MHz, DMSO) d 0.27 (9H, s), 1.42 (18H, s), 8.50 (1H, s); MS (ES$^+$) 472.09

Step 3: tert-butyl N-(5-bromo-3-ethynyl-pyrazin-2-yl)-N-tert-butoxycarbonyl-carbamate Sodium carbonate (918.5 µL of 2 M, 1.837 mmol) was added to a solution of tert-butyl N-[5-bromo-3-(2-trimethylsilylethynyl)pyrazin-2-yl]-N-tert-butoxycarbonyl-carbamate (720 mg, 1.531 mmol) in DMF (2 mL) and the resulting solution heated at 90° C. for 20 minutes. The reaction mixture was allowed to cool to RT and diluted with EtOAc and water and the layers separated. The aqueous layer was extracted further with EtOAc and the combined organics washed with water, dried (MgSO$_4$) and concentrated in vacuo to give the product as a yellow solid (574 mg, 94% Yield). 1H NMR (400.0 MHz, DMSO) d 1.43 (18H, s), 3.53 (1H, s), 8.55 (1H, s); MS (ES$^+$) 400.03

Step 4: tert-butyl N-[5-bromo-3-(3-phenylisoxazol-5-yl)pyrazin-2-yl]-N-tert-butoxycarbonyl-carbamate Triethylamine (50.82 mg, 70.00 µL, 0.5022 mmol) was added to a solution of tert-butyl N-(5-bromo-3-ethynyl-pyrazin-2-yl)-N-tert-butoxycarbonyl-carbamate (200 mg, 0.5022 mmol) and N-hydroxybenzimidoyl chloride (78.13 mg, 0.5022 mmol) in THF (16.00 mL) and the reaction mixture stirred at RT for 1 hour. After this time the reaction mixture was heated under reflux for 3 hours, cooled to RT and concentrated in vacuo. The residue was purified by column chromatography eluting with 10% EtOAc/Petroleum ether to give the product as a colourless oil that crystallised on standing (182 mg, 70% Yield). 1H NMR (400.0 MHz, DMSO) d 1.41 (18H, s), 7.37 (1H, s), 7.52 (3H, m), 7.90 (2H, m), 8.68 (1H, s); MS (ES$^+$) 519.05

Step 5: 4-(5-(bis(tert-butoxycarbonyl)amino)-6-(3-phenylisoxazol-5-yl)pyrazin-2-yl)benzoic Acid Tert-butyl N-[5-bromo-3-(3-phenylisoxazol-5-yl)pyrazin-2-yl]-N-tert-butoxycarbonyl-carbamate (184 mg, 0.3379 mmol), 4-boronobenzoic acid (56.07 mg, 0.3379 mmol) and Na$_2$CO$_3$ (71.63 mg, 0.6758 mmol) were suspended in MeCN (2.896 mL)/water (2.896 mL) and the mixture de-gassed (×5) and treated with Pd(PPh$_3$)$_4$ (39.05 mg, 0.03379 mmol). The reaction was de-gassed again and heated at 110° C. in the microwave for 30 minutes. The reaction mixture was concentrated to half its original volume and washed with DCM. The aqueous phase was acidified to pH4 by (2M HCl) and resulting precipitate collected, washed with water and dried under vacuum (120 mg, 99% Yield). MS (ES$^+$) 359.12

Step 6: 4-(5-amino-6-(3-phenylisoxazol-5-yl)pyrazin-2-yl)phenyl)(1,4-diazepan-1-yl)methanone To a solution of 4-[5-amino-6-(3-phenylisoxazol-5-yl)pyrazin-2-yl]benzoic acid (120 mg, 0.3349 mmol), CDI (108.6 mg, 0.6698 mmol), DIPEA (129.9 mg, 175.1 μL, 1.005 mmol), DMAP (4.091 mg, 0.03349 mmol) in DMSO (2.054 mL) was added tert-butyl 1,4-diazepane-1-carboxylate (201.3 mg, 1.005 mmol) and the resulting solution stirred at RT for 3 hours. After this time water was added and the aqueous layer extracted with EtOAc, and the combined organics dried (MgSO₄) and concentrated in vacuo. The resultant residue was taken up in DCM (3.000 mL) and treated with TFA (763.7 mg, 516.0 μL, 6.698 mmol) and the mixture stirred overnight at RT. The mixture was concentrated in vacuo and the residue taken up in dichloromethane (5 mL) and washed with NaHCO₃ aqueous solution. The organic layer was dried (MgSO₄), concentrated in vacuo and purified by reverse phase preparative HPLC [Waters Sunfire C18, 10 mM, 100 Å column, gradient 10%-95% B (solvent A: 0.05% TFA in water; solvent B: CH₃CN) over 16 minutes at 25 mL/min]. The fractions were collected and freeze-dried to give the title compound as a yellow solid (68.7 mg, 37% Yield). 1H NMR (400.0 MHz, DMSO) d 1.95 (2H, m), 3.25-3.96 (8H, m partially hidden by water peak), 7.08 (2H, br s), 7.54-7.61 (5H, m), 7.78 (1H, s), 8.03-8.05 (2H, m), 8.19 (2H, m), 8.72 (2H, br s), 8.89 (1H, s); MS (ES⁺) 441.21

Example 7

5-(pyridin-3-yl)-3-(5-(thiophen-2-yl)-4H-1,2,4-triazol-3-yl)pyrazin-2-amine (Compound IIIA-4)

Compound IIIA-4 was prepared using Method IV-G, Steps 1-5.

Method IV-G

Step 1: Methyl 3-amino-6-bromopyrazine-2-carboxylate

A mixture of methyl 3-aminopyrazine-2-carboxylate (8.35 g, 54.53 mmol) and N-bromo-succinimide (9.705 g, 54.53 mmol) were stirred in MeCN (100 mL) at room temp for 16 hours. The resultant precipitate was filtered, washed with MeCN and dried under vacuum to give the desired product as a yellow solid (11.68 g, 92%). 1H NMR (400.0 MHz, DMSO) d 3.85 (3H, s), 7.55 (2H, br s), 8.42 (1H, s); MS (ES⁺) 233.78

Step 2: 3-amino-6-(pyridin-3-yl)pyrazine-2-carboxylic Acid

A mixture of methyl 3-amino-6-bromo-pyrazine-2-carboxylate (8 g, 34.48 mmol), diethyl-(3-pyridyl)borane (6.084 g, 41.38 mmol), dichloropalladium; triphenylphosphane (1.210 g, 1.724 mmol), disodium carbonate (51.70 mL of 2 M, 103.4 mmol) in DME (100 mL) were heated at 80° C. for 16 hours. The reaction mixture was cooled and treated with EtOAc and the resultant precipitate was isolated by filtration. Water was added to the solid and then the suspension heated and filtered hot. The solution was then allowed to cool and then acidified (AcOH) to approx pH 5. The precipitate was collected and washed with MeOH and dried under vacuum (6.23 g, 84% Yield). 1H NMR (400.0 MHz, DMSO) d 7.47 (1H, m), 7.60 (2H, br s), 8.42-8.57 (2H, m), 8.97 (1H, s), 9.26 (1H, m); MS (ES⁺) 216.89

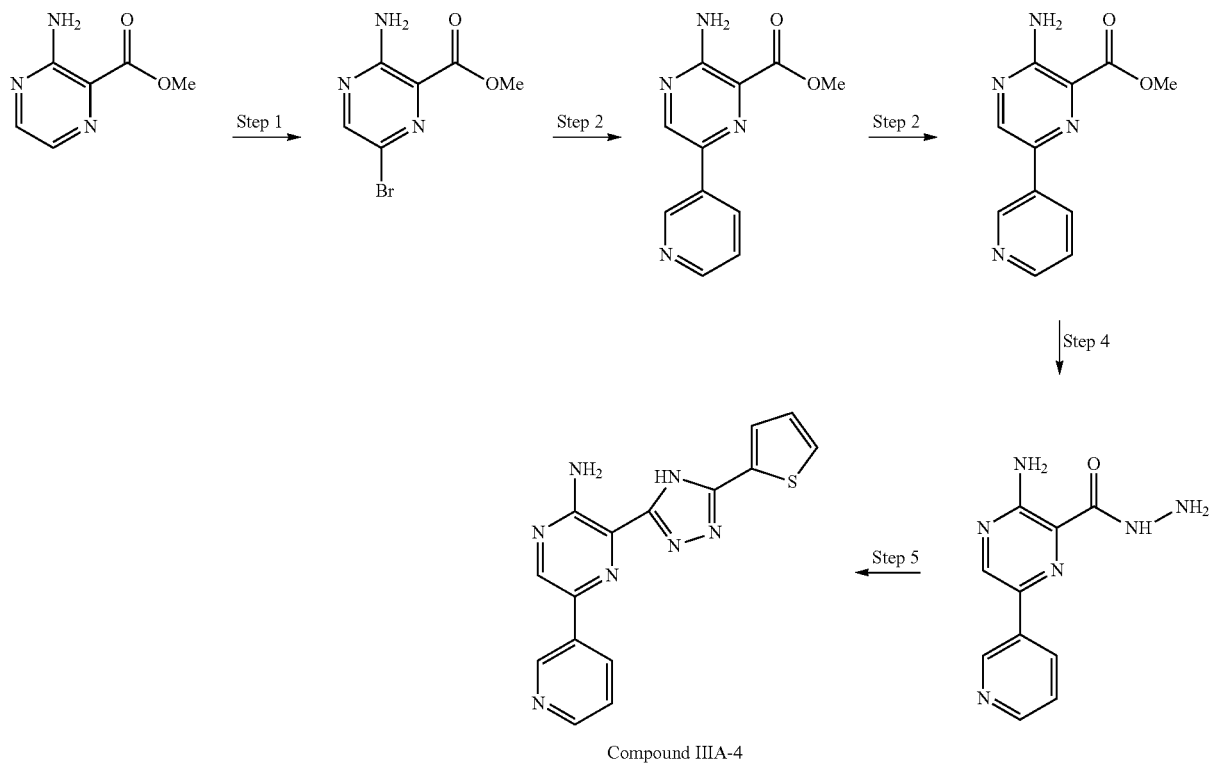

Compound IIIA-4

Step 3: Methyl 3-amino-6-(pyridin-3-yl)pyrazine-2-carboxylate

To 3-amino-6-(3-pyridyl)pyrazine-2-carboxylic acid (2 g, 9.251 mmol) in MeOH (50 mL) was added conc. $H_2SO_4$ (907.3 mg, 493.1 μL, 9.251 mmol) and the mixture heated to reflux for 2 hours. The solvent was removed under vacuum and the mixture neutralised with aqueous $Na_2CO_3$ and the resulting solid collected by filtration and dried to give the desired product (2.08 g, 97% Yield). MS (ES$^+$) 231.87

Step 4: 3-amino-6-(pyridin-3-yl)pyrazine-2-carbohydrazide

Methyl 3-amino-6-(3-pyridyl)pyrazine-2-carboxylate (2 g, 8.687 mmol) was heated in hydrazine (1.392 g, 1.363 mL, 43.43 mmol) with a minimal amount of MeOH (5 mL) added at 80° C. for 2 hours. The reaction was treated with water and the product collected by filtration, washed with methanol and dried to give the desired product as a brown solid (1.17 g, 58% Yield). 1H NMR (400.0 MHz, DMSO) d 7.43 (1H, m), 7.47 (2H, br s), 8.54 (2H, m), 8.90 (1H, s), 9.38 (1H, m), 10.16 (1H, br s); MS (ES$^+$) 231.96

Step 5: 5-(pyridin-3-yl)-3-(5-(thiophen-2-yl)-4H-1,2,4-triazol-3-yl)pyrazin-2-amine 3-amino-6-(3-pyridyl)pyrazine-2-carbohydrazide (40 mg, 0.173 mmoles), thiophene-2-carboxamidine (21.92 mg, 0.173 mmoles) and sodium ethanolate (11.82 mg, 0.173 mmoles) were added to a microwave vial. DMF (1 mL) was then added and the vial sealed and heated in the microwave at 160° C. for 40 minutes. The reaction mixture was filtered and purified by reverse phase preparative HPLC [Waters Sunfire C18, 10 mM, 100 Å column, gradient 10%-95% B (solvent A: 0.05% TFA in water; solvent B: $CH_3CN$) over 16 minutes at 25 mL/min]. The fractions were collected and freeze-dried to give the title compound (23.4 mg, 31% Yield). 1H NMR (400.0 MHz, DMSO-d6) δ 14.96 (s, 1H), 9.55 (s, 1H), 8.99 (s, 1H), 8.84 (d, J=6.1 Hz, 1H), 8.69 (dd, J=1.2, 4.9 Hz, 1H), 7.95 (s, 2H), 7.81 (d, J=3.0 Hz, 1H), 7.73-7.68 (m, 2H) and 7.22 (dd, J=3.8, 4.8 Hz, 1H) ppm; MS (ES$^+$) 323.10

Example 8A

N-(2-(5-amino-6-(5-phenyl-1,3,4-oxadiazol-2-yl)pyrazin-2-yl)phenyl)ethanamide (Compound IA-267)

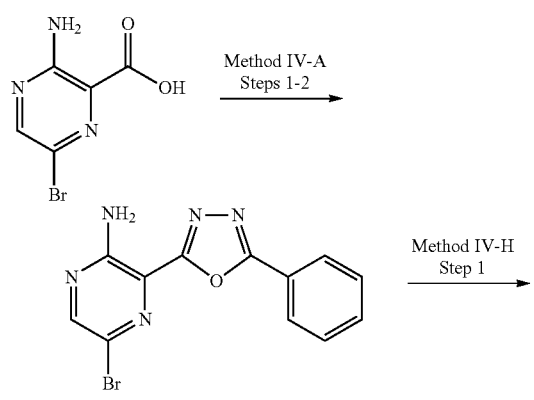

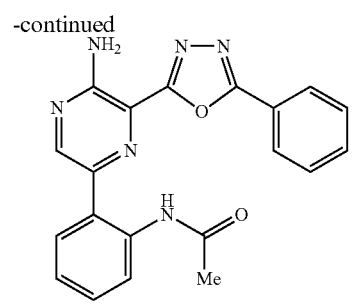

Compound IA-267

Compound IA-267 was prepared using Method IV-A, Steps 1-2, followed by Method IV-H, Step 1.

Method II-H: Step 1: N-(2-(5-amino-6-(5-phenyl-1,3,4-oxadiazol-2-yl)pyrazin-2-yl)phenyl)ethanamide A solution of 5-bromo-3-(5-phenyl-1,3,4-oxadiazol-2-yl)pyrazin-2-amine (100 mg, 0.31 mmol), 2-ethanamidophenylboronic acid (56.25 mg, 0.31 mmol), tetrakis(triphenylphosphine)palladium (18.17 mg, 0.015 mmol) and $Na_2CO_3$ (471 μL, 2M aqueous solution) were added to a 10 mL microwave vial. Dioxane (3 mL) was then added and the vial sealed. The reaction mixture was heated in the microwave at 150° C. for 30 min. After this time methanol was added and the reaction mixture filtered. The solid was then washed with water (5 mL) and MeOH (5 mL) and dried under vacuum to give the product (31.0 mg, 28% yield); 1H NMR (400.0 MHz, DMSO) d 2.04 (s, 3H), 7.26 (t, 1H), 7.44-7.40 (m, 1H), 7.69-7.67 (m, 4H), 7.80 (d, 2H), 8.15-8.13 (m, 3H), 8.73 (s, 1H) and 10.76 (s, 1H) ppm; MS (ES$^+$) 373.0

The following compounds were all prepared using the method described for Compound IA-267 above.

Compound IA-75 1H NMR (400.0 MHz, DMSO) 3.25 (s, 3H), 7.63 (s, 1H), 7.63 (dd, 2H), 7.74 (t, 3H), 7.90 (dd, 1H), 8.09 (dd, 2H), 8.40 (dd, 1H), 8.54 (t, 1H) and 9.00 (s, 1H) ppm; MS (ES$^+$) 394.0

Compound IA-89 5-(4-methylsulfonylphenyl)-3-(5-phenyl-1,3,4-oxadiazol-2-yl)pyrazin-2-amine; MS (ES$^+$) 393.0

Compound IA-93 5-(1-naphthyl)-3-(5-phenyl-1,3,4-oxadiazol-2-yl)pyrazin-2-amine; MS (ES$^+$) 365.0

Compound IA-94 5-(2-(dimethylamino)phenyl)-3-(5-phenyl-1,3,4-oxadiazol-2-yl)pyrazin-2-amine; MS (ES$^+$) 359.0

Compound IA-96 3-(5-phenyl-1,3,4-oxadiazol-2-yl)-5-[3-(trifluoromethyl)phenyl]pyrazin-2-amine; MS (ES$^+$) 384.0

Compound IA-100 3-[5-amino-6-(5-phenyl-1,3,4-oxadiazol-2-yl)pyrazin-2-yl]benzamide; MS (ES$^+$) 359.0

Compound IA-104 3-(5-phenyl-1,3,4-oxadiazol-2-yl)-5-(3-thienyl)pyrazin-2-amine; MS (ES$^+$) 322.0

Compound IA-105 methyl 2-[5-amino-6-(5-phenyl-1,3,4-oxadiazol-2-yl)pyrazin-2-yl]benzoate; 1H NMR (400.0 MHz, DMSO) d 3.61 (s, 3H), 7.56 (m, 1H), 7.65-7.72 (m, 7H), 7.87 (d, 1H), 8.16 (m, 2H) and 8.72 (s, 1H) ppm; MS (ES$^+$) 374.0

Compound IA-110 1-[4-[5-amino-6-(5-phenyl-1,3,4-oxadiazol-2-yl)pyrazin-2-yl]phenyl]ethanone; MS (ES$^+$) 358.0

Compound IA-116 5-(4-isopropylsulfonylphenyl)-3-(5-phenyl-1,3,4-oxadiazol-2-yl)pyrazin-2-amine; 1H NMR (400.0 MHz, DMSO) d 1.20 (d, 6H), 3.47 (t, 1H), 7.66-7.72 (m, 3H), 7.98 (d, 4H), 8.17-8.19 (m, 2H), 8.40 (dd, 2H), and 9.60 (s, 1H) ppm; MS (ES$^+$) 422.0

Compound IA-118 5-(2-((dimethylamino)methyl)phenyl)-3-(5-phenyl-1,3,4-oxadiazol-2-yl)pyrazin-2-amine; MS (ES$^+$) 373.0

Compound IA-125 5-[2-(methoxymethyl)phenyl]-3-(5-phenyl-1,3,4-oxadiazol-2-yl)pyrazin-2-amine; MS (ES$^+$) 360.0

Compound IA-137 2-[2-[5-amino-6-(5-phenyl-1,3,4-oxadiazol-2-yl)pyrazin-2-yl]phenyl]ethanol; 1H NMR (400.0 MHz, DMSO) d 2.89 (t, 2H), 3.74 (s, 2H), 4.61 (s, 1H), 7.32-7.43 (m, 3H), 7.47-7.49 (m, 1H), 7.61-7.69 (m, 5H), 8.13-8.16 (m, 2H) and 8.49 (s, 1H) ppm; MS (ES$^+$) 360.0

Compound IA-141 5-(4-pyridyl)-3-[5-(2-thienyl)-1,3,4-oxadiazol-2-yl]pyrazin-2-amine; 1H NMR (400.0 MHz, DMSO) d 7.22 (t, 1H), 7.38 (t, 1H), 7.80-7.82 (m, 1H), 8.04-8.09 (m, 4H), 8.70 (dd, 2H) and 9.08 (s, 1H) ppm; MS (ES$^+$) 323.1

Compound IA-144 N-[3-[5-amino-6-(5-phenyl-1,3,4-oxadiazol-2-yl)pyrazin-2-yl]phenyl]methanesulfonamide; MS (ES$^+$) 408.0

Compound IA-149 5-(4-ethylsulfonylphenyl)-3-(5-phenyl-1,3,4-oxadiazol-2-yl)pyrazin-2-amine; MS (ES$^+$) 408.0

Compound IA-150 3-(5-phenyl-1,3,4-oxadiazol-2-yl)-5-[3-(trifluoromethoxy)phenyl]pyrazin-2-amine; MS (ES$^+$) 400.0

Compound IA-169 5-[4-(2-dimethylaminoethylsulfonyl)phenyl]-3-(5-phenyl-1,3,4-oxadiazol-2-yl)pyrazin-2-amine 1H NMR (400.0 MHz, DMSO) d 2.81 (s, 6H), 3.43-3.40 (m, 2H), 3.89-3.93 (m, 2H), 7.68-7.73 (m, 3H), 7.90 (br s, 2H), 8.07 (d, 2H), 8.17-8.19 (m, 2H), 8.45 (d, 2H) and 9.10 (s, 1H) ppm; MS (ES$^+$) 451.0

Compound IA-170 5-(3-furyl)-3-(5-phenyl-1,3,4-oxadiazol-2-yl)pyrazin-2-amine; MS (ES$^+$) 306.0

Compound IA-174 3-(5-phenyl-1,3,4-oxadiazol-2-yl)-5-[2(-trifluoromethyl)phenyl]pyrazin-2-amine; MS (ES$^+$) 384.0

Compound IA-176 5-(2-bromophenyl)-3-(5-phenyl-1,3,4-oxadiazol-2-yl)pyrazin-2-amine; MS (ES$^+$) 393.0

Compound IA-182 5-(m-tolyl)-3-(5-phenyl-1,3,4-oxadiazol-2-yl)pyrazin-2-amine; MS (ES$^+$) 330.0

Compound IA-190 5-(2-methylsulfonylphenyl)-3-(5-phenyl-1,3,4-oxadiazol-2-yl)pyrazin-2-amine; MS (ES$^+$) 394.0

Compound IA-197 3-(5-phenyl-1,3,4-oxadiazol-2-yl)-5-[4-(4-piperidylsulfonyl)phenyl]pyrazin-2-amine 1H NMR (400 MHz, DMSO) d 1.76-1.70 (m, 2H), 2.08 (d, 2H), 2.89 (d, 2H), 3.37 (d, 2H), 3.66 (d, 1H), 7.70 (d, 2H), 7.82 (s, 1H), 7.86 (s, 1H), 7.98 (d, 2H), 8.13 (s, 1H), 8.18 (d, 2H), 8.44 (d, 2H), 8.63 (s, 1H) and 9.08 (s, 1H) ppm; MS (ES$^+$) 463.0

Compound IA-202 [3-[5-amino-6-(5-phenyl-1,3,4-oxadiazol-2-yl)pyrazin-2-yl]phenyl]methanol; MS (ES$^+$) 346.0

Compound IA-210 5-(1-ethylpyrazol-4-yl)-3-(5-phenyl-1,3,4-oxadiazol-2-yl)pyrazin-2-amine; MS (ES$^+$) 334.0

Compound IA-216 3-(5-phenyl-1,3,4-oxadiazol-2-yl)-5-(8-quinolyl)pyrazin-2-amine; 1H NMR (400.0 MHz, DMSO) d 7.63-7.71 (m, 4H), 7.82 (t, 3H), 8.10-8.15 (m, 3H), 8.26 (m, 1H), 8.53 (m, 1H), 9.01 (dd, 1H) and 9.14 (s, 1H) ppm; MS (ES$^+$) 366.023

Compound IA-218 4-[5-amino-6-(5-phenyl-1,3,4-oxadiazol-2-yl)pyrazin-2-yl]benzamide; MS (ES$^+$) 359.0

Compound IA-221 2-[2-[5-amino-6-(5-phenyl-1,3,4-oxadiazol-2-yl)pyrazin-2-yl]phenyl]acetonitrile; MS (ES$^+$) 355.0

Compound IA-230 5-(2-methylsulfanylphenyl)-3-(5-phenyl-1,3,4-oxadiazol-2-yl)pyrazin-2-amine; MS (ES$^+$) 362.0

Compound IA-241 5-(2-methylsulfinylphenyl)-3-(5-phenyl-1,3,4-oxadiazol-2-yl)pyrazin-2-amine; MS (ES$^+$) 378.0

Compound IA-244 2-[5-amino-6-(5-phenyl-1,3,4-oxadiazol-2-yl)pyrazin-2-yl]-N,N-dimethyl-benzamide; MS (ES$^+$) 387.0

Compound IA-247 N-[4-[5-amino-6-(5-phenyl-1,3,4-oxadiazol-2-yl)pyrazin-2-yl]phenyl]acetamide; MS (ES$^+$) 373.0

Compound IA-249 1-[3-[5-amino-6-(5-phenyl-1,3,4-oxadiazol-2-yl)pyrazin-2-yl]phenyl]ethanone; 1H NMR (400.0 MHz, DMSO) d 2.70 (s, 3H), 7.67-7.71 (m, 4H), 8.00-8.02 (m, 1H), 8.17 (dd, 2H), 8.39 (d, 1H), 8.64 (d, 1H) and 9.05 (s, 1H) ppm; MS (ES$^+$) 358.0

Compound IA-252 3-[5-amino-6-(5-phenyl-1,3,4-oxadiazol-2-yl)pyrazin-2-yl]benzonitrile; MS (ES$^+$) 341.0

Compound IA-253 3-(5-phenyl-1,3,4-oxadiazol-2-yl)-5-(2-vinylphenyl)pyrazin-2-amine; MS (ES$^+$) 342.0

Compound IA-259 5-(benzothiophen-7-yl)-3-(5-phenyl-1,3,4-oxadiazol-2-yl)pyrazin-2-amine; MS (ES$^+$) 371.0

Compound IA-260 3-(5-phenyl-1,3,4-oxadiazol-2-yl)-5-(5-quinolyl)pyrazin-2-amine; MS (ES$^+$) 366.0

Compound IA-266 2-[2-[5-amino-6-(5-phenyl-1,3,4-oxadiazol-2-yl)pyrazin-2-yl]phenyl]acetamide; 1H NMR (400.0 MHz, DMSO) d 3.64 (s, 2H), 6.88 (s, 1H), 7.40 (dd, 4H), 7.51-7.53 (m, 1H), 7.62 (s, 1H), 7.67 (dd, 4H), 8.12 (d, 2H) and 8.49 (s, 1H) ppm; MS (ES$^+$) 373.0

Compound IA-271 3-(5-phenyl-1,3,4-oxadiazol-2-yl)-5-(2-piperazin-1-yl-4-pyridyl)pyrazin-2-amine; MS (ES$^+$) 400.0

Compound IA-274 5-(4-methylsulfinylphenyl)-3-(5-phenyl-1,3,4-oxadiazol-2-yl)pyrazin-2-amine 1H NMR (400.0 MHz, DMSO) d 2.81 (s, 3H), 7.69 (d, 3H), 7.83 (d, 3H), 8.16-8.19 (m, 2H), 8.30-8.33 (m, 2H) and 9.02 (s, 1H) ppm; MS (ES$^+$) 377.0

Example 9A

4-[5-amino-6-[5-(2-chloroanilino)-1,3,4-oxadiazol-2-yl]pyrazin-2-yl]-N,N-dimethyl-benzamide (Compound IA-151)

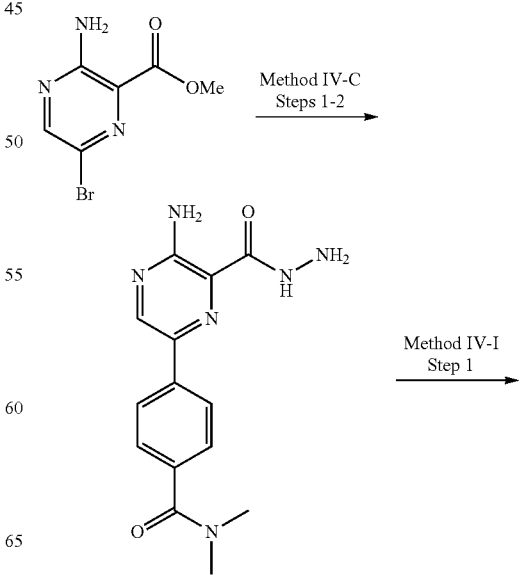

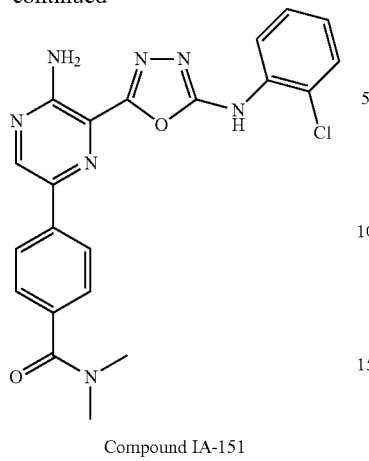

Compound IA-151

Compound IA-151 was prepared using Method IV-C, Steps 1-2, followed by Method IV-I, Step 1.

Method IV-I

Step 1: 4-[5-amino-6-[5-(2-chloroanilino)-1,3,4-oxadiazol-2-yl]pyrazin-2-yl]-N,N-dimethylbenzamide A solution of 2-chloroaniline (31.85 mg, 41.15 µL, 0.2497 mmol) in dichloromethane (2 mL) was slowly added dropwise to a solution of 1,1'-thiocarbonyldiimidazole (53.39 mg, 0.2996 mmol) in dichloromethane (1.5 mL) and the resulting solution stirred at room temperature for 1 h. Additional 1,1'-thiocarbonyldiimidazole (8.9 mg, 0.05 mmol) was added, and the reaction mixture stirred at room temperature overnight. The reaction mixture diluted with water and extracted with dichloromethane (3×5 mL). The organic extracts were dried over MgSO₄, filtered and evaporated to dryness to leave a yellow solid. The solid was re-dissolved in dichloromethane (1.5 mL) and 4-(5-amino-6-(hydrazinecarbonyl)pyrazin-2-yl)-N,N-dimethylbenzamide (75 mg, 0.2497 mmol) added and the reaction mixture stirred at room temperature for 48 h. The reaction mixture was evaporated to dryness and then triturated with EtOAc/Petrol/Ether to give a yellow solid, 4-[5-amino-6-[[(2 chlorophenyl)carbamothioylamino]carbamoyl]pyrazin-2-yl]-N,N-dimethyl-benzamide. This was re-dissolved in dichloromethane (1.5 mL) and EDC (71.81 mg, 0.3746 mmol) added and the resulting solution heated at 40° C. for 3 h. The reaction mixture was cooled to room temperature and concentrated in vacuo and the solid triturated with EtOAc and petroleum ether to yield the product as a yellow solid (28.9 mg, 26% yield); 1H NMR (400.0 MHz, DMSO) d 2.96 (s, 3H), 3.01 (s, 3H), 7.15-7.25 (m, 1H), 7.40-7.49 (m, 1H), 7.53 (d, 3H), 7.70 (br s, 2H), 8.11 (d, 3H), 8.89 (s, 1H) and 10.45 (s, 1H) ppm; MS (ES⁺) 436.11

Example 10A

4-[5-amino-6-[5-(p-tolyl)-1,3,4-oxadiazol-2-yl]pyrazin-2-yl]-N,N-dimethylbenzamide (Compound IA-263)

SCHEME

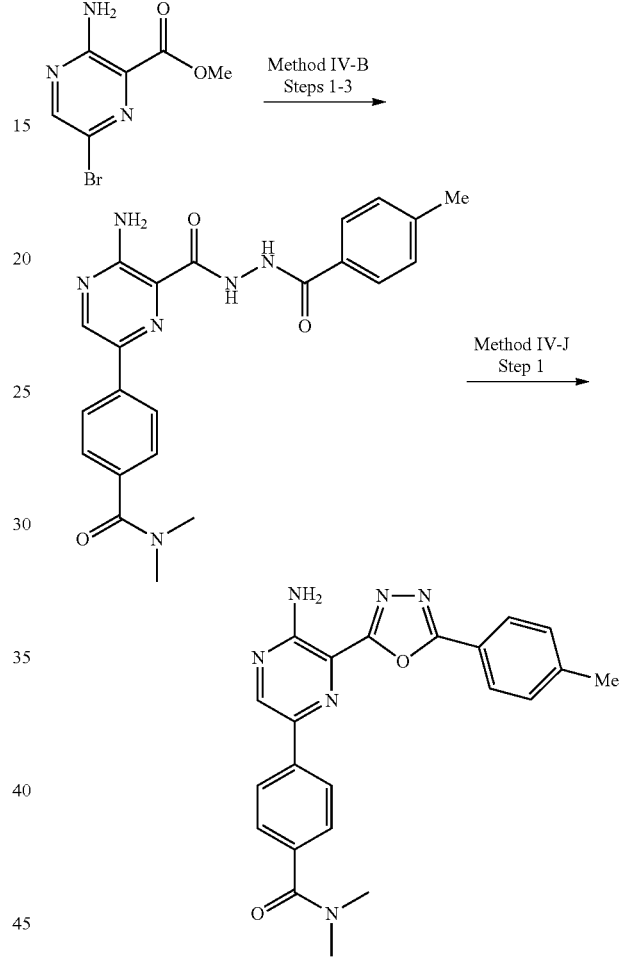

Compound IA-263

Compound IA-263 was prepared using Method IV-B, Steps 1-2, followed by Method IV-J, Step 1.

Method IV-J

Step 1: 4-[5-amino-6-[5-(p-tolyl)-1,3,4-oxadiazol-2-yl]pyrazin-2-yl]-N,N-dimethylbenzamide A solution of 4-[5-amino-6-[[(4-methylbenzoyl)amino]carbamoyl]pyrazin-2-yl]-N,N-dimethyl-benzamide (90 mg, 0.2151 mmol) and POCl₃ (3.298 g, 2.005 mL, 21.51 mmol) was heated at 110° C. for 2 h. After this time the reaction mixture was cooled to room temperature and ice added. Once all of the ice had melted the reaction mixture was extracted with dichloromethane (3×5 mL) and the combined organics dried over MgSO₄ and concentrated in vacuo. The residue was purified by reverse phase preparative HPLC

[Waters Sunfire C18, 10 mM, 100 Å column, gradient 10%-95% B (solvent A: 0.05% TFA in water; solvent B: $CH_3CN$) over 16 minutes at 25 mL/min]. The product fractions combined and lyophilised to leave the product as a yellow solid (21.2 mg, 20% yield); 1H NMR (400.0 MHz, DMSO) d 2.22 (s, 3H), 2.75 (m, 6H), 7.26 (m, 2H), 7.32 (m, 2H), 7.58 (br s, 2H), 7.83 (m, 2H), 7.95 (m, 2H) and 8.77 (1H, s); MS ($ES^+$) 401.15

The following compounds were all prepared using the method described for Compound IA-263 above.

Compound IA-135 4-[5-amino-6-[5-(1-methylpyrrol-2-yl)-1,3,4-oxadiazol-2-yl]pyrazin-2-yl]-N,N-dimethyl-benzamide 1H NMR (400.0 MHz, DMSO) d 2.97 (m, 6H), 4.06 (s, 3H), 6.30 (m, 1H), 7.03 (m, 1H), 7.26 (m, 1H), 7.53-7.55 (m, 2H), 7.77 (br s, 2H), 8.15 (m, 2H) and 8.97 (1H, s) ppm; MS ($ES^+$) 390.14

Example 11A

4-[5-amino-6-[5-(azetidin-1-yl)-1,3,4-oxadiazol-2-yl]pyrazin-2-yl]-N,N-dimethyl-benzamide (Compound IA-192)

SCHEME

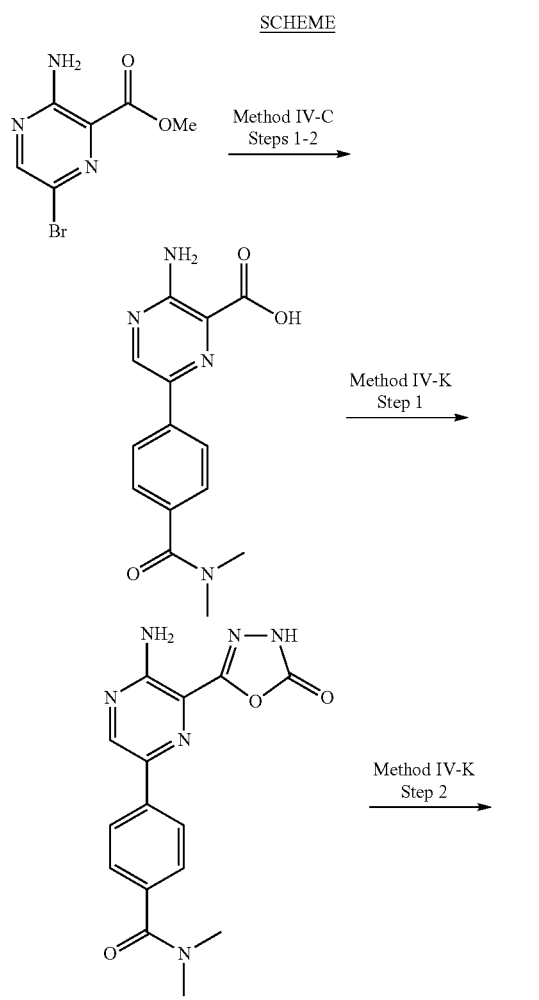

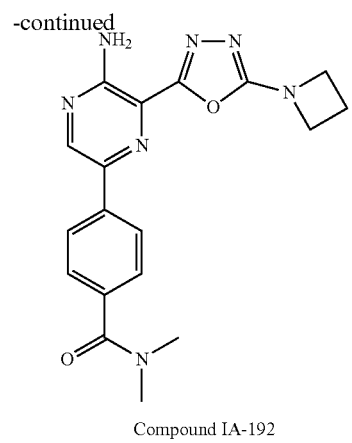

Compound IA-192

Compound IA-192 was prepared using Method IV-C, Steps 1-2, followed by Method IV-K, Steps 1-2.

Method IV-K

Step 1: 4-(5-amino-6-(5-oxo-4,5-dihydro-1,3,4-oxadiazol-2-yl)pyrazin-2-yl)-N,N-dimethylbenzamide DIPEA (86.08 mg, 116.0 µL, 0.6660 mmol) was added to a solution of 4-(5-amino-6-(hydrazine carbonyl)pyrazin-2-yl)-N,N-dimethylbenzamide (100 mg, 0.3330 mmol) in DCM (6.500 mL) under nitrogen. A solution of triphosgene (39.53 mg, 0.1332 mmol) in DCM (100.0 µL) was then added dropwise to the stirred solution. The reaction mixture was stirred at room temperature for 2 h. The reaction mixture was filtered and the solid obtained dried under vacuum to yield the product (106.g mg, 98% yield); 1H NMR (400.0 MHz, DMSO) d 2.96 (s, 3H), 3.00 (s, 3H), 7.33 (br s, 2H), 7.52 (d, 2H), 8.09 (d, 2H), 8.89 (s, 1H) and 12.98 (br s, 1H) ppm; MS ($ES^+$) 327.12

Step 2: 4-[5-amino-6-[5-(azetidin-1-yl)-1,3,4-oxadiazol-2-yl]pyrazin-2-yl]-N,N-dimethylbenzamide DIPEA (38.44 mg, 51.81 µL, 0.2974 mmol), azetidine (8.490 mg, 0.1487 mmol) and bromo(tripyrrolidin-1-yl) phosphonium hexafluorophosphate (76.27 mg, 0.1636 mmol) were added to a solution of 4-(5-amino-6-(5-oxo-4,5-dihydro-1,3,4-oxadiazol-2-yl)pyrazin-2-yl)-N,N-dimethylbenzamide (50 mg, 0.1487 mmol) in DMF (485.1 µL) and the resulting solution stirred at room temperature for 2 h. The reaction mixture was filtered and purified by reverse phase preparative HPLC [Waters Sunfire C18, 10 mM, 100 Å column, gradient 10%-95% B (solvent A: 0.05% TFA in water; solvent B: $CH_3CN$) over 16 minutes at 25 mL/min]. Product fractions were concentrated in vacuo and triturated with dichloromethane/diethyl ether to give the product (8.6 mg, 15% yield); 1H NMR (400.0 MHz, DMSO) d 2.96 (s, 3H), 3.00 (s, 6H), 4.25 (t, 4H), 7.52 (dd, 2H), 7.65 (br s, 1H), 8.04-8.06 (m, 2H) and 8.83 (s, 1H) ppm; MS ($ES^+$) 366.21

The following compounds were all prepared using the method described for Compound IA-192 above.

Compound IA-250 4-[5-amino-6-[5-(N-methylanilino)-1,3,4-oxadiazol-2-yl]pyrazin-2-yl]-N,N-dimethyl-benzamide; MS ($ES^+$) 416.18

Example 12A

4-[5-amino-6-[5-(2-furyl)-1,3,4-oxadiazol-2-yl]pyrazin-2-yl]-N,N-dimethylbenzamide (Compound IA-115)

SCHEME

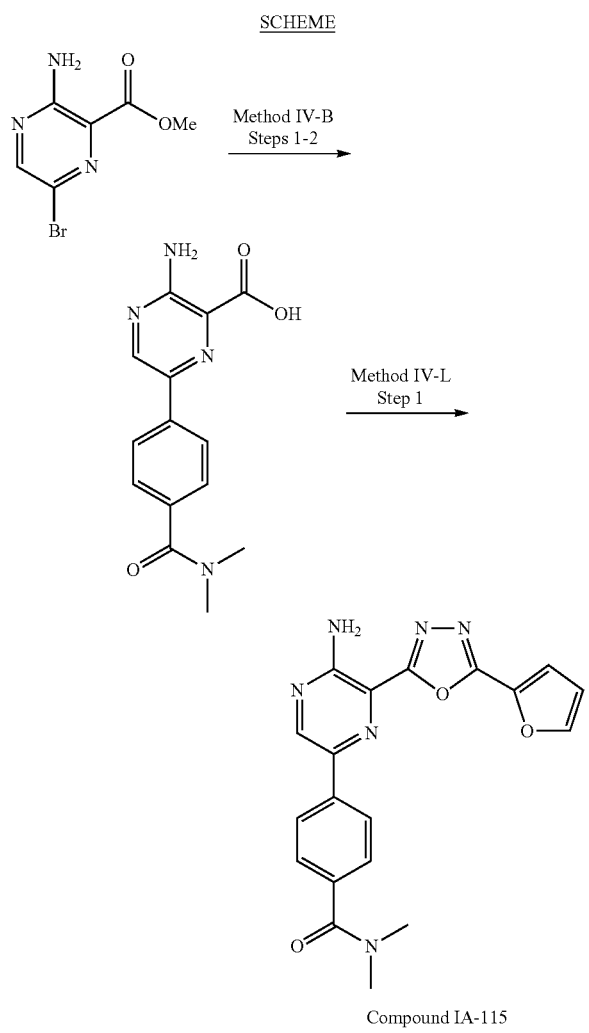

Compound IA-115

Compound IA-115 was prepared using Method IV-B, Steps 1-2, followed by Method IV-L, Step 1.

Method IV-L

Step 1: 4-[5-amino-6-[5-(2-furyl)-1,3,4-oxadiazol-2-yl]pyrazin-2-yl]-N,N-dimethylbenzamide Dibromo(triphenyl)phosphorane was added to a solution of 3-amino-6-[4-(dimethylcarbamoyl)phenyl]pyrazine-2-carboxylic acid (100 mg, 0.35 mmol) and furan 2-carbohydrazide (44.1 mg, 0.35 mmol) in acetonitrile (3.0 mL) at room temperature. Bright yellow solution observed. The resulting solution was stirred at room temperature for 30 min. After this time, DIPEA (304 µL, 1.75 mmol) was added dropwise and the reaction mixture stirred at room temperature for 30 min. The reaction mixture was filtered to leave a yellow solid. The solid was purified by reverse phase preparative HPLC [Waters Sunfire C18, 10 mM, 100 Å column, gradient 10%-95% B (solvent A: 0.05% TFA in water; solvent B: $CH_3CN$) over 16 minutes at 25 mL/min]. Product fractions were freeze dried to give the product as a yellow solid (67.6 mg, 51% yield); 1H NMR (400.0 MHz, DMSO) d 2.97 (m, 6H), 6.87 (m, 1H), 7.54-7.56 (m, 3H), 7.57 (br s, 2H), 8.15 (m, 3H) and 8.98 (1H, s) ppm; MS ($ES^+$) 377.17

The following compounds were all prepared using a method similar to the one described for Compound IA-115 above.

Compound IA-71 4-[5-amino-6-[5-(o-tolyl)-1,3,4-oxadiazol-2-yl]pyrazin-2-yl]-N,N-dimethyl-benzamide 1H NMR (400.0 MHz, DMSO) d 2.74 (s, 3H), 2.98 (m, 6H), 7.48-7.62 (m, 5H), 7.80 (br s, 2H), 8.07 (m, 1H), 8.15 (m, 2H) and 8.99 (1H, s) ppm; MS ($ES^+$) 401.21

Compound IA-87 4-[5-amino-6-[5-(4-hydroxyphenyl)-1,3,4-oxadiazol-2-yl]pyrazin-2-yl]-N,N-dimethyl-benzamide 1H NMR (400.0 MHz, DMSO) d 2.98 (m, 6H), 7.04 (m, 2H), 7.54 (m, 2H), 7.76 (br s, 2H), 8.01 (m, 2H), 8.16 (m, 2H), 8.97 (s, 1H) and 10.42 (s, 1H) ppm; MS ($ES^+$) 403.16

Compound IA-101 4-[5-amino-6-(5-cyclopropyl-1,3,4-oxadiazol-2-yl)pyrazin-2-yl]-N,N-dimethyl-benzamide 1H NMR (400.0 MHz, DMSO) d 1.14-1.18 (m, 2H), 1.22-1.25 (m, 2H), 2.40 (m, 1H), 3.01 (m, 6H), 7.54 (m, 2H), 7.68 (br s, 2H), 8.10 (m, 2H) and 8.93 (s, 1H) ppm; MS ($ES^+$) 351.17

Compound IA-157 4-[5-amino-6-[5-(4-methoxyphenyl)-1,3,4-oxadiazol-2-yl]pyrazin-2-yl]-N,N-dimethyl-benzamide 1H NMR (400.0 MHz, DMSO) d 2.98 (m, 6H), 3.89 (s, 3H), 7.22 (m, 2H), 7.54 (m, 2H), 7.76 (br s, 2H), 8.10 (m, 2H), 8.16 (m, 2H) and 8.98 (s, 1H) ppm; MS ($ES^+$) 417.18

Compound IA-167 4-[5-amino-6-[5-(3-methyl-2-thienyl)-1,3,4-oxadiazol-2-yl]pyrazin-2-yl]-N,N-dimethyl-benzamide MS ($ES^+$) 407.18

Compound IA-205 4-[5-amino-6-[5-(2-iodophenyl)-1,3,4-oxadiazol-2-yl]pyrazin-2-yl]-N,N-dimethyl-benzamide 1H NMR (400.0 MHz, DMSO) d 2.96 (m, 6H), 7.43 (m, 1H), 7.52 (m, 2H), 7.69 (m, 1H), 7.81 (br s, 2H), 7.96 (m, 1H), 8.16 (m, 2H), 8.20 (m, 1H) and 9.01 (s, 1H) ppm; MS ($ES^+$) 513.01

Compound IA-237 4-[5-amino-6-[5-(m-tolyl)-1,3,4-oxadiazol-2-yl]pyrazin-2-yl]-N,N-dimethyl-benzamide 1H NMR (400.0 MHz, DMSO) d 2.53 (s, 3H), 3.05 (m, 6H), 7.57-7.65 (m, 4H), 7.84 (br s, 2H), 8.04 (m, 2H), 8.23 (m, 2H) and 9.05 (s, 1H) ppm; MS ($ES^+$) 401.2

Compound IA-242 4-[5-amino-6-[5-(2-methoxyphenyl)-1,3,4-oxadiazol-2-yl]pyrazin-2-yl]-N,N-dimethyl-benzamide 1H NMR (400.0 MHz, DMSO) d 2.97 (m, 6H), 3.97 (s, 3H), 7.19-7.23 (dt, 1H) 7.35 (m, 1H), 7.56 (m, 2H), 7.65-7.70 (m, 1H), 7.77 (br s, 2H), 7.99 (dd, 1H), 8.14 (m, 2H) and 8.98 (s, 1H) ppm; MS ($ES^+$) 417.19

Compound IA-245 4-[5-amino-6-[5-(5-methyl-2-thienyl)-1,3,4-oxadiazol-2-yl]pyrazin-2-yl]-N,N-dimethyl-benzamide 1H NMR (400.0 MHz, DMSO) d 2.60 (s, 3H), 2.98 (m, 6H), 7.08 (d, 1H), 7.53 (m, 2H), 7.74 (br s, 2H), 7.82 (m, 1H), 8.15 (m, 2H) and 8.97 (1H, s) ppm; MS ($ES^+$) 407.12

Compound IA-262 4-[5-amino-6-[5-(3-thienyl)-1,3,4-oxadiazol-2-yl]pyrazin-2-yl]-N,N-dimethyl-benzamide 1H NMR (400.0 MHz, DMSO) d 2.98 (m, 6H), 7.53 (m, 2H), 7.75-7.77 (m, 3H), 7.89 (m, 1H), 8.17 (m, 2H), 8.57 (m, 1H) and 8.98 (s, 1H) ppm; MS ($ES^+$) 393.12

Example 13A

4-[5-amino-6-(5-phenyl-1,3,4-oxadiazol-2-yl) pyrazin-2-yl]-3-(difluoromethyl)-N,N-dimethyl-benzamide (Compound IA-126)

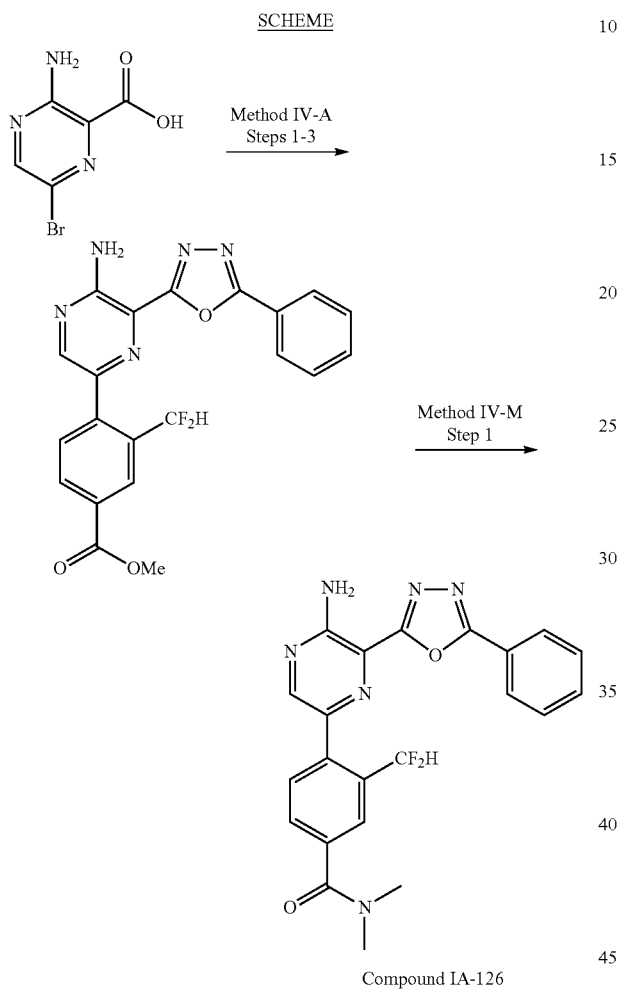

Compound IA-126

Compound IA-126 was prepared using Method IV-A, Steps 1-3, followed by Method IV-M, Step 1.

Method IV-M

Step 1: 4-[5-amino-6-(5-phenyl-1,3,4-oxadiazol-2-yl)pyrazin-2-yl]-3-(difluoromethyl)-N,N-dimethyl-benzamide LiOH (495.9 µL of 1 M aq solution, 0.4959 mmol) was added to a suspension of methyl 4-[5-amino-6-(5-phenyl-1,3,4-oxadiazol-2-yl)pyrazin-2-yl]-3-(difluoromethyl)benzoate (70 mg, 0.1653 mmol) in THF (5 mL) and methanol (2 mL). The reaction mixture was stirred for 4 h at room temperature and then concentrated in vacuo. The residue was acidified to pH2 by the addition of 1M HCl. A precipitate formed which was then filtered and washed with water, ethylacetate and ether. The solid was taken up in DMF (2 mL) and TBTU (79.63 mg, 0.2480 mmol) and DIPEA (64.09 mg, 86.37 µL, 0.4959 mmol) added followed by N-methyl-methanamine (495.9 µL of 1 M, 0.4959 mmol) in THF. The resulting mixture was stirred at room temperature for 2 h, diluted with ethylacetate (5 mL), washed with water (2×5 mL) and concentrated in vacuo. The residue was purified by reverse phase preparative HPLC [Waters Sunfire C18, 10 mM, 100 Å column, gradient 10%-95% B (solvent A: 0.05% TFA in water; solvent B: $CH_3CN$) over 16 minutes at 25 mL/min]. Product fractions were freeze dried to leave the product as a solid (29.6 mg, 40% yield); 1H NMR (400.0 MHz, DMSO) d 3.0 (d, 6H), 7.6-7.7 (m, 4H), 7.82 (s, 1H), 7.9 (d, 2H), 8.15-8.18 (m, 2H) and 8.7 (s, 1H) ppm; MS ($ES^+$) 437.2

The following compounds were all prepared using a method similar to the one described for Compound IA-126 above.

Compound IA-148 4-[5-amino-6-(5-phenyl-1,3,4-oxadiazol-2-yl)pyrazin-2-yl]-3-(2-fluorovinyl)-N,N-dimethyl-benzamide 1H NMR (400.0 MHz, DMSO) d 3.05 (d, 6H), 6.15 (dd, 0.5H), 6.85-6.95 (m, 1H), 7.1 (d, 0.25H), 7.45-7.55 (m, 2H), 7.6-7.7 (m, 5H), 7.8 (br s, 2H), 8.1-8.15 (m, 2H) and 8.45-8.48 (m, 1H) ppm; MS ($ES^+$) 431.2

Compound IA-161 4-[5-amino-6-(5-phenyl-1,3,4-oxadiazol-2-yl)pyrazin-2-yl]-N,N-dimethyl-3-oxazol-5-yl-benz-amide 1H NMR (400.0 MHz, DMSO) d 3.02 (d, 6H), 7.6-7.75 (m, 4H), 7.75-7.8 (m, 3H), 8.1 (d, 2H), 8.19 (s, 1H) and 8.19 (s, 1H) ppm; MS ($ES^+$) 454.1

Example 14A

5-(2-ethynylphenyl)-3-(5-phenyl-1,3,4-oxadiazol-2-yl)pyrazin-2-amine (Compound IA-194)

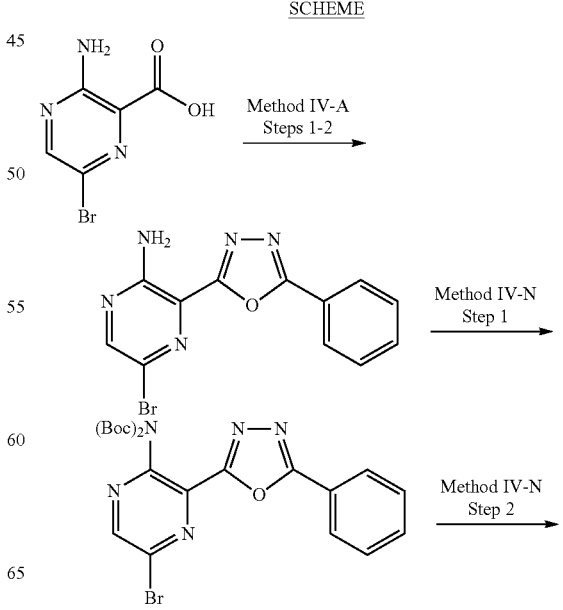

411

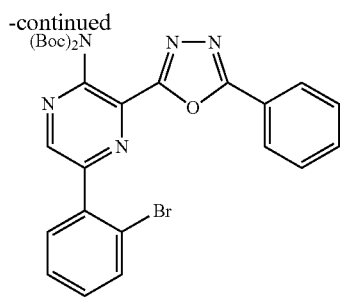

Method IV-N
Step 3

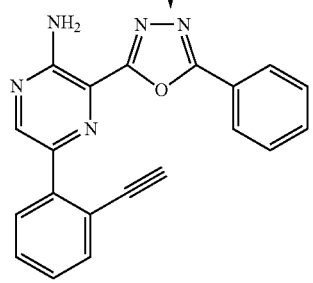

Compound IA-194

Compound IA-194 was prepared using Method IV-A, Steps 1-2, followed by Method IV-N, Steps 1-3.

Method IV-N

Step 1: di-tert-butyl 5-bromo-3-(5-phenyl-1,3,4-oxadiazol-2-yl)pyrazin-2-yliminodicarbonate 5-bromo-3-(5-phenyl-1,3,4-oxadiazol-2-yl)pyrazin-2-amine (4 g, 12.57 mmol) was suspended in DCM (59.76 mL) and THF (59.76 mL) and DMAP (153.6 mg, 1.257 mmol) was added. Di-tert-butyl dicarbonate (8.230 g, 8.663 mL, 37.71 mmol) was added in portions and the reaction allowed to stir at room temperature overnight. The reaction mixture was concentrated under reduced pressure and purified by column chromatography on silica gel eluting 10-20% EtAc/petrol to give the product as a cream coloured solid (5.72 g, 88% yield); 1H NMR (400.0 MHz, DMSO) d 1.29 (s, 18H), 7.69 (d, 3H), 8.13 (d, 2H) and 9.17 (s, 1H) ppm Step 2: tert butyl-5-(2-bromophenyl)-3-(5-phenyl-1,3,4-oxadiazol-2-yl)pyrazin-2-yl(tert-butoxycarbonyl)carbamate A mixture of (2-bromophenyl)boronic acid (100 mg, 0.4979 mmol), tert-butyl N-[5-bromo-3-(5-phenyl-1,3,4-oxadiazol-2-yl)pyrazin-2-yl]-N-tert-butoxycarbonyl-carbamate (258.1 mg, 0.4979 mmol), potassium carbonate (206.5 mg, 1.494 mmol) and triphenylphosphane palladium (13.06 mg, 11.54 µL, 0.04979 mmol) in DMF (3 mL) was heated at 50° C. for 1 h. The reaction mixture was cooled to room temperature and filtered through a Celite™ pad. The pad was washed with ethyl acetate (1×10 mL) and the combined filtrates were washed with water (2×10 mL) and brine (1×10 mL), dried over MgSO$_4$ and concentrated to leave the product as a solid which was used directly in the next step without further purification.

412

Step 3: 5-(2-ethynylphenyl)-3-(5-phenyl-1,3,4-oxadiazol-2-yl)pyrazin-2-amine

A suspension of tert-butyl N-[5-(2-bromophenyl)-3-(5-phenyl-1,3,4-oxadiazol-2-yl)pyrazin-2-yl]-N-tert-butoxycarbonyl-carbamate (100 mg, 0.1682 mmol), copper iodided (9.612 mg, 0.05047 mmol), dichloropalladium; triphenylphosphane (35.42 mg, 0.05046 mmol), triethylamine (211.0 µL, 1.514 mmol) and ethynyl(trimethyl)silane (85.58 µL, 0.6056 mmol) were heated at 60° C. in toluene (10 mL) for 1 h. The reaction mixture was cooled to room temperature and filtered through a Celite™ pad and the filtrate concentrated in vacuo to leave an oil. This was purified by column chromatography on silica eluting with diethyl ether/petroleum ether as eluent to yield the product as a yellow oil. This oil was dissolved in THF (2 mL) followed by the addition of tetrabutylammonium fluoride (336.4 µL of 1 M, 0.3364 mmol) and the resulting solution stirred at room temperature for 1 h. The mixture was diluted with ethylacetate (5 mL), washed with water and brine and concentrated in vacuo to leave a solid. The solid was dissolved in dichloromethane (10 mL) and trifluoroacetic acid (19.18 mg, 12.96 µL, 0.1682 mmol) was added. The resulting mixture was stirred at room temperature for 1 h and then concentrated in vacuo to leave an oil which was purified by reverse phase preparative HPLC [Waters Sunfire C18, 10 mM, 100 Å column, gradient 10%-95% B (solvent A: 0.05% TFA in water; solvent B: CH$_3$CN) over 16 minutes at 25 mL/min]. Product fractions were freeze dried to leave the product as a solid (12.0 mg, 24% yield); 1H NMR (400.0 MHz, MeOD) d 2.77 (s, 1H), 6.42-6.5 (m, 1H), 6.55-6.62 (m, 1H), 6.6-6.75 (m, 4H), 6.82 (d, 1H), 7.3 (d, 1H) and 7.83 (s, 1H) ppm; MS (ES$^+$) 340.1

Example 15A 4-(5-amino-6-(5-(2-vinylphenyl)-1,3,4-oxadiazol-2-yl)pyrazin-2-yl)-N,N-dimethylbenzamide (Compound IA-77)

SCHEME

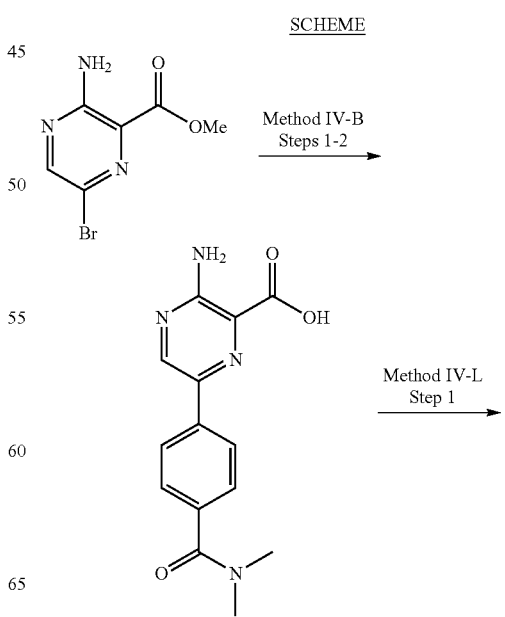

Method IV-B
Steps 1-2

Method IV-L
Step 1

413
-continued

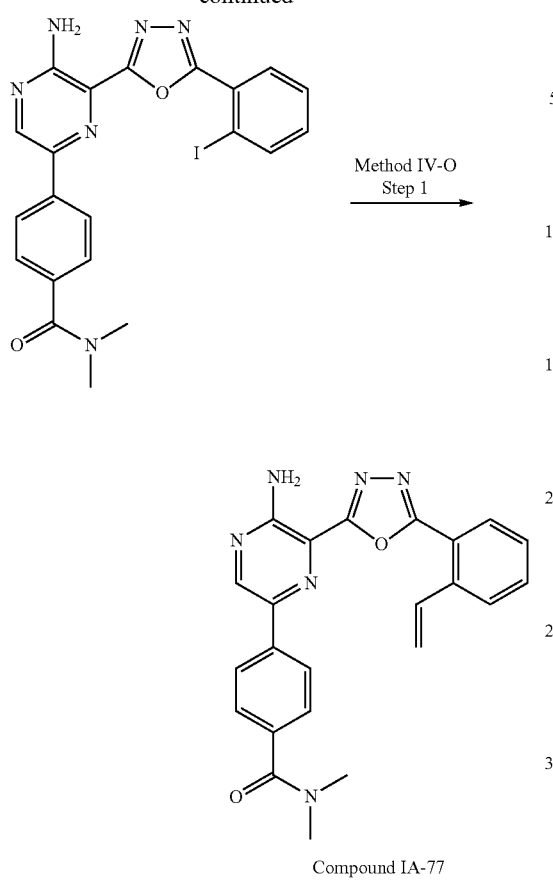

Compound IA-77

Compound IA-77 was prepared using Method IV-B, Steps 1-2, followed by Method IV-L, Step 1, followed by Method IV-O, Step 1.

Method IV-O

Step 1: 4-(5-amino-6-(5-(2-vinylphenyl)-1,3,4-oxadiazol-2-yl)pyrazin-2-yl)-N,N-dimethylbenzamide A solution of 4-[5-amino-6-[5-(2-iodophenyl)-1,3,4-oxadiazol-2-yl]pyrazin-2-yl]-N,N-dimethyl-benzamide (100 mg, 0.1952 mmol), potassium trifluoro-vinyl-boron (31.37 mg, 0.2342 mmol), triethyl amine (81.63 µL, 0.5857 mmol) and cyclopenta-1,4-dien-1-yl(diphenyl)phosphane; dichloromethane; dichloropalladium; iron (31.88 mg, 0.03904 mmol) in propanol (2.000 mL) was degassed and flushed with nitrogen (3×) and the resulting solution heated at 100° C. for 1 h. The reaction mixture cooled to room temperature and concentrated in vacuo. The residue was purified by column chromatography on silica eluting with ethyl acetate. Product fractions were combined and concentrated in vacuo to leave the product as a yellow solid (43.1 mg, 53% yield); 1H NMR (400.0 MHz, DMSO) d 2.97 (m, 6H), 5.51 (m, 1H), 5.98 (m, 1H), 7.54 (m, 2H), 7.58-7.70 (m, 3H), 7.78 (br s, 2H), 7.89 (m, 1H), 8.06 (m, 2H) and 9.00 (s, 1H) ppm; MS (ES$^+$) 413.15

414

Example 16A 2-(5-amino-6-(5-(thiophen-2-yl)-1,3,4-oxadiazol-2-yl)pyrazin-2-yl)-5-(1,4-diazepane-1-carbonyl)benzonitrile (Compound IA-152)

SCHEME

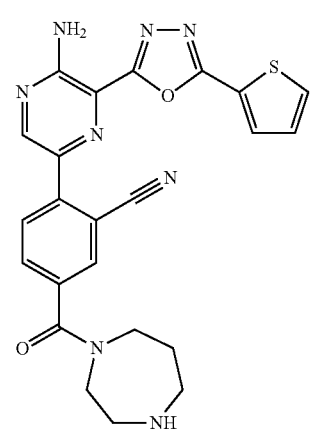

Compound IA-152

Compound IA-152 was prepared using Method IV-P, Steps 1-2.

Method IV-P

Step 1: 5-bromo-3-(5-(thiophen-2-yl)-1,3,4-oxadiazol-2-yl)pyrazin-2-amine 3-amino-6-bromo-pyrazine-2-carboxylic acid (3.2 g, 14.68 mmol) and thiophene-2-carbohydrazide (2.152 g, 14.68 mmol) were suspended in acetonitrile (48.00 mL) at room temperature and dibromo(triphenyl)phosphorane (24.79 g, 58.72 mmol) was added, followed by additional acetonitrile (16.00 mL). The reaction mixture turned bright yellow in colour and was stirred at room temperature for 1 h. After this time, the reaction mixture cooled in an icebath and DIPEA (7.209 g, 9.716 mL, 55.78 mmol) was added dropwise. The reaction mixture was stirred in the ice bath for 1 h and then additional DIPEA (2.277 g, 3.069 mL, 17.62 mmol) added and the reaction mixture stirred for left for 30 mins and further DIPEA (1.897 g, 2.557 mL, 14.68 mmol) added. The reaction mixture was stirred for 1 h and then filtered. The solid was washed with ether, isolated and then triturated with acetonitrile and washed with ether to give the product as a yellow solid (2.776 g, 57% yield); 1H NMR (400.0 MHz, DMSO) 7.35 (s, 1H), 7.80 (br s, 2H), 7.98 (m, 1H), 8.04 (m, 1H) and 8.45 (s, 1H); MS (ES$^+$) 326.04

Step 2: 2-(5-amino-6-(5-(thiophen-2-yl)-1,3,4-oxadiazol-2-yl)pyrazin-2-O-5-(1,4-diazepane-1-carbonyl)benzonitrile tert-Butyl 4-(4-bromo-3-cyano-benzoyl)-1,4-diazepane-1-carboxylate (126.0 mg, 0.3085 mmol), potassium acetate (90.83 mg, 0.9255 mmol), 4,4,5,5-tetramethyl-2-(4,4,5,5-tetramethyl-1,3,2-dioxaborolan-2-yl)-1,3,2-dioxaborolane (117.5 mg, 0.4628 mmol) and 1-cyclopenta-1,4-dienyl-diphenyl-phosphane; dichloromethane; dichloropalladium; iron (25.19 mg, 0.03085 mmol) were heated in dioxane (3 mL) at 80° C. for 3 h. Sodium carbonate (462.8 µL of 2 M, 0.9255 mmol) was added to the reaction mixture followed by tert-butyl 4-(4-bromo-3-cyano-benzoyl)-1,4-diazepane-1-carboxylate (126.0 mg, 0.3085 mmol) and palladium; triphenylphosphane (35.65 mg, 0.03085 mmol) and the reaction mixture evacuated and flushed with nitrogen (3 cycles) and then heated at 150° C. in the microwave for 1 h.

The reaction mixture was diluted with water (10 mL) and EtOAc (10 ml). The layers were separated and the aqueous layer extracted with EtOAc (3×10 mL). The combined organic extracted were dried over MgSO$_4$, filtered and evaporated to dryness to give a brown/black solid. This solid was re-dissolved in MeOH/DCM (4 mL) and solution filtered through thiol cartridges to leave a brown solid. This was triturated with acetonitrile to give the product as a yellow solid. The yellow solid was redissolved in DCM (3 mL) and TFA (500 µL, 6.490 mmol) added and the resulting mixture stirred at room temperature for 15 mins. This solution was evaporated to dryness and then MeOH/DCM added and the mixture concentrated in vacuo again. The solid was then re-dissolved in acetonitrile/water and passed through a bicarbonate cartridge. The filtrate was then freeze dried to leave the product as a yellow solid (29.8 mg, 20% yield); 1H NMR (400.0 MHz, DMSO) d 1.60 (br s, 1H), 1.75 (br s, 1H), 2.70-2.80 (m, 3H), 2.90 (m, 1H), 3.35 (m, 3H), 3.60-3.70 (m, 2H), 7.30-7.40 (m, 1H), 7.80-7.90 (m, 2H), 7.95-8.15 (m, 5H) and 8.89 (s, 1H) ppm; MS (ES$^+$) 473.26

The following compounds were all prepared using a method similar to the one described for Compound IA-152 above.

Compound IA-179 5-(2-methylsulfinylphenyl)-3-[5-(3-methyl-2-thienyl)-1,3,4-oxadiazol-2-yl]pyrazin-2-amine 1H NMR (400.0 MHz, DMSO) d 2.7 (s, 3H), 3.1 (s, 3H), 7.2-7.25 (m, 1H), 7.6-7.8 (m, 3H), 7.9 (s, 1H), 8.05 (d, 1H), 8.25 (d, 1H) and 8.95 (s, 1H) ppm; MS (ES$^+$) 398.1

Example 17A 3-(5-amino-6-(5-phenyl-1,3,4-oxadiazol-2-yl)pyrazin-2-yl)pyridine-4-carbonitrile (Compound IA-153)

SCHEME

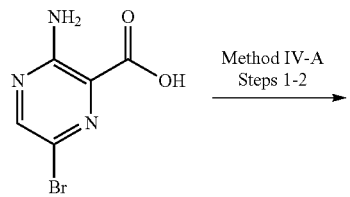

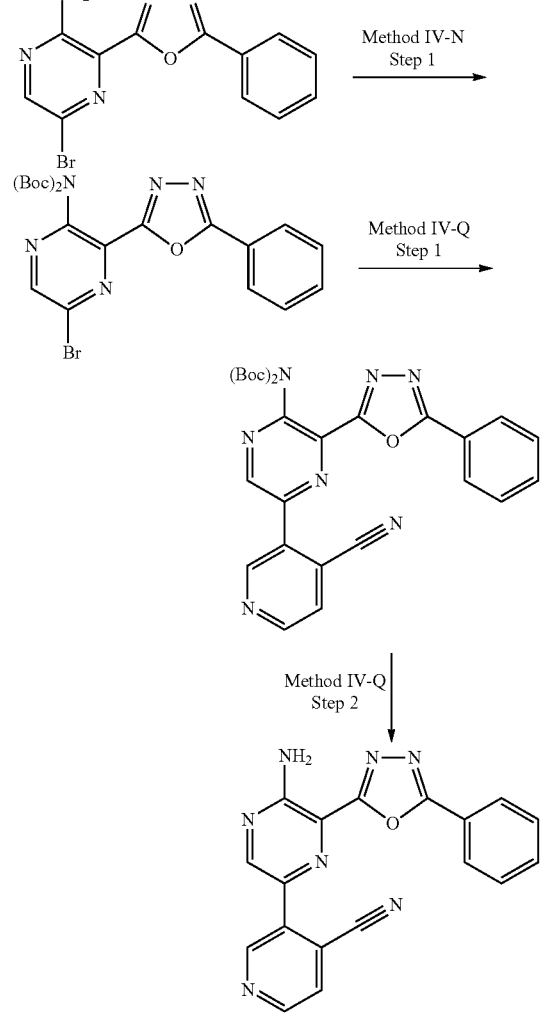

Compound IA-153

Compound IA-153 was prepared using Method IV-A, Steps 1-2, followed by Method IV-N, Step 1, followed by Method IV-Q, Steps 1-2.

Method IV-Q

Step 1: di-tert-butyl 5-(4-cyanopyridin-3-yl)-3-(5-phenyl-1,3,4-oxadiazol-2-yl)pyrazin-2-yliminodicarbonate tert-Butyl N-[5-bromo-3-(5-phenyl-1,3,4-oxadiazol-2-yl)pyrazin-2-yl]-N-tert-butoxycarbonyl-carbamate (150 mg, 0.2894 mmol), 3-(5,5-dimethyl-1,3,2-dioxaborinan-2-yl)pyridine-2-carbonitrile (75.03 mg, 0.3473 mmol), cesium fluoride (87.92 mg, 0.5788 mmol), copper iodide (5.512 mg, 0.9790 µL, 0.02894 mmol), and palladium; triphenylphosphane (16.72 mg, 0.01447 mmol) were placed in a microwave tube which was evacuated and nitrogen flushed (×5). Dioxane (2.486 mL) was added and the reaction mixture stirred during 5 further vacuum/flush cycles. The resulting solution was heated at 85° C. overnight, cooled to room temperature diluted with ethyl acetate. The mixture was washed with aq NaHCO$_3$ solution (1×10 mL) and brine (1×10 mL), dried over MgSO$_4$ and concentrated under reduced pressure. The material was purified by column chromatography on silica gel eluting 50-60% ethyl acetate/petroleum ether to give the product as a colourless foam. (136 mg, 86.8%); 1H NMR (400.0 MHz, DMSO) 1.34 (s, 18H), 7.19 (s, 2H), 7.49 (m, 3H), 7.75 (m, 1H), 8.17 (m, 2H), 8.40 (m, 1H), 8.90 (m, 1H) and 9.12 (s, 1H) ppm Step 2: 3-(5-amino-6-(5-phenyl-1,3,4-oxadiazol-2-yl)pyrazin-2-yl)pyridine-4-carbonitrile tert-Butyl N-tert-butoxycarbonyl-N-[5-(4-cyano-3-pyridyl)-3-(5-phenyl-1,3,4-oxadiazol-2-yl)pyrazin-2-yl]carbamate (140 mg, 0.2585 mmol) in dichloromethane (2 mL) was treated with TFA (2 mL, 25.96 mmol) and stirred at room temperature for 1 h. The mixture was concentrated under reduced pressure, re-dissolved in MeOH/DCM and concentrated (2×), dissolved MeOH/DCM and passed through bicarbonate cartridge, concentrated under reduced pressure to give a yellow solid. The solid was triturated with acetonitrile and filtered to give yellow solid (83 mg, 94%); 1H NMR (400.0 MHz, DMSO) d 7.69-7.77 (m, 3H), 8.07 (d, 1H), 8.24-8.26 (m, 2H), 7.80-8.40 (br s, 2H), 8.90 (d, 1H), 9.09 (s, 1H) and 9.47 (s, 1H) ppm; MS (ES+) 342.16

The following compounds were all prepared using a method similar to the one described for Compound IA-153 above.

Compound IA-74 3-[5-amino-6-(5-phenyl-1,3,4-oxadiazol-2-yl)pyrazin-2-yl]pyridine-2-carbonitrile 1H NMR (400.0 MHz, DMSO) d 7.64-7.70 (m, 3H), 7.86-7.89 (m, 1H), 8.18-8.20 (m, 2H), 8.54-8.57 (m, 1H), 8.79-8.81 (m, 1H) and 8.94 (s, 1H) ppm; MS (ES+) 342.16

Compound IA-132 2-[5-amino-6-(5-phenyl-1,3,4-oxadiazol-2-yl)pyrazin-2-yl]-5-isopropylsulfonyl-benzonitrile 1H NMR (400.0 MHz, CDCl3) d 1.35 (d, 6H), 7.5-7.6 (m, 4H), 8.0-8.05 (m, 1H), 8.1-8.15 (m, 1H), 8.2-8.25 (m, 2H), 8.3-8.32 (m, 1H) and 8.7 (s, 1H) ppm; MS (ES+) 447.2

Example 18A 4-(5-amino-6-(5-(3-nitrophenyl)-1,3,4-oxadiazol-2-yl)pyrazin-2-yl)-N,N-dimethylbenzamide (Compound IA-286)

SCHEME

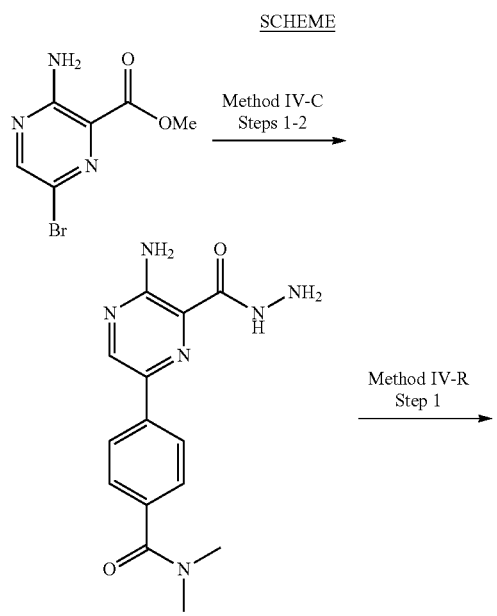

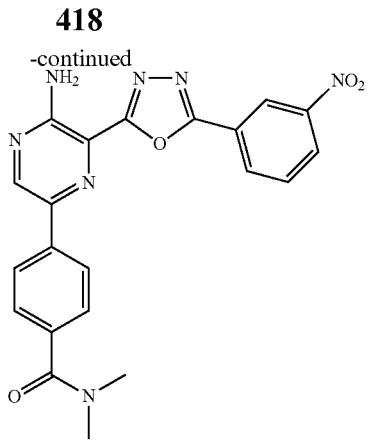

Compound IA-286

Compound IA-286 was prepared using Method IV-C, Steps 1-2, followed by Method IV-R, Step 1.

Method IV-R

Step 1: 4-(5-amino-6-(5-(3-nitrophenyl)-1,3,4-oxadiazol-2-yl)pyrazin-2-yl)-N,N-dimethylbenzamide Dibromo(triphenyl)phosphorane (707.8 mg, 1.68 mmol) was added to a solution of 3-amino-6-[4-(dimethylcarbamoyl)phenyl]pyrazine-2-carboxylic acid (100 mg, 0.35 mmol) and 4-(5-amino-6-(hydrazinecarbonyl)pyrazin-2-yl)-N,N-dimethylbenzamide (63.28 mg, 0.35 mmol) in acetonitrile (5 mL) at room temperature. A bright yellow solution was observed. The reaction mixture was stirred at room temperature for 30 min. DIPEA (304 µL, 1.75 mmol) was added dropwise and the reaction mixture was stirred at room temperature for 30 min. The reaction mixture was filtered and the solid triturated with acetonitrile to give the product as a yellow solid (78.5 mg, 51.3% yield); 1H NMR (400.0 MHz, DMSO) d 2.98 (m, 6H), 7.56 (m, 2H), 7.85 (br s, 1H), 7.99 (t, 1H), 8.17 (m, 2H), 8.52 (m, 1H), 8.56 (m, 1H), 8.82 (m, 1H) and 9.02 (s, 1H) ppm; MS (ES+) 432.2

The following compounds were all prepared using a method similar to the one described for Compound IA-286 above.

Compound IA-85 4-[5-amino-6-[5-(3-hydroxyphenyl)-1,3,4-oxadiazol-2-yl]pyrazin-2-yl]-N,N-dimethyl-benzamide 1H NMR (400.0 MHz, DMSO) d 3.02 (m, 6H), 7.11 (m, 1H), 7.52 (m, 1H), 7.59 (m, 3H), 7.64 (m, 1H), 7.84 (br s, 2H), 8.22 (m, 2H), 9.04 (s, 1H) and 10.13 (1H, s) ppm; MS (ES+) 402.23

Compound IA-180 4-[5-amino-6-(5-thiazol-4-yl-1,3,4-oxadiazol-2-yl)pyrazin-2-yl]-N,N-dimethyl-benzamide 1H NMR (400.0 MHz, DMSO) d 2.78 (m, 6H), 7.35 (m, 2H), 7.60 (br s, 1H), 7.94 (m, 2H), 8.62 (m, 1H), 8.79 (s, 1H) and 9.22 (m, 1H) ppm; MS (ES+) 394.15

Compound IA-187 3-[5-[3-amino-6-(4-isopropylsulfonylphenyl)pyrazin-2-yl]-1,3,4-oxadiazol-2-yl]benzonitrile 1H NMR (400.0 MHz, DMSO) d 1.20 (d, 6H), 3.47 (q, 1H), 7.92 (br s, 2H), 7.90 (t, 1H), 7.99 (m, 2H), 8.19 (dt, 1H), 8.41-8.43 (m, 2H), 8.48-8.51 (m, 1H), 8.58 (t, 1H) and 9.09 (s, 1H) ppm; MS (ES+) 447.2

Compound IA-189 4-[5-amino-6-[5-(3-cyano-2-thienyl)-1,3,4-oxadiazol-2-yl]pyrazin-2-yl]-N,N-dimethyl-benzamide 1H NMR (400.0 MHz, DMSO) d 2.97 (m, 6H), 7.50 (m, 2H), 7.80 (m, 1H), 8.21 (m, 3H) and 9.05 (s, 1H) ppm; MS (ES+) 418.15

Compound IA-215 4-[5-amino-6-[5-(2-hydroxyphenyl)-1,3,4-oxadiazol-2-yl]pyrazin-2-yl]-N,N-dimethyl-benzamide 1H NMR (400.0 MHz, DMSO) d 2.97 (s, 3H), 3.01 (s, 3H), 7.09-7.14 (m, 2H), 7.53-7.55 (m, 3H), 7.80 (br s, 2H), 7.93 (dd, 1H), 8.16 (d, 2H), 8.99 (s, 1H) and 10.45 (s, 1H) ppm; MS (ES+) 403.23

Compound IA-246 4-[5-amino-6-[5-(4-methyl-2-thienyl)-1,3,4-oxadiazol-2-yl]pyrazin-2-yl]-N,N-dimethyl-benzamide 1H NMR (400.0 MHz, DMSO) d 2.34 (s, 3H), 2.98 (m, 6H), 7.54 (m, 2H), 7.62 (s, 1H), 7.75 (br s, 2H), 7.85 (s, 1H), 8.15 (m, 2H) and 8.98 (s, 1H) ppm; MS (ES+) 407.18

Compound IA-273 4-[5-[3-amino-6-(4-isopropylsulfonylphenyl)pyrazin-2-yl]-1,3,4-oxadiazol-2-yl]benzonitrile 1H NMR (400.0 MHz, DMSO) d 1.20 (d, 6H), 3.48 (m, 1H), 7.99 (d, 2H), 7.80-8.30 (br s, 2H), 8.15 (d, 2H), 8.34 (d, 2H), 8.40 (d, 2H) and 9.09 (s, 1H) ppm; MS (ES+) 447.19

Example 19A 5-(2-(isopropylsulfinyl)phenyl)-3-(5-phenyl-1,3,4-oxadiazol-2-yl)pyrazin-2-amine (Compound IA-136)

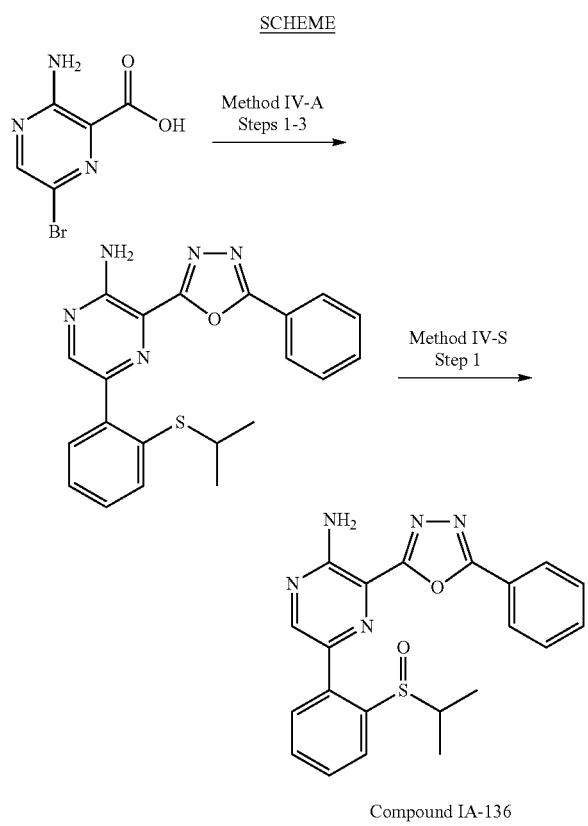

Compound IA-136

Compound IA-136 was prepared using Method IV-A, Steps 1-3, followed by Method IV-S, Step 1.

Method IV-S

Step 1: 5-(2-(isopropylsulfinyl)phenyl)-3-(5-phenyl-1,3,4-oxadiazol-2-yl)pyrazin-2-amine 5-(2-isopropylsulfanylphenyl)-3-(5-phenyl-1,3,4-oxadiazol-2-yl)pyrazin-2-amine (50 mg, 0.1284 mmol) was dissolved in dichloromethane (10 mL) and cooled to 0° C. in an ice-bath. 3-Chlorobenzenecarboperoxoic acid (26.59 mg, 0.1541 mmol) was added in one portion with rapid stirring. The mixture was stirred at 0° C. for 15 min, washed with saturated aqueous NaHCO$_3$ solution (1×5 mL) and brine (1×5 mL), dried over MgSO$_4$ and concentrated in vacuo to leave a solid which was purified by column chromatography on silica eluting with ether/petroleum ether to yield the product as a yellow solid (16.1 mg, 31% yield); 1H NMR (400.0 MHz, CDCl$_3$) d 1.2 (d, 3H), 1.35 (d, 3H), 3.5-3.6 (m, 1H), 7.5-7.75 (m, 2H), 7.5-7.65 (m, 7H), 8.25 (d, 2H) and 8.55 (s, 1H) ppm; MS (ES+) 406.1

The following compounds were all prepared using a method similar to the one described for Compound IA-136 above.

Compound IA-256 5-(2-ethylsulfinylphenyl)-3-(5-phenyl-1,3,4-oxadiazol-2-yl)pyrazin-2-amine 1H NMR (400.0 MHz, CDCl$_3$) d 1.25-1.4 (m, 3H), 3.3-3.6 (m, 2H), 7.6-7.8 (m, 6H), 8.2 (d, 2H), 8.4 (d, 1H) and 8.6 (s, 1H) ppm; MS (ES+) 392.2

Example 20A 5-(2-isopropylsulfonylphenyl)-3-(5-phenyl-1,3,4-oxadiazol-2-yl)pyrazin-2-amine (Compound IA-121)

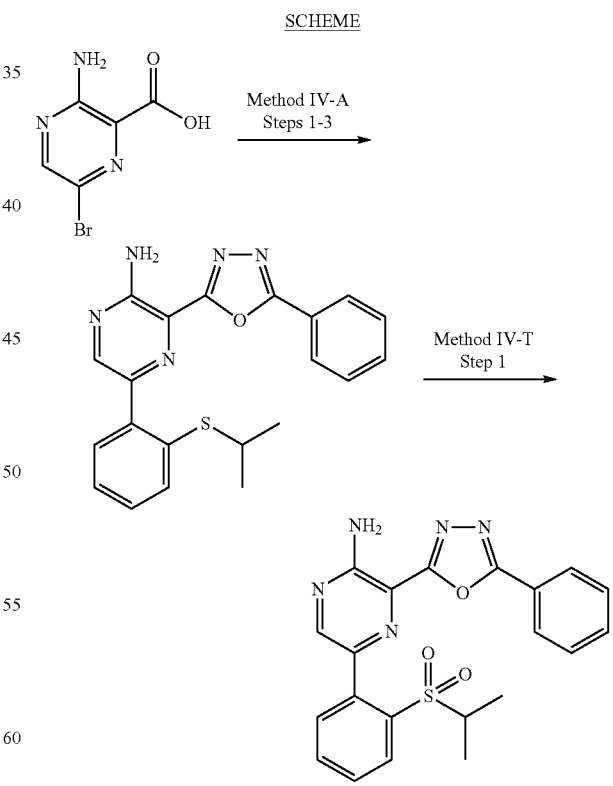

Compound IA-121

Compound IA-121 was prepared using Method IV-A, Steps 1-3, followed by Method IV-T, Step 1.

Method IV-T

Step 1: 5-(2-isopropylsulfonylphenyl)-3-(5-phenyl-1,3,4-oxadiazol-2-yl)pyrazin-2-amine 5-(2-isopropylsulfanylphenyl)-3-(5-phenyl-1,3,4-oxadiazol-2-yl)pyrazin-2-amine (40 mg, 0.1027 mmol) was dissolved in dichloromethane (10 mL) followed by the portionwise addition of 3-chlorobenzenecarboperoxoic acid (70.89 mg, 0.4108 mmol) over 10 min. The resulting mixture was stirred at room temperature for 2 h, and poured onto a 50/50 mixture of saturated aqueous sodium thiosulfate solution and saturated aqueous sodium bicarbonate solution (20 mL). The layers were separated and the organic layer was washed with dilute $NaHCO_3$ solution (1×10 mL) and brine (1×10 mL) and then concentrated in vacuo to leave a solid. The solid was purified by column chromatography on silica eluting with 50% ether/petroleum ether to afford the product as a yellow solid. (20.25 mg, 36% yield); 1H NMR (400.0 MHz, $CDCl_3$) d 1.4 (d, 6H), 4.48-4.52 (m, 1H), 7.0 (br s, 2H), 7.5-7.7 (m, 5H), 7.7-7.75 (m, 1H), 8.2 (d, 1H), 8.3 (d, 1H) and 8.55 (s, 1H) ppm; MS ($ES^+$) 422.2

The following compounds were all prepared using a method similar to the one described for Compound IA-121 above.

Compound IA-164 tert-butyl N-[2-[2-[5-amino-6-(5-phenyl-1,3,4-oxadiazol-2-yl)pyrazin-2-yl]phenyl]sulfinylethyl]carbamate 1H NMR (400.0 MHz, $CDCl_3$) d 1.55 (s, 9H), 3.45-3.5 (m, 1H), 3.6-3.7 (m, 3H), 5.5 (br s, 1H), 7.6-7.8 (m, 6H), 8.2-8.25 (m, 2H), 8.3 (d, 1H) and 8.6 (s, 1H) ppm; MS ($ES^+$) 507.2

Compound IA-203 5-(2-ethylsulfonylphenyl)-3-(5-phenyl-1,3,4-oxadiazol-2-yl)pyrazin-2-amine 1H NMR (400.0 MHz, $CDCl_3$) d 1.2 (d, 3H), 1.35 (d, 3H), 3.5-3.6 (m, 1H), 7.5-7.75 (m, 2H), 7.5-7.65 (m, 7H), 8.25 (d, 2H) and 8.55 (s, 1H) ppm; MS ($ES^+$) 408.2

Compound IA-280 5-(4-tert-butylsulfonylphenyl)-3-(5-phenyl-1,3,4-oxadiazol-2-yl)pyrazin-2-amine 1H NMR (400.0 MHz, DMSO) d 1.32 (s, 9H), 7.7-7.8 (m, 3H), 7.9-8.0 (m, 3H), 8.20-8.25 (m, 2H), 8.45 (d, 2H) and 9.1 (s, 1H) ppm; MS ($ES^+$) 436.2

Example 21A

4-(5-amino-6-(5-(2-ethoxyphenyl)-1,3,4-oxadiazol-2-yl)pyrazin-2-yl)-N,N-dimethylbenzamide (Compound IA-277)

SCHEME

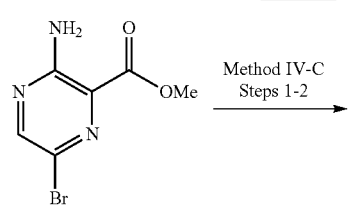

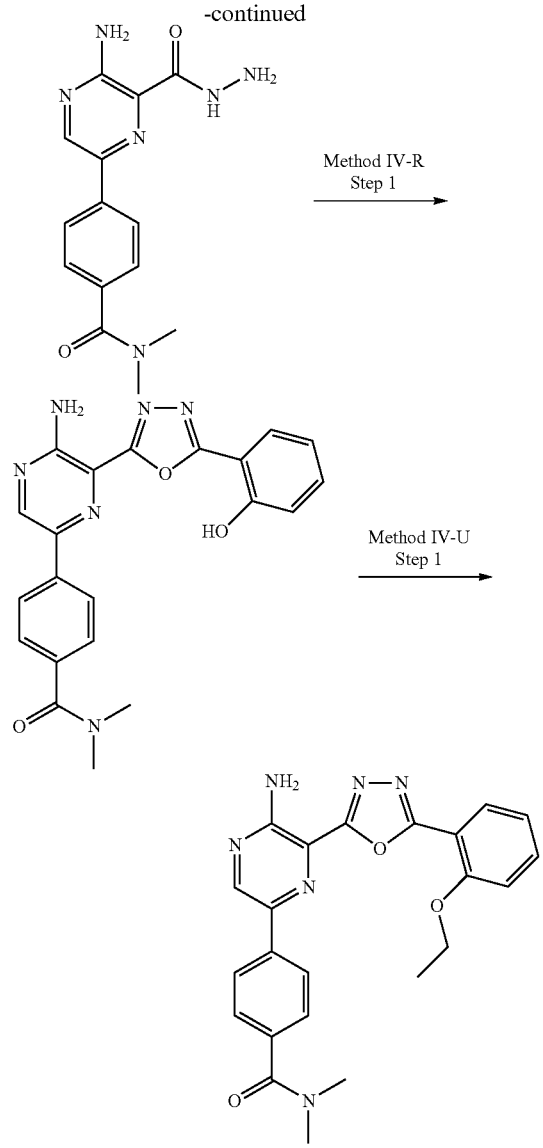

Compound IA-277

Compound IA-277 was prepared using Method IV-C, Steps 1-2, followed by Method IV-R, Step 1, followed by Method IV-U, Step 1.

Method IV-U: Step 1: 4-(5-amino-6-(5-(2-ethoxyphenyl)-1,3,4-oxadiazol-2-yl)pyrazin-2-yl)-N,N-dimethylbenzamide Potassium carbonate (25.46 mg, 0.1842 mmol) was added to a mixture of 4-[5-amino-6-[5-(2-hydroxyphenyl)-1,3,4-oxadiazol-2-yl]pyrazin-2-yl]-N,N-dimethyl-benzamide (50 mg, 0.1228 mmol) in DMF (1 mL) at room temperature. Colour change observed from yellow to orange. The resulting suspension was heated at 60-65° C. and bromoethane (14.72 mg, 10.01 μL, 0.1351 mmol) was added slowly. After the addition is complete the reaction heated at 60-65° C. for 30 min. The reaction mixture was cooled to room temperature. Water (2 mL) was added slowly at and the mixture stirred at room temperature for 20 min. A precipitate formed and was filtered and washed with water. The solid was re-dissolved in DCM and dried over MgSO$_4$, filtered and evaporated to dryness. The solid was triturated with acetonitrile to give the product as a yellow solid (38.3 mg, 73% yield); 1H NMR (400.0 MHz, DMSO) d 1.49 (t, 3H), 2.97-3.02 (m, 6H), 4.24-4.29 (m, 2H), 7.17-7.18 (m, 1H), 7.20 (d, 1H), 7.32-7.35 (m, 2H), 7.53 (d, 1H), 7.65 (br s, 2H), 8.05 (d, 1H), 8.17 (d, 2H) and 8.99 (s, 1H) ppm; MS (ES$^+$) 431.24

The following compounds were all prepared using a method similar to the one described for Compound IA-277 above.

Compound IA-108 4-[5-amino-6-[5-(2-isopropoxyphenyl)-1,3,4-oxadiazol-2-yl]pyrazin-2-yl]-N,N-dimethyl-benzamide 1H NMR (400.0 MHz, DMSO) d 1.40 (d, 6H), 2.99 (s, 3H), 3.01 (s, 3H), 4.90 (q, 1H), 7.20 (t, 1H), 7.39 (d, 1H), 7.51-7.53 (m, 2H), 7.55-7.65 (m, 1H), 7.80 (br s, 2H), 8.05-8.10 (m, 1H), 8.17-8.20 (m, 2H) and 8.99 (s, 1H) ppm; MS (ES$^+$) 445.27

Compound IA-175 tert-butyl N-[2-[2-[5-[3-amino-6-[4-(dimethylcarbamoyl)phenyl]pyrazin-2-yl]-1,3,4-oxadiazol-2-yl]phenoxy]ethyl]carbamate 1H NMR (400.0 MHz, DMSO) d 1.29 (s, 9H), 2.96 (s, 3H), 3.00 (s, 3H), 3.50 (d, 2H), 4.18 (s, 2H), 6.96-6.99 (m, 1H), 7.19-7.25 (m, 1H), 7.35 (d, 1H), 7.53 (d, 2H), 7.66-7.67 (m, 1H), 7.80 (br s, 2H), 8.06-8.08 (m, 1H), 8.16 (d, 2H) and 8.99 (s, 1H) ppm; MS (ES$^+$) 546.27

Compound IA-196 4-[5-amino-6-[5-[2-(2-hydroxyethoxy)phenyl]-1,3,4-oxadiazol-2-yl]pyrazin-2-yl]-N,N-dimethyl-benzamide 1H NMR (400.0 MHz, DMSO) d 2.98 (s, 3H), 3.00 (s, 3H), 3.86-3.89 (m, 2H), 4.23 (s, 2H), 4.85 (t, 1H), 7.19-7.22 (m, 1H), 7.35-7.37 (m, 1H), 7.54 (d, 2H), 7.63-7.67 (m, 1H), 7.79 (br s, 2H), 8.02-8.04 (m, 1H), 8.18 (s, 2H) and 8.99 (s, 1H) ppm; MS (ES$^+$) 447.24

Compound IA-284 4-[5-amino-6-[5-[2-(3-hydroxypropoxy)phenyl]-1,3,4-oxadiazol-2-yl]pyrazin-2-yl]-N,N-dimethyl-benzamide 1H NMR (400.0 MHz, DMSO) d 2.00 (s, 2H), 2.97 (s, 3H), 3.01 (s, 3H), 3.65 (d, 2H), 4.26 (s, 2H), 4.55 (s, 1H), 7.19 (s, 1H), 7.35 (s, 1H), 7.54 (d, 2H), 7.70 (br s, 2H), 8.03 (d, 1H), 8.16 (d, 2H) and 8.98 (s, 1H) ppm; MS (ES$^+$) 461.26

Example 22A 4-(5-amino-6-(5-(2-aminophenyl)-1,3,4-oxadiazol-2-yl)pyrazin-2-yl)-N,N-dimethylbenzamide (Compound IA-99)

SCHEME

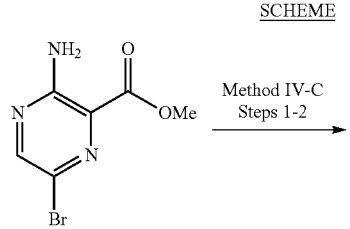

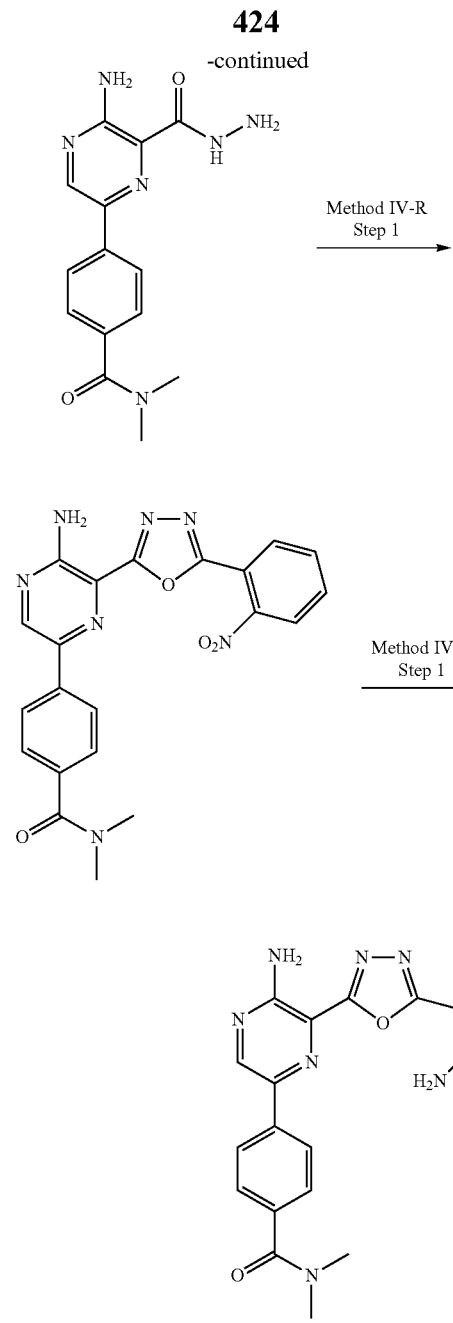

Compound IA-99

Compound IA-99 was prepared using Method IV-C, Steps 1-2, followed by Method IV-R, Step 1, followed by Method IV-V, Step 1.

Method IV-V

Step 1: 4-(5-amino-6-(5-(2-aminophenyl)-1,3,4-oxadiazol-2-yl)pyrazin-2-yl)-N,N-dimethylbenzamide SnCl$_2$.2H$_2$O (151.6 mg, 0.6720 mmol) was added to a solution of 4-[5-amino-6-[5-(2-nitrophenyl)-1,3,4-oxadiazol-2-yl]pyrazin-2-yl]-N,N-dimethyl-benzamide (58 mg, 0.1344 mmol) in EtOAc (3 mL) and dichloromethane (1 mL) at room temperature and the resulting solution stirred overnight at room temperature. The reaction mixture was poured carefully onto saturated aqueous sodium hydrogen carbonate solution (5 mL) and the layers separated. The aqueous layer extracted further with dichloromethane (2×15 mL) and the combined organics dried over MgSO₄ and concentrated in vacuo to leave a yellow solid. This was purified using by reverse phase preparative HPLC [Waters Sunfire C18, 10 mM, 100 Å column, gradient 10%-95% B (solvent A: 0.05% TFA in water; solvent B: CH₃CN) over 16 minutes at 25 mL/min]. The product fractions were freeze dried to give the product as a yellow solid (17.2 mg, 34% yield); 1H NMR (400.0 MHz, DMSO) d 2.98 (m, 6H), 6.78 (t, 1H), 6.88 (br s, 1H), 7.34 (m, 1H), 7.55 (m, 2H), 7.79 (br s, 2H), 7.85 (m, 1H), 8.18 (m, 2H) and 8.99 (s, 1H) ppm; MS (ES⁺) 402.26

The following compounds were all prepared using a method similar to the one described for Compound IA-99 above.

Compound IA-142 4-[5-amino-6-[5-(3-aminophenyl)-1,3,4-oxadiazol-2-yl]pyrazin-2-yl]-N,N-dimethyl-benzamide 1H NMR (400.0 MHz, DMSO) d 2.98 (m, 6H), 6.88 (m, 1H), 7.31 (m, 2H), 7.41 (m, 1H), 7.56 (m, 2H), 7.78 (br s, 2H), 8.15 (m, 2H) and 8.98 (s, 1H) ppm; MS (ES⁺) 402.19

Example 23A 5-(6-(4-methylpiperazin-1-yl)pyridin-3-yl)-3-(5-phenyl-1,3,4-oxadiazol-2-yl)pyrazin-2-amine (Compound IA-200)

SCHEME

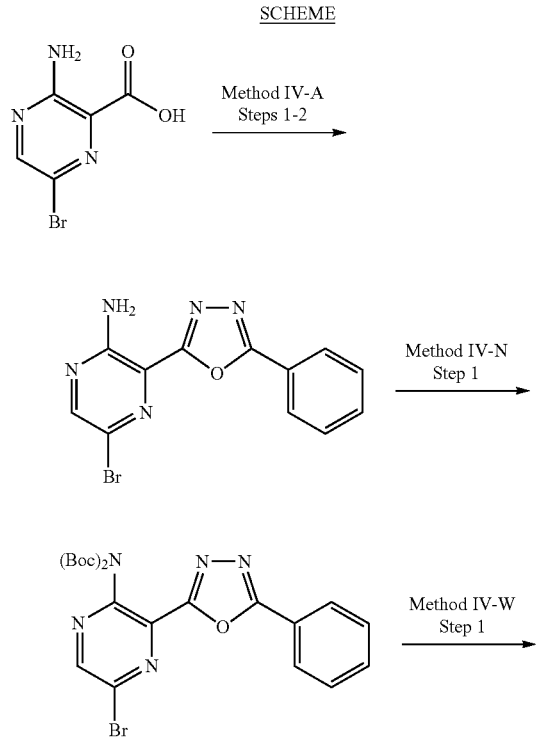

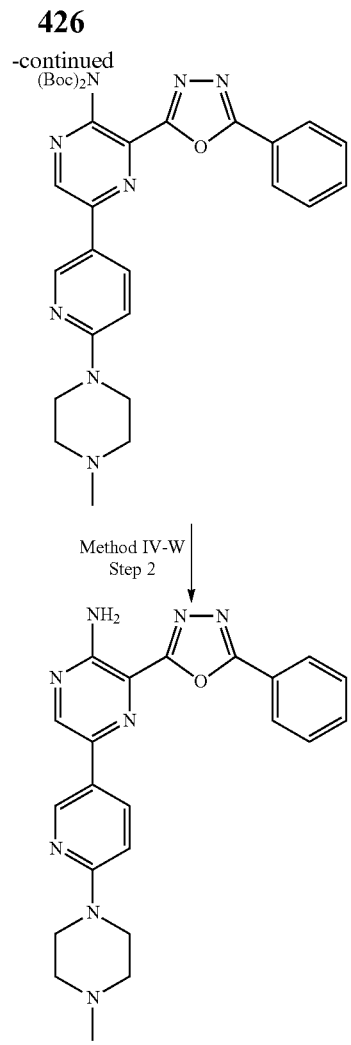

Compound IA-200 was prepared using Method IV-A, Steps 1-2, followed by Method IV-N, Step 1, followed by Method IV-W, Steps 1-2.

Method IV-W

Step 1: Di-tert-butyl(5-(6-(4-methylpiperazin-1-yl)pyridin-3-yl)-3-(5-phenyl-1,3,4-oxadiazol-2-yl)pyrazin-2-yl)iminodicarbonate tert-Butyl N-[5-bromo-3-(5-phenyl-1,3,4-oxadiazol-2-yl)pyrazin-2-yl]-N-tert-butoxycarbonyl-carbamate (100 mg, 0.19 mmol) was dissolved in DMF (1 mL) and 1-methyl-4-(5-(4,4,5,5-tetramethyl-1,3,2-dioxaborolan-2-yl)pyridin-2-yl)piperazine (70.19 mg, 0.23 mmol) and Pd(PPh₃)₂Cl₂ (13.54 mg, 0.019 mmol) were added. K₂CO₃ (289 μL, 0.58 mmol, 2M aqueous solution) was added and the reaction mixture heated at 100° C. for 12 hours. The reaction mixture was cooled to room temperature and taken onto the next step without further purification.

Step 2: 5-(6-(4-methylpiperazin-1-yl)pyridin-3-yl)-3-(5-phenyl-1,3,4-oxadiazol-2-yl)pyrazin-2-amine Di-tert-butyl(5-(6-(4-methylpiperazin-1-yl)pyridin-3-yl)-3-(5-phenyl-1,3,4-oxadiazol-2-yl)pyrazin-2-yl)iminodicarbonate (118.6 mg, 0.19 mmol) as a solution in DMF (1 mL) was diluted with dichloromethane (5 mL) and was treated with TFA (1 mL, 12.98 mmol). The resulting solution was stirred at room temperature for 18 h and then concentrated in vacuo. The residue was purified by reverse phase preparative HPLC [Waters Sunfire C18, 10 mM, 100 Å column, gradient 10%-95% B (solvent A: 0.05% TFA in water; solvent B: $CH_3CN$) over 16 minutes at 25 mL/min]. The fractions were collected and freeze-dried to give the product as a yellow solid (27.3 mg, 27% yield); 1H NMR (400.0 MHz, DMSO) d 2.87 (d, 3H), 3.08-3.21 (m, 4H), 3.40-3.53 (m, 2H), 4.52 (d, 2H), 7.12 (d, 1H), 7.66-7.70 (m, 5H), 8.16-8.18 (m, 2H), 8.33 (dd, 1H), 8.92 (s, 1H), 8.93 (d, 1H) and 9.75 (br s, 1H) ppm; MS (ES$^+$) 415.2

The following compounds were all prepared using a method similar to the one described for Compound IA-200 above.

Compound IA-72 5-[6-(2-morpholinoethylamino)-3-pyridyl]-3-(5-phenyl-1,3,4-oxadiazol-2-yl)pyrazin-2-amine 1H NMR (400.0 MHz, CDCl$_3$) d 3.17 (br s, 4H), 3.29 (t, 2H), 3.92-3.94 (m, 6H), 7.03 (d, 1H), 7.51-7.58 (m, 3H), 8.18-8.21 (m, 2H), 8.38 (d, 1H), 8.49 (s, 1H) and 8.52 (s, 1H) ppm; MS (ES$^+$) 445.2

Compound IA-86 5-(3-methoxy-4-pyridyl)-3-(5-phenyl-1,3,4-oxadiazol-2-yl)pyrazin-2-amine 1H NMR (400.0 MHz, DMSO) d 4.09 (s, 3H), 7.66-7.72 (m, 3H), 7.96 (br s, 2H), 8.12 (br d, 1H), 8.17 (dd, 2H), 8.47 (d, 1H), 8.64 (s, 1H) and 9.03 (s, 1H) ppm; MS (ES$^+$) 347.1

Compound IA-117 5-(6-methoxy-3-pyridyl)-3-(5-phenyl-1,3,4-oxadiazol-2-yl)pyrazin-2-amine 1H NMR (400.0 MHz, DMSO) d 3.93 (s, 3H), 6.99 (d, 1H), 7.67-7.73 (m, 5H), 8.17-8.20 (m, 2H), 8.42 (dd, 1H), 8.93 (d, 1H) and 8.95 (s, 1H) ppm; MS (ES$^+$) 347.1

Compound IA-165 5-[2-(2-dimethylaminoethyloxy)-4-pyridyl]-3-(5-phenyl-1,3,4-oxadiazol-2-yl)pyrazin-2-amine 1H NMR (400.0 MHz, DMSO) d 2.23 (s, 6H), 2.65 (t, 2H), 4.41 (t, 2H), 7.49 (s, 1H), 7.69-7.73 (m, 4H), 7.95 (br s, 2H), 8.16-8.19 (m, 2H), 8.28 (d, 1H) and 9.07 (s, 1H) ppm; MS (ES$^+$) 404.1

Compound IA-186 3-(5-phenyl-1,3,4-oxadiazol-2-yl)-5-(6-piperazin-1-yl-3-pyridyl)pyrazin-2-amine 1H NMR (400.0 MHz, DMSO) d 3.00 (br d, 4H), 3.58 (br t, 4H), 6.86 (d, 1H), 7.42-7.48 (m, 5H), 7.94 (dd, 2H), 8.09 (dd, 1H), 8.53 (br s, 2H), 8.68 (s, 1H) and 8.69 (d, 1H) ppm Compound IA-265 N'-[4-[5-amino-6-(5-phenyl-1,3,4-oxadiazol-2-yl)pyrazin-2-yl]-2-pyridyl]-N,N-dimethyl-ethane-1,2-diamine 1H NMR (400.0 MHz, DMSO) d 2.20 (s, 6H), 2.45 (t, 2H), 3.41 (q, 2H), 6.54 (t, 1H), 7.18 (dd, 1H), 7.21 (s, 1H), 7.67-7.74 (m, 3H), 7.86 (br s, 2H), 8.08 (d, 1H), 8.18 (dd, 2H) and 8.89 (s, 1H) ppm; MS (ES$^+$) 403.2

Compound IA-279 5-[6-[3-(dimethylamino)propoxy]-3-pyridyl]-3-(5-phenyl-1,3,4-oxadiazol-2-yl)pyrazin-2-amine 1H NMR (400.0 MHz, DMSO) d 1.89 (quin, 2H), 2.16 (s, 6H), 2.36 (t, 2H), 4.35 (t, 2H), 6.96 (d, 1H), 7.68-7.71 (m, 5H), 8.17-8.19 (m, 2H), 8.40 (dd, 1H), 8.91 (d, 1H) and 8.94 (s, 1H) ppm; MS (ES$^+$) 418.2

Compound IA-283 5-(6-morpholino-3-pyridyl)-3-(5-phenyl-1,3,4-oxadiazol-2-yl)pyrazin-2-amine 1H NMR (400.0 MHz, DMSO) d 3.33-3.35 (m, 4H), 3.52-3.54 (m, 4H), 6.79 (d, 1H), 7.42-7.51 (m, 5H), 7.95-7.97 (m, 2H), 8.07 (dd, 1H) and 8.69 (s, 2H) ppm; MS (ES$^+$) 402.1

Example 24A 5-(2-(2-aminoethylthio)phenyl)-3-(5-phenyl-1,3,4-oxadiazol-2-yl)pyrazin-2-amine (Compound IA-224)

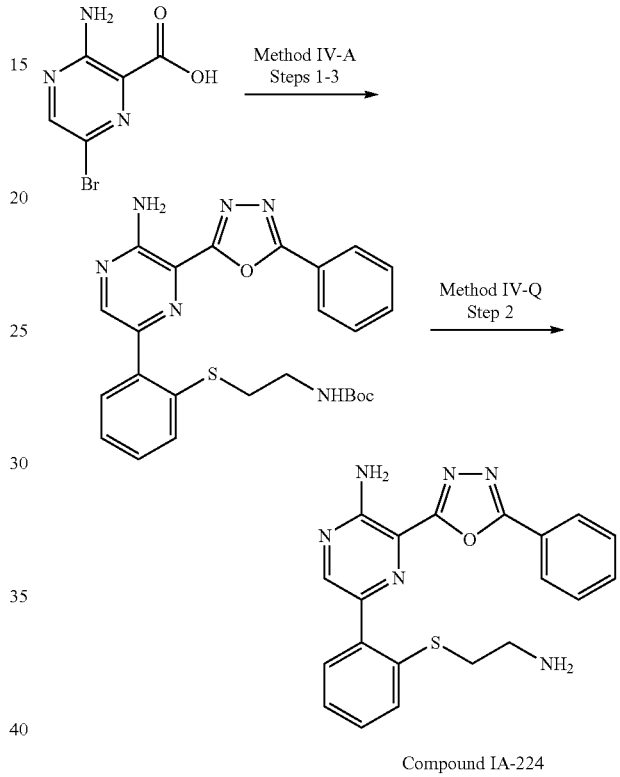

Compound IA-224

Compound IA-224 was prepared using Method IV-A, Steps 1-3, followed by Method IV-Q, Step 2.

Compound IA-224 5-(2-(2-aminoethylthio)phenyl)-3-(5-phenyl-1,3,4-oxadiazol-2-yl)pyrazin-2-amine 1H NMR (400 MHz, DMSO) d 2.9-3.0 (m, 2H), 3.2 (t, 2H), 7.8 (t, 1H), 7.95 (t, 1H), 7.6-7.75 (m, 5H), 7.75-7.85 (br s, 3H), 8.15 (d, 2H) and 8.55 (s, 1H) ppm; MS (ES$^+$) 391.2

Example 25A 5-(2-(2-aminoethylsulfinyl)phenyl)-3-(5-phenyl-1,3,4-oxadiazol-2-yl)pyrazin-2-amine (Compound IA-261)

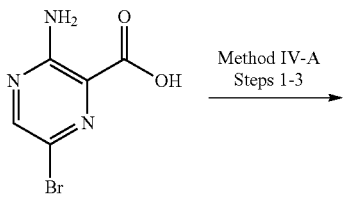

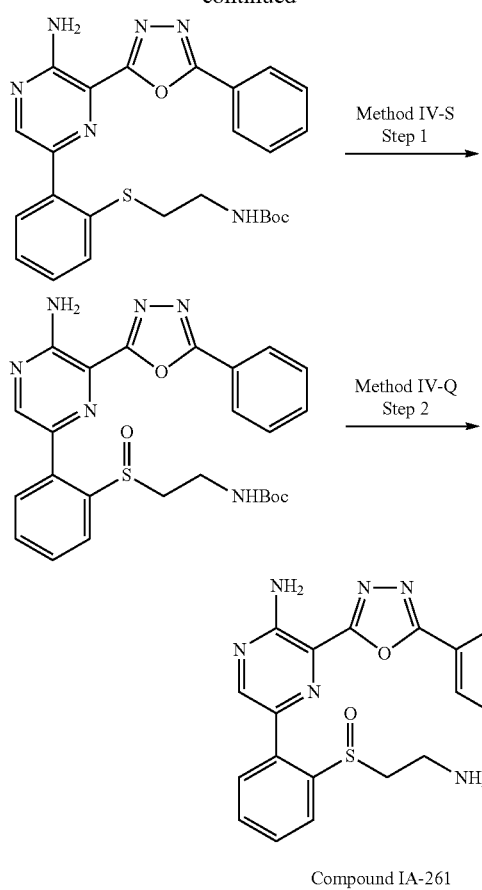

Compound IA-261

Compound IA-261 was prepared using Method IV-A, Steps 1-3, followed by Method IV-S, Step 1, followed by Method IV-Q, Step 2.

Compound IA-261 5-(2-(2-amino ethylsulfinyl)phenyl)-3-(5-phenyl-1,3,4-oxadiazol-2-yl)pyrazin-2-amine 1H NMR (400 MHz, DMSO) d 2.9-3.0 (m, 1H), 3.1-3.2 (m, 1H), 3.3-3.4 (m, 1H), 3.55-3.62 (m, 1H), 7.6-7.75 (m, 8H), 7.8-7.9 (m, 2H), 8.2-8.3 (m, 4H) and 8.55 (s, 1H) ppm; MS (ES+) 407.2

Example 26A

4-[5-amino-6-[5-(6-amino-2-pyridyl)-1,3,4-oxadiazol-2-yl]pyrazin-2-yl]-N,N-dimethyl-benzamide (Compound IA-231)

SCHEME

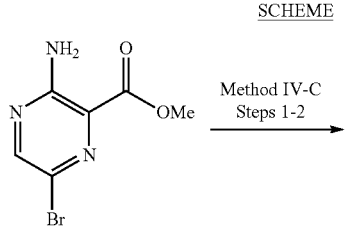

Method IV-C
Steps 1-2

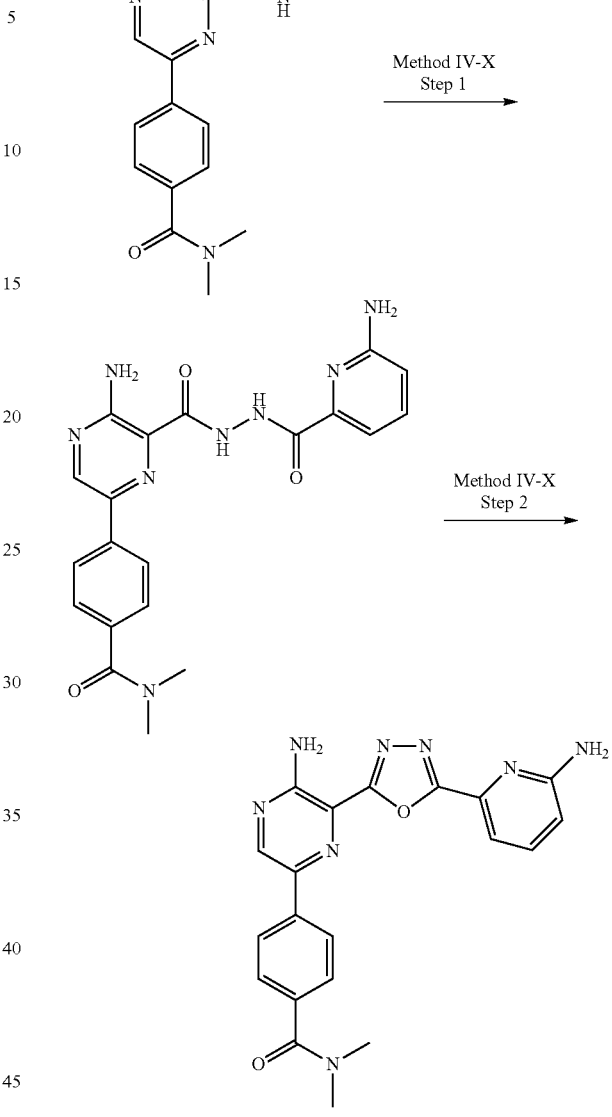

Compound IA-231

Compound IA-231 was prepared using Method IV-C, Steps 1-2, followed by Method IV-X, Steps 1-2.

Method IV-X

Step 1: 4-(5-amino-6-(2-(6-aminopyridine-2-carbonyl)hydrazinecarbonyl)pyrazin-2-yl)-N,N-dimethyl-benzamide A solution of 4-[5-amino-6-(hydrazinecarbonyl)pyrazin-2-yl]-N,N-dimethylbenzamide (100 mg, 0.3163 mmol) and 6-aminopyridine-2-carboxylic acid (43.69 mg, 0.3163 mmol) in DMF (1.000 mL) was treated with triethylamine (32.01 mg, 44.09 μL, 0.3163 mmol) then warmed slightly. The mixture was cooled to room temperature and then treated with (benzotriazol-1-yloxy-dimethylamino-methylene)-dimethyl-ammonium tetrafluoroborate (121.9 mg, 0.3796 mmol) and stirred at room temperature overnight.

The mixture was poured dropwise onto water (5 ml) with rapid stirring, stirred at room temperature for 1 h then filtered to give a wet paste which was dried under high vacuum at 100° C. overnight. Used directly in the next step without purification.

Step 2: 4-[5-amino-6-[5-(6-amino-2-pyridyl)-1,3,4-oxadiazol-2-yl]pyrazin-2-yl]-N,N-dimethyl-benzamide To a suspension of 4-[5-amino-6-[[(6-aminopyridine-2-carbonyl)amino]carbamoyl]pyrazin-2-yl]-N,N-dimethyl-benzamide (80 mg, 0.1903 mmol) in anhydrous acetonitrile (1.600 mL) cooled in an ice bath, was added DIPEA (73.78 mg, 99.43 µL, 0.5709 mmol) followed by dibromo(triphenyl)phosphorane (104.4 mg, 0.2474 mmol) portionwise. The resulting mixture was stirred at room temperature for 30 min. The precipitate was isolated by filtration, washed with small amount of acetonitrile giving a pale yellow solid. The solid was triturated in hot acetonitrile, cooled, filtered and washed acetonitrile then ether to give the pure product (36.1 mg, 54% yield); 1H NMR (400 MHz, DMSO) d 2.98-3.02 (m, 6H), 6.53 (br s, 2H), 6.69 (m, 1.5H), 7.16 (m, 0.5H), 7.16 (m, 1H), 7.53-7.66 (m, 3H), 8.11 (m, 2H) and 8.94 (s, 1H) ppm; MS (ES$^+$) 403.29

The following compounds were all prepared using a method similar to the one described for Compound IA-231 above.

Compound IA-73 tert-butyl N-[[3-[5-[3-amino-6-[4-(dimethylcarbamoyl)phenyl]pyrazin-2-yl]-1,3,4-oxadiazol-2-yl]phenyl]methyl]carbamate 1H NMR (400.0 MHz, DMSO) d 1.41 (s, 9H), 2.98 (m, 6H), 4.27 (m, 2H), 7.54-7.60 (m, 4H), 7.65 (m, 1H), 7.79 (br s, 2H), 8.03-8.05 (m, 2H), 8.16 (m, 2H) and 8.99 (s, 1H) ppm; MS (ES$^+$) 516.3

Compound IA-95 tert-butyl 4-[5-[3-amino-6-(4-isopropylsulfonylphenyl)pyrazin-2-yl]-1,3,4-oxadiazol-2-yl]-3,6-dihydro-2H-pyridine-1-carboxylate 1H NMR (400 MHz, DMSO) d 1.19 (d, 6H), 1.45 (s, 9H), 2.64 (s, 2H), 3.39-3.53 (m, 1H), 3.60 (s, 2H), 4.18 (s, 2H), 7.01 (s, 1H), 7.85 (s, 2H), 7.95 (d, 2H), 8.36 (d, 2H) and 9.05 (s, 1H) ppm; MS (ES$^+$) 527.3

Compound IA-143 5-[5-[3-amino-6-(4-isopropylsulfonylphenyl)pyrazin-2-yl]-1,3,4-oxadiazol-2-yl]thiophene-3-carbonitrile 1H NMR (400 MHz, DMSO) d 1.20 (d, 6H), 3.47 (t, 1H), 7.97 (d, 2H), 8.40 (dd, 2H), 8.46 (d, 1H), 8.97 (d, 1H) and 9.08 (s, 1H) ppm; MS (ES$^+$) 453.0

Compound IA-154 tert-butyl N-[1-[3-[5-[3-amino-6-(4-isopropylsulfonylphenyl)pyrazin-2-yl]-1,3,4-oxadiazol-2-yl]phenyl]ethyl]carbamate 1H NMR (400 MHz, DMSO) d 1.19 (m, 6H), 1.38 (m, 12H), 3.48 (m, 1H), 4.77 (m, 1H), 7.64 (m, 3H), 7.97 (m, 2H), 8.03 (m, 1H), 8.10 (s, 1H), 8.39 (m, 2H) and 9.07 (s, 1H) ppm; MS (ES$^+$) 565.35

Compound IA-162 tert-butyl N-[[4-[5-[3-amino-6-[4-(dimethylcarbamoyl)phenyl]pyrazin-2-yl]-1,3,4-oxadiazol-2-yl]phenyl]methyl]carbamate 1H NMR (400.0 MHz, DMSO) d 1.42 (s, 9H), 2.98-3.02 (m, 6H), 4.25 (d, 2H), 7.51-7.56 (m, 5H), 7.79 (br s, 2H), 8.12-8.19 (m, 4H) and 8.98 (s, 1H) ppm; MS (ES$^+$) 516.24

Compound IA-223 4-[5-amino-6-[5-(2-amino-4-pyridyl)-1,3,4-oxadiazol-2-yl]pyrazin-2-yl]-N,N-dimethyl-benzamide 1H NMR (400 MHz, DMSO) d 2.98-3.02 (m, 6H), 6.49 (br s, 2H), 7.13-7.17 (m, 2H), 7.54-7.56 (m, 2H), 7.80 (br s, 2H), 8.14-8.19 (m, 3H) and 9.00 (1H, s) ppm; MS (ES$^+$) 403.21

Compound IA-251 tert-butyl N-[2-[5-[3-amino-6-(4-isopropylsulfonylphenyl)pyrazin-2-yl]-1,3,4-oxadiazol-2-yl]ethyl]carbamate 1H NMR (400 MHz, DMSO) d 1.19 (d, 6H), 1.32 (s, 9H), 2.08 (s, 2H), 3.13 (s, 2H), 3.31 (d, 2H), 3.40 (d, 1H), 7.05-7.08 (m, 1H), 7.96 (d, 2H), 8.32 (d, 2H) and 9.02 (s, 1H) ppm; MS (ES$^+$) 489.27

Example 27A 4-(5-amino-6-(5-(2-ethylphenyl)-1,3,4-oxadiazol-2-yl)pyrazin-2-yl)-N,N-dimethylbenzamide (Compound IA-155)

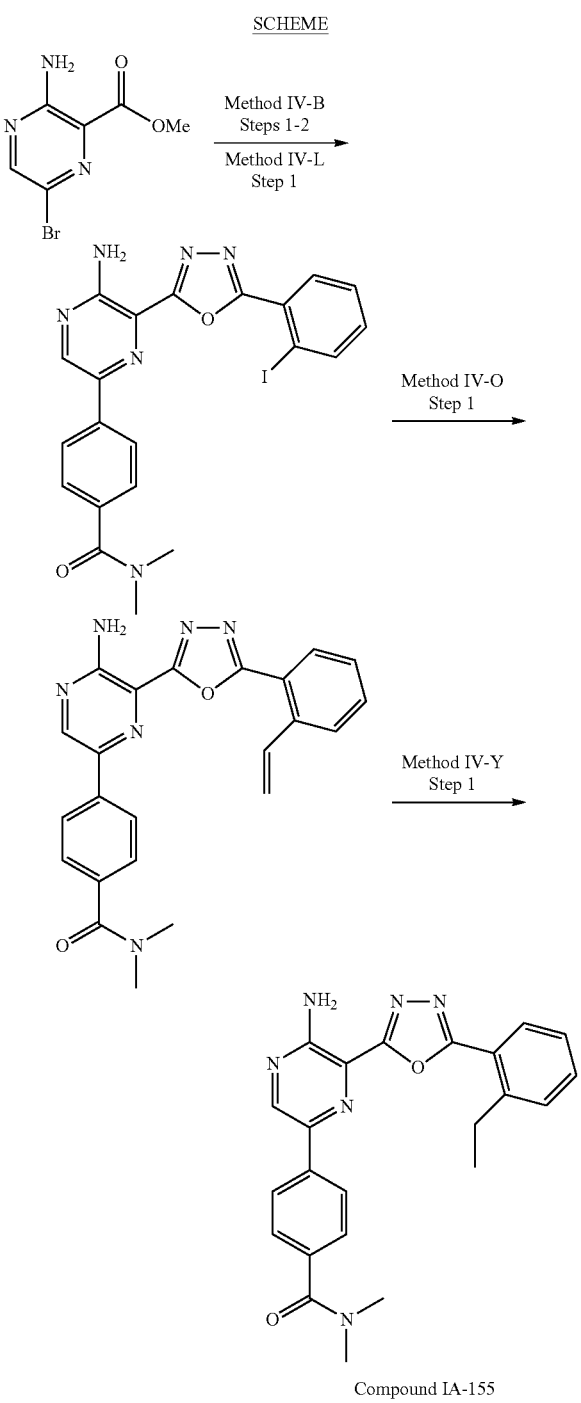

Compound IA-155

Compound IA-155 was prepared using Method IV-B, Steps 1-2, followed by Method IV-L, Step 1, followed by Method IV-O, Step 1, followed by Method IV-Y, Step 1.

Method IV-Y

Step 1: 4-(5-amino-6-(5-(2-ethylphenyl)-1,3,4-oxadiazol-2-yl)pyrazin-2-yl)-N,N-dimethylbenzamide A suspension of 4-[5-amino-6-[5-(2-vinylphenyl)-1,3,4-oxadiazol-2-yl]pyrazin-2-yl]-N,N-dimethyl-benzamide (45 mg, 0.1091 mmol) in a mixture of ethanol (5 mL) and acetic acid (0.5 mL) in the presence of Pd on C, wet, Degussa (116.1 mg, 0.1091 mmol) was hydrogenated at 60 psi overnight using the parr apparatus. The reaction mixture was filtered through a Celite pad and washed with more ethanol (5 mL) and ethyl acetate (5 mL). The filtrate was dried over MgSO$_4$ and filtered and concentrated in vacuo. Purified by reverse phase preparative HPLC [Waters Sunfire C18, 10 mM, 100 Å column, gradient 10%-95% B (solvent A: 0.05% TFA in water; solvent B: CH$_3$CN) over 16 minutes at 25 mL/min]. The product fractions were combined and freeze dried to give the product as a yellow solid (14.2 mg, 38% yield); 1H NMR (400 MHz, DMSO) d 1.30 (t, 3H), 2.98 (m, 6H), 3.13 (q, 2H), 7.48-7.55 (m, 4H), 7.62 (m, 1H), 7.78 (br s, 2H), 8.05 (m, 1H), 8.14 (m, 2H) and 8.99 (1H, s) ppm; MS (ES$^+$) 415.27

Example 28A

4-[5-amino-6-(5-phenyl-1,3,4-oxadiazol-2-yl)pyrazin-2-yl]-N,N-dimethyl-3-prop-1-ynyl-benzamide (Compound IA-268)

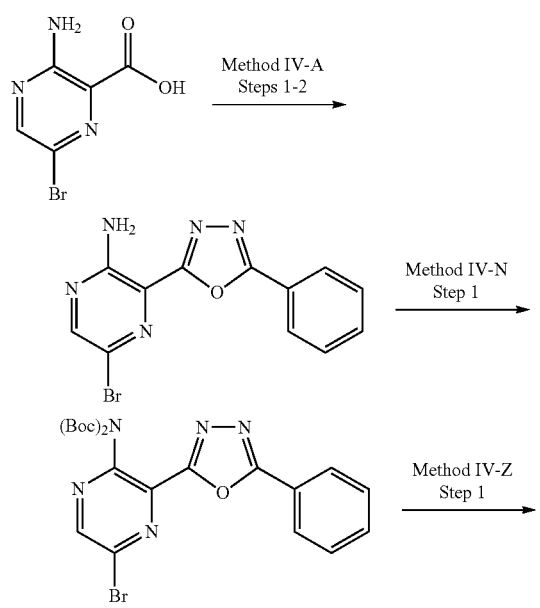

Compound IA-268

Compound IA-268 was prepared using Method IV-A, Steps 1-2, followed by Method IV-N, Step 1, followed by Method IV-Z, Steps 1-2.

Method IV-Z

Step 1: di-tert-butyl(5-(4-(dimethylcarbamoyl)-2-(prop-1-ynyl)phenyl)-3-(5-phenyl-1,3,4-oxadiazol-2-yl)pyrazin-2-yl)iminodicarbonate 4-(dimethylcarbamoyl)-2-(prop-1-ynyl)phenylboronic acid (52 mg, 0.225 mmol) was treated with tert-butyl N-[5-bromo-3-(5-phenyl-1,3,4-oxadiazol-2-yl)pyrazin-2-yl]-N-tert-butoxycarbonyl-carbamate (77.91 mg, 0.1503 mmol), sodium carbonate (75.15 µL of 2 M, 0.1503 mmol) and dichloropalladium; triphenylphosphane (10.55 mg, 0.01503 mmol) and DMF (1.122 mL), and the resulting mixture heated at 95° C. in the microwave for 1 h. The reaction mixture was diluted with EtOAc and washed NaHCO$_3$/NaCl aqueous solution (3×5 mL), dried over MgSO$_4$ and concentrated in vacuo. Purified by column chromatography on silica gel eluting with 30-100% EtOAc/petroleum ether. Product fractions were combined and concentrated in vacuo to leave a brown oil which was used directly in the next step.

Step 2: 4-[5-amino-6-(5-phenyl-1,3,4-oxadiazol-2-yl)pyrazin-2-yl]-N,N-dimethyl-3-prop-1-ynyl-benzamide di-tert-butyl(5-(4-(dimethylcarbamoyl)-2-(prop-1-ynyl)phenyl)-3-(5-phenyl-1,3,4-oxadiazol-2-yl)pyrazin-2-yl)iminodicarbonate (10 mg, 0.01601 mmol) in CH₂Cl₂ (200 µL) was treated with TFA (200 µL, 2.596 mmol) and stirred at room temperature for 1 h. The reaction mixture was concentrated under reduced pressure then passed through carbonate cartridge with eluting with DCM/MeOH. The product was purified by column chromatography on silica gel eluting with 20-100% EtOAc/CH₂Cl₂ to yield the product (2.6 mg, 34% yield); 1H NMR (400 MHz, CDCl₃) d 1.97 (s, 3H), 2.98-3.07 (m, 6H), 7.40-7.52 (m, 5H), 7.82 (m, 1H), 8.19 (m, 2H) and 8.90 (s, 1H) ppm; MS (ES⁺) 425.21

Example 29A

4-[5-amino-6-[5-[3-(aminomethyl)phenyl]-1,3,4-oxadiazol-2-yl]pyrazin-2-yl]-N,N-dimethyl-benzamide (Compound IA-183)

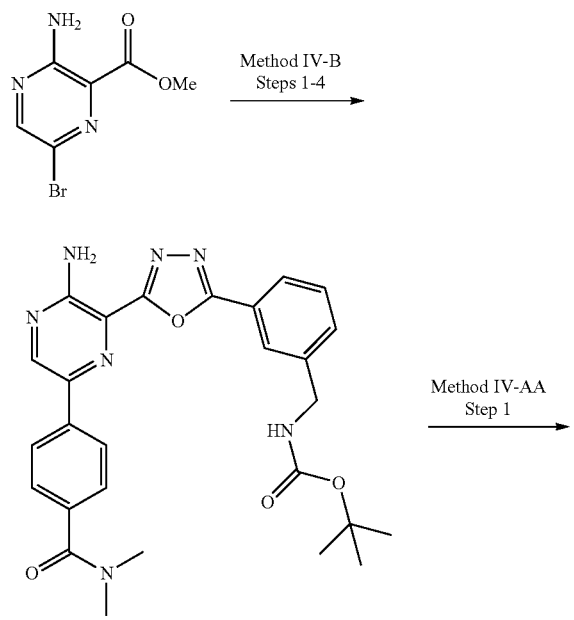

Compound IA-183

Compound IA-183 was prepared using Method IV-B, Steps 1-4, followed by Method IV-AA, Step 1.

Method IV-AA

Step 1: 4-[5-amino-6-[5-[3-(aminomethyl)phenyl]-1,3,4-oxadiazol-2-yl]pyrazin-2-yl]-N,N-dimethyl-benzamide TFA (131.1 mg, 88.58 µL, 1.150 mmol) was added to a solution of tert-butyl N-[[3-[5-[3-amino-6-[4-(dimethylcarbamoyl)phenyl]pyrazin-2-yl]-1,3,4-oxadiazol-2-yl]phenyl]methyl]carbamate (60 mg, 0.1150 mmol) in dichloromethane (2 mL) and the resulting solution stirred at room temperature overnight. The reaction mixture was passed through a bicarbonate cartridge, which was flushed further with methanol (5 mL). The filtrate was concentrated in vacuo to leave a yellow/orange solid. The solid was taken up in a mixture of methanol and dichloromethane and passed through an SCX cartridge. The cartridge was washed initially with methanol and then the product eluted with 2M ammonia in methanol solution over 4 fractions. A yellow solid crystallised out of the filtrate which was isolated by filtration to give the product (44 mg, 90% yield) 1H NMR (400 MHz, DMSO) d 2.98 (m, 6H), 3.87 (s, 2H), 7.55 (m, 2H), 7.59-7.66 (m, 2H), 7.81 (br s, 2H), 8.00 (m, 1H), 8.17 (m, 3H) and 8.99 (s, 1H) ppm; MS (ES⁺) 416.26

The following compounds were all prepared using a method similar to the one described for Compound IA-183 above.

Compound IA-234 4-[5-amino-6-[5-[4-(aminomethyl)phenyl]-1,3,4-oxadiazol-2-yl]pyrazin-2-yl]-N,N-dimethyl-benzamide 1H NMR (400 MHz, DMSO) d 2.99-3.02 (m, 6H), 4.20 (s, 2H), 7.56 (d, 2H), 7.75 (d, 2H), 7.80 (br s, 2H), 8.18 (d, 2H), 8.23 (d, 2H), 8.34 (br s, 2H) and 9.00 (s, 1H) ppm; MS (ES⁺) 416.25

Example 30A

4-[5-amino-6-[5-[2-(2-aminoethoxy)phenyl]-1,3,4-oxadiazol-2-yl]pyrazin-2-yl]-N,N-dimethyl-benzamide (Compound IA-213)

SCHEME

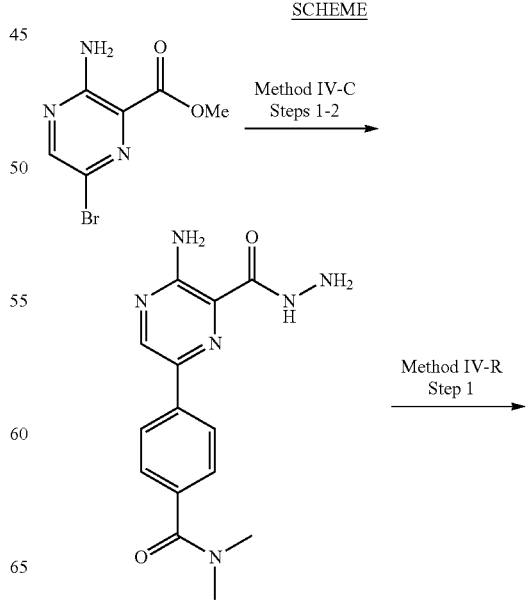

7.69-7.71 (m, 2H), 7.87 (s, 3H), 8.04 (dd, 1H), 8.16 (d, 2H) and 9.01 (s, 1H) ppm; MS (ES+) 446.28

Example 31A 4-(5-amino-6-(5-(3-methoxythiophen-2-yl)-1,3,4-oxadiazol-2-yl)pyrazin-2-yl)-N,N-dimethylbenzamide (Compound IA-172)

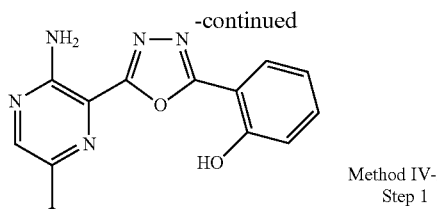

Method IV-AB
Step 1

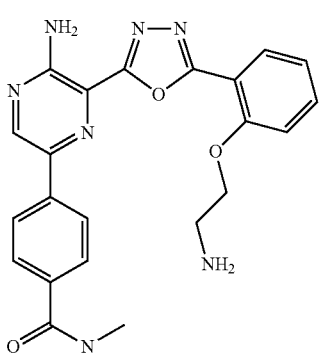

Compound IA-213

Compound IA-213 was prepared using Method IV-C, Steps 1-2, followed by Method IV-R, Step 1, followed by Method IV-AB, Step 1.

Method IV-AB

Step 1: 4-[5-amino-6-[5-[2-(2-amino ethoxy)phenyl]-1,3,4-oxadiazol-2-yl]pyrazin-2-yl]-N,N-dimethyl-benzamide A mixture of 4-[5-amino-6-[5-(2-hydroxyphenyl)-1,3,4-oxadiazol-2-yl]pyrazin-2-yl]-N,N-dimethyl-benzamide (50 mg, 0.1228 mmol) in DMF (1.000 mL) was stirred at room temperature and potassium carbonate (25.46 mg, 0.1842 mmol) added. The resulting suspension was heated at 60-65° C. and tert-butyl N-(2-bromoethyl)carbamate (30.28 mg, 0.1351 mmol) was added slowly. After addition is complete the reaction mixture was heated overnight at 65° C. The reaction mixture was cooled to room temperature and water (2 mL) added slowly and the mixture stirred at room temperature for 20 min. A precipitate formed and was isolated by filtration and washed with water (3×5 mL). The solid was re-dissolved in $CH_2Cl_2$ and dried ($MgSO_4$), filtered and evaporated to dryness. The solid was triturated with DCM/Ether, and filtered to leave a yellow solid. The yellow solid was in $CH_2Cl_2$ (1 mL) and TFA (150 μL, 1.947 mmol) added and the resulting solution stirred at room temperature for 2 h. The reaction mixture was concentrated in vacuo and the residue taken up in a mixture of MeOH/$CH_2Cl_2$ (4 mL) and passed through a bicarbonate cartridge eluting with MeOH/DCM. The filtrate was evaporated to dryness and then triturated with acetonitrile to give the product as a yellow solid (36.7 mg, 69% yield) 1H NMR (400 MHz, DMSO) d 2.98 (s, 3H), 3.02 (s, 3H), 3.31 (t, 2H), 4.41 (t, 2H), 7.30 (t, 1H), 7.40 (d, 1H), 7.56 (d, 2H),

SCHEME

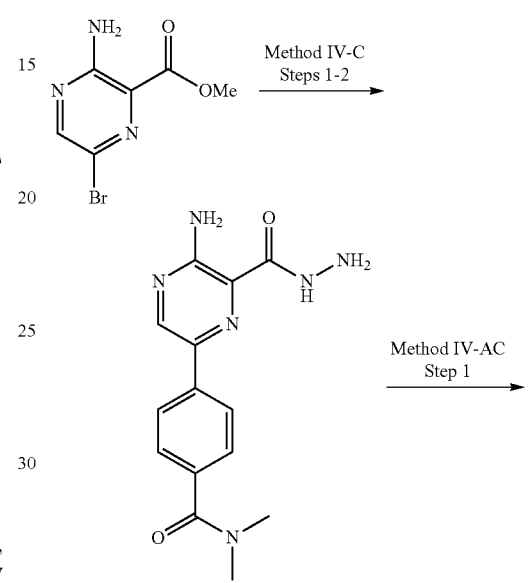

Method IV-AC
Step 1

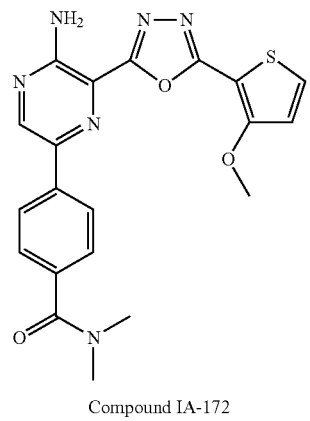

Compound IA-172

Compound IA-172 was prepared using Method IV-C, Steps 1-2, followed by Method IV-AC, Step 1.

Method IV-AC

Step 1: 4-(5-amino-6-(5-(3-methoxythiophen-2-yl)-1,3,4-oxadiazol-2-yl)pyrazin-2-yl)-N,N-dimethyl-benzamide TBTU (160.4 mg, 0.4995 mmol) and $Et_3N$ (33.70 mg, 46.42 μL, 0.3330 mmol) were added to a solution of 4-(5-amino-6-(hydrazinecarbonyl)pyrazin-2-yl)-N,N-dimethylbenzamide (100 mg, 0.3330 mmol) and 3-methoxythiophene-2-carboxylic acid (52.67 mg, 0.3330 mmol) in $CH_2Cl_2$ (2.000 mL) and the resulting solution stirred at room temperature for 72 h. The reaction mixture was diluted with dichloromethane (5 mL) and water (5 mL) and the layers separated. The aqueous layer was extracted further with dichloromethane (3×5 mL), and the combined organic extracts dried over MgSO$_4$, filtered and concentrated in vacuo to leave 4-[5-amino-6-[[(3-methoxythiophene-2-carbonyl)amino]carbamoyl]pyrazin-2-yl]-N,N-dimethyl-benzamide as a yellow oil. POCl$_3$ (1.788 g, 1.087 mL, 11.66 mmol) was added to 4-[5-amino-6-[[(3-methoxythiophene-2-carbonyl)amino]carbamoyl]pyrazin-2-yl]-N,N-dimethyl-benzamide and the resulting mixture heated at 100° C. for 2 h. The reaction mixture was cooled to room temperature and ice/water added carefully with vigorous stirring between additions. The mixture was left to stir at room temperature for 20 min and then diluted with dichloromethane (10 mL) and the layers separated. The aqueous layer was extracted further with dichloromethane (2×5 mL) and combined organics dried over MgSO$_4$ and concentrated in vacuo. Solid obtained is re-dissolved in CH$_2$Cl$_2$ and purified by column chromatography on the ISCO column companion system (12 g column, 0-5% MeOH/CH$_2$Cl$_2$). Product fractions were combined and concentrated in vacuo. This was purified further by reverse phase preparative HPLC [Waters Sunfire C18, 10 mM, 100 Å column, gradient 10%-95% B (solvent A: 0.05% TFA in water; solvent B: CH$_3$CN) over 16 minutes at 25 mL/min]. The product fractions were combined and freeze dried to give the product as a yellow solid (33.0 mg, 23% yield) 1H NMR (400 MHz, DMSO) d 2.98 (s, 3H), 3.01 (s, 3H), 4.07 (s, 3H), 7.30 (d, 1H), 7.56 (d, 2H), 7.70 (br s, 2H), 7.96 (d, 1H), 8.14 (d, 2H) and 8.97 (s, 1H) ppm; MS (ES$^+$) 423.19

Example 31A 2-(5-amino-6-(5-(3-methylthiophen-2-yl)-1,3,4-oxadiazol-2-yl)pyrazin-2-yl)-5-(1,4-diazepane-1-carbonyl)benzonitrile (Compound IA-181)

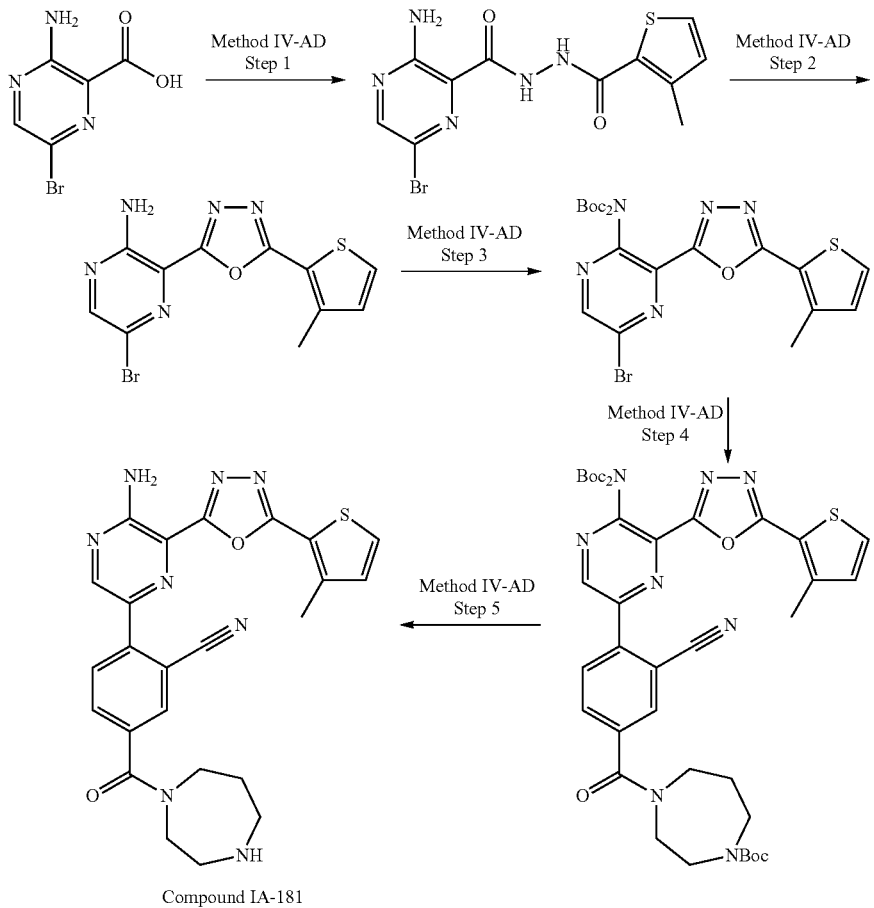

Compound IA-181 was prepared using Method IV-AD, Steps 1-5.

Method IV-AD

Step 1: 3-amino-6-bromo-N'-(3-methylthiophene-2-carbonyl)pyrazine-2-carbohydrazide To a suspension of 3-amino-6-bromo-pyrazine-2-carboxylic acid (13.26 g, 60.82 mmol) and 3-methylthiophene-2-carbohydrazide (10 g, 60.82 mmol) in DMF (95.00 mL) cooled in an ice bath was added Et$_3$N (7.385 g, 10.17 mL, 72.98 mmol) followed by TBTU (23.43 g, 72.98 mmol) portionwise after complete addition, the reaction mixture was allowed to warm to room temperature and stirred overnight. The reaction mixture was diluted with EtOAc (50 mL) and water (50 mL). The layers were separated and the organic extracts washed with water (1×50 mL) and brine (1×50 mL), dried over MgSO₄ and concentrated to leave a brown solid (7.85 g, 36% yield) which was used directly in the next step without further purification.

Step 2: 5-bromo-3-(5-(3-methylthiophen-2-yl)-1,3,4-oxadiazol-2-yl)pyrazin-2-amine To a suspension of 3-amino-6-bromo-N'-(3-methylthiophene-2-carbonyl)pyrazine-2-carbohydrazide (7.85 g, 22.04 mmol) in anhydrous acetonitrile (117.8 mL) cooled in an ice bath was added DIPEA (8.546 g, 11.52 mL, 66.12 mmol) followed by dibromo(triphenyl)phosphorane (12.09 g, 28.65 mmol) portionwise. The resulting suspension was stirred at room temperature for 30 min and the precipitate isolated by filtration and washed with acetonitrile to give the product as a yellow solid (4.42 g, 52% yield); 1H NMR (400 MHz, DMSO) d 2.64 (s, 3H), 7.21 (d, 1H), 7.91 (3H, m) and 8.44 (s, 1H) ppm; MS (ES⁺) 340.04

Step 3: tert-butyl-5-bromo-3-(5-(3-methylthiophen-2-yl)-1,3,4-oxadiazol-2-yl)pyrazin-2-yl(tert-butoxycarbonyl)carbamate 5-bromo-3-[5-(3-methyl-2-thienyl)-1,3,4-oxadiazol-2-yl]pyrazin-2-amine (10.68 g, 31.58 mmol) and DMAP (385.8 mg, 3.158 mmol) were suspended in CH₂Cl₂ (160.2 mL) and THF (160.2 mL) and cooled in an icebath. tert-Butoxycarbonyl tert-butyl carbonate (20.68 g, 94.74 mmol) was added portionwise to the stirred mixture. The reaction mixture was stirred at room temperature for 1 h and then diluted with CH₂Cl₂ (100 ml) and saturated aqueous sodium hydrogen carbonate solution (100 ml). The layers were separated and the organic layer washed with saturated aqueous sodium hydrogen carbonate solution (2×100 ml), dried over MgSO₄, filtered and concentrated in vacuo. The residue was recrystallised from a mixture of ethyl acetate and petroleum ether to give the product as a brown crystalline material (14.29 g, 84% yield); 1H NMR (400 MHz, DMSO) d 1.41 (s, 9H), 2.72 (s, 3H), 7.10 (m, 1H), 7.55 (m, 1H) and 8.74 (s, 1H) ppm

Step 4: tert-butyl 4-(4-(5-(bis(tert-butoxycarbonyl)amino)-6-(5-(3-methylthiophen-2-yl)-1,3,4-oxadiazol-2-yl)pyrazin-2-yl)-3-cyanophenylcarbonyl)-1,4-diazepane-1-carboxylate tert-Butyl N-[5-bromo-3-[5-(3-methyl-2-thienyl)-1,3,4-oxadiazol-2-yl]pyrazin-2-yl]-N-tert-butoxycarbonyl-carbamate (13.52 g, 25.12 mmol) and tert-butyl 4-[3-cyano-4-(4,4,5,5-tetramethyl-1,3,2-dioxaborolan-2-yl)benzoyl]-1,4-diazepane-1-carboxylate (11.44 g, 25.12 mmol) were taken up in DMF (160 mL) and Na₂CO₃ (37.68 mL of 2 M, 75.36 mmol) (4:1 mixture) and reaction mixture degassed with nitrogen and Pd (tBu₃P)₂ (1.027 g, 2.010 mmol) added in one portion. The resulting mixture was heated at 75° C. 2.5 h. The reaction mixture was cooled to room temperature and diluted with EtOAc (50 mL) and water (50 mL). The organic extracts were washed with water (1×100 mL) and brine (1×100 mL) and then the aqueous layers back extracted with ethyl acetate (3×100 mL), dried over MgSO₄, filtered and concentrated in vacuo. The material was passed through a silica pad eluting with 50-100% EtOAc/Petroleum ether. The material was purified further by column chromatography on silica (500 mL) eluting with 30-100% EtOAc/petroleum ether. Product fractions were combined and concentrated in vacuo to leave the product as a yellow solid (11.9 g, 55% yield)

Step 5: 2-[5-amino-6-[5-(3-methyl-2-thienyl)-1,3,4-oxadiazol-2-yl]pyrazin-2-yl]-5-(1,4-diazepane-1-carbonyl)benzonitrile tert-Butyl 4-[4-[5-[bis(tert-butoxycarbonyl)amino]-6-[5-(3-methyl-2-thienyl)-1,3,4-oxadiazol-2-yl]pyrazin-2-yl]-3-cyano-benzoyl]-1,4-diazepane-1-carboxylate (9.9 g, 11.32 mmol) was dissolved in anhydrous CH₂Cl₂ (100 mL) at room temperature and TFA (10 mL, 129.8 mmol) added. Additional TFA (10 mL, 129.8 mmol) was added and the reaction mixture stirred at room temperature for 3.5 h and then concentrated in vacuo. The material was dissolved in a mixture of acetonitrile and methanol (10:1 mixture) and PS-HCO₃ (5 eq) added. The mixture was stirred for 1 h at room temperature and then the resin removed by filtration and washed with acetonitrile and methanol. The filtrate was concentrated in vacuo and the residue recrystallised from acetonitrile. The isolated solid was washed with ether and dried to give the product as a yellow solid (2.41 g, 35% yield); 1H NMR (400 MHz, DMSO) d 1.76-1.84 (m, 2H), 2.67 (s, 3H), 2.88-2.93 (m, 4H), 3.42-3.44 (m, 2H), 3.67-3.74 (m, 2H), 7.2 (d, 1H), 7.84-7.87 (m, 1H), 7.89-7.99 (m, 1H), 8.04-8.09 (m, 2H) and 8.85 (s, 1H) ppm; MS (ES⁺) 487.26

Example 32A

1-[5-amino-6-(5-phenyl-1,3,4-oxadiazol-2-yl)pyrazin-2-yl]pyrrole-2-carbonitrile (Compound IA-264)

SCHEME

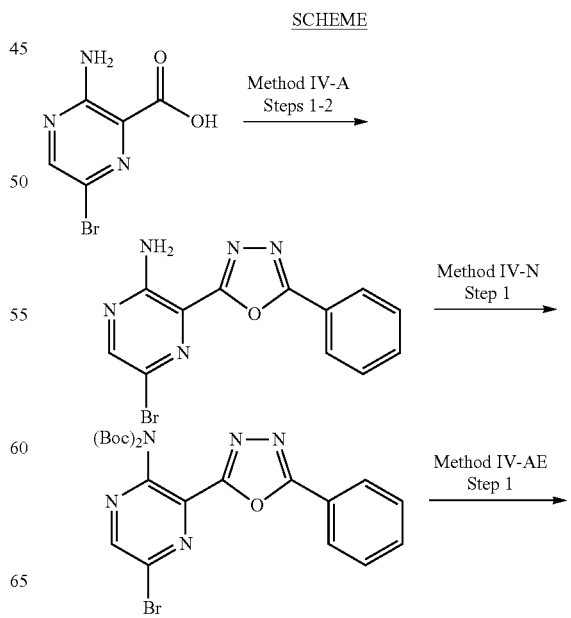

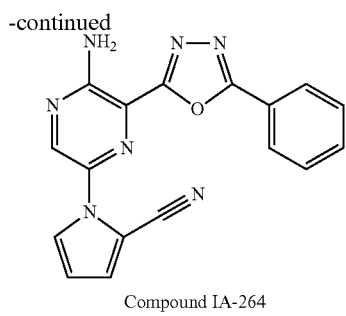

Compound IA-264

Compound IA-264 was prepared using Method IV-A, Steps 1-2, followed by Method IV-N, Step 1, followed by Method IV-AE, Step 1.

Method IV-AE

Step 1: 1-[5-amino-6-(5-phenyl-1,3,4-oxadiazol-2-yl)pyrazin-2-yl]pyrrole-2-carbonitrile tert-Butyl N-[5-bromo-3-(5-phenyl-1,3,4-oxadiazol-2-yl)pyrazin-2-yl]-N-tert-butoxycarbonyl-carbamate (100 mg, 0.1929 mmol) and cesium carbonate (125.7 mg, 0.3858 mmol) were added to DMF (5 mL) followed by the addition of 1H-pyrrole-2-carbonitrile (26.65 mg, 0.2894 mmol). The resulting mixture was heated at 50° C. for 1 h. The mixture was cooled to room temperature, filtered and diluted with ethyl acetate (5 mL). The organics were washed with water (1×10 mL) and brine (1×10 mL) and the organic layer concentrated in vacuo to leave an oil. This was dissolved in CH$_2$Cl$_2$ (10 mL) and TFA (659.9 mg, 445.9 μL, 5.787 mmol) was added. The reaction mixture was stirred at room temperature for 1 h, and then concentrated in vacuo to an oil. The oil was dissolved in CH$_2$Cl$_2$ and the product precipitated by slow addition of petroleum ether (28.3 mg, 45% yield); 1H NMR (400 MHz, DMSO) d 6.6 (s, 1H), 7.3 (s, 1H), 7.7-7.85 (m, 3H), 7.9 (br s, 2H), 7.95 (s, 1H), 8.2-8.25 (m, 2H) and 8.8 (s, 1H) ppm; MS (ES$^+$) 330.2

Example 33A

4-[5-amino-6-(5-phenyl-1,3,4-oxadiazol-2-yl)pyrazin-2-yl]-2-(2-dimethylaminoethylamino)pyridine-3-carbonitrile (Compound IA-209)

SCHEME

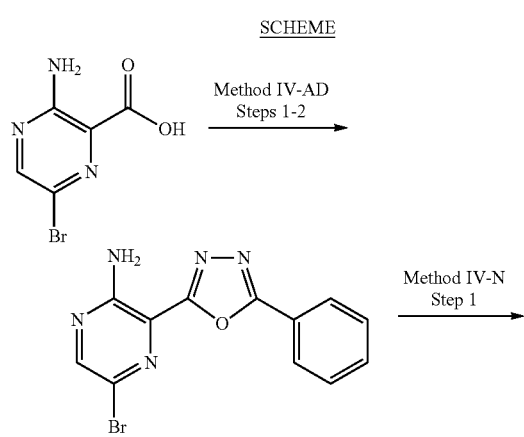

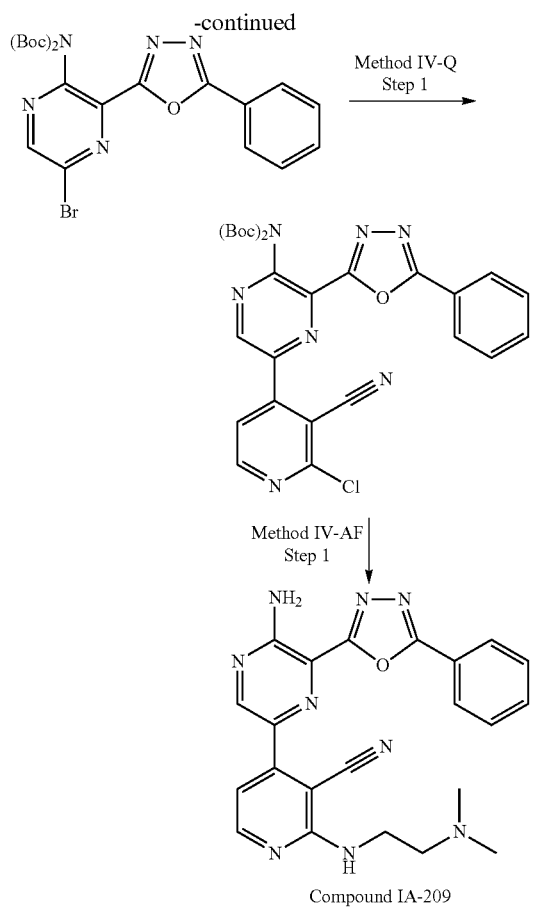

Compound IA-209

Compound IA-209 was prepared using Method IV-A, Steps 1-2, followed by Method IV-N, Step 1, followed by Method IV-Q, Step 1, followed by Method IV-AF, Step 1.

Method IV-AF

Step 1: 4-[5-amino-6-(5-phenyl-1,3,4-oxadiazol-2-yl)pyrazin-2-yl]-2-(2-dimethylaminoethylamino)pyridine-3-carbonitrile N,N-dimethylethane-1,2-diamine (22.04 mg, 27.45 μL, 0.2500 mmol) was added to a solution of di-tert-butyl 5-(2-chloro-3-cyanopyridin-4-yl)-3-(5-phenyl-1,3,4-oxadiazol-2-yl)pyrazin-2-yliminodicarbonate (36 mg, 0.06250 mmol) and Et$_3$N (25.30 mg, 34.85 μL, 0.2500 mmol) in NMP (1 mL) and the reaction was heated at 150° C. for 2 hours under microwave conditions. The material was purified by reverse phase preparative HPLC [Waters Sunfire C18, 10 μM, 100 Å column, gradient 10%-95% B (solvent A: 0.05% TFA in water; solvent B: CH3CN) over 16 minutes at 25 mL/min]. The fractions were collected and freeze-dried to give the title compound as a yellow solid (7.6 mg, 24% yield); 1H NMR (400 MHz, DMSO) d 2.88 (d, 6H), 3.38 (br m, 2H), 3.81-3.83 (m, 2H), 7.34 (d, 1H), 7.63-7.71 (m, 3H), 8.22-8.24 (m, 2H), 8.38 (d, 1H), 8.96 (s, 1H) and 9.23 (br s, 1H) ppm; MS (ES$^+$) 428.3

Example 34A

4-[5-amino-6-[5-[3-(hydroxymethyl)phenyl]-1,3,4-oxadiazol-2-yl]pyrazin-2-yl]-N,N-dimethyl-benzamide (Compound IA-198)

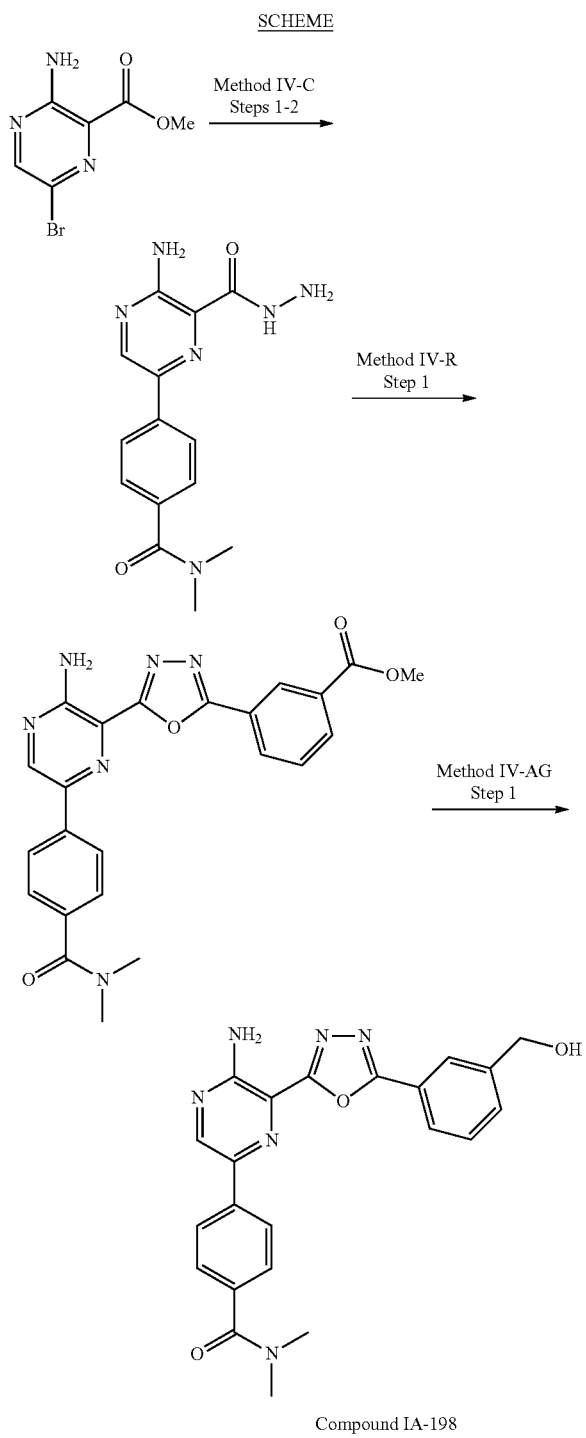 [SMILES: COC(=O)c1nc(Br)cnc1N ; CN(C)C(=O)c1ccc(-c2cnc(N)c(C(=O)NN)n2)cc1 ; COC(=O)c1cccc(-c2nnc(-c3nc(-c4ccc(C(=O)N(C)C)cc4)cnc3N)o2)c1 ; CN(C)C(=O)c1ccc(-c2cnc(N)c(-c3nnc(-c4cccc(CO)c4)o3)n2)cc1]

Compound IA-198

Compound IA-198 was prepared using Method IV-C, Steps 1-2, followed by Method IV-R, Step 1, followed by Method IV-AG, Step 1.

Method IV-AG: Step 1: 4-[5-amino-6-[5-[3-(hydroxymethyl)phenyl]-1,3,4-oxadiazol-2-yl]pyrazin-2-yl]-N,N-dimethyl-benzamide Diisobutylaluminium hydride (810.0 μL of 1 M, 0.8100 mmol) in dichloromethane was added dropwise to a solution of methyl 3-[5-[3-amino-6-[4-(dimethylcarbamoyl)phenyl]pyrazin-2-yl]-1,3,4-oxadiazol-2-yl]benzoate (120 mg, 0.2700 mmol) in $CH_2Cl_2$ (6 mL) at 0° C., the solution darkened upon addition. The resulting solution was stirred at 0° C. for 30 min and allowed to warm slowly to room temperature. The reaction mixture was stirred at room temperature for 4 h and then quenched by addition of 1M HCl (3 mL). The resulting mixture was filtered through a Celite pad and washed with dichloromethane (2×5 mL). The layers were separated and the aqueous layer extracted further with dichloromethane (2×10 mL) and combined organic extracts dried over $MgSO_4$ and concentrated in vacuo. The residue was purified using by reverse phase preparative HPLC [Waters Sunfire C18, 10 μM, 100 Å column, gradient 10%-95% B (solvent A: 0.05% TFA in water; solvent B: CH3CN) over 16 minutes at 25 mL/min]. Product fractions were combined and lypholised to give the product as a yellow solid (20.3 mg, 18% yield); 1H NMR (400 MHz, DMSO) d 2.98 (m, 6H), 4.66 (s, 2H), 7.55 (m, 2H), 7.63 (m, 2H), 7.80 (br s, 2H), 8.04 (m, 1H), 8.16 (m, 3H) and 8.99 (s, 1H) ppm; MS (ES$^+$) 417.23

Example 35A

4-[5-amino-6-[5-[3-(2-hydroxyethyl)phenyl]-1,3,4-oxadiazol-2-yl]pyrazin-2-yl]-N,N-dimethyl-benzamide (Compound IA-69)

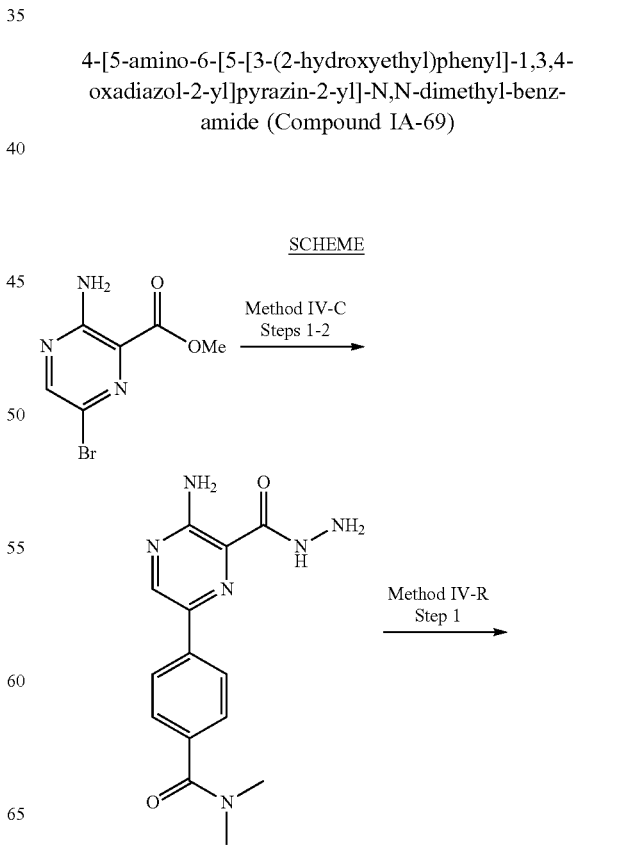

447

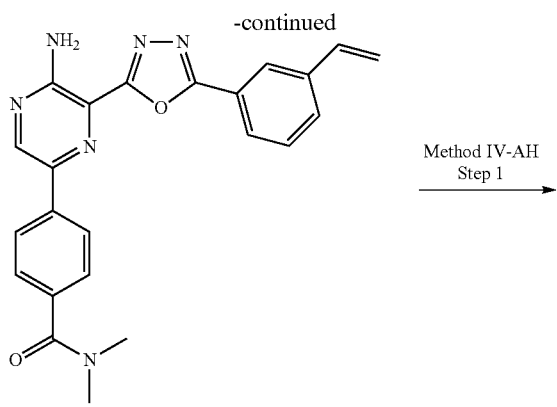

Method IV-AH
Step 1

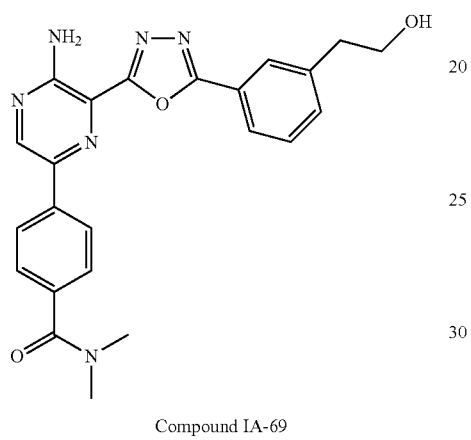

Compound IA-69

Compound IA-69 was prepared using Method IV-C, Steps 1-2, followed by Method IV-R, Step 1, followed by Method IV-AH, Step 1.

Method IV-AH

Step 1: 4-[5-amino-6-[5-[3-(2-hydroxyethyl)phenyl]-1,3,4-oxadiazol-2-yl]pyrazin-2-yl]-N,N-dimethyl-benzamide To a solution of 4-[5-amino-6-[5-(3-vinylphenyl)-1,3,4-oxadiazol-2-yl]pyrazin-2-yl]-N,N-dimethyl-benzamide (100 mg, 0.2425 mmol) in THF (9.172 mL) at 0° C., borane-THF complex (606.3 μL of 1 M, 0.6063 mmol) was added dropwise and the reaction mixture stirred overnight at room temperature. Water (43.69 mg, 43.69 μL, 2.425 mmol) was added to the reaction mixture followed by hydrogen peroxide (299.9 μL of 27.5% w/v, 2.425 mmol) and NaOH (606.5 μL of 2 M, 1.213 mmol) and the mixture stirred vigorously for 1 h. The mixture was partitioned between ethyl acetate (5 mL) and water (5 mL) and the layers separated. The aqueous layer was extracted further with ethyl acetate (2×5 mL) and combined organic extracts dried over MgSO$_4$ and concentrated in vacuo. The residue was purified by reverse phase preparative HPLC [Waters Sunfire C18, 10 μM, 100 Å column, gradient 10%-95% B (solvent A: 0.05% TFA in water; solvent B: CH3CN) over 16 minutes at 25 mL/min]. Product fractions were combined and lypholised to give the product as a yellow solid (5.8 mg, 11% yield); 1H NMR (400 MHz, DMSO) d 2.89 (t, 2H), 2.98 (m, 6H), 3.70 (q, 2H), 4.75 (t, 1H), 7.55-7.62 (m, 4H), 7.80 (br s, 2H), 8.01 (m, 2H), 8.17 (m, 2H) and 8.99 (s, 1H) ppm; MS (ES$^+$) 431.24

The following compounds were all prepared using a method similar to the one described for Compound IA-69 above.

Compound IA-275 4-[5-amino-6-[5-[3-(1-hydroxyethyl)phenyl]-1,3,4-oxadiazol-2-yl]pyrazin-2-yl]-N,N-dimethyl-benzamide 1H NMR (400 MHz, DMSO) d 1.40 (d, 3H), 2.98 (m, 6H), 4.88 (m, 1H), 5.46 (m, 1H), 7.55 (m, 2H), 7.62 (m, 2H), 7.81 (br s, 2H), 8.03 (m, 1H), 8.16 (m, 3H) and 8.99 (s, 1H) ppm; MS (ES$^+$) 431.24

Example 36A

4-[5-amino-6-[5-[2-(3-thienyl)phenyl]-1,3,4-oxadiazol-2-yl]pyrazin-2-yl]-N,N-dimethyl-benzamide (Compound IA-127)

SCHEME

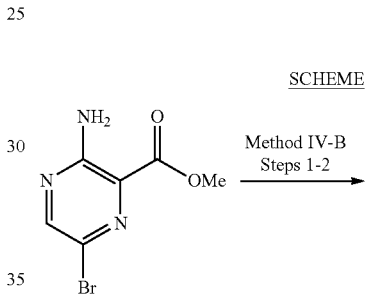

Method IV-B
Steps 1-2

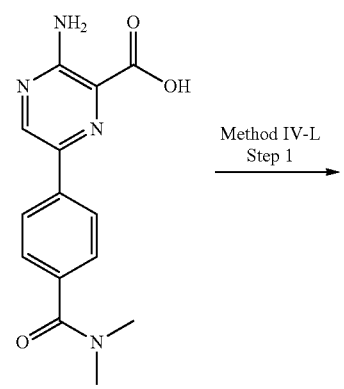

Method IV-L
Step 1

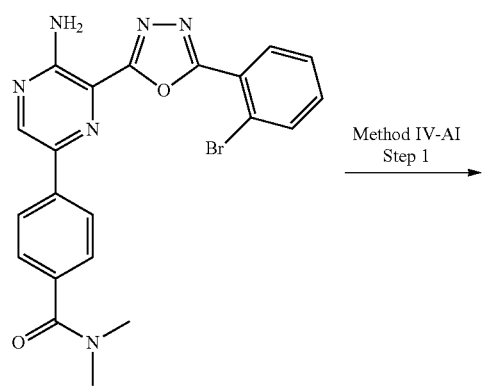

Method IV-AI
Step 1

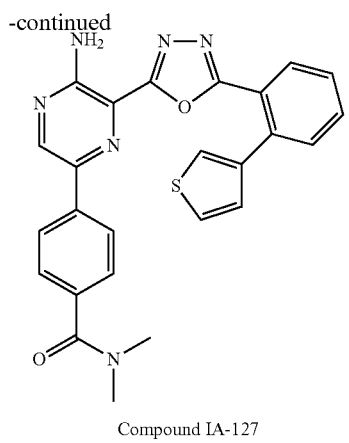

Compound IA-127

Compound IA-127 was prepared using Method IV-B, Steps 1-2, followed by Method IV-L, Step 1, followed by Method IV-AI, Step 1.

Method IV-AI

Step 1: 4-[5-amino-6-[5-[2-(3-thienyl)phenyl]-1,3,4-oxadiazol-2-yl]pyrazin-2-yl]-N,N-dimethyl-benzamide A solution of 4-[5-amino-6-[5-(2-bromophenyl)-1,3,4-oxadiazol-2-yl]pyrazin-2-yl]-N,N-dimethyl-benzamide (50 mg, 0.108 mmol), thiophen-3-ylboronic acid (13.8 mg, 0.108 mmol), cesium carbonate (107 μL of 2M aqueous solution) and dichloropalladium; triphenylphosphane (7.55 mg, 0.0108 mmol) in dioxane (2 mL) was heated at 110° C. in the microwave for 1 h. The reaction mixture was cooled to room temperature and filtered. The filtrated was purified by reverse phase preparative HPLC [Waters Sunfire C18, 10 μM, 100 Å column, gradient 10%-95% B (solvent A: 0.05% TFA in water; solvent B: CH3CN) over 16 minutes at 25 mL/min]. Product fractions were combined and lypholised to give the product as a yellow solid (7.4 mg, 17% yield); 1H NMR (400 MHz, DMSO) d 2.97 (m, 6H), 7.09 (m, 1H), 7.53 (m, 2H), 7.60 (m, 2H), 7.64 (m, 2H), 7.71-7.76 (m, 3H), 8.01 (m, 2H), 8.07 (m, 1H) and 8.95 (s, 1H) ppm; MS (ES+) 469.22

Example 37A

3-[5-[3-(aminomethyl)phenyl]-1,3,4-oxadiazol-2-yl]-5-(4-isopropylsulfonylphenyl)pyrazin-2-amine (Compound IA-220)

SCHEME

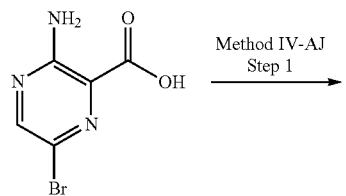

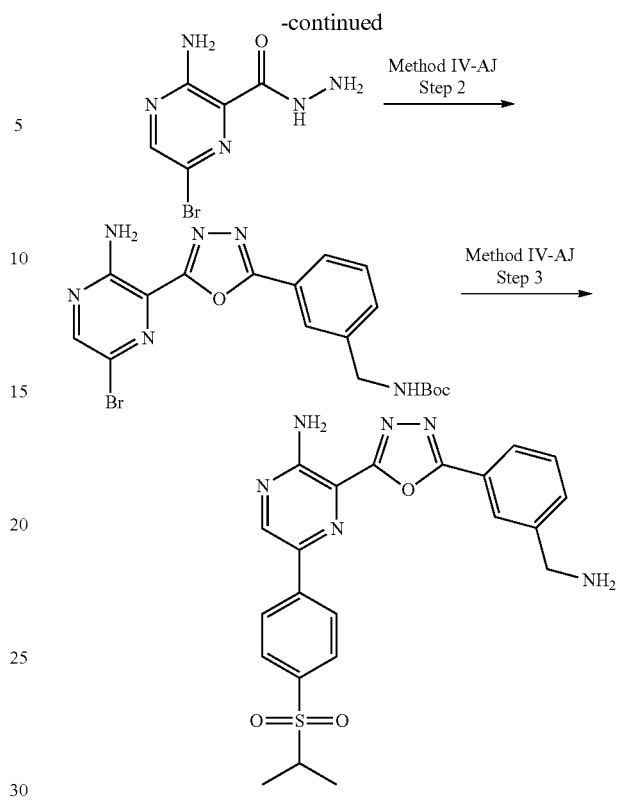

Compound IA-220

Compound IA-220 was prepared using Method IV-AJ, Steps 1-4.

Method IV-AJ

Step 1: 3-amino-6-bromopyrazine-2-carbohydrazide

Methyl 3-amino-6-bromo-pyrazine-2-carboxylate (10.18 g, 43.87 mmol) was suspended in EtOH (50.90 mL) and hydrazine hydrate (4.392 g, 4.268 mL, 87.74 mmol) was added and the reaction mixture heated at 70° C. for 2 h. Water (50 mL) was added and the precipitate isolated by filtration. The solid was washed with methanol and dried under vacuum to leave the product as a pale yellow powder (9.8 g, 96% yield); 1H NMR (400 MHz, DMSO) d 4.53 (bs s, 2H), 7.62 (br s, 2H) and 9.78 (br s, 1H) ppm; MS (ES+) 232.06

Step 2: tert-butyl 3-(5-(3-amino-6-bromopyrazin-2-yl)-1,3,4-oxadiazol-2-yl)benzylcarbamate 3-amino-6-bromo-pyrazine-2-carbohydrazide (1.2 g, 5.172 mmol), TBTU (1.333 g, 5.689 mmol), 3-[(tert-butoxycarbonylamino)methyl]benzoic acid (1.300 g, 5.172 mmol) and DIPEA (1.338 g, 1.803 mL, 10.35 mmol) in a solution in DMF (13.98 mL) were stirred at room temperature for 1 h. The reaction mixture was diluted with ethyl acetate (35 mL), washed with water (2×50 mL) and brine (1×50 mL). The organic layer was dried over MgSO4 and concentrated in vacuo to a solid. This solid was suspended in MeCN (83.89 mL) at room temperature followed by the addition of dibromo(triphenyl)phosphorane (2.183 g, 5.172 mmol) and DIPEA (1.338 g, 1.803 mL, 10.35 mmol). The resulting mixture was stirred at room temperature for 2 h and then concentrated in vacuo to leave a solid. This was purified by column chromatography on silica eluting with EtOAc/petroleum ether, Product fractions were combined and concentrated in vacuo to leave the product as a white solid. The mixture was conc. to a solid and purified by column chromatography using ethylacetate/pet ether as elaunt to afford the product as a white solid (924 mg, 40% yield); 1H NMR (400 MHz, DMSO) d 1.43 (s, 9H), 4.26 (m, 2H), 7.55 (m, 3H), 7.80 (br s, 2H), 7.97 (m, 1H) and 8.45 (s, 1H) ppm; MS (ES$^+$) 449.08

Step 3: 3-[5-[3-(aminomethyl)phenyl]-1,3,4-oxadiazol-2-yl]-5-(4-isopropylsulfonylphenyl)pyrazin-2-amine Sodium carbonate (335.4 μL of 2 M, 0.6708 mmol) was added to a solution of tert-butyl N-[[3-[5-(3-amino-6-bromo-pyrazin-2-yl)-1,3,4-oxadiazol-2-yl]phenyl]methyl]carbamate (100 mg, 0.2236 mmol), (4-isopropylsulfonyl-phenyl)boronic acid (66.30 mg, 0.2907 mmol), palladium; triphenylphosphane (25.84 mg, 0.02236 mmol) in dioxane (5 mL) and the resulting mixture heated at 110° C. under microwave conditions for 90 min. The mixture was placed directly onto silica gel pad and washed through with diethyl ether and followed by 50% EtOAc/petroleum ether. Product fractions were combined and concentrated in vacuo. The residue was dissolved in CH$_2$Cl$_2$ (10 mL) and TFA (764.9 mg, 516.8 μL, 6.708 mmol) was added. The reaction mixture was stirred at room temperature for 1 h and then concentrated in vacuo to leave an oil. This was purified by reverse phase preparative HPLC [Waters Sunfire C18, 10 μM, 100 Å column, gradient 10%-95% B (solvent A: 0.05% TFA in water; solvent B: CH3CN over 16 minutes at 25 mL/min]. Product fractions were combined and lypholised to give the product as a yellow solid (36.05 mg, 35% yield); 1H NMR (400 MHz, DMSO) d 1.3 (d, 6H), 3.45-3.55 (m, 1H), 4.24-4.3 (m, 2H), 7.7-7.8 (m, 2H), 7.95 (d, 2H), 8.25 (d, 1H), 8.3-8.4 (br s, 2H), 8.4 (s, 1H), 8.45 (d, 2H) and 9.1 (s, 1H) ppm; MS (ES$^+$) 451.2

The following compounds were all prepared using a method similar to the one described for Compound IA-220 above.

Compound IA-88 3-[4-[5-amino-6-[5-[4-(methylaminomethyl)phenyl]-1,3,4-oxadiazol-2-yl]pyrazin-2-yl]phenyl]sulfonylbutan-1-ol 1H NMR (400 MHz, DMSO) d 1.21 (d, 3H), 1.38-1.47 (m, 1H), 1.97-2.05 (m, 1H), 2.64 (t, 3H), 3.38-3.46 (m, 2H), 3.51-3.56 (m, 1H), 4.29 (t, 2H), 7.77 (d, 2H), 7.97-8.01 (m, 2H), 8.26 (d, 2H), 8.40-8.44 (m, 2H), 8.97 (s, 2H) and 9.09 (d, 1H) ppm; MS (ES$^+$) 495.0

Compound IA-257 3-[5-[3-(aminomethyl)phenyl]-1,3,4-oxadiazol-2-yl]-5-(2-methylsulfinylphenyl)pyrazin-2-amine 1H NMR (400 MHz, DMSO) d 3.1 (s, 3H), 4.3 (s, 2H), 7.6-7.75 (m, 4H), 8.05 (d, 1H), 8.15 (d, 1H), 8.35-8.5 (m, 4H) and 8.9 (s, 1H) ppm; MS (ES$^+$) 407.1

Compound IA-321 5-(3-fluoro-4-isopropylsulfonyl-phenyl)-3-[5-[2-fluoro-4-(methylaminomethyl)phenyl]-1,3,4-oxadiazol-2-yl]pyrazin-2-amine 1H NMR (400 MHz, DMSO) d 1.25 (d, 6H), 2.7 (s, 3H), 3.5-3.6 (m, 1H), 4.4 (s, 2H), 7.6 (d, 1H), 7.7 (d, 1H), 7.9 (t, 1H), 8.2-8.3 (m, 2H), 8.35 (t, 1H), 8.9-9.0 (br s, 2H) and 9.1 (s, 1H) ppm; MS (ES$^+$) 501.3

Compound IA-329 5-(3-chloro-4-isopropylsulfonyl-phenyl)-3-[5-[2-fluoro-4-(methylaminomethyl)phenyl]-1,3,4-oxadiazol-2-yl]pyrazin-2-amine 1H NMR (400 MHz, DMSO) d 1.25 (d, 6H), 2.7 (s, 3H), 3.7-3.8 (m, 1H), 4.4 (s, 2H), 7.6 (d, 1H), 7.7 (d, 1H), 8.1 (d, 1H), 8.25-8.35 (m, 2H), 8.4 (s, 1H), 8.9-9.0 (br s, 2H) and 9.1 (s, 1H) ppm; MS (ES$^+$) 517.2

Compound IA-342 3-[4-[5-amino-6-[5-[2-fluoro-4-(methylaminomethyl)phenyl]-1,3,4-oxadiazol-2-yl]pyrazin-2-yl]phenyl]sulfonylbutan-1-ol 1H NMR (400 MHz, DMSO) d 1.25 (d, 3H), 1.4-1.5 (m, 1H), 1.95-2.03 (m, 1H), 2.7 (s, 3H), 3.4-3.5 (m, 1H), 3.5-3.6 (m, 1H), 4.45 (s, 2H), 4.6-4.7 (m, 1H), 7.6 (d, 1H), 7.7 (d, 1H), 8.0 (d, 2H), 8.3 (t, 1H), 8.4 (d, 2H), 9.0 (br s, 2H) and 9.1 (s, 1H) ppm; MS (ES$^+$) 513.2

Example 38A

3-[5-[3-(dimethylaminomethyl)phenyl]-1,3,4-oxadiazol-2-yl]-5-(4-isopropylsulfonylphenyl)pyrazin-2-amine (Compound IA-204)

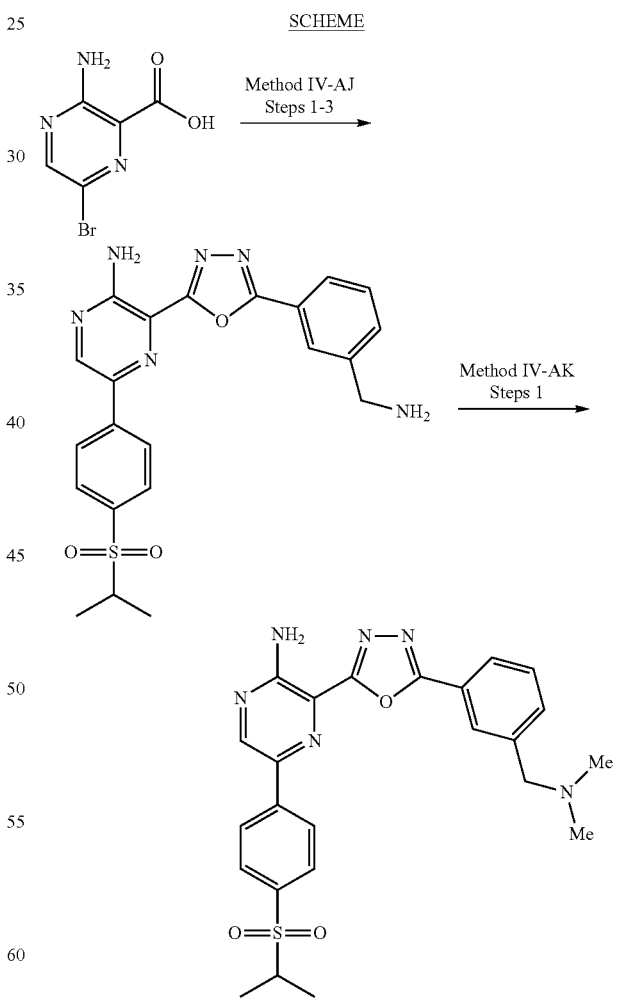

Compound IA-204

Compound IA-204 was prepared using Method IV-AJ, Steps 1-3, followed by Method IV-AK, Step 1.

Method IV-AK

Step 1: 3-[5-[3-(dimethylaminomethyl)phenyl]-1,3,4-oxadiazol-2-yl]-5-(4-isopropylsulfonylphenyl)pyrazin-2-amine 3-[5-[3-(aminomethyl)phenyl]-1,3,4-oxadiazol-2-yl]-5-(4-isopropylsulfonylphenyl)pyrazin-2-amine (12 mg, 0.02108 mmol) was added to a solution of MeI (8.976 mg, 3.937 μL, 0.06324 mmol) and potassium carbonate (8.740 mg, 0.06324 mmol) in DMF (2 mL). The resulting mixture was stirred at room temperature for 30 min. The reaction mixture was diluted with ethyl acetate (3 mL) and washed successively with water (1×5 mL) and brine (1×5 mL). The organic extracts were dried over MgSO$_4$ and concentrated in vacuo. The residue was purified by reverse phase preparative HPLC [Waters Sunfire C18, 10 μM, 100 Å column, gradient 10%-95% B (solvent A: 0.05% TFA in water; solvent B: CH3CN) over 16 minutes at 25 mL/min]. Product fractions were combined and lypholised to give the product as a yellow solid (3.0 mg, 24% yield); 1H NMR (400 MHz, MeOD) d 1.35-1.4 (m, 6H), 2.95 (s, 6H), 4.65 (s, 2H), 7.8-7.85 (m, 2H), 8.05-8.1 (m, 2H), 8.4-8.5 (m, 4H) and 9.95 (s, 1H) ppm; MS (ES$^+$) 479.3

Example 39A

5-(4-isopropylsulfonylphenyl)-3-[5-(3-methyl-2-thienyl)-1,3,4-oxadiazol-2-yl]pyrazin-2-amine (Compound IA-276)

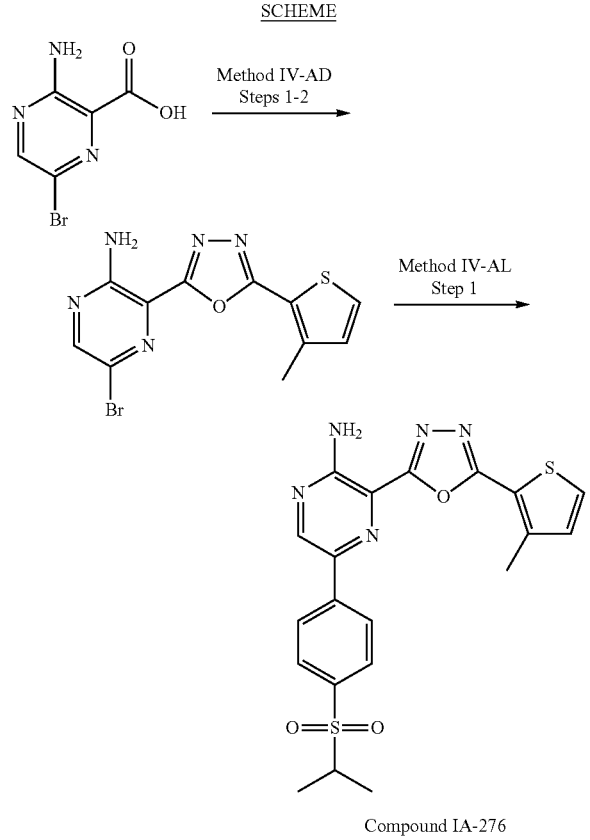

Compound IA-276

Compound IA-276 was prepared using Method IV-AJ, Steps 1-3, followed by Method IV-AL, Step 1.

Method IV-AL: Step 1: 5-(4-isopropylsulfonylphenyl)-3-[5-(3-methyl-2-thienyl)-1,3,4-oxadiazol-2-yl]pyrazin-2-amine A microwave vial was charged with 5-bromo-3-[5-(3-methyl-2-thienyl)-1,3,4-oxadiazol-2-yl]pyrazin-2-amine (75 mg, 0.2218 mmol), (4-isopropylsulfonylphenyl)boronic acid (50.59 mg, 0.2218 mmol), palladium; triphenylphosphane (12.82 mg, 0.01109 mmol) and an aqueous sodium carbonate (332.7 μL of 2 M, 0.6654 mmol) solution was then added followed by DMF (1 mL) and the vial sealed. The reaction mixture was heated in the microwave at 150° C. for 30 min. After this time water was added and the resulting precipitate collected by filtration. The precipitate was passed through a palladium scavenging column eluting with MeCN and MeOH. The solvent was removed to give the product as a yellow solid (19.2 mg, 19% yield); 1H NMR (400 MHz, DMSO) d 1.20 (d, 6H), 2.69 (s, 3H), 3.48 (t, 1H), 7.23 (d, 1H), 7.92 (d, 2H), 7.98 (d, 2H), 8.36-8.34 (m, 2H) and 9.06 (s, 1H) ppm; MS (ES$^+$) 442.0

The following compounds were all prepared using a method similar to the one described for Compound IA-276 above.

Compound IA-269 5-[4-(2-dimethylaminoethylsulfonyl)phenyl]-3-[5-(3-methyl-2-thienyl)-1,3,4-oxadiazol-2-yl]pyrazin-2-amine 1H NMR (400 MHz, DMSO) d 2.69 (s, 3H), 2.78 (s, 6H), 3.36 (s, 2H), 3.91-3.87 (m, 2H), 7.23 (d, 1H), 7.93 (d, 1H), 8.07 (d, 2H), 8.39 (d, 2H) and 9.08 (s, 1H) ppm; MS (ES$^+$) 471.0

Example 40A

[4-[5-[3-amino-6-[4-(dimethylaminomethyl)phenyl]pyrazin-2-yl]-1,3,4-oxadiazol-2-yl]phenyl]methanol (Compound IA-240)

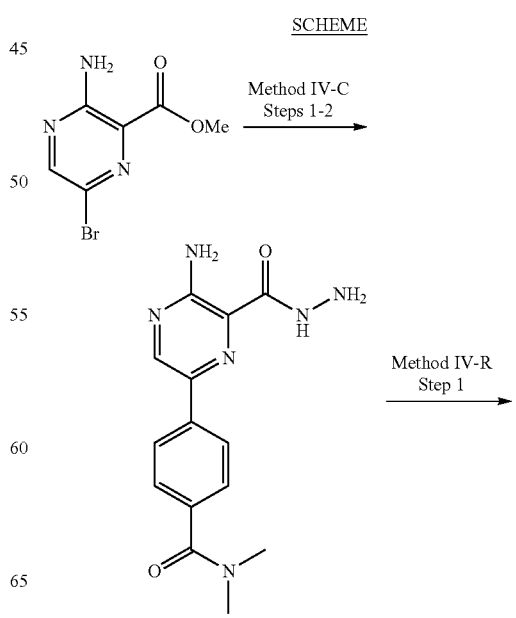

-continued

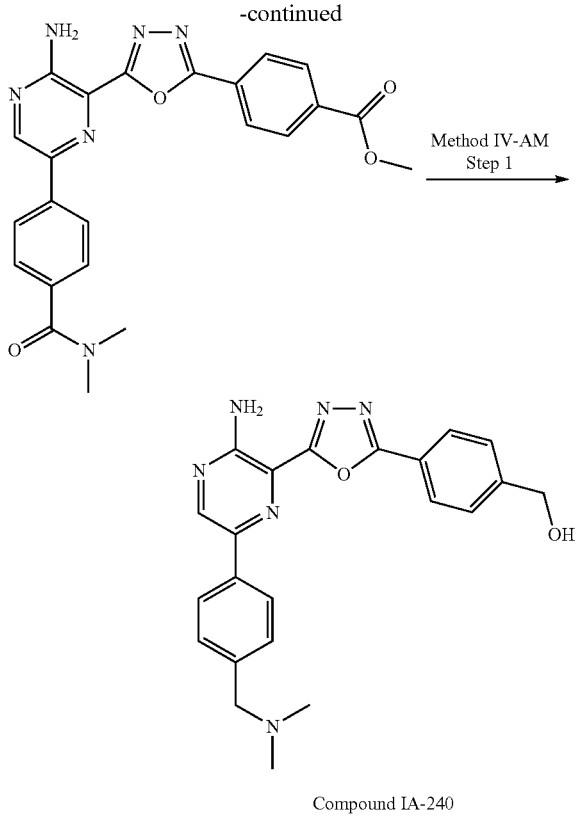

Compound IA-240

Compound IA-240 was prepared using Method IV-C, Steps 1-2, followed by Method IV-R, Step 1, followed by Method IV-AM, Step 1.

Method IV-AM

Step 1: [4-[5-[3-amino-6-[4-(dimethylaminomethyl) phenyl]pyrazin-2-yl]-1,3,4-oxadiazol-2-yl]phenyl] methanol Methyl 4-[5-[3-amino-6-[4-(dimethylcarbamoyl)phenyl] pyrazin-2-yl]-1,3,4-oxadiazol-2-yl]benzoate (154 mg, 0.3465 mmol) in dry THF (1.5 mL) was cooled in ice-bath then treated dropwise with DIBAL (346.5 μL of 1 M solution in hexanes, 0.3465 mmol). The resulting mixture was stirred 0-20° C. over 90 min and then at room temperature overnight. Additional DIBAL (1.732 mL of 1 M solution in hexanes, 1.732 mmol) was added at room temperature. The reaction mixture was poured onto water (10 mL) and acidified with 2M HCl, adjusted to pH 10 with aq NaOH solution and extracted EtOAc (6×10 mL) to give an orange solid. This was purified by reverse phase preparative HPLC [Waters Sunfire C18, 10 μM, 100 Å column, gradient 10%-95% B (solvent A: 0.05% TFA in water; solvent B: CH3CN) over 16 minutes at 25 mL/min]. Product fractions were combined and passed through a bicarbonate cartridge. The eluent was concentrated in vacuo and taken up in acetonitrile and water and lypholised to leave the product as a yellow powder (13.1 mg, 33% yield); 1H NMR (400 MHz, DMSO) d 2.18 (s, 6H), 4.64 (s, 2H), 5.43 (br s, 1H), 4.43-4.45 (m, 2H), 7.65-7.63 (m, 2H), 7.69 (br s, 2H), 8.05-8.30 (m, 4H) and 8.92 (s, 1H) ppm; MS (ES+) 403.18

Example 41A

4-[5-amino-6-[5-[4-(methylaminomethyl)phenyl]-1, 3,4-oxadiazol-2-yl]pyrazin-2-yl]-N,N-dimethyl-benzamide (Compound IA-281)

SCHEME

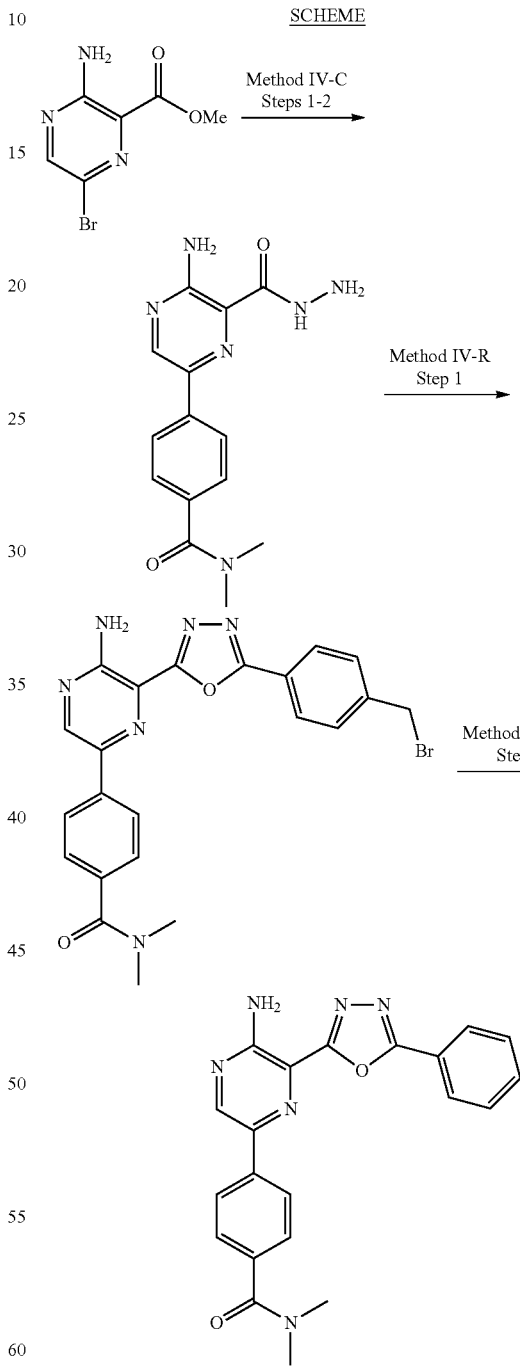

Compound IA-281

Compound IA-281 was prepared using Method IV-C, Steps 1-2, followed by Method IV-R, Step 1, followed by Method IV-AN, Step 1.

Method IV-AN

Step 1: 4-[5-amino-6-[5-[4-(methylaminomethyl)phenyl]-1,3,4-oxadiazol-2-yl]pyrazin-2-yl]-N,N-dimethyl-benzamide 4-[5-amino-6-[5-[4-(bromomethyl)phenyl]-1,3,4-oxadiazol-2-yl]pyrazin-2-yl]-N,N-dimethyl-benzamide (70 mg, 0.1460 mmol) was treated with methylamine (2 mL of 33% w/w solution in ethanol), and the resulting mixture stirred heated at 100° C. for 10 min. The reaction mixture was cooled to room temperature and filtered. The filtrate was collected and purified by reverse phase preparative HPLC [Waters Sunfire C18, 10 μM, 100 Å column, gradient 10%-95% B (solvent A: 0.05% TFA in water; solvent B: $CH_3CN$) over 16 minutes at 25 mL/min]. The product fractions were passed through a carbonate cartridge leuting with $MeOH/CH_2Cl_2$. The eluent was concentrated in vacuo and the solid triturated with acetonitrile to give the product as a yellow solid (11.4 mg, 19% yield); 1H NMR (400 MHz, DMSO) d 2.30 (s, 3H), 2.98-3.02 (m, 6H), 3.77 (s, 2H), 7.55 (d, 2H), 7.61 (d, 2H), 7.78 (br s, 2H), 8.11 (d, 2H), 8.17 (d, 2H) and 8.98 (s, 1H) ppm; MS ($ES^+$) 430.31

Example 42A

[4-[5-[3-amino-6-[4-(dimethylcarbamoyl)phenyl]pyrazin-2-yl]-1,3,4-oxadiazol-2-yl]phenyl]methyl acetate (Compound IA-131)

SCHEME

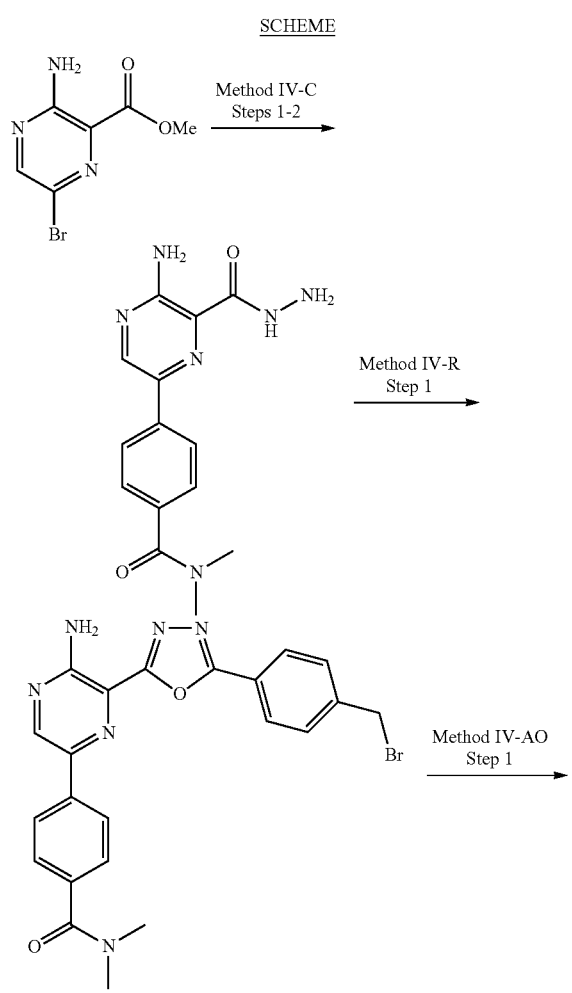

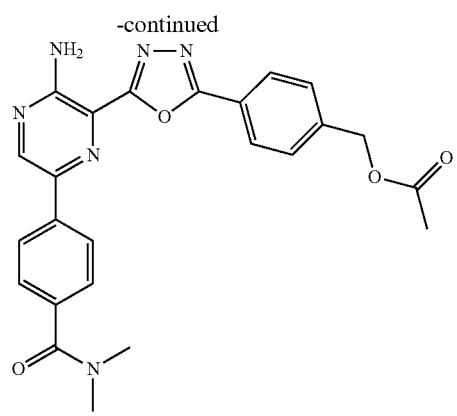

Compound IA-131

Compound IA-131 was prepared using Method IV-C, Steps 1-2, followed by Method IV-R, Step 1, followed by Method IV-AO, Step 1.

Method IV-AO

Step 1: [4-[5-[3-amino-6-[4-(dimethylcarbamoyl)phenyl]pyrazin-2-yl]-1,3,4-oxadiazol-2-yl]phenyl]methyl acetate A mixture of 4-[5-amino-6-[5-[4-(bromomethyl)phenyl]-1,3,4-oxadiazol-2-yl]pyrazin-2-yl]-N,N-dimethyl-benzamide (200 mg, 0.4172 mmol) and potassium acetate (102.4 mg, 1.043 mmol) in DMF (5.714 mL) was heated at 100° C. for 4 h in a sealed microwave tube. The reaction mixture was cooled to room temperature and poured onto ice/water and acidified by HCl (1.043 mL of 1 M, 1.043 mmol). The mixture was extracted with ethyl acetate (3×10 mL) and the combined organic extracts washed with brine (3×10 mL). The extracts were dried over $MgSO_4$ and concentrated under reduced pressure to give a yellow solid (150 mg, 74% yield); 1H NMR (400 MHz, DMSO) d 2.13 (s, 3H), 2.98-3.02 (m, 6H), 5.22 (s, 2H), 7.55 (d, 2H), 7.66 (d, 2H), 7.78 (br s, 2H), 8.16-8.19 (m, 4H) and 8.99 (s, 1H) ppm; MS ($ES^+$) 459.18

Example 43A

4-[5-amino-6-[5-[4-(hydroxymethyl)phenyl]-1,3,4-oxadiazol-2-yl]pyrazin-2-yl]-N,N-dimethyl-benzamide (Compound IA-76)

SCHEME

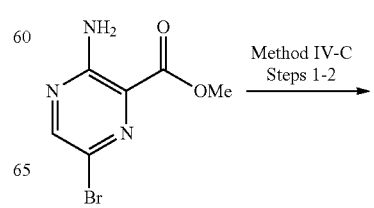

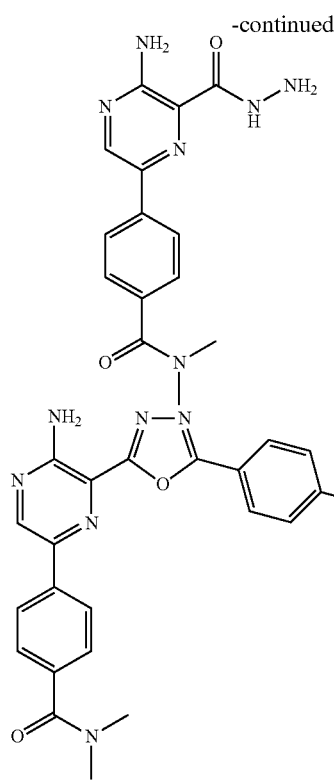

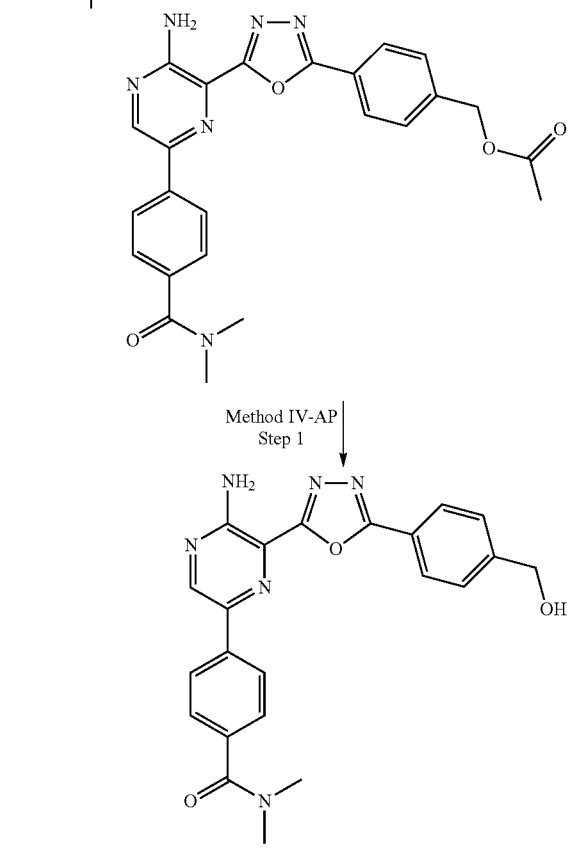

Compound IA-76

Compound IA-76 was prepared using Method IV-C, Steps 1-2, followed by Method IV-R, Step 1, followed by Method IV-AO, Step 1, followed by Method IV-AP, Step 1.

Method IV-AP

Step 1: 4-[5-amino-6-[5-[4-(hydroxymethyl)phenyl]-1,3,4-oxadiazol-2-yl]pyrazin-2-yl]-N,N-dimethyl-benzamide

[4-[5-[3-amino-6-[4-(dimethylcarbamoyl)phenyl]pyrazin-2-yl]-1,3,4-oxadiazol-2-yl]phenyl]methyl acetate (118 mg, 0.2445 mmol) was suspended in methanol (2 mL) and treated with NaOH (489.0 μL of 1 M, 0.4890 mmol). The resulting mixture was stirred at 55° C. for 1 h. The reaction mixture was cooled to room temperature and then neutralised with HCl (978.0 μL of 1 M, 0.9780 mmol), filtered and washed with acetonitrile. The resulting yellow powder was heated in acetonitrile (5 mL), cooled and filtered to give a pale yellow powder. This was purified by column chromatography on silica gel eluting with 5% MeOH/CH$_2$Cl$_2$ to give the product as a pale yellow powder (73 mg, 70%); 1H NMR (400 MHz, DMSO) d 2.98-3.02 (m, 6H), 4.64 (d, 2H), 5.44 (t, 1H), 7.54-7.62 (dd, 4H), 7.78 (br s, 2H), 8.12-8.18 (dd, 4H) and 8.98 (s, 1H) ppm; MS (ES$^+$) 417.23

Example 44A

4-[5-amino-6-[5-[4-(1,2-dihydroxyethyl)phenyl]-1,3,4-oxadiazol-2-yl]pyrazin-2-yl]-N,N-dimethyl-benzamide (Compound IA-106)

SCHEME

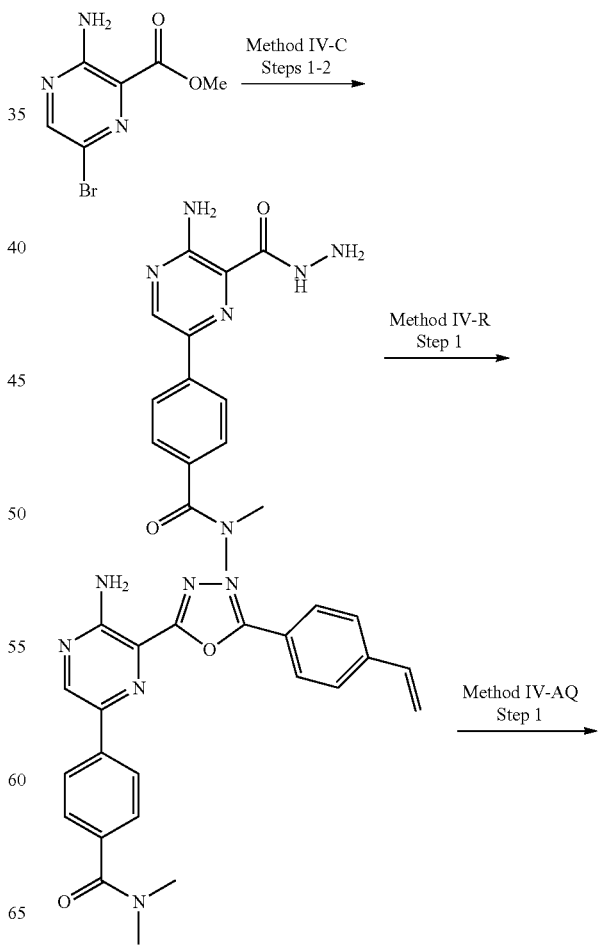

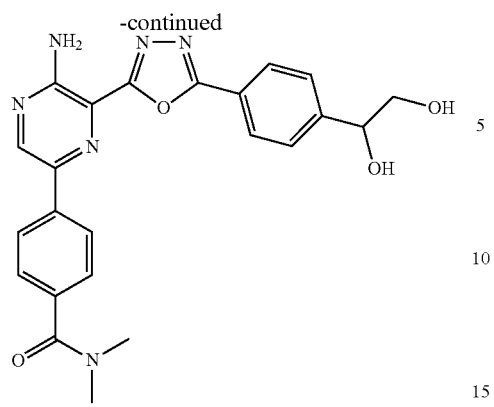

Compound IA-106

Compound IA-106 was prepared using Method IV-C, Steps 1-2, followed by Method IV-R, Step 1, followed by Method IV-AQ, Step 1.

Method IV-AQ

Step 1: 4-[5-amino-6-[5-[4-(1,2-dihydroxyethyl) phenyl]-1,3,4-oxadiazol-2-yl]pyrazin-2-yl]-N,N-dimethyl-benzamide AD-mix-Alpha (450 mg) and methanesulfonamide (20.53 mg, 0.2158 mmol) in a mixture of t-butanol (2 mL)/water (2 mL) were stirred at room temperature until dissolved, then cooled to 0° C. and treated with 4-[5-amino-6-[5-(4-vinyl-phenyl)-1,3,4-oxadiazol-2-yl]pyrazin-2-yl]-N,N-dimethyl-benzamide (89 mg, 0.2158 mmol). The reaction mixture was stirred vigorously and warmed to room temperature overnight. A further portion of AD-mix (300 g) was added and the reaction mixture stirred overnight at room temperature to give complete conversion. The reaction mixture was treated with $Na_2S_2O_3$/NaCl solution and extracted into ethyl acetate (10 mL), dried over $MgSO_4$ and concentrated under reduced pressure to give a yellow solid. This was purified by reverse phase preparative HPLC [Waters Sunfire C18, 10 µM, 100 Å column, gradient 10%-95% B (solvent A: 0.05% TFA in water; solvent B: $CH_3CN$) over 16 minutes at 25 mL/min]. Product fractions were combined and lypholised to give the product as a pale yellow powder (28.4 mg, 36% yield); 1H NMR (400 MHz, DMSO) d 2.9-3.02 (m, 6H), 3.51 (m, 2H), 4.67 (m, 1H), 4.83 (m, 1H), 5.49 (m, 1H), 7.55 (d, 2H), 7.64 (d, 2H), 7.78 (br s, 2H), 8.11 (d, 2H), 8.18 (d, 2H) and 8.98 (s, 1H) ppm; MS (ES$^+$) 447.25

Example 45A

3-[5-[4-(aminomethyl)phenyl]-1,3,4-oxadiazol-2-yl]-5-(4-isopropylsulfonylphenyl)pyrazin-2-amine (Compound IA-222)

SCHEME

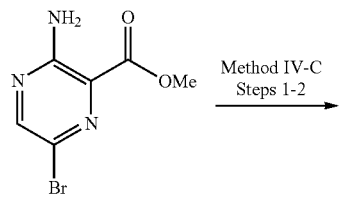

Method IV-C
Steps 1-2

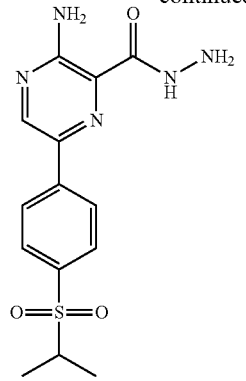

Method IV-AR
Step 1

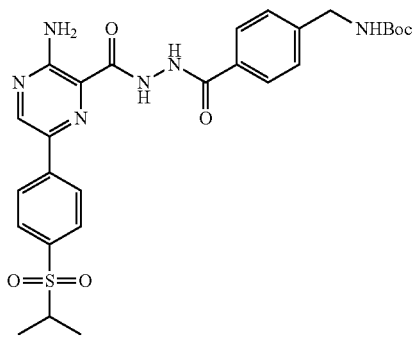

Method IV-AR
Step 2

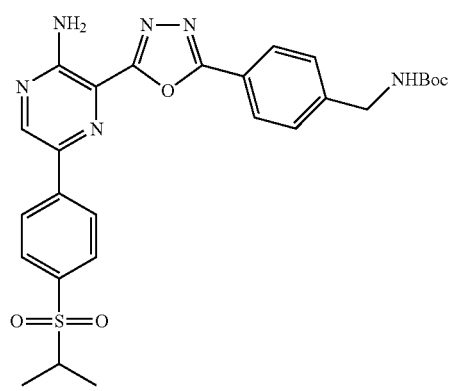

Method IV-AR
Step 3

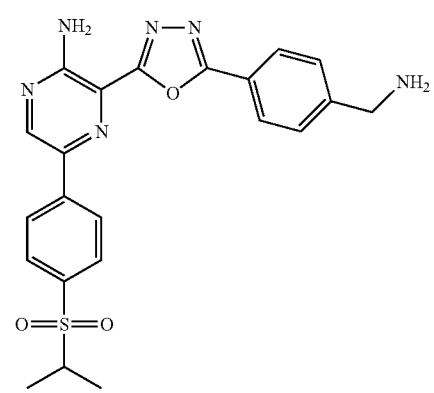

Compound IA-222

Compound IA-222 was prepared using Method IV-C, Steps 1-2, followed by Method IV-AR, Steps 1-3.

Method IV-AR

Step 1: tert-butyl 4-(2-(3-amino-6-(4-(isopropylsulfonyl)phenyl)pyrazine-2-carbonyl)hydrazinecarbonyl)benzylcarbamate 3-amino-6-(4-isopropylsulfonylphenyl)pyrazine-2-carbohydrazide (100 mg, 0.2833 mmol) and 4-[(tert-butoxycarbonylamino)methyl]benzoic acid (71.19 mg, 0.2833 mmol) in dmf (1.000 mL) was treated with triethylamine (28.67 mg, 39.49 µL, 0.2833 mmol) followed by TBTU (109.2 mg, 0.3400 mmol) and the resulting solution stirred at room temperature overnight. The solution was poured dropwise onto rapidly stirred water (15 ml), stirred at room temperature for 1 h and then filtered to give the product as a pale yellow solid which was dried under high vacuum at 83° C. and then used directly in the next step without further purification (136 mg, 84%)

Step 2: tert-butyl 4-(5-(3-amino-6-(4-(isopropylsulfonyl)phenyl)pyrazin-2-yl)-1,3,4-oxadiazol-2-yl)benzylcarbamate A mixture of tert-butyl 4-(2-(3-amino-6-(4-(isopropylsulfonyl)phenyl)pyrazine-2-carbonyl)hydrazinecarbonyl)benzylcarbamate (136 mg, 0.24 mmol) and DIPEA (109.8 mg, 148.0 µL, 0.8499 mmol) in acetonitrile (3.000 mL) at 0° C. was treated portionwise with dibromo(triphenyl)phosphorane (143.5 mg, 0.3400 mmol) and the resulting mixture stirred at room temperature for 48 h. The mixture was concentrated in vacuo and pre-absorbed onto silica gel and purified by column chromatography on silica gel eluting with 50% EtOAc/CH$_2$Cl$_2$ to give the product (46.8 mg, 30% yield); MS (ES$^+$) 551.31

Step 3: 3-[5-[4-(aminomethyl)phenyl]-1,3,4-oxadiazol-2-yl]-5-(4-isopropylsulfonylphenyl)pyrazin-2-amine A solution of tert-butyl N-[[4-[5-[3-amino-6-(4-isopropylsulfonylphenyl)pyrazin-2-yl]-1,3,4-oxadiazol-2-yl]phenyl]methyl]carbamate (45 mg, 0.08172 mmol) in CH$_2$Cl$_2$ (1 mL) was treated with TFA (1 mL, 12.98 mmol) and stirred at room temperature for 1 h. The solution was concentrated under reduced pressure then azeotroped with methanol/CH$_2$Cl$_2$ (×2), dissolved in CH$_2$Cl$_2$/MeOH and passed through a carbonate cartridge. The eluent was concentrated then crystallised from hot acetonitrile giving a yellow crystalline solid (18 mg, 41% yield); 1H NMR (400 MHz, DMSO) d 1.20 (d, 6H), 1.97 (br s, 2H), 3.47 (m, 1H), 3.85 (s, 2H), 7.63 (d, 2H), 7.89 (br s, 2H), 7.98 (d, 2H), 8.11 (d, 2H), 8.40 (d, 2H) and 9.06 (s, 1H) ppm; MS (ES$^+$) 451.41

The following compounds were all prepared using a method similar to the one described for Compound IA-222 above.

Compound IA-80 3-[5-[3-[(1R)-1-aminoethyl]phenyl]-1,3,4-oxadiazol-2-yl]-5-(4-isopropylsulfonylphenyl)pyrazin-2-amine 1H NMR (400 MHz, DMSO) d 1.19 (m, 6H), 1.32 (m, 3H), 3.48 (m, 1H), 4.17 (m, 1H), 7.61 (m, 1H), 7.69 (m, 1H), 7.99 (m, 5H), 8.19 (m, 1H), 8.39 (m, 2H) and 9.07 (s, 1H) ppm; MS (ES$^+$) 465.32

Compound IA-84 5-(4-isopropylsulfonylphenyl)-3-[5-(3-pyrrolidin-2-ylphenyl)-1,3,4-oxadiazol-2-yl]pyrazin-2-amine 1H NMR (400 MHz, DMSO) d 1.19 (d, 6H), 1.57 (m, 1H), 1.80 (m, 2H), 2.20 (m, 1H), 2.97 (m, 1H), 3.01 (m, 1H), 3.45 (m, 1H), 4.24 (m, 1H), 7.59 (m, 1H), 7.67 (m, 1H), 7.97-8.03 (m, 4H), 8.19 (s, 1H), 8.39 (m, 2H) and 9.07 (s, 1H) ppm; MS (ES$^+$) 491.33

Compound IA-91 3-[5-(3-aminopropyl)-1,3,4-oxadiazol-2-yl]-5-(4-isopropylsulfonylphenyl)pyrazin-2-amine 1H NMR (400 MHz, DMSO) d 1.18-1.20 (m, 7H), 1.23 (s, 1H), 1.99 (t, 2H), 3.46 (t, 1H), 7.16 (s, 1H), 7.87 (d, 2H), 8.46 (d, 2H), 8.93 (s, 1H) and 10.20 (s, 1H) ppm; MS (ES$^+$) 403.23

Compound IA-92 3-[5-(4-aminobutyl)-1,3,4-oxadiazol-2-yl]-5-(4-isopropylsulfonylphenyl)pyrazin-2-amine 1H NMR (400 MHz, DMSO) d 1.18-1.20 (m, 7H), 1.50 (t, 2H), 1.84 (t, 2H), 2.62 (t, 2H), 3.03 (t, 3H), 3.46 (t, 1H), 7.85 (br s, 1H), 7.96 (d, 2H), 8.31 (d, 2H) and 9.02 (s, 1H) ppm; MS (ES$^+$) 417.23

Compound IA-102 5-(4-isopropylsulfonylphenyl)-3-[5-(4-pyrrolidin-2-ylphenyl)-1,3,4-oxadiazol-2-yl]pyrazin-2-amine 1H NMR (400 MHz, DMSO) d 1.20 (d, 6H), 1.45-1.58 (m, 1H), 1.71-1.86 (m, 2H), 2.15-2.26 (m, 1H), 2.90-3.08 (m, 2H), 3.48 (m, 1H), 4.18 (t, 1H), 7.65 (d, 2H), 7.97 (br s, 2H), 7.98 (d, 2H), 8.09 (d, 2H), 8.40 (d, 2H) and 9.07 (s, 1H) ppm; MS (ES$^+$) 491.34

Compound IA-107 3-[5-[4-(2-amino ethyl)phenyl]-1,3,4-oxadiazol-2-yl]-5-(4-isopropylsulfonylphenyl)pyrazin-2-amine 1H NMR (400 MHz, DMSO) d 1.20 (d, 6H), 2.79 (m, 2H), 2.85 (m, 2H), 3.47 (m, 1H), 7.51 (d, 2H), 7.92 (br s, 2H), 7.98 (d, 2H), 8.09 (d, 2H), 8.39 (d, 2H) and 9.06 (s, 1H) ppm; MS (ES$^+$) 465.34

Compound IA-123 3-[5-[3-[(1S)-1-aminoethyl]phenyl]-1,3,4-oxadiazol-2-yl]-5-(4-isopropylsulfonylphenyl)pyrazin-2-amine 1H NMR (400 MHz, DMSO) d 1.19 (m, 6H), 1.32 (m, 3H), 3.49 (m, 1H), 4.18 (m, 1H), 7.61 (m, 1H), 7.69 (m, 1H), 7.99 (m, 4H), 8.19 (m, 1H), 8.39 (m, 2H) and 9.07 (s, 1H) ppm; MS (ES$^+$) 465.32

Compound IA-124 3-[5-[4-[(1R)-1-aminoethyl]phenyl]-1,3,4-oxadiazol-2-yl]-5-(4-isopropylsulfonylphenyl)pyrazin-2-amine 1H NMR (400 MHz, DMSO) d 1.20 (d, 6H), 1.30 (d, 3H), 3.48 (m, 1H), 4.11 (q, 1H), 7.67 (d, 2H), 7.96 (v br s, 2H), 7.98 (d, 2H), 8.10 (d, 2H), 8.40 (d, 2H) and 9.07 (s, 1H) ppm; MS (ES$^+$) 465.37

Compound IA-130 3-[5-[2-fluoro-4-(methylaminomethyl)phenyl]-1,3,4-oxadiazol-2-yl]-5-(4-isopropylsulfonylphenyl)pyrazin-2-amine 1H NMR (400 MHz, DMSO) d 1.3 (d, 6H), 2.7 (s, 3H), 3.4-3.6 (m, 1H), 4.35 (s, 2H), 7.6 (d, 1H), 7.7 (d, 1H), 8.0 (d, 2H), 8.3 (t, 1H), 8.38 (d, 2H), 8.92 (br s, 2H) and 9.1 (s, 1H) ppm; MS (ES$^+$) 483.4

Compound IA-145 5-(4-isopropylsulfonylphenyl)-3-[5-(1,2,3,4-tetrahydroisoquinolin-6-yl)-1,3,4-oxadiazol-2-yl]pyrazin-2-amine 1H NMR (400 MHz, DMSO) d 1.19 (m, 6H), 2.89 (m, 2H), 3.08 (m, 2H), 3.47 (m, 1H), 4.03 (s, 1H), 7.34 (m, 1H), 7.90-7.99 (m, 5H), 8.26 (s, 1H), 8.38 (m, 2H) and 9.03 (s, 1H) ppm; MS (ES$^+$) 477.41

Compound IA-147 5-(4-isopropylsulfonylphenyl)-3-[5-(5-pyrrolidin-2-yl-2-thienyl)-1,3,4-oxadiazol-2-yl]pyrazin-2-amine 1H NMR (400 MHz, DMSO) d 1.25 (d, 6H), 2.0-2.2 (m, 3H), 3.3-3.6 (m, 4H), 5.0-5.1 (m, 1H), 7.9-8.0 (m, 4H), 8.4 (d, 2H), 9.05-9.1 (m, 2H) and 9.6 (br s, 1H) ppm; MS (ES$^+$) 497.4

Compound IA-168 3-[5-(aminomethyl)-1,3,4-oxadiazol-2-yl]-5-(4-isopropylsulfonylphenyl)pyrazin-2-amine 1H NMR (400 MHz, DMSO) d 1.16-1.19 (m, 6H), 1.23 (s, 3H), 3.46 (t, 1H), 4.06 (s, 2H), 7.96 (d, 2H), 8.31 (d, 2H) and 9.02 (s, 1H) ppm; MS (ES$^+$) 375.17

Compound IA-173 3-[5-[5-(aminomethyl)-2-thienyl]-1,3,4-oxadiazol-2-yl]-5-(4-isopropylsulfonylphenyl)pyrazin-2-amine 1H NMR (400 MHz, DMSO) d 1.20 (d, 6H), 3.46-

3.51 (m, 1H), 4.41 (s, 2H), 7.45 (d, 1H), 7.96 (d, 1H), 7.98 (d, 2H), 8.30 (br s, 2H), 8.37 (d, 2H) and 9.08 (s, 1H) ppm; MS (ES+) 457.3

Compound IA-185 3-[5-[3-(azetidin-3-yl)phenyl]-1,3,4-oxadiazol-2-yl]-5-(4-isopropylsulfonylphenyl)pyrazin-2-amine 1H NMR (400 MHz, DMSO) d 1.20 (d, 6H), 3.48 (m, 1H), 4.19 (m, 2H), 4.34 (m, 3H), 7.71-7.79 (m, 2H), 7.97 (m, 2H), 8.12 (m, 1H), 8.20 (m, 1H), 8.41 (m, 2H), 8.69 (br s, 1H) and 9.09 (s, 1H) ppm; MS (ES+) 477.29

Compound IA-201 3-[5-(4-aminophenyl)-1,3,4-oxadiazol-2-yl]-5-(4-isopropylsulfonylphenyl)pyrazin-2-amine 1H NMR (400 MHz, DMSO) d 1.21 (d, 6H), 3.47 (m, 1H), 6.10 (s, 2H), 6.75 (d, 2H), 7.83 (d, 2H), 7.89 (br s, 2H), 7.97 (d, 2H), 8.39 (d, 2H) and 9.02 (s, 1H) ppm; MS (ES+) 437.22

Compound IA-214 3-[5-(2-aminoethyl)-1,3,4-oxadiazol-2-yl]-5-(4-isopropylsulfonylphenyl)pyrazin-2-amine 1H NMR (400 MHz, DMSO) d 1.19 (d, 6H), 3.05 (m, 4H), 3.33 (d, 1H), 3.46 (s, 1H), 7.96 (d, 2H), 8.31 (d, 2H) and 9.02 (s, 1H) ppm; MS (ES+) 389.24

Compound IA-228 3-[5-[4-[(1S)-1-aminoethyl]phenyl]-1,3,4-oxadiazol-2-yl]-5-(4-isopropylsulfonylphenyl)pyrazin-2-amine 1H NMR (400 MHz, DMSO) d 1.20 (d, 6H), 1.30 (d, 3H), 3.48 (m, 1H), 4.11 (q, 1H), 7.67 (d, 2H), 7.96 (v br s, 2H), 7.98 (d, 2H), 8.10 (d, 2H), 8.40 (d, 2H) and 9.07 (s, 1H) ppm; MS (ES+) 465.42

Compound IA-232 5-(4-isopropylsulfonylphenyl)-3-[5-(1,2,3,6-tetrahydropyridin-4-yl)-1,3,4-oxadiazol-2-yl]pyrazin-2-amine 1H NMR (400 MHz, DMSO) d 1.19 (d, 6H), 2.50 (s, 2H), 2.98 (br t, 2H), 3.46 (m, 1H), 3.55 (dr d, 2H), 7.03 (s, 1H), 7.90 (br s, 2H), 7.95 (d, 2H), 8.35 (d, 2H) and 9.04 (s, 1H) ppm; MS (ES+) 427.4

Compound IA-282 3-[5-[3-(1-aminoethyl)phenyl]-1,3,4-oxadiazol-2-yl]-5-(4-isopropylsulfonylphenyl)pyrazin-2-amine 1H NMR (400 MHz, DMSO) d 1.20 (m, 6H), 1.33 (m, 3H), 3.48 (m, 1H), 4.18 (m, 1H), 7.61 (m, 1H), 7.70 (m, 1H), 7.98-8.03 (m, 4H), 8.20 (m, 1H), 8.39 (m, 2H) and 9.07 (s, 1H) ppm; MS (ES+) 465.3

Compound IA-285 3-[5-[4-(azetidin-3-yl)phenyl]-1,3,4-oxadiazol-2-yl]-5-(4-isopropylsulfonylphenyl)pyrazin-2-amine 1H NMR (400 MHz, DMSO) d 1.20 (d, 6H), 3.48 (m, 1H), 3.65 (m, 2H), 3.87 (m, 2H), 3.99 (m, 1H), 7.65 (d, 2H), 7.91 (br s, 2H), 7.98 (d, 2H), 8.14 (d, 2H), 8.39 (d, 2H) and 9.06 (s, 1H) ppm; MS (ES+) 477.44

Compound IA-306 3-[5-[2-chloro-4-(methylaminomethyl)phenyl]-1,3,4-oxadiazol-2-yl]-5-(4-isopropylsulfonylphenyl)pyrazin-2-amine MS (ES+) 499.2

Compound IA-309 3-[5-[3-chloro-4-(methylaminomethyl)phenyl]-1,3,4-oxadiazol-2-yl]-5-(4-isopropylsulfonylphenyl)pyrazin-2-amine 1H NMR (400 MHz, DMSO) d 1.25 (d, 6H), 2.7 (s, 3H), 3.4-3.5 (m, 1H), 4.45 (s, 2H), 7.7 (d, 1H), 8.0 (d, 2H), 8.3 (d, 1H), 8.4 (d, 2H), 9.0 (br s, 2H) and 9.1 (s, 1H) ppm; MS (ES+) 499.2

Compound IA-311 3-[5-[4-(1-amino-1-methyl-ethyl)phenyl]-1,3,4-oxadiazol-2-yl]-5-(4-isopropylsulfonylphenyl)pyrazin-2-amine 1H NMR (400 MHz, DMSO) d 1.19 (m, 6H), 1.43 (s, 6H), 3.51 (m, 1H), 7.83 (m, 2H), 7.97 (m, 2H), 8.09 (m, 2H), 8.39 (m, 2H) and 9.07 (s, 1H) ppm; MS (ES+) 479.27

Example 46A

2-[5-[3-amino-6-(4-isopropylsolfonylphenyl)pyrazin-2-yl]-1,3,4-oxadiazol-2-yl]phenol (Compound IA-235)

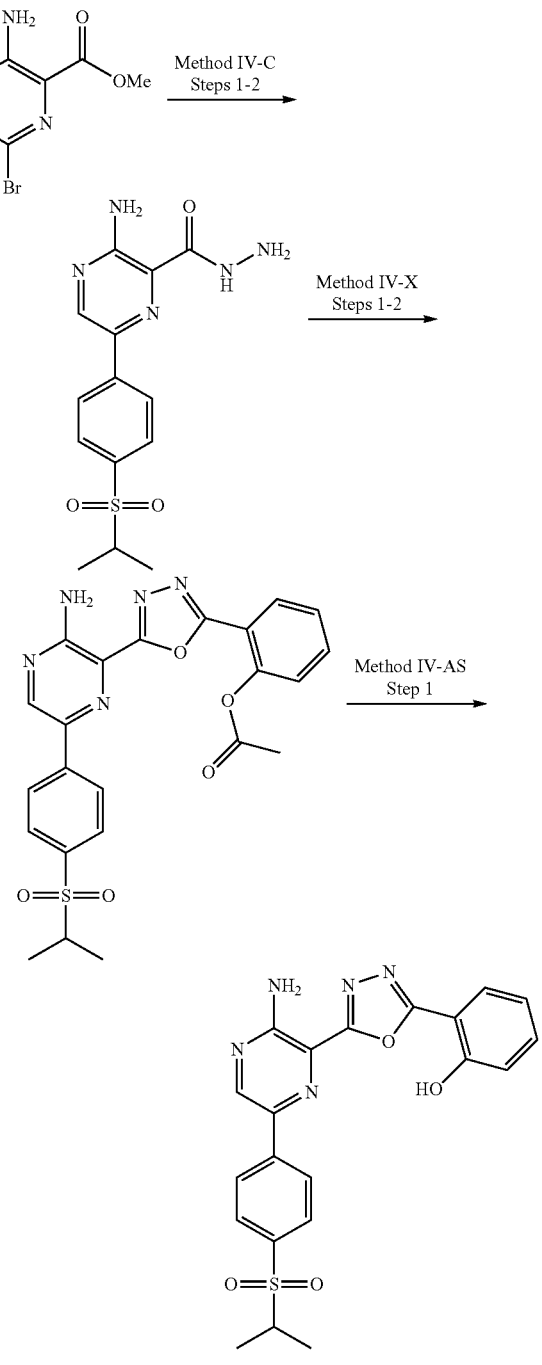

Compound IA-235

Compound IA-235 was prepared using Method IV-C, Steps 1-2, followed by Method IV-X, Steps 1-2, followed by Method IV-AS, Step 1.

Method IV-AS

Step 1: 2-[5-[3-amino-6-(4-isopropylsulfonylphenyl)pyrazin-2-yl]-1,3,4-oxadiazol-2-yl]phenol LiOH (292.0 μL of 1 M, 0.2920 mmol) was added to a suspension of 2-(5-(3-amino-6-(4-(isopropylsulfonyl)phenyl)pyrazin-2-yl)-1,3,4-oxadiazol-2-yl)phenyl acetate (14 mg, 0.02920 mmol) in THF (5 mL) at ambient temperature. After 3 h, a further portion of LiOH (292.0 μL of 1 M, 0.2920 mmol) was added and the reaction continued to stir at room temperature for 1 h. 1M HCl was added dropwise until the reaction mixture was acidic and the resultant precipitate isolated by filtration. The solid residue was dissolved in a mixture of MeCN and water and lypholised to give the product as a green solid (5.1 mg, 38% yield); 1H NMR (400 MHz, DMSO) d 1.20 (d, 6H), 3.46 (m, 1H), 6.98-7.22 (m, 2H), 7.36-7.59 (m, 1H), 7.75-8.16 (m, 5H), 8.37 (d, 2H), 9.06 (s, 1H) and 10.43 (s, 1H) ppm; MS (ES+) 438.2

The following compounds were all prepared using a method similar to the one described for Compound IA-235 above.

Compound IA-193 4-[5-[3-amino-6-(4-isopropylsulfonylphenyl)pyrazin-2-yl]-1,3,4-oxadiazol-2-yl]phenol 1H NMR (400 MHz, DMSO) d 1.20 (d, 6H), 3.47 (m, 1H), 7.03 (dd, 2H), 7.89 (br s, 2H), 7.97 (dd, 2H), 8.02 (dd, 2H), 8.39 (dd, 2H), 9.04 (s, 1H) and 10.44 (s, 1H) ppm; MS (ES+) 438.2

Example 47A 5-(4-isopropylsulfonylphenyl)-3-[5-[4-(methylaminomethyl)phenyl]-1,3,4-oxadiazol-2-yl]pyrazin-2-amine (Compound IA-159)

SCHEME

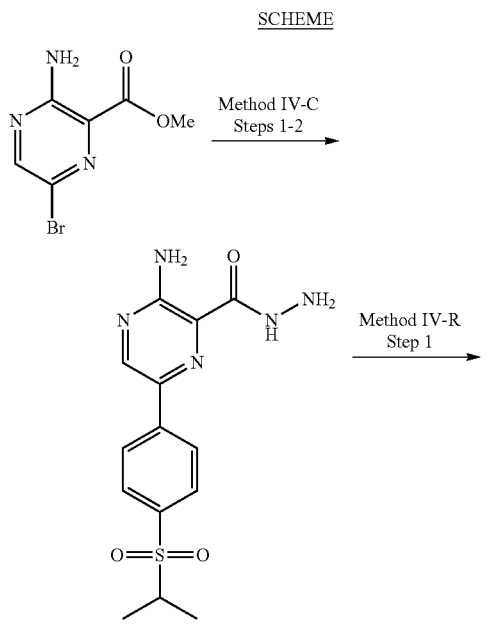

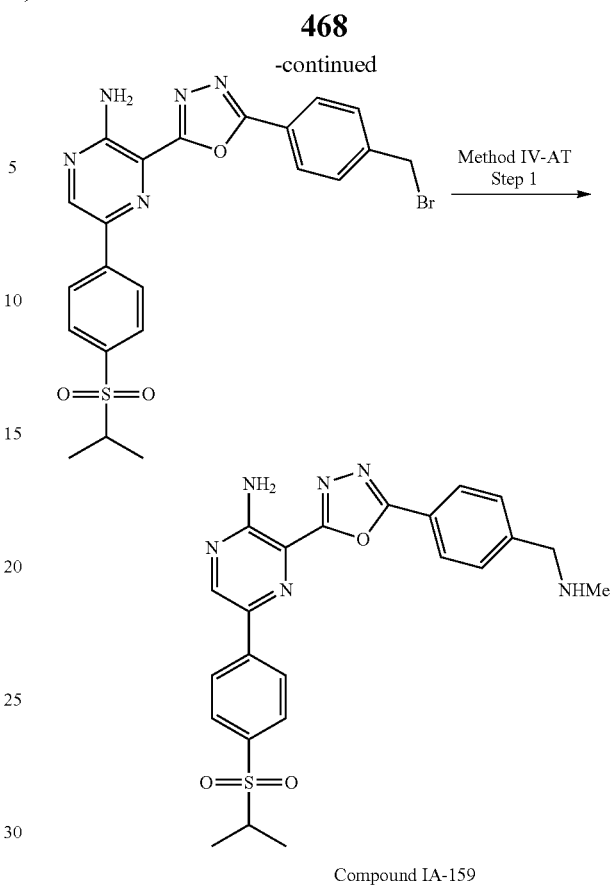

Compound IA-159

Compound IA-159 was prepared using Method IV-C, Steps 1-2, followed by Method IV-R, Step 1, followed by Method IV-AT, Step 1.

Method IV-AT

Step 1: 5-(4-isopropylsulfonylphenyl)-3-[5-[4-(methylaminomethyl)phenyl]-1,3,4-oxadiazol-2-yl]pyrazin-2-amine MeNH$_2$ in ethanol (184.9 g, 243.6 mL of 33% w/w, 1.965 mol) was added in one portion to a stirred solution of 3-[5-[4-(bromomethyl)phenyl]-1,3,4-oxadiazol-2-yl]-5-(4-isopropylsulfonylphenyl)pyrazin-2-amine (10.11 g, 19.65 mmol) in CH$_2$Cl$_2$ (1.01 L) and methanol (1.01 L) and the resulting mixture stirred overnight at room temperature. Nitrogen was bubbled through reaction for 2 h and then the reaction mixture was concentrated in vacuo. The crude material was stirred in K$_2$CO$_3$ (393.0 mL of 0.25 M, 98.25 mmol) for 2 h and then isolated by filtration and washed with water. Triturated with warm acetonitrile to leave the product as a yellow solid (7.19 g, 75% yield); 1H NMR (400 MHz, DMSO) d 1.19-1.21 (d, 6H), 2.30 (m, 3H), 3.35-3.49 (m, 1H), 3.77 (m, 2H), 7.61-7.63 (d, 2H), 7.97-7.99 (d, 2H), 8.11-8.13 (d, 2H), 8.39-8.41 (d, 2H) and 9.06 (s, 1H) ppm; MS (ES+) 465.4

The following compounds were all prepared using a method similar to the one described for Compound IA-159 above.

Compound IA-119 5-(4-isopropylsulfonylphenyl)-3-[5-[4-[(2-methoxyethylamino) methyl]phenyl]-1,3,4-oxadiazol-2-yl]pyrazin-2-amine 1H NMR (400 MHz, DMSO) d 1.20 (d, 6H), 2.67 (t, 2H), 3.25 (s, 3H), 3.43 (t, 2H), 3.48 (m, 1H), 3.84 (s, 2H), 7.62 (d, 2H), 7.97 (d, 2H), 7.98 (v br s, 2H), 8.12 (d, 2H), 8.40 (d, 2H) and 9.07 (s, 1H) ppm; MS (ES+) 509.37

Compound IA-122 3-[5-[4-(ethylaminomethyl)phenyl]-1,3,4-oxadiazol-2-yl]-5-(4-isopropylsulfonylphenyl)pyrazin-2-amine 1H NMR (400 MHz, DMSO) d 1.17-1.22 (m, 9H), 2.89 (q, 2H), 3.48 (m, 1H), 4.15 (s, 2H), 7.77 (d, 2H), 7.98 (d, 2H), 7.99 (br s, 2H), 8.21 (d, 2H), 8.41 (d, 2H) and 9.08 (s, 1H) ppm; MS (ES+) 479.41

Compound IA-139 2-[[4-[5-[3-amino-6-(4-isopropylsulfonylphenyl)pyrazin-2-yl]-1,3,4-oxadiazol-2-yl]phenyl]methylamino]-2-(hydroxymethyl)propane-1,3-diol 1H NMR (400 MHz, DMSO) d 1.20 (d, 6H), 3.44 (s, 6H), 3.45 (m, 1H), 3.90 (s, 2H), 4.37 (br s, 3H), 7.66 (d, 2H), 7.95 (br s, 2H), 7.98 (d, 2H), 8.11 (d, 2H), 8.40 (d, 2H) and 9.07 (s, 1H) ppm; MS (ES+) 555.32

Compound IA-146 5-(4-isopropylsulfonylphenyl)-3-[5-[3-(methylaminomethyl)phenyl]-1,3,4-oxadiazol-2-yl]pyrazin-2-amine 1H NMR (400 MHz, DMSO) d 1.19 (d, 6H), 2.33 (s, 3H), 3.48 (m, 1H), 3.83 (s, 2H), 7.61-7.67 (m, 2H), 7.97 (m, 3H), 8.05 (m, 1H), 8.15 (m, 1H), 8.39 (m, 2H) and 9.07 (s, 1H) ppm; MS (ES+) 465.29

Compound IA-158 3-[5-[4-[(cyclopropylamino)methyl]phenyl]-1,3,4-oxadiazol-2-yl]-5-(4-isopropylsulfonylphenyl)pyrazin-2-amine 1H NMR (400 MHz, DMSO) d 0.28 (m, 2H), 0.36 (m, 2H), 1.20 (d, 6H), 2.07 (m, 1H), 3.48 (m, 1H), 3.85 (s, 2H), 7.61 (d, 2H), 7.96 (br s, 2H), 7.98 (d, 2H), 8.11 (d, 2H), 8.40 (d, 2H) and 9.07 (s, 1H) ppm; MS (ES+) 491.42

Compound IA-178 2-(4-(5-(3-amino-6-(4-(isopropylsulfonyl)phenyl)pyrazin-2-yl)-1,3,4-oxadiazol-2-yl)benzylamino)ethanol 1H NMR (400 MHz, DMSO) d 1.20 (d, 6H), 2.61 (t, 2H), 3.42-3.51 (m, 3H), 3.86 (s, 2H), 4.54 (br s, 1H), 7.63 (d, 2H), 7.80 (br s, 2H), 7.98 (d, 2H), 8.12 (d, 2H), 8.39 (d, 2H) and 9.06 (s, 1H) ppm; MS (ES+) 495.31

Compound IA-225 N-[[4-[5-[3-amino-6-(4-isopropylsulfonylphenyl)pyrazin-2-yl]-1,3,4-oxadiazol-2-yl]phenyl]methyl]-N',N'-dimethyl-ethane-1,2-diamine 1H NMR (400 MHz, DMSO) d 1.20 (d, 6H), 3.07 (s, 3H), 3.29-3.49 (m, 5H), 4.74 (s, 2H), 7.91 (d, 2H), 7.97 (d, 2H), 7.98 (v br s, 2H), 8.27 (d, 2H), 8.40 (d, 2H) and 9.07 (s, 1H) ppm; MS (ES+) 522.23

Compound IA-238 [4-[5-[3-amino-6-(4-isopropylsulfonylphenyl)pyrazin-2-yl]-1,3,4-oxadiazol-2-yl]phenyl]methanol 1H NMR (400 MHz, DMSO) d 1.20 (d, 6H), 3.48 (m, 1H), 6.64 (d, 2H), 5.46 (t, 1H), 7.61 (d, 2H), 7.98 (d, 2H), 7.99 (br s, 2H), 8.15 (d, 2H), 8.40 (d, 2H) and 9.07 (s, 1H) ppm; MS (ES+) 452.26

Compound IA-243 3-[5-[4-(dimethylaminomethyl)phenyl]-1,3,4-oxadiazol-2-yl]-5-(4-isopropylsulfonylphenyl)pyrazin-2-amine 1H NMR (400 MHz, DMSO) d 1.20 (m, 6H), 2.21 (s, 6H), 3.47 (m, 1H), 3.54 (s, 2H), 7.59 (d, 2H), 7.90 (br s, 2H), 7.97 (d, 2H), 8.13 (d, 2H), 8.39 (d, 2H) and 9.06 (s, 1H) ppm; MS (ES+) 479.37

Compound IA-333 (R)-2-(4-(5-(3-amino-6-(4-(isopropylsulfonyl)phenyl)pyrazin-2-yl)-1,3,4-oxadiazol-2-yl)-3-fluorobenzylamino)propan-1-ol 1H NMR (400 MHz, DMSO) d 1.06 (3H, d), 1.20 (d, 6H), 2.44 (m, 1H), 3.35 (obscured, 2H), 3.48 (m, 1H), 3.85 (m, 2H), 4.53 (m, 1H), 7.47 (d, 1H), 7.52 (d, 1H), 7.97 (br s, 2H), 7.98 (d, 2H), 8.12 (t, 1H), 8.37 (d, 2H) and 9.08 (s, 1H) ppm; MS (ES+) 527.2

Compound IA-334 (S)-1-(4-(5-(3-amino-6-(4-(isopropylsulfonyl)phenyl)pyrazin-2-yl)-1,3,4-oxadiazol-2-yl)-3-fluorobenzylamino)propan-2-ol 1H NMR (400 MHz, DMSO) d 1.06 (3H, d), 1.20 (d, 6H), 3.45 (m, 1H), 3.71 (m, 1H), 4.53 (d, 1H), 7.46 (d, 1H), 7.52 (d, 1H), 7.97 (br s, 2H), 7.98 (d, 2H), 8.12 (t, 1H), 8.37 (d, 2H) and 9.07 (s, 1H) ppm; MS (ES+) 527.2

Compound IA-335 (S)-2-(4-(5-(3-amino-6-(4-(isopropylsulfonyl)phenyl)pyrazin-2-yl)-1,3,4-oxadiazol-2-yl)-3-fluorobenzylamino)propan-1-ol 1H NMR (400 MHz, DMSO) d 0.97 (d, 3H), 1.20 (d, 6H), 2.62 (m, 1H), 3.30 (m, 2H), 3.48 (m, 1H), 3.88 (m, 2H), 4.58 (m, 1H), 7.47 (d, 1H), 7.53 (d, 1H), 7.97 (br s, 2H), 7.98 (d, 2H), 8.12 (t, 1H), 8.37 (d, 2H) and 9.07 (s, 1H) ppm; MS (ES+) 527.2

Compound IA-336 3-[5-[3-fluoro-4-(methylaminomethyl)phenyl]-1,3,4-oxadiazol-2-yl]-5-(4-isopropylsulfonylphenyl)pyrazin-2-amine 1H NMR (400 MHz, DMSO) d 1.20 (m, 6H), 2.68 (m, 3H), 3.48 (m, 1H), 4.34 (m, 2H), 7.86 (t, 1H), 7.99 (m, 2H), 8.09 (m, 1H), 8.14 (dd, 1H), 8.42 (m, 2H), 8.96 (br s, 2H) and 9.11 (s, 1H) ppm; MS (ES+) 483.1

Compound IA-340 3-[5-[2-fluoro-4-[(2-fluoroethylamino)methyl]phenyl]-1,3,4-oxadiazol-2-yl]-5-(4-isopropylsulfonylphenyl)pyrazin-2-amine 1H NMR (400 MHz, DMSO) d 1.20 (d, 6H), 2.81 (m, 2H), 3.48 (m, 1H), 3.88 (s, 2H), 4.51 (m, 2H), 7.47 (d, 1H), 7.52 (d, 1H), 7.97 (br s, 2H), 7.98 (d, 2H), 8.12 (t, 1H), 8.37 (d, 2H) and 9.07 (s, 1H) ppm; MS (ES+) 515.2

Compound IA-341 (R)-1-(4-(5-(3-amino-6-(4-(isopropylsulfonyl)phenyl)pyrazin-2-yl)-1,3,4-oxadiazol-2-yl)-3-fluorobenzylamino)propan-2-ol 1H NMR (400 MHz, DMSO) d 1.06 (dd, 3H), 1.20 (dd, 6H), 3.45 (m, 1H), 3.71 (m, 1H), 4.53 (m, 1H), 7.46 (d, 1H), 7.52 (d, 1H), 7.97 (br s, 2H), 7.98 (d, 2H), 8.12 (t, 1H), 8.37 (d, 2H) and 9.07 (s, 1H) ppm; MS (ES+) 527.2

Compound IA-345 3-[5-[2-fluoro-4-[(tetrahydrofuran-3-ylamino)methyl]phenyl]-1,3,4-oxadiazol-2-yl]-5-(4-isopropylsulfonylphenyl)pyrazin-2-amine 1H NMR (400 MHz, DMSO) d 1.20 (d, 6H), 1.70-1.74 (m, 1H), 1.90-1.98 (m, 1H), 3.25-3.32 (m, 1H), 3.41-3.50 (m, 2H), 3.60-3.85 (m, 5H), 7.47 (d, 1H), 7.53 (d, 1H), 7.97 (br s, 2H), 7.98 (d, 2H), 8.12 (t, 1H), 8.37 (d, 2H) and 9.08 (s, 1H) ppm; MS (ES+) 539.3

Compound IA-346 3-[5-[4-[(2-fluoroethylamino)methyl]phenyl]-1,3,4-oxadiazol-2-yl]-5-(4-isopropylsulfonylphenyl)pyrazin-2-amine 1H NMR (400 MHz, DMSO) d 1.20 (d, 6H), 2.82 (m, 2H), 3.48 (m, 1H), 3.87 (s, 2H), 4.50 (m, 2H), 7.64 (d, 2H), 7.97 (br s, 2H), 7.98 (d, 2H), 8.13 (d, 2H), 8.40 (d, 2H) and 9.06 (s, 1H) ppm; MS (ES+) 497.2

Compound IA-348 1-(4-(5-(3-amino-6-(4-(isopropylsulfonyl)phenyl)pyrazin-2-yl)-1,3,4-oxadiazol-2-yl)-3-fluorobenzylamino)-2-methylpropan-2-ol 1H NMR (400 MHz, DMSO) d 1.13 (s, 6H), 1.20 (d, 6H), 2.39 (s, 2H), 3.48 (m, 1H), 3.88 (s, 2H), 4.27 (s, 1H), 7.45 (d, 1H), 7.51 (d, 1H), 7.97 (br s, 2H), 7.98 (d, 2H), 8.12 (t, 1H), 8.37 (d, 2H) and 9.07 (s, 1H) ppm; MS (ES+) 541.2

Compound IA-319 3-[5-[2-fluoro-4-[(oxetan-3-ylamino)methyl]phenyl]-1,3,4-oxadiazol-2-yl]-5-(4-isopropylsulfonylphenyl)pyrazin-2-amine 1H NMR (400 MHz, DMSO) d 1.20 (d, 6H), 4.48 (m, 1H), 3.77 (s, 2H), 3.80 (m, 1H), 4.34 (t, 2H), 4.59 (t, 2H), 7.45 (d, 1H), 7.51 (d, 1H), 7.97 (br s, 2H), 7.98 (d, 2H), 8.12 (t, 1H), 8.37 (d, 2H) and 9.07 (s, 1H) ppm; MS (ES+) 525.2

Example 48A

4-[5-[3-amino-6-(4-isopropylsulfonylphenyl)pyrazin-2-yl]-1,3,4-oxadiazol-2-yl]benzamidine (Compound IA-70)

SCHEME

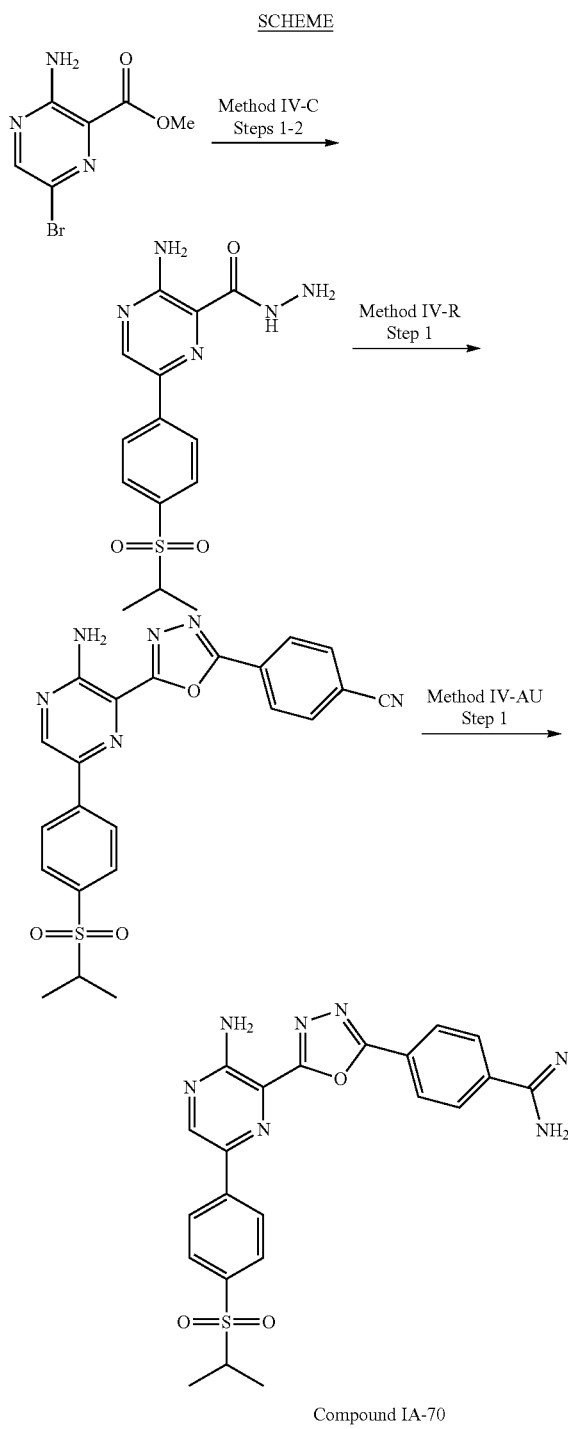

Compound IA-70

Compound IA-70 was prepared using Method IV-C, Steps 1-2, followed by Method IV-R, Step 1, followed by Method IV-AU, Step 1

Method IV-AU

Step 1: 4-[5-[3-amino-6-(4-isopropylsulfonylphenyl)pyrazin-2-yl]-1,3,4-oxadiazol-2-yl]benzamidine 4-[5-[3-amino-6-(4-isopropylsulfonylphenyl)pyrazin-2-yl]-1,3,4-oxadiazol-2-yl]benzonitrile (58 mg, 0.1299 mmol) was suspended in a mixture of $CH_2Cl_2$ (3 mL)/ethanol (4 mL, 68.51 mmol), sonicated then stirred at 0° C. during the addition of HCl gas until saturated. The resulting suspension was stirred at room temperature for 4 h, then warmed to 40° C. and stirred overnight. The mixture was concentrated to dryness under reduced pressure then suspended in absolute ethanol (60 ml), cooled in ice bath and ammonia gas bubbled through for 5 min. The reaction vessel was sealed and then stirred at room temperature for 3 h, then heated at 50° C. overnight. The reaction mixture was concentrated in vacuo and purified by reverse phase preparative HPLC [Waters Sunfire C18, 10 μM, 100 Å column, gradient 10%-95% B (solvent A: 0.05% TFA in water; solvent B: $CH_3CN$) over 16 minutes at 25 mL/min]. Product fractions were combined and lypholised to give the product as a pale yellow powder (16.7 mg, 32% yield); 1H NMR (400 MHz, DMSO) d 1.21 (d, 6H), 3.48 (m, 1H), 6.80 (br s, 2H), 7.98 (d, 2H), 8.05 (d, 2H), 8.21 (d, 2H), 8.41 (d, 2H) and 9.08 (s, 1H) ppm; MS $(ES^+)$ 464.24

The following compounds were all prepared using a method similar to the one described for Compound IA-70 above.

Compound IA-208 4-[5-[3-amino-6-(4-isopropylsulfonylphenyl)pyrazin-2-yl]-1,3,4-oxadiazol-2-yl]-N-methylbenzamidine 1H NMR (400 MHz, DMSO) d 1.20 (d, 6H), 2.88 (s, 3H), 3.48 (m, 1H), 6.83 (br s, 1H), 7.98 (br s, 2H), 7.99 (d, 2H), 8.03 (d, 2H) 8.19 (d, 2H), 8.41 (d, 2H) and 9.07 (s, 1H) ppm; MS $(ES^+)$ 478.24

Example 49A

4-[5-[3-amino-6-[4-(2-dimethylaminoethylsulfonyl)phenyl]pyrazin-2-yl]-1,3,4-oxadiazol-2-yl]phenol (Compound IA-191)

SCHEME

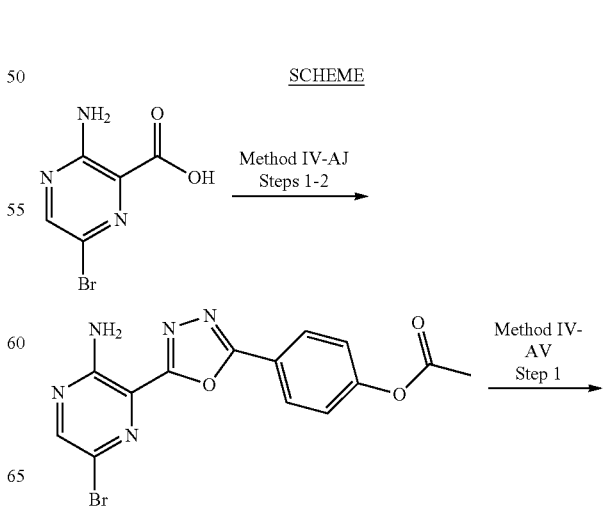

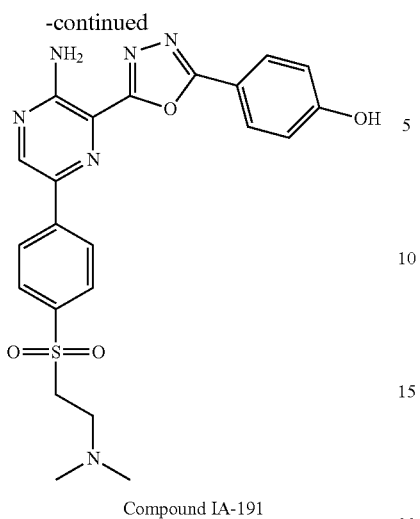

Compound IA-191

Compound IA-191 was prepared using Method IV-AJ, Steps 1-2, followed by Method IV-AV, Step 1.

Method IV-AV

Step 1: 4-[5-[3-amino-6-[4-(2-dimethylaminoethyl-sulfonyl)phenyl]pyrazin-2-yl]-1,3,4-oxadiazol-2-yl]phenol 2-(4-bromophenyl)sulfonyl-N,N-dimethyl-ethanamine (181.8 mg, 0.6221 mmol) was dissolved in dioxane (2 mL) and bis(pinacolato)diboron (237.0 mg, 0.9332 mmol) and potassium acetate (183.1 mg, 1.866 mmol) were added. The reaction mixture was degassed and filled with nitrogen (5×) then Pd(dppf)Cl$_2$.CH$_2$Cl$_2$ (50.80 mg, 0.06221 mmol) was added and the reaction heated to 90° C. for 2 hours. The reaction mixture was cooled to ambient temperature and diluted with DMF (2 mL). [4-[5-(3-amino-6-bromo-pyrazin-2-yl)-1,3,4-oxadiazol-2-yl]phenyl]acetate (234 mg, 0.6221 mmol), Na$_2$CO$_3$ (933.0 μL of 2 M aqueous solution, 1.866 mmol) and Pd(PPh$_3$)$_2$Cl$_2$ (43.67 mg, 0.06221 mmol) were added and the reaction heated at 150° C. under microwave conditions for 30 minutes. The reaction mixture was partitioned between EtOAc (5 mL) and water (5 mL) and any precipitate removed by filtration. The layers were separated and the aqueous layer extracted with EtOAc (3×5 mL) and the combined organic extracts dried over MgSO$_4$, filtered and concentrated in vacuo. The residue was triturated form EtOAc/MeOH to give the title compound as a brown solid (44.3 mg, 15%); 1H NMR (400 MHz, DMSO) d 2.07 (s, 6H), 2.56 (t, 2H), 3.52 (t, 2H), 7.03 (d, 2H), 7.87 (br s, 2H), 8.02 (dd, 4H), 8.38 (d, 2H), 9.05 (s, 1H) and 10.44 (s, 1H) ppm; MS (ES$^+$) 467.2

Example 50A

5-[3-amino-6-(4-isopropylsulfonylphenyl)pyrazin-2-yl]-1,3,4-oxadiazol-2-amine (Compound IA-270)

SCHEME

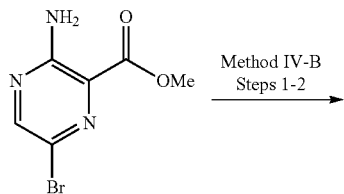

Method IV-B
Steps 1-2

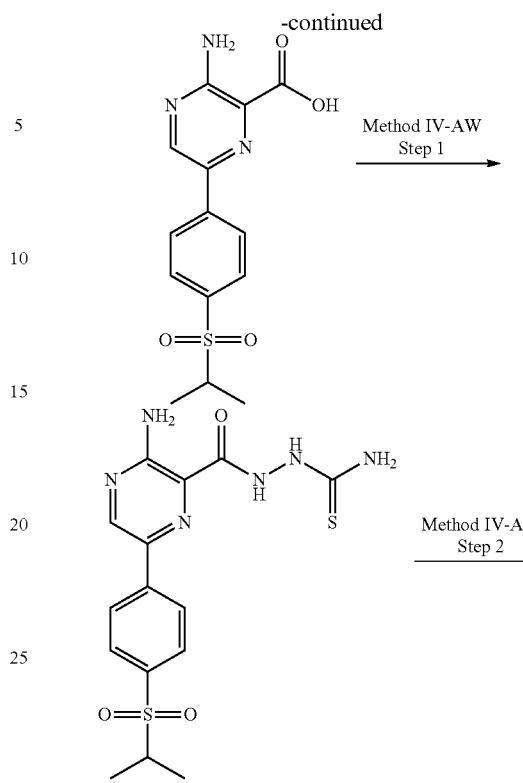

Compound IA-270

Compound IA-270 was prepared using Method IV-B, Steps 1-2, followed by Method IV-AW, Steps 1-2.

Method IV-AW

Step 1: 2-(3-amino-6-(4-(isopropylsulfonyl)phenyl)pyrazine-2-carbonyl)hydrazinecarbothioamide TBTU (749.4 mg, 2.334 mmol) and Et$_3$N (157.5 mg, 216.9 μL, 1.556 mmol) were added to a suspension of 3-amino-6-(4-isopropylsulfonylphenyl)pyrazine-2-carboxylic acid (500 mg, 1.556 mmol) and aminothiourea (141.8 mg, 1.556 mmol) in DMF (10 mL). The reaction was allowed to stir at ambient temperature for 1 h. The reaction mixture was added to rapidly stirring water and the resultant precipitate isolated by filtration to give the product as a khaki solid (587 mg, 96%) 1H NMR (400 MHz, DMSO) d 1.18 (d, 6H), 3.40-3.56 (m, 1H), 7.64 (s, 2H), 7.79 (s, 2H), 7.88 (d, 2H), 8.56 (d, 1H), 9.03 (s, 1H), 9.41 (s, 1H) and 10.75 (s, 1H) ppm; MS (ES$^+$) 395.2

Step 2: 5-[3-amino-6-(4-isopropylsulfonylphenyl)pyrazin-2-yl]-1,3,4-oxadiazol-2-amine EDC (109.3 mg, 0.5704 mmol) was added to a stirred suspension of [[3-amino-6-(4-isopropylsulfonylphenyl)pyrazine-2-carbonyl]amino]thiourea (150 mg, 0.3803 mmol) in DCE (3.000 mL) and the reaction mixture heated at reflux for 22 h. The solvent was removed in vacuo and the residue partitioned between EtOAc and water. The aqueous layer was extracted with EtOAc (3×10 mL) and the combined organic extracts dried MgSO$_4$, filtered and concentrated in vacuo to give the sub-title compound as a yellow solid (118 mg, 86%)

1H NMR (400 MHz, DMSO) d 1.19 (d, 6H), 3.45 (dt, 1H), 7.65-7.80 (m, 4H), 7.95 (d, 2H), 8.26 (d, 2H) and 8.89 (s, 1H) ppm; MS (ES$^+$) 361.0

Example 51

3-[5-[5-(ethylaminomethyl)-2-thienyl]-1,3,4-oxadiazol-2-yl]-5-(4-isopropylsulfonylphenyl)pyrazin-2-amine (Compound IA-83)

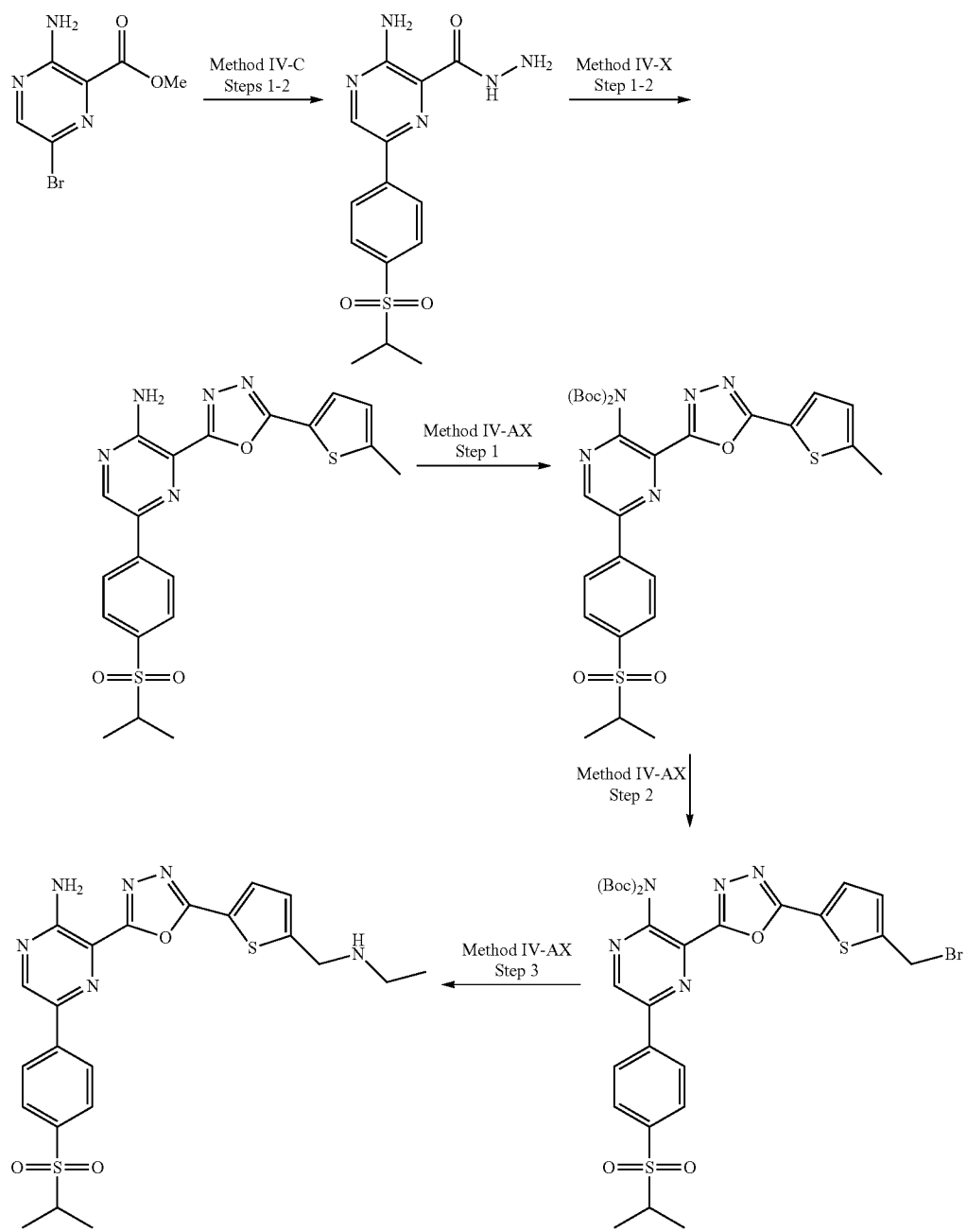

SCHEME

Compound IA-83

Compound IA-83 was prepared using Method IV-C, Steps 1-2, followed by Method IV-X, Steps 1-2, followed by Method IV-AX, Steps 1-3.

Method IV-AX

Step 1: di-tert-butyl N-[5-(4-isopropylsulfonylphenyl)-3-[5-(5-methyl-2-thienyl)-1,3,4-oxadiazol-2-yl]pyrazin-2-yl]iminodicarbonate 5-(4-isopropylsulfonylphenyl)-3-[5-(5-methyl-2-thienyl)-1,3,4-oxadiazol-2-yl]pyrazin-2-amine (600 mg, 1.359 mmol) was added to MeCN (50 mL) followed by the addition of $BOC_2O$ (889.8 mg, 936.6 µL, 4.077 mmol) and DMAP (8.301 mg, 0.06795 mmol). The resulting mixture was stirred overnight at room temperature. The reaction mixture was concentrated in vacuo to leave a solid which was purified by column chromatography on silica gel eluting with 50% EtOAc/petroleum ether (544.6 mg, 74%) 1H NMR (400 MHz, $CDCl_3$) d 1.29 (d, 6H), 1.36 (s, 9H), 2.54 (s, 3H, 3.20 (m, 1H), 6.83 (m, 1H), 7.71 (m, 1H), 8.03 (m, 2H), 8.31 (m, 2H) and 9.06 (s, 1H) ppm Step 2: di-tert-butyl 3-(5-(5-(bromomethyl)thiophen-2-yl)-1,3,4-oxadiazol-2-yl)-5-(4-(isopropylsulfonyl)phenyl)pyrazin-2-yliminodicarbonate To a solution of di-tert-butyl N-[5-(4-isopropylsulfonylphenyl)-3-[5-(5-methyl-2-thienyl)-1,3,4-oxadiazol-2-yl]pyrazin-2-yl]iminodicarbonate (700 mg, 1.292 mmol) in ethyl acetate (50 mL) was added NBS (299.0 mg, 1.680 mmol) and AIBN (42.43 mg, 0.2584 mmol). The resulting mixture was heated to reflux for 2 h. The reaction mixture was cooled to room temperature and filtered, washed with water and the organic layer was dried over $MgSO_4$ and concentrated in vacuo to a yellow solid which was used in the next stage without further purification.

Step 3: 3-[5-[5-(ethylaminomethyl)-2-thienyl]-1,3,4-oxadiazol-2-yl]-5-(4-isopropylsulfonylphenyl)pyrazin-2-amine To a solution of di-tert-butyl 3-(5-(5-(bromomethyl)thiophen-2-yl)-1,3,4-oxadiazol-2-yl)-5-(4-(isopropylsulfonyl)phenyl)pyrazin-2-yliminodicarbonate (90 mg, 0.1450 mmol) in ethanol (2 mL) at room temperature was added ethylamine (7.250 mL of 2 M in ethanol, 14.50 mmol). The resulting mixture was stirred at room temperature 1 h. The mixture was concentrated in vacuo to leave a solid. The solid was redissolved in $CH_2Cl_2$ and concentrated to a solid to remove any remaining methanol. The solid was dissolved in $CH_2Cl_2$ (3 mL) and TFA (165.3 mg, 111.7 µL, 1.450 mmol) was added. The mixture was stirred at room temperature for 2 h and then concentrated in vacuo and the residue purified by reverse phase preparative HPLC [Waters Sunfire C18, 10 µM, 100 Å column, gradient 10%-95% B (solvent A: 0.05% TFA in water; solvent B: $CH_3CN$) over 16 minutes at 25 mL/min]. Product fractions were combined and lypholised to give the product as a pale yellow powder (63 mg, 73.5%); 1H NMR (400 MHz, DMSO) d 1.20-1.25 (m, 9H), 3.0-3.1 (m, 2H), 3.42-3.46 (m, 1H), 4.5 (s, 2H), 7.5 (d, 1H), 7.95 (d, 1H), 8.01 (d, 1H), 8.38 (d, 1H), 9.0 (br s, 2H) and 9.18 (s, 1H) ppm; MS ($ES^+$) 485.4

The following compounds were all prepared using a method similar to the one described for Compound IA-83 above.

Compound IA-140 5-(4-isopropylsulfonylphenyl)-3-[5-[5-(methylaminomethyl)-2-thienyl]-1,3,4-oxadiazol-2-yl]pyrazin-2-amine 1H NMR (400 MHz, DMSO) d 1.22 (d, 6H), 2.65 (s, 3H), 3.42-3.46 (m, 1H), 4.5 (s, 2H), 7.5 (d, 1H), 8.0 (d, 1H), 8.05 (d, 1H), 8.4 (d, 1H), 9.05 (br s, 2H) and 9.1 (s, 1H) ppm; MS ($ES^+$) 471.3

Compound IA-226 5-(4-isopropylsulfonylphenyl)-3-[5-[4-(methylaminomethyl)-2-thienyl]-1,3,4-oxadiazol-2-yl]pyrazin-2-amine 1H NMR (400 MHz, MeOD) d 1.4 (d, 6H), 2.8 (s, 3H), 4.4 (s, 2H), 3.3-3.4 (m, 1H), 8.0-8.1 (m, 3H), 8.12 (s, 1H), 8.35 (d, 2H) and 9.0 (s, 1H) ppm; MS ($ES^+$) 471.3

Compound IA-236 3-[5-[5-[(2,2-difluoroethylamino)methyl]-2-thienyl]-1,3,4-oxadiazol-2-yl]-5-(4-isopropylsulfonylphenyl)pyrazin-2-amine 1H NMR (400 MHz, DMSO) d 1.25 (d, 6H), 3.4-3.6 (m, 3H), 4.55 (s, 2H), 6.2-6.5 (m, 1H), 7.5 (d, 1H), 7.8-8.1 (m, 4H), 8.45 (d, 2H) and 9.1 (s, 1H) ppm; MS ($ES^+$) 521.3

Compound IA-248 3-[5-[5-[(isopropylamino)methyl]-2-thienyl]-1,3,4-oxadiazol-2-yl]-5-(4-isopropylsulfonylphenyl)pyrazin-2-amine 1H NMR (400 MHz, DMSO) d 1.25 (m, 6H), 1.35 (d, 6H), 3.4-3.6 (m, 2H), 4.6 (s, 2H), 7.5 (d, 1H), 7.95-8.1 (m, 4H), 8.45 (d, 2H), 8.9-9.0 (br s, 2H) and 9.1 (s, 1H) ppm; MS ($ES^+$) 499.4

Example 52A

N-[5-[3-amino-6-(4-isopropylsulfonylphenyl)pyrazin-2-yl]-1,3,4-oxadiazol-2-yl]acetamide (Compound IA-177)

SCHEME

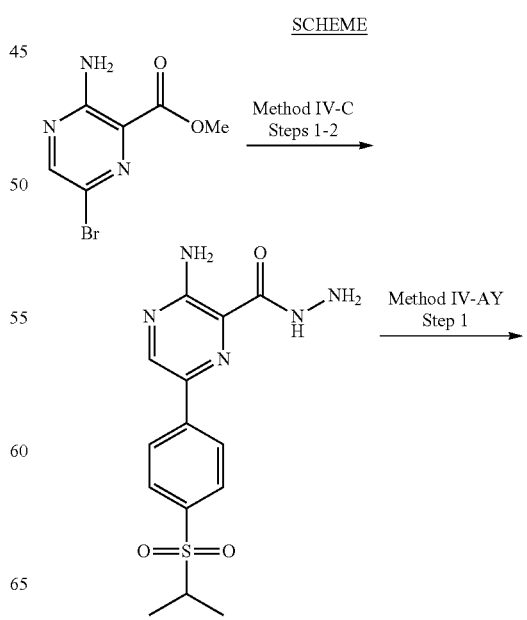

-continued

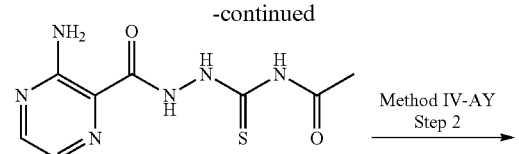

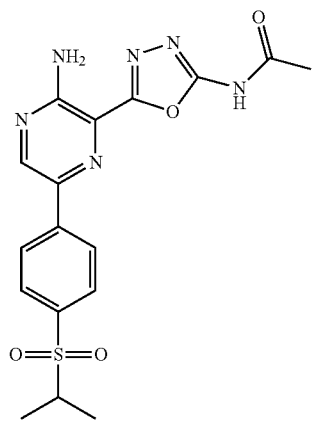

Compound IA-177

Compound IA-177 was prepared using Method IV-C, Steps 1-2, followed by Method IV-AY, Steps 1-2.

Method IV-AY

Step 1: N-(2-(3-amino-6-(4-(isopropylsulfonyl)phenyl)pyrazine-2-carbonyl) hydrazinecarbonothioyl) ethanamide A mixture of 3-amino-6-(4-isopropylsulfonylphenyl)pyrazine-2-carbohydrazide (100 mg, 0.2982 mmol), acetyl isothiocyanate (30.16 mg, 26.20 μL, 0.2982 mmol) and dry DCE (2.000 mL) were stirred at ambient temperature for 2 h and then concentrated in vacuo. Used directly in the next step without further purification; MS (ES+) 437.20

Step 2: N-[5-[3-amino-6-(4-isopropylsulfonylphenyl)pyrazin-2-yl]-1,3,4-oxadiazol-2-yl]acetamide N-(2-(3-amino-6-(4-(isopropylsulfonyl)phenyl)pyrazine-2-carbonyl)hydrazinecarbonothioyl)acetamide (47 mg, 0.1077 mmol) was dissolved in DMF (2 mL) and EDC (30.98 mg, 0.1616 mmol) was added. The reaction was allowed to stir at ambient temperature for 45 minutes then warmed to 100° C. for 1 hour. The reaction mixture was cooled to ambient temperature then added slowly to stirred water. The resultant precipitate was isolated by filtration to give the sub-title product as a yellow solid (31 mg, 68%); 1H NMR (400 MHz, DMSO) d 1.18 (d, 6H), 2.20 (s, 3H), 3.41-3.49 (m, 1H), 7.81 (br s, 2H), 8.14 (d, 2H), 8.27 (d, 2H), 8.99 (s, 1H) and 11.98 (s, 1H) ppm; MS (ES+) 403.2

Example 53A 2-amino-N-[5-[3-amino-6-(4-isopropylsulfonylphenyl)pyrazin-2-yl]-1,3,4-oxadiazol-2-yl]acetamide (Compound IA-82)

SCHEME

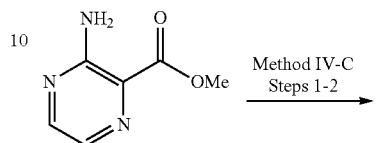

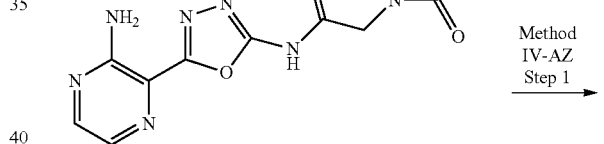

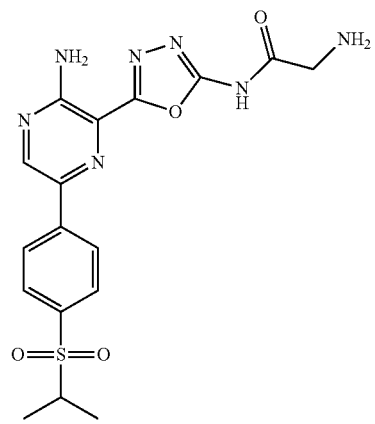

Compound IA-82

Compound IA-82 was prepared using Method IV-C, Steps 1-2, followed by Method IV-AY, Steps 1-2, followed by Method IV-AZ, Step 1.

Method IV-AZ

Step 1: 2-amino-N-[5-[3-amino-6-(4-isopropylsulfonylphenyl)pyrazin-2-yl]-1,3,4-oxadiazol-2-yl]acetamide Hydrazine hydrate (8.065 mg, 7.838 μL, 0.1611 mmol) was added to a stirred suspension of N-(5-(3-amino-6-(4-(isopropylsulfonyl)phenyl)pyrazin-2-yl)-1,3,4-oxadiazol-2-yl)-2-(1,3-dioxoisoindolin-2-yl)acetamide (147 mg, 0.1611 mmol) in MeOH (5 mL)/CH$_2$Cl$_2$ (5 mL) and the reaction mixture was allowed to stir at ambient temperature for 2 hours. A further portion of hydrazine hydrate (16.13 mg, 15.68 μL, 0.3222 mmol) was added and the reaction stirred for a further 16 hours. The solvent was removed in vacuo and residue was purified by reverse phase preparative HPLC [Waters Sunfire C18, 10 μM, 100 Å column, gradient 10%-95% B (solvent A: 0.05% TFA in water; solvent B: CH$_3$CN) over 16 minutes at 25 mL/min]. The fractions were collected and freeze-dried to give the title compound as a yellow solid (10 mg, 11%); 1H NMR (400.0 MHz, DMSO) d 1.18 (d, 6H), 3.50-3.53 (m, 1H), 4.11 (s, 1.4H), 4.33 (s, 0.6H), 7.81 (s, 2H), 7.91 (d, 2H), 8.53 (d, 2H), 9.07 (s, 1H), 10.99 (s, 0.7H) and 11.16 (s, 0.3H) ppm; MS (ES$^+$) 418.2

The following compounds were all prepared using a method similar to the one described for Compound IA-82 above.

Compound IA-219 2-amino-N-[5-[3-amino-6-(4-isopropylsulfonylphenyl)pyrazin-2-yl]-1,3,4-oxadiazol-2-yl]-2-methyl-propanamide 1H NMR (400.0 MHz, DMSO) d 1.18 (d, 6H), 1.21 (s, 6H), 3.43-3.53 (m, 1H), 7.80 (br s, 2H), 7.88 (d, 2H), 8.08 (s, 1H), 8.54 (d, 2H), 9.01 (s, 1H), 10.49 (br s, 1H) and 10.62 (s, 1H) ppm; MS (ES$^+$) 446.2

Compound IA-272 2-amino-N-[5-[3-amino-6-(4-isopropylsulfonylphenyl)pyrazin-2-yl]-1,3,4-oxadiazol-2-yl]propanamide 1H NMR (400.0 MHz, DMSO) d 1.19 (d, 6H), 1.30 (d, 1.8H), 1.39 (d, 1.2H), 3.46-3.53 (m, 1H), 4.34 (br s, 0.6H), 4.54 (br s, 0.4H), 7.82 (br s, 2H), 7.91 (d, 2H), 8.50-8.55 (m, 2H), 9.09 (s, 1H), 11.06 (br s, 0.6H) and 11.17 (br s, 0.4H) ppm; MS (ES$^+$) 432.2

Example 54A

5-[3-amino-6-(4-isopropylsulfonylphenyl)pyrazin-2-yl]-N-(3-piperidyl)-1,3,4-oxadiazol-2-amine (Compound IA-199)

SCHEME

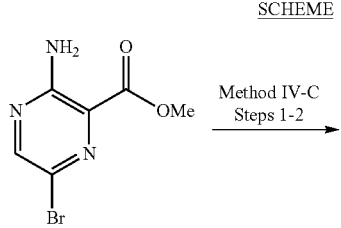

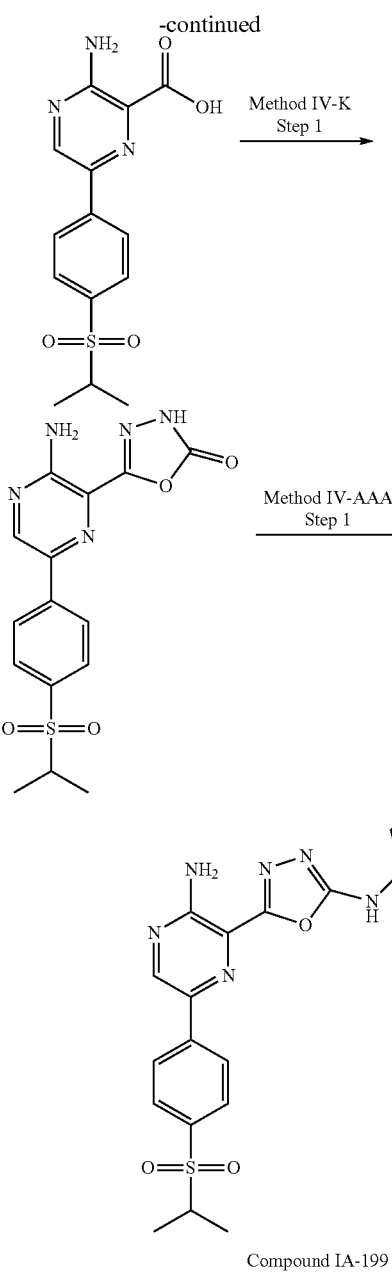

Compound IA-199

Compound IA-199 was prepared using Method IV-C, Steps 1-2, followed by Method IV-K, Step 1, followed by Method IV-AAA, Step 1.

Method IV-AAA

Step 1: 5-[3-amino-6-(4-isopropylsulfonylphenyl)pyrazin-2-yl]-N-(3-piperidyl)-1,3,4-oxadiazol-2-amine DIPEA (173.6 μL, 1.0 mmol), tert-butyl 3-aminopiperidine-1-carboxylate (99.7 mg, 0.50 mmol) and bromo(tripyrrolidin-1-yl)phosphonium hexafluorophosphate (340.6 mg, 0.73 mmol) were added to a mixture of 5-[3-amino-6-(4-isopropylsulfonylphenyl)pyrazin-2-yl]-3H-1,3,4-oxadiazol-2-one (120 mg, 0.33 mmol) in DMF (600 μL) and DMSO (600 L). The resulting mixture was stirred at room temperature for 4.5 h. The reaction mixture was diluted with EtOAc (5 mL) and saturated aqueous sodium hydrogen carbonate solution (5 mL). The aqueous layer was washed with EtOAc (3×5 mL) and the combined organic extracts dried over MgSO₄, filtered and concentrated in vacuo. The residue was taken up in methanol (1.2 mL) and HCl (332 μL, 1.0 mmol, 3M solution in methanol) and the resulting solution stirred at room temperature overnight. The reaction mixture was evaporated to dryness and the solid triturated with acetonitrile and then purified further by reverse phase preparative HPLC [Waters Sunfire C18, 10 μM, 100 Å column, gradient 10%-95% B (solvent A: 0.05% TFA in water; solvent B: CH₃CN) over 16 minutes at 25 mL/min]. The product fractions were passed through a bicarbonate cartridge and lypholised to give the title compound as a yellow solid (29.6 mg, 20%); H NMR (400.0 MHz, DMSO) d 1.19 (d, 6H), 1.43-1.48 (m, 2H), 1.64-1.67 (m, 1H), 1.99-2.01 (m, 1H), 2.40-2.46 (m, 2H), 2.77-2.80 (m, 1H), 3.10-3.14 (m, 1H), 3.46-3.55 (m, 2H), 7.80 (br s, 1H), 7.95 (d, 2H), 8.23 (t, 2H), 8.27 (s, 1H) and 8.89 (s, 1H) ppm; MS (ES⁺) 444.25

The following compounds were all prepared using a method similar to the one described for Compound IA-199 above.

Compound IA-97 N-[5-[3-amino-6-(4-isopropylsulfonylphenyl)pyrazin-2-yl]-1,3,4-oxadiazol-2-yl]propane-1,3-diamine 1H NMR (400.0 MHz, DMSO) d 1.18 (d, 7H), 1.67 (t, 2H), 2.64 (t, 2H), 3.00-3.01 (m, 2H), 3.46-3.50 (m, 1H), 6.75 (br s, 1H), 7.80 (br s, 1H), 7.95 (d, 2H), 8.26 (d, 2H) and 8.89 (s, 1H) ppm; MS (ES⁺) 418.21

Compound IA-109 3-[5-(4-amino-1-piperidyl)-1,3,4-oxadiazol-2-yl]-5-(4-isopropylsulfonylphenyl)pyrazin-2-amine 1H NMR (400.0 MHz, DMSO) d 1.19 (d, 6H), 1.45-1.60 (m, 2H), 1.94 (s, 2H), 2.08 (s, 1H), 3.17-3.25 (m, 4H), 3.45 (t, 2H), 4.00 (s, 2H), 7.75 (br s, 1H), 7.93 (d, 2H), 8.32 (d, 2H) and 8.93 (s, 1H) ppm; MS (ES⁺) 444.21

Compound IA-111 3-[5-(3-aminoazetidin-1-yl)-1,3,4-oxadiazol-2-yl]-5-(4-isopropylsulfonylphenyl)pyrazin-2-amine 1H NMR (400.0 MHz, DMSO) d 1.18 (dd, 6H), 2.35 (br s, 2H), 2.95 (br s, 2H), 3.40-3.55 (m, 1H), 3.85-4.01 (m, 2H), 4.00-4.30 (m, 2H), 7.75 (br s, 1H), 7.94 (d, 2H), 8.27 (d, 2H) and 8.91 (s, 1H) ppm; MS (ES⁺) 416.2

Compound IA-138 3-[5-[4-(aminomethyl)-1-piperidyl]-1,3,4-oxadiazol-2-yl]-5-(4-isopropylsulfonylphenyl)pyrazin-2-amine 1H NMR (400.0 MHz, DMSO) d 1.16-1.19 (m, 6H), 1.20-1.40 (m, 3H), 1.50-1.95 (m, 3H), 2.08 (s, 1H), 2.54 (s, 1H), 2.85-3.35 (m, 3H), 3.40-3.50 (m, 1H), 3.95-4.10 (m, 2H), 7.75 (br s, 1H), 7.94 (d, 2H), 8.31 (d, 2H) and 8.92 (s, 1H) ppm; MS (ES⁺) 458.21

Compound IA-188 3-[5-(3-aminopyrrolidin-1-yl)-1,3,4-oxadiazol-2-yl]-5-(4-isopropylsulfonylphenyl)pyrazin-2-amine 1H NMR (400.0 MHz, DMSO) d 1.05 (d, 6H), 1.95-2.05 (m, 1H), 2.20-2.30 (m, 1H), 2.95 (t, 3H), 3.40-3.55 (m, 2H), 3.60-3.70 (m, 1H), 3.70-3.80 (m, 2H), 3.80-3.90 (m, 1H), 5.15 (s, 1H), 7.80 (d, 2H), 8.16 (d, 2H) and 8.78 (s, 1H) ppm; MS (ES⁺) 430.27

Compound IA-227 3-[5-[3-(aminomethyl)-1-piperidyl]-1,3,4-oxadiazol-2-yl]-5-(4-isopropylsulfonylphenyl)pyrazin-2-amine MS (ES⁺) 458.23

Compound IA-206 3-[5-(3-amino-1-piperidyl)-1,3,4-oxadiazol-2-yl]-5-(4-isopropylsulfonylphenyl)pyrazin-2-amine 1H NMR (400.0 MHz, DMSO) d 1.19 (d, 6H), 1.45-1.65 (m, 1H), 1.75-1.90 (m, 2H), 2.08 (s, 1H), 2.75-3.20 (m, 5H), 3.40-3.50 (m, 1H), 3.75-3.95 (m, 2H), 7.75 (s, 2H), 7.94 (d, 2H), 8.32 (d, 2H) and 8.91 (s, 1H) ppm; MS (ES⁺) 444.21

Compound IA-239 5-(4-isopropylsulfonylphenyl)-3-(5-piperazin-1-yl-1,3,4-oxadiazol-2-yl)pyrazin-2-amine 1H NMR (400.0 MHz, DMSO) d 1.18 (d, 6H), 2.67 (s, 1H), 2.98 (s, 3H), 3.10 (d, 2H), 3.40-3.50 (m, 1H), 3.57-3.60 (m, 4H), 7.75 (br s, 1H), 7.93 (d, 2H), 8.32 (d, 2H) and 8.93 (s, 1H) ppm; MS (ES⁺) 430.23

Compound IA-318 5-[3-amino-6-(4-isopropylsulfonylphenyl)pyrazin-2-yl]-N-(4-piperidyl)-1,3,4-oxadiazol-2-amine 1H NMR (400.0 MHz, DMSO) d 1.18 (d, 6H), 1.35-1.45 (m, 2H), 1.95-2.00 (m, 2H), 2.95-3.00 (m, 2H), 3.40-3.55 (m, 2H), 7.95 (d, 2H), 8.25-8.35 (m, 3H) and 8.90 (s, 1H) ppm; MS (ES⁺) 444.2

Example 55

5-[3-amino-6-(4-isopropylsulfonylphenyl)pyrazin-2-yl]-N-pyrrolidin-3-yl-1,3,4-oxadiazole-2-carboxamide (Compound IA-114)

SCHEME

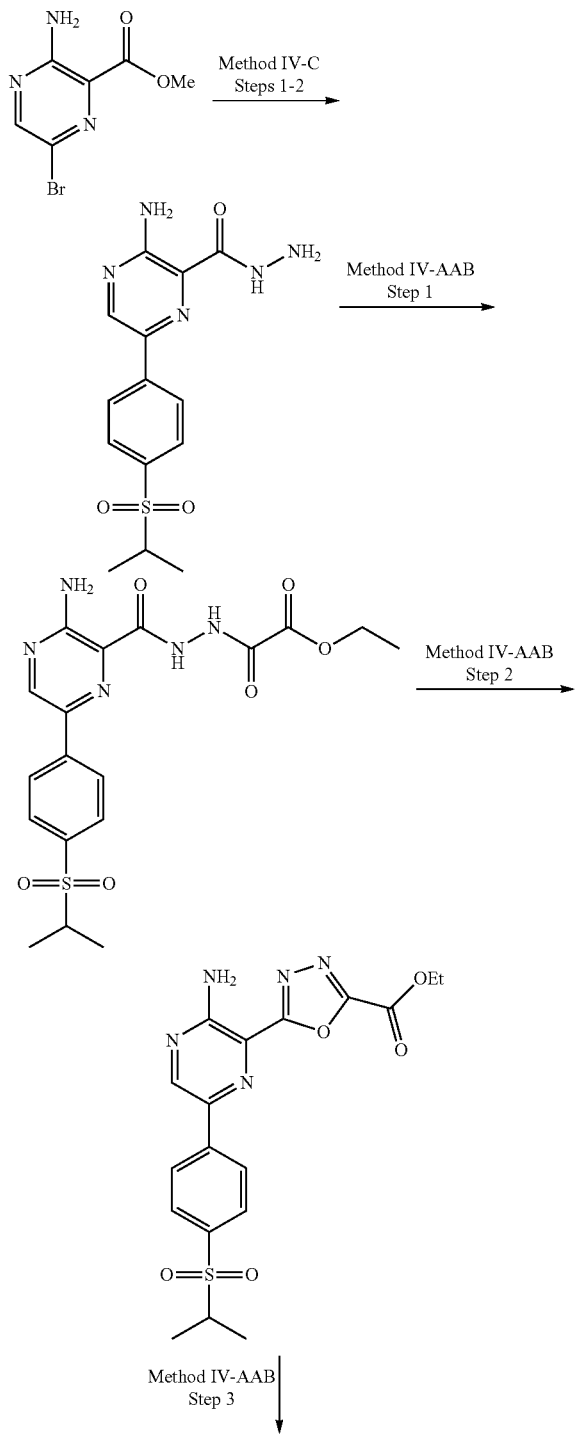

-continued

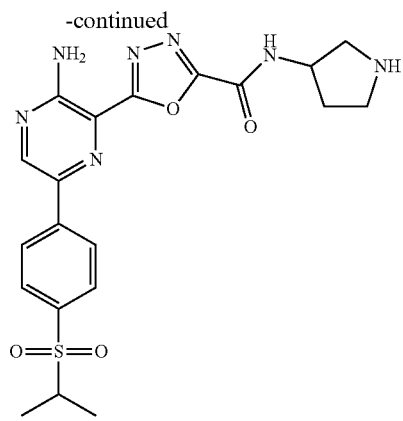

Compound IA-114

Compound IA-114 was prepared using Method IV-C, Steps 1-2, followed by Method IV-AAB, Steps 1-3.

Method IV-AAB

Step 1: ethyl 2-(2-(3-amino-6-(4-(isopropylsulfonyl)phenyl)pyrazine-2-carbonyl)hydrazinyl)-2-oxoethanoate 3-amino-6-(4-isopropylsulfonylphenyl)pyrazine-2-carbohydrazide (2 g, 5.963 mmol) and Et₃N (1.810 g, 2.493 mL, 17.89 mmol) were dissolved in THF (128.0 mL) and treated dropwise with ethyl 2-chloro-2-oxo-acetate (814.2 mg, 666.3 µL, 5.963 mmol) at 0° C. The reaction mixture was warmed slowly to room temperature and stirred for 1.5 h. The reaction mixture was filtered and grey solid washed with THF. The filtrate was evaporated to dryness azeotroping with acetonitrile. Then residue was then triturated with acetonitrile to give the product as a yellow solid (1.52 g, 58%); 1H NMR (400 MHZ, DMSO) d 1.19 (m, 6H), 1.32 (m, 3H), 3.34 (m, 1H), 4.32 (m, 2H), 7.88 (m, 2H), 8.56 (m, 2H), 9.07 (s, 1H), 10.95 (s, 1H) and 11.05 (s, 1H) ppm; MS (ES⁺) 436.32

Step 2: ethyl 5-(3-amino-6-(4-(isopropylsulfonyl)phenyl)pyrazin-2-yl)-1,3,4-oxadiazole-2-carboxylate To a stirred solution of ethyl 2-(2-(3-amino-6-(4-(isopropylsulfonyl)phenyl)pyrazine-2-carbonyl)hydrazinyl)-2-oxoacetate (1.1894 g, 2.731 mmol) was in CH₂Cl₂ (23.78 mL) was added triethylamine (552.7 mg, 761.3 µL, 5.462 mmol), followed by 4-methylbenzenesulfonyl chloride (520.7 mg, 2.731 mmol) and the resulting solution stirred at room temperature for 3 h. The reaction mixture is diluted with CH₂Cl₂ and washed with water (1×20 mL), saturated aqueous sodium hydrogen carbonate solution (1×20 mL) and brine (1×20 mL). The organic extracts were dried over MgSO₄, filtered and concentrated in vacuo. The residue was triturated with acetonitrile to give the product as a yellow solid (1.03 g, 90%); 1H NMR (400 MHz, DMSO) d 1.37 (m, 6H), 1.54 (m, 3H), 3.25 (m, 1H), 4.64 (m, 2H), 8.00 (m, 2H), 8.20 (m, 2H) and 8.83 (s, 1H) ppm; MS (ES⁺) 418.19

Step 3: 5-[3-amino-6-(4-isopropylsulfonylphenyl)pyrazin-2-yl]-N-pyrrolidin-3-yl-1,3,4-oxadiazole-2-carboxamide To a suspension of ethyl 5-[3-amino-6-(4-isopropylsulfonylphenyl)pyrazin-2-yl]-1,3,4-oxadiazole-2-carboxylate (100 mg, 0.34 mmol) in ethanol (2 mL), tert-butyl 3-aminopyrrolidine-1-carboxylate (49.1 mg, 0.26 mmol) was added and the resulting mixture heated under reflux overnight. The reaction mixture was cooled to room temperature and evaporated to dryness. The residue was taken up in CH₂Cl₂ (2.0 mL) and TFA (400 µL) was added and the reaction mixture stirred overnight at room temperature. The reaction mixture was passed through a bicarbonate cartridge and the filtrate concentrated in vacuo. The residue was passed through a TsOH cartridge eluting the product with 2M Ammonia in methanol (5 mL). The solid was triturated form acetonitrile to give the product as a yellow solid (44.94 mg, 41%); 1H NMR (400.0 MHz, DMSO) d 1.19 (d, 6H), 1.75 (s, 1H), 2.00 (d, 1H), 2.73-2.78 (m, 2H), 2.94 (s, 1H), 2.95 (dd, 1H), 3.47 (t, 1H), 4.40 (br s, 1H), 7.85 (br s, 2H), 7.98 (d, 2H), 8.32-8.34 (m, 2H), 9.09 (s, 1H) and 9.46 (d, 1H) ppm; MS (ES⁺) 458.22

The following compounds were all prepared using a method similar to the one described for Compound IA-114 above.

Compound IA-79 [5-[3-amino-6-(4-isopropylsulfonylphenyl)pyrazin-2-yl]-1,3,4-oxadiazol-2-yl]-(1,4-diazepan-1-yl)methanone; MS (ES⁺) 472.3

Compound IA-81 N-(2-aminocyclohexyl)-5-[3-amino-6-(4-isopropylsulfonylphenyl)pyrazin-2-yl]-1,3,4-oxadiazole-2-carboxamide 1H NMR (400.0 MHz, DMSO) d 1.19 (d, 6H), 1.21-1.30 (br s, 1H), 1.40-1.50 (m, 1H), 1.65-1.75 (m, 2H), 1.80-1.95 (m, 2H), 2.75 (br s, 2H), 3.45-3.50 (m, 3H), 3.65 (br s, 1H), 7.95 (s, 2H), 8.45 (s, 2H), 9.10 (s, 1H) and 9.30 (br s, 1H) ppm; MS (ES⁺) 486.35

Compound IA-98 [5-[3-amino-6-(4-isopropylsulfonylphenyl)pyrazin-2-yl]-1,3,4-oxadiazol-2-yl]-(3-amino-1-piperidyl)methanone 1H NMR (400.0 MHz, DMSO) d 1.19 (d, 6H), 1.34-1.38 (m, 1H), 1.48-1.51 (m, 1H), 1.76-1.92 (m, 3H), 2.67-2.81 (m, 2H), 3.17-3.29 (m, 2H), 3.50-3.99 (m, 1H), 4.09-4.10 (m, 0.5H), 4.12-4.23 (m, 0.5H), 4.24-4.30 (m, 1H), 7.85 (br s, 1H), 7.98 (d, 2H), 8.32 (dd, 2H) and 9.09 (s, 1H) ppm; MS (ES⁺) 472.28

Compound IA-113 butyl 5-[3-amino-6-(4-isopropylsulfonylphenyl)pyrazin-2-yl]-1,3,4-oxadiazole-2-carboxylate 1H NMR (400.0 MHz, DMSO) d 0.97 (t, 3H), 1.19 (d, 6H), 1.46 (d, 2H), 1.75-1.78 (m, 2H), 2.08 (s, 1H), 3.47-3.55 (m, 1H), 4.46 (t, 2H), 7.75 (br s, 1H), 7.99 (d, 2H), 8.31 (d, 2H) and 9.10 (s, 1H) ppm; MS (ES⁺) 446.22

Compound IA-120 (3-aminoazetidin-1-yl)-[5-[3-amino-6-(4-isopropylsulfonylphenyl)pyrazin-2-yl]-1,3,4-oxadiazol-2-yl]methanone 1H NMR (400.0 MHz, DMSO) d 1.18-1.20 (m, 6H), 2.50 (br s, 1H), 2.55 (s, 1H), 3.05 (br s, 2H), 3.45-3.52 (m, 1H), 3.76-3.80 (m, 1H), 3.82-3.87 (m, 1H), 4.22-4.26 (m, 1H), 4.31-4.36 (m, 1H), 4.76-4.79 (m, 1H), 7.98 (d, 2H), 8.32 (d, 2H) and 9.09 (s, 1H) ppm; MS (ES⁺) 444.28

Compound IA-133 [5-[3-amino-6-(4-isopropylsulfonylphenyl)pyrazin-2-yl]-1,3,4-oxadiazol-2-yl]-(3-aminopyrrolidin-1-yl)methanone 1H NMR (400.0 MHz, DMSO) d 1.19 (d, 6H), 1.65-1.80 (m, 1H), 1.95-2.10 (m, 1H), 3.45-3.50 (m, 2H), 3.55-3.75 (m, 3H), 3.95-4.10 (m, 1H), 7.75 (br s, 1H), 7.98 (d, 2H), 8.32 (d, 2H) and 9.09 (s, 1H) ppm; MS (ES⁺) 458.37

Compound IA-255 5-[3-amino-6-(4-isopropylsulfonylphenyl)pyrazin-2-yl]-N-(3-piperidylmethyl)-1,3,4-oxadiazole-2-carboxamide 1H NMR (400.0 MHz, DMSO) d 1.05-1.10 (m, 1H), 1.19 (d, 6H), 1.25-1.35 (m, 1H), 1.55-1.59 (m, 1H), 1.73-1.75 (m, 1H), 2.19-2.22 (m, 1H), 2.33-2.40 (m, 1H), 2.80-2.82 (m, 1H), 2.91-2.94 (m, 1H), 3.18 (s, 1H), 3.18-3.21 (m, 2H), 3.47-3.50 (m, 1H), 7.85 (br s, 1H), 7.98 (d, 2H), 8.33 (d, 2H), 9.09 (s, 1H) and 9.44-9.47 (m, 1H) ppm; MS (ES⁺) 486.29

487

Example 56A (2S)—N-[5-[3-amino-6-(4-isopropylsulfonylphenyl)pyrazin-2-yl]-1,3,4-oxadiazol-2-yl]piperidine-2-carboxamide (Compound IA-211)

SCHEME

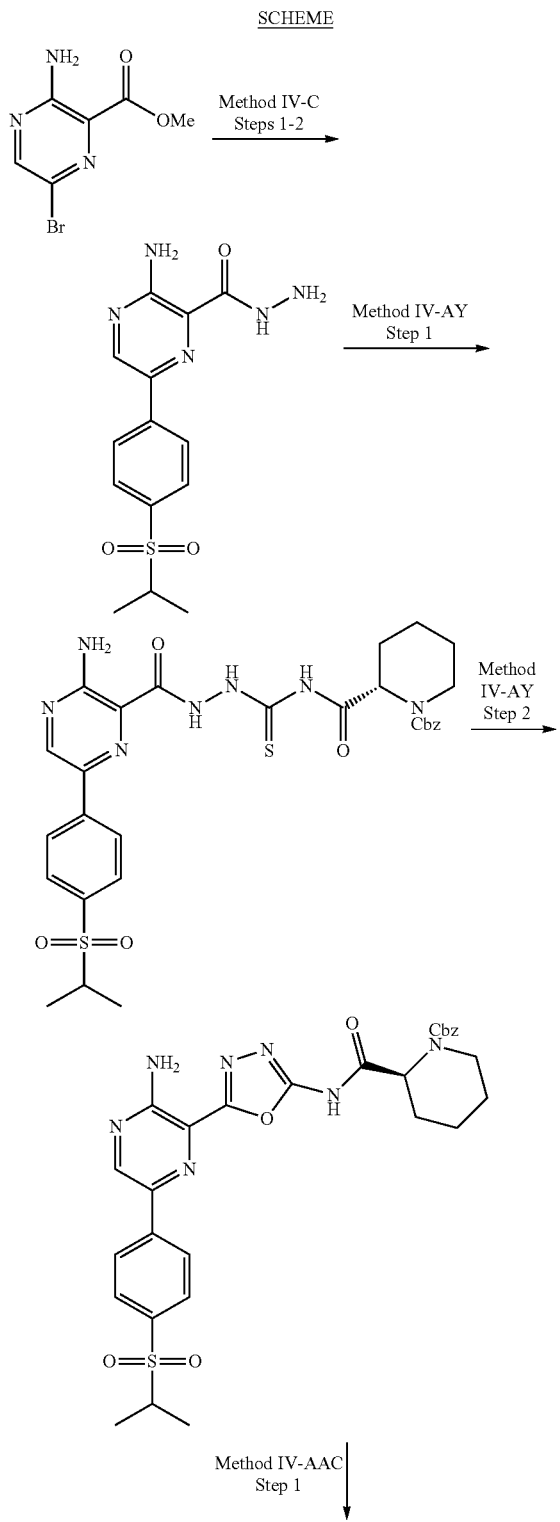

Method IV-AAC
Step 1

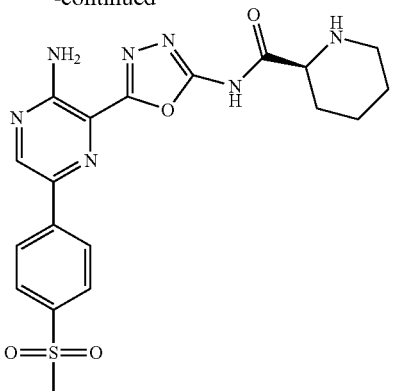

Compound IA-211

Compound IA-211 was prepared using Method IV-C, Steps 1-2, followed by Method IV-AY, Steps 1-2, followed by Method IV-AAC, Step 1.

Method IV-AAC

Step 1: (2S)-N-[5-[3-amino-6-(4-isopropylsulfonyl-phenyl)pyrazin-2-yl]-1,3,4-oxadiazol-2-yl]piperidine-2-carboxamide Pd on C, wet, degussa (50 mg) was added to a stirred solution of (S)-benzyl 2-(5-(3-amino-6-(4-(isopropylsulfonyl)phenyl)pyrazin-2-yl)-1,3,4-oxadiazol-2-ylcarbamoyl)piperidine-1-carboxylate (251 mg, 0.25 mmol) in MeOH (5 mL)/EtOAc (5 mL) and the reaction mixture was placed under an atmosphere of $H_2$. The reaction was stirred at ambient temperature for 17 hours. Once the reaction had gone to completion, the Pd was removed by filtration and the solvent was removed in vacuo. The material was purified by reverse phase preparative HPLC [Waters Sunfire C18, 10 μM, 100 Å column, gradient 10%-95% B (solvent A: 0.05% TFA in water; solvent B: CH3CN) over 16 minutes at 25 mL/min]. The fractions were collected and freeze-dried to give the product as a yellow solid (56.4 mg, 39%); 1H NMR (400.0 MHz, DMSO) d 1.19 (d, 6H), 1.38-1.49 (m, 2H), 1.51-1.61 (m, 1H), 1.80-1.83 (m, 1H), 1.89-1.92 (m, 1H), 2.09-2.11 (m, 1H), 3.01 (br s, 2H), 3.19-3.23 (m, 1H), 3.47-3.51 (m, 1H), 4.13 (d, 1H), 4.31 (br s, 1H), 7.81 (s, 2H), 7.91 (d, 2H), 8.52 (d, 2H), 9.06 (s, 1H) and 11.04 (br s, 1H) ppm; MS ($ES^+$) 472.3

The following compounds were all prepared using a method similar to the one described for Compound IA-211 above.

Compound IA-160 (1R,4S,6S)—N-[5-[3-amino-6-(4-isopropylsulfonylphenyl)pyrazin-2-yl]-1,3,4-oxadiazol-2-yl]-5-azabicyclo[2.2.1]heptane-6-carboxamide 1H NMR (400.0 MHz, DMSO) d 1.18 (d, 6H), 1.34-1.45 (m, 2H), 1.55-1.76 (m, 4H), 2.68 (br d, 1H), 3.44-3.52 (m, 1H), 3.64 (s, 0.6H), 3.76 (s, 0.4H), 4.25 (s, 0.6H), 4.33 (s, 0.4H), 7.88 (d, 1.2H), 7.90 (br s, 2H), 7.92 (d, 0.8H), 8.31 (d, 0.8H), 8.53 (d, 1.2H), 9.00 (d, 1H), 10.43 (s, 0.4H) and 10.86 (s, 0.6H) ppm; MS ($ES^+$) 484.3

Compound IA-217 (2S)-N-[5-[3-amino-6-(4-isopropylsulfonylphenyl)pyrazin-2-yl]-1,3,4-oxadiazol-2-yl]pyrrolidine-2-carboxamide 1H NMR (400.0 MHz, DMSO) d 1.18 (d, 6H), 1.67-1.72 (m, 1H), 2.04-2.21 (m, 2H), 3.00 (br s, 2H), 3.35-3.41 (m, 1H), 3.45-3.59 (m, 3H), 4.28-4.34 (m, 1H), 7.82 (br s, 2H), 7.88-7.92 (m, 2H), 8.44-8.53 (m, 2H), 9.00-9.01 (2×s, 1H) and 10.87 (s, 1H) ppm; MS ($ES^+$) 458.3

Example 57A
5-(4-isopropylsulfonylphenyl)-3-[3-[4-(methylamin-
omethyl)phenyl]isoxazol-5-yl]pyrazin-2-amine
(Compound IIA-7)
SCHEME
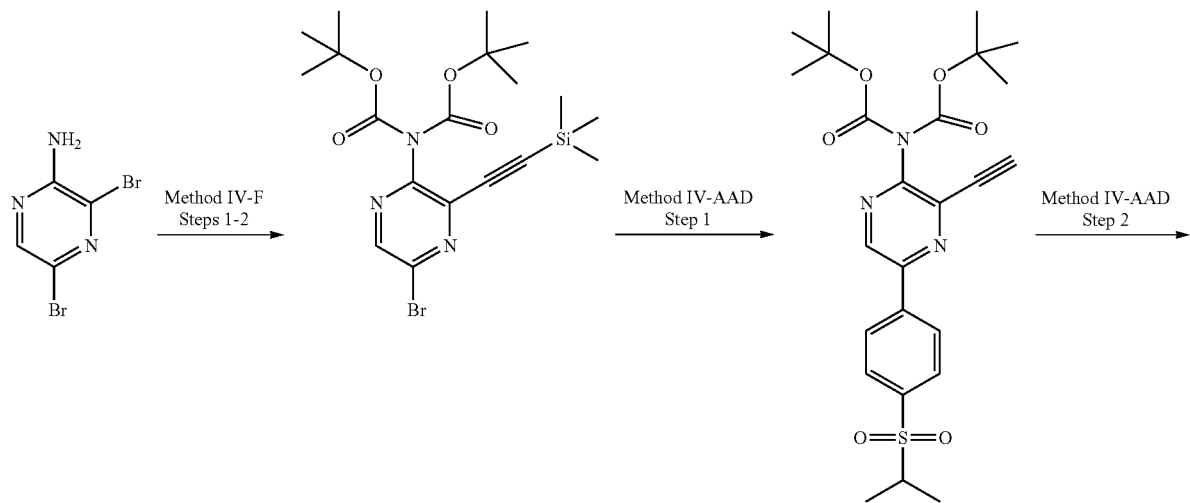
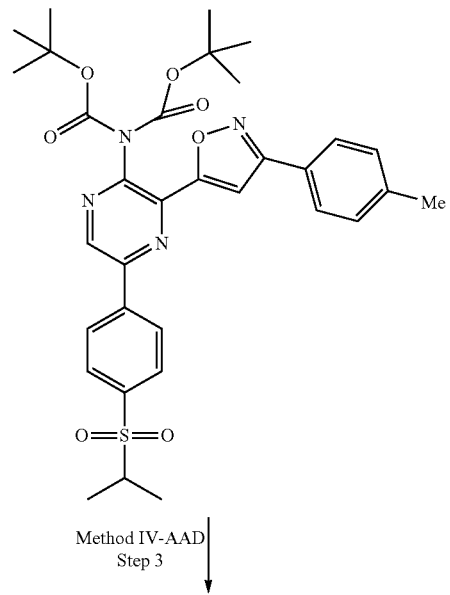

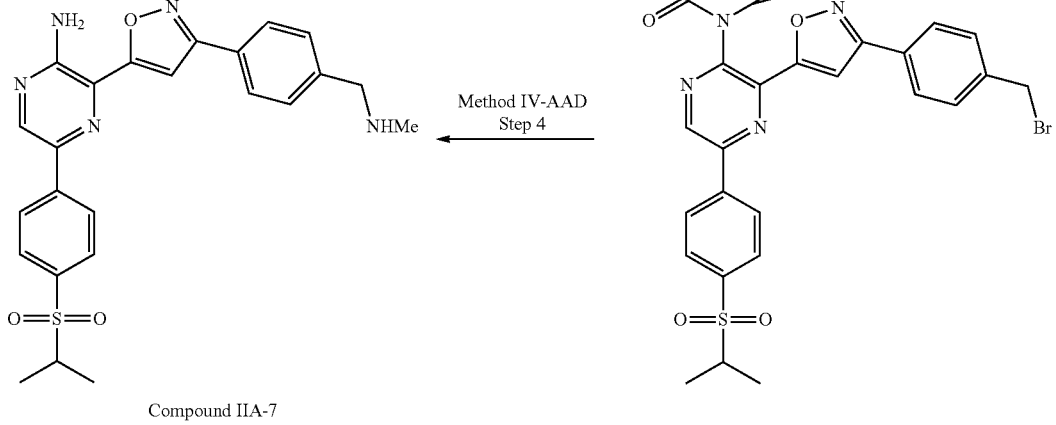

Compound IIA-7

Compound IIA-7 was prepared using Method IV-F, Steps 1-2, followed by Method IV-AAD, Steps 1-4.

Method IV-AAD

Step 1: tert-butyl N-(3-ethynyl-5-(4-(isopropylsulfonyl)phenyl)pyrazin-2-yl)N-tert-butoxycarbonyl-carbamate tert-butyl N-[5-bromo-3-(2-trimethylsilylethynyl)pyrazin-2-yl]-N-tert-butoxycarbonyl-carbamate (3 g, 6.377 mmol) and (4-isopropylsulfonylphenyl)boronic acid (1.491 g, 6.536 mmol) were dissolved in MeCN (60.00 mL) then treated with water (12.00 mL) and $K_3PO_4$ (2.706 g, 12.75 mmol) then degassed/flushed nitrogen (×5 cycles). Treated with Pd[P(tBu)$_3$]$_2$ (162.9 mg, 0.3188 mmol) and reflushed Vac/Nitrogen ×5. The resulting mixture was stirred at room temperature for 1 h. The reaction mixture was poured quickly into a mixture of ethyl acetate (500 mL), water (90 mL) and 1% aqueous sodium metabisulphite at 4° C., shaken well and the layer separated. The organic fraction was dried over MgSO$_4$, filtered and the filtrate was treated with 3-mercaptopropyl ethyl sulphide on silica (0.8 mmol/g) (1 g), pre-absorbed onto silica gel then purified by column chromatography on silica gel eluting with 30-40% EtOAc/petroleu ether. Product fractions were combined and concentrated in vacuo to leave the product as a yellow/brown viscous oil. Triturated with petroleum ether and some diethyl ether and a small amount of dichloromethane added. Left to stand at room temperature for 30 min and beige crystals formed, isolated by filtration to leave the product as a beige solid (1.95 g, 61%); 1H NMR (400 MHz, DMSO) d 1.20 (m, 6H), 1.39 (s, 18H), 3.50 (m, 1H), 5.01 (s, 1H), 8.03 (m, 2H), 8.46 (m, 2H) and 9.37 (s, 1H) ppm.

Step 2: tert-butyl N-[5-(4-(isopropylsulfonyl)phenyl)-3-(3-(4-methyl)phenylisoxazol-5-yl)pyrazin-2-yl]-N-tert-butoxycarbonyl-carbamate To a solution of tert-butyl N-tert-butoxycarbonyl-N-[3-ethynyl-5-(4-isopropylsulfonylphenyl)pyrazin-2-yl]carbamate (6.8 g, 13.56 mmol) and N-hydroxy-4-methyl-benzimidoyl chloride (2.706 g, 13.56 mmol) in THF (141.6 mL) at room temperature was added TEA (1.646 g, 2.267 mL, 16.27 mmol) dropwise over 10 min. The mixture was stirred at room temperature overnight then at 60° C. for 2 h. The reaction mixture was concentrated under reduced pressure, dissolved in CH$_2$Cl$_2$ (30 mL) and washed with brine (1×50 mL) and aqueous NaHCO$_3$ (1×50 mL). The organic extracts were dried over MgSO$_4$ then decanted onto a silica gel column (300 ml). Elution with 20% EtOAc/petroleum ether to give the product (7.1 g, 82%); 1H NMR (400 Mhz, DMSO) d 1.21 (m, 6H), 1.33 (s, 18H), 3.34 (s, 3H), 3.55 (m, 1H), 7.39 (m, 2H), 7.92 (m, 2H), 8.01 (s, 1H), 8.07 (m, 2H), 8.66 (m, 2H0 and 9.51 (s, 1H) ppm Step 3: tert-butyl N-[5-(4-(isopropylsulfonyl)phenyl)-3-(3-(4-bromomethyl)phenylisoxazol-5-yl)pyrazin-2-yl]-N-tert-butoxycarbonyl-carbamate tert-butyl N-tert-butoxycarbonyl-N-[5-(4-isopropylsulfonylphenyl)-3-[3-(p-tolyl)isoxazol-5-yl]pyrazin-2-yl]carbamate (1 g, 1.575 mmol) was dissolved in ethylacetate (10 mL) and NBS (364.5 mg, 2.048 mmol) and AIBN (25.86 mg, 0.1575 mmol) were added. The resulting mixture was heated to 75° C. and placed under a bright lamp for 1 h. After this time, the reaction mixture was concentrated in vacuo to an oil and this was used directly in the next stage without further purification Step 4: 5-(4-isopropylsulfonylphenyl)-3-[3-[4-(methylaminomethyl)phenyl]isoxazol-5-yl]pyrazin-2-amine tert-butyl N-[3-[3-[4-(bromomethyl)phenyl]isoxazol-5-yl]-5-(4-isopropylsulfonylphenyl)pyrazin-2-yl]-N-tert-butoxycarbonyl-carbamate (60 mg, 0.08408 mmol) was added to a solution of methylamine in ethanol solution (791.3 mg, 8.408 mmol) in ethanol (3 mL). The reaction mixture was stirred at room temperature for 1 h and then the solvent removed in vacuo to an oil. The oil was redissolved in CH$_2$Cl$_2$ (10 ml) and concentrated to an oil to remove any excess amine. The oil was taken up in CH$_2$Cl$_2$ (5 mL) and TFA (479.4 mg, 323.9 µL, 4.204 mmol) added. The mixture was stirred at room temperature for 1 h, and the reaction mixture concentrated in vacuo. The residue was purified by reverse phase preparative HPLC [Waters Sunfire C18, 10 μM, 100 Å column, gradient 10%-95% B (solvent A: 0.05% TFA in water; solvent B: CH₃CN) over 16 minutes at 25 mL/min]. The product fractions were passed through a bicarbonate cartridge and lypholised to give the title compound as a yellow solid (13.6 g, 28% yield); 1H NMR (400 MHz, DMSO) d 1.22 (d, 6H), 2.6-2.65 (m, 3H), 3.5-3.6 (m, 1H), 4.2-4.25 (m, 2H), 7.2-73 (br s, 2H), 7.65 (d, 2H), 7.82 (s, 1H), 7.85 (d, 2H), 8.1 (d, 2H), 8.4 (d, 2H), 8.85 (br s, 2H) and 8.92 (s, 1H) ppm; MS (ES⁺) 464.4

The following compounds were all prepared using a method similar to the one described for Compound IIA-7 above.

Compound IIA-4 2-(2-(4-(5-(3-amino-6-(4-(isopropylsulfonyl)phenyl)pyrazin-2-yl)isoxazol-3-yl)benzylamino)ethoxy)ethanol 1H NMR (400 MHz, DMSO) d 1.22 (d, 6H), 3.2-3.25 (m, 2H), 3.5-3.6 (m, 2H), 3.6-3.63 (m, 2H), 3.5-3.8 (m, 2H), 4.3-4.35 (m, 2H), 4.75 (br s, 1H), 7.2-73 (br s, 2H), 7.65 (d, 2H), 7.82 (s, 1H), 7.95 (d, 2H), 8.1 (d, 2H), 8.4 (d, 2H) and 8.9-9.05 (m, 3H) ppm; MS (ES⁺) 538.4

Compound IIA-5 3-[3-[4-(aminomethyl)phenyl]isoxazol-5-yl]-5-(4-isopropylsulfonylphenyl)pyrazin-2-amine 1H NMR (400 MHz, DMSO) d 1.22 (d, 6H), 3.5-3.6 (m, 1H), 4.2-4.25 (m, 2H), 7.2-73 (br s, 2H), 7.65 (d, 2H), 7.82 (s, 1H), 7.95 (d, 2H), 8.1 (d, 2H), 8.4 (d, 2H), 8.2 (br s, 2H) and 8.97 (s, 1H) ppm; MS (ES⁺) 450.4

Compound IIA-6 5-(4-(isopropylsulfonyl)phenyl)-3-(3-(4-((propylamino)methyl)phenyl)isoxazol-5-yl)pyrazin-2-amine 1H NMR (400 MHz, DMSO) d 0.95 (t, 3H), 1.22 (d, 6H), 1.6-1.7 (m, 2H), 2.9-3.0 (m, 2H), 3.5-3.6 (m, 1H), 4.2-4.25 (m, 2H), 7.2-73 (br s, 2H), 7.65 (d, 2H), 7.82 (s, 1H), 7.95 (d, 2H), 8.1 (d, 2H), 8.4 (d, 2H), 8.8 (br s, 2H) and 8.97 (s, 1H) ppm; MS (ES⁺) 492.4

Compound IIA-8 3-[3-[4-[(isopropylamino)methyl]phenyl]isoxazol-5-yl]-5-(4-isopropylsulfonylphenyl)pyrazin-2-amine 1H NMR (400 MHz, DMSO) d 1.2 (d, 6H), 1.3 (d, 6H), 3.5-3.6 (m, 1H), 4.2-4.25 (m, 2H), 7.2-73 (br s, 2H), 7.65 (d, 2H), 7.82 (s, 1H), 7.95 (d, 2H), 8.1 (d, 2H), 8.4 (d, 2H), 8.7 (br s, 2H) and 8.95 (s, 1H) ppm; MS (ES⁺) 492.4

Compound IIA-9 2-(4-(5-(3-amino-6-(4-(isopropylsulfonyl)phenyl)pyrazin-2-yl)isoxazol-3-yl)benzylamino)ethanol 1H NMR (400 MHz, DMSO) d 1.22 (d, 6H), 3.0-3.1 (m, 2H), 3.5-3.6 (m, 1H), 3.65-3.7 (m, 2H), 4.2-4.25 (m, 2H), 5.3 (br s, 1H), 7.2-73 (br s, 2H), 7.65 (d, 2H), 7.82 (s, 1H), 7.95 (d, 2H), 8.1 (d, 2H), 8.4 (d, 2H), 8.8 (br s, 2H) and 8.87 (s, 1H) ppm; MS (ES⁺) 494.3

Compound IIA-10 3-[3-[4-(ethylaminomethyl)phenyl]isoxazol-5-yl]-5-(4-isopropylsulfonylphenyl)pyrazin-2-amine 1H NMR (400 MHz, DMSO) d 1.22 (d, 6H), 1.25 (t, 3H), 3.0-3.1 (m, 2H), 3.5-3.6 (m, 1H), 4.2-4.25 (m, 2H), 7.2-73 (br s, 2H), 7.65 (d, 2H), 7.82 (s, 1H), 7.95 (d, 2H), 8.1 (d, 2H), 8.4 (d, 2H), 8.8 (br s, 2H) and 8.97 (s, 1H) ppm; MS (ES⁺) 478.4

Compound IIA-11 1-(4-(5-(3-amino-6-(4-(isopropylsulfonyl)phenyl)pyrazin-2-yl)isoxazol-3-yl)benzylamino)propan-2-ol 1H NMR (400 MHz, DMSO) d 1.05 (d, 3H), 1.22 (d, 6H), 3.0-3.1 (m, 2H), 2.65-2.7 (m, 1H), 2.8-2.85 (m, 1H), 3.5-3.6 (m, 1H), 3.8-3.85 (m, 1H), 4.2-4.25 (m, 2H), 5.3-5.33 (m, 1H), 7.2 (br s, 2H), 7.65 (d, 2H), 7.82 (s, 1H), 7.85 (d, 2H), 8.02 (d, 2H), 8.35 (d, 2H), 8.8 (br s, 2H) and 8.87 (s, 1H) ppm; MS (ES⁺) 508.4

Example 58A 5-(4-isopropylsulfonylphenyl)-3-[5-[4-[1-(methylamino)ethyl]phenyl]-1,3,4-oxadiazol-2-yl]pyrazin-2-amine (Compound IA-212)

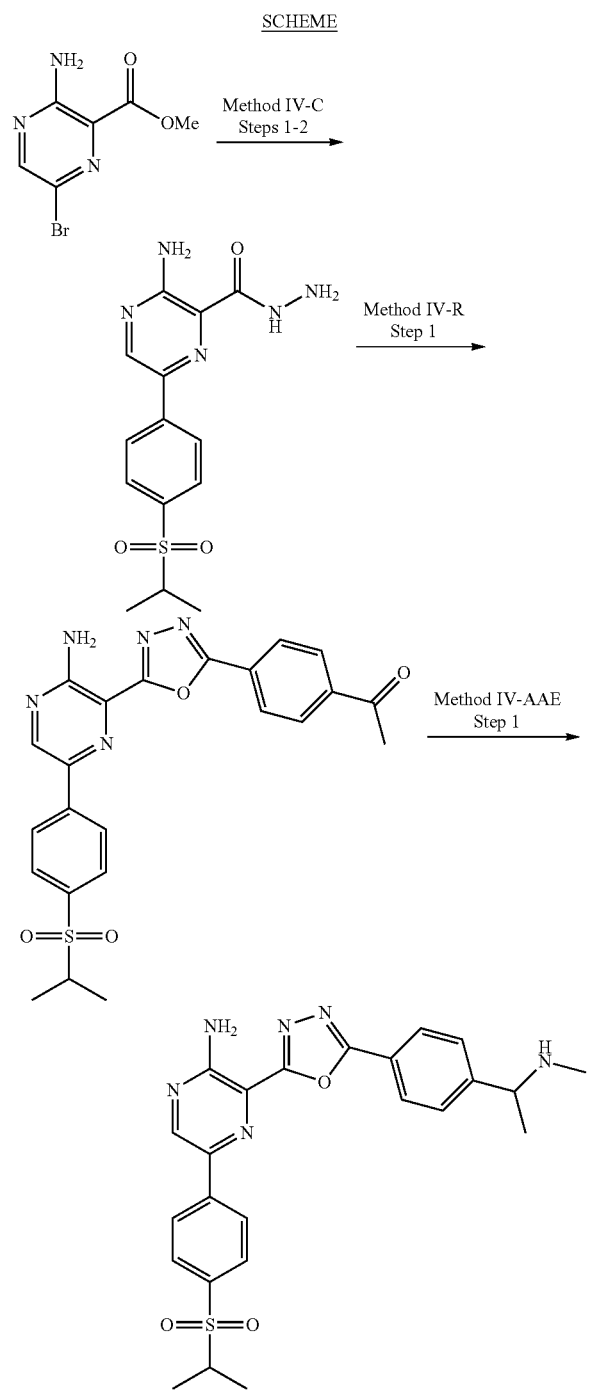

Compound IA-212

Compound IA-212 was prepared using Method IV-C, Steps 1-2, followed by Method IV-R, Step 1, followed by Method IV-AAE, Step 1.

Method IV-AAE

Step 1: 5-(4-isopropylsulfonylphenyl)-3-[5-[4-[1-(methylamino)ethyl]phenyl]-1,3,4-oxadiazol-2-yl]pyrazin-2-amine A mixture of 1-[4-[5-[3-amino-6-(4-isopropylsulfonylphenyl)pyrazin-2-yl]-1,3,4-oxadiazol-2-yl]phenyl]ethanone (130 mg, 0.2805 mmol), methylamine hydrochloride (37.88 mg, 0.5610 mmol), Ti(OiPr)$_4$ (159.4 mg, 165.5 µL, 0.5610 mmol) and triethylamine (56.77 mg, 78.20 µL, 0.5610 mmol) was stirred at room temperature in ethanol (2 mL) under nitrogen overnight. The reaction mixture was treated with sodium borohydride (15.92 mg, 16.85 µL, 0.4208 mmol) and stirred at room temperature over weekend and then was quenched with aqueous ammonia (1 mL conc in 4 mL water). The mixture was extracted with dichloromethane and the organic extracts dried over MgSO$_4$ and concentrated in vacuo. The residue was purified by reverse phase preparative HPLC [Waters Sunfire C18, 10 µM, 100 Å column, gradient 10%-95% B (solvent A: 0.05% TFA in water; solvent B: CH$_3$CN) over 16 minutes at 25 mL/min]. The product fractions were passed through a bicarbonate cartridge and concentrated in vacuo. The solid was triturated with acetonitrile to give the product as a pale yellow solid (27.0 mg, 22%); 1H NMR (400 MHz, DMSO) d 1.20 (d, 6H), 1.28 (d, 3H), 4.48 (m, 1H), 3.69 (q, 1H), 7.72 (d, 2H), 7.97 (d, 2H), 7.98 (v br s, 2H), 8.12 (d, 2H) and 9.07 (s, 1H) ppm; MS (ES$^+$) 479.3

Example 59A

5-(4-isopropylsulfonylphenyl)-3-[5-[2-methyl-4-(methylaminomethyl)phenyl]-1,3,4-oxadiazol-2-yl]pyrazin-2-amine (Compound IA-166)

SCHEME

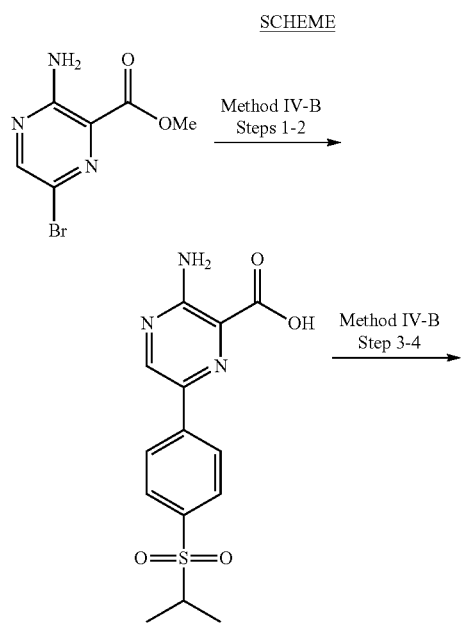

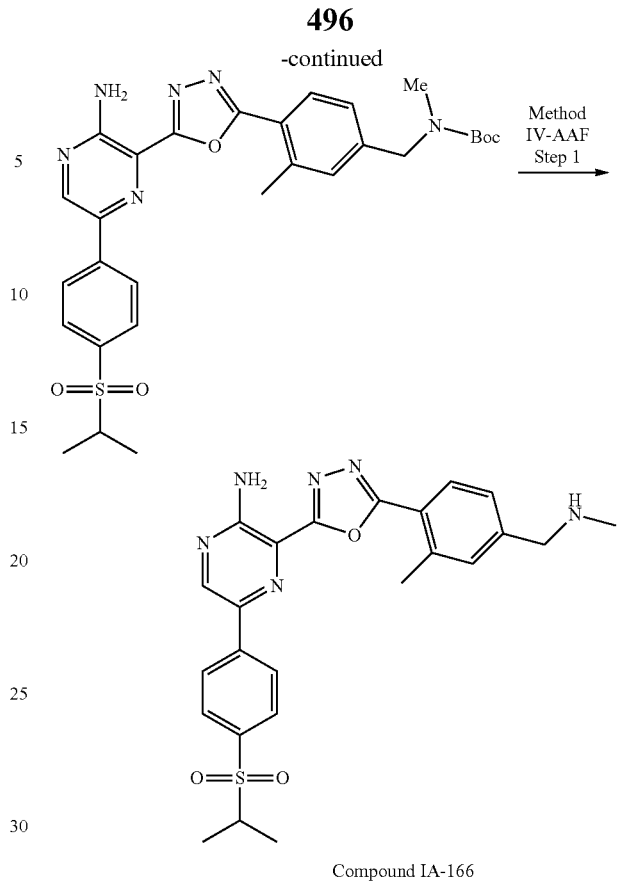

Compound IA-166

Compound IA-166 was prepared using Method IV-B, Steps 1-4, followed by Method IV-AAF, Step 1.

Method IV-AAF

Step 1: 5-(4-isopropylsulfonylphenyl)-3-[5-[2-methyl-4-(methylaminomethyl)phenyl]-1,3,4-oxadiazol-2-yl]pyrazin-2-amine To a solution of tert-butyl N-[[4-[5-[3-amino-6-(4-isopropylsulfonylphenyl)pyrazin-2-yl]-1,3,4-oxadiazol-2-yl]-3-methyl-phenyl]methyl]-N-methyl-carbamate (120 mg, 0.2074 mmol) in CH$_2$Cl$_2$ (10 mL) was added TFA (709.5 mg, 479.4 µL, 6.222 mmol) and the resulting solution stirred at room temperature for 1 h. The reaction mixture was concentrated in vacuo and redissolved in CH$_2$Cl$_2$ (20 ml) and concentrated. The residue was purified by reverse phase preparative HPLC [Waters Sunfire C18, 10 µM, 100 Å column, gradient 10%-95% B (solvent A: 0.05% TFA in water; solvent B: CH$_3$CN) over 16 minutes at 25 mL/min]. Product fractions were combined and lypholised to give the product as a yellow solid (48.0 mg, 39%); 1H NMR (400 MHz, DMSO) d 1.2 (d, 6H), 2.6 (s, 3H), 2.75 (s, 3H), 3.4-3.5 (m, 1H), 4.25 (s, 2H), 7.7 (d, 1H), 7.72 (s, 1H), 8.0-8.1 (m, 3H), 8.2 (d, 1H), 8.4 (d, 2H), 8.8 (br s, 2H) and 9.2 (s, 1H) ppm; MS (ES$^+$) 479.4

Example 60A

5-[3-amino-6-(4-isopropylsulfonylphenyl)pyrazin-2-yl]-1,3,4-oxadiazole-2-carboxylic Acid (Compound IA-128)

SCHEME

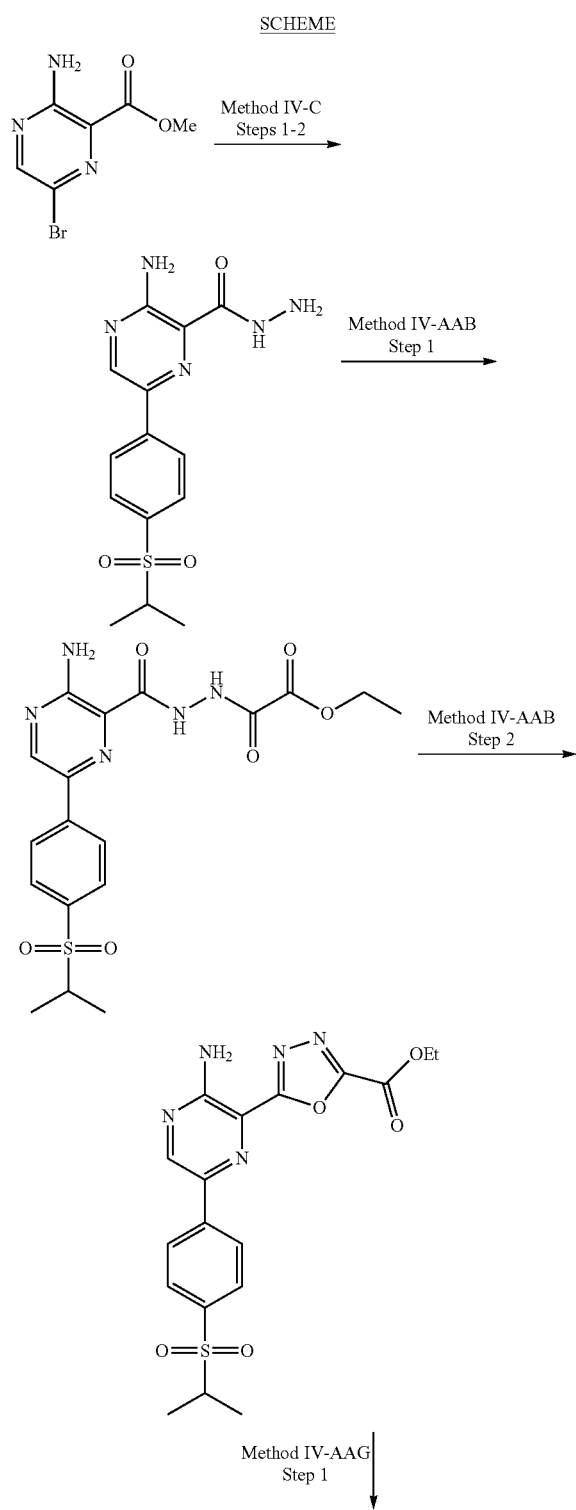

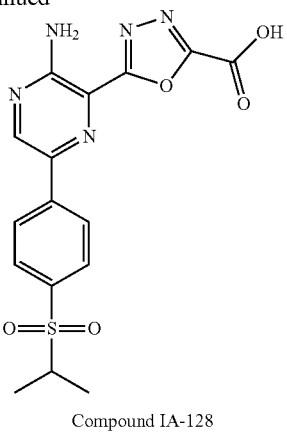

Compound IA-128

Compound IA-128 was prepared using Method IV-C, Steps 1-2, followed by Method IV-AAB, Steps 1-2, followed by Method IV-AAG, Step 1.

Method IV-AAG

Step 1: 5-[3-amino-6-(4-isopropylsulfonylphenyl)pyrazin-2-yl]-1,3,4-oxadiazole-2-carboxylic Acid A solution of ethyl 5-[3-amino-6-(4-isopropylsulfonylphenyl)pyrazin-2-yl]-1,3,4-oxadiazole-2-carboxylate (50 mg, 0.1198 mmol) in NaOH (59.90 μL of 1 M, 0.05990 mmol) was stirred at room temperature for 1 h. Water (0.5 mL) was added and the reaction mixture stirred at room temperature for 5 min and then filtered. The yellow solid obtained was dried under vacuum to give the product (30.93 mg, 62%); 1H NMR (400 MHz, DMSO) d 1.19 (d, 6H), 3.40-3.49 (m, 1H), 7.90 (br s, 2H), 7.96 (d, 2H), 8.32 (d, 2H) and 9.00 (s, 1H) ppm; MS (ES$^+$) 390.13

Example 61A 3-(5-ethynyl-1,3,4-oxadiazol-2-yl)-5-(4-isopropylsulfonylphenyl)pyrazin-2-amine (Compound IA-258)

SCHEME

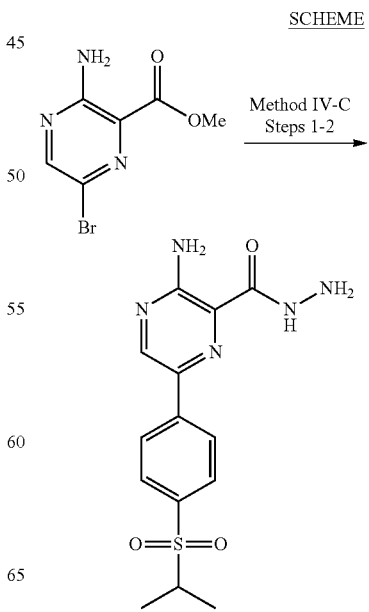

-continued

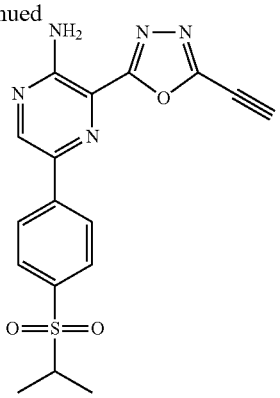

Compound IA-258

Compound IA-258 was prepared using Method IV-C, Steps 1-2, followed by Method IV-AAH, Step 1.

Method IV-AAH

Step 1: 3-(5-ethynyl-1,3,4-oxadiazol-2-yl)-5-(4-isopropylsulfonylphenyl)pyrazin-2-amine Dibromo(triphenyl)phosphorane (1.208 g, 2.862 mmol) was added to a suspension of 3-trimethylsilylprop-2-ynoic acid (84.8 mg, 0.60 mmol) and 3-amino-6-(4-(isopropylsulfonyl)phenyl)pyrazine-2-carbohydrazide (200 mg, 0.60 mmol) in acetonitrile (3.000 mL) at room temperature and the resulting solution stirred for 30 min. DIPEA (385.4 mg, 519.4 µL, 2.982 mmol) was then added and a precipitate quickly formed. The resulting mixture was stirred at room temperature for 1 h and was then filtered. The reaction mixture was concentrated in vacuo and the residue taken up in methanol (5 mL) and potassium carbonate (131.9 mg, 0.9541 mmol) added and the resulting solution stirred at room temperature overnight. The reaction mixture was diluted with ethyl acetate (5 mL) and water (5 mL) and the layers separated. The aqueous layer was extracted further with ethyl acetate (2×5 mL), dried over MgSO$_4$ and concentrated in vacuo. The material was purified by reverse phase preparative HPLC [Waters Sunfire C18, 10 µM, 100 Å column, gradient 10%-95% B (solvent A: 0.05% TFA in water; solvent B: CH$_3$CN) over 16 minutes at 25 mL/min]. Product fractions were freeze dried to leave the product as a yellow solid (56.1 mg, 27% yield); 1H NMR (400 MHz, DMSO) d 1.18 (m, 6H), 3.44 (m, 1H), 5.48 (s, 1H), 7.96 (m, 2H), 8.32 (m, 2H) and 9.08 (s, 1H) ppm; MS (ES$^+$) 370.14

Example 62A

2-[5-[3-amino-6-(4-isopropylsulfonylphenyl)pyrazin-2-yl]-1,3,4-oxadiazol-2-yl]acetic Acid (Compound IA-78)

SCHEME

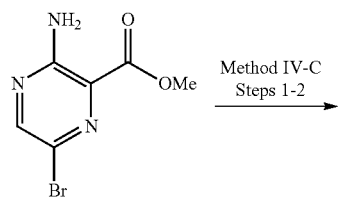 Method IV-C Steps 1-2

-continued

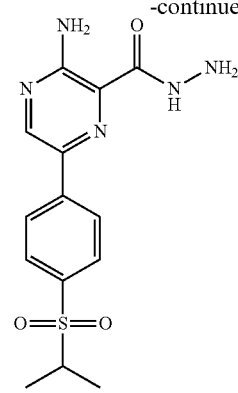

Method IV-X Steps 1-2

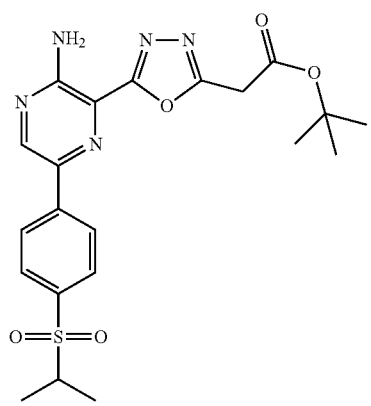

Method IV-AAI Step 1

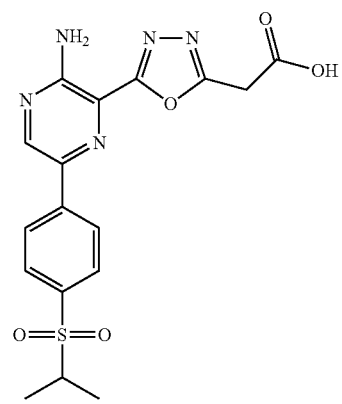

Compound IA-78

Compound IA-78 was prepared using Method IV-C, Steps 1-2, followed by Method IV-X, Steps 1-2, followed by Method IV-AAI, Step 1.

Method IV-AAI

Step 1: 2-[5-[3-amino-6-(4-isopropylsulfonylphenyl)pyrazin-2-yl]-1,3,4-oxadiazol-2-yl]acetic Acid TFA (500 µL, 6.490 mmol) was added to a stirred solution of tert-butyl 2-(5-(3-amino-6-(4-(isopropylsulfonyl)phenyl)pyrazin-2-yl)-1,3,4-oxadiazol-2-yl)acetate (45 mg, 0.083 mmol) in CH$_2$Cl$_2$ (5 mL) and the reaction stirred at ambient temperature for 18 h. The solvent was removed in vacuo and the residue azeotroped with CH₂Cl₂ (2×5 mL) and ether (2×5 mL). The material was purified by reverse phase preparative HPLC [Waters Sunfire C18, 10 μM, 100 Å column, gradient 10%-95% B (solvent A: 0.05% TFA in water; solvent B: CH₃CN) over 16 minutes at 25 mL/min]. The fractions were collected and freeze-dried to give the title compound as a yellow solid (16.7 mg, 49%); 1H NMR (400 MHz, DMSO) d 1.19 (d, 6H), 3.45 (m, 1H), 4.27 (s, 2H), 7.85 (br s, 2H), 7.96 (d, 2H), 8.30 (d, 2H), 9.04 (s, 1H) and 13.30 (s, 1H) ppm; MS (ES⁺) 404.2

Example 63A 5-(4-isopropylsulfonylphenyl)-3-[5-[2-methoxy-4-(methylaminomethyl)phenyl]-1,3,4-oxadiazol-2-yl]pyrazin-2-amine (Compound IA-171)

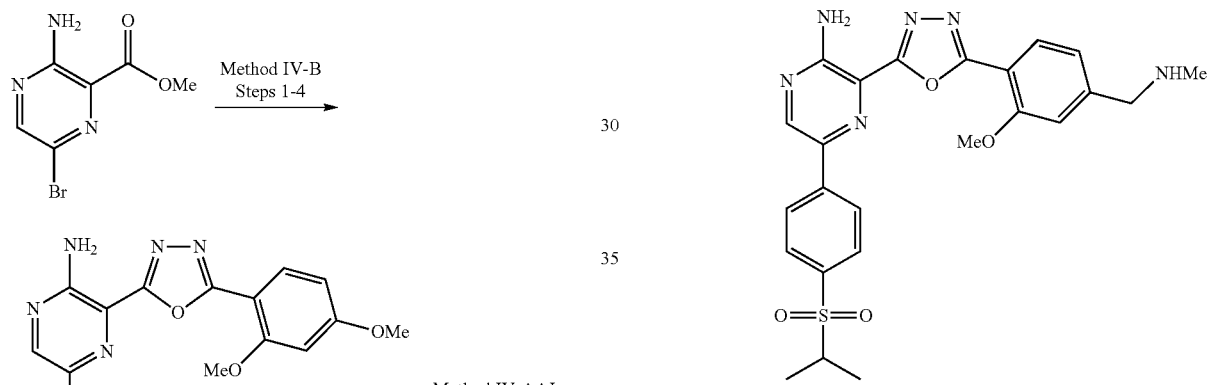

Compound IA-171 was prepared using Method IV-B, Steps 1-4, followed by Method IV-AAJ, Steps 1-3.

Method IV-AAJ

Step 1: di-tert-butyl(5-(4-(isopropylsulfonyl)phenyl)-3-(5-(2-methoxy-4-methylphenyl)-1,3,4-oxadiazol-2-yl)pyrazin-2-yl)iminodicarbonate Di-tert-butyldicarbonate (703.2 mg, 740.2 μL, 3.222 mmol) and DMAP (7.872 mg, 0.06444 mmol) were added to a suspension of 5-(4-isopropylsulfonylphenyl)-3-[5-(2-methoxy-4-methyl-phenyl)-1,3,4-oxadiazol-2-yl]pyrazin-2-amine (300 mg, 0.6444 mmol) in a mixture of acetonitrile (10 mL) and THF (10 mL). The reaction mixture was stirred at room temperature for 2 h and then heated at 50° C. for 2 h. The reaction mixture was cooled to room temperature and concentrated in vacuo. The residue was purified by column chromatography on silica eluting with 20% diethyl ether/petroleum ether. Product fractions were combined and concentrated in vacuo to leave the product (253 mg, 59%); MS (ES⁺) 666.31

Step 2: Di-tert-butyl(5-(4-(isopropylsulfonyl)phenyl)-3-(5-(2-methoxy-4-methylaminomethylphenyl)-1,3,4-oxadiazol-2-yl)pyrazin-2-yl)iminodicarbonate NBS (120.3 mg, 0.6760 mmol) and AIBN (17.08 mg, 0.1040 mmol) were added to a solution of tert-butyl N-tert-butoxycarbonyl-N-[5-(4-isopropylsulfonylphenyl)-3-[5-(2-methoxy-4-methyl-phenyl)-1,3,4-oxadiazol-2-yl]pyrazin-2-yl]carbamate (346.2 mg, 0.5200 mmol) in ethylacetate (40 mL). The resulting mixture was heated to reflux for 2 h while under a bright lamp. The reaction mixture was cooled to room temperature and added directly to methylamine in ethanol (2.447 g, 26.00 mmol) at room temperature. The reaction mixture was stirred at room temperature for 30 min and then concentrated in vacuo to leave an oil. The oil was redissolved in $CH_2Cl_2$ (50 ml) and concentrated in vacuo to remove any excess amine. The product was purified by column chromatography on silica eluting with 5% MeOH/$CH_2Cl_2$. Product fractions were combined and concentrated in vacuo to leave the product as a yellow oil. (148 mg, 41%)

Step 3: 5-(4-isopropylsulfonylphenyl)-3-[5-[2-methoxy-4-(methylaminomethyl)phenyl]-1,3,4-oxadiazol-2-yl]pyrazin-2-amine TFA (393.7 mg, 266.0 µL, 3.453 mmol) was added to a solution of tert-butyl N-tert-butoxycarbonyl-N-[5-(4-isopropylsulfonylphenyl)-3-[5-[2-methoxy-4-(methylaminomethyl)phenyl]-1,3,4-oxadiazol-2-yl]pyrazin-2-yl]carbamate (80 mg, 0.1151 mmol) $CH_2Cl_2$ (10 mL). The resulting mixture was stirred at room temperature for 1 h, and then concentrated in vacuo to leave an oil. The oil was re-dissolved in $CH_2Cl_2$ (10 ml), and evaporated to dryness. The residue was purified by reverse phase preparative HPLC [Waters Sunfire C18, 10 µM, 100 Å column, gradient 10%-95% B (solvent A: 0.05% TFA in water; solvent B: $CH_3CN$) over 16 minutes at 25 mL/min]. The fractions were collected and freeze-dried to give the title compound as a yellow solid (27.1 mg, 39%); 1H NMR (400 MHz, DMSO) d 1.3 (d, 6H), 2.65-2.7 (m, 3H), 3.4-3.5 (m, 1H), 4.0 (s, 3H), 4.25-4.3 (m, 2H), 7.25 (d, 1H), 7.5 (s, 1H), 8.0 (d, 2H), 8.1 (d, 1H), 8.38 (d, 2H), 8.92 (br s, 2H) and 9.1 (s, 1H) ppm; MS (ES$^+$) 495.3

Example 64A 5-(2-fluoro-4-isopropylsulfonyl-phenyl)-3-[5-[4-(methylaminomethyl)phenyl]-1,3,4-oxadiazol-2-yl]pyrazin-2-amine (Compound IA-292)

SCHEME

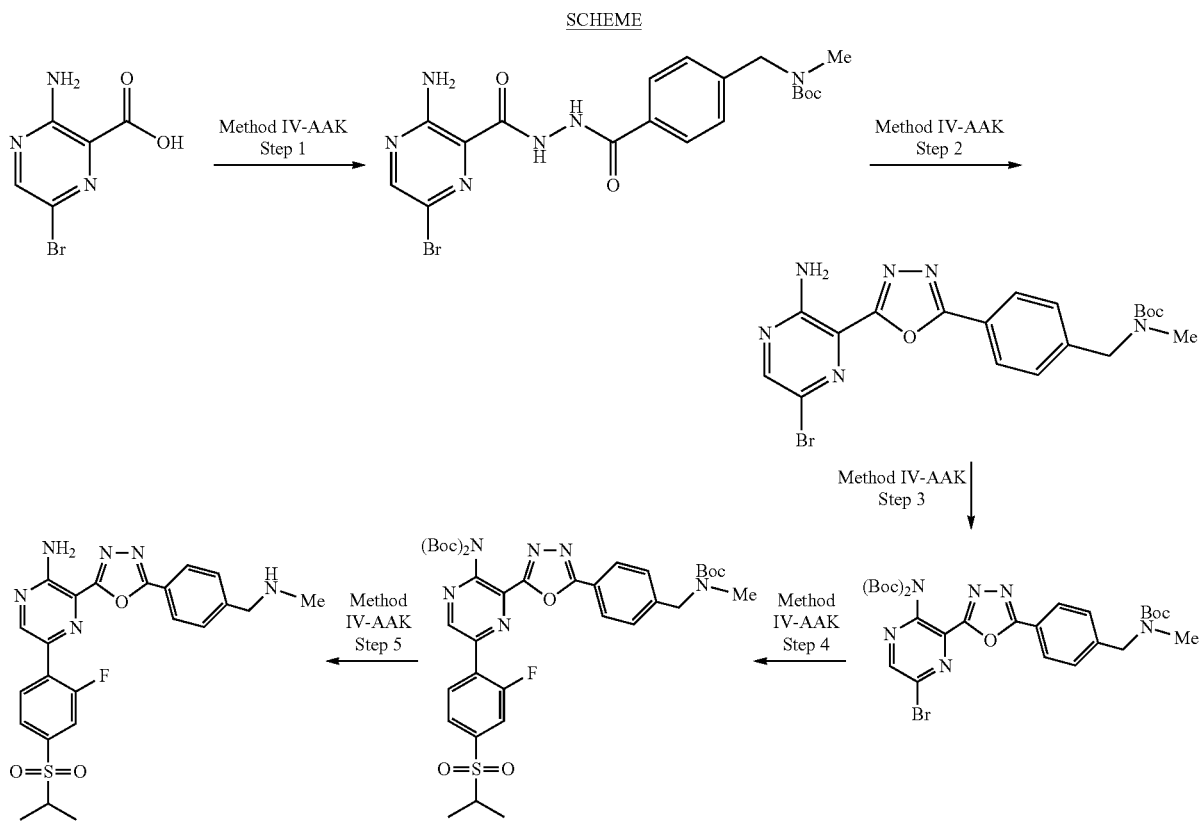

Compound
IA-292

Compound IA-292 was prepared using Method IV-AAK, Steps 1-5.

Method IV-AAK

Step 1: tert-butyl 4-(2-(3-amino-6-bromopyrazine-2-carbonyl)hydrazinecarbonyl)benzyl(methyl)carbamate To a solution of tert-butyl N-[[4-(hydrazinecarbonyl)phenyl]methyl]-N-methyl-carbamate (1 g, 3.580 mmol) in DMF (7.769 mL) and 2-amino-5-bromo-pyridine-3-carboxylic acid (776.9 mg, 3.580 mmol) was added triethylamine (724.5 mg, 997.9 µL, 7.160 mmol) followed by TBTU (1.724 g, 5.370 mmol). The resulting mixture was stirred at room temperature for 48 h. The reaction mixture was diluted with ethyl acetate (20 mL) and water (20 mL) and the layers separated. The aqueous layer was extracted further with ethyl acetate (2×20 mL) and combined organic extracts washed with saturated aqueous sodium hydrogen carbonate solution (1×20 mL), brine (1×20 mL), dried over $MgSO_4$ and concentrated in vacuo. The residue was triturated with $CH_2Cl_2$ to give the product as a white solid (1.71 g, 58% yield); 1H NMR (400.0 MHz, DMSO) d 1.39-1.45 (m, 9H), 2.80 (s, 3H), 4.45 (s, 2H), 4.45 (s, 2H), 7.28 (s, 2H), 7.35 (d, 2H), 7.90 (d, 2H), 8.20 (d, 2H), 8.24 (d, 1H), 10.50 (s, 1H) and 10.54 (s, 1H) ppm; MS ($ES^+$) 480.16

Step 2: tert-butyl 4-(5-(3-amino-6-bromopyrazin-2-yl)-1,3,4-oxadiazol-2-yl)methyl)benzyl(methyl)carbamate To a solution of tert-butyl N-[[4-[[(2-amino-5-bromo-pyridine-3-carbonyl)amino]carbamoyl]phenyl]methyl]-N-methyl-carbamate (992.3 mg, 2.074 mmol) in dry MeCN (14.88 mL) at 0° C. was added DIPEA (804.2 mg, 1.084 mL, 6.222 mmol) followed by dibromo(triphenyl)phosphorane (1.185 g, 2.696 mmol) portionwise and the resulting mixture stirred at 0° C. for 1 h and then at room temperature overnight. The reaction mixture was evaporated to dryness and then purified by column chromatography using the ISCO column companion system (40 g column, 0-20% EtOAc/petroleum ether. Product fractions were combined and concentrated in vacuo to leave the product as a white solid (681.6 mg, 63% yield); 1H NMR (400.0 MHZ, DMSO) d 1.39-1.46 (d, 9H, 4.48 (d, 2H), 7.46 (d, 2H), 8.22 (d, 2H), 8.32 (d, 1H) and 8.49 (d, 1H) ppm; MS ($ES^+$) 462.12

Step 3: tert-butyl N-[[4-[5-[3-[bis(tert-butoxycarbonyl)amino]-6-bromo-pyrazin-2-yl]-1,3,4-oxadiazol-2-yl]phenyl]methyl]-N-methyl-carbamate Di-tert-butyl dicarbonate (1.306 g, 1.375 mL, 5.984 mmol) was added to a stirred solution of tert-butyl N-[[4-[5-(3-amino-6-bromo-pyrazin-2-yl)-1,3,4-oxadiazol-2-yl]phenyl]methyl]-N-methyl-carbamate (885 mg, 1.496 mmol) and DMAP (18.28 mg, 0.1496 mmol) in anhydrous THF (20 mL) at room temperature. The reaction was allowed to stir at room temperature for 18 h. Additional DIPEA (580.0 mg, 781.7 µL, 4.488 mmol) and di-tert-butyl dicarbonate (1.306 g, 1.375 mL, 5.984 mmol) were added and the reaction stirred at room temperature for a further 2 h. $CH_2Cl_2$ (10 mL) was added to aid solubility and the reaction stirred at room temperature overnight. The solvent was removed in vacuo and the residue purified by column chromatography (ISCO Companion, 40 g column, eluting with 0 to 50% EtOAc/Petroleum Ether, loaded in $CH_2Cl_2$) to give the product as an off-white solid (810 mg, 82% yield); 1H NMR (400.0 MHz, DMSO) d 1.26 (s, 18H), 1.37-1.45 (m, 9H), 2.85 (br s, 3H), 4.49 (s, 2H), 7.50 (d, 2H), 8.15 (d, 2H) and 8.95 (d, 2H) ppm Step 4: tert-butyl 4-(5-(3-bis(tert-butoxycarbonyl)amino-6-(2-fluoro-4-(isopropylsulfonyl)phenyl)pyrazin-2-yl)-1,3,4-oxadiazol-2-yl)benzyl(methyl)carbamate tert-butyl N-[[4-[5-[3-[bis(tert-butoxycarbonyl)amino]-6-bromo-pyrazin-2-yl]-1,3,4-oxadiazol-2-yl]phenyl]methyl]-N-methyl-carbamate (100 mg, 0.1512 mmol) was dissolved in DMF (1 mL) and 2-(2-fluoro-4-isopropylsulfonyl-phenyl)-4,4,5,5-tetramethyl-1,3,2-dioxaborolane (74.44 mg, 0.2268 mmol) and $Pd(PPh_3)_2Cl_2$ (6.254 mg, 0.01512 mmol) were added. $Na_2CO_3$ (226.8 µL of 2 M, 0.4536 mmol) was added and the reaction heated at 80° C. under an atmosphere of nitrogen for 1 h in a sealed tube. The reaction mixture was partitioned between EtOAc (5 mL) and water (5 mL) and the aqueous layer extracted with EtOAc (2×5 mL). The combined organic extracts were washed with water (3×5 mL), brine (2×5 mL), dried over $MgSO_4$, filtered and concentrated in vacuo. The residue was purified by column chromatography (ISCO Companion, 24 g column, eluting with 0 to 50% EtOAc/Petroleum Ether, loaded in $CH_2Cl_2$) to give the product as an off-white solid that was used without further purification (114.4 mg, 96% yield)

Step 5: 5-(2-fluoro-4-isopropylsulfonyl-phenyl)-3-[5-[4-(methylaminomethyl)phenyl]-1,3,4-oxadiazol-2-yl]pyrazin-2-amine TFA (1 mL, 12.98 mmol) was added to a solution of tert-butyl 4-(5-(3-bis(tert-butoxycarbonyl)amino-6-(2-fluoro-4-(isopropylsulfonyl)phenyl)pyrazin-2-yl)-1,3,4-oxadiazol-2-yl)benzyl(methyl)carbamate (114 mg, 0.1456 mmol) in $CH_2Cl_2$ (5 mL). The reaction was stirred at room temperature for 2 h. The solvent was removed in vacuo and the residue azeotroped with $CH_2Cl_2$ (×2) and ether (×2). The material was purified by reverse phase preparative HPLC [Waters Sunfire C18, 10 µM, 100 Å column, gradient 10%-95% B (solvent A: 0.05% TFA in water; solvent B: $CH_3CN$) over 16 minutes at 25 mL/min]. The product fractions were collected, passed through a sodium bicarbonate cartridge and freeze-dried to give the title compound as a yellow solid (43.5 mg, 62% yield); 1H NMR (400.0 MHz, DMSO) d 1.23 (d, 6H), 2.29 (s, 3H), 3.58 (m, 1H), 3.76 (s, 2H), 7.60 (d, 2H), 7.88 (d, 2H), 8.00 (br s, 2H), 8.10 (d, 2H), 8.32 (t, 1H) and 8.80 (s, 1H) ppm; MS ($ES^+$) 483.3

The following compounds were all prepared using a method similar to the one described for Compound IA-292 above. Additionally, compounds P1 to P72, P146 and P149 can also be made using a methodology similar to the one described in Method AAK.

Compound IA-290 5-[4-isopropylsulfonyl-3-(trifluoromethoxy)phenyl]-3-[5-[4-(methylaminomethyl)phenyl]-1,3,4-oxadiazol-2-yl]pyrazin-2-amine 1H NMR (400.0 MHz, DMSO) d 1.24 (d, 6H), 2.61 (s, 3H), 3.53 (sept, 1H), 4.24 (s, 2H), 7.76 (d, 2H), 8.08 (d, 1H), 8.19 (d, 2H), 8.35 (s, 1H), 8.41 (dd, 1H) and 9.17 (s, 1H) ppm; MS ($ES^+$) 549.2

Compound IA-293 5-(4-isopropylsulfonyl-2-methyl-phenyl)-3-[5-[4-(methylaminomethyl)phenyl]-1,3,4-oxadiazol-2-yl]pyrazin-2-amine 1H NMR (400.0 MHz, DMSO) d 1.22 (d, 6H), 2.28 (s, 3H), 2.58 (s, 3H), 3.48 (d, 1H), 3.74 (s, 2H), 7.58 (d, 2H), 7.81-7.85 (m, 4H), 8.05 (d, J=8.2 Hz, 2H) and 8.60 (s, 1H) ppm; MS (ES+) 479.3

Compound IA-294 5-(4-(cyclopentylsulfonyl)phenyl)-3-(5-(4-((methylamino)methyl)phenyl)-1,3,4-oxadiazol-2-yl)pyrazin-2-amine Compound IA-295 5-[5-amino-6-[5-[4-(methylaminomethyl)phenyl]-1,3,4-oxadiazol-2-yl]pyrazin-2-yl]-2-isopropylsulfonyl-benzonitrile 1H NMR (400.0 MHz, DMSO) d 1.28 (d, 6H), 2.30 (s, 3H), 3.63 (m, 1H), 3.77 (s, 2H), 7.62 (d, 2H), 8.13 (d, 2H), 8.22 (d, 1H), 8.71 (dd, 1H), 8.87 (s, 1H) and 9.19 (s, 1H) ppm; MS (ES+) 490.3

Compound IA-298 3-(5-(4-((methylamino)methyl)phenyl)-1,3,4-oxadiazol-2-yl)-5-(4-(1-methylpyrrolidin-3-ylsulfonyl)phenyl)pyrazin-2-amine Compound IA-300 5-(5-isopropylsulfonyl-2-pyridyl)-3-[5-[4-(methylaminomethyl)phenyl]-1,3,4-oxadiazol-2-yl]pyrazin-2-amine 1H NMR (400.0 MHz, DMSO) d 1.23 (d, 6H), 2.64 (s, 3H), 3.59 (m, 1H), 4.29 (s, 2H), 7.77 (d, 2H), 8.28 (d, 2H), 8.37-8.39 (m, 1H), 8.56 (d, 1H), 8.87 (br s, 2H), 9.05 (s, 1H) and 9.30 (s, 1H) ppm; MS (ES+) 466.2

Compound IA-303 5-(6-isopropylsulfonyl-3-pyridyl)-3-[5-[4-(methylaminomethyl)phenyl]-1,3,4-oxadiazol-2-yl]pyrazin-2-amine 1H NMR (400.0 MHz, DMSO) d 1.24 (d, 6H), 2.31 (s, 3H), 3.76 (m, 1H), 3.78 (s, 2H), 7.62 (d, 2H), 7.91 (br s, 2H), 8.14-8.20 (m, 3H), 8.81 (dd, 1H), 9.15 (s, 1H) and 9.54 (d, 1H) ppm; MS (ES+) 466.2

Compound IA-305 5-(3-chloro-4-isopropylsulfonyl-phenyl)-3-[5-[4-(methylaminomethyl)phenyl]-1,3,4-oxadiazol-2-yl]pyrazin-2-amine 1H NMR (400.0 MHz, DMSO) d 1.24 (d, 6H), 2.30 (s, 3H), 3.77 (s, 2H), 3.79 (m, 1H), 7.62 (d, 2H), 8.11-8.14 (m, 3H), 8.38 (dd, 1H), 8.44 (d, 1H) and 9.12 (s, 1H) ppm; MS (ES+) 499.3

Compound IA-312 5-(4-isopropylsulfonyl-3-methyl-phenyl)-3-[5-[4-(methylaminomethyl)phenyl]-1,3,4-oxadiazol-2-yl]pyrazin-2-amine 1H NMR (400.0 MHz, DMSO) d 1.20 (d, 6H), 2.33 (s, 3H), 2.74 (s, 3H), 3.50 (m, 1H), 3.82 (s, 2H), 7.64 (d, 2H), 7.96-7.98 (m, 1H), 8.14 (d, 2H), 8.20-8.23 (m, 2H) and 9.06 (s, 1H) ppm; MS (ES+) 479.3

Compound IA-314 5-(3-fluoro-4-isopropylsulfonyl-phenyl)-3-[5-[4-(methylaminomethyl)phenyl]-1,3,4-oxadiazol-2-yl]pyrazin-2-amine 1H NMR (400.0 MHz, DMSO) d 1.25 (d, 6H), 2.30 (s, 3H), 3.76 (s, 1H), 3.77 (s, 2H), 7.62 (d, 2H), 7.93-7.97 (m, 1H), 8.13 (d, 2H), 8.24 (s, 1H), 8.24 (dd, 1H) and 9.10 (s, 1H) ppm; MS (ES+) 483.2

Compound IA-316 5-(2-chloro-4-isopropylsulfonyl-phenyl)-3-[5-[4-(methylaminomethyl)phenyl]-1,3,4-oxadiazol-2-yl]pyrazin-2-amine 1H NMR (400.0 MHz, DMSO) d 1.24 (d, 6H), 2.28 (s, 3H), 3.63 (t, 1H), 3.74 (s, 2H), 7.58 (d, 2H), 7.99-8.07 (m, 5H) and 8.71 (s, 1H) ppm; MS (ES+) 499.2

Compound IA-322 5-[2-(difluoromethyl)-4-isopropylsulfonyl-phenyl]-3-[5-[4-(methylaminomethyl)phenyl]-1,3,4-oxadiazol-2-yl]pyrazin-2-amine 1H NMR (400.0 MHz, DMSO) d 1.23 (d, 6H), 2.28 (s, 3H), 3.55-3.65 (m, 1H), 3.75 (s, 2H), 7.59-7.62 (m, 3H), 8.06 (d, 2H), 8.16 (s, 2H), 8.20 (s, 1H) and 8.80 (s, 1H) ppm; MS (ES+) 515.3

Compound IA-326 5-(3-ethyl-4-isopropylsulfonyl-phenyl)-3-[5-[4-(methylaminomethyl)phenyl]-1,3,4-oxadiazol-2-yl]pyrazin-2-amine 1H NMR (400.0 MHz, DMSO) d 1.21 (d, 6H), 1.34 (t, 3H), 2.68 (t, 3H), 3.09 (m, 2H), 3.45 (m, 1H), 4.29 (s, 2H), 7.77 (d, 2H), 7.97 (d, 1H), 8.21-8.27 (m, 4H), 8.88 (s, 2H) and 9.11 (s, 1H) ppm; MS (ES+) 493.3

Compound IA-331 2-[5-amino-6-[5-[4-(methylaminomethyl)phenyl]-1,3,4-oxadiazol-2-yl]pyrazin-2-yl]-5-isopropylsulfonyl-benzonitrile 1H NMR (400.0 MHz, DMSO) d 1.23 (d, 6H), 2.29 (s, 3H), 3.66 (s, 1H), 3.75 (s, 2H), 7.60 (d, 2H), 8.13 (d, 2H), 8.24 (m, 1H), 8.38-8.42 (m, 2H) and 9.00 (s, 1H) ppm; MS (ES+) 490.1

Example 65A 5-(4-isopropylsulfonylphenyl)-3-[3-[2-methyl-4-(methylaminomethyl)phenyl]isoxazol-5-yl]pyrazin-2-amine (Compound IIA-12)

SCHEME

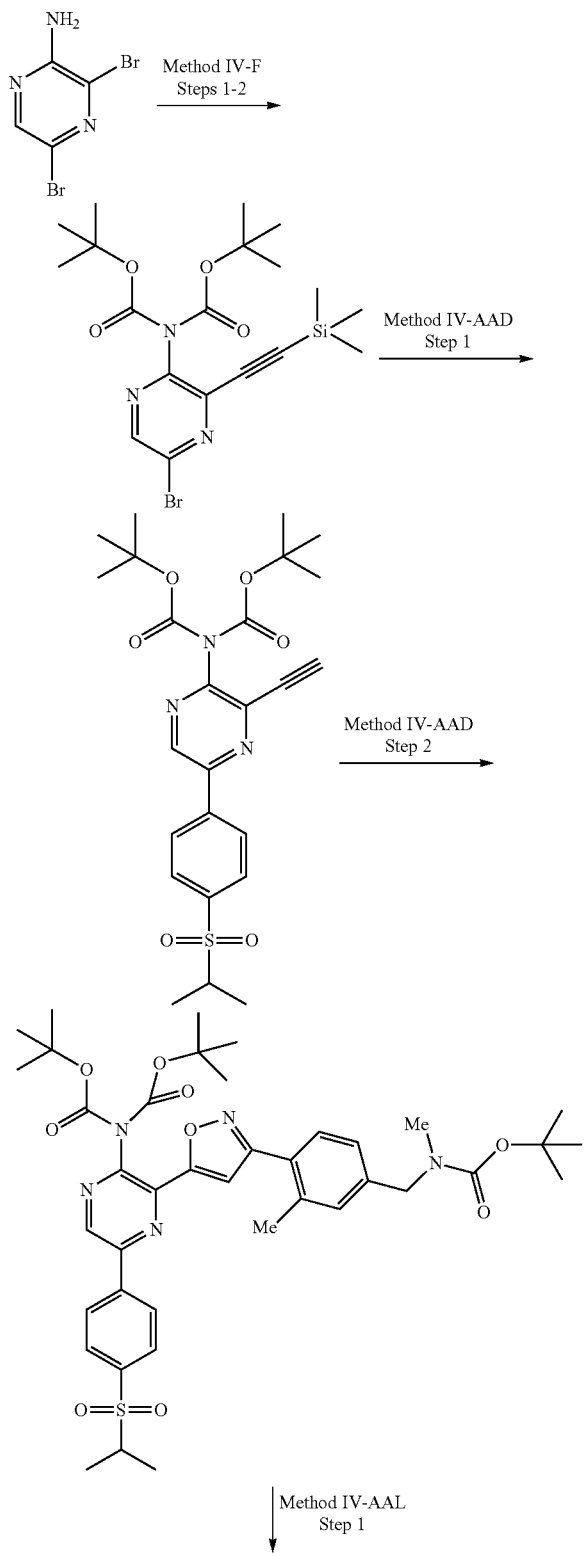

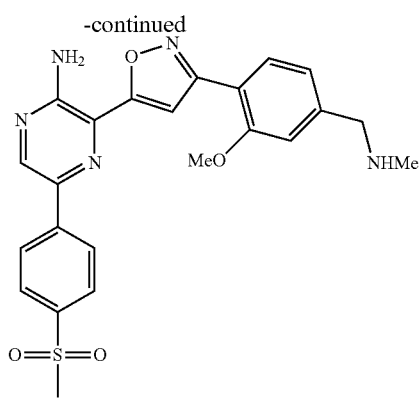

Compound IIA-12

Compound IIA-12 was prepared using Method IV-F, Steps 1-2, followed by Method IV-AAD, Steps 1-2, followed by Method IV-AAL, Step 1.

Method IV-AAL

Step 1: 5-(4-isopropylsulfonylphenyl)-3-[3-[2-methyl-4-(methylaminomethyl)phenyl]isoxazol-5-yl]pyrazin-2-amine TFA (556.9 mg, 376.3 μL, 4.884 mmol) was added to a solution of tert-butyl N-[[4-[5-[3-[bis(tert-butoxycarbonyl)amino]-6-(4-isopropylsulfonylphenyl)pyrazin-2-yl]isoxazol-3-yl]-3-methyl-phenyl]methyl]-N-methyl-carbamate (190 mg, 0.2442 mmol) in dichloromethane (4.750 mL) and the resulting yellow solution stirred overnight at room temperature. The reaction mixture was concentrated in vacuo and the residue taken up in methanol (2 mL) and dichloromethane (1 mL) and passed through an SCX cartridge and the product eluted with 2M ammonia in methanol and concentrated in vacuo. The filtrate was purified further by reverse phase preparative HPLC [Waters Sunfire C18, 10 μM, 100 Å column, gradient 10%-95% B (solvent A: 0.05% TFA in water; solvent B: CH$_3$CN) over 16 minutes at 25 mL/min]. The product fractions were collected and lypholised to give the product as a yellow solid (96.4 mg, 69% yield); 1H NMR (400.0 MHz, DMSO) d 1.18 (d, 6H), 2.61 (s, 3H), 2.62 (m, 3H), 3.48 (m, 1H), 4.20 (m, 2H), 7.24 (br s, 2H), 7.48-7.52 (m, 2H), 7.63 (s, 1H), 7.84 (m, 1H), 7.93 (m, 2H), 8.37 (m, 2H), 8.81 (br s, 2H) and 8.97 (s, 1H) ppm; MS (ES$^+$) 478.3

The following compounds were all prepared using a method similar to the one described for Compound IIA-12 above.

Compound IIA-13 3-[3-[3-chloro-4-(methylaminomethyl)phenyl]isoxazol-5-yl]-5-(4-isopropylsulfonylphenyl)pyrazin-2-amine 1H NMR (400.0 MHz, DMSO) d 1.19 (m, 6H), 2.71 (s, 3H), 3.48 (m, 1H), 4.37 (s, 2H), 7.24 (br s, 2H), 7.79 (m, 1H), 7.95 (m, 2H), 8.12 (m, 1H), 8.25 (m, 1H), 8.38 (m, 2H) and 8.98 (br s, 2H) ppm; MS (ES$^+$) 498.25

Compound IIA-14 3-[3-[2-fluoro-4-(methylaminomethyl)phenyl]isoxazol-5-yl]-5-(4-isopropylsulfonylphenyl)pyrazin-2-amine 1H NMR (400.0 MHz, DMSO) d 1.18 (m, 6H), 2.63 (m, 3H), 3.47 (m, 1H), 4.26 (m, 2H), 7.26 (br s, 2H), 7.51 (m, 1H), 7.60 (m, 1H), 7.65 (m, 1H), 7.94 (m, 2H), 8.13 (t, 1H), 8.36 (m, 2H), 8.88 (br s, 2H) amd 8.98 (s, 1H) ppm; MS (ES$^+$) 482.0

Compound IIA-15 3-[3-[2-chloro-4-(methylaminomethyl)phenyl]isoxazol-5-yl]-5-(4-isopropylsulfonylphenyl) pyrazin-2-amine 1H NMR (400.0 MHz, DMSO) d 1.18 (d, 6H), 2.63 (t, 3H), 3.49 (m, 1H), 4.26 (m, 2H), 7.25 (br s, 2H), 7.63-7.65 (m, 2H), 7.85 (m, 1H), 7.93 (m, 3H), 8.36 (m, 2H), 8.87 (br s, 2H) amd 8.98 (s, 1H) ppm; MS (ES$^+$) 498.2

Example 66A 5-(4-(ethylsulfonyl)phenyl)-3-(5-(3-((methylamino)methyl)phenyl)-1,3,4-oxadiazol-2-yl)pyrazin-2-amine (Compound IA-307)

SCHEME

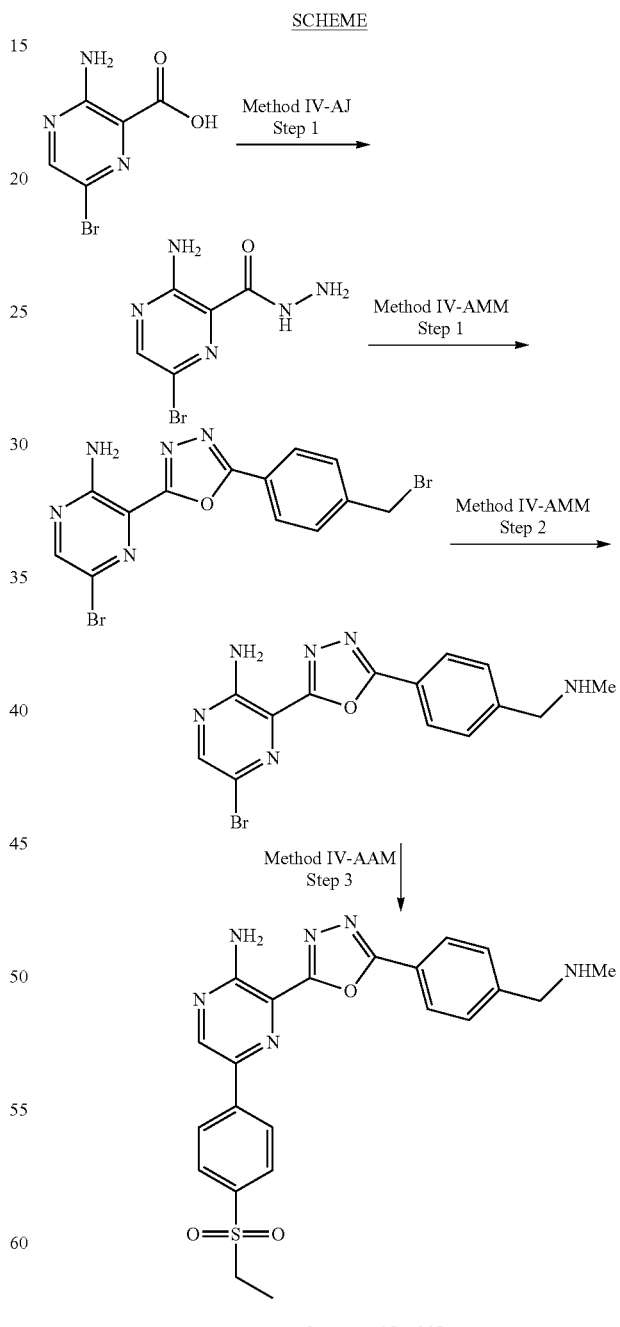

Compound IA-307

Compound IA-307 was prepared using Method IV-AJ, Step 1, followed by Method IV-AAM, Steps 1-3.

Method IV-AAM

Step 1: 5-bromo-3-(5-(4-(bromomethyl)phenyl)-1,3,4-oxadiazol-2-yl)pyrazin-2-amine Dibromo(triphenyl)phosphorane (37.29 g, 88.35 mmol) was added to a suspension of 4-(bromomethyl)benzoic acid (4.318 g, 20.08 mmol) and 3-amino-6-bromo-pyrazine-2-carbohydrazide (4.66 g, 20.08 mmol) in acetonitrile (143.4 mL). The resulting mixture was stirred at room temperature for 2 h and then Hunig's base (15.57 g, 20.98 mL, 120.5 mmol) was added and the reaction was stirred overnight. Exotherm observed during Hunig's base addition; moderated with ice bath (temp. kept around 20+/−4). The reaction mixture was filtered and the solid obtained washed with cold acetonitrile to leave the product as a yellow solid (5.45 g, 66.7% yield); 1H NMR (400.0 MHz, DMSO) d 4.82 (s, 2H), 7.72 (d, 2H), 7.80 (s, 1H), 8.11 (d, 2H) and 8.45 (s, 1H) ppm; MS (ES$^+$) 412.1.

Step 2: 5-bromo-3-(5-(4-((methylamino)methyl)phenyl)-1,3,4-oxadiazol-2-yl)pyrazin-2-amine 5-bromo-3-(5-(4-(bromomethyl)phenyl)-1,3,4-oxadiazol-2-yl)pyrazin-2-amine (100 mg, 0.2433 mmol) and Na$_2$CO$_3$ (77.36 mg, 0.7299 mmol) were suspended in and treated with methylamine (182.4 µL of 2 M, 0.36 mmol). The reaction was heated at 60° C. for 10 min and then additional methylamine (426.0 µL of 2 M, 0.86 mmol) was then added and the reaction heated at 60° C. or another 10 min. The reaction was cooled, diluted with water (5 mL) and extracted into dichloromethane (3×5 mL). The organic layer was dried over Na$_2$SO$_4$, filtered and concentrated in vacuo to yield 5-bromo-3-[5-[4-(methylaminomethyl)phenyl]-1,3,4-oxadiazol-2-yl]pyrazin-2-amine (74.7 mg, 85.34% yield) as a yellow solid; MS (ES$^+$) 362.3

Step 3: 5-(4-(ethylsulfonyl)phenyl)-3-(5-(4-((methylamino)methyl)phenyl)-1,3,4-oxadiazol-2-yl)pyrazin-2-amine To a 0.5-2.0 mL microwave vial 5-bromo-3-[5-[4-(methylaminomethyl)phenyl]-1,3,4-oxadiazol-2-yl]pyrazin-2-amine (100 mg, 0.24 mmol), 4-(ethylsulfonyl)phenylboronic acid (56.72 mg, 0.265 mmol), dioxane (1 mL) and aqueous solution of Na$_2$CO$_3$ (361.3 µL of 2M solution, 0.72 mmol) were added. Palladium; triphenylphosphane (13.91 mg, 0.012 mmol) was then added and the vial sealed. The reaction mixture was heated in the microwave at 150° C. for 30 min. After this time the reaction mixture was diluted with DMSO (2 mL) and filtered before purification by reverse phase preparative HPLC [Waters Sunfire C18, 10 µM, 100 Å column, gradient 10%-95% B (solvent A: 0.05% TFA in water; solvent B: CH$_3$CN over 16 minutes at 25 mL/min]. The product fractions were collected and evaporated to dryness to give the product as a yellow solid (64.35 mg, 65% yield); 1H NMR (400.0 MHz, DMSO) d 1.14 (t, 3H), 2.64 (s, 3H), 3.33-3.39 (m, 2H), 4.29 (s, 2H), 7.77 (d, 2H), 8.02 (d, 2H), 8.26 (d, 2H), 8.41 (d, 2H), 8.93 (s, 2H) and 9.09 (s, 1H) ppm; MS (ES$^+$) 451.0

The following compounds were all prepared using a method similar to the one described for Compound IA-307 above.

Compound IA-289 5-[4-(2-dimethylaminoethylsulfonyl)phenyl]-3-[5-[4-(methylaminomethyl)phenyl]-1,3,4-oxadiazol-2-yl]pyrazin-2-amine MS (ES$^+$) 494.0

Compound IA-296 4-[5-amino-6-[5-[4-(methylaminomethyl)phenyl]-1,3,4-oxadiazol-2-yl]pyrazin-2-yl]-N,N-dimethyl-benzenesulfonamide 1H NMR (400.0 MHz, DMSO) d 2.64 (t, 3H), 2.67 (s, 6H), 4.28-4.30 (m, 2H), 7.76 (d, 2H), 7.88 (d, 2H), 8.26 (d, 2H), 8.40 (d, 2H), 8.92 (s, 2H) and 9.08 (s, 1H) ppm; MS (ES$^+$) 466.0

Compound IA-297 5-[4-(azetidin-1-ylsulfonyl)phenyl]-3-[5-[4-(methylaminomethyl)phenyl]-1,3,4-oxadiazol-2-yl]pyrazin-2-amine 1H NMR (400.0 MHz, DMSO) d 2.01 (td, 2H), 2.64 (s, 3H), 3.72 (t, 4H), 4.29 (s, 2H), 7.77 (d, 2H), 7.94 (d, 2H), 8.26 (d, 2H), 8.45 (d, 2H), 8.94 (s, 2H) and 9.10 (s, 1H) ppm; MS (ES$^+$) 478.0

Compound IA-301 3-[4-[5-amino-6-[5-[4-(methylaminomethyl)phenyl]-1,3,4-oxadiazol-2-yl]pyrazin-2-yl]phenyl]sulfonylpropan-1-ol 1H NMR (400.0 MHz, DMSO) d 1.71 (dd, 2H), 2.64 (s, 3H), 3.28-3.45 (m, 4H), 4.29 (s, 2H), 4.68 (s, 1H), 7.77 (d, 2H), 8.02 (d, 2H), 8.27 (d, 2H), 8.41 (d, 2H), 8.90 (s, 2H) and 9.09 (s, 1H) ppm; MS (ES$^+$) 481.0

Compound IA-302 3-[5-[4-(methylaminomethyl)phenyl]-1,3,4-oxadiazol-2-yl]-5-(4-tetrahydrofuran-3-ylsulfonylphenyl)pyrazin-2-amine 1H NMR (400.0 MHz, DMSO) d 2.14-2.20 (m, 2H), 2.64 (s, 3H), 3.66 (dd, 1H), 3.77 (dd, 1H), 3.86 (dd, 1H), 4.05 (dd, 1H), 4.23-4.26 (m, 1H), 4.29 (s, 2H), 7.77 (d, 2H), 8.05 (d, 2H), 8.26 (d, 2H), 8.42 (d, 2H), 8.94 (s, 2H) and 9.09 (s, 1H) ppm; MS (ES$^+$) 493.0

Compound IA-304 4-[5-amino-6-[5-[4-(methylaminomethyl)phenyl]-1,3,4-oxadiazol-2-yl]pyrazin-2-yl]-N-(2-hydroxyethyl)benzenesulfonamide 1H NMR (400.0 MHz, DMSO) d 2.63 (d, 3H), 2.84 (q, 2H), 3.39 (t, 2H), 4.29 (s, 2H), 7.74 (q, 1H), 7.78 (s, 2H), 7.93 (d, 2H), 8.26 (d, 2H), 8.34 (d, 2H), 8.99 (s, 2H) and 9.05 (s, 1H) ppm; MS (ES$^+$) 482.0

Compound IA-308 3-[5-[4-(methylaminomethyl)phenyl]-1,3,4-oxadiazol-2-yl]-5-[4-(oxetan-3-ylsulfonyl)phenyl]pyrazin-2-amine 1H NMR (400.0 MHz, DMSO) d 2.64 (s, 3H), 4.29 (s, 2H), 4.77-4.82 (m, 4H), 4.96 (s, 1H), 7.77 (d, 2H), 8.05 (d, 2H), 8.26 (d, 2H), 8.41-8.43 (m, 2H), 8.89 (s, 2H) and 9.09 (s, 1H) ppm; MS (ES$^+$) 479.0

Compound IA-310 3-[5-[4-(methylaminomethyl)phenyl]-1,3,4-oxadiazol-2-yl]-5-(4-propylsulfonylphenyl)pyrazin-2-amine 1H NMR (400.0 MHz, DMSO) d 0.94 (t, 3H), 1.60 (q, 2H), 2.64 (s, 3H), 3.32-3.36 (m, 1H), 4.29 (s, 2H), 7.77 (d, 2H), 8.02 (d, 2H), 8.26 (d, 2H), 8.39-8.41 (m, 2H), 8.95 (d, 2H) and 9.08 (s, 1H) ppm; MS (ES$^+$) 465.0

Compound IA-313 3-[5-[4-(methylaminomethyl)phenyl]-1,3,4-oxadiazol-2-yl]-5-(4-sec-butylsulfonylphenyl)pyrazin-2-amine 1H NMR (400.0 MHz, DMSO) d 0.94 (t, 3H), 1.19 (d, 3H), 1.32-1.40 (m, 1H), 1.89-1.83 (m, 1H), 2.28 (d, 3H), 3.26-3.31 (m, 1H), 3.76 (s, 2H), 7.61 (d, 2H), 7.98 (d, 2H), 8.12 (d, 2H), 8.40 (d, 2H) and 9.06 (s, 1H) ppm; MS (ES$^+$) 479.0

Compound IA-288 3-[5-[4-(methylaminomethyl)phenyl]-1,3,4-oxadiazol-2-yl]-5-(4-methylsulfonylphenyl)pyrazin-2-amine 1H NMR (400.0 MHz, DMSO) d 2.64 (s, 3H), 3.29 (s, 3H), 4.29 (s, 2H), 7.77 (d, 2H), 8.06 (d, 2H), 8.26 (d, 2H), 8.39-8.41 (m, 2H), 8.92 (s, 2H) and 9.09 (s, 1H) ppm; MS (ES$^+$) 437.0

Compound IA-323 3-[5-[4-(methylaminomethyl)phenyl]-1,3,4-oxadiazol-2-yl]-5-(4-tetrahydropyran-4-ylsulfonylphenyl)pyrazin-2-amine 1H NMR (400.0 MHz, DMSO) d 1.52-1.63 (m, 2H), 11.78 (d, 2H), 2.64 (s, 3H), 3.30 (dd, 2H), 3.57-3.64 (m, 1H), 3.92 (dd, 2H), 4.28-4.30 (m, 2H), 7.77 (d, 2H), 7.98 (d, 2H), 8.26 (d, 2H), 8.41-8.43 (m, 2H), 8.91 (s, 2H) and 9.01 (s, 1H) ppm; MS (ES$^+$) 507

Compound IA-324 5-[4-[2-(dimethylamino)-1-methyl-ethyl]sulfonylphenyl]-3-[5-[4-(methylaminomethyl)phenyl]-1,3,4-oxadiazol-2-yl]pyrazin-2-amine 1H NMR (400.0 MHz, DMSO) d 1.30 (d, 3H), 2.64 (s, 3H), 2.81 (s, 3H), 2.90 (s, 3H), 3.35 (s, 1H), 3.56 (s, 1H), 4.09 (s, 1H), 4.29 (s, 2H), 7.77 (d, 2H), 7.90-7.97 (m, 2H), 8.06 (d, 2H), 8.25 (d, 2H), 8.47 (d, 2H), 9.03 (s, 2H), 9.13 (s, 1H) and 9.65 (s, 1H) ppm; MS (ES+) 508

Compound IA-328 4-[4-[5-amino-6-[5-[2-fluoro-4-(methylaminomethyl)phenyl]-1,3,4-oxadiazol-2-yl]pyrazin-2-yl]phenyl]sulfonyl-2-methyl-pentan-2-ol MS (ES+) 541

Compound IA-332 3-[5-[2-fluoro-4-(methylaminomethyl)phenyl]-1,3,4-oxadiazol-2-yl]-5-[4-(3-methoxy-1-methyl-propyl)sulfonylphenyl]pyrazin-2-amine 1H NMR (400.0 MHz, DMSO) d 1.24 (d, 3H), 1.51-1.57 (m, 1H), 2.07-2.14 (m, 1H), 2.67 (s, 3H), 3.22 (s, 3H), 3.40-3.45 (m, 3H),), 4.33 (s, 2H), 7.62 (m, 1H), 7.72 (d, 1H), 8.02 (d, 2H), 8.31 (t, 1H), 8.40 (d, 2H), 9.06 (s, 2H) and 9.12 (s, 1H) ppm; MS (ES+) 528

Compound IA-338 3-[5-[2-fluoro-4-(methylaminomethyl)phenyl]-1,3,4-oxadiazol-2-yl]-5-(4-sec-butylsulfonyl-phenyl)pyrazin-2-amine MS (ES+) 497

Compound IA-344 3-[5-[2-fluoro-4-(methylaminomethyl)phenyl]-1,3,4-oxadiazol-2-yl]-5-(4-tetrahydropyran-4-ylsulfonylphenyl)pyrazin-2-amine 1H NMR (400.0 MHz, DMSO) d 1.52-1.63 (m, 2H), 1.77 (d, 2H), 2.64 (s, 3H), 3.30 (dd, 2H), 3.56-3.64 (m, 1H), 3.92 (dd, 2H), 4.31 (s, 2H), 7.60 (dd, 1H), 7.68-7.70 (m, 1H), 7.98 (d, 2H), 8.28 (t, 1H), 8.37-8.39 (m, 1H), 8.98 (s, 2H) and 9.09 (s, 1H) ppm; MS (ES+) 525

Compound IA-347 3-[5-[2-fluoro-4-(methylaminomethyl)phenyl]-1,3,4-oxadiazol-2-yl]-5-(4-tetrahydrofuran-3-ylsulfonylphenyl)pyrazin-2-amine 1H NMR (400.0 MHz, DMSO) d 2.13-2.20 (m, 2H), 2.64 (s, 3H), 3.66 (dd, 1H), 3.74-3.80 (m, 1H), 3.86 (m, 1H), 4.04 (m, 1H), 4.22-4.28 (m, 1H), 4.31 (s, 2H), 7.60 (dd, 1H), 7.69 (d, 1H), 8.05 (d, 2H), 8.29 (t, 1H), 8.38 (d, 2H), 8.96 (s, 2H) and 9.10 (s, 1H) ppm; MS (ES+) 511

Compound IA-330 5-[4-(3-methoxy-1-methyl-propyl)sulfonylphenyl]-3-[5-[4-(methylaminomethyl)phenyl]-1,3,4-oxadiazol-2-yl]pyrazin-2-amine MS (ES+) 509

Example 67A

2-[5-[3-amino-6-(4-isopropylsolfonylphenyl)pyrazin-2-yl]-1,3,4-oxadiazol-2-yl]-5-(methylaminomethyl)phenol (Compound IA-291)

SCHEME

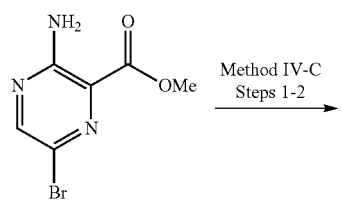

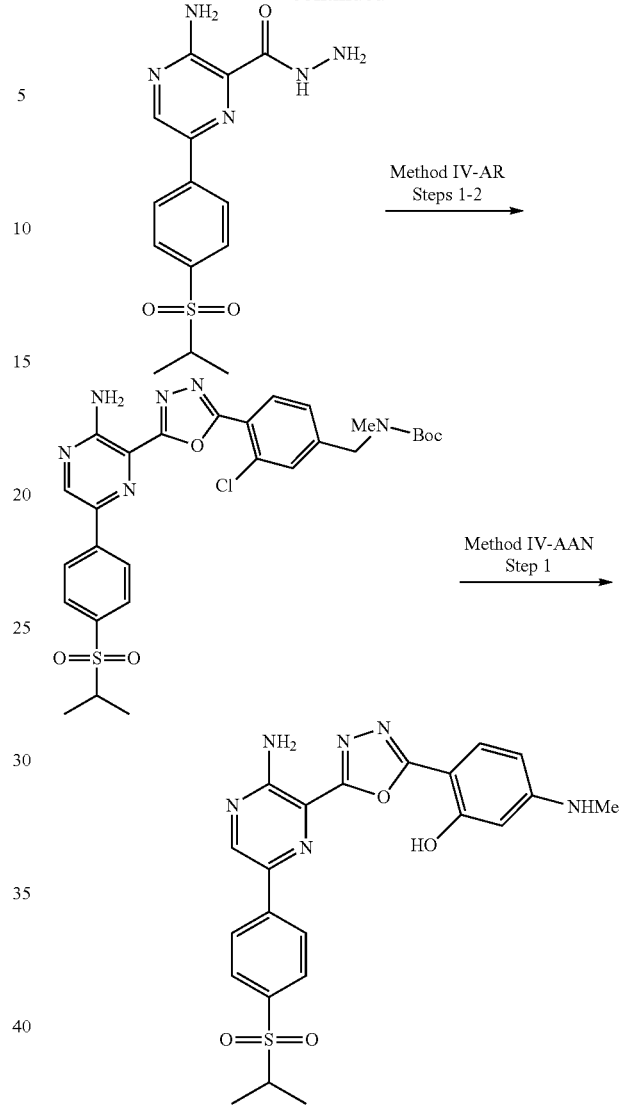

Compound IA-291

Compound IA-291 was prepared using Method IV-C, Steps 1-2, followed by Method IV-AR, Steps 1-2, followed by Method IV-AAN, Step 1.

Method IV-AAN

Step 1: 2-[5-[3-amino-6-(4-isopropylsulfonylphenyl)pyrazin-2-yl]-1,3,4-oxadiazol-2-yl]-5-(methylaminomethyl)phenol To a solution of tert-butyl N-[[4-[5-[3-amino-6-(4-isopropylsulfonylphenyl)pyrazin-2-yl]-1,3,4-oxadiazol-2-yl]-3-chloro-phenyl]methyl]-N-methyl-carbamate (130 mg, 0.2170 mmol) in dioxane (3 mL) was added of 1,5-diphenylpenta-1,4-dien-3-one; palladium (6.239 mg, 0.01085 mmol), di-tert-butyl-[2-(2,4,6-triisopropylphenyl)phenyl]phosphane (13.82 mg, 0.03255 mmol) and potassium hydroxide (434.0 µL of 1 M, 0.4340 mmol). The resulting mixture was heated to 100° C. for 2 h. Additional 1,5-diphenylpenta-1,4-dien-3-one; palladium (6.239 mg, 0.01085 mmol), ditert-butyl-[2-(2,4,6-triisopropylphenyl)phenyl]phosphane (13.82 mg, 0.03255 mmol) and potassium hydroxide (434.0 µL of 1 M, 0.4340 mmol) were added and the resulting mixture heated for a further 2 h at 100° C. The reaction mixture was evaporated to dryness and the residue purified by column chromatography on silica eluting with 20% EtOAc/petroleum ether. Product fractions were combined and concentrated in vacuo. This mixture was dissolved in DCM (10 mL) and TFA (247.4 mg, 167.2 µL, 2.170 mmol) added. The resulting mixture was stirred at room temperature for 1 h and then concentrated in vacuo to an oil. This was purified by reverse phase preparative HPLC [Waters Sunfire C18, 10 µM, 100 Å column, gradient 10%-95% B (solvent A: 0.05% TFA in water; solvent B: CH$_3$CN) over 16 minutes at 25 mL/min]. The product fractions were collected and lypholised to give the product as a yellow solid (24.0 mg, 18% yield); 1H NMR (400.0 MHz, DMSO) d 1.31 (m, 6H), 2.80 (s, 3H), 3.43 (m, 1H), 4.27 (s, 2H), 7.23 (m, 1H), 7.30 (m, 1H), 8.04 (m, 2H), 8.19 (m, 1H), 8.41 (m, 2H) and 8.95 (s, 1H) ppm; MS (ES$^+$) 481.2

The following compounds were all prepared using a method similar to the one described for Compound I-291 above.

Compound I-320 5-[5-[3-amino-6-(4-isopropylsulfonyl-phenyl)pyrazin-2-yl]-1,3,4-oxadiazol-2-yl]-2-(methylaminomethyl)phenol 1H NMR (400.0 MHz, DMSO) d 1.3 (d, 6H), 2.7 (s, 3H), 3.4-3.5 (m, 1H), 4.45 (s, 2H), 7.7 (d, 1H), 7.8-7.83 (m, 2H), 8.05 (d, 2H), 8.4 (d, 2H) and 8.95 (s, 1H) ppm; MS (ES$^+$) 481.2

Example 67A

2-[5-amino-6-(5-phenyl-1,3,4-thiadiazol-2-yl)pyrazin-2-yl]-5-(1,4-diazepane-1-carbonyl)benzonitrile (Compound IV-2)

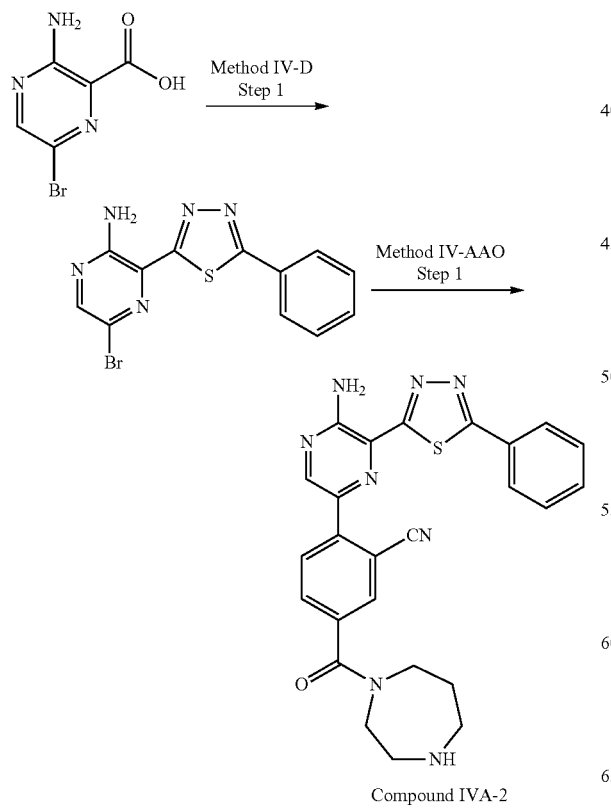

Compound IVA-2

Compound IVA-2 was prepared using Method IV-D, Step 1, followed by Method IV-AAO, Step 1.

Method IV-AAO

Step 1: 2-[5-amino-6-(5-phenyl-1,3,4-thiadiazol-2-yl)pyrazin-2-yl]-5-(1,4-diazepane-1-carbonyl)benzonitrile A mixture of methyl 4-bromo-3-cyano-benzoate (100 mg, 0.4166 mmol), potassium acetate (122.7 mg, 1.250 mmol), 4,4,5,5-tetramethyl-2-(4,4,5,5-tetramethyl-1,3,2-dioxaborolan-2-yl)-1,3,2-dioxaborolane (158.7 mg, 0.6249 mmol) and 1-cyclopenta-1,4-dienyl-diphenyl-phosphane; dichloromethane; dichloropalladium; iron (34.02 mg, 0.04166 mmol) was heated in dioxane (10 mL) at 80° C. for 2 h. After this time, the reaction mixture was cooled and palladium; triphenylphosphane (48.14 mg, 0.04166 mmol), sodium carbonate (625.0 µL of 2 M, 1.250 mmol) and 5-bromo-3-(5-phenyl-1,3,4-thiadiazol-2-yl)pyrazin-2-amine (139.2 mg, 0.4166 mmol) were added and heated at 140° C. under microwave conditions for 1 h. After cooling to room temperature, the resulting carboxylic acid was filtered off as brown solid. The solid was dissolved in DMF (3 mL) and 1,4-diazepane (208.3 mg, 2.083 mmol) and TBTU (267.5 mg, 0.8332 mmol) were added. The resulting mixture was stirred at room temperature for 2 h then diluted with ethyl acetate (5 mL), and the organic extract washed with water (1×5 mL) and brine (1×5 mL), dried over MgSO$_4$ and concentrated in vacuo to a solid. This solid was purified by reverse phase preparative HPLC [Waters Sunfire C18, 10 µM, 100 Å column, gradient 10%-95% B (solvent A: 0.05% TFA in water; solvent B: CH$_3$CN) over 16 minutes at 25 mL/min]. The product fractions were collected and lypholised to give the product as a yellow solid (60 mg, 25% yield); 1H NMR (400.0 MHz, DMSO) d 1.9-2.1 (m, 2H), 3.3-3.4 (m, 4H), 3.5-3.55 (m, 2H), 3.65-3.7 (m, 1H), 3.7-3.75 (m, 1H), 3.8-3.9 (m, 2H), 7.5-7.6 (m, 3H), 7.8 (d, 1H), 8.1-8.22 (m, 3H), 8.25 (br s, 1H), 8.75 (br s, 2H) and 8.8 (s, 1H) ppm; MS (ES$^+$) 483.2

The following compounds were all prepared using a method similar to the one described for Compound IVA-2 above.

Compound IVA-1 4-[5-amino-6-(5-phenyl-1,3,4-thiadiazol-2-yl)pyrazin-2-yl]-3-cyano-N,N-dimethyl-benzamide 1H NMR (400.0 MHz, DMSO) d 3.0 (d, 6H), 7.6-7.65 (m, 3H), 7.85 (d, 1H), 8.1-8.2 (m, 4H), 8.25 (br s, 1H) and 8.8 (s, 1H) ppm; MS (ES$^+$) 428.1

Example 68A

4-[5-amino-6-[5-(2-cyanoanilino)-1,3,4-thiadiazol-2-yl]pyrazin-2-yl]-N,N-dimethyl-benzamide (Compound IVA-3)

SCHEME

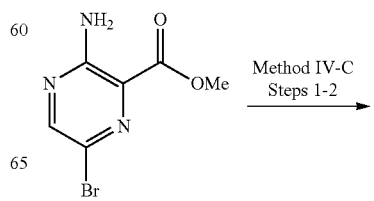

517
-continued

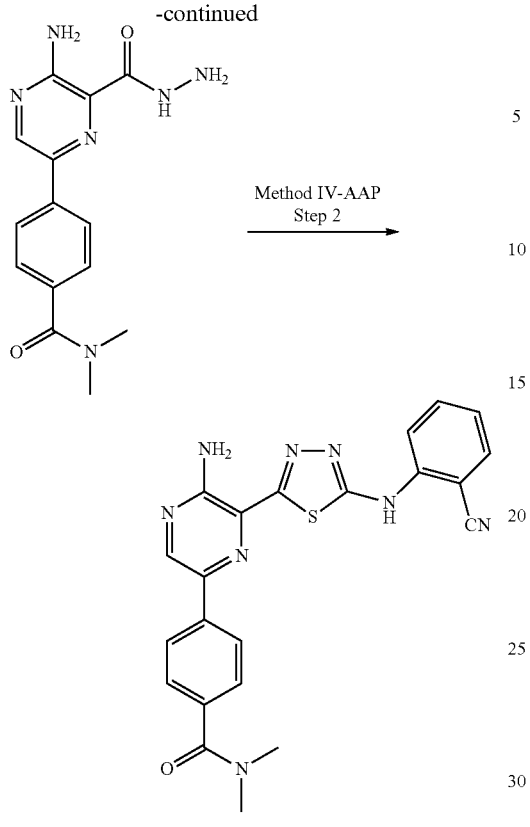

Compound IVA-3

Compound IVA-3 was prepared using Method IV-C, Steps 1-2, followed by Method IV-AAP, Step 1.

Method IV-AAP

Step 1: 2-[5-amino-6-(5-phenyl-1,3,4-thiadiazol-2-yl)pyrazin-2-yl]-5-(1,4-diazepane-1-carbonyl)benzonitrile A mixture of 4-(5-amino-6-(hydrazinecarbonyl)pyrazin-2-yl)-N,N-dimethylbenzamide (75 mg, 0.2373 mmol), 2-isothiocyanatobenzonitrile (38.01 mg, 0.2373 mmol) in $CH_2Cl_2$ (1.425 mL) was stirred at room temperature for 2 h. Ether was added and the reaction mixture filtered to give a yellow solid. This was taken up in anhydrous acetonitrile (1.5 mL) and then cooled in an ice bath. DIPEA (92.01 mg, 124.0 μL, 0.7119 mmol) was added, followed by portionwise addition of dibromo(triphenyl)phosphorane (130.2 mg, 0.3085 mmol). The resulting mixture was stirred at room temperature overnight and then heated under reflux for 1 h. The reaction mixture was cooled to room temperature and then filtered. The solid was washed further with acetonitrile (5 mL) and dried under vacuum to give the product as a bright yellow solid (68.0 mg, 62% yield); 1H NMR (400.0 MHz, DMSO) d 3.01 (d, 6H), 5.76 (s, 2H), 7.55-7.60 (m, 3H), 7.73 (d, 1H), 7.83-7.87 (m, 2H), 8.18 (d, 2H), 8.43-8.45 (m, 1H) and 8.91 (s, 1H) ppm; MS (ES+) 443.17

518
Example 69A

3-[3-[2-fluoro-4-(methylaminomethyl)phenyl]isoxazol-5-yl]-5-(4-tetrahydrofuran-3-ylsulfonylphenyl)pyrazin-2-amine (Compound IIA-16)

SCHEME

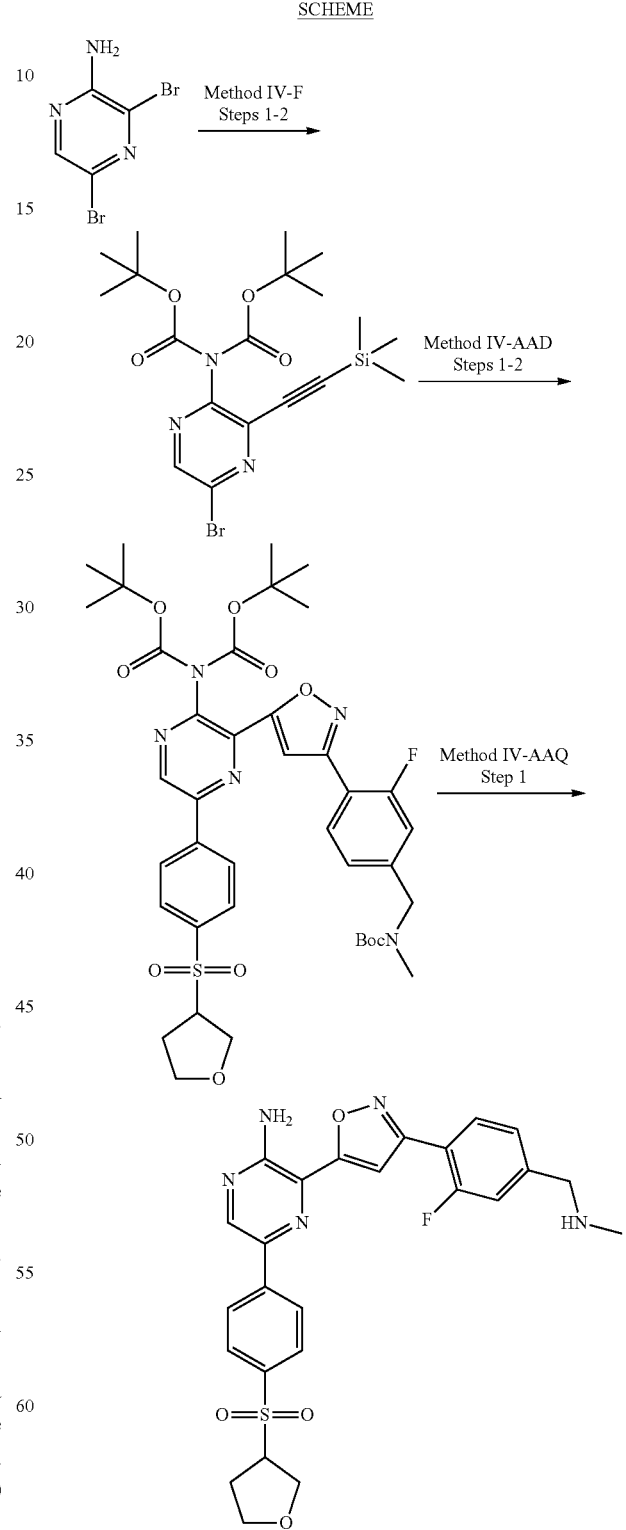

Compound IIA-16

Compound IIA-16 was prepared using Method IV-F, Steps 1-2, followed by Method IV-AAD, Steps 1-2, followed by Method IV-AAQ, Step 1.

Method IV-AAQ

Step 1: 3-[3-[2-fluoro-4-(methylaminomethyl)phenyl]isoxazol-5-yl]-5-(4-tetrahydrofuran-3-ylsulfonylphenyl)pyrazin-2-amine TFA (281.6 mg, 190.3 μL, 2.470 mmol) was added to a solution of tert-butyl N-[[4-[5-[3-[bis(tert-butoxycarbonyl)amino]-6-(4-tetrahydrofuran-3-ylsulfonylphenyl)pyrazin-2-yl]isoxazol-3-yl]-3-fluoro-phenyl]methyl]-N-methyl-carbamate (100 mg, 0.1235 mmol) in dichloromethane (2.069 mL) at room temperature and the resulting solution stirred for 2 h. The reaction mixture was concentrated in vacuo and purified by reverse phase preparative HPLC [Waters Sunfire C18, 10 μM, 100 Å column, gradient 10%-95% B (solvent A: 0.05% TFA in water; solvent B: CH₃CN) over 16 minutes at 25 mL/min]. The product fractions were collected and lypholised to give the product as a yellow solid (34.0 mg, 44% yield); 1H NMR (400.0 MHz, DMSO) d 2.13-2.19 (m, 2H), 2.63 (m, 3H), 3.66 (m, 1H), 3.76 (m, 1H), 3.85 (m, 1H), 4.04 (m, 1H), 4.21-4.28 (m, 3H), 7.27 (m, 2H), 7.52 (m, 1H), 7.60-7.65 (m, 2H), 8.00 (m, 2H), 8.12 (t, 1H), 8.36 (m, 2H) and 8.94 (m, 3H) ppm; MS (ES⁺) 510.2

Example 70A

3-[5-[4-[(1S)-1-amino-2,2,2-trifluoro-ethyl]phenyl]-1,3,4-oxadiazol-2-yl]-5-(4-isopropylsulfonylphenyl)pyrazin-2-amine (Compound IA-325)

SCHEME

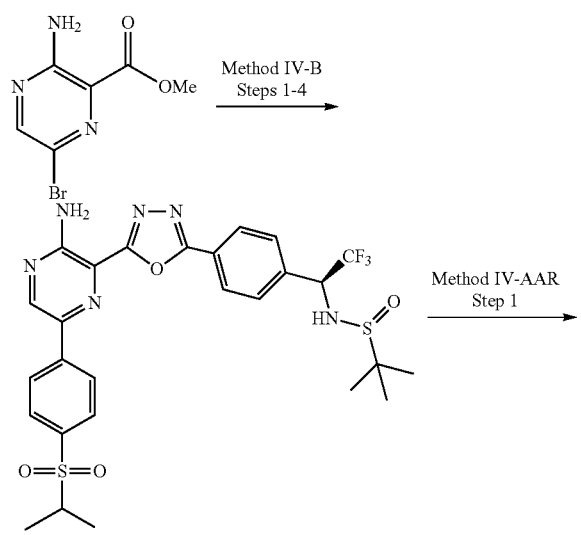

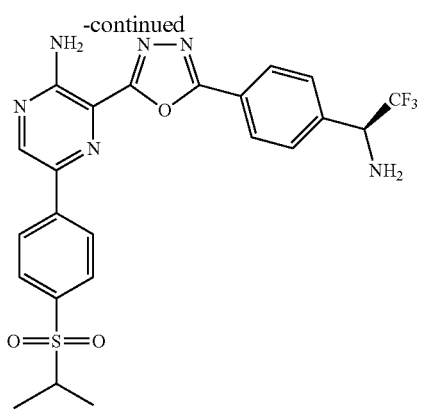

Compound IA-325

Compound IA-325 was prepared using Method IV-B, Steps 1-4, followed by Method IV-AAR, Step 1.

Method IV-AAR

Step 1: 3-[5-[4-[(1S)-1-amino-2,2,2-trifluoro-ethyl]phenyl]-1,3,4-oxadiazol-2-yl]-5-(4-isopropylsulfonylphenyl)pyrazin-2-amine HCl (35.27 μL of 3 M, 0.1058 mmol) was added to a solution of N-[(1S)-1-[4-[5-[3-amino-6-(4-isopropylsulfonylphenyl)pyrazin-2-yl]-1,3,4-oxadiazol-2-yl]phenyl]-2,2,2-trifluoro-ethyl]-2-methyl-propane-2-sulfinamide (253.3 mg, 0.05288 mmol) in MeOH (1 mL) and the resulting solution stirred at room temperature overnight. The reaction mixture was concentrated to dryness under reduced pressure and the residue triturated with acetonitrile and filtered. The solid was taken up in a mixture of acetonitrile/water/MeOH and passed through the bicarbonate cartridge. The eluent was concentrated in vacuo and then triturated with acetonitrile to give the product as a yellow solid (26 mg, 99% yield); 1H NMR (400.0 MHz, DMSO) d 1.20 (d, 6H), 2.68 (d, 2H), 3.41-3.51 (m, 1H), 4.65-4.75 (m, 1H), 7.81 (d, 2H), 7.98 (d, 2H), 8.20 (d, 2H), 8.41 (d, 2H) and 9.08 (s, 1H) ppm; MS (ES⁺) 519.1

Example 71A

5-[4-[2-(dimethylamino)-1-methyl-ethyl]sulfonylphenyl]-3-[5-(2-fluorophenyl)-1,3,4-oxadiazol-2-yl]pyrazin-2-amine (Compound IA-337)

SCHEME

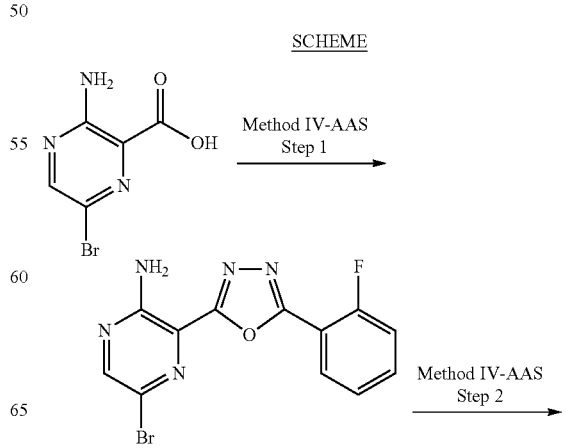

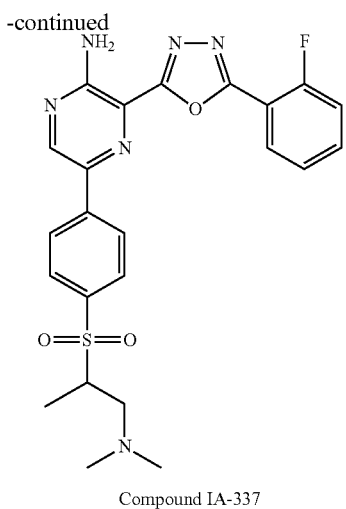

Compound IA-337

Compound IA-337 was prepared using Method IV-AAS, Steps 1-2.

Method IV-AAS

Step 1: 5-bromo-3-(5-(2-fluorophenyl)-1,3,4-oxadiazol-2-yl)pyrazin-2-amine

To a suspension of 2-fluorobenzohydrazide (2 g, 12.98 mmol), 3-amino-6-bromo-pyrazine-2-carboxylic acid (2.830 g, 12.98 mmol), and TBTU (5.002 g, 15.58 mmol) in DMF (20.00 mL) was added DIPEA (3.691 g, 4.974 mL, 28.56 mmol). The resulting mixture was stirred at room temperature for 2 h. The reaction mixture was diluted with water (20 mL) and extracted with EtOAc (3×20 mL), the combined organic extracts were washed with water (3×20 mL) and brine (1×20 mL), dried over $MgSO_4$ and concentrated in vacuo. The residue was then triturated with acetonitrile and filted and dried to give 3-amino-6-bromo-N-(2-fluorophenylcarbonyl)pyrazine-2-carbohydrazide as an orange solid. This was taken up in MeCN (20.00 mL) and added bromo(triphenyl)phosphonium (5.331 g, 15.58 mmol) was added followed by DIPEA (3.691 g, 4.974 mL, 28.56 mmol). The reaction mixture was stirred for 30 min, and then filtered. The solid was washed with acetonitrile to give the product as a yellow solid (1.46 g, 67%); 1H NMR (400 MHz, DMSO) d 7.48-7.54 (m, 2H), 7.75 (m, 3H), 8.12 (m, 1H) and 8.45 (m, 1H) ppm; MS (ES$^+$) 338.03

Step 2: 5-[4-[2-(dimethylamino)-1-methyl-ethyl]sulfonylphenyl]-3-[5-(2-fluorophenyl)-1,3,4-oxadiazol-2-yl]pyrazin-2-amine 2-(4-bromophenyl)sulfonyl-N,N-dimethyl-propan-1-amine (100 mg, 0.3233 mmol) was dissolved in dioxane (1.774 mL) and Bis(pinacolato)diboron (123.6 mg, 0.4866 mmol) and potassium acetate (95.50 mg, 0.9731 mmol) were added. The reaction was degassed and filled with nitrogen five times then Pd(dppf)Cl$_2$.DCM (26.40 mg, 0.03233 mmol) was added and the reaction heated to 90° C. for 2 h. The reaction mixture was cooled to room temperature and N$_2$ bubbled through for 10 min. Then 5-bromo-3-(5-phenyl-1,3,4-oxadiazol-2-yl)pyrazin-2-amine (102.9 mg, 0.3233 mmol) and an aqueous solution of Na$_2$CO$_3$ (485.0 μL of 2 M, 0.9699 mmol) was added. N$_2$ was bubbled through for a further 10 min then Pd(PPh$_3$)$_4$ (37.47 mg, 0.03243 mmol) was added and the reaction mixture heated under microwave conditions at 150° C. for 30 min. The reaction mixture was passed through an SCX-2 cartridge eluting with MeCN/MeOH, washing with 200 mL, followed by 2M NH$_3$ in MeOH with MeCN to elute the compound. Evaporation of the solvent gave a brown solid which was purified by reverse phase preparative HPLC [Waters Sunfire C18, 10 μM, 100 Å column, gradient 10%-95% B (solvent A: 0.05% TFA in water; solvent B: CH$_3$CN) over 16 minutes at 25 mL/min]. The product fractions were collected and lypholised to give the product as a yellow solid (67.1 mg, 33% yield); 1H NMR (400.0 MHz, DMSO) d 1.29 (d, 3H), 2.80 (s, 3H), 2.90 (s, 3H), 3.35 (d, 1H), 3.48 (d, 1H), 4.09 (s, 1H), 7.50-7.60 (m, 2H), 7.76-7.81 (m, 1H), 8.06 (d, 2H), 8.20 (m, 1H), 8.43 (d, 2H), 9.12 (s, 1H) and 9.41 (s, 1H) ppm; MS (ES$^+$) 483

The following compounds were all prepared using a method similar to the one described for Compound IA-337 above.

Compound IA-327 3-[5-(2-fluorophenyl)-1,3,4-oxadiazol-2-yl]-5-(4-tetrahydropyran-4-ylsulfonylphenyl)pyrazin-2-amine MS (ES$^+$) 482

Compound IA-339 3-[4-[5-amino-6-[5-(2-fluorophenyl)-1,3,4-oxadiazol-2-yl]pyrazin-2-yl]phenyl]sulfonylbutan-1-ol 1H NMR (400.0 MHz, DMSO) d 1.20 (d, 3H), 1.37-1.46 (m, 1H), 1.99-2.02 (m, 1H), 3.38-3.43 (m, 2H), 3.52 (s, 1H), 4.66 (t, 1H), 7.50-7.59 (m, 2H), 7.77 (d, 1H), 7.97 (d, 2H), 8.20 (s, 1H), 8.37 (d, 2H) and 9.08 (s, 1H) ppm; MS (ES$^+$) 470

Compound IA-343 5-[4-[3-(dimethylamino)-1-methylpropyl]sulfonylphenyl]-3-[5-(2-fluorophenyl)-1,3,4-oxadiazol-2-yl]pyrazin-2-amine 1H NMR (400.0 MHz, DMSO) d 1.20 (d, 3H), 1.76-1.82 (m, 1H), 2.14-2.20 (m, 1H), 2.79 (s, 6H), 3.21 (s, 2H), 3.47-3.55 (m, 1H), 7.50-7.59 (m, 2H), 7.75-7.81 (m, 1H), 8.01 (d, 2H), 8.19 (m, 1H), 8.40 (d, 2H), 9.10 (s, 1H) and 9.58 (s, 1H) ppm; MS (ES$^+$) 497

Compound IA-349 3-[5-(2-fluorophenyl)-1,3,4-oxadiazol-2-yl]-5-(4-tetrahydrofuran-3-ylsulfonylphenyl)pyrazin-2-amine 1H NMR (400.0 MHz, DMSO) d 2.13-2.19 (m, 2H), 3.65 (m, 1H), 3.74-3.80 (m, 1H), 3.86 (dd, 1H), 4.04 (dd, 1H), 4.22-4.28 (m, 1H), 7.50-7.60 (m, 2H), 7.75-7.80 (m, 1H), 8.04 (d, 2H), 8.20 (m, 1H0, 8.38 (d, 2H) and 9.09 (s, 1H) ppm; MS (ES$^+$) 468

Example 72A 3-(3-(4-((dimethylamino)methyl)-2-fluorophenyl)isoxazol-5-yl)-5-(3-fluoro-4-(isopropylsulfonyl)phenyl)pyrazin-2-amine (Compound IIA-17)

SCHEME

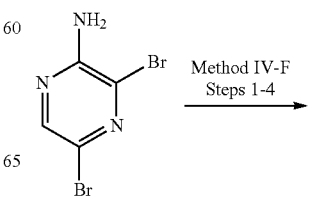

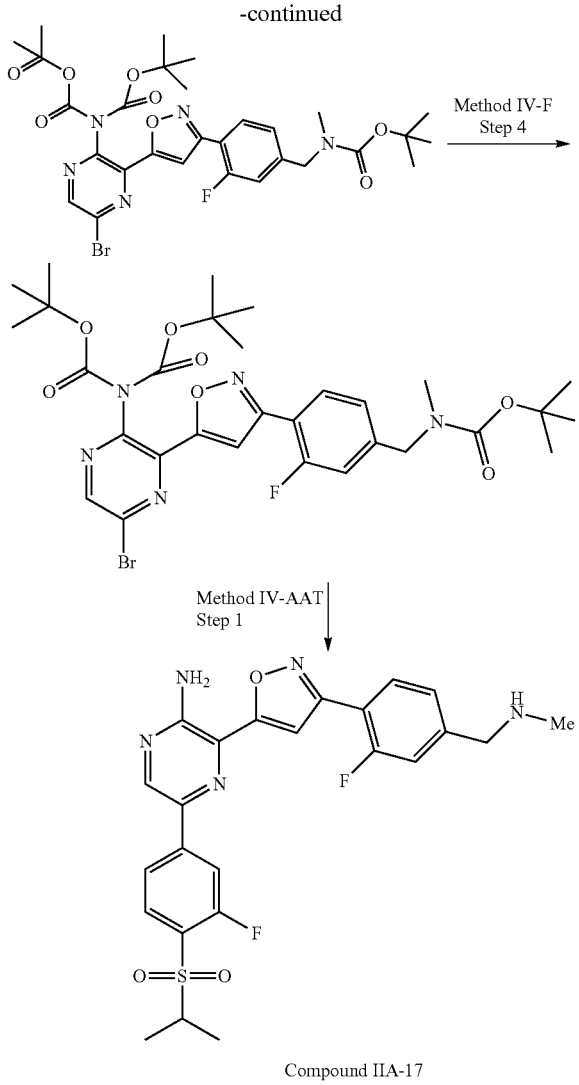

Compound IIA-17

Compound IIA-17 was prepared using Method IV-F, Steps 1-4, followed by Method IV-AAT, Step 1.

tert-Butyl N-[[4-[5-[3-[bis(tert-butoxycarbonyl)amino]-6-bromo-pyrazin-2-yl]isoxazol-3-yl]-3-fluoro-phenyl]methyl]-N-methyl-carbamate (150 mg, 0.2211 mmol), 2-(3-fluoro-4-isopropylsulfonyl-phenyl)-4,4,5,5-tetramethyl-1,3,2-dioxaborolane (72.57 mg, 0.2211 mmol) and $Na_2CO_3$ (46.87 mg, 0.4422 mmol) suspended in MeCN (2.486 mL)/water (2.486 mL). Mixture de-gassed (×5 $N_2$-vacuum cycles) and $Pd(PPh_3)_4$ (25.55 mg, 0.02211 mmol) added. Mixture de-gassed again and the reaction mixture was heated at 90° C. under microwave conditions for 20 min. The reaction mixture was diluted with water (5 mL) and ethyl acetate (5 mL) and the layers separated. The aqueous layer was extracted further with ethyl acetate (2×10 mL) and the combined organic extracts dried over $MgSO_4$ and concentrated in vacuo. The residue was taken up in dichloromethane (3 mL) and TFA (504.2 mg, 340.7 µL, 4.422 mmol) was added. The resulting solution was stirred at room temperature for 4 h and then concentrated in vacuo. The residue was purified by reverse phase preparative HPLC [Waters Sunfire C18, 10 µM, 100 Å column, gradient 10%-95% B (solvent A: 0.05% TFA in water; solvent B: $CH_3CN$) over 16 minutes at 25 mL/min]. The product fractions were collected and lypholised to give the product as a yellow solid (47.5 mg, 45% yield); MS ($ES^+$) 500.1

Compounds P73 to P144, P145, P147-P148 and P150 can be made using a methodology similar to the one described in Method AAT.

The compounds of Table A were synthesized using the methods described herein as well as those known in the art. More specifically, the compounds were made using one or more of the following methods: Oxadiazolyl compounds (Formula IA compounds) can be made according to methods described in Schemes I-B2 and I-B3; Isoxazolyl compounds (Formula HA compounds) can be made according to methods described in Schemes I-E1 and I-E2. Triazolyl compounds (Formula IIIA) can be made according to methods described in Schemes I-F1 and I-F2.

TABLE A

| Patent Cmpd | LCMS (M + 1) | LCMS Rt (min) | HNMR |
|---|---|---|---|
| IA-1 | 442.02 | 3.12 | (DMSO) 1.90 (2H, m), 3,10 (4H, m), 3.34 (2H, m), 3.34-3.70 (2H, m), 7.46 (2H, m), 7.53-7.57 (3H, m), 7.66 (1H, br s), 8.02-8.07 (4H, m), 8.58 (2H, br s), 8.86 (1H, s) |
| IA-2 | 442.02 | 3.2 | (DMSO) 1.96-2.04 (2H, m), 3.25-3.85 (8H, m - with water signal), 7.47 (2H, br s), 7.60 (2H, m), 7.71 (2H, m), 7.79 (1H, m), 8.16 (2H, m), 8.29 (2H, m), 8.77 (2H, m), 8.97 (1H, s) |
| IA-4 | 488.31 | 2.49 | — |
| IA-5 | 474.29 | 2.46 | 1.78 (1H, m), 2.02 (1H, m), 2.73 (1H, m), 3.11-3.50 (3H, m), 3.68-3.79 (1H, m), 7.58 (1H, m), 7.68 (3H, m), 7.88 (2H, br hump), 8.00 (2H, m), 8.19 (2H, m), 9.03 (1H, m) |
| IA-6 | 460.23 | 2.47 | dmso d6 1.581H, m), 1.76 (1H, m), 2.69-2.89 (4H, m), 3.28-3.41 (2H, m), 3.62 + 3.68 (2H, 2xm), 7.54 (1H, m), 7.70 (3H, m), 7.89 (2H, br hump(, 8.03 (2H, m), 8.18 (2H, m), 9.03 (1H, d) |
| IA-7 | 446.21 | 2.45 | — |
| IA-8 | 596.15 | 3.77 | dmso d6 1.21 + 1.25 (6H, 2xt), 1.60 + 1.83 (2H, 2xm), 3.15-3.41 (4H, m), 3.72 (2H, m), 3.90 (2H, 2xq), 7.54 (1H, m), 7.70 (3H, m), 8.04 (2H, m), 8.18 (2H, m), 9.03 (1H, s) |

TABLE A-continued

| Patent Cmpd | LCMS (M + 1) | LCMS Rt (min) | HNMR |
|---|---|---|---|
| IA-9 | 442.2 | 2.42 | — |
| IA-10 | 456.16 | 3.4 | — |
| IA-11 | 500.17 | 3.6 | — |
| IA-12 | 428.13 | 3.1 | — |
| IA-13 | 429.07 | 3.17 | dmso d6 3.32-3.62 (8H, m), 7.57 (2H, d), 7.69 (3H, m), 7.81 (2H, br s), 8.18 (4H, m), 9.00 (1H, s) |
| IA-14 | 431.1 | 3.27 | — |
| IA-15 | 443.09 | 3.18 | — |
| IA-16 | 496.08 | 2.79 | — |
| IA-17 | 442.12 | 2.46 | — |
| IA-18 | 456.15 | 2.51 | — |
| IA-19 | 567.22 | 3.68 | CDCl3 1.18 (1H, m), 1.36 (1H, m), 1.70 (1H, m), 1.93 (1H, m), 3.35-3.53 (5H, m), 3.59 (1H, m), 3.67 (1H, m), 3.77 (1H, m), 7.49 (3H, m), 7.66 (1H, m), 7.80 (1H, s), 7.87 (1H, m), 8.21 (2H, m), 8.64 (1H, m) |
| IA-20 | 467.22 | 2.93 | dmso d6 1.60 (1H, m), 1.76 (1H, m), 2.68-2.89 (3H, m), 3.34-3.41 (2H, m), 3.61-3.68 (2H, m), 7.65-7.70 (3H, m), 7.83 (1H, d), 7.92 (1H, d), 8.10-8.20 (3H, m), 8.91 (1H, s) |
| IA-21 | 506 | 2.58 | H NMR (400.0 MHz, DMSO) d 9.61 (s, 1H), 9.08 (s, 1H), 8.21-8.18 (m, 2H), 7.98 (d, J = 9.8 Hz, 2H), 7.72-7.67 (m, 4H), 4.69 (d, J = 11.6 Hz, 1H), 3.67 (d, J = 12.9 Hz, 1H), 3.54 (t, J = 6.1 Hz, 1H), 3.23-3.15 (m, 1H), 2.91-2.85 (m, 1H), 2.79 (s, 6H), 2.17 (d, J = 11.1 Hz, 1H), 2.05 (d, J = 12.6 Hz, 1H), 1.57 (dd, J = 4.2, 12.4 Hz, 1H) and 1.48 (dd, J = 3.8, 12.0 Hz, 1H) ppm |
| IA-22 | 538 | 2.6 | H NMR (400.0 MHz, DMSO) d 9.57 (s, 1H), 8.52 (s, 1H), 8.08-8.06 (m, 2H), 7.95 (s, 1H), 7.88-7.82 (m, 3H), 7.71-7.62 (m, 3H), 4.70 (s, 1H), 3.74 (s, 1H), 3.49 (s, 1H), 3.19 (s, 1H), 2.79 (s, 3H), 2.77 (s, 3H), 2.68 (t, J = 1.8 Hz, 1H), 2.09 (s, 1H), 1.91 (s, 1H) and 1.71-1.66 (m, 2H) ppm |
| IA-23 | 387.13 | 3.48 | (DMSO) 2.98 (6H, m), 7.55 (2H, m), 7.69-7.71 (3H, m), 7.83 (2H, br s), 8.17-8.20 (4H, m), 9.00 (1H, s) |
| IA-24 | 464 | 2.68 | H NMR (400.0 MHz, DMSO) d 9.09 (s, 1H), 8.43 (d, J = 8.6 Hz, 3H), 8.19-8.17 (m, 2H), 7.92 (d, J = 8.5 Hz, 2H), 7.71 (dd, J = 4.5, 7.0 Hz, 2H), 7.69 (s, 1H), 3.21 (d, J = 5.0 Hz, 4H) and 3.15 (s, 4H) ppm |
| IA-25 | 492 | 2.68 | — |
| IA-26 | 439 | 3.06 | H NMR (400.0 MHz, DMSO) d 9.10 (s, 1H), 8.39 (dd, J = 1.6, 7.0 Hz, 2H), 8.27-8.24 (m, 2H), 7.99 (d, J = 8.5 Hz, 2H), 7.78-7.74 (m, 4H), 4.78 (t, J = 5.6 Hz, 1H), 3.45 (q, J = 6.1 Hz, 2H) and 2.90 (t, J = 6.1 Hz, 2H) ppm |
| IA-27 | 526.2 | 2.83 | dmso d6 0.85 + 0.90 (9H, 2xs), 1.29 + 1.38 (2H, 2xt), 1.71 + 1.83 (2H, 2xm), 2.39-2.72 (6H, m), 3.41 (2H, m), 3.65 (2H, m), 7.52 (2H, m), 7.69 (3H, m), 7.80 (2H, br s), 8.18 (4H, m), 8.99 (1H, s) |
| IA-28 | 542.17 | 3.67 | 1.44 (9H, s), 1.59 (1H, m), 1.80 (1H, m), 3.32-3.40 (4H, m), 3.37-3.43 (2H, m), 3.63 (1H, m), 3.73 (1H, m), 7.45-7.54 (2H, m), 7.66-7.73 (3H, m), 7.80 (2H, br s), 8.16-8.20 (4H, m), 9.00 (1H, s) |
| IA-29 | 470.1 | 2.92 | 1.58 (1H, m), 1.83 (1H, m), 3.32-3.65 (7H, m), 3.79 (1H, m), 7.45-7.50 (2H, m), 7.67-7.71 (3H, m), 7.80 (2H, br s), 8.04 (1H, m), 8.14-8.20 (4H, m), 9.00 (1H, s) |
| IA-30 | 405.11 | 3.42 | (DMSO) 2.97 (6H, m), 7.50-7.60 (4H, m), 7.75-7.80 (2H, m), 8.15-8.21 (3H, m), 9.01 (1H, s) |
| IA-31 | 540.2 | 3.52 | dmso d6 1.01, 1.02 (9H, 2xs), 1.54, 1.83 (2H, 2xm), 2.25, m, 3.32-3.79 (8H, m), 7.43-7.52 (2H, m), 7.68-7.73 (3H, m), 7.80 (2H, br s), 8.14-8.20 (4H, m), 9.00 (1H, s) |
| IA-32 | 402.13 | 3.34 | H NMR (400.0 MHz, DMSO) d 2.97 (s, 3H), 3.01 (s, 3H), 7.06 (d, J = 7.4 Hz, 1H), 7.38-7.42 (m, 2H), 7.54-7.56 (m, 2H), 7.68-7.70 (m, 3H), 8.10 (dd, J = 1.5, 6.8 Hz, 2H), 8.88 (s, 1H) and 11.04 (s, 1H) ppm |
| IA-33 | 340.15 | 2.63 | H NMR (400.0 MHz, DMSO) d 2.92 (d, J = 4.7 Hz, 3H), 2.96 (s, 3H), 3.00 (s, 3H), 7.52 (d, J = 8.3 Hz, 2H), 7.55 (br s, 1H), 8.06 (d, J = 8.4 Hz, 3H) and 8.82 (s, 1H) ppm |
| IA-34 | 500.1 | 3.23 | 1.61, 1.81 (2H, 2xM), 3.17-3.73 (8H, m), 3.64 (3H, s), 7.48 (2H, m), 7.70-7.80 (5H, m), 8.15-8.24 (4H, m), 8.99 (1H, s) |
| IA-35 | 342.03 | 3.2 | 7.64-7.72 (4H, m), 7.72 (1H, v br s), 8.21-8.24 (3H, m), 8.91 (1H, d), 9.09 (2H, d) |
| IA-36 | 405.16 | 3.52 | (DMSO) 2.98-3.02 (6H, m), 7.52-7.56 (4H, m), 7.80 (2H, br s), 8.17 (2H, m), 8.24 (2H, m), 9.00 (1H, s) |

TABLE A-continued

| Patent Cmpd | LCMS (M + 1) | LCMS Rt (min) | HNMR |
|---|---|---|---|
| IA-37 | 444 | 2.28 | H NMR (400.0 MHz, DMSO) d 9.58 (d, J = 2.1 Hz, 2H), 9.14 (d, J = 3.4 Hz, 1H), 8.85 (BR S, 2H), 8.22-8.20 (m, 2H), 7.72-7.67 (m, 3H), 3.90 (t, J = 5.1 Hz, 1H), 3.76 (s, 1H), 3.58 (d, J = 5.1 Hz, 1H), 3.42 (t, J = 6.0 Hz, 2H), 3.28 (s, 1H), 3.24 (s, 1H), 3.17 (s, 1H) and 2.00 (d, J = 5.1 Hz, 2H) ppm |
| IA-38 | 478 | 2.56 | H NMR (400.0 MHz, DMSO) d 9.08 (d, J = 2.4 Hz, 1H), 8.77 (s, 2H), 8.21-8.17 (m, 2H), 8.00-7.98 (m, 2H), 7.74-7.67 (m, 3H), 3.91-3.88 (m, 1H), 3.79 (t, J = 5.9 Hz, 1H), 3.70-3.67 (m, 1H), 3.50 (t, J = 6.0 Hz, 2H), 3.44 (s, 1H), 3.32 (s, 1H), 3.17 (s, 1H), 2.10 (d, J = 5.3 Hz, 1H) and 2.00 (t, J = 4.9 Hz, 1H) ppm |
| IA-39 | 510 | 2.6 | H NMR (400.0 MHz, DMSO) d 8.69 (s, 2H), 8.45 (s, 1H), 8.01-7.99 (m, 2H), 7.95 (s, 1H), 7.79 (dd, J = 8.0, 18.7 Hz, 3H), 7.64-7.55 (m, 3H), 7.45-7.30 (m, 1H), 3.82-3.79 (m, 1H), 3.67 (d, J = 5.4 Hz, 1H), 3.41 (t, J = 5.8 Hz, 2H), 3.28 (s, 1H), 3.20 (s, 1H), 3.10 (s, 1H), 1.98 (s, 1H) and 1.89 (s, 1H) ppm |
| IA-40 | 405.16 | 3.54 | (DMSO) 2.98 (6H, m), 7.55-7.61 (3H, m), 7.73-7.85 (3H, m), 7.96 (1H, m), 8.02 (1H, m), 8.19 (2H, m), 9.01 (1H, s) |
| IA-41 | 388.19 | 3.02 | (DMSO) 2.98 (6H, m), 7.54 (2H, m), 7.71-7.75 (1H, m), 7.80 (2H, br s), 8.19 (2H, m), 8.55 (1H, m), 8.87 (1H, m), 9.02 (1H, s), 9.35 (1H, m) |
| IA-42 | 436.1 | 3.6 | H NMR (400.0 MHz, DMSO) d 2.97 (s, 3H), 3.01 (s, 3H), 7.46 (d, J = 8.9 Hz, 2H), 7.55 (d, J = 8.4 Hz, 2H), 7.69-7.71 (m, 3H), 8.09 (d, J = 8.3 Hz, 2H), 8.89 (s, 1H) and 11.22 (s, 1H) ppm |
| IA-43 | 436.1 | 3.6 | H NMR (400.0 MHz, DMSO) d 2.97 (s, 3H), 3.01 (s, 3H), 7.05 (d, 1H), 7.35 (d, J = 8.4 Hz, 1H), 7.50 (d, 3H), 7.65 (br s, 2H), 7.85 (s, 2H), 8.70 (s, 1H) and 11.30 (s, 1H) ppm |
| IA-44 | 403.16 | 2.98 | H NMR (400.0 MHz, DMSO) d 2.95 (s, 3H), 3.00 (s, 3H), 3.30 (s, 1H), 7.41 (s, 1H), 7.54 (d, J = 8.4 Hz, 2H), 7.68 (br s, 2H), 8.08 (d, J = 8.3 Hz, 1H), 8.11 (s, 0.5H), 8.13 (s, 0.5H), 8.25 (s, 1H), 8.81 (s, 1H), 8.88 (s, 1H) and 11.32 (s, 1H) ppm |
| IA-45 | 396.16 | 2.87 | H NMR (400.0 MHz, DMSO) d 2.96 (s, 3H), 3.00 (s, 3H), 3.55-3.57 (m, 4H), 3.76-3.78 (m, 4H), 7.51 (d, 2H), 7.63 (br s, 2H), 8.10 (d, 2H) and 8.86 (s, 1H) ppm |
| IA-46 | 421.1 | 3.55 | DMSO 3.03 (6H, d), 7.5 (1H, d), 7.6-7.7 (3H, m), 7.75 (1H, d), 7.85 (1H, brs), 8.1 (1H, d), 8.62 (1H, s) |
| IA-47 | 443 | 2.87 | H NMR (400.0 MHz, DMSO) d 9.32 (d, J = 1.9 Hz, 1H), 9.09 (d, J = 2.8 Hz, 1H), 8.87 (s, 2H), 8.65-8.61 (m, 1H), 8.19-8.17 (m, 2H), 7.82 (dd, J = 8.2, 14.6 Hz, 1H), 7.73-7.66 (m, 3H), 3.89-3.87 (m, 1H), 3.79-3.73 (m, 2H), 3.62 (t, J = 5.9 Hz, 1H), 3.35 (d, J = 3.0 Hz, 2H), 3.27 (s, 2H) and 2.09-2.03 (m, 2H) ppm |
| IA-48 | 492 | 3.23 | H NMR (400.0 MHz, DMSO) d 8.92 (s, 2H), 8.62 (d, J = 2.2 Hz, 1H), 8.32-8.29 (m, 1H), 8.07-8.04 (m, 2H), 7.91-7.84 (m, 2H), 7.79 (d, J = 7.2 Hz, 1H), 7.73-7.60 (m, 6H), 4.19-4.10 (m, 2H), 3.89-3.69 (m, 2H), 3.51-3.11 (m, 4H), 2.15 (t, J = 5.6 Hz, 1H) and 1.88 (s, 1H) ppm |
| IA-49 | 316 | 3.9 | H NMR (400.0 MHz, DMSO) d 9.00 (s, 1H), 8.24-8.17 (m, 4H), 7.78-7.71 (m, 5H), 7.61-7.57 (m, 2H) and 7.48 (t, J = 7.3 Hz, 1H) ppm |
| IA-50 | 341 | 3.65 | H NMR (400.0 MHz, DMSO) d 8.88 (s, 1H), 8.20-8.18 (m, 2H), 8.09 (d, J = 7.7 Hz, 1H), 8.01 (dd, J = 1.0, 7.9 Hz, 1H), 7.85 (td, J = 7.7, 3.0 Hz, 1H) and 7.70-7.62 (m, 4H) ppm |
| IA-51 | 388.14 | 3.02 | (DMSO) 2.95 (6H, m), 7.56 (2H, m), 7.69-7.73 (1H, m), 7.83 (2H, br s), 8.11-8.16 (3H, m), 8.32 (1H, m), 8.87 (1H, m), 9.01 (1H, s) |
| IA-52 | 393.12 | 3.35 | (DMSO) 3.02 (6H, m), 7.36-7.38 (1H, m), 7.54 (2H, m), 7.78 (2H, br s), 8.01-8.05 (2H, m), 8.17 (2H, m), 8.99 (1H, s) |
| IA-53 | 404.16 | 2.62 | (DMSO) 3.00 (6H, m), 6.47 (1H, t), 7.53-7.56 (2H, m), 7.65 (1H, m), 7.78 (2H, m), 8.13 (2H, m), 8.29-8.31 (1H, m), 8.98 (1H, s) |
| IA-54 | 409.19 | 2.34 | H NMR (400.0 MHz, DMSO) d 1.69-1.80 (m, 2H), 2.10-2.20 (m, 2H), 2.96 (s, 3H), 3.01 (s, 3H), 3.05-3.10 (m, 2H), 3.31-3.34 (m, 2H), 3.85 (br s, 1H), 7.53 (d, J = 8.3 Hz, 2H), 7.65 (br s, 2H), 8.06 (d, J = 8.3 Hz, 2H), 8.45 (d, J = 7.0 Hz, 1H) and 8.84 (s, 1H) ppm |

TABLE A-continued

| Patent Cmpd | LCMS (M + 1) | LCMS Rt (min) | HNMR |
|---|---|---|---|
| IA-55 | 416.2 | 3.27 | H NMR (400.0 MHz, DMSO) d 2.96 (s, 3H), 3.00 (s, 3H), 4.50 (d, J = 6.1 Hz, 2H), 7.29 (d, J = 7.2 Hz, 1H), 7.35-7.42 (m, 4H), 7.51-7.53 (m, 2H), 7.65 (br s, 2H), 8.06 (dd, J = 1.5, 6.9 Hz, 2H) and 8.81 (d, J = 12.4 Hz, 2H) ppm |
| IA-56 | 358 | 4.26 | H NMR (400.0 MHz, DMSO) d 8.44 (s, 1H), 8.08-8.06 (m, 2H), 7.68-7.62 (m, 5H), 7.52 (dd, J = 0.8, 7.9 Hz, 1H), 7.47-7.40 (m, 2H), 7.32 (dd, J = 1.0, 7.4 Hz, 1H), 3.21 (qn, J = 6.8 Hz, 1H) and 1.27 (d, J = 6.8 Hz, 6H) ppm |
| IA-57 | 344 | 4.14 | — |
| IA-58 | 331 | 2.98 | — |
| IA-59 | 355 | 3.56 | — |
| IA-60 | 317 | 2.37 | — |
| IA-61 | 332 | 3.85 | — |
| IA-62 | 346 | 3.41 | — |
| IA-63 | 367 | 2.63 | — |
| IA-64 | 317 | 2.39 3.87 | — |
| IA-65 | 346 | | — |
| IA-66 | 373 | 3.22 | H NMR (400.0 MHz, DMSO) d 10.13 (s, 1H), 8.83 (s, 1H), 8.24 (s, 1H), 8.19-8.17 (m, 2H), 7.76-7.69 (m, 7H), 7.44 (t, J = 7.9 Hz, 1H) and 2.10 (s, 3H) ppm |
| IA-67 | 388.17 | 3.1 | (DMSO) 3.02 (6H, m), 7.55 (2H, m), 7.83 (2H, br s), 8/10 (2H, m), 8.20 (2H, m), 8.92 (2H, m), 9.03 (1H, s) |
| IA-68 | 458.07 | 2.62 | dmso d6 1.60 (1H, m), 1.77 (1H, m), 2.72-2.39 (4H, m_, 3.40 (2H, m), 3.60-3.67 (2H, m), 7.52 (2H, d), 7.58-7.65 (3H, m), 7.99 (1H, m), 8.00 (2H, br hump), 8.10-8.14 (3h, m), 8.95 (1H, s) |
| IIA-1 | 317 | 3.4 | 1H NMR (400.0 MHz, DMSO) d 7.32 (br s, 2H), 7.38 (dd, J = 4.3, 8.0 Hz, 1H), 7.52-7.56 (m, 2H), 7.59-7.64 (m, 1H), 8.12-8.14 (m, 2H), 8.24-8.27 (m, 1H), 8.44 (dd, J = 1.6, 4.8 Hz, 1H), 8.82 (s, 1H) and 9.11 (d, J = 1.8 Hz, 1H) ppm |
| IIA-2 | 394 | 3.4 | 1H NMR (400.0 MHz, DMSO) d 3.27 (s, 3H), 7.58 (br s, 2H), 7.69-7.73 (m, 2H), 7.77-7.81 (m, 1H), 8.05 (d, J = 8.5 Hz, 2H), 8.32 (dd, J = 8.5, 18.0 Hz, 4H) and 9.04 (s, 1H) ppm |
| IIA-3 | 441.21 | 3.13 | (DMSO) 1.95 (2H, m), 3.25-3.96 (8H, m partially hidden by water peak), 7.08 (2H, br s), 7.54-7.61 (5H, m), 7.78 (1H, s), 8.03-8.05 (2H, m), 8.19 (2H, m), 8.72 (2H, br s), 8.89 (1H, s) |
| IIIA-1 | 331.2 | 1.5 | 1H NMR (400.0 MHz, DMSO) d 15.03 (br s, 1H), 9.60 (s, 1H), 9.02 (s, 1H), 8.96 (d, J = 7.9 Hz, 1H), 8.74 (dd, J = 1.3, 5.2 Hz, 1H), 8.06 (s, 2H), 7.82 (dd, J = 5.2, 8.1 Hz, 1H), 7.74 (s, 2H), 7.39 (t, J = 7.8 Hz, 1H) and 7.03-6.98 (m, 1H) ppm |
| IIIA-2 | 330 | 2.46 | — |

TABLE A-continued

| Patent Cmpd | LCMS (M + 1) | LCMS Rt (min) | HNMR |
|---|---|---|---|
| IIIA-3 | 322 | 2.25 | 1H NMR (400.0 MHz, DMSO-d6) d 14.96 (s, 1H), 9.55 (s, 1H), 8.99 (s, 1H), 8.84 (d, J = 6.1 Hz, 1H), 8.69 (dd, J = 1.2, 4.9 Hz, 1H), 7.95 (s, 2H), 7.81 (d, J = 3.0 Hz, 1H), 7.73-7.68 (m, 2H) and 7.22 (dd, J = 3.8, 4.8 Hz, 1H) ppm |
| IIIA-4 | 345 | 1.79 | — |
| IIIA-5 | 345 | 1.75 | — |
| IIIA-6 | 331.2 | 1.5 | 1H NMR (400.0 MHz, DMSO) d 15.03 (br s, 1H), 9.60 (s, 1H), 9.02 (s, 1H), 8.96 (d, J = 7.9 Hz, 1H), 8.74 (dd, J = 1.3, 5.2 Hz, 1H), 8.06 (s, 2H), 7.82 (dd, J = 5.2, 8.1 Hz, 1H), 7.74 (s, 2H), 7.39 (t, J = 7.8 Hz, 1H) and 7.03-6.98 (m, 1H) ppm |

Example 73A

3-amino-N-(1H-benzo[d]imidazol-2-yl)-6-(4-(dimethylcarbamoyl)phenyl)pyrazine-2-carboxamide (Compound V-1)

SCHEME

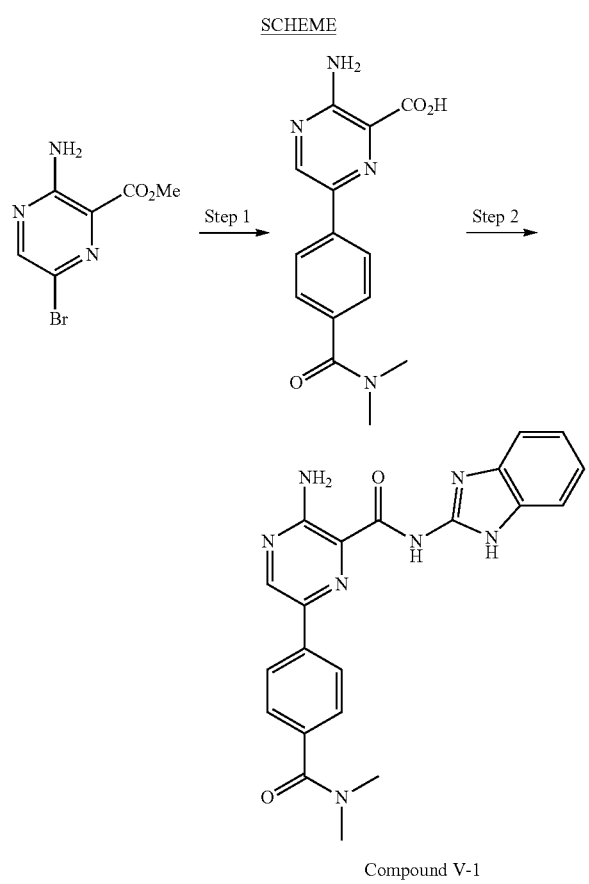

Compound V-1

Compound V-1 was prepared using Method V-A, Steps 1-2

Method V-A

Step 1: 3-Amino-6-(4-(dimethylcarbamoyl)phenyl)pyrazine-2-carboxylic acid

Methyl 3-amino-6-bromo-pyrazine-2-carboxylate (6.01 g, 25.9 mmol, 1.0 Eq.), 4-(dimethylcarbamoyl)phenylboronic acid (5.00 g, 25.9 mmol, 1.0 Eq.), $Na_2CO_3$ (5.49 g, 51.8 mmol, 2.0 Eq.) and $Pd(PPh_3)_4$ (2.99 g, 2.59 mmol, 0.1 Eq.) in acetonitrile (30 mL) and water (30 mL) were heated at 90° C. for 16 hours. After cooling to ambient temperature the precipitate was removed by filtration. The aqueous filtrate was acidified to pH4 by addition of 1M HCl and then extracted with dichloromethane (3×20 mL), dried over $MgSO_4$ and concentrated in vacuo to give the sub-title product as a yellow solid (2.42 g, 65% Yield). 1H NMR (400.0 MHz, DMSO) δ 2.95 (3H, br s), 3.00 (3H, br s), 7.49-7.51 (2H, m), 7.58 (2H, br s), 8.15 92H, d), 8.95 (1H, s), 13.25 (1H, br s) ppm; MS (ES+) 287.13.

Step 2: 3-amino-N-(1H-benzo[d]imidazol-2-yl)-6-(4-(dimethylcarbamoyl)phenyl)pyrazine-2-carboxamide Amino-6-(4-(dimethylcarbamoyl)phenyl)pyrazine-2-carboxylic acid (112.5 mg, 0.3930 mmol, 1.0 Eq.) in DMF (1.1 mL) was treated with 1H-benzimidazol-2-amine (62.8 mg, 0.4716 mmol, 1.2 Eq.) and triethylamine (39.8 mg, 54.8 μL, 0.3930 mmol, 1.0 Eq.) followed by the addition of TBTU (176.7 mg, 0.5502 mmol, 1.4 Eq.). The reaction mixture was allowed to stir at ambient temperature overnight then added dropwise to stirred water (15 ml). This was stirred at ambient temperature for 1 hour and the resultant precipitate isolated by filtration and washed with water. The residue was recrystallised from hot acetonitrile to give the title compound as a yellow solid (63.1 mg, 40% Yield). 1H NMR (400.0 MHz, DMSO) δ 2.97 (3H, br s), 3.02 (3H, br s), 7.15-7.18 (2H, m), 7.51-7.55 (4H, m), 7.83 (2H, br s), 8.34 (2H, d), 9.04 (1H, s), 11.50 (1H, br s), 12.35 (1H, br s) ppm; MS (ES+) 402.08.

Compounds V-1 to V-30 can also be prepared using a method similar to the one used to prepare compound V-1.

| Cmpd No. | LCMS ES+ | LCMS R(t) min | HNMR |
|---|---|---|---|
| V-1 | 402.08 | 2.35 | dmso d6 2.97, 3.02 (2x3H, 2xs), 7.15-7.18 (2H, m), 7.51-7.55 (4H, m), 7.83 (2H, br s), 8.34 (2H, d), 9.04 (1H, s), 11.50 (1H, br hump), 12.35 (1H, br hump) |

-continued

| Cmpd No. | LCMS ES+ | LCMS R(t) min | HNMR |
|---|---|---|---|
| V-2 | 482.2 | 2.72 | 1.61 + 1.76 (2H, 2xm), 2.74-2.82 (3H, m), 2.90 (1H, m), 3.40 (2H, m), 3.53 (2H, m), 7.15 (2H, dt), 7.52 (2H, dt), 7.86 (1H, dq), 8.00-8.18 (2H, br hump), 8.06 (1H, m), 8.29 (1H, dd), 9.00 (1H, s) |
| V-3 | 357.13 | 3 | dmso d6 7.26 (2H, m), 7.60 (2H, m), 8.29 (1H, d), 8.0-8.5 (2H, br hump), 8.96 (1H, d), 9.15 (2H, d), |
| V-4 | 457.3 | 2.42 | MeOD 2.1-2.3 (2H, m), 3.3-3.4 (2H, m), 3.5-3.55 (1.5H, m), 3.6-3.65 (1.5H, m), 3.85-3.9 (1H, m), 4.1-4.15 (1.5H, m), 7.65 (2H, d), 7.6 (2H, d), 7.75-7.8 (2H, m), 8.25 (2H, d), 8.65 (1H, s), 8.8 (1H, s), 9.4 (1H, s), 10.7 (1H, s) |
| V-5 | 458.2 | 2.77 | DMSO 1.8-2.0 (2H, m), 3.5-3.6 (2H, m), 3.7-3.8 (2H, m), 3.8-3.85 (2H, m), 7.35-7.4 (H, m), 7.6 (2H, d), 7.7 (2H, t), 7.8 (2H, s), 8.4 (2H, d), 8.7-8.8 (2H, m), 9.03 (1H, s), 11.8 (1H, s) |
| V-6 | 456.2 | 2.45 | DMSO 1.8-2.0 (2H, m), 3.5-3.6 (2H, m), 3.7-3.8 (2H, m), 3.8-3.85 (2H, m), 6.6-6.7 (2H, m), 6.75 (1H, bs), 6.85 (1H, t), 7.2 (1H, d), 7.45 (2H, d), 7.9 (1.5H, s), 8.02 (2H, d), 8.7 (2H, brs), 8.7 (1H, s), 11.0 (1H, s) |
| V-7 | 471.2 | 2.67 | DMSO 1.8-2.0 (2H, m), 3.2-3.3 (3H, m), 3.3-3.4 (1H, m), 3.4-3.5 (1H, m), 3.6-3.75 (2H, m), 3.77 (3H, s), 3.8-3.9 (1H, m), 7.3-7.4 (2H, m), 7.55 (1H, d), 7.7 (1H, d), 7.9 (1H, vbrs), 8.33-8.4 (2H, m), 8.7-8.8 (2H, m), 9.05 (1H, s), |
| V-8 | 457 | 2.77 | DMSO 1.6-1.7 (1H, m), 1.8-1.85 (1H, m), 2.65-2.8 (3H, m), 2.85-2.9 (1H, m), 3.4-3.5 (2H, m), 3.55-3.6 (2H, m), 7.1-7.2 (1H, m), 7.3-7.5 (3H, m), 7.7-7.8 (2H, m), 8.3-8.4 (2H, m), 9.0 (1H, s), 10.9 (1H, s), 13.0 (1H, s), |
| V-9 | 474.1 | 2.63 | DMSO 2.8-2.9 (3H, m), 2.95-3.02 (1H.m), 3.35-3.45 (2H, m), 3.65-3.7 (2H, m), 7.35 (1H, t), 7.5-7.6 (4H, m), 7.7-7.8 (3H, m), 8.1 (1H, d), 8.35-8.4 (2H, m), 8.05 (1H, s) |
| V-10 | 457.23 | 2.85 | dmso d6 1.60 (1H, m), 1.76 (1H, m), 2.67-2.90 (4H, m), 3.35-3.44 (2H, m), 3.55-3.70 (2H, m), 7.14-7.16 (2H, m), 7.48-7.54 (4H, m), 7.82 (2H, br s), 8.30-8.37 (2H, m), 9.03 (1H, s) |
| V-11 | 409 | 2.43 | — |
| V-12 | 409 | 3.11 | — |
| V-13 | 409 | 3.05 | — |
| V-14 | 333 | 2.06 | — |
| V-15 | 331 | 2.41 | 1H NMR (400.0 MHz, DMSO) d 11.00 (s, 1H), 10.67 (s, 1H), 9.65 (d, J = 1.9 Hz, 1H), 9.09 (s, 1H), 9.03 (d, J = 8.2 Hz, 1H), 8.73 (dd, J = 1.2, 5.2 Hz, 1H), 7.79 (dd, J = 5.2, 8.0 Hz, 3H), 7.50 (d, J = 7.8 Hz, 1H), 7.35 (t, J = 2.8 Hz, 1H), 7.21 (d, J = 7.4 Hz, 1H), 7.04 (t, J = 7.7 Hz, 1H) and 6.50 (dd, J = 2.0, 2.9 Hz, 1H) ppm |
| V-16 | 331 | 8.42 | — |
| V-17 | 331 | 7.99 | — |
| V-18 | 409 | 3.05 | — |
| V-19 | 409 | 3.11 | — |
| V-20 | 409 | 2.43 | — |
| V-21 | 402.08 | 2.35 | dmso d6 2.97, 3.02 (2x3H, 2xs), 7.15-7.18 (2H, m), 7.51-7.55 (4H, m), 7.83 (2H, br s), 8.34 (2H, d), 9.04 (1H, s), 11.50 (1H, br hump), 12.35 (1H, br hump) |
| V-22 | 474.1 | 2.63 | DMSO 2.8-2.9 (3H, m), 2.95-3.02 (1H.m), 3.35-3.45 (2H, m), 3.65-3.7 (2H, m), 7.35 (1H, t), 7.5-7.6 (4H, m), 7.7-7.8 (3H, m), 8.1 (1H, d), 8.35-8.4 (2H, m), 8.05 (1H, s) |
| V-23 | 457 | 2.77 | DMSO 1.6-1.7 (1H, m), 1.8-1.85 (1H, m), 2.65-2.8 (3H, m), 2.85-2.9 (1H, m), 3.4-3.5 (2H, m), 3.55-3.6 (2H, m), 7.1-7.2 (1H, m), 7.3-7.5 (3H, m), 7.7-7.8 (2H, m), 8.3-8.4 (2H, m), 9.0 (1H, s), 10.9 (1H, s), 13.0 (1H, s), |
| V-24 | 457.23 | 2.85 | dmso d6 1.60 (1H, m), 1.76 (1H, m), 2.67-2.90 (4H, m), 3.35-3.44 (2H, m), 3.55-3.70 (2H, m), 7.14-7.16 (2H, m), 7.48-7.54 (4H, m), 7.82 (2H, br s), 8.30-8.37 (2H, m), 9.03 (1H, s) |
| V-25 | 471.2 | 2.67 | DMSO 1.8-2.0 (2H, m), 3.2-3.3 (3H, m), 3.3-3.4 (1H, m), 3.4-3.5 (1H, m), 3.6-3.75 (2H, m), 3.77 (3H, s), 3.8-3.9 (1H, m), 7.3-7.4 (2H, m), 7.55 (1H, d), 7.7 (1H, d), 7.9 (1H, vbrs), 8.33-8.4 (2H, m), 8.7-8.8 (2H, m), 9.05 (1H, s), |
| V-26 | 456.2 | 2.45 | DMSO 1.8-2.0 (2H, m), 3.5-3.6 (2H, m), 3.7-3.8 (2H, m), 3.8-3.85 (2H, m), 6.6-6.7 (2H, m), 6.75 (1H, bs), 6.85 (1H, t), 7.2 (1H, d), 7.45 (2H, d), 7.9 (1.5H, s), 8.02 (2H, d), 8.7 (2H, brs), 8.7 (1H, s), 11.0 (1H, s) |
| V-27 | 458.2 | 2.77 | DMSO 1.8-2.0 (2H, m), 3.5-3.6 (2H, m), 3.7-3.8 (2H, m), 3.8-3.85 (2H, m), 7.35-7.4 (H, m), 7.6 (2H, d), 7.7 (2H, t), 7.8 (2H, s), 8.4 (2H, d), 8.7-8.8 (2H, m), 9.03 (1H, s), 11.8 (1H, s) |

-continued

| Cmpd No. | LCMS ES+ | LCMS R(t) min | HNMR |
|---|---|---|---|
| V-28 | 457.3 | 2.42 | MeOD 2.1-2.3 (2H, m), 3.3-3.4 (2H, m), 3.5-3.55 (1.5H, m), 3.6-3.65 (1.5H, m), 3.85-3.9 (1H, m), 4.1-4.15 (1.5H, m), 7.65 (2H, d), 7.6 (2H, d), 7.75-7.8 (2H, m), 8.25 (2H, d), 8.65 (1H, s), 8.8 (1H, s), 9.4 (1H, s), 10.7 (1H, s) |
| V-29 | 482.2 | 2.72 | 1.61 + 1.76 (2H, 2xm), 2.74-2.82 (3H, m), 2.90 (1H, m), 3.40 (2H, m), 3.53 (2H, m), 7.15 (2H, dt), 7.52 (2H, dt), 7.86 (1H, dq), 8.00-8.18 (2H, br hump), 8.06 (1H, m), 8.29 (1H, dd), 9.00 (1H, s) |
| V-30 | 357.13 | 3.00 | dmso d6 7.26 (2H, m), 7.60 (2H, m), 8.29 (1H, d), 8.0-8.5 (2H, br hump), 8.96 (1H, d), 9.15 (2H, d), |

The compounds of Table B were synthesized using the methods described herein as well as those known in the art. More specifically, the compounds were made using one or more of the following methods: benzothiazolyl compounds can be made according to methods described in Schemes I-H1 and I-H2; benzoxazolyl compounds can be made according to methods described in Schemes I-G1. Benzimidazolyl compounds can be made according to methods described in Schemes I-I1 and I-I2. Heteroaromatic amides can be made according to methods described in Schemes I-A1 and I-A2.

TABLE B

| Cmpd No. | LCMS ES+ | LCMS R(t) min | HNMR |
|---|---|---|---|
| III-7 | 532.34 | 3.71 | Lot 1: dmso d6 1.28 + 1.44 (9H, 2xs), 1.59 + 1.80 (2H, 2xs), 3.35-3.73 (8H, m), 7.12 (1H, m), 7.32 (1H, m), 7.49 (3H, m), 8.36 (2H, m), 8.91 (1H, s), 13.36 (1H, s) |
| III-8 | 432.22 | 2.53 | Lot 1: dmso d6 1.60 + 1.76 (2H, 2xs), 2.75-2.88 (4H, m), 3.38 (2H, d), 3.64 (2H, d), 7.11 (1H, m), 7.32 (1H, m), 7.52 (3H, m), 8.36 (2H, m), 8.89 (1H, s) |
| III-9 | 460.28 | 2.55 | — |
| III-10 | 446.28 | 2.53 | — |
| III-11 | 418.19 | 2.51 | — |
| III-12 | 414.00 | 2.44 | Lot 1: H NMR (400.0 MHz, DMSO) d 8.88 (s, 1H), 8.79 (s, 2H), 8.39 (d, J = 8.3 Hz, 2H), 7.72 (s, 2H), 7.58 (d, J = 8.3 Hz, 2H), 7.31 (q, J = 3.0 Hz, 2H), 3.86 (br s, 1H), 3.73 (br s, 1H), 3.65 (br s, 1H), 3.50 (br s, 1H), 3.34 (br s, 1H), 3.26 (br s, 3H), 2.06 (br s, 1H) and 1.96 (br s, 1H) ppm |
| III-13 | 432.00 | 2.51 | — |
| III-14 | 428.00 | 2.56 | — |
| III-15 | 444.00 | 2.43 | — |
| III-16 | 442.00 | 2.45 | Lot 1: H NMR (400.0 MHz, DMSO) d 9.65 (s, 1H), 8.88 (s, 1H), 8.39 (d, J = 8.3 Hz, 2H), 7.72 (s, 2H), 7.55 (d, J = 8.3 Hz, 2H), 7.31 (q, J = 2.9 Hz, 2H), 4.66 (br s, 1H), 3.80-2.97 (m, 2H), 2.79 (s, 3H), 2.78 (s, 3H), 2.00 (br s, 3H) and 1.64 (d, J = 9.7 Hz, 3H) ppm |
| III-17 | 460.00 | 2.53 | — |
| III-18 | 456.00 | 2.58 | — |
| III-19 | 474.00 | 2.65 | — |
| III-20 | 472.00 | 2.45 | Lot 1: H NMR (400.0 MHz, DMSO) d 9.63 (s, 1H), 8.85 (s, 1H), 8.37 (d, J = 8.4 Hz, 2H), 7.62 (d, J = 7.2 Hz, 1H), 7.55 (d, J = 8.3 Hz, 2H), 7.15 (s, 1H), 6.94 (dd, J = 2.1, 8.8 Hz, 1H), 4.65 (br s, 2H), 3.85 (s, 3H), 3.47 (br s, 3H), 2.78 (d, J = 4.9 Hz, 6H), 2.00 (br s, 2H) and 1.63 (d, J = 9.1 Hz, 2H) ppm |
| III-21 | 510.00 | 2.79 | — |
| III-22 | 400.00 | 2.43 | — |
| III-23 | 418.00 | 2.50 | — |
| III-24 | 414.00 | 2.55 | — |
| III-25 | 432.00 | 2.64 | — |
| III-26 | 430.00 | 2.42 | — |
| III-27 | 468.00 | 2.76 | — |
| III-28 | 428.00 | 2.44 | — |
| III-29 | 446.00 | 2.51 | — |
| III-30 | 442.00 | 2.56 | Lot 1: H NMR (400.0 MHz, DMSO) d 13.05 (s, 1H), 9.96 (s, 1H), 8.88 (s, 1H), 8.39 (d, J = 7.2 Hz, 2H), 7.67 (d, J = 8.4 Hz, 2H), 7.49 (s, 1H), 7.22 (t, J = 7.6 Hz, 1H), 7.09 (d, J = 7.2 Hz, 1H), 3.95-3.88 (m, 1H), 3.71-3.61 (m, 3H), 2.90-2.76 (m, 6H), 2.68-2.65 (m, 3H), 2.33 (s, 1H), 2.13 (d, J = 6.8 Hz, 1H) and 1.21 (t, J = 7.0 Hz, 1H) ppm |

TABLE B-continued

| Cmpd No. | LCMS ES+ | LCMS R(t) min | HNMR |
|---|---|---|---|
| III-31 | 460.00 | 2.63 | — |
| III-32 | 458.00 | 2.43 | — |
| III-33 | 433.00 | 3.26 | Lot 1: H NMR (400.0 MHz, DMSO) d 13.35 (s, 1H), 8.90 (s, 1H), 8.36 (d, J = 7.3 Hz, 2H), 7.53-7.49 (m, 3H), 7.35-7.31 (m, 1H), 7.14-7.09 (m, 1H), 3.77-3.64 (m, 7H), 3.49 (d, J = 5.4 Hz, 1H), 1.91 (s, 1H) and 1.76 (s, 1H) ppm |
| III-34 | 446.00 | 3.40 | — |
| III-35 | 482.00 | 2.79 | — |
| VI-1 | 431.12 | 3.47 | (DMSO) 1.91-1.96 (2H, m), 3.25-3.49 (6H, m - partially hidden by water peak), 3.64-3.85 (3H, m), 7.51 (1H, m), 7.55 (3H, m), 8.16-8.19 (4H, m), 8.73 (1H, m), 8.97 (1H, s) |
| VI-2 | 415.16 | 3.20 | (DMSO) 2.00-2.12 (2H, m), 3.29-3.89 (8H, m) signal partially obscured by water peak, 7.51-7.59 (2H, m), 7.63-7.65 (2H, m), 7.96-7.99 (2H, m), 8.15 (2H, br s), 8.22-8.24 (2H, m), 8.77 (1H, s), 9.02 (1H, s) |
| VI-3 | 531.19 | 4.09 | (DMSO) 1.25-1.44 (12H, m), 1.62 (1H, m), 1.79 (1H, m), 3.41-3.63 (8H, m), 3.72 (1H, m)7.45-7.58 (3H, m), 7.61 (1H, m), 7.73 (1H, m), 8.16 (4H, m ), 8.97 (1H, s) |
| VII-1 | 400 | 3.55 | — |
| VII-2 | 384 | 3.23 | — |
| VII-3 | 387 | 2.98 | H NMR (400.0 MHz, DMSO) d 10.56 (s, 1H), 9.08 (s, 1H), 8.55 (d, J = 8.7 Hz, 2H), 7.98 (d, J = 8.5 Hz, 2H), 7.86 (s, 2H), 6.08 (s, 1H), 3.64 (s, 3H), 3.27 (s, 3H) and 2.16 (s, 3H) ppm |
| VII-4 | 398 | 2.88 | — |
| VII-5 | 384 | 3.45 | H NMR (400.0 MHz, DMSO) d 10.37 (s, 1H), 9.05 (s, 1H), 8.36 (dd, J = 1.8, 8.5 Hz, 2H), 8.08-8.02 (m, 3H), 7.93 (s, 2H), 7.80 (t, J = 7.8 Hz, 1H), 7.09 (d, J = 7.5 Hz, 1H), 3.28 (s, 3H) and 2.47 (s, 3H) ppm |
| VII-6 | 370 | 2.63 | — |
| VII-7 | 377 | 2.90 | — |
| VII-8 | 390 | 3.13 | — |
| VII-9 | 400 | 2.22 | — |
| VII-10 | 412.2 | 2.33 | H NMR (400.0 MHz, DMSO) d 2.27 (s, 3H), 2.98 (br s, 1H), 3.28 (s, 3H), 3.63 (s, 2H), 7.34 (d, J = 8.4 Hz, 2H), 7.75 (d, J = 8.5 Hz, 2H), 7.89 (Br s, 2H), 8.01 (d, J = 8.6 Hz, 2H), 8.51 (d, J = 8.5 Hz, 2H), 9.04 (s, 1H) and 10.43 (s, 1H) ppm |
| VII-11 | 440.3 | 2.48 | H NMR (400.0 MHz, DMSO) d 1.04 (d, J = 6.8 Hz, 6H), 2.11 (s, 3H), 2.89 (br s, 1H), 3.33 (sept, 1H), 3.48 (s, 2H), 7.18 (d, J = 8.4 Hz, 2H), 7.60 (d, J = 8.5 Hz, 2H), 7.73 (br s, 2H), 7.77 (d, J = 8.6 Hz, 2H), 8.37 (d, J = 8.5 Hz, 2H), 8.89 (s, 1H) and 10.28 (s, 1H) ppm |
| VII-12 | 440.2 | 1.08 | H NMR (400.0 MHz, DMSO) d 1.20 (d, J = 6.9 Hz, 6H), 2.30 (s, 3H), 3.46 (sept, 1H), 3.68 (s, 2H), 7.13 (d, 1H), 7.34 (t, 1H), 7.70 (d, 1H), 7.78 (br s, 1H), 7.93 (d, 2H), 7.94 (br s, 2H), 8.53 (d, 2H), 9.04 (s, 1H) and 10.43 (s, 1H) ppm |
| VII-13 | 412.2 | 1.00 | H NMR (400.0 MHz, DMSO) d 2.29 (s, 3H), 3.28 (s, 3H), 3.67 (s, 2H), 7.13 (d, 1H), 7.34 (t, 1H), 7.70 (d, 1H), 7.77 (s, 1H), 7.90 (br s, 2H), 8.01 (d, 2H), 8.51 (d, 2H), 9.04 (s, 1H) and 10.43 (s, 1H) ppm |

Examples 75A

Cellular ATR Inhibition Assay

Compounds can be screened for their ability to inhibit intracellular ATR using an immunofluorescence microscopy assay to detect phosphorylation of the ATR substrate histone H2AX in hydroxyurea treated cells. HT29 cells are plated at 14,000 cells per well in 96-well black imaging plates (BD 353219) in McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media from a final concentration of 25 μM in 3-fold serial dilutions and the cells are incubated at 37° C. in 5% $CO_2$. After 15 min, hydroxyurea (Sigma H8627) is added to a final concentration of 2 mM.

After 45 min of treatment with hydroxyurea, the cells are washed in PBS, fixed for 10 min in 4% formaldehyde diluted in PBS (Polysciences Inc 18814), washed in 0.2% Tween-20 in PBS (wash buffer), and permeabilised for 10 min in 0.5% Triton X-100 in PBS, all at room temperature. The cells are then washed once in wash buffer and blocked for 30 min at room temperature in 10% goat serum (Sigma G9023) diluted in wash buffer (block buffer). To detect H2AX phosphorylation levels, the cells are then incubated for 1 h at room temperature in primary antibody (mouse monoclonal anti-phosphorylated histone H2AX Ser139 antibody; Upstate 05-636) diluted 1:250 in block buffer. The cells are then washed five times in wash buffer before incubation for 1 h at room temperature in the dark in a mixture of secondary antibody (goat anti-mouse Alexa Fluor 488 conjugated antibody; Invitrogen A11029) and Hoechst stain (Invitrogen H3570); diluted 1:500 and 1:5000, respectively, in wash buffer. The cells are then washed five times in wash buffer and finally 100 ul PBS is added to each well before imaging.

Cells are imaged for Alexa Fluor 488 and Hoechst intensity using the BD Pathway 855 Bioimager and Attovision software (BD Biosciences, Version 1.6/855) to quantify phosphorylated H2AX Ser139 and DNA staining, respectively. The percentage of phosphorylated H2AX-positive nuclei in a montage of 9 images at 20× magnification is then calculated for each well using BD Image Data Explorer software (BD Biosciences Version 2.2.15). Phosphorylated H2AX-positive nuclei are defined as Hoechst-positive regions of interest containing Alexa Fluor 488 intensity at 1.75-fold the average Alexa Fluor 488 intensity in cells not treated with hydroxyurea. The percentage of H2AX positive nuclei is finally plotted against concentration for each compound and IC50s for intracellular ATR inhibition are determined using Prism software (GraphPad Prism version 3.0 cx for Macintosh, GraphPad Software, San Diego Calif., USA).

The compounds described herein can also be tested according to other methods known in the art (see Sarkaria et al, "Inhibition of ATM and ATR Kinase Activities by the Radiosensitizing Agent, Caffeine: *Cancer Research* 59: 4375-5382 (1999); Hickson et al, "Identification and Characterization of a Novel and Specific Inhibitor of the Ataxia-Telangiectasia Mutated Kinase ATM" *Cancer Research* 64: 9152-9159 (2004); Kim et al, "Substrate Specificities and Identification of Putative Substrates of ATM Kinase Family Members" *The Journal of Biological Chemistry*, 274(53): 37538-37543 (1999); and Chiang et al, "Determination of the catalytic activities of mTOR and other members of the phosphoinositide-3-kinase-related kinase family" *Methods Mol. Biol.* 281:125-41 (2004)).

Example 76A

ATR Inhibition Assay

Compounds were screened for their ability to inhibit ATR kinase using a radioactive-phosphate incorporation assay. Assays were carried out in a mixture of 50 mM Tris/HCl (pH 7.5), 10 mM MgCl2 and 1 mM DTT. Final substrate concentrations were 10 µM [γ-33P]ATP (3mCi 33P ATP/mmol ATP, Perkin Elmer) and 800 µM target peptide (ASELPASQPQPFSAKKK (SEQ ID NO: 1)).

Assays were carried out at 25° C. in the presence of 5 nM full-length ATR. An assay stock buffer solution was prepared containing all of the reagents listed above, with the exception of ATP and the test compound of interest. 13.5 µL of the stock solution was placed in a 96 well plate followed by addition of 2 µL of DMSO stock containing serial dilutions of the test compound (typically starting from a final concentration of 15 µM with 3-fold serial dilutions) in duplicate (final DMSO concentration 7%). The plate was pre-incubated for 10 minutes at 25° C. and the reaction initiated by addition of 15 µL [γ-33P]ATP (final concentration 10 µM).

The reaction was stopped after 24 hours by the addition of 30 µL 0.1M phosphoric acid containing 2 mM ATP. A multiscreen phosphocellulose filter 96-well plate (Millipore, Cat no. MAPHN0B50) was pretreated with 100 µL 0.2M phosphoric acid prior to the addition of 45 µL of the stopped assay mixture. The plate was washed with 5×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

Below is a chart showing the ATR Inhibition Ki values of compounds of the disclosure. Compounds with a Ki value of ≤10 nM are marked with "+++." Compounds with a Ki value >10 nM but ≤100 nM are marked with "++." Compounds with a Ki value >100 nM but ≤5 uM are marked with "+."

| Cmpd #: | ATR Ki |
|---|---|
| I-1 | + |
| I-2 | +++ |
| I-3 | + |
| I-4 | + |
| I-5 | ++ |
| I-6 | + |
| I-7 | ++ |
| I-8 | + |
| I-9 | + |
| I-10 | + |
| I-11 | + |
| I-12 | + |
| I-13 | + |
| I-14 | + |
| I-15 | + |
| I-16 | + |
| I-17 | + |
| I-18 | + |
| I-19 | ++ |
| I-20 | ++ |
| I-21 | ++ |
| I-22 | ++ |
| I-23 | ++ |
| I-24 | ++ |
| I-25 | ++ |
| I-26 | + |
| I-27 | ++ |
| I-28 | +++ |
| I-29 | ++ |
| I-30 | ++ |
| I-31 | ++ |
| I-32 | ++ |
| I-33 | + |
| I-34 | ++ |
| I-35 | ++ |
| I-36 | ++ |
| I-37 | ++ |
| I-38 | ++ |
| I-39 | ++ |
| I-40 | + |
| I-41 | + |
| I-42 | + |
| I-43 | ++ |
| I-44 | ++ |
| I-45 | ++ |
| I-46 | + |
| I-47 | ++ |
| I-48 | + |
| I-49 | + |
| I-50 | + |
| I-51 | ++ |
| I-52 | + |
| I-53 | + |
| I-54 | + |
| I-55 | + |
| I-56 | + |
| I-57 | + |
| I-58 | + |
| I-59 | + |
| I-60 | + |
| I-61 | + |
| I-62 | + |
| I-63 | + |

| Cmpd #: | ATR Ki |
|---|---|
| I-64 | + |
| I-65 | + |
| I-66 | ++ |
| I-67 | ++ |
| I-68 | ++ |
| I-69 | + |
| I-70 | ++ |
| I-71 | ++ |
| I-72 | ++ |
| I-73 | ++ |
| I-74 | ++ |
| I-75 | ++ |
| I-76 | ++ |
| I-77 | ++ |
| I-78 | ++ |
| I-79 | ++ |
| I-80 | ++ |
| I-81 | +++ |
| I-82 | ++ |
| I-83 | + |
| I-84 | + |
| I-85 | ++ |
| I-86 | ++ |
| I-87 | + |
| I-88 | + |
| I-89 | + |
| I-90 | + |
| I-91 | + |
| I-92 | + |
| I-93 | + |
| I-94 | + |
| I-95 | + |
| I-96 | + |
| I-97 | + |
| I-98 | + |
| I-99 | + |
| I-100 | + |
| I-101 | ++ |
| I-102 | ++ |
| I-103 | ++ |
| I-104 | ++ |
| I-105 | ++ |
| I-106 | ++ |
| I-107 | ++ |
| I-108 | +++ |
| I-109 | +++ |
| I-110 | + |
| I-111 | ++ |
| I-112 | +++ |
| I-113 | + |
| I-114 | +++ |
| I-115 | ++ |
| I-116 | + |
| I-117 | ++ |
| I-118 | +++ |
| I-119 | ++ |
| I-120 | ++ |
| I-121 | ++ |
| I-122 | ++ |
| I-123 | ++ |
| I-124 | ++ |
| I-125 | ++ |
| I-126 | + |
| I-127 | + |
| I-128 | ++ |
| I-129 | ++ |
| I-130 | + |
| I-131 | ++ |
| I-132 | ++ |
| I-133 | ++ |
| I-134 | +++ |
| I-135 | + |
| I-136 | + |
| I-137 | ++ |
| I-138 | ++ |
| I-139 | ++ |
| I-140 | ++ |
| I-141 | ++ |
| I-142 | ++ |
| I-143 | ++ |
| I-144 | +++ |
| I-145 | ++ |
| I-146 | ++ |
| I-147 | +++ |
| I-148 | ++ |
| I-149 | ++ |
| I-150 | ++ |
| I-151 | ++ |
| I-152 | ++ |
| I-153 | ++ |
| IA-1 | +++ |
| IA-2 | ++ |
| IA-4 | +++ |
| IA-5 | +++ |
| IA-6 | +++ |
| IA-7 | ++ |
| IA-8 | +++ |
| IA-9 | +++ |
| IA-10 | +++ |
| IA-11 | ++ |
| IA-12 | ++ |
| IA-13 | ++ |
| IA-14 | +++ |
| IA-15 | +++ |
| IA-16 | +++ |
| IA-17 | ++ |
| IA-18 | +++ |
| IA-19 | +++ |
| IA-20 | +++ |
| IA-21 | ++ |
| IA-22 | ++ |
| IA-23 | +++ |
| IA-24 | ++ |
| IA-25 | ++ |
| IA-26 | +++ |
| IA-27 | ++ |
| IA-28 | +++ |
| IA-29 | +++ |
| IA-30 | +++ |
| IA-31 | +++ |
| IA-32 | ++ |
| IA-33 | + |
| IA-34 | +++ |
| IA-35 | +++ |
| IA-36 | ++ |
| IA-37 | ++ |
| IA-38 | ++ |
| IA-39 | +++ |
| IA-40 | ++ |
| IA-41 | ++ |
| IA-42 | ++ |
| IA-43 | ++ |
| IA-44 | ++ |
| IA-45 | + |
| IA-46 | ++ |
| IA-47 | +++ |
| IA-48 | ++ |
| IA-49 | ++ |
| IA-50 | ++ |
| IA-51 | ++ |
| IA-52 | +++ |
| IA-53 | ++ |
| IA-54 | + |
| IA-55 | + |
| IA-56 | + |
| IA-57 | + |
| IA-58 | ++ |
| IA-59 | ++ |
| IA-60 | +++ |
| IA-61 | ++ |
| IA-62 | ++ |
| IA-63 | ++ |
| IA-64 | ++ |
| IA-65 | + |

| Cmpd #: | ATR Ki |
|---|---|
| IA-66 | ++ |
| IA-67 | ++ |
| IA-68 | +++ |
| IA-69 | ++ |
| IA-70 | +++ |
| IA-71 | +++ |
| IA-72 | + |
| IA-73 | +++ |
| IA-74 | +++ |
| IA-75 | ++ |
| IA-76 | +++ |
| IA-77 | +++ |
| IA-78 | ++ |
| IA-79 | ++ |
| IA-80 | +++ |
| IA-81 | + |
| IA-82 | + |
| IA-83 | +++ |
| IA-84 | +++ |
| IA-85 | ++ |
| IA-86 | + |
| IA-87 | +++ |
| IA-88 | +++ |
| IA-89 | +++ |
| IA-90 | +++ |
| IA-91 | + |
| IA-92 | + |
| IA-93 | + |
| IA-94 | + |
| IA-95 | + |
| IA-96 | + |
| IA-97 | ++ |
| IA-98 | ++ |
| IA-99 | +++ |
| IA-100 | ++ |
| IA-101 | + |
| IA-102 | +++ |
| IA-103 | ++ |
| IA-104 | ++ |
| IA-105 | + |
| IA-106 | ++ |
| IA-107 | +++ |
| IA-108 | +++ |
| IA-109 | + |
| IA-110 | ++ |
| IA-111 | + |
| IA-112 | +++ |
| IA-113 | ++ |
| IA-114 | + |
| IA-115 | ++ |
| IA-116 | +++ |
| IA-117 | + |
| IA-118 | + |
| IA-119 | +++ |
| IA-120 | ++ |
| IA-121 | + |
| IA-122 | +++ |
| IA-123 | +++ |
| IA-124 | +++ |
| IA-125 | + |
| IA-126 | +++ |
| IA-127 | ++ |
| IA-128 | +++ |
| IA-129 | ++ |
| IA-130 | +++ |
| IA-131 | ++ |
| IA-132 | +++ |
| IA-133 | + |
| IA-134 | + |
| IA-135 | +++ |
| IA-136 | ++ |
| IA-137 | ++ |
| IA-138 | ++ |
| IA-139 | +++ |
| IA-140 | +++ |
| IA-141 | +++ |
| IA-142 | +++ |
| IA-143 | ++ |
| IA-144 | ++ |
| IA-145 | +++ |
| IA-146 | +++ |
| IA-147 | +++ |
| IA-148 | + |
| IA-149 | +++ |
| IA-150 | + |
| IA-151 | ++ |
| IA-152 | +++ |
| IA-153 | ++ |
| IA-154 | +++ |
| IA-155 | ++ |
| IA-156 | + |
| IA-157 | ++ |
| IA-158 | +++ |
| IA-159 | +++ |
| IA-160 | + |
| IA-161 | ++ |
| IA-162 | ++ |
| IA-163 | + |
| IA-164 | + |
| IA-165 | ++ |
| IA-166 | +++ |
| IA-167 | +++ |
| IA-168 | + |
| IA-169 | +++ |
| IA-170 | ++ |
| IA-171 | +++ |
| IA-172 | +++ |
| IA-173 | +++ |
| IA-174 | + |
| IA-175 | +++ |
| IA-176 | + |
| IA-177 | ++ |
| IA-178 | +++ |
| IA-179 | +++ |
| IA-180 | ++ |
| IA-181 | +++ |
| IA-182 | + |
| IA-183 | +++ |
| IA-184 | ++ |
| IA-185 | ++ |
| IA-186 | + |
| IA-187 | ++ |
| IA-188 | + |
| IA-189 | ++ |
| IA-190 | + |
| IA-191 | +++ |
| IA-192 | + |
| IA-193 | +++ |
| IA-194 | + |
| IA-195 | ++ |
| IA-196 | +++ |
| IA-197 | +++ |
| IA-198 | ++ |
| IA-199 | + |
| IA-200 | + |
| IA-201 | +++ |
| IA-202 | + |
| IA-203 | + |
| IA-204 | ++ |
| IA-205 | +++ |
| IA-206 | + |
| IA-207 | + |
| IA-208 | +++ |
| IA-209 | ++ |
| IA-210 | ++ |
| IA-211 | + |
| IA-212 | +++ |
| IA-213 | ++ |
| IA-214 | ++ |
| IA-215 | +++ |
| IA-216 | + |
| IA-217 | + |
| IA-218 | ++ |
| IA-219 | + |

| Cmpd #: | ATR Ki | | Cmpd #: | ATR Ki |
|---|---|---|---|---|
| IA-220 | +++ | | IA-299 | +++ |
| IA-221 | + | | IA-300 | +++ |
| IA-222 | +++ | | IA-301 | +++ |
| IA-223 | ++ | | IA-302 | +++ |
| IA-224 | + | | IA-303 | +++ |
| IA-225 | ++ | | IA-304 | +++ |
| IA-226 | +++ | | IA-305 | +++ |
| IA-227 | + | | IA-306 | +++ |
| IA-228 | +++ | | IA-307 | +++ |
| IA-229 | + | | IA-308 | +++ |
| IA-230 | ++ | | IA-309 | +++ |
| IA-231 | ++ | | IA-310 | +++ |
| IA-232 | ++ | | IA-311 | +++ |
| IA-233 | ++ | | IA-312 | +++ |
| IA-234 | +++ | | IA-313 | +++ |
| IA-235 | +++ | | IA-314 | +++ |
| IA-236 | ++ | | IA-315 | +++ |
| IA-237 | ++ | | IA-316 | +++ |
| IA-238 | +++ | | IA-318 | + |
| IA-239 | + | | IA-319 | +++ |
| IA-240 | + | | IA-320 | +++ |
| IA-241 | +++ | | IA-321 | +++ |
| IA-242 | +++ | | IA-322 | +++ |
| IA-243 | +++ | | IA-323 | +++ |
| IA-244 | + | | IA-324 | +++ |
| IA-245 | ++ | | IA-325 | ++ |
| IA-246 | +++ | | IA-326 | +++ |
| IA-247 | ++ | | IA-327 | +++ |
| IA-248 | +++ | | IA-328 | +++ |
| IA-249 | ++ | | IA-329 | +++ |
| IA-250 | + | | IA-330 | +++ |
| IA-251 | + | | IA-331 | +++ |
| IA-252 | ++ | | IA-332 | +++ |
| IA-253 | + | | IA-333 | +++ |
| IA-254 | + | | IA-334 | +++ |
| IA-255 | + | | IA-335 | +++ |
| IA-256 | +++ | | IA-336 | +++ |
| IA-257 | +++ | | IA-337 | +++ |
| IA-258 | +++ | | IA-338 | +++ |
| IA-259 | ++ | | IA-339 | +++ |
| IA-260 | ++ | | IA-340 | +++ |
| IA-261 | ++ | | IA-341 | +++ |
| IA-262 | +++ | | IA-342 | +++ |
| IA-263 | ++ | | IA-343 | +++ |
| IA-264 | +++ | | IA-344 | +++ |
| IA-265 | + | | IA-345 | +++ |
| IA-266 | ++ | | IA-346 | +++ |
| IA-267 | ++ | | IA-347 | +++ |
| IA-268 | ++ | | IA-348 | +++ |
| IA-269 | +++ | | IA-349 | +++ |
| IA-270 | +++ | | IIA-1 | ++ |
| IA-271 | + | | IIA-2 | +++ |
| IA-272 | + | | IIA-3 | +++ |
| IA-273 | ++ | | IIA-4 | +++ |
| IA-274 | +++ | | IIA-5 | +++ |
| IA-275 | ++ | | IIA-6 | +++ |
| IA-276 | +++ | | IIA-7 | +++ |
| IA-277 | +++ | | IIA-8 | +++ |
| IA-278 | + | | IIA-9 | +++ |
| IA-279 | + | | IIA-10 | +++ |
| IA-280 | +++ | | IIA-11 | +++ |
| IA-281 | +++ | | IIA-12 | +++ |
| IA-282 | +++ | | IIA-13 | +++ |
| IA-283 | ++ | | IIA-14 | +++ |
| IA-284 | +++ | | IIA-15 | |
| IA-285 | +++ | | IIA-16 | +++ |
| IA-286 | + | | IIIA-1 | ++ |
| IA-287 | + | | IIIA-2 | ++ |
| IA-288 | +++ | | IIIA-3 | ++ |
| IA-289 | +++ | | IIIA-4 | ++ |
| IA-290 | +++ | | IIIA-5 | ++ |
| IA-291 | +++ | | IIIA-6 | ++ |
| IA-292 | +++ | | IVA-1 | +++ |
| IA-293 | +++ | | IVA-2 | +++ |
| IA-295 | +++ | | IVA-3 | + |
| IA-296 | +++ | | III-1 | ++ |
| IA-297 | +++ | | III-2 | ++ |

-continued

| Cmpd #: | ATR Ki |
|---|---|
| III-3 | ++ |
| III-4 | ++ |
| III-5 | ++ |
| III-6 | ++ |
| III-7 | +++ |
| III-8 | +++ |
| III-9 | ++ |
| III-10 | ++ |
| III-11 | +++ |
| III-12 | ++ |
| III-13 | ++ |
| III-14 | ++ |
| III-15 | ++ |
| III-16 | ++ |
| III-17 | ++ |
| III-18 | ++ |
| III-19 | ++ |
| III-20 | ++ |
| III-21 | ++ |
| III-22 | ++ |
| III-23 | ++ |
| III-24 | ++ |
| III-25 | ++ |
| III-26 | ++ |
| III-27 | + |
| III-28 | ++ |
| III-29 | ++ |
| III-30 | ++ |
| III-31 | ++ |
| III-32 | ++ |
| III-33 | +++ |
| III-34 | ++ |
| III-35 | ++ |
| V-1 | +++ |
| V-2 | +++ |
| V-3 | +++ |
| V-4 | ++ |
| V-5 | ++ |
| V-6 | + |
| V-7 | + |
| V-8 | +++ |
| V-9 | ++ |
| V-10 | +++ |
| V-11 | +++ |
| V-12 | +++ |
| V-13 | + |
| V-14 | + |
| V-15 | + |
| V-16 | ++ |
| V-17 | ++ |
| V-18 | + |
| V-19 | +++ |
| V-20 | +++ |
| V-21 | +++ |
| V-22 | ++ |
| V-23 | +++ |
| V-24 | +++ |
| V-25 | + |
| V-26 | + |
| V-27 | ++ |
| V-28 | ++ |
| V-29 | +++ |
| V-30 | +++ |
| VI-1 | ++ |
| VI-2 | ++ |
| VI-3 | ++ |
| VII-1 | ++ |
| VII-2 | ++ |
| VII-3 | + |
| VII-4 | ++ |
| VII-5 | ++ |
| VII-6 | ++ |
| VII-7 | ++ |
| VII-8 | ++ |
| VII-9 | +++ |
| VII-10 | + |
| VII-11 | ++ |

-continued

| Cmpd #: | ATR Ki |
|---|---|
| VII-12 | +++ |
| VII-13 | ++ |

Example 77A

Cisplatin Sensitization Assay

Compounds were screened for their ability to sensitize HCT116 colorectal cancer cells to Cisplatin using a 96 h cell viability (MTS) assay. HCT116 cells, which possess a defect in ATM signaling to Cisplatin (see, Kim et al.; *Oncogene* 21:3864 (2002); see also, Takemura et al.; *JBC* 281:30814 (2006)) were plated at 470 cells per well in 96-well polystyrene plates (Costar 3596) in 150 µl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds and Cisplatin were then both added simultaneously to the cell media in 2-fold serial dilutions from a top final concentration of 10 µM as a full matrix of concentrations in a final cell volume of 200 µl, and the cells were then incubated at 37° C. in 5% $CO_2$. After 96 h, 40 µl of MTS reagent (Promega G358a) was added to each well and the cells were incubated for 1 h at 37° C. in 5% $CO_2$. Finally, absorbance was measured at 490 nm using a SpectraMax Plus 384 reader (Molecular Devices) and the concentration of compound required to reduce the IC50 of Cisplatin alone by at least 3-fold (to 1 decimal place) was reported.

Compounds with an IC50 or Ki value of ≤100 nM are marked with "+++." Compounds with an IC50 or Ki value >100 nM but ≤1 uM are marked with "++." Compounds with an IC50 or Ki value >1 uM but ≤20 uM are marked with "+."

TABLE C

| Compound No. | ATR Inhibition Assay Ki (uM) | Cellular ATR Inhibition IC50 (uM) | HTC116 (MTS) IC50 (uM) | Synergy with Cisplatin (uM) |
|---|---|---|---|---|
| I-82 | +++ | + | + | ++ |
| IA-159 | +++ | +++ | ++ | +++ |
| IIA-11 | +++ | +++ | ++ | +++ |
| III-8 | +++ | ++ | | |

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:

1. A compound of Formula II:

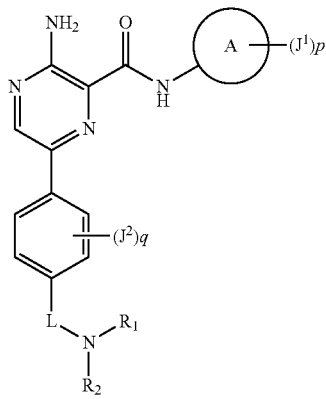

II or a pharmaceutically acceptable salt thereof, wherein:
Ring A is phenyl;
L is C(O);
$R^1$ is $C_1$-$C_6$alkyl;
$R^2$ is —($C_2$-$C_6$alkyl)-Z or a 4-8 membered cyclic ring containing 0-2 nitrogen atoms, wherein said ring is bonded via a carbon atom and is optionally substituted with one occurrence of $J^Z$;
or $R^1$ and $R^2$, taken together with the atom to which they are bound, form a 4-8 membered heterocyclic ring containing 1-2 nitrogen atoms, wherein said heterocyclic ring is optionally substituted with one occurrence of $J^{Z1}$;
$J^{Z1}$ is —(X)$_t$—CN, $C_1$-$C_6$alkyl, or —(X)$_r$—Z;
X is $C_1$-$C_4$alkylene;
each t, p, and r is independently 0 or 1;
Z is —$NR^3R^4$;
$R^3$ is H or $C_1$-$C_2$alkyl;
$R^4$ is H or $C_1$-$C_6$alkyl;
or $R^3$ and $R^4$, taken together with the atom to which they are bound, form a 4-8 membered heterocyclic ring containing 1-2 nitrogen atoms, wherein said ring optionally substituted with one occurrence of $J^Z$;
each of $J^Z$ and $J^1$ is, independently, $NH_2$, $NH(C_1$-$C_4$aliphatic), $N(C_1$-$C_4$aliphatic)$_2$, halogen, $C_1$-$C_4$aliphatic, OH, O($C_1$-$C_4$aliphatic), $NO_2$, CN, $CO_2H$, CO($C_1$-$C_4$aliphatic), $CO_2(C_1$-$C_4$aliphatic), O(halo$C_1$-$C_4$aliphatic), or halo$C_1$-$C_4$aliphatic;
$J^2$ is halo, $C_1$-$C_2$alkyl optionally substituted with 1-3 fluoro, or CN; and
q is 0, 1, or 2.

2. The compound of claim 1, wherein $R^1$ and $R^2$, taken together with the atom to which they are bound, form a 4-8 membered heterocyclic ring containing 1-2 nitrogen atoms.

3. The compound of claim 2, wherein t is 1.

4. The compound of claim 2, wherein t is 0.

5. The compound of claim 2, wherein the heterocyclic ring formed by $R^1$ and $R^2$ is pyrrolidinyl, piperidinyl, piperazinyl, azepanyl, or 1,4-diazepanyl.

6. The compound of claim 5, wherein the heterocyclic ring formed by $R^1$ and $R^2$ is

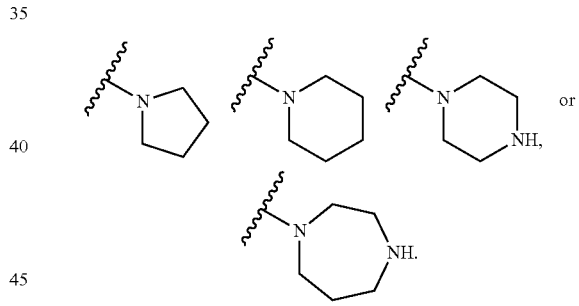

7. The compound of claim 6, wherein the ring formed by $R^1$ and $R^2$ is optionally substituted with $CH_2$pyrrolidinyl, $C_1$-$C_4$alkyl, $N(C_1$-$C_2$alkyl)$_2$, or $CH_2CH_2CN$.

8. The compound of claim 7, wherein $R^3$ and $R^4$ are both $C_1$-$C_2$alkyl.

9. The compound of claim 7, wherein $R^3$ and $R^4$, taken together with the atom to which they are bound, form a ring selected from the group consisting of pyrrolidinyl, piperidinyl, piperazinyl, azepanyl, and 1,4-diazepanyl.

10. The compound of claim 9, wherein said ring is pyrrolidinyl or piperidinyl.

11. The compound of claim 1, wherein $R^2$ is —($C_2$-$C_6$alkyl)-Z.

12. The compound of claim 1, wherein p is 0, q is 0, and -L-$NR^1R^2$ is C(O)-pyrrolidinyl, C(O)-piperidinyl, C(O)-piperazinyl, C(O)-azepanyl, C(O)-1,4-diazepanyl, or C(O)—N(CH$_3$)CH$_2$CH$_2$N(CH$_3$)$_2$, wherein said pyrrolidinyl, piperidinyl, piperazinyl, azepanyl, or 1,4-diazepanyl is optionally substituted with $CH_2$pyrrolidinyl, $C_1$-$C_4$alkyl, N($C_1$-$C_2$alkyl)$_2$, or $CH_2CH_2CN$.

13. The compound of claim 1, the compound is:
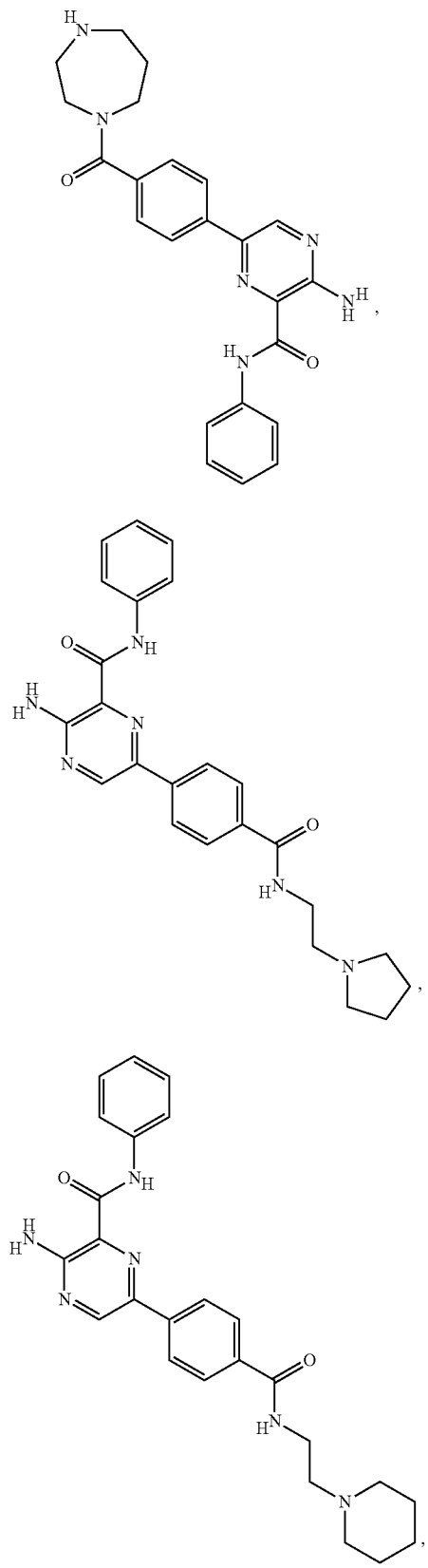
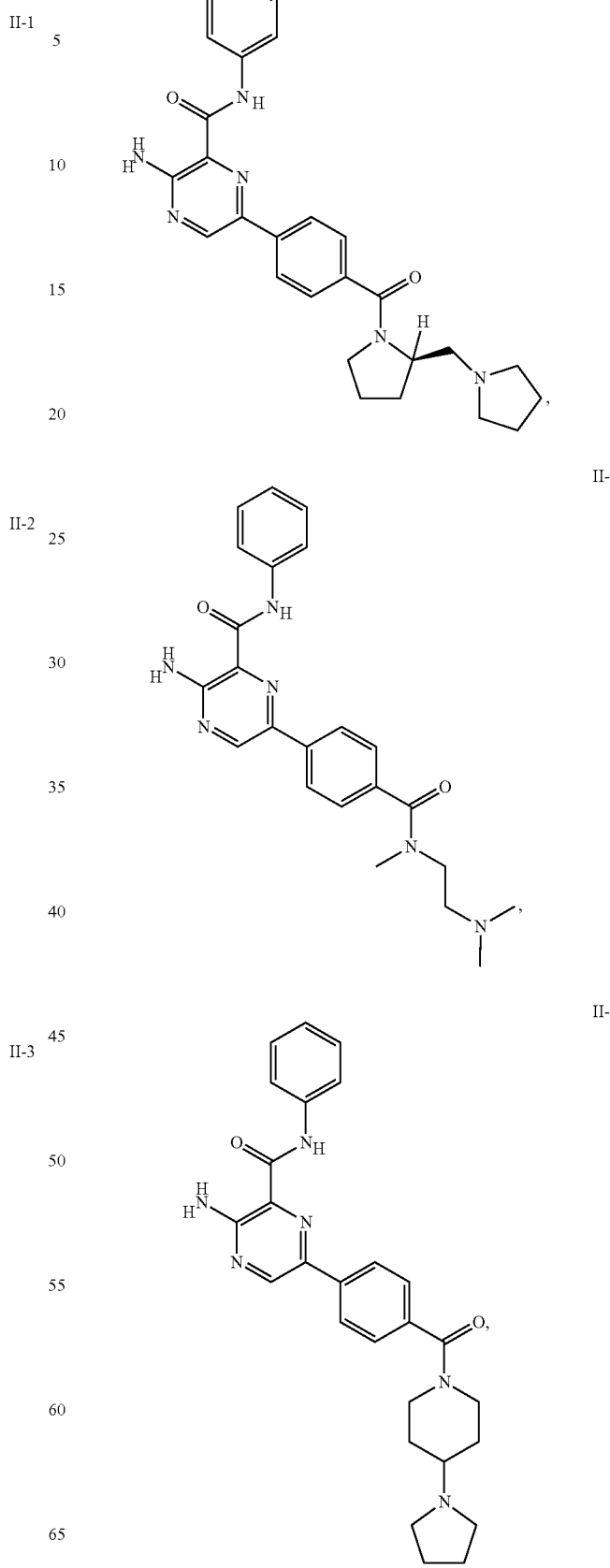

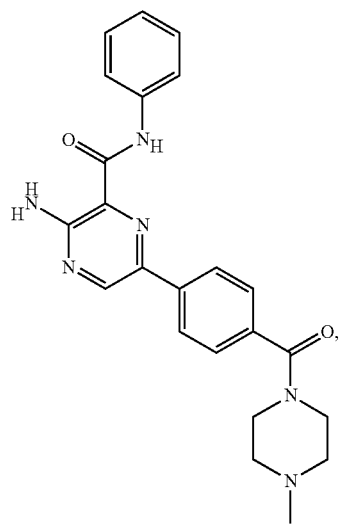
II-7
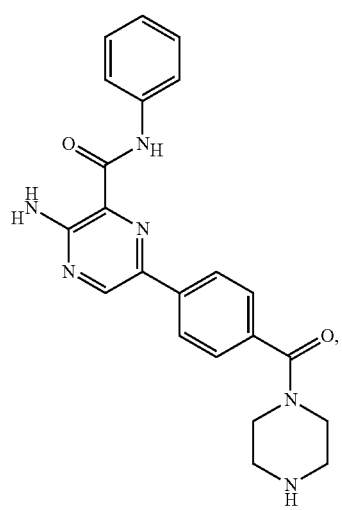
II-8
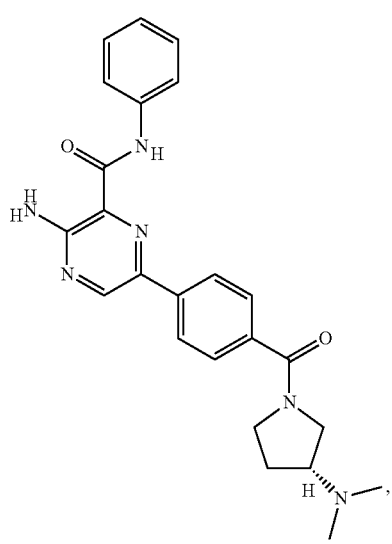
II-9
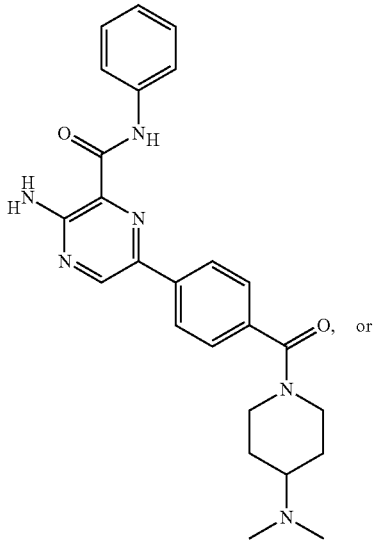
II-10
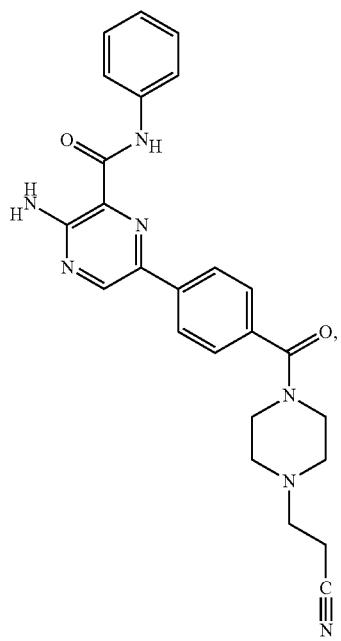
II-11
or a pharmaceutically acceptable salt thereof.
14. A method if inhibiting ATR in a biological sample, comprising the step of contacting a compound of claim 1 with said biological sample.
15. The method of claim 14, wherein said biological sample is a cell.
16. A pharmaceutical composition comprising a compound of formula II,

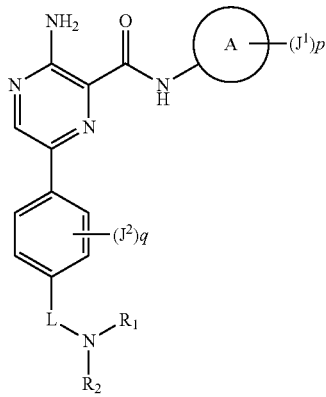

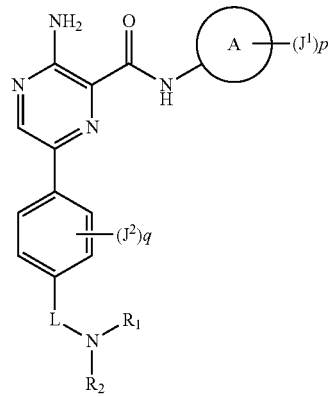

or a pharmaceutically acceptable salt thereof; wherein

Ring A is phenyl;

L is —C(O)—;

$R^1$ is $C_1$-$C_6$alkyl;

$R^2$ is —($C_2$-$C_6$alkyl)—Z or a 4-8 membered cyclic ring containing 0-2 nitrogen atoms; wherein said ring is bonded via a carbon atom and is optionally substituted with one occurrence of $J^z$;

or $R^1$ and $R^2$, taken together with the atom to which they are bound, form a 4-8 membered heterocyclic ring containing 1-2 nitrogen atoms, wherein said heterocyclic ring is optionally substituted with one occurrence of $J^{Z1}$;

$J^{Z1}$ is $(X)_r$—CN, $C_1$-$C_6$alkyl, or —$(X)_r$—Z;

X is $C_1$-$C_4$alkylene;

each t, p, and r is independently 0 or 1;

Z is —$NR^3R^4$;

$R^3$ is H or $C_1$-$C_2$alkyl;

$R^4$ is H or $C_1$-$C_6$alkyl;

or $R^3$ and $R^4$, taken together with the atom to which they are bound, form a 4-8 membered heterocyclic ring containing 1-2 nitrogen atoms, wherein said ring is optionally substituted with one occurrence of $J^z$;

each $J^z$ and $J^1$ is independently $NH_2$, $NH(C_1$-$C_4$aliphatic), $N(C_1$-$C_4$aliphatic$)_2$, halogen, $C_1$-$C_4$aliphatic, OH, O($C_1$-$C_4$aliphatic), $NO_2$, CN, $CO_2H$, CO($C_1$-$C_4$aliphatic), $CO_2(C_1$-$C_4$aliphatic), O(halo$C_1$-$C_4$aliphatic), or halo$C_1$-$C_4$aliphatic;

$J^2$ is halo, $C_1$-$C_2$alkyl optionally substituted with 1-3 fluoro, or CN; and q is 0, 1, or 2;

and a pharmaceutically acceptable carrier.

17. A method of promoting cell death in cancer cells of a patient comprising administering to the patient a compound of formula II, or a pharmaceutically acceptable salt thereof; wherein Ring A is phenyl;

L is —C(O)—;

$R^1$ is $C_1$-$C_6$alkyl;

$R^2$ is —($C_2$-$C_6$alkyl)—Z or a 4-8 membered cyclic ring containing 0-2 nitrogen atoms, wherein said ring is bonded via a carbon atom and is optionally substituted with one occurrence of $J^z$;

or $R^1$ and $R^2$, taken together with the atom to which they are bound, form a 4-8 membered heterocyclic ring containing 1-2 nitrogen atoms, wherein said heterocyclic ring is optionally substituted with one occurrence of $J^{Z1}$;

$j^{Z1}$ is $(X)_r$—CN, $C_1$-$C_6$alkyl, or —$(X)_r$—Z;

X is $C_1$-$C_4$alkylene;

each t, p, and r is independently 0 or 1;

Z is —NR3R4;

$R^3$ is H or $C_1$-$C_2$alkyl;

$R^4$ is H or $C_1$-$C_6$alkyl;

or $R^3$ and $R^4$, taken together with the atom to which they are bound, form a 4-8 membered heterocyclic ring containing 1-2 nitrogen atoms, wherein said ring is optionally substituted with one occurrence of $J^z$;

each $J^z$ and $J^1$ is independently $NH_2$, $NH(C_1$-$C_4$aliphatic), $N(C_1$-$C_4$aliphatic$)_2$, halogen, $C_1$-$C_4$aliphatic, OH, O($C_1$-$C_4$aliphatic), $NO_2$, CN, $CO_2H$, CO($C_1$-$C_4$aliphatic), $CO_2(C_1$-$C_4$aliphatic), O(halo$C_1$-$C_4$aliphatic), or halo$C_1$-$C_4$aliphatic;

$J^2$ is halo, $C_1$-$C_2$alkyl optionally substituted with 1-3 fluoro, or CN; and q is 0, 1, or 2.

18. A method of preventing cell repair from DNA damage in a patient comprising administering to the patient a compound of formula II,

II

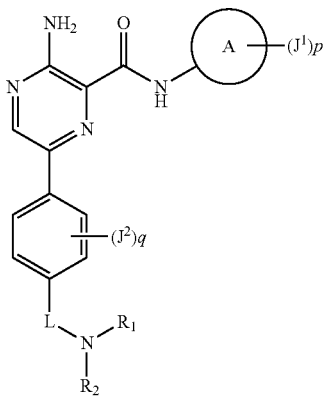

or a pharmaceutically acceptable salt thereof; wherein
Ring A is phenyl;
L is —C(O)—;
$R^1$ is $C_1$-$C_6$alkyl;
$R^2$ is —($C_2$-$C_6$alkyl)—Z or a 4-8 membered cyclic ring containing 0-2 nitrogen atoms, wherein said ring is bonded via a carbon atom and is optionally substituted with one occurrence of $J^Z$;
or $R^1$ and $R^2$, taken together with the atom to which they are bound, form a 4-8 membered heterocyclic ring containing 1-2 nitrogen atoms, wherein said heterocyclic ring is optionally substituted with one occurrence of $J^{Z1}$;
$J^{Z1}$ is $(X)_t$—CN, $C_1$-$C_6$alkyl, or —$(X)_t$—Z;
X is $C_1$-$C_4$alkylene;
each t, p, and r is independently 0 or 1;
Z is —$NR^3R^4$;
$R^3$ is H or $C_1$-$C_2$alkyl;
$R^4$ is H or $C_1$-$C_6$alkyl;
or $R^3$ and $R^4$, taken together with the atom to which they are bound, form a 4-8 membered heterocyclic ring containing 1-2 nitrogen atoms, wherein said ring is optionally substituted with one occurrence of $J^Z$;
each $J^Z$ and $J^1$ is independently $NH_2$, $NH(C_1$-$C_4$aliphatic), $N(C_1$-$C_4$aliphatic)$_2$, halogen, $C_1$-$C_4$aliphatic, OH, O($C_1$-$C_4$aliphatic), $NO_2$, CN, $CO_2H$, CO($C_1$-$C_4$aliphatic), $CO_2(C_1$-$C_4$aliphatic), O(halo$C_1$-$C_4$aliphatic), or halo$C_1$-$C_4$aliphatic;
$J^2$ is halo, $C_1$-$C_2$alkyl optionally substituted with 1-3 fluoro, or CN; and
q is 0, 1, or 2.

19. A compound of Formula V:

V

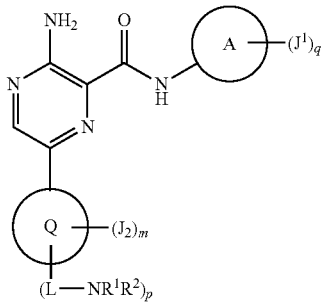

or a pharmaceutically acceptable salt thereof, wherein:
Ring A is an 8-9 membered bicyclic heteroaryl ring having 1-4 heteroatoms selected from the group consisting of oxygen, nitrogen, and sulfur;
Ring Q is a 5-6 membered monocyclic aromatic ring containing 0-3 heteroatoms independently selected from the group consisting of nitrogen, oxygen, and sulfur;
L is a $C_1$-$C_4$alkylene chain, wherein up to two methylene units of the alkylene chain are optionally replaced with O, $NR^6$, S, —C(O)—, —S(O)—, or —$S(O)_2$—;
$R^1$ is H or $C_1$-$C_6$alkyl;
$R^2$ is H, $C_1$-$C_6$alkyl, —($C_2$-$C_6$alkyl)-Z, or a 3-8 membered cyclic ring containing 0-2 nitrogen atoms, wherein said ring is bonded via a carbon atom and is optionally substituted with one occurrence of $J^Z$;
or $R^1$ and $R^2$, taken together with the atom to which they are bound, form a 3-8 membered monocyclic or 8-9 membered bicyclic heterocyclic ring containing 1-2 heteroatoms selected the group consisting of oxygen, nitrogen, and sulfur, wherein said heterocyclic ring is optionally substituted with one occurrence of $J^{Z1}$;
$J^{Z1}$ is —$(X)_t$—CN, $C_1$-$C_6$alkyl or —$(X)_r$—$Z^1$;
X is $C_1$-$C_4$alkylene;
Z is —$NR^3R^4$;
$R^3$ is H or $C_1$-$C_2$alkyl;
$R^4$ is H or $C_1$-$C_6$alkyl;
or $R^3$ and $R^4$, taken together with the atom to which they are bound, form a 4-8 membered heterocyclic ring containing 1-2 nitrogen atoms, wherein said ring is optionally substituted with one occurrence of $J^Z$;
$Z^1$ is —$NR^5R^6$;
$R^5$ is H or $C_1$-$C_2$alkyl;
$R^6$ is H or $C_1$-$C_6$alkyl;
or $R^5$ and $R^6$, taken together with the atom to which they are bound, form a 4-8 membered heterocyclic ring containing 1-2 nitrogen atoms, wherein said ring is optionally substituted with one occurrence of $J^{Z1}$;
$J^1$ is halo, CN, or a $C_1$-$C_6$aliphatic group wherein up to 2 methylene units are optionally replaced with O, NR", C(O), S, S(O), or $S(O)_2$, wherein said $C_1$-$C_6$aliphatic group is optionally substituted with 1-3 fluoro or CN;
$J^2$ is halo; CN; or a $C_1$-$C_6$aliphatic group wherein up to 2 methylene units are optionally replaced with O, NR", C(O), S, S(O), or $S(O)_2$, wherein said $C_1$-$C_6$aliphatic group is optionally substituted with 1-3 fluoro or CN;
$J^Z$ is independently $NH_2$, $NH(C_1$-$C_4$aliphatic), $N(C_1$-$C_4$aliphatic)$_2$, halogen, $C_1$-$C_4$aliphatic, OH, O($C_1$-$C_4$aliphatic), $NO_2$, CN, $CO_2H$, CO($C_1$-$C_4$aliphatic), $CO_2(C_1$-$C_4$aliphatic), O(halo $C_1$-$C_4$aliphatic), or halo $C_1$-$C_4$aliphatic;
R' is independently H or $C_1$-$C_4$ alkyl;
each q and m is independently 0, 1, or 2; and
each t, p, and r is independently 0 or 1.

20. The compound of claim 14, wherein Ring A is a 9-membered bicyclic heteroaryl ring.

21. The compound of claim 20, wherein L is C(O) or $S(O)_2$.

22. The compound of claim 21, wherein $R^1$ and $R^2$ are both $C_1$-$C_4$alkyl.

23. The compound of claim 19, wherein Ring A is benzimidazolyl, benzoxazolyl, indazolyl, benzothiazolyl, or indolyl.

24. The compound of claim 19, wherein Ring A is benzimidazolyl, benzoxazolyl, indazolyl, benzothiazolyl, indolyl, or pyrrolopyridinyl.

25. The compound of claim 24, wherein said 4-7 membered monocyclic heterocyclic ring is 1,4-diazepanyl.

26. The compound of claim 14, wherein Ring A has 1-2 heteroatoms.

27. The compound of claim 26, wherein p is 1 and Ring Q is substituted in the para position with L-NR$^1$R$^2$ as shown in Formula V-a:

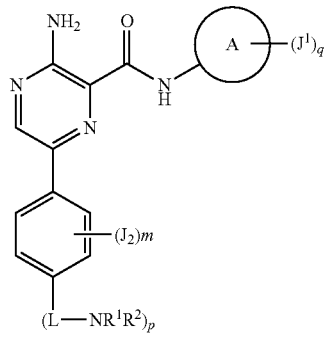

V-a or a pharmaceutically acceptable salt thereof.

28. The compound of claim 20, wherein L is C(O) or S(O)$_2$.

29. The compound of claim 14, wherein Ring A is a 9-membered bicyclic heteroaryl ring.

30. The compound of claim 14, wherein Ring A is an 8-membered bicyclic heteroaryl ring.

31. The compound of claim 23, wherein said 4-7 membered monocyclic heterocyclic ring is selected from the group consisting of pyrrolidinyl, piperidinyl, piperazinyl, azepanyl, and 1,4-diazepanyl.

32. The compound of claim 24, wherein said 4-7 membered monocyclic heterocyclic ring is 1,4-diazepanyl.

33. The compound of claim 15, wherein Ring Q is pyridyl.

34. The compound of claim 16, wherein p is 0.

35. The compound of claim 33, wherein m is 1, and J$^2$ is CN.

36. The compound of claim 19, wherein the compound is:

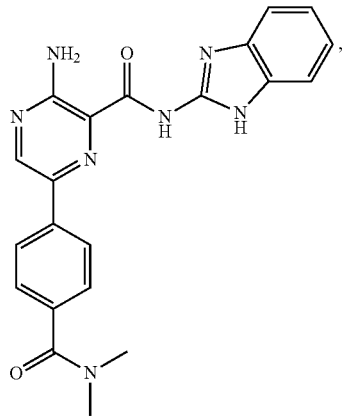

V-1

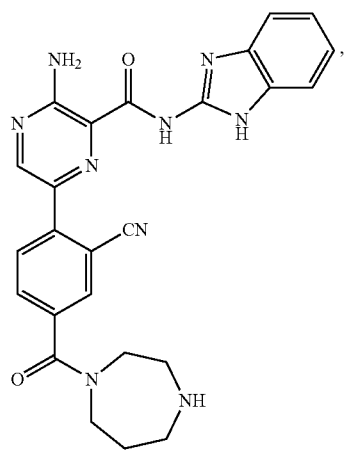

V-2

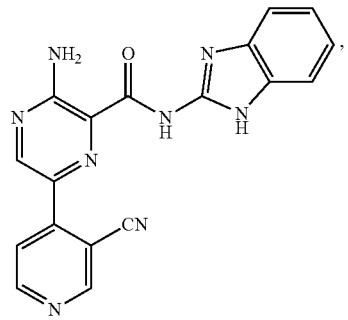

V-3

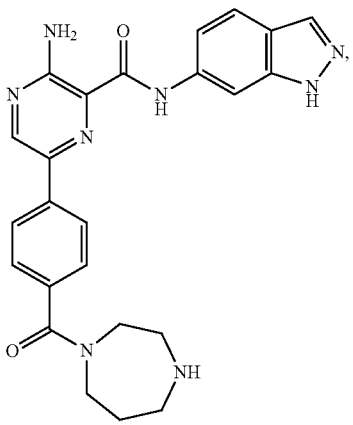

V-4

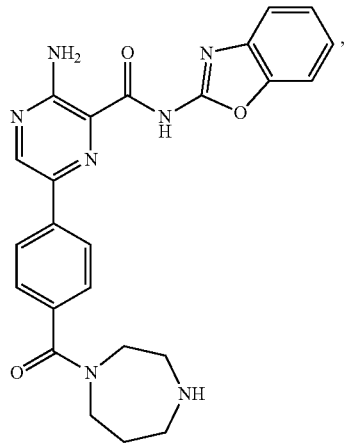

V-5

V-6
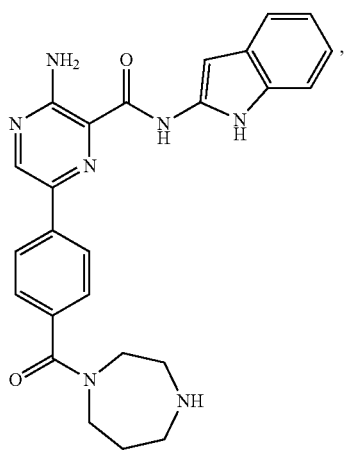
V-7
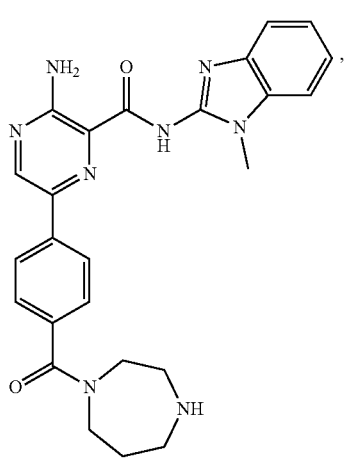
V-8
V-9
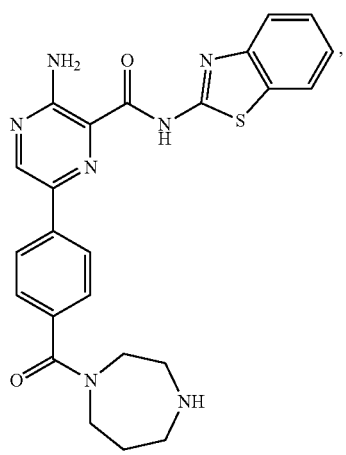
V-10
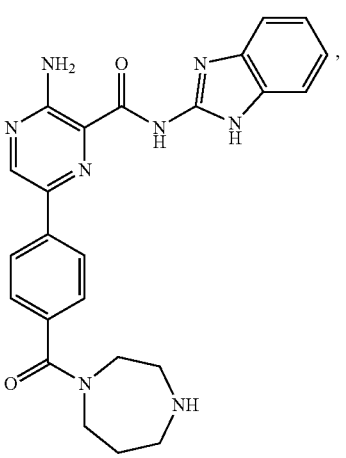
V-11
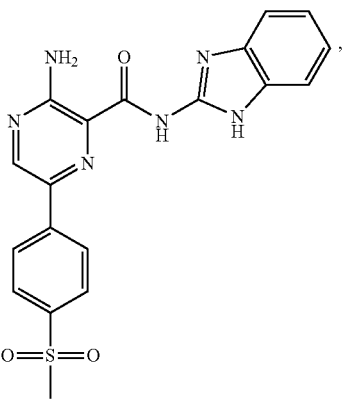

V-12 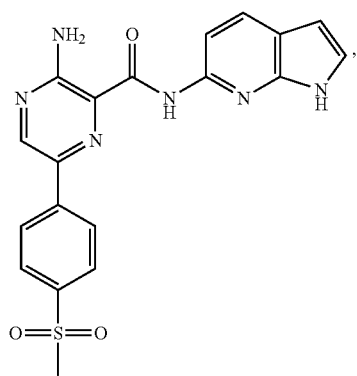
V-13 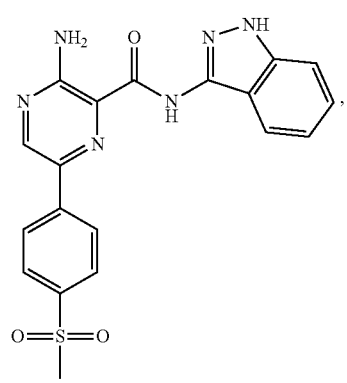
V-14 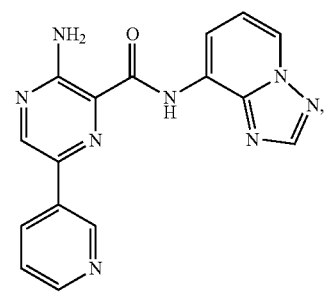
V-15 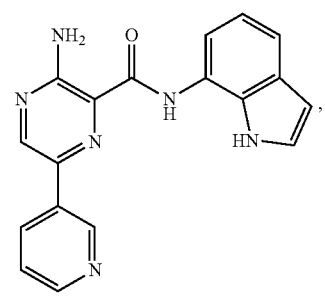
V-16 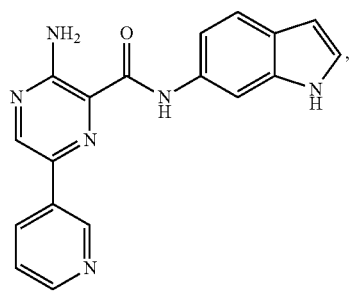
V-17 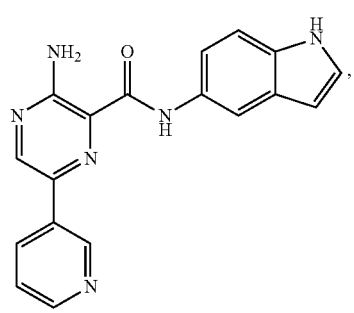
or a pharmaceutically acceptable salt thereof.
37. The compound of claim 19, wherein the compound is:
V18 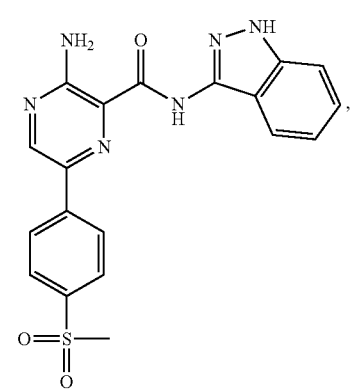
V19 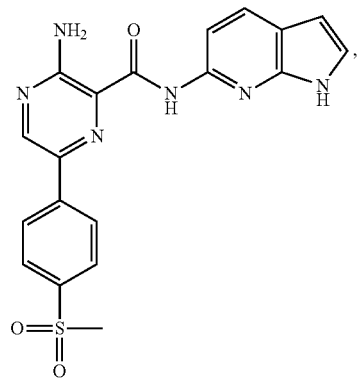
V20 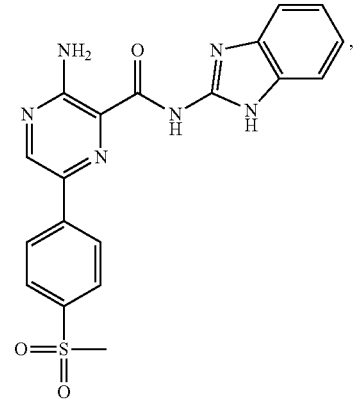

565
-continued
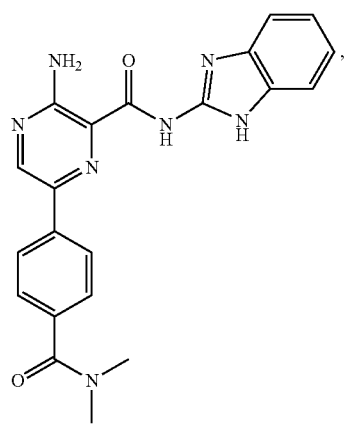
V21
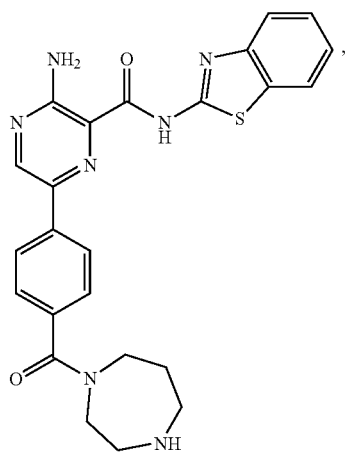
V22
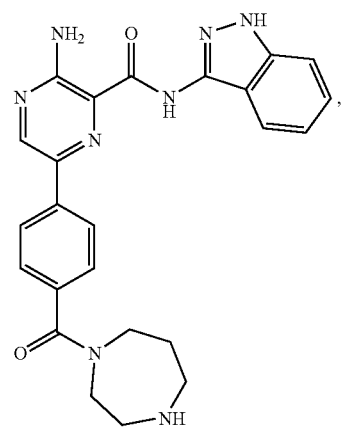
V23
566
-continued
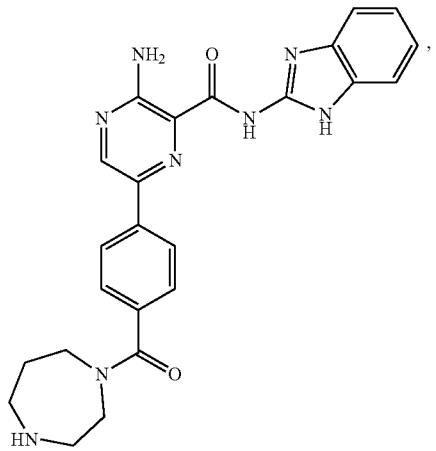
V24
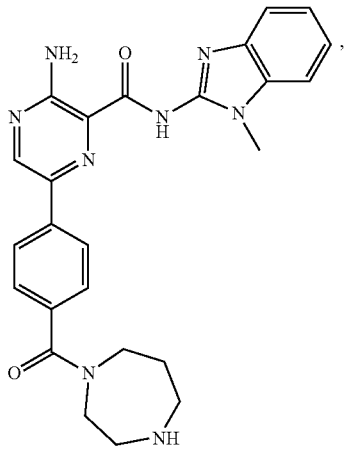
V25
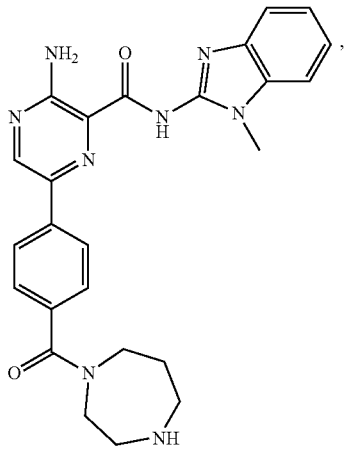
V26

567
-continued

V27
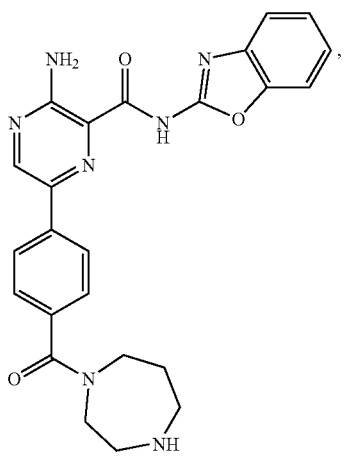

V28
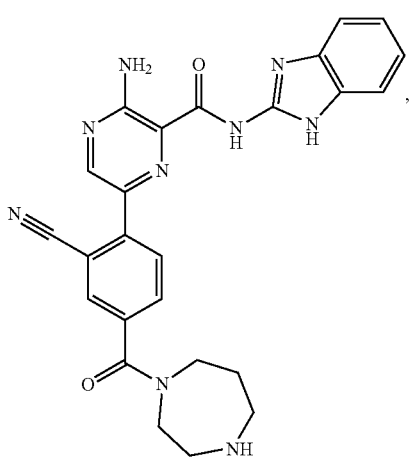

V29
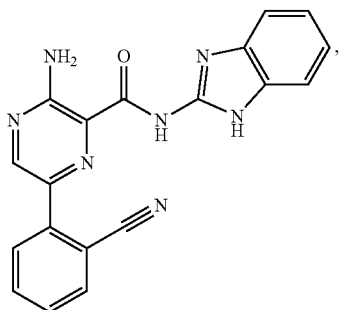

568
-continued

V-30

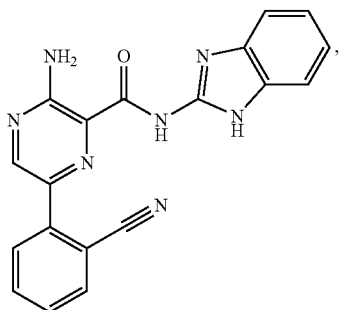

or a pharmaceutically acceptable salt thereof.

38. A method of inhibiting ATR in a biological sample comprising the step of contacting a compound of claim 19 with said biological sample.

39. A pharmaceutical composition comprising a compound of formula V,

V or a pharmaceutically acceptable salt thereof,
wherein:
Ring A is an 8-9 membered bicyclic heteroaryl ring having 1-4 heteroatoms selected from the group consisting of oxygen, nitrogen, and sulfur;
Ring Q is a 5-6 membered monocyclic aromatic ring containing 0-3 heteroatoms independently selected from the group consisting of nitrogen, oxygen, and sulfur;
L is a $C_1$-$C_4$alkyl chain, wherein up to two methylene units of the alkyl chain are optionally replaced with O, $NR^6$, S, —C(O)—, —S(O)—, or —S(O)$_2$—;
$R^1$ is H or $C_1$-$C_6$alkyl;
$R^2$ is H, $C_1$-$C_6$alkyl, —($C_2$-$C_6$alkyl)—Z, or a 3-8 membered cyclic ring containing 0-2 nitrogen atoms, wherein said ring is bonded via a carbon atom and is optionally substituted with one occurrence of $J^Z$;
or $R^1$ and $R^2$, taken together with the atom to which they are bound, form a 3-8 membered monocyclic or 8-9 membered bicyclic heterocyclic ring containing 1-2 heteroatoms selected the group consisting of oxygen, nitrogen, and sulfur, wherein said heterocyclic ring is optionally substituted with one occurrence of $J^{Z1}$;
$J^{Z1}$ is —(X)$_t$—CN, $C_1$-$C_6$alkyl or —(X)$_t$—$Z^1$;
X is $C_1$-$C_4$alkylene;
Z is —$NR^3R^4$;
$R^3$ is H or $C_1$-$C_2$alkyl;
$R^4$ is H or $C_1$-$C_6$alkyl;
or $R^3$ and $R^4$, taken together with the atom to which they are bound, form a 4-8 membered heterocyclic ring containing 1-2 nitrogen atoms, wherein said ring is optionally substituted with one occurrence of $J^{Z1}$;
$Z^1$ is —$NR^5R^6$;
$R^5$ is H or $C_1$-$C_2$alkyl;
$R^6$ is H or $C_1$-$C_6$alkyl;
or $R^5$ and $R^6$, taken together with the atom to which they are bound, form a 4-8 membered heterocyclic ring containing 1-2 nitrogen atoms; wherein said ring is optionally substituted with one occurrence of $J^{Z1}$;
$J^1$ is halo, CN, or a $C_1$-$C_6$aliphatic group wherein up to 2 methylene units are optionally replaced with O, C(O), S, S(O), or S(O)$_2$, wherein said $C_1$-$C_6$aliphatic group is optionally substituted with 1-3 fluoro or CN;
$J^2$ is halo, CN, or a $C_1$-$C_6$aliphatic group wherein up to 2 methylene units are optionally replaced with O, C(O), S, S(O), or S(O)$_2$, wherein said $C_1$-$C_6$aliphatic group is optionally substituted with 1-3 fluoro or CN;
$J^Z$ is independently $NH_2$, NH($C_1$-$C_4$aliphatic), N($C_1$-$C_4$aliphatic)$_2$, halogen, $C_1$-$C_4$aliphatic, OH, O($C_1$-$C_4$aliphatic), $NO_2$, CN, $CO_2H$, CO($C_1$-$C_4$aliphatic), $CO_2$($C_1$-$C_4$aliphatic), O(halo $C_1$-$C_4$aliphatic), or halo $C_1$-$C_4$aliphatic;
each q and m is independently 0, 1, or 2; and
each t, p, and r is independently 0 or 1;
and a pharmaceutically acceptable carrier.

40. A method of promoting cell death in cancer cells of a patient comprising administering to the patient a compound of formula V,

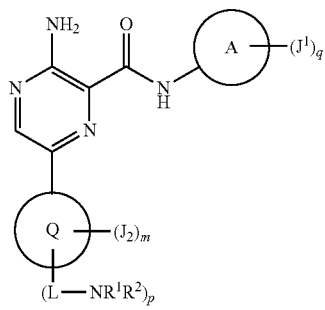

V or a pharmaceutically acceptable salt thereof,
wherein:
Ring A is an 8-9 membered bicyclic heteroaryl ring having 1-4 heteroatoms selected from the group consisting of oxygen, nitrogen, and sulfur;
Ring Q is a 5-6 membered monocyclic aromatic ring containing 0-3 heteroatoms independently selected from the group consisting of nitrogen, oxygen, and sulfur;
L is a $C_1$-$C_4$alkyl chain, wherein up to two methylene units of the alkyl chain are optionally replaced with O, $NR^6$, S, —C(O)—, —S(O)—, or —S(O)$_2$—;
$R^1$ is H or $C_1$-$C_6$alkyl;
$R^2$ is H, $C_1$-$C_6$alkyl, —($C_2$-$C_6$alkyl)—Z, or a 3-8 membered cyclic ring containing 0-2 nitrogen atoms, wherein said ring is bonded via a carbon atom and is optionally substituted with one occurrence of $J^Z$;
or $R^1$ and $R^2$, taken together with the atom to which they are bound, form a 3-8 membered monocyclic or 8-9 membered bicyclic heterocyclic ring containing 1-2 heteroatoms selected the group consisting of oxygen, nitrogen, and sulfur, wherein said heterocyclic ring is optionally substituted with one occurrence of $J^{Z1}$;

$J^{Z1}$; is $(X)_t$-CN, $C_1$-$C_6$alkyl or —$(X)_t$-$Z^1$;
X is $C_1$-$C_4$alkylene;
Z is -$R^3R^4$;
$R^3$ is H or $C_1$-$C_2$alkyl;
$R^4$ is H or $C_1$-$C_6$alkyl;
or $R^3$ and $R^4$, taken together with the atom to which they are bound, form a 4-8 membered heterocyclic ring containing 1-2 nitrogen atoms, wherein said ring is optionally substituted with one occurrence of $J^Z$;
$Z^1$ is —$NR^5R^6$;
$R^5$ is H or $C_1$-$C_2$alkyl;
$R^6$ is H or $C_1$-$C_6$alkyl;
or $R^5$ and $R^6$, taken together with the atom to which they are bound, form a 4-8 membered heterocyclic ring containing 1-2 nitrogen atoms, wherein said ring is optionally substituted with one occurrence of $J^{Z1}$;
$J^1$ is halo, CN, or a $C_1$-$C_6$aliphatic group wherein up to 2 methylene units are optionally replaced with O, C(O), S, S(O), or S(O)$_2$, wherein said $C_1$-$C_6$aliphatic group is optionally substituted with 1-3 fluoro or CN;
$J^2$ is halo, CN, or a $C_1$-$C_6$aliphatic group wherein up to 2 methylene units are optionally replaced with O, C(O), S, S(O), or S(O)$_2$, wherein said $C_1$-$C_6$aliphatic group is optionally substituted with 1-3 fluoro or CN;
$J^Z$ is independently $NH_2$, NH($C_1$-$C_4$aliphatic), N($C_1$-$C_4$aliphatic)$_2$, halogen, $C_1$-$C_4$aliphatic, OH, O($C_1$-$C_4$aliphatic), $NO_2$, CN, $CO_2H$, CO($C_1$-$C_4$aliphatic), $CO_2$($C_1$-$C_4$aliphatic), O(halo $C_1$-$C_4$aliphatic), or halo $C_1$-$C_4$aliphatic;
each q and m is independently 0, 1, or 2; and
each t, p, and r is independently 0 or 1.

41. A method of preventing cell repair from DNA damage in a patient, comprising administering to the patient a compound of formula V,

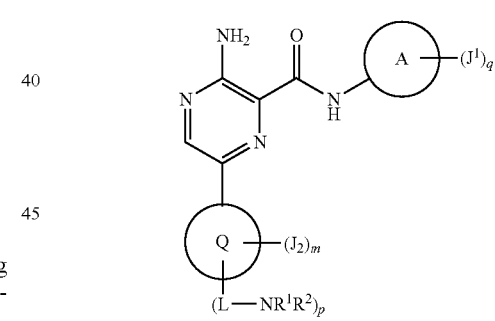

V or a pharmaceutically acceptable salt thereof,
wherein:
Ring A is an 8-9 membered bicyclic heteroaryl ring having 1-4 heteroatoms selected from the group consisting of oxygen, nitrogen, and sulfur;
Ring Q is a 5-6 membered monocyclic aromatic ring containing 0-3 heteroatoms independently selected from the group consisting of nitrogen, oxygen, and sulfur;
L is a $C_1$-$C_4$alkyl chain, wherein up to two methylene units of the alkyl chain are optionally replaced with O, $NR^6$, S, —C(O)—, —S(O)—, or —S(O)$_2$—;
$R^1$ is H or $C_1$-$C_6$alkyl;
$R^2$ is H, $C_1$-$C_6$alkyl, —($C_2$-$C_6$alkyl)—Z, or a 3-8 membered cyclic ring containing 0-2 nitrogen atoms, wherein said ring is bonded via a carbon atom and is optionally substituted with one occurrence of $J^Z$;

or R¹ and R², taken together with the atom to which they are bound, form a 3-8 membered monocyclic or 8-9 membered bicyclic heterocyclic ring containing 1-2 heteroatoms selected the group consisting of oxygen, nitrogen, and sulfur, wherein said heterocyclic ring is optionally substituted with one occurrence of $J^{Z1}$;

$J^{Z1}$ is —(X)$_t$-CN, $C_1$-$C_6$alkyl or —(X)$_t Z^1$;

X is $C_1$-$C_4$alkylene;

Z is —NR³R⁴;

R³ is H or $C_1$-$C_2$alkyl;

R⁴ is H or $C_1$-$C_6$alkyl;

or R³ and R⁴, taken together with the atom to which they are bound, form a 4-8 membered heterocyclic ring containing 1-2 nitrogen atoms, wherein said ring is optionally substituted with one occurrence of $J^Z$;

$Z^1$ is —NR⁵R⁶;

R⁵ is H or $C_1$-$C_2$alkyl;

R⁶ is H or $C_1$-$C_6$alkyl;

or R⁵ and R⁶, taken together with the atom to which they are bound, form a 4-8 membered heterocyclic ring containing 1-2 nitrogen atoms, wherein said ring is optionally substituted with one occurrence of $J^{Z1}$;

J¹ is halo, CN, or a $C_{1\text{-}C_6}$aliphatic group wherein up to 2 methylene units are optionally replaced with O, C(O), S, S(O), or S(O)$_2$, wherein said $C_1$-$C_6$aliphatic group is optionally substituted with 1-3 fluoro or CN;

J² is halo, CN, or a $C_1$-$C_6$aliphatic group wherein up to 2 methylene units are optionally replaced with O, C(O), S, S(O), or S(O)$_2$, wherein said $C_1$-$C_6$aliphatic group is optionally substituted with 1-3 fluoro or CN;

$J^Z$ is independently NH$_2$, NH($C_1$-$C_4$aliphatic), N($C_1$-$C_4$aliphatic)$_2$, halogen, $C_1$-$C_4$aliphatic, OH, O($C_1$-$C_4$aliphatic), NO$_2$, CN, CO$_2$H, CO($C_1$-$C_4$aliphatic), CO$_2$($C_1$-$C_4$aliphatic), O(halo $C_1$-$C_4$aliphatic), or halo $C_1$-$C_4$aliphatic;

each q and m is independently 0, 1, or 2; and each t, p, and r is independently 0 or 1.

42. A compound of Formula VII:

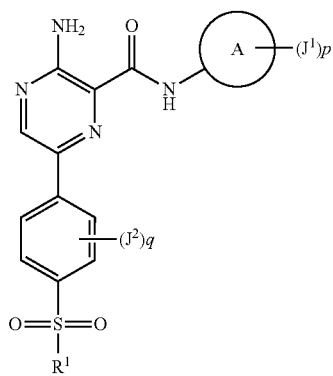

VII or a pharmaceutically acceptable salt thereof, wherein:

Ring A is a 5-6 membered monocyclic aryl or heteroaryl ring having 0-3 heteroatoms independently selected from the group consisting of nitrogen, oxygen, and sulfur, wherein said ring is optionally substituted with J¹;

R¹ is $C_1$-$C_6$alkyl;

J¹ is a $C_1$-$C_6$alkyl chain wherein 1-2 methylene units are optionally replaced with O, NR*, S, or C(O), wherein J¹ is optionally substituted with 1-3 occurrences of halo;

R* is H or $C_1$-$C_4$alkyl;

J² is halo, $C_1$-$C_2$alkyl optionally substituted with 1-3 fluoro, or CN; and each p and q is independently 0, 1, or 2.

43. The compound of claim 42, wherein Ring A is a 5-6 membered monocyclic heteroaryl having 1-3 heteroatoms independently selected from the group consisting of nitrogen, oxygen, and sulfur.

44. The compound of claim 34, wherein Ring A is pyridinyl, pyrimidinyl, pyrazinyl, triazinyl, pyrrolyl, pyrazolyl, triazolyl, thienyl, thiazolyl, thiadiazolyl, furanyl, oxazolyl, or oxadiazolyl.

45. The compound of claim 43, wherein Ring A is pyridinyl, pyrazolyl, thiadiazolyl, or thiazolyl, wherein Ring A is optionally substituted with $C_{1\text{-}4}$alkyl.

46. The compound of claim 33, wherein Ring A is phenyl.

47. The compound of claim 46, wherein said phenyl is substituted with one occurrence of J¹.

48. The compound of claim 47, wherein J¹ is a $C_1$-$C_6$alkyl chain wherein 1 methylene unit is replaced with NR* or O.

49. The compound of claim 38, wherein J¹ is O($C_1$-$C_4$alkyl) or —($C_1$-$C_4$alkyl)NH($C_1$-$C_4$alkyl).

50. The compound of claim 39, wherein J¹ is —($C_1$-$C_4$alkyl)NH($C_1$-$C_4$alkyl).

51. The compound of claim 42, wherein the compound is:

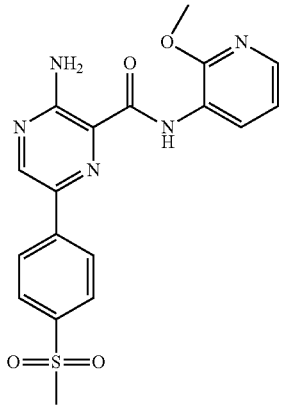

VII-1

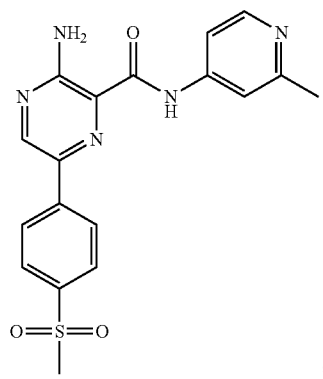

VII-2

VII-3 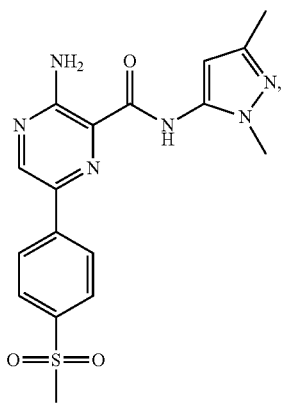
VII-4 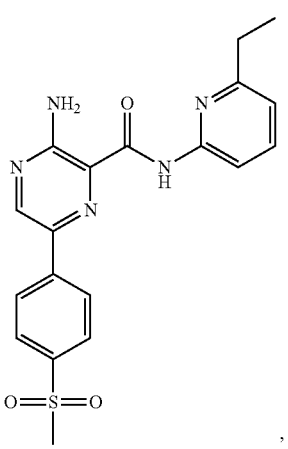
VII-5 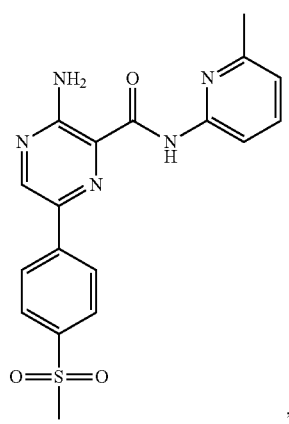
VII-6 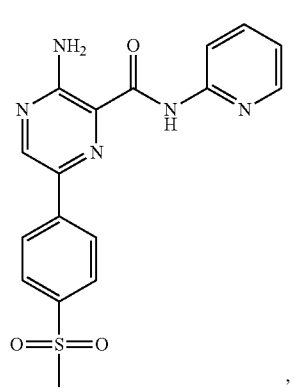
VII-7 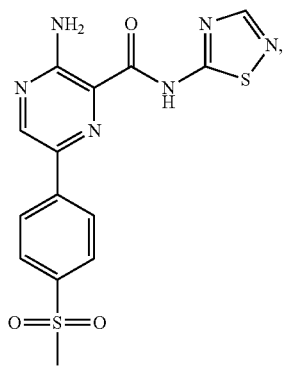
VII-8 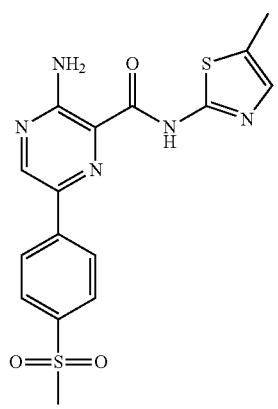
VII-9 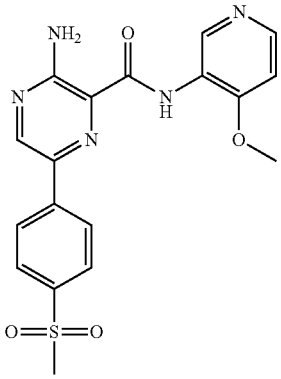
VII-10 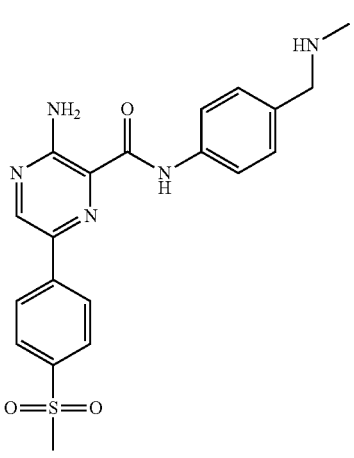

-continued

VII-11
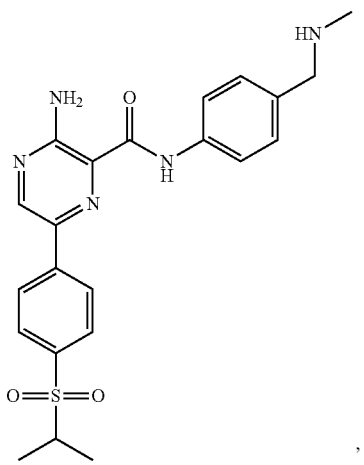

VII-12
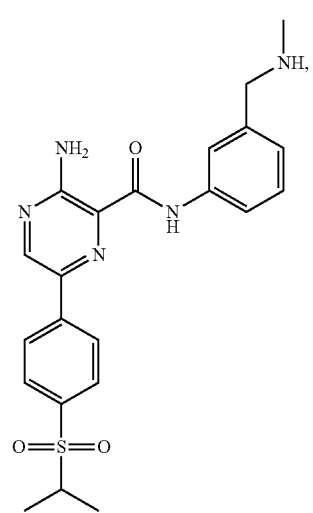

VII-13
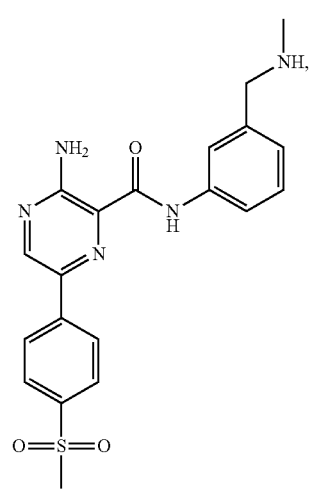

or a pharmaceutically acceptable salt thereof.

52. A method of inhibiting ATR in a biological sample comprising the step of contacting a compound of claim 42 with said biological sample.

53. A pharmaceutical composition comprising a compound of formula VII,

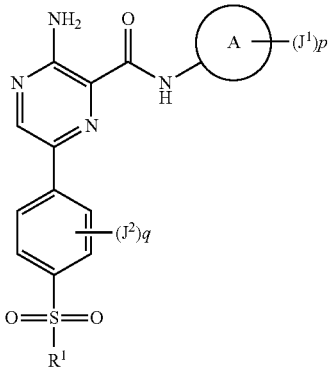

or a pharmaceutically acceptable salt thereof, wherein:
Ring A is a 5-6 membered monocyclic aryl or heteroaryl ring having 0-3 heteroatoms independently selected from the group consisting of nitrogen, oxygen, and sulfur, wherein said ring is optionally substituted with $J^1$;
$R^1$ is $C_1$-$C_6$alkyl;
$J^1$ is a $C_1$-$C_6$alkyl chain, wherein 1-2 methylene units are optionally replaced with O, NR*, S, or C(O), wherein $J^1$ is optionally substituted with 1-3 occurrences of halo;
R* is H or $C_1$-$C_4$alkyl;
$J^2$ is halo, $C_1$-$C_2$alkyl optionally substituted with 1-3 fluoro, or CN; and each p and q is independently 0, 1, or 2;
and a pharmaceutically acceptable carrier.

54. A method of promoting cell death in cancer cells of a patient comprising administering to the patient a compound of formula VII,

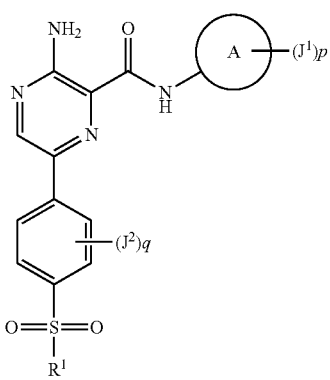

or a pharmaceutically acceptable salt thereof, wherein:
Ring A is a 5-6 membered monocyclic aryl or heteroaryl ring having 0-3 heteroatoms independently selected from the group consisting of nitrogen, oxygen, and sulfur, wherein said ring is optionally substituted with $J^1$;
$R^1$ is $C_1$-$C_6$alkyl;
$J^1$ is a $C_1$-$C_6$alkyl chain, wherein 1-2 methylene units are optionally replaced with O, NR*, S, or C(O), wherein $J^1$ is optionally substituted with 1-3 occurrences of halo;
R* is H or $C^1$-$C^4$alkyl;
$J^2$ is halo, $C_1$-$C_2$alkyl optionally substituted with 1-3 fluoro, or CN; and
each p and q is independently 0, 1, or 2.

55. A method of preventing cell repair from DNA damage in a patient comprising administering to the patient a compound of formula VII,

VII or a pharmaceutically acceptable salt thereof, wherein:
Ring A is a 5-6 membered monocyclic aryl or heteroaryl ring having 0-3 heteroatoms independently selected from the group consisting of nitrogen, oxygen, and sulfur, wherein said ring is optionally substituted with $J^1$;
$R^1$ is $C_1$-$C_6$alkyl;
$J^1$ is a $C_1$-$C_6$alkyl chain, wherein 1-2 methylene units are optionally replaced with O, NR*, S, or C(O), wherein $J^1$ is optionally substituted with 1-3 occurrences of halo;
R* is H or $C_1$-$C_4$alkyl;
$J^2$ is halo, $C_1$-$C_2$alkyl optionally substituted with 1-3 fluoro, or CN; and
each p and q is independently 0, 1, or 2.

56. A method of sensitizing cells of a patient to DNA damaging agents comprising administering to the patient a compound of any one of claims 1, 14, and 33.

57. The method of claim 49, wherein said cells are cancer cells having defects in the ATM signaling cascade.

58. The method of claim 57, wherein said defect is altered expression or activity of one or more selected from the group consisting of ATM, p53, CHK2, MRE11, RAD50, NBS1, 53BP1, MDC1, and H2AX.

59. The method of claim 56, wherein said cells are cancer cells expressing DNA damaging oncogenes.

60. The method of claim 19, wherein said cancer cell has altered expression or activity of one or more selected from the group consisting of K-Ras, N-Ras, H-Ras, Raf, Myc, Mos, E2F, Cdc25A, CDC4, CDK2, Cyclin E, Cyclin A, and Rb.

61. A compound selected from the group consisting of:

I-7
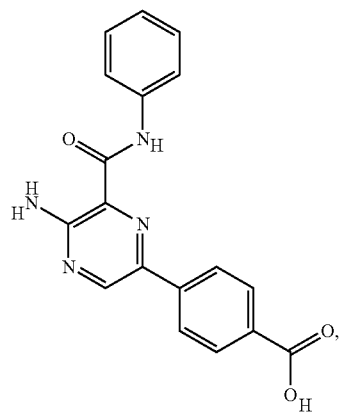
I-8
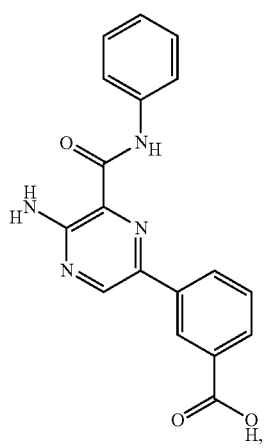
I-9
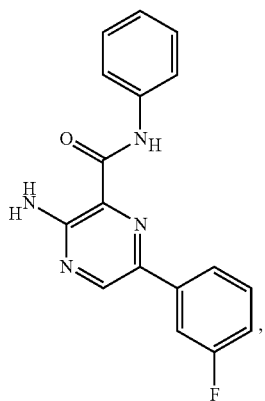
I-10
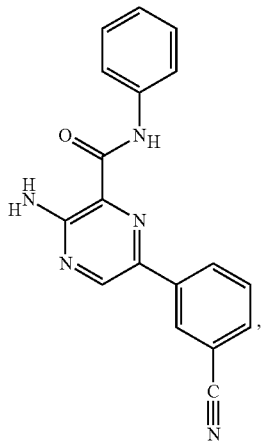
I-11
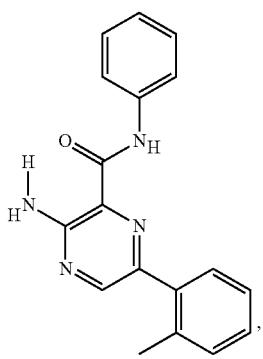
I-12
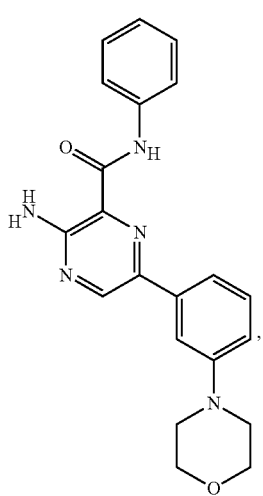

I-13
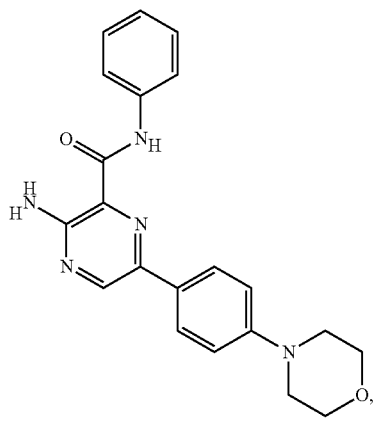
I-14
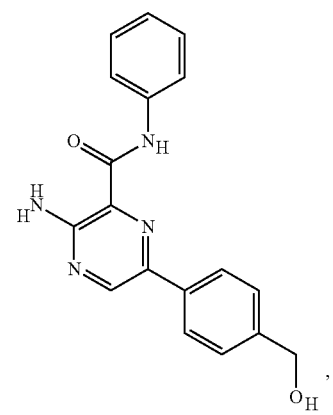
I-16
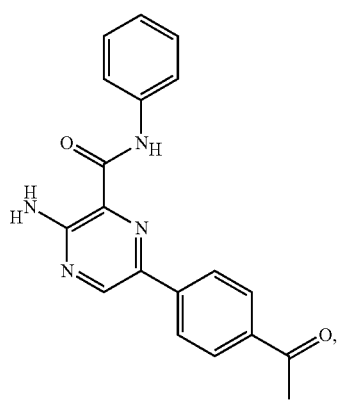
I-17
I-18
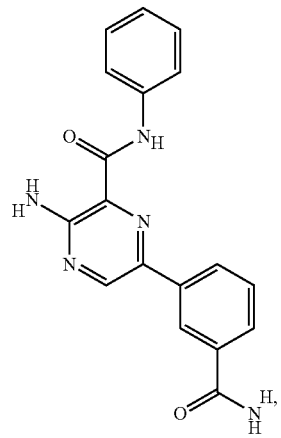
I-19
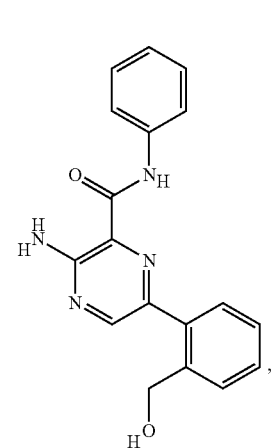
I-20
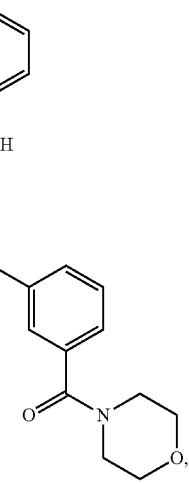

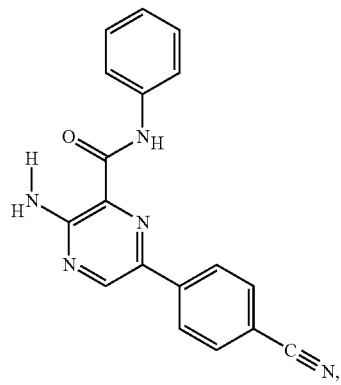
I-21
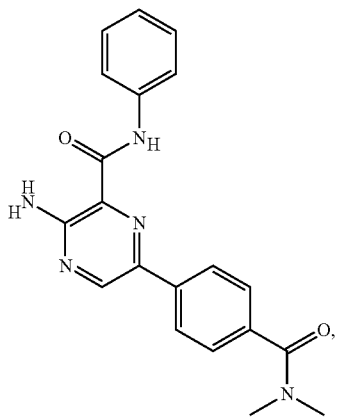
I-24
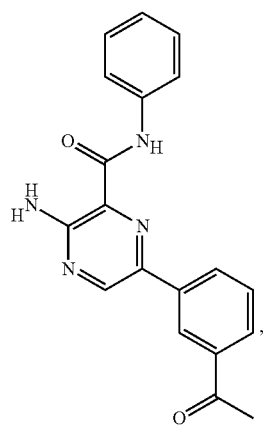
I-22
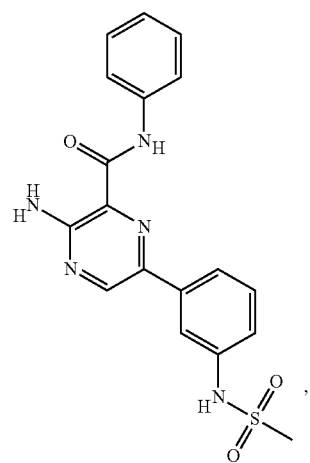
I-25
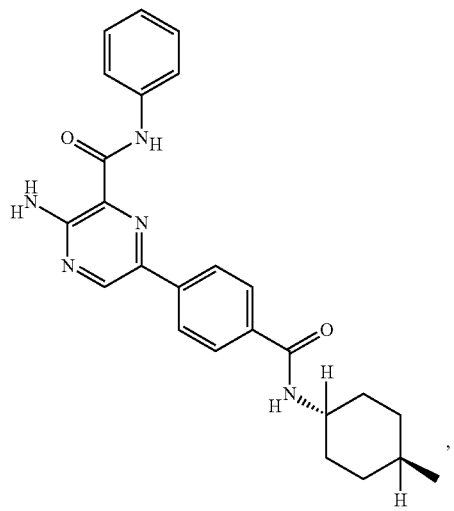
I-23
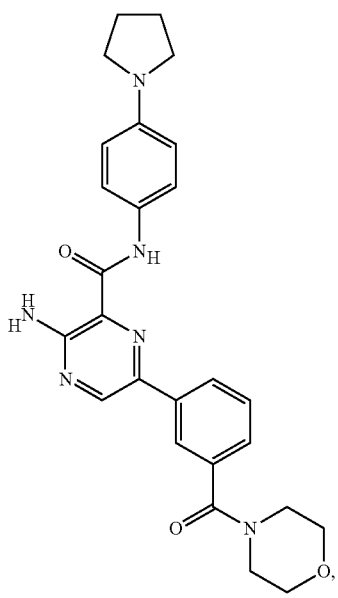
I-26

-continued
I-27
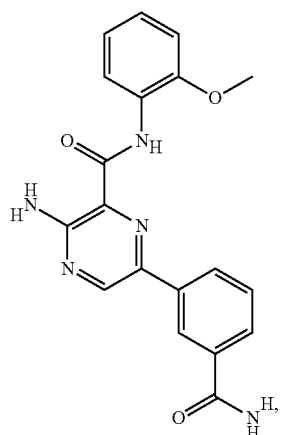
I-28
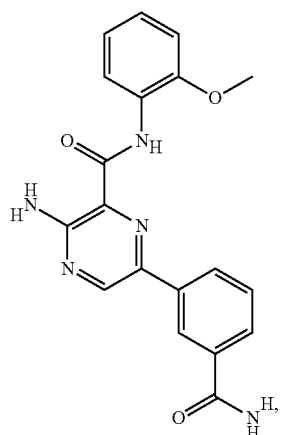
I-29
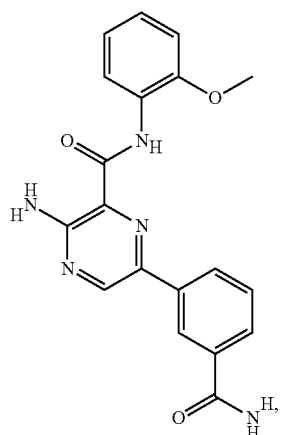
I-30
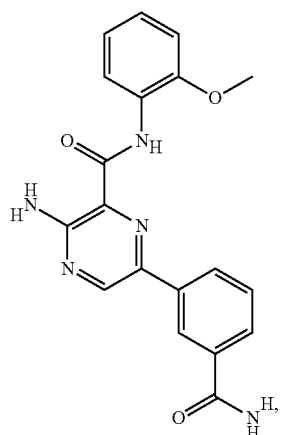
-continued
I-31
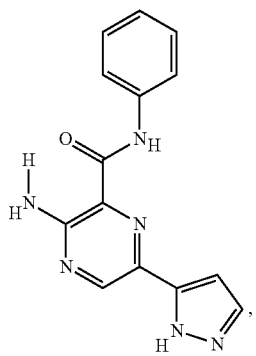
I-32
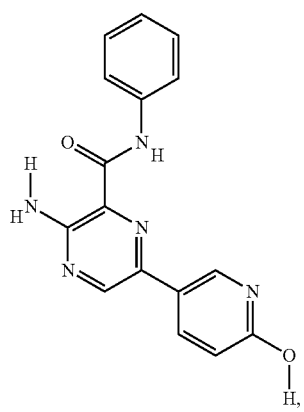
I-33
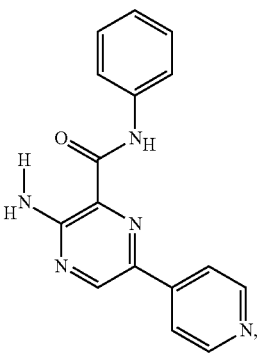
I-34
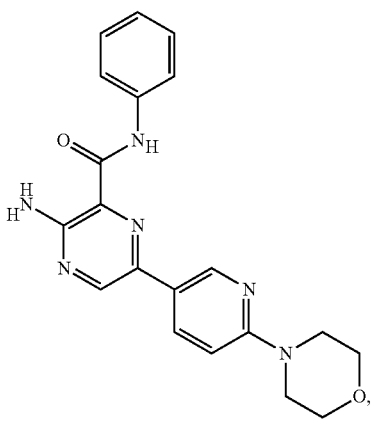

I-35
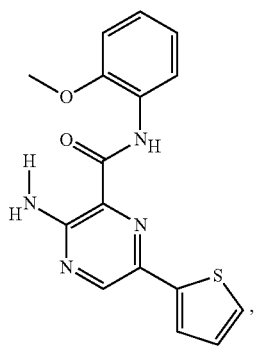
I-36
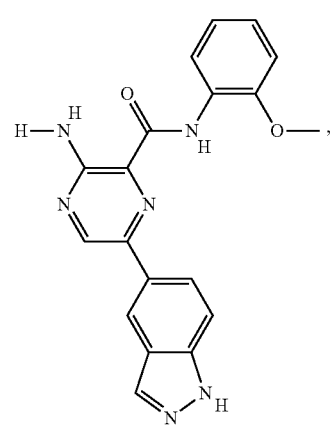
I-37
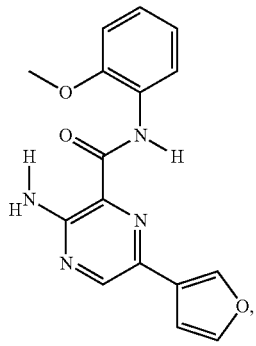
I-38
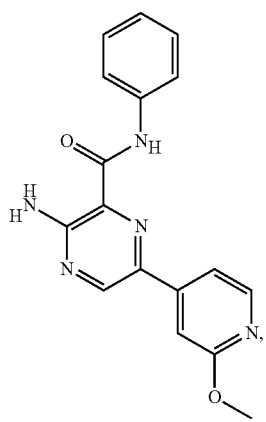
I-39
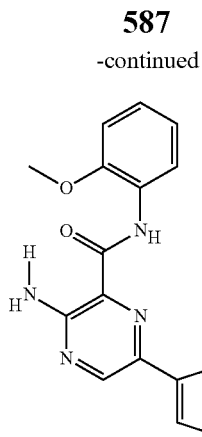
I-40
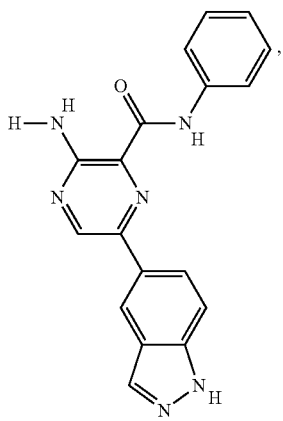
I-41
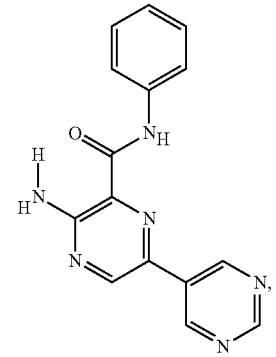
I-42
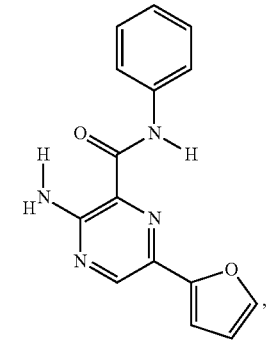

I-43
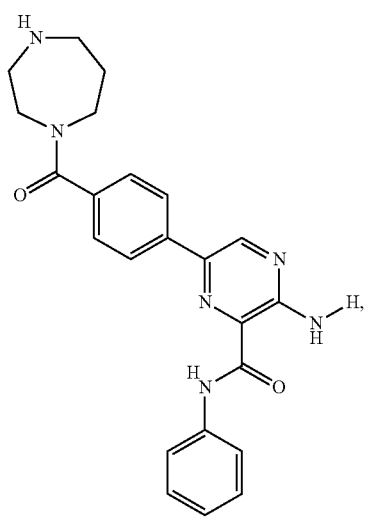
I-44
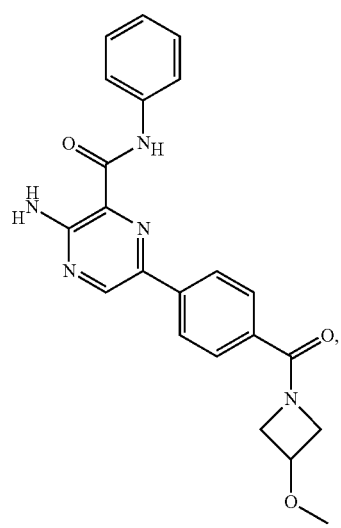
I-45
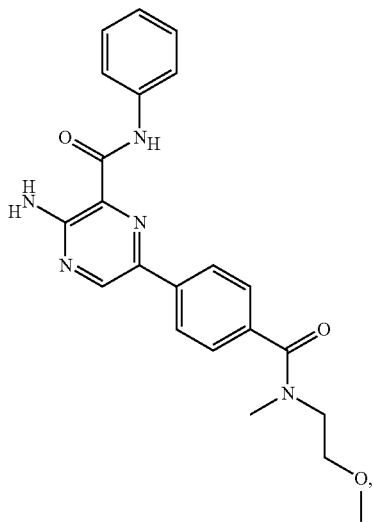
I-46
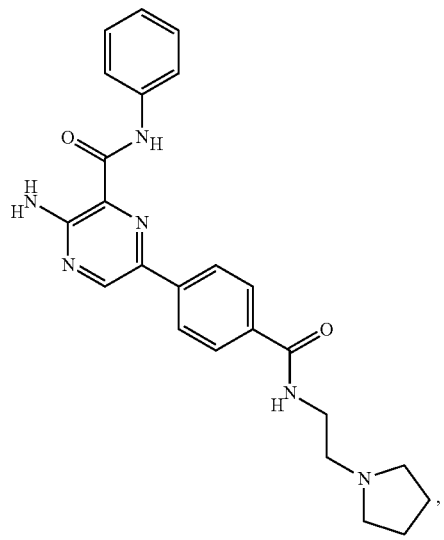
I-47
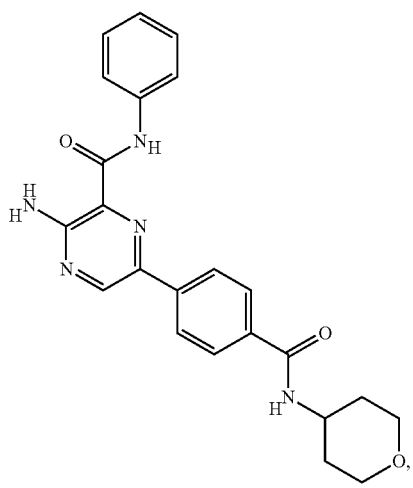
I-48
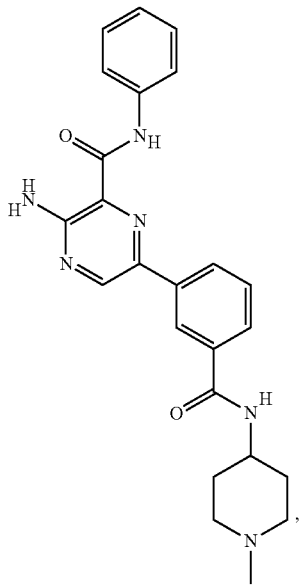

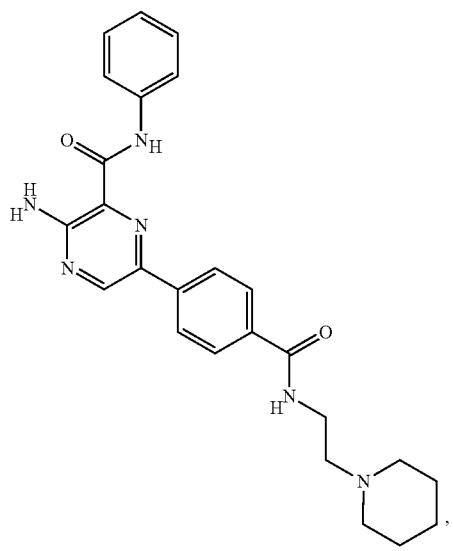
I-49
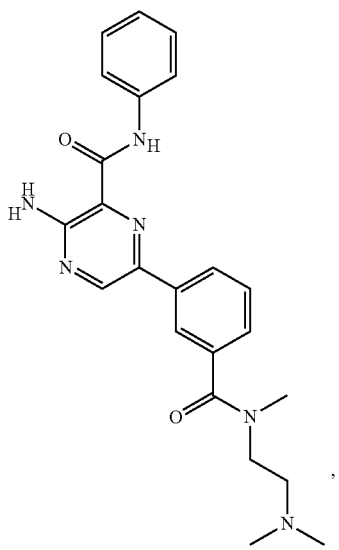
I-52
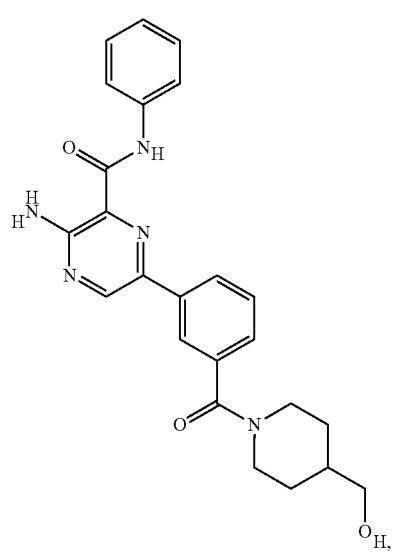
I-50
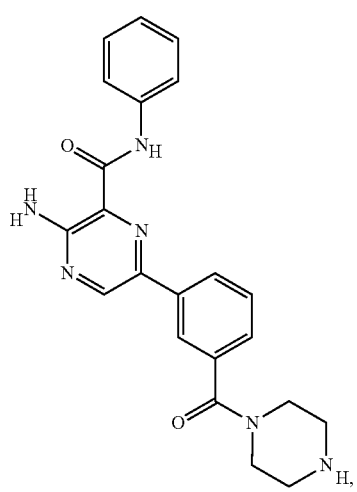
I-53
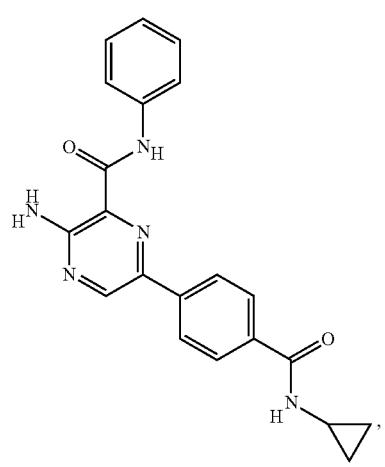
I-51
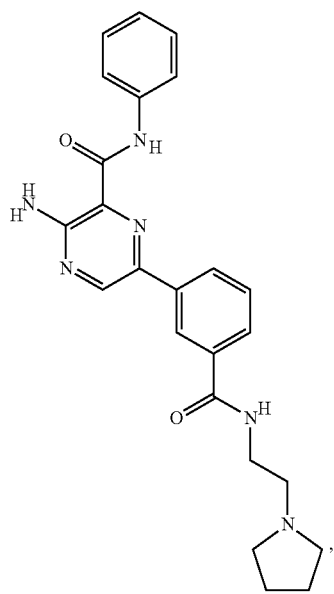
I-54

I-55
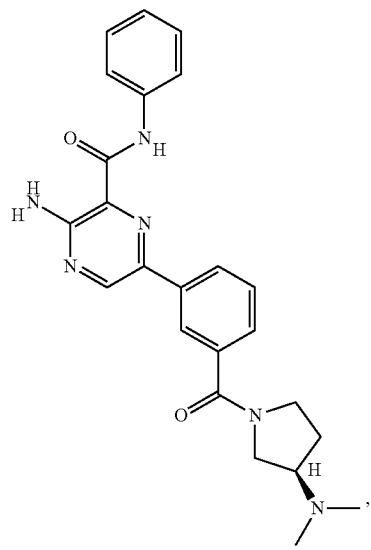
I-56
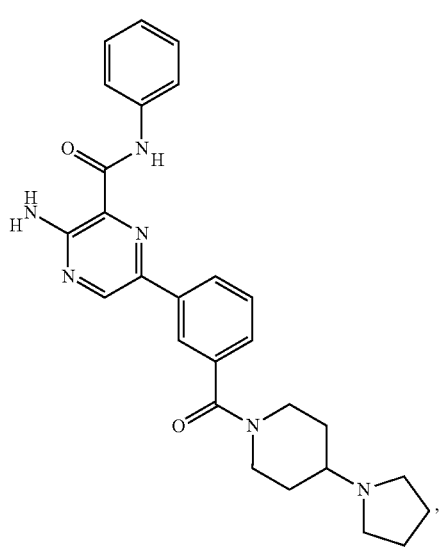
I-57
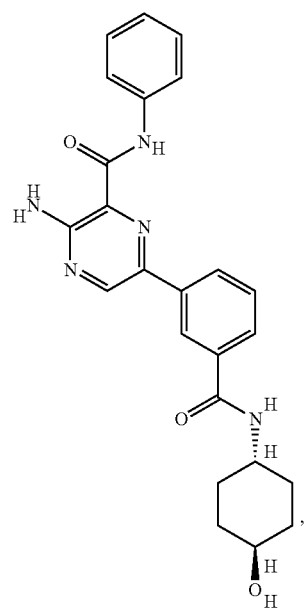
I-58
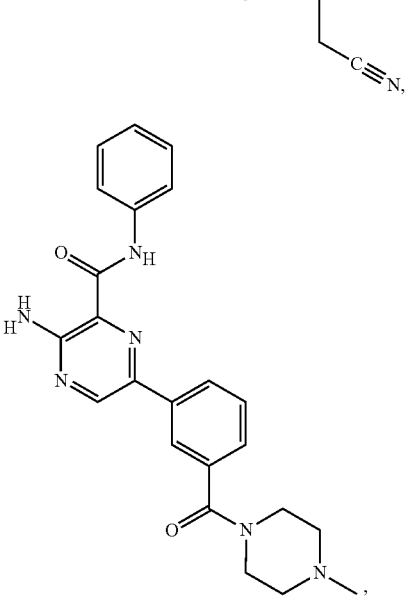
I-59

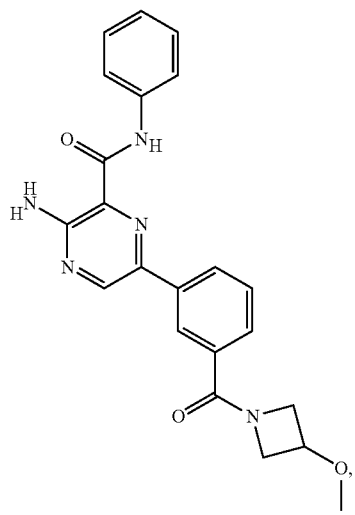
I-60
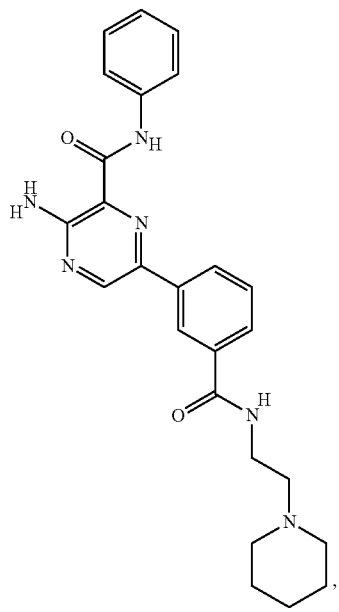
I-61
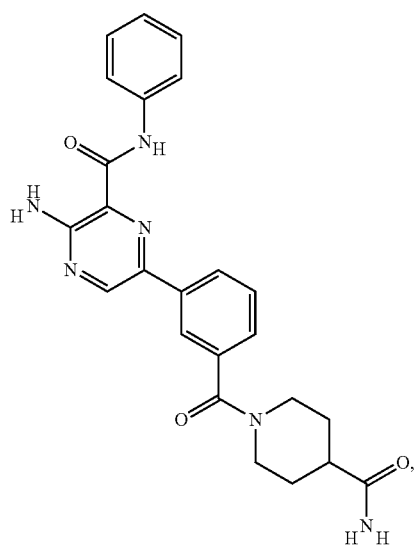
I-62
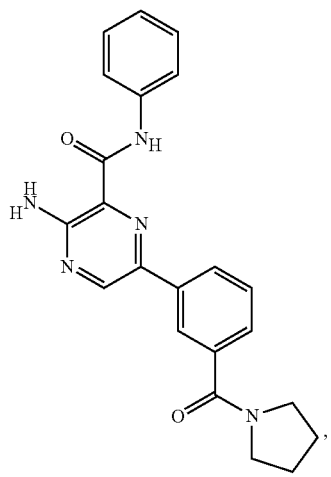
I-63
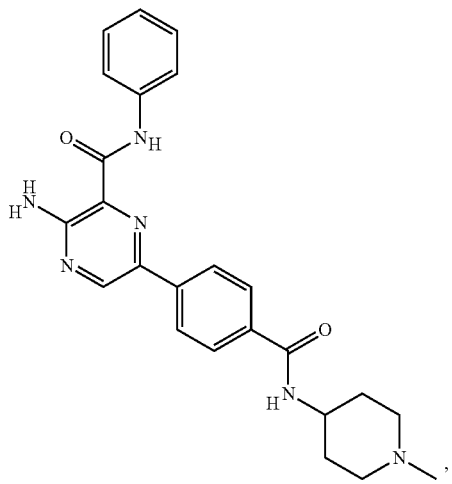
I-64
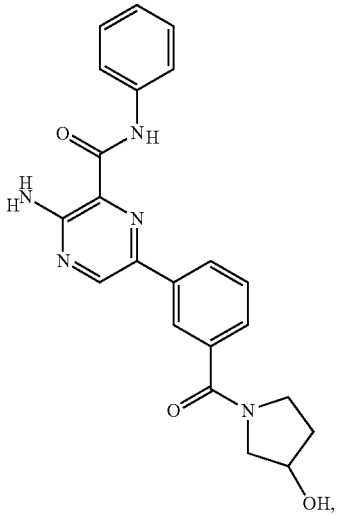
I-65

I-66
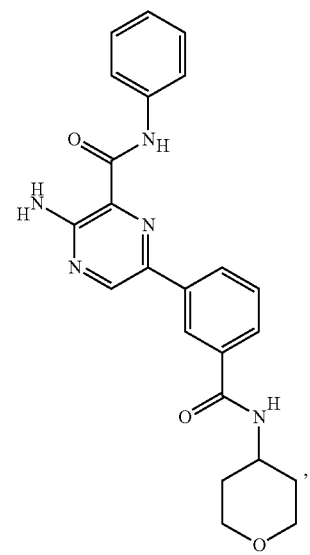
I-67
I-68
I-69
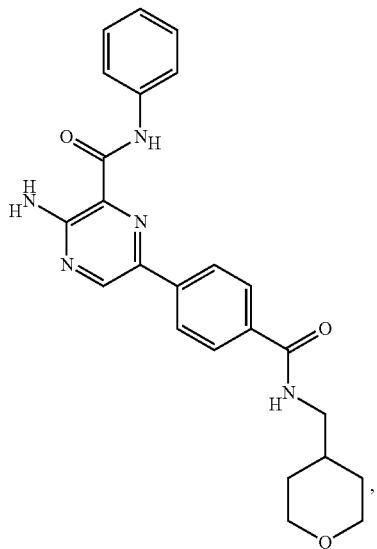
I-70
I-71
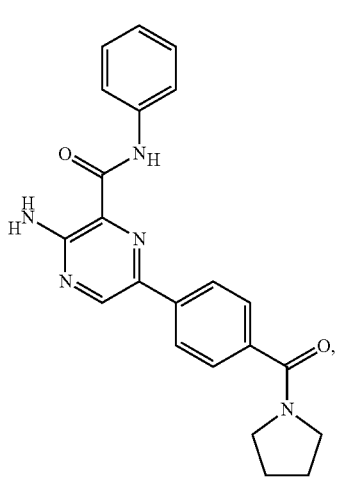

I-72

I-73

I-74

I-75

I-76

I-77

I-78
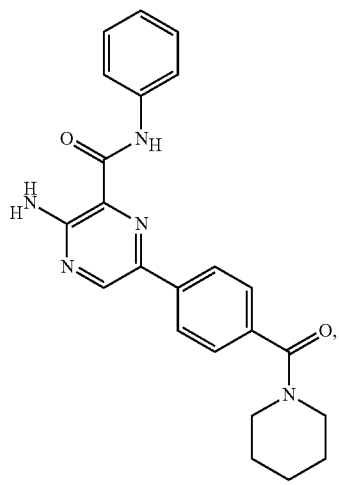
I-79
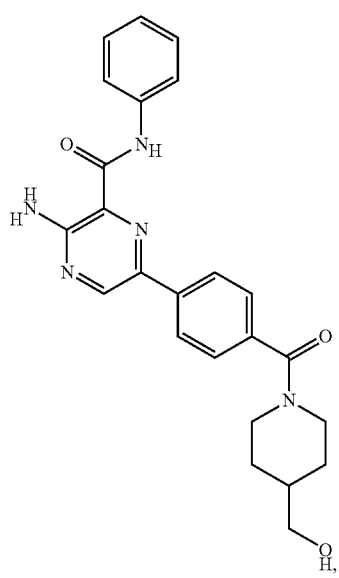
I-80
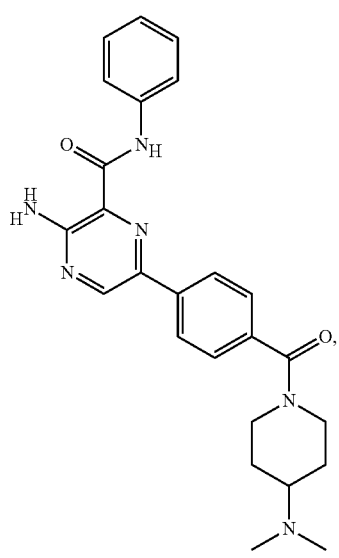
I-81
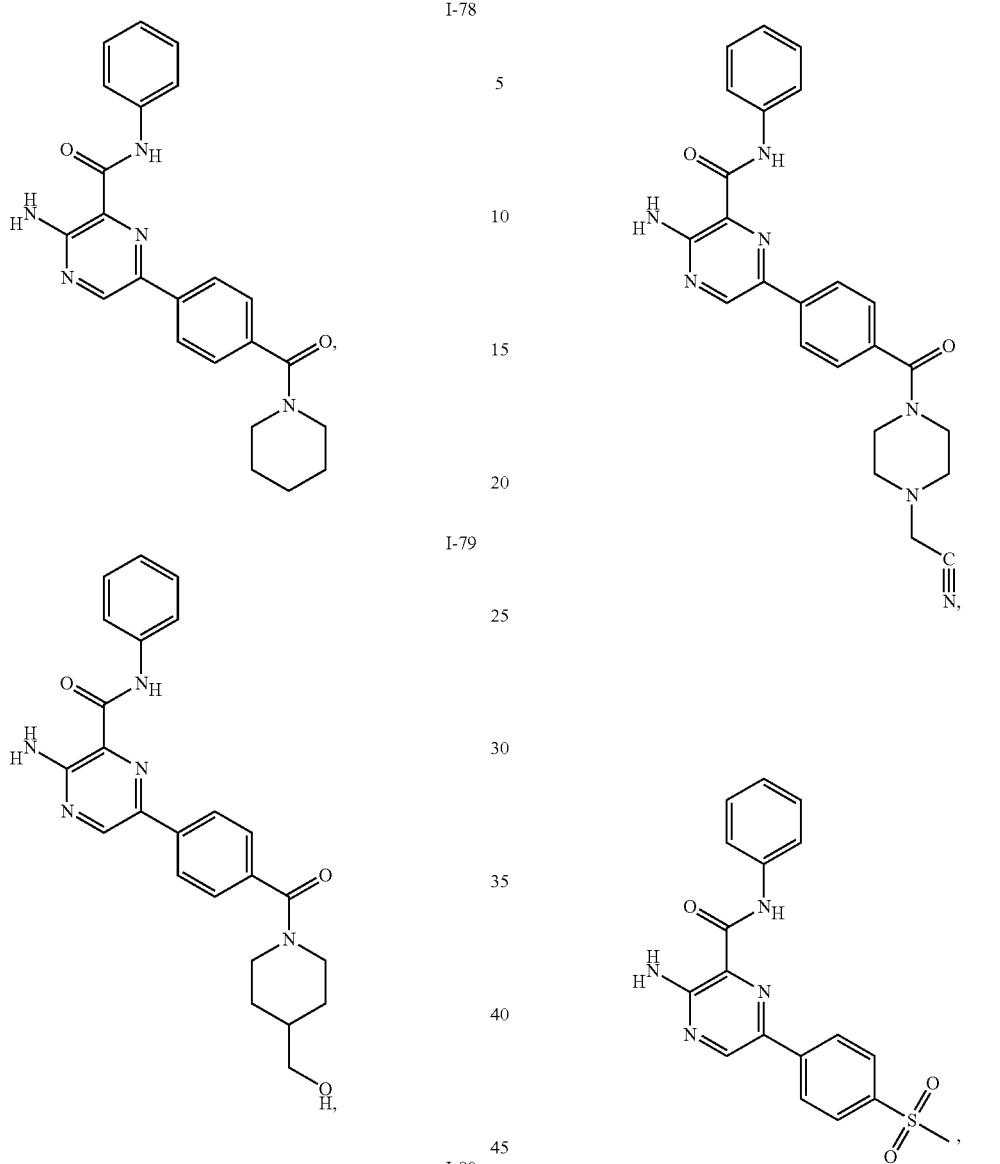
I-82
I-83
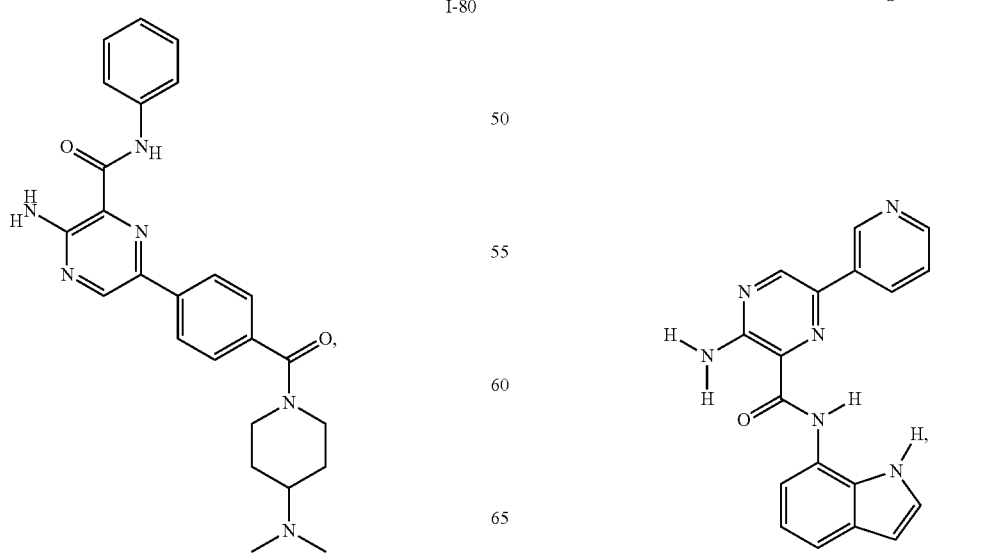

| | |
|---|---|
| 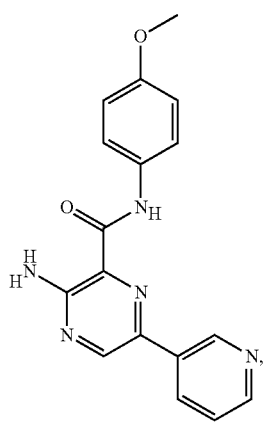 | I-84 |
| 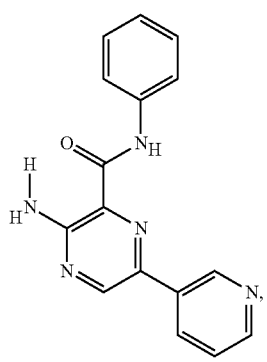 | I-85 |
| 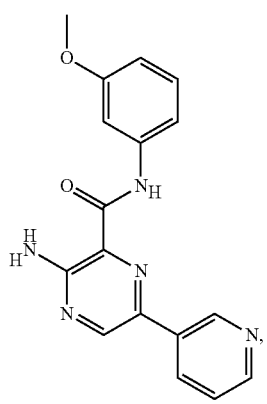 | I-86 |
| 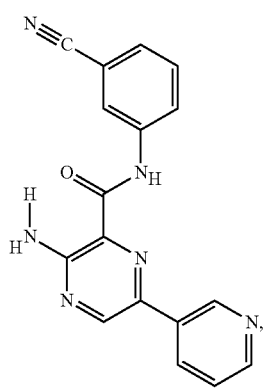 | I-87 |
| 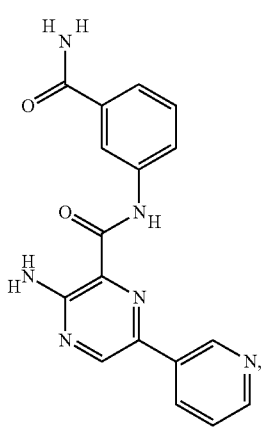 | I-88 |
| 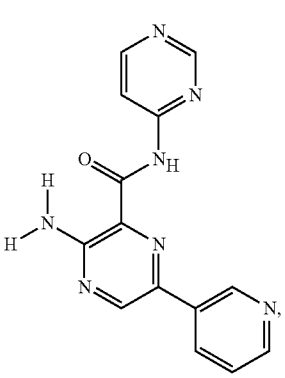 | I-89 |
| 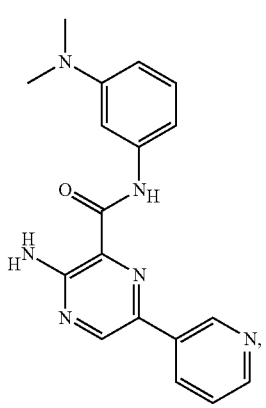 | I-90 |
| 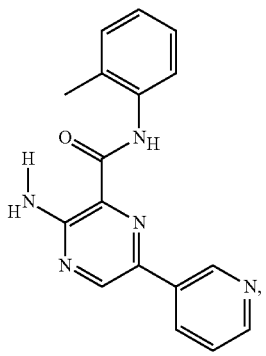 | I-91 |

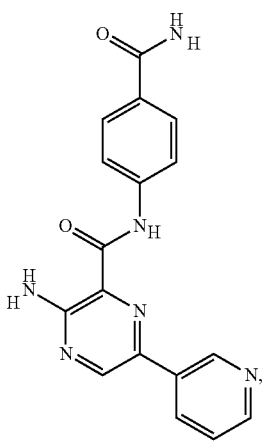
I-92
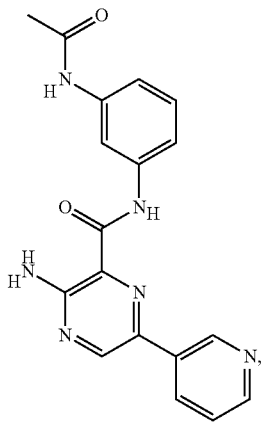
I-95
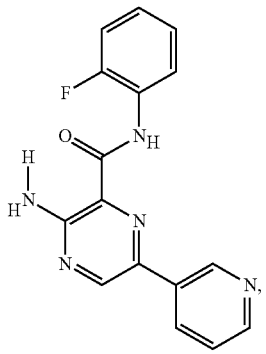
I-96
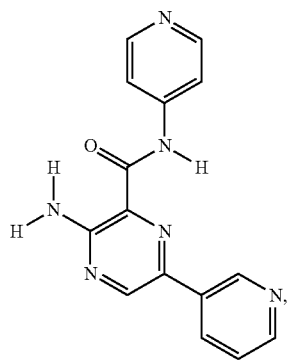
I-98
I-93
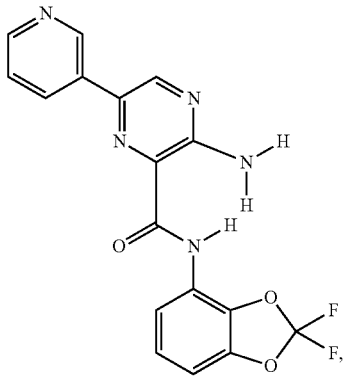
I-99
I-94

US 9,701,674 B2
607
-continued
I-100
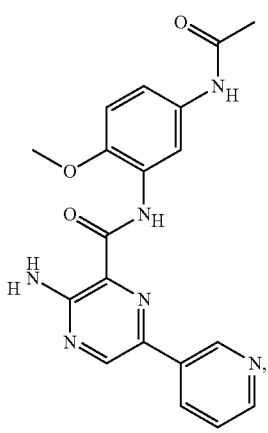
I-101
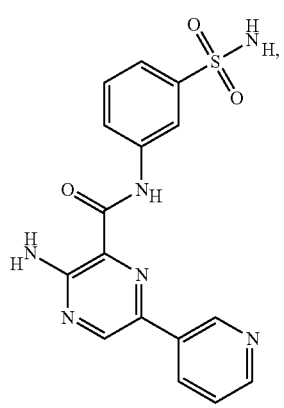
I-102
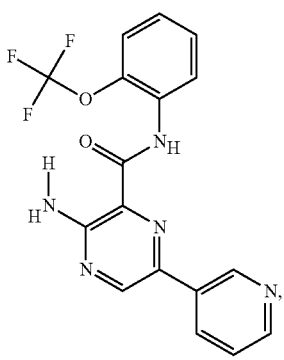
I-103
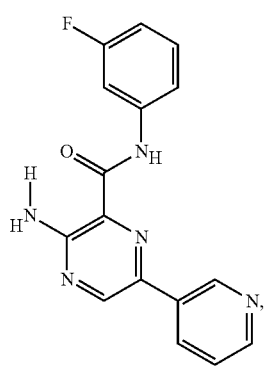
608
-continued
I-104
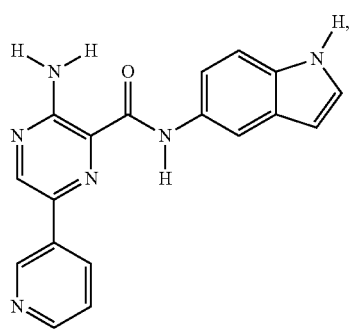
I-105
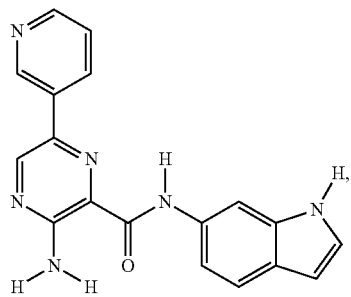
I-106
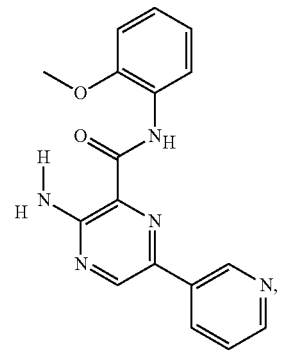
I-107
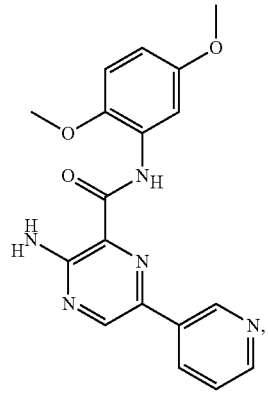

I-108
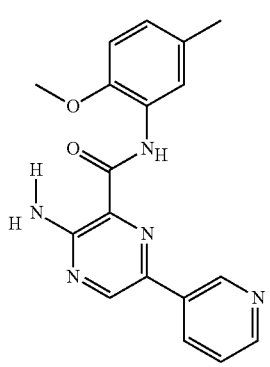
and pharmaceutically acceptable salts thereof.
* * * * *

SEQUENCE LISTING

```
<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ser Glu Leu Pro Ala Ser Gln Pro Gln Pro Phe Ser Ala Lys Lys
1               5                   10                  15

Lys
```